US008367390B2

(12) United States Patent
De Maria et al.

(10) Patent No.: US 8,367,390 B2
(45) Date of Patent: Feb. 5, 2013

(54) GALACTANASE VARIANTS

(75) Inventors: Leonardo De Maria, Frederiksberg (DK); Allan Svendsen, Hoersholm (DK); Torben Vedel Borchert, Birkeroed (DK); Lars Lehmann Hylling Christensen, Alleroed (DK); Sine Larsen, Grenoble (FR); Carsten Ryttersgaard, Los Angeles, CA (US)

(73) Assignee: Novozymes A/S, Bagsvaerd (DK)

( * ) Notice: Subject to any disclaimer, the term of this patent is extended or adjusted under 35 U.S.C. 154(b) by 516 days.

(21) Appl. No.: 12/420,446

(22) Filed: Apr. 8, 2009

(65) Prior Publication Data

US 2009/0203106 A1 Aug. 13, 2009

Related U.S. Application Data

(62) Division of application No. 10/537,746, filed as application No. PCT/DK03/00851 on Dec. 11, 2003, now Pat. No. 7,537,921.

(60) Provisional application No. 60/437,615, filed on Jan. 2, 2003, provisional application No. 60/461,230, filed on Apr. 8, 2003.

(30) Foreign Application Priority Data

Dec. 20, 2002 (DK) ................. 2002 01968
Apr. 8, 2003 (DK) ................. 2003 00537

(51) Int. Cl.
*C12N 9/24* (2006.01)
*G01N 33/53* (2006.01)
*C12Q 1/34* (2006.01)
*C07H 21/04* (2006.01)
*A23C 17/00* (2006.01)

(52) U.S. Cl. ............ 435/200; 435/7.6; 435/18; 426/42; 536/23.2

(58) Field of Classification Search ................. None
See application file for complete search history.

(56) References Cited

U.S. PATENT DOCUMENTS 6,242,237 B1 * 6/2001 Kofod et al. ................. 435/200
6,329,185 B1 12/2001 Kofod

FOREIGN PATENT DOCUMENTS

WO WO 97/32014 9/1997
WO WO-00-47711 * 8/2000
WO WO 00/47711 8/2000

OTHER PUBLICATIONS

Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry.*
De Vries et al, Eur J Biochem, vol. 269, No. 20, pp. 4985-4993 (2002).
De Vries et al, Uniprot Acces No. Q8X168 (2002).
Bergmans et al, Biotechnol Tech, vol. 13, No. 1, pp. 87-92 (1999).
Ryttersgaard et al., "Crystallization and Preliminary X-Ray Studies of Beta-1,4-Galactanasse From *Aspergillus aculeatus*" Acta Crystallographica, vol. D55, pp. 929-930 (1999).
Le Nours et al., "Structure of Two Fungal Beta-1,4 Galactanases: Searching for the Basis for Temperature and pH Optimum", Protein Science, vol. 12, pp. 1195-1204 (2003).
Abstract of JP 2003174892 (Jun. 24, 2003).
Braithwaite et al., "Evidence That Galactanase From *Pseudomonas Fluorescence Subspecies Cellulosa* is a Retaining Family 53 Glyscosyl Hydrolase in Which E161 and E270 are in the Catalytic Residues", Biochemistry, vol. 36, No. 49, pp. 15489-15500 (1997).
Ryttersgaard et al., "*Aspergillus aculeatus* Beta-1,4-Galactanase: Substrate Recognition and Relations to Other Glycoside Hydrolases in Clan GH-A", Biochemistry, vol. 41, No. 51, pp. 15135-15143 (2002).
Database UniProt—Accession No. Q9Y7F8 (1999).
Branden et al., Introduction to Protein Structure, pp. 247, (1991).
Witkowski et al., Biochemistry, vol. 38, No. 36, pp. 11643-11650, (1999).
Seffernick et al., Journal of Bacteriology, vol. 183, No. 8, pp. 2405-2410 (2001).

* cited by examiner

*Primary Examiner* — Anand Desai
*Assistant Examiner* — Iqbal H Chowdhury
(74) *Attorney, Agent, or Firm* — Elias Lambiris

(57) ABSTRACT

The present invention relates to variants of Glycoside Hydrolase family 53 galactanases, e.g., variants of the galactanases from strains of *Yersinia, Aspergillus, Humicola, Meripilus, Myceliophthora, Thermomyces, Bacillus, Bifidobacterium, Cellvibrio, Clostridium, Pseudomonas, Thermotoga,* or *Xanthomonas*.

12 Claims, 174 Drawing Sheets

```
HEADER                                                                    MTGL
ATOM    1   CB   ALA   1    15.214   -2.789   18.265   1.00  29.91        MTGL
ATOM    2   C    ALA   1    17.670   -3.053   17.823   1.00  27.24        MTGL
ATOM    3   O    ALA   1    18.335   -2.394   17.026   1.00  27.44        MTGL
ATOM    4   N    ALA   1    16.132   -5.006   17.678   1.00  29.26        MTGL
ATOM    5   CA   ALA   1    16.268   -3.540   17.450   1.00  28.32        MTGL
ATOM    6   N    LEU   2    18.116   -3.378   19.034   1.00  25.13        MTGL
ATOM    7   CA   LEU   2    19.439   -2.955   19.486   1.00  23.17        MTGL
ATOM    8   CB   LEU   2    19.648   -3.322   20.957   1.00  23.07        MTGL
ATOM    9   CG   LEU   2    18.891   -2.507   22.005   1.00  23.57        MTGL
ATOM   10   CD1  LEU   2    19.156   -3.090   23.384   1.00  23.95        MTGL
ATOM   11   CD2  LEU   2    19.330   -1.057   21.940   1.00  23.31        MTGL
ATOM   12   C    LEU   2    20.560   -3.574   18.664   1.00  22.07        MTGL
ATOM   13   O    LEU   2    20.524   -4.757   18.340   1.00  21.83        MTGL
ATOM   14   N    THR   3    21.557   -2.767   18.329   1.00  20.29        MTGL
ATOM   15   CA   THR   3    22.699   -3.257   17.575   1.00  19.63        MTGL
ATOM   16   CB   THR   3    23.506   -2.100   16.978   1.00  20.33        MTGL
ATOM   17   OG1  THR   3    22.674   -1.360   16.083   1.00  20.92        MTGL
ATOM   18   CG2  THR   3    24.728   -2.626   16.227   1.00  20.96        MTGL
ATOM   19   C    THR   3    23.610   -4.038   18.515   1.00  19.16        MTGL
ATOM   20   O    THR   3    24.131   -5.092   18.156   1.00  19.29        MTGL
ATOM   21   N    TYR   4    23.796   -3.514   19.724   1.00  18.09        MTGL
ATOM   22   CA   TYR   4    24.652   -4.159   20.715   1.00  17.42        MTGL
ATOM   23   CB   TYR   4    25.724   -3.180   21.202   1.00  17.15        MTGL
ATOM   24   CG   TYR   4    26.514   -2.544   20.082   1.00  18.02        MTGL
ATOM   25   CD1  TYR   4    27.516   -3.251   19.412   1.00  17.43        MTGL
ATOM   26   CE1  TYR   4    28.210   -2.678   18.348   1.00  18.07        MTGL
ATOM   27   CD2  TYR   4    26.229   -1.246   19.661   1.00  17.07        MTGL
ATOM   28   CE2  TYR   4    26.916   -0.666   18.598   1.00  18.55        MTGL
ATOM   29   CZ   TYR   4    27.902   -1.386   17.948   1.00  17.59        MTGL
ATOM   30   OH   TYR   4    28.564   -0.814   16.891   1.00  18.07        MTGL
ATOM   31   C    TYR   4    23.858   -4.657   21.912   1.00  16.29        MTGL
ATOM   32   O    TYR   4    23.210   -3.876   22.615   1.00  16.95        MTGL
ATOM   33   N    ARG   5    23.907   -5.964   22.125   1.00  15.87        MTGL
ATOM   34   CA   ARG   5    23.232   -6.611   23.244   1.00  16.37        MTGL
ATOM   35   CB   ARG   5    22.281   -7.711   22.746   1.00  17.04        MTGL
ATOM   36   CG   ARG   5    21.203   -7.235   21.764   1.00  18.21        MTGL
ATOM   37   CD   ARG   5    20.189   -8.348   21.482   1.00  18.30        MTGL
ATOM   38   NE   ARG   5    20.839   -9.547   20.950   1.00  19.36        MTGL
ATOM   39   CZ   ARG   5    21.243   -9.681   19.692   1.00  20.62        MTGL
ATOM   40   NH1  ARG   5    21.054   -8.696   18.824   1.00  19.45        MTGL
ATOM   41   NH2  ARG   5    21.864  -10.790   19.307   1.00  21.29        MTGL
ATOM   42   C    ARG   5    24.390   -7.238   24.009   1.00  16.18        MTGL
ATOM   43   O    ARG   5    24.869   -8.311   23.642   1.00  16.58        MTGL
ATOM   44   N    GLY   6    24.853   -6.577   25.064   1.00  16.16        MTGL
ATOM   45   CA   GLY   6    25.991   -7.135   25.770   1.00  16.79        MTGL
ATOM   46   C    GLY   6    26.064   -7.065   27.275   1.00  15.64        MTGL
ATOM   47   O    GLY   6    25.129   -6.664   27.968   1.00  15.46        MTGL
ATOM   48   N    VAL   7    27.213   -7.497   27.775   1.00  15.87        MTGL
ATOM   49   CA   VAL   7    27.491   -7.500   29.199   1.00  15.12        MTGL
ATOM   50   CB   VAL   7    27.178   -8.877   29.846   1.00  14.43        MTGL
ATOM   51   CG1  VAL   7    25.750   -9.293   29.537   1.00  12.85        MTGL
ATOM   52   CG2  VAL   7    28.170   -9.931   29.348   1.00  13.29        MTGL
ATOM   53   C    VAL   7    28.977   -7.238   29.363   1.00  16.14        MTGL
ATOM   54   O    VAL   7    29.768   -7.469   28.440   1.00  17.27        MTGL
ATOM   55   N    ASP   8    29.354   -6.737   30.531   1.00  15.62        MTGL
ATOM   56   CA   ASP   8    30.755   -6.514   30.842   1.00  15.20        MTGL
ATOM   57   CB   ASP   8    30.920   -5.292   31.751   1.00  14.35        MTGL
```

Fig. 1

```
ATOM   58  CG  ASP   8    32.373  -4.975  32.034  1.00 15.24      MTGL
ATOM   59  OD1 ASP   8    33.105  -5.881  32.486  1.00 14.12      MTGL
ATOM   60  OD2 ASP   8    32.784  -3.817  31.805  1.00 14.89      MTGL
ATOM   61  C   ASP   8    31.108  -7.793  31.602  1.00 14.33      MTGL
ATOM   62  O   ASP   8    30.573  -8.040  32.683  1.00 15.61      MTGL
ATOM   63  N   TRP   9    31.980  -8.614  31.027  1.00 13.27      MTGL
ATOM   64  CA  TRP   9    32.365  -9.872  31.653  1.00 13.40      MTGL
ATOM   65  CB  TRP   9    32.124 -11.020  30.663  1.00 12.58      MTGL
ATOM   66  CG  TRP   9    33.183 -11.146  29.585  1.00 13.96      MTGL
ATOM   67  CD2 TRP   9    33.682 -12.362  29.012  1.00 13.39      MTGL
ATOM   68  CE2 TRP   9    34.661 -12.008  28.057  1.00 13.29      MTGL
ATOM   69  CE3 TRP   9    33.396 -13.719  29.214  1.00 14.51      MTGL
ATOM   70  CD1 TRP   9    33.860 -10.128  28.964  1.00 14.11      MTGL
ATOM   71  NE1 TRP   9    34.752 -10.640  28.046  1.00 13.31      MTGL
ATOM   72  CZ2 TRP   9    35.357 -12.964  27.305  1.00 14.73      MTGL
ATOM   73  CZ3 TRP   9    34.093 -14.673  28.463  1.00 14.84      MTGL
ATOM   74  CH2 TRP   9    35.059 -14.287  27.523  1.00 14.12      MTGL
ATOM   75  C   TRP   9    33.832  -9.860  32.102  1.00 13.91      MTGL
ATOM   76  O   TRP   9    34.454 -10.915  32.272  1.00 13.71      MTGL
ATOM   77  N   SER  10    34.373  -8.660  32.295  1.00 13.08      MTGL
ATOM   78  CA  SER  10    35.770  -8.481  32.692  1.00 14.15      MTGL
ATOM   79  CB  SER  10    35.983  -7.052  33.193  1.00 13.75      MTGL
ATOM   80  OG  SER  10    35.691  -6.114  32.168  1.00 14.07      MTGL
ATOM   81  C   SER  10    36.321  -9.460  33.726  1.00 14.36      MTGL
ATOM   82  O   SER  10    37.414  -9.994  33.553  1.00 14.45      MTGL
ATOM   83  N   SER  11    35.561  -9.697  34.789  1.00 14.45      MTGL
ATOM   84  CA  SER  11    35.985 -10.588  35.870  1.00 15.55      MTGL
ATOM   85  CB  SER  11    35.053 -10.416  37.069  1.00 15.32      MTGL
ATOM   86  OG  SER  11    33.795 -11.014  36.792  1.00 13.85      MTGL
ATOM   87  C   SER  11    36.043 -12.080  35.544  1.00 16.02      MTGL
ATOM   88  O   SER  11    36.438 -12.870  36.401  1.00 16.91      MTGL
ATOM   89  N   VAL  12    35.656 -12.472  34.330  1.00 16.04      MTGL
ATOM   90  CA  VAL  12    35.640 -13.890  33.969  1.00 14.89      MTGL
ATOM   91  CB  VAL  12    35.367 -14.090  32.448  1.00 14.61      MTGL
ATOM   92  CG1 VAL  12    36.418 -13.371  31.604  1.00 13.79      MTGL
ATOM   93  CG2 VAL  12    35.336 -15.583  32.124  1.00 13.78      MTGL
ATOM   94  C   VAL  12    36.861 -14.726  34.373  1.00 15.76      MTGL
ATOM   95  O   VAL  12    36.709 -15.751  35.034  1.00 14.51      MTGL
ATOM   96  N   VAL  13    38.065 -14.312  33.990  1.00 16.87      MTGL
ATOM   97  CA  VAL  13    39.246 -15.100  34.343  1.00 17.35      MTGL
ATOM   98  CB  VAL  13    40.496 -14.656  33.534  1.00 17.20      MTGL
ATOM   99  CG1 VAL  13    41.775 -15.198  34.177  1.00 16.12      MTGL
ATOM  100  CG2 VAL  13    40.391 -15.193  32.109  1.00 15.88      MTGL
ATOM  101  C   VAL  13    39.534 -15.043  35.841  1.00 18.53      MTGL
ATOM  102  O   VAL  13    40.002 -16.024  36.430  1.00 19.44      MTGL
ATOM  103  N   VAL  14    39.242 -13.907  36.466  1.00 17.79      MTGL
ATOM  104  CA  VAL  14    39.463 -13.785  37.900  1.00 18.35      MTGL
ATOM  105  CB  VAL  14    39.106 -12.368  38.411  1.00 18.68      MTGL
ATOM  106  CG1 VAL  14    39.117 -12.347  39.939  1.00 19.58      MTGL
ATOM  107  CG2 VAL  14    40.113 -11.352  37.876  1.00 17.40      MTGL
ATOM  108  C   VAL  14    38.588 -14.816  38.620  1.00 17.85      MTGL
ATOM  109  O   VAL  14    39.034 -15.495  39.543  1.00 17.72      MTGL
ATOM  110  N   GLU  15    37.341 -14.941  38.181  1.00 17.47      MTGL
ATOM  111  CA  GLU  15    36.420 -15.889  38.800  1.00 18.52      MTGL
ATOM  112  CB  GLU  15    34.985 -15.585  38.373  1.00 19.09      MTGL
ATOM  113  CG  GLU  15    34.392 -14.361  39.056  1.00 20.86      MTGL
ATOM  114  CD  GLU  15    34.147 -14.579  40.542  1.00 22.32      MTGL
ATOM  115  OE1 GLU  15    35.113 -14.887  41.273  1.00 23.29      MTGL
```

Fig. 1 cont.

| ATOM | 116 | OE2 | GLU | 15 | 32.984 | -14.445 | 40.981 | 1.00 | 22.28 | MTGL |
|------|-----|-----|-----|----|--------|---------|--------|------|-------|------|
| ATOM | 117 | C | GLU | 15 | 36.753 | -17.346 | 38.502 | 1.00 | 18.21 | MTGL |
| ATOM | 118 | O | GLU | 15 | 36.640 | -18.196 | 39.377 | 1.00 | 19.29 | MTGL |
| ATOM | 119 | N | GLU | 16 | 37.151 | -17.639 | 37.272 | 1.00 | 18.79 | MTGL |
| ATOM | 120 | CA | GLU | 16 | 37.504 | -19.006 | 36.921 | 1.00 | 19.07 | MTGL |
| ATOM | 121 | CB | GLU | 16 | 37.827 | -19.103 | 35.424 | 1.00 | 19.33 | MTGL |
| ATOM | 122 | CG | GLU | 16 | 36.645 | -18.735 | 34.530 | 1.00 | 19.54 | MTGL |
| ATOM | 123 | CD | GLU | 16 | 36.970 | -18.798 | 33.049 | 1.00 | 19.73 | MTGL |
| ATOM | 124 | OE1 | GLU | 16 | 38.143 | -18.577 | 32.683 | 1.00 | 19.62 | MTGL |
| ATOM | 125 | OE2 | GLU | 16 | 36.048 | -19.048 | 32.244 | 1.00 | 20.12 | MTGL |
| ATOM | 126 | C | GLU | 16 | 38.706 | -19.425 | 37.767 | 1.00 | 18.57 | MTGL |
| ATOM | 127 | O | GLU | 16 | 38.766 | -20.557 | 38.250 | 1.00 | 17.78 | MTGL |
| ATOM | 128 | N | ARG | 17 | 39.640 | -18.492 | 37.960 | 1.00 | 17.17 | MTGL |
| ATOM | 129 | CA | ARG | 17 | 40.842 | -18.759 | 38.756 | 1.00 | 18.26 | MTGL |
| ATOM | 130 | CB | ARG | 17 | 41.872 | -17.646 | 38.568 | 1.00 | 17.11 | MTGL |
| ATOM | 131 | CG | ARG | 17 | 42.593 | -17.719 | 37.240 | 1.00 | 16.83 | MTGL |
| ATOM | 132 | CD | ARG | 17 | 43.446 | -16.496 | 37.009 | 1.00 | 15.44 | MTGL |
| ATOM | 133 | NE | ARG | 17 | 44.246 | -16.636 | 35.801 | 1.00 | 15.36 | MTGL |
| ATOM | 134 | CZ | ARG | 17 | 45.084 | -15.708 | 35.357 | 1.00 | 15.76 | MTGL |
| ATOM | 135 | NH1 | ARG | 17 | 45.225 | -14.570 | 36.025 | 1.00 | 15.62 | MTGL |
| ATOM | 136 | NH2 | ARG | 17 | 45.788 | -15.922 | 34.254 | 1.00 | 15.66 | MTGL |
| ATOM | 137 | C | ARG | 17 | 40.502 | -18.887 | 40.225 | 1.00 | 18.97 | MTGL |
| ATOM | 138 | O | ARG | 17 | 41.279 | -19.407 | 41.017 | 1.00 | 19.60 | MTGL |
| ATOM | 139 | N | ALA | 18 | 39.330 | -18.396 | 40.590 | 1.00 | 19.85 | MTGL |
| ATOM | 140 | CA | ALA | 18 | 38.890 | -18.486 | 41.967 | 1.00 | 21.00 | MTGL |
| ATOM | 141 | CB | ALA | 18 | 38.071 | -17.262 | 42.339 | 1.00 | 21.45 | MTGL |
| ATOM | 142 | C | ALA | 18 | 38.066 | -19.756 | 42.154 | 1.00 | 21.18 | MTGL |
| ATOM | 143 | O | ALA | 18 | 37.495 | -19.982 | 43.216 | 1.00 | 21.53 | MTGL |
| ATOM | 144 | N | GLY | 19 | 37.994 | -20.577 | 41.110 | 1.00 | 20.78 | MTGL |
| ATOM | 145 | CA | GLY | 19 | 37.265 | -21.827 | 41.218 | 1.00 | 21.14 | MTGL |
| ATOM | 146 | C | GLY | 19 | 35.833 | -21.845 | 40.716 | 1.00 | 21.86 | MTGL |
| ATOM | 147 | O | GLY | 19 | 35.124 | -22.833 | 40.901 | 1.00 | 20.92 | MTGL |
| ATOM | 148 | N | VAL | 20 | 35.386 | -20.769 | 40.080 | 1.00 | 21.60 | MTGL |
| ATOM | 149 | CA | VAL | 20 | 34.021 | -20.755 | 39.578 | 1.00 | 21.91 | MTGL |
| ATOM | 150 | CB | VAL | 20 | 33.533 | -19.321 | 39.264 | 1.00 | 23.06 | MTGL |
| ATOM | 151 | CG1 | VAL | 20 | 32.126 | -19.370 | 38.674 | 1.00 | 22.39 | MTGL |
| ATOM | 152 | CG2 | VAL | 20 | 33.530 | -18.475 | 40.530 | 1.00 | 22.53 | MTGL |
| ATOM | 153 | C | VAL | 20 | 33.877 | -21.589 | 38.305 | 1.00 | 21.53 | MTGL |
| ATOM | 154 | O | VAL | 20 | 34.673 | -21.473 | 37.377 | 1.00 | 21.65 | MTGL |
| ATOM | 155 | N | SER | 21 | 32.864 | -22.444 | 38.283 | 0.50 | 21.24 | MTGL |
| ATOM | 156 | CA | SER | 21 | 32.596 | -23.272 | 37.116 | 0.50 | 21.35 | MTGL |
| ATOM | 157 | CB | SER | 21 | 32.602 | -24.757 | 37.488 | 0.50 | 22.01 | MTGL |
| ATOM | 158 | OG | SER | 21 | 33.897 | -25.165 | 37.901 | 0.50 | 22.69 | MTGL |
| ATOM | 159 | C | SER | 21 | 31.227 | -22.857 | 36.605 | 0.50 | 20.74 | MTGL |
| ATOM | 160 | O | SER | 21 | 30.205 | -23.167 | 37.214 | 0.50 | 20.32 | MTGL |
| ATOM | 161 | N | TYR | 22 | 31.216 | -22.134 | 35.491 | 1.00 | 20.34 | MTGL |
| ATOM | 162 | CA | TYR | 22 | 29.972 | -21.659 | 34.914 | 1.00 | 20.72 | MTGL |
| ATOM | 163 | CB | TYR | 22 | 30.270 | -20.511 | 33.952 | 1.00 | 19.18 | MTGL |
| ATOM | 164 | CG | TYR | 22 | 30.765 | -19.280 | 34.682 | 1.00 | 18.50 | MTGL |
| ATOM | 165 | CD1 | TYR | 22 | 29.909 | -18.548 | 35.503 | 1.00 | 17.85 | MTGL |
| ATOM | 166 | CE1 | TYR | 22 | 30.357 | -17.428 | 36.202 | 1.00 | 17.95 | MTGL |
| ATOM | 167 | CD2 | TYR | 22 | 32.092 | -18.865 | 34.578 | 1.00 | 17.87 | MTGL |
| ATOM | 168 | CE2 | TYR | 22 | 32.552 | -17.744 | 35.275 | 1.00 | 17.81 | MTGL |
| ATOM | 169 | CZ | TYR | 22 | 31.676 | -17.031 | 36.083 | 1.00 | 17.46 | MTGL |
| ATOM | 170 | OH | TYR | 22 | 32.107 | -15.915 | 36.767 | 1.00 | 17.47 | MTGL |
| ATOM | 171 | C | TYR | 22 | 29.152 | -22.742 | 34.239 | 1.00 | 21.41 | MTGL |
| ATOM | 172 | O | TYR | 22 | 29.688 | -23.634 | 33.588 | 1.00 | 21.91 | MTGL |
| ATOM | 173 | N | LYS | 23 | 27.839 | -22.654 | 34.414 | 1.00 | 22.66 | MTGL |

Fig. 1 cont.

| | | | | | | | | | |
|---|---|---|---|---|---|---|---|---|---|
| ATOM | 174 | CA | LYS | 23 | 26.918 | -23.619 | 33.836 | 1.00 23.97 | MTGL |
| ATOM | 175 | CB | LYS | 23 | 26.387 | -24.537 | 34.936 | 1.00 24.47 | MTGL |
| ATOM | 176 | CG | LYS | 23 | 27.479 | -25.094 | 35.839 | 1.00 26.17 | MTGL |
| ATOM | 177 | CD | LYS | 23 | 26.894 | -25.778 | 37.066 | 1.00 28.12 | MTGL |
| ATOM | 178 | CE | LYS | 23 | 27.985 | -26.217 | 38.040 | 1.00 29.23 | MTGL |
| ATOM | 179 | NZ | LYS | 23 | 28.750 | -25.069 | 38.615 | 1.00 28.37 | MTGL |
| ATOM | 180 | C | LYS | 23 | 25.748 | -22.915 | 33.158 | 1.00 24.07 | MTGL |
| ATOM | 181 | O | LYS | 23 | 25.344 | -21.823 | 33.570 | 1.00 23.42 | MTGL |
| ATOM | 182 | N | ASN | 24 | 25.210 | -23.557 | 32.125 | 1.00 25.34 | MTGL |
| ATOM | 183 | CA | ASN | 24 | 24.074 | -23.020 | 31.390 | 1.00 26.76 | MTGL |
| ATOM | 184 | CB | ASN | 24 | 23.907 | -23.741 | 30.042 | 1.00 27.22 | MTGL |
| ATOM | 185 | CG | ASN | 24 | 23.925 | -25.258 | 30.174 | 1.00 28.00 | MTGL |
| ATOM | 186 | OD1 | ASN | 24 | 23.306 | -25.825 | 31.075 | 1.00 28.00 | MTGL |
| ATOM | 187 | ND2 | ASN | 24 | 24.626 | -25.923 | 29.258 | 1.00 28.41 | MTGL |
| ATOM | 188 | C | ASN | 24 | 22.802 | -23.171 | 32.216 | 1.00 27.53 | MTGL |
| ATOM | 189 | O | ASN | 24 | 22.830 | -23.727 | 33.315 | 1.00 26.87 | MTGL |
| ATOM | 190 | N | THR | 25 | 21.691 | -22.668 | 31.687 | 1.00 29.20 | MTGL |
| ATOM | 191 | CA | THR | 25 | 20.408 | -22.754 | 32.378 | 1.00 31.61 | MTGL |
| ATOM | 192 | CB | THR | 25 | 19.299 | -21.968 | 31.619 | 1.00 31.89 | MTGL |
| ATOM | 193 | OG1 | THR | 25 | 19.269 | -22.380 | 30.245 | 1.00 32.33 | MTGL |
| ATOM | 194 | CG2 | THR | 25 | 19.558 | -20.468 | 31.689 | 1.00 30.90 | MTGL |
| ATOM | 195 | C | THR | 25 | 19.968 | -24.209 | 32.540 | 1.00 33.20 | MTGL |
| ATOM | 196 | O | THR | 25 | 19.107 | -24.518 | 33.362 | 1.00 34.49 | MTGL |
| ATOM | 197 | N | ASN | 26 | 20.561 | -25.101 | 31.754 | 1.00 33.98 | MTGL |
| ATOM | 198 | CA | ASN | 26 | 20.229 | -26.521 | 31.831 | 1.00 34.91 | MTGL |
| ATOM | 199 | CB | ASN | 26 | 20.595 | -27.233 | 30.529 | 1.00 37.07 | MTGL |
| ATOM | 200 | CG | ASN | 26 | 19.515 | -27.114 | 29.479 | 1.00 38.98 | MTGL |
| ATOM | 201 | OD1 | ASN | 26 | 19.743 | -27.405 | 28.305 | 1.00 40.46 | MTGL |
| ATOM | 202 | ND2 | ASN | 26 | 18.325 | -26.696 | 29.898 | 1.00 39.01 | MTGL |
| ATOM | 203 | C | ASN | 26 | 21.000 | -27.153 | 32.967 | 1.00 33.95 | MTGL |
| ATOM | 204 | O | ASN | 26 | 20.752 | -28.294 | 33.356 | 1.00 34.07 | MTGL |
| ATOM | 205 | N | GLY | 27 | 21.952 | -26.402 | 33.493 | 1.00 32.34 | MTGL |
| ATOM | 206 | CA | GLY | 27 | 22.739 | -26.928 | 34.583 | 1.00 30.16 | MTGL |
| ATOM | 207 | C | GLY | 27 | 24.009 | -27.629 | 34.140 | 1.00 29.51 | MTGL |
| ATOM | 208 | O | GLY | 27 | 24.692 | -28.244 | 34.950 | 1.00 28.86 | MTGL |
| ATOM | 209 | N | ASN | 28 | 24.350 | -27.547 | 32.864 | 1.00 29.22 | MTGL |
| ATOM | 210 | CA | ASN | 28 | 25.565 | -28.205 | 32.419 | 1.00 28.62 | MTGL |
| ATOM | 211 | CB | ASN | 28 | 25.323 | -28.945 | 31.108 | 1.00 30.49 | MTGL |
| ATOM | 212 | CG | ASN | 28 | 24.313 | -30.063 | 31.258 | 1.00 31.94 | MTGL |
| ATOM | 213 | OD1 | ASN | 28 | 24.453 | -30.930 | 32.124 | 1.00 32.14 | MTGL |
| ATOM | 214 | ND2 | ASN | 28 | 23.288 | -30.049 | 30.417 | 1.00 32.11 | MTGL |
| ATOM | 215 | C | ASN | 28 | 26.714 | -27.228 | 32.264 | 1.00 27.80 | MTGL |
| ATOM | 216 | O | ASN | 28 | 26.537 | -26.085 | 31.831 | 1.00 26.86 | MTGL |
| ATOM | 217 | N | ALA | 29 | 27.897 | -27.695 | 32.629 | 1.00 26.54 | MTGL |
| ATOM | 218 | CA | ALA | 29 | 29.103 | -26.889 | 32.547 | 1.00 26.11 | MTGL |
| ATOM | 219 | CB | ALA | 29 | 30.290 | -27.687 | 33.067 | 1.00 25.81 | MTGL |
| ATOM | 220 | C | ALA | 29 | 29.351 | -26.456 | 31.110 | 1.00 25.11 | MTGL |
| ATOM | 221 | O | ALA | 29 | 29.232 | -27.254 | 30.184 | 1.00 24.31 | MTGL |
| ATOM | 222 | N | GLN | 30 | 29.713 | -25.192 | 30.932 | 1.00 23.82 | MTGL |
| ATOM | 223 | CA | GLN | 30 | 29.967 | -24.655 | 29.603 | 1.00 23.10 | MTGL |
| ATOM | 224 | CB | GLN | 30 | 28.620 | -24.424 | 28.901 | 1.00 23.68 | MTGL |
| ATOM | 225 | CG | GLN | 30 | 28.676 | -23.687 | 27.578 | 1.00 26.45 | MTGL |
| ATOM | 226 | CD | GLN | 30 | 27.335 | -23.695 | 26.858 | 1.00 27.43 | MTGL |
| ATOM | 227 | OE1 | GLN | 30 | 26.282 | -23.584 | 27.486 | 1.00 27.66 | MTGL |
| ATOM | 228 | NE2 | GLN | 30 | 27.371 | -23.815 | 25.537 | 1.00 27.00 | MTGL |
| ATOM | 229 | C | GLN | 30 | 30.748 | -23.350 | 29.740 | 1.00 21.50 | MTGL |
| ATOM | 230 | O | GLN | 30 | 30.556 | -22.609 | 30.700 | 1.00 21.61 | MTGL |
| ATOM | 231 | N | PRO | 31 | 31.661 | -23.066 | 28.797 | 1.00 20.08 | MTGL |

Fig. 1 cont.

| | | | | | | | | | |
|---|---|---|---|---|---|---|---|---|---|
| ATOM | 232 | CD | PRO | 31 | 32.110 | -23.886 | 27.657 | 1.00 20.60 | MTGL |
| ATOM | 233 | CA | PRO | 31 | 32.432 | -21.820 | 28.886 | 1.00 19.48 | MTGL |
| ATOM | 234 | CB | PRO | 31 | 33.262 | -21.834 | 27.603 | 1.00 20.47 | MTGL |
| ATOM | 235 | CG | PRO | 31 | 33.489 | -23.309 | 27.369 | 1.00 20.52 | MTGL |
| ATOM | 236 | C | PRO | 31 | 31.492 | -20.617 | 28.960 | 1.00 18.32 | MTGL |
| ATOM | 237 | O | PRO | 31 | 30.491 | -20.558 | 28.246 | 1.00 17.02 | MTGL |
| ATOM | 238 | N | LEU | 32 | 31.811 | -19.664 | 29.828 | 1.00 18.30 | MTGL |
| ATOM | 239 | CA | LEU | 32 | 30.971 | -18.477 | 29.987 | 1.00 18.52 | MTGL |
| ATOM | 240 | CB | LEU | 32 | 31.623 | -17.476 | 30.954 | 1.00 17.22 | MTGL |
| ATOM | 241 | CG | LEU | 32 | 30.828 | -16.190 | 31.227 | 1.00 17.71 | MTGL |
| ATOM | 242 | CD1 | LEU | 32 | 29.443 | -16.536 | 31.767 | 1.00 15.78 | MTGL |
| ATOM | 243 | CD2 | LEU | 32 | 31.588 | -15.319 | 32.235 | 1.00 15.40 | MTGL |
| ATOM | 244 | C | LEU | 32 | 30.655 | -17.776 | 28.669 | 1.00 17.46 | MTGL |
| ATOM | 245 | O | LEU | 32 | 29.504 | -17.413 | 28.429 | 1.00 18.85 | MTGL |
| ATOM | 246 | N | GLU | 33 | 31.660 | -17.581 | 27.818 | 1.00 16.99 | MTGL |
| ATOM | 247 | CA | GLU | 33 | 31.421 | -16.903 | 26.546 | 1.00 17.55 | MTGL |
| ATOM | 248 | CB | GLU | 33 | 32.716 | -16.763 | 25.735 | 1.00 17.22 | MTGL |
| ATOM | 249 | CG | GLU | 33 | 33.426 | -18.077 | 25.424 | 1.00 16.64 | MTGL |
| ATOM | 250 | CD | GLU | 33 | 34.496 | -18.417 | 26.453 | 1.00 16.72 | MTGL |
| ATOM | 251 | OE1 | GLU | 33 | 34.234 | -18.270 | 27.667 | 1.00 14.95 | MTGL |
| ATOM | 252 | OE2 | GLU | 33 | 35.597 | -18.840 | 26.048 | 1.00 16.02 | MTGL |
| ATOM | 253 | C | GLU | 33 | 30.369 | -17.630 | 25.712 | 1.00 18.39 | MTGL |
| ATOM | 254 | O | GLU | 33 | 29.576 | -16.988 | 25.021 | 1.00 19.97 | MTGL |
| ATOM | 255 | N | ASN | 34 | 30.354 | -18.959 | 25.779 | 1.00 18.00 | MTGL |
| ATOM | 256 | CA | ASN | 34 | 29.381 | -19.739 | 25.019 | 1.00 19.90 | MTGL |
| ATOM | 257 | CB | ASN | 34 | 29.793 | -21.214 | 24.955 | 1.00 21.66 | MTGL |
| ATOM | 258 | CG | ASN | 34 | 31.121 | -21.420 | 24.251 | 1.00 24.08 | MTGL |
| ATOM | 259 | OD1 | ASN | 34 | 31.355 | -20.886 | 23.168 | 1.00 25.77 | MTGL |
| ATOM | 260 | ND2 | ASN | 34 | 31.995 | -22.207 | 24.861 | 1.00 26.27 | MTGL |
| ATOM | 261 | C | ASN | 34 | 27.991 | -19.618 | 25.640 | 1.00 19.84 | MTGL |
| ATOM | 262 | O | ASN | 34 | 26.988 | -19.598 | 24.931 | 1.00 19.75 | MTGL |
| ATOM | 263 | N | ILE | 35 | 27.932 | -19.553 | 26.967 | 1.00 18.73 | MTGL |
| ATOM | 264 | CA | ILE | 35 | 26.656 | -19.404 | 27.656 | 1.00 18.63 | MTGL |
| ATOM | 265 | CB | ILE | 35 | 26.845 | -19.440 | 29.188 | 1.00 18.28 | MTGL |
| ATOM | 266 | CG2 | ILE | 35 | 25.556 | -19.028 | 29.890 | 1.00 17.35 | MTGL |
| ATOM | 267 | CG1 | ILE | 35 | 27.270 | -20.844 | 29.623 | 1.00 18.06 | MTGL |
| ATOM | 268 | CD1 | ILE | 35 | 27.652 | -20.946 | 31.091 | 1.00 19.14 | MTGL |
| ATOM | 269 | C | ILE | 35 | 26.048 | -18.053 | 27.258 | 1.00 18.92 | MTGL |
| ATOM | 270 | O | ILE | 35 | 24.867 | -17.966 | 26.907 | 1.00 18.51 | MTGL |
| ATOM | 271 | N | LEU | 36 | 26.866 | -17.005 | 27.313 | 1.00 18.03 | MTGL |
| ATOM | 272 | CA | LEU | 36 | 26.416 | -15.665 | 26.956 | 1.00 17.16 | MTGL |
| ATOM | 273 | CB | LEU | 36 | 27.563 | -14.660 | 27.110 | 1.00 17.06 | MTGL |
| ATOM | 274 | CG | LEU | 36 | 28.076 | -14.411 | 28.538 | 1.00 16.94 | MTGL |
| ATOM | 275 | CD1 | LEU | 36 | 29.323 | -13.516 | 28.504 | 1.00 14.36 | MTGL |
| ATOM | 276 | CD2 | LEU | 36 | 26.969 | -13.761 | 29.372 | 1.00 16.43 | MTGL |
| ATOM | 277 | C | LEU | 36 | 25.891 | -15.636 | 25.522 | 1.00 17.26 | MTGL |
| ATOM | 278 | O | LEU | 36 | 24.795 | -15.132 | 25.270 | 1.00 16.08 | MTGL |
| ATOM | 279 | N | ALA | 37 | 26.675 | -16.174 | 24.589 | 1.00 17.12 | MTGL |
| ATOM | 280 | CA | ALA | 37 | 26.278 | -16.203 | 23.187 | 1.00 17.86 | MTGL |
| ATOM | 281 | CB | ALA | 37 | 27.362 | -16.863 | 22.338 | 1.00 16.93 | MTGL |
| ATOM | 282 | C | ALA | 37 | 24.961 | -16.948 | 23.014 | 1.00 18.20 | MTGL |
| ATOM | 283 | O | ALA | 37 | 24.062 | -16.480 | 22.314 | 1.00 19.46 | MTGL |
| ATOM | 284 | N | ALA | 38 | 24.850 | -18.105 | 23.658 | 1.00 18.38 | MTGL |
| ATOM | 285 | CA | ALA | 38 | 23.643 | -18.917 | 23.560 | 1.00 20.05 | MTGL |
| ATOM | 286 | CB | ALA | 38 | 23.809 | -20.212 | 24.358 | 1.00 19.05 | MTGL |
| ATOM | 287 | C | ALA | 38 | 22.419 | -18.154 | 24.049 | 1.00 20.48 | MTGL |
| ATOM | 288 | O | ALA | 38 | 21.294 | -18.447 | 23.634 | 1.00 21.25 | MTGL |
| ATOM | 289 | N | ASN | 39 | 22.637 | -17.173 | 24.923 | 1.00 20.10 | MTGL |

Fig. 1 cont.

| ATOM | 290 | CA | ASN | 39 | 21.531 | -16.390 | 25.460 | 1.00 | 19.15 | MTGL |
|------|-----|-----|-----|----|--------|---------|--------|------|-------|------|
| ATOM | 291 | CB | ASN | 39 | 21.717 | -16.168 | 26.963 | 1.00 | 19.77 | MTGL |
| ATOM | 292 | CG | ASN | 39 | 21.416 | -17.414 | 27.774 | 1.00 | 19.60 | MTGL |
| ATOM | 293 | OD1 | ASN | 39 | 22.241 | -18.327 | 27.872 | 1.00 | 22.00 | MTGL |
| ATOM | 294 | ND2 | ASN | 39 | 20.224 | -17.467 | 28.346 | 1.00 | 18.25 | MTGL |
| ATOM | 295 | C | ASN | 39 | 21.253 | -15.056 | 24.768 | 1.00 | 18.64 | MTGL |
| ATOM | 296 | O | ASN | 39 | 20.544 | -14.213 | 25.317 | 1.00 | 19.42 | MTGL |
| ATOM | 297 | N | GLY | 40 | 21.803 | -14.862 | 23.572 | 1.00 | 17.47 | MTGL |
| ATOM | 298 | CA | GLY | 40 | 21.535 | -13.635 | 22.837 | 1.00 | 17.26 | MTGL |
| ATOM | 299 | C | GLY | 40 | 22.585 | -12.537 | 22.880 | 1.00 | 17.22 | MTGL |
| ATOM | 300 | O | GLY | 40 | 22.523 | -11.594 | 22.095 | 1.00 | 17.12 | MTGL |
| ATOM | 301 | N | VAL | 41 | 23.544 | -12.641 | 23.791 | 1.00 | 16.80 | MTGL |
| ATOM | 302 | CA | VAL | 41 | 24.589 | -11.631 | 23.893 | 1.00 | 15.92 | MTGL |
| ATOM | 303 | CB | VAL | 41 | 25.510 | -11.908 | 25.103 | 1.00 | 16.19 | MTGL |
| ATOM | 304 | CG1 | VAL | 41 | 26.630 | -10.888 | 25.144 | 1.00 | 14.75 | MTGL |
| ATOM | 305 | CG2 | VAL | 41 | 24.707 | -11.875 | 26.397 | 1.00 | 15.59 | MTGL |
| ATOM | 306 | C | VAL | 41 | 25.441 | -11.645 | 22.626 | 1.00 | 15.77 | MTGL |
| ATOM | 307 | O | VAL | 41 | 25.832 | -12.715 | 22.158 | 1.00 | 14.76 | MTGL |
| ATOM | 308 | N | ASN | 42 | 25.724 | -10.469 | 22.064 | 1.00 | 16.34 | MTGL |
| ATOM | 309 | CA | ASN | 42 | 26.559 | -10.406 | 20.864 | 1.00 | 16.57 | MTGL |
| ATOM | 310 | CB | ASN | 42 | 25.771 | -9.889 | 19.646 | 1.00 | 17.06 | MTGL |
| ATOM | 311 | CG | ASN | 42 | 25.299 | -8.443 | 19.798 | 1.00 | 18.15 | MTGL |
| ATOM | 312 | OD1 | ASN | 42 | 25.727 | -7.709 | 20.694 | 1.00 | 18.63 | MTGL |
| ATOM | 313 | ND2 | ASN | 42 | 24.416 | -8.028 | 18.898 | 1.00 | 16.75 | MTGL |
| ATOM | 314 | C | ASN | 42 | 27.812 | -9.560 | 21.048 | 1.00 | 16.81 | MTGL |
| ATOM | 315 | O | ASN | 42 | 28.651 | -9.478 | 20.147 | 1.00 | 17.52 | MTGL |
| ATOM | 316 | N | THR | 43 | 27.952 | -8.951 | 22.221 | 1.00 | 16.55 | MTGL |
| ATOM | 317 | CA | THR | 43 | 29.108 | -8.108 | 22.502 | 1.00 | 15.96 | MTGL |
| ATOM | 318 | CB | THR | 43 | 28.827 | -6.634 | 22.136 | 1.00 | 16.50 | MTGL |
| ATOM | 319 | OG1 | THR | 43 | 28.192 | -6.565 | 20.850 | 1.00 | 17.26 | MTGL |
| ATOM | 320 | CG2 | THR | 43 | 30.123 | -5.840 | 22.102 | 1.00 | 15.22 | MTGL |
| ATOM | 321 | C | THR | 43 | 29.487 | -8.144 | 23.976 | 1.00 | 15.93 | MTGL |
| ATOM | 322 | O | THR | 43 | 28.618 | -8.180 | 24.849 | 1.00 | 16.10 | MTGL |
| ATOM | 323 | N | VAL | 44 | 30.786 | -8.148 | 24.251 | 1.00 | 14.74 | MTGL |
| ATOM | 324 | CA | VAL | 44 | 31.251 | -8.136 | 25.626 | 1.00 | 15.41 | MTGL |
| ATOM | 325 | CB | VAL | 44 | 32.038 | -9.418 | 26.012 | 1.00 | 16.13 | MTGL |
| ATOM | 326 | CG1 | VAL | 44 | 31.084 | -10.603 | 26.096 | 1.00 | 16.11 | MTGL |
| ATOM | 327 | CG2 | VAL | 44 | 33.146 | -9.689 | 25.004 | 1.00 | 14.58 | MTGL |
| ATOM | 328 | C | VAL | 44 | 32.137 | -6.922 | 25.849 | 1.00 | 15.69 | MTGL |
| ATOM | 329 | O | VAL | 44 | 32.974 | -6.574 | 25.014 | 1.00 | 16.22 | MTGL |
| ATOM | 330 | N | ARG | 45 | 31.916 | -6.271 | 26.981 | 1.00 | 14.86 | MTGL |
| ATOM | 331 | CA | ARG | 45 | 32.662 | -5.091 | 27.383 | 1.00 | 15.51 | MTGL |
| ATOM | 332 | CB | ARG | 45 | 31.702 | -4.129 | 28.087 | 1.00 | 16.51 | MTGL |
| ATOM | 333 | CG | ARG | 45 | 32.297 | -2.828 | 28.597 | 1.00 | 17.41 | MTGL |
| ATOM | 334 | CD | ARG | 45 | 31.143 | -1.971 | 29.107 | 1.00 | 18.63 | MTGL |
| ATOM | 335 | NE | ARG | 45 | 31.519 | -0.636 | 29.554 | 1.00 | 19.44 | MTGL |
| ATOM | 336 | CZ | ARG | 45 | 31.756 | -0.309 | 30.820 | 1.00 | 19.56 | MTGL |
| ATOM | 337 | NH1 | ARG | 45 | 31.671 | -1.225 | 31.777 | 1.00 | 18.15 | MTGL |
| ATOM | 338 | NH2 | ARG | 45 | 32.032 | 0.949 | 31.130 | 1.00 | 19.68 | MTGL |
| ATOM | 339 | C | ARG | 45 | 33.752 | -5.561 | 28.342 | 1.00 | 15.10 | MTGL |
| ATOM | 340 | O | ARG | 45 | 33.516 | -6.446 | 29.168 | 1.00 | 13.85 | MTGL |
| ATOM | 341 | N | GLN | 46 | 34.938 | -4.965 | 28.232 | 1.00 | 14.87 | MTGL |
| ATOM | 342 | CA | GLN | 46 | 36.071 | -5.331 | 29.074 | 1.00 | 14.52 | MTGL |
| ATOM | 343 | CB | GLN | 46 | 37.030 | -6.246 | 28.296 | 1.00 | 14.23 | MTGL |
| ATOM | 344 | CG | GLN | 46 | 36.376 | -7.512 | 27.746 | 1.00 | 14.12 | MTGL |
| ATOM | 345 | CD | GLN | 46 | 37.310 | -8.358 | 26.902 | 1.00 | 13.86 | MTGL |
| ATOM | 346 | OE1 | GLN | 46 | 36.895 | -9.363 | 26.335 | 1.00 | 15.22 | MTGL |
| ATOM | 347 | NE2 | GLN | 46 | 38.575 | -7.958 | 26.814 | 1.00 | 13.21 | MTGL |

Fig. 1 cont.

```
ATOM  348  C    GLN  46   36.831  -4.089  29.534  1.00  15.79      MTGL
ATOM  349  O    GLN  46   37.153  -3.211  28.728  1.00  15.74      MTGL
ATOM  350  N    ARG  47   37.111  -4.005  30.830  1.00  15.01      MTGL
ATOM  351  CA   ARG  47   37.851  -2.866  31.350  1.00  15.05      MTGL
ATOM  352  CB   ARG  47   37.524  -2.631  32.828  1.00  13.91      MTGL
ATOM  353  CG   ARG  47   37.649  -3.868  33.710  1.00  13.56      MTGL
ATOM  354  CD   ARG  47   37.391  -3.520  35.175  1.00  13.26      MTGL
ATOM  355  NE   ARG  47   37.207  -4.710  36.004  1.00  12.49      MTGL
ATOM  356  CZ   ARG  47   36.063  -5.382  36.117  1.00  13.71      MTGL
ATOM  357  NH1  ARG  47   34.983  -4.981  35.457  1.00  13.79      MTGL
ATOM  358  NH2  ARG  47   36.004  -6.477  36.876  1.00  12.61      MTGL
ATOM  359  C    ARG  47   39.347  -3.107  31.182  1.00  15.50      MTGL
ATOM  360  O    ARG  47   39.849  -4.209  31.433  1.00  15.21      MTGL
ATOM  361  N    VAL  48   40.056  -2.072  30.745  1.00  15.84      MTGL
ATOM  362  CA   VAL  48   41.496  -2.171  30.557  1.00  15.53      MTGL
ATOM  363  CB   VAL  48   41.899  -1.874  29.102  1.00  16.38      MTGL
ATOM  364  CG1  VAL  48   43.418  -1.906  28.975  1.00  15.45      MTGL
ATOM  365  CG2  VAL  48   41.258  -2.892  28.160  1.00  14.39      MTGL
ATOM  366  C    VAL  48   42.222  -1.185  31.459  1.00  16.31      MTGL
ATOM  367  O    VAL  48   41.941   0.013  31.433  1.00  14.76      MTGL
ATOM  368  N    TRP  49   43.139  -1.707  32.270  1.00  16.64      MTGL
ATOM  369  CA   TRP  49   43.938  -0.890  33.172  1.00  17.13      MTGL
ATOM  370  CB   TRP  49   43.893  -1.458  34.598  1.00  17.19      MTGL
ATOM  371  CG   TRP  49   42.525  -1.365  35.239  1.00  17.50      MTGL
ATOM  372  CD2  TRP  49   42.129  -1.903  36.510  1.00  17.36      MTGL
ATOM  373  CE2  TRP  49   40.773  -1.550  36.710  1.00  17.08      MTGL
ATOM  374  CE3  TRP  49   42.786  -2.651  37.497  1.00  16.24      MTGL
ATOM  375  CD1  TRP  49   41.426  -0.728  34.736  1.00  17.53      MTGL
ATOM  376  NE1  TRP  49   40.370  -0.832  35.614  1.00  17.76      MTGL
ATOM  377  CZ2  TRP  49   40.063  -1.915  37.860  1.00  16.34      MTGL
ATOM  378  CZ3  TRP  49   42.079  -3.014  38.642  1.00  17.30      MTGL
ATOM  379  CH2  TRP  49   40.729  -2.645  38.812  1.00  16.66      MTGL
ATOM  380  C    TRP  49   45.369  -0.870  32.632  1.00  17.96      MTGL
ATOM  381  O    TRP  49   45.819  -1.830  32.007  1.00  16.92      MTGL
ATOM  382  N    VAL  50   46.078   0.228  32.874  1.00  18.74      MTGL
ATOM  383  CA   VAL  50   47.438   0.408  32.373  1.00  18.43      MTGL
ATOM  384  CB   VAL  50   47.898   1.865  32.604  1.00  17.51      MTGL
ATOM  385  CG1  VAL  50   49.310   2.061  32.069  1.00  16.69      MTGL
ATOM  386  CG2  VAL  50   46.931   2.814  31.912  1.00  16.38      MTGL
ATOM  387  C    VAL  50   48.492  -0.568  32.910  1.00  20.17      MTGL
ATOM  388  O    VAL  50   49.035  -1.359  32.141  1.00  20.17      MTGL
ATOM  389  N    ASN  51   48.809  -0.513  34.203  1.00  20.54      MTGL
ATOM  390  CA   ASN  51   49.800  -1.438  34.780  1.00  22.14      MTGL
ATOM  391  CB   ASN  51   51.181  -0.778  34.894  1.00  22.82      MTGL
ATOM  392  CG   ASN  51   51.899  -0.671  33.564  1.00  24.64      MTGL
ATOM  393  OD1  ASN  51   52.211   0.430  33.102  1.00  25.29      MTGL
ATOM  394  ND2  ASN  51   52.180  -1.813  32.945  1.00  24.48      MTGL
ATOM  395  C    ASN  51   49.416  -1.943  36.173  1.00  22.18      MTGL
ATOM  396  O    ASN  51   50.177  -1.771  37.119  1.00  23.10      MTGL
ATOM  397  N    PRO  52   48.242  -2.584  36.317  1.00  21.49      MTGL
ATOM  398  CD   PRO  52   47.333  -3.089  35.273  1.00  20.91      MTGL
ATOM  399  CA   PRO  52   47.847  -3.079  37.642  1.00  20.88      MTGL
ATOM  400  CB   PRO  52   46.509  -3.769  37.370  1.00  20.37      MTGL
ATOM  401  CG   PRO  52   46.683  -4.283  35.963  1.00  20.56      MTGL
ATOM  402  C    PRO  52   48.905  -4.041  38.177  1.00  21.68      MTGL
ATOM  403  O    PRO  52   49.390  -4.902  37.449  1.00  20.78      MTGL
ATOM  404  N    ALA  53   49.261  -3.891  39.448  1.00  22.20      MTGL
ATOM  405  CA   ALA  53   50.278  -4.739  40.061  1.00  23.49      MTGL
```

Fig. 1 cont.

| | | | | | | | | | | |
|---|---|---|---|---|---|---|---|---|---|---|
| ATOM | 406 | CB | ALA | 53 | 50.409 | -4.407 | 41.549 | 1.00 | 23.83 | MTGL |
| ATOM | 407 | C | ALA | 53 | 50.037 | -6.235 | 39.883 | 1.00 | 23.68 | MTGL |
| ATOM | 408 | O | ALA | 53 | 50.937 | -6.960 | 39.466 | 1.00 | 23.33 | MTGL |
| ATOM | 409 | N | ASP | 54 | 48.831 | -6.704 | 40.195 | 1.00 | 24.06 | MTGL |
| ATOM | 410 | CA | ASP | 54 | 48.539 | -8.126 | 40.058 | 1.00 | 24.64 | MTGL |
| ATOM | 411 | CB | ASP | 54 | 47.400 | -8.540 | 40.994 | 1.00 | 26.42 | MTGL |
| ATOM | 412 | CG | ASP | 54 | 46.109 | -7.805 | 40.706 | 1.00 | 27.54 | MTGL |
| ATOM | 413 | OD1 | ASP | 54 | 45.834 | -7.515 | 39.522 | 1.00 | 29.32 | MTGL |
| ATOM | 414 | OD2 | ASP | 54 | 45.360 | -7.529 | 41.664 | 1.00 | 27.59 | MTGL |
| ATOM | 415 | C | ASP | 54 | 48.207 | -8.560 | 38.631 | 1.00 | 24.00 | MTGL |
| ATOM | 416 | O | ASP | 54 | 47.878 | -9.720 | 38.396 | 1.00 | 24.44 | MTGL |
| ATOM | 417 | N | GLY | 55 | 48.286 | -7.630 | 37.686 | 1.00 | 22.74 | MTGL |
| ATOM | 418 | CA | GLY | 55 | 48.013 | -7.959 | 36.296 | 1.00 | 21.74 | MTGL |
| ATOM | 419 | C | GLY | 55 | 46.566 | -8.102 | 35.854 | 1.00 | 20.84 | MTGL |
| ATOM | 420 | O | GLY | 55 | 46.294 | -8.150 | 34.652 | 1.00 | 20.70 | MTGL |
| ATOM | 421 | N | ASN | 56 | 45.627 | -8.173 | 36.791 | 1.00 | 20.23 | MTGL |
| ATOM | 422 | CA | ASN | 56 | 44.229 | -8.320 | 36.399 | 1.00 | 19.77 | MTGL |
| ATOM | 423 | CB | ASN | 56 | 43.329 | -8.530 | 37.623 | 1.00 | 21.09 | MTGL |
| ATOM | 424 | CG | ASN | 56 | 43.569 | -9.876 | 38.301 | 1.00 | 22.81 | MTGL |
| ATOM | 425 | OD1 | ASN | 56 | 43.921 | -10.859 | 37.647 | 1.00 | 20.74 | MTGL |
| ATOM | 426 | ND2 | ASN | 56 | 43.359 | -9.926 | 39.611 | 1.00 | 22.17 | MTGL |
| ATOM | 427 | C | ASN | 56 | 43.751 | -7.108 | 35.612 | 1.00 | 18.30 | MTGL |
| ATOM | 428 | O | ASN | 56 | 43.972 | -5.968 | 36.016 | 1.00 | 17.82 | MTGL |
| ATOM | 429 | N | TYR | 57 | 43.108 | -7.376 | 34.480 | 1.00 | 16.29 | MTGL |
| ATOM | 430 | CA | TYR | 57 | 42.570 | -6.353 | 33.591 | 1.00 | 15.51 | MTGL |
| ATOM | 431 | CB | TYR | 57 | 41.680 | -5.376 | 34.368 | 1.00 | 15.50 | MTGL |
| ATOM | 432 | CG | TYR | 57 | 40.756 | -6.062 | 35.348 | 1.00 | 16.25 | MTGL |
| ATOM | 433 | CD1 | TYR | 57 | 39.969 | -7.150 | 34.955 | 1.00 | 15.93 | MTGL |
| ATOM | 434 | CE1 | TYR | 57 | 39.137 | -7.799 | 35.859 | 1.00 | 16.29 | MTGL |
| ATOM | 435 | CD2 | TYR | 57 | 40.681 | -5.642 | 36.671 | 1.00 | 16.32 | MTGL |
| ATOM | 436 | CE2 | TYR | 57 | 39.847 | -6.288 | 37.585 | 1.00 | 17.00 | MTGL |
| ATOM | 437 | CZ | TYR | 57 | 39.080 | -7.363 | 37.172 | 1.00 | 15.31 | MTGL |
| ATOM | 438 | OH | TYR | 57 | 38.254 | -8.000 | 38.066 | 1.00 | 15.12 | MTGL |
| ATOM | 439 | C | TYR | 57 | 43.627 | -5.579 | 32.807 | 1.00 | 15.53 | MTGL |
| ATOM | 440 | O | TYR | 57 | 43.315 | -4.561 | 32.189 | 1.00 | 14.98 | MTGL |
| ATOM | 441 | N | ASN | 58 | 44.877 | -6.033 | 32.825 | 1.00 | 14.46 | MTGL |
| ATOM | 442 | CA | ASN | 58 | 45.876 | -5.327 | 32.032 | 1.00 | 15.65 | MTGL |
| ATOM | 443 | CB | ASN | 58 | 47.314 | -5.594 | 32.522 | 1.00 | 15.44 | MTGL |
| ATOM | 444 | CG | ASN | 58 | 47.783 | -7.030 | 32.319 | 1.00 | 16.49 | MTGL |
| ATOM | 445 | OD1 | ASN | 58 | 48.869 | -7.390 | 32.779 | 1.00 | 18.71 | MTGL |
| ATOM | 446 | ND2 | ASN | 58 | 46.995 | -7.844 | 31.640 | 1.00 | 13.70 | MTGL |
| ATOM | 447 | C | ASN | 58 | 45.660 | -5.763 | 30.582 | 1.00 | 16.00 | MTGL |
| ATOM | 448 | O | ASN | 58 | 44.774 | -6.579 | 30.317 | 1.00 | 14.12 | MTGL |
| ATOM | 449 | N | LEU | 59 | 46.447 | -5.235 | 29.649 | 1.00 | 16.39 | MTGL |
| ATOM | 450 | CA | LEU | 59 | 46.241 | -5.564 | 28.242 | 1.00 | 17.31 | MTGL |
| ATOM | 451 | CB | LEU | 59 | 47.192 | -4.751 | 27.356 | 1.00 | 17.07 | MTGL |
| ATOM | 452 | CG | LEU | 59 | 46.797 | -4.743 | 25.874 | 1.00 | 17.21 | MTGL |
| ATOM | 453 | CD1 | LEU | 59 | 45.367 | -4.208 | 25.722 | 1.00 | 16.29 | MTGL |
| ATOM | 454 | CD2 | LEU | 59 | 47.769 | -3.882 | 25.085 | 1.00 | 16.17 | MTGL |
| ATOM | 455 | C | LEU | 59 | 46.333 | -7.046 | 27.880 | 1.00 | 17.51 | MTGL |
| ATOM | 456 | O | LEU | 59 | 45.517 | -7.537 | 27.096 | 1.00 | 17.20 | MTGL |
| ATOM | 457 | N | ASP | 60 | 47.317 | -7.754 | 28.432 | 1.00 | 17.48 | MTGL |
| ATOM | 458 | CA | ASP | 60 | 47.460 | -9.183 | 28.152 | 1.00 | 18.05 | MTGL |
| ATOM | 459 | CB | ASP | 60 | 48.700 | -9.768 | 28.837 | 1.00 | 20.82 | MTGL |
| ATOM | 460 | CG | ASP | 60 | 49.995 | -9.286 | 28.217 | 1.00 | 23.01 | MTGL |
| ATOM | 461 | OD1 | ASP | 60 | 50.012 | -9.009 | 26.999 | 1.00 | 25.11 | MTGL |
| ATOM | 462 | OD2 | ASP | 60 | 51.002 | -9.204 | 28.946 | 1.00 | 25.50 | MTGL |
| ATOM | 463 | C | ASP | 60 | 46.237 | -9.943 | 28.647 | 1.00 | 17.40 | MTGL |

Fig. 1 cont.

```
ATOM    464  O    ASP    60      45.749 -10.856  27.984  1.00 16.59      MTGL
ATOM    465  N    TYR    61      45.756  -9.573  29.827  1.00 15.42      MTGL
ATOM    466  CA   TYR    61      44.580 -10.215  30.398  1.00 15.67      MTGL
ATOM    467  CB   TYR    61      44.266  -9.581  31.759  1.00 15.24      MTGL
ATOM    468  CG   TYR    61      43.000 -10.071  32.427  1.00 15.21      MTGL
ATOM    469  CD1  TYR    61      41.746  -9.597  32.032  1.00 15.96      MTGL
ATOM    470  CE1  TYR    61      40.578 -10.025  32.670  1.00 14.87      MTGL
ATOM    471  CD2  TYR    61      43.058 -10.990  33.473  1.00 15.54      MTGL
ATOM    472  CE2  TYR    61      41.899 -11.428  34.120  1.00 14.46      MTGL
ATOM    473  CZ   TYR    61      40.662 -10.943  33.714  1.00 16.75      MTGL
ATOM    474  OH   TYR    61      39.511 -11.379  34.345  1.00 14.25      MTGL
ATOM    475  C    TYR    61      43.400 -10.042  29.434  1.00 15.36      MTGL
ATOM    476  O    TYR    61      42.651 -10.987  29.175  1.00 15.76      MTGL
ATOM    477  N    ASN    62      43.257  -8.834  28.897  1.00 14.42      MTGL
ATOM    478  CA   ASN    62      42.174  -8.509  27.971  1.00 16.00      MTGL
ATOM    479  CB   ASN    62      42.072  -6.990  27.811  1.00 15.99      MTGL
ATOM    480  CG   ASN    62      41.231  -6.354  28.895  1.00 18.27      MTGL
ATOM    481  OD1  ASN    62      39.998  -6.396  28.840  1.00 18.23      MTGL
ATOM    482  ND2  ASN    62      41.887  -5.780  29.901  1.00 16.02      MTGL
ATOM    483  C    ASN    62      42.306  -9.172  26.600  1.00 16.04      MTGL
ATOM    484  O    ASN    62      41.306  -9.546  25.990  1.00 15.56      MTGL
ATOM    485  N    ILE    63      43.534  -9.311  26.110  1.00 16.06      MTGL
ATOM    486  CA   ILE    63      43.732  -9.952  24.824  1.00 17.20      MTGL
ATOM    487  CB   ILE    63      45.202  -9.827  24.350  1.00 16.83      MTGL
ATOM    488  CG2  ILE    63      45.481 -10.814  23.214  1.00 17.67      MTGL
ATOM    489  CG1  ILE    63      45.463  -8.391  23.887  1.00 17.41      MTGL
ATOM    490  CD1  ILE    63      46.910  -8.105  23.521  1.00 18.09      MTGL
ATOM    491  C    ILE    63      43.333 -11.420  24.945  1.00 17.68      MTGL
ATOM    492  O    ILE    63      42.664 -11.964  24.068  1.00 18.06      MTGL
ATOM    493  N    ALA    64      43.722 -12.058  26.046  1.00 17.70      MTGL
ATOM    494  CA   ALA    64      43.379 -13.463  26.253  1.00 17.86      MTGL
ATOM    495  CB   ALA    64      44.000 -13.971  27.555  1.00 17.49      MTGL
ATOM    496  C    ALA    64      41.860 -13.703  26.262  1.00 17.48      MTGL
ATOM    497  O    ALA    64      41.370 -14.616  25.599  1.00 17.31      MTGL
ATOM    498  N    ILE    65      41.104 -12.895  27.002  1.00 16.55      MTGL
ATOM    499  CA   ILE    65      39.665 -13.117  27.030  1.00 16.75      MTGL
ATOM    500  CB   ILE    65      38.991 -12.503  28.289  1.00 16.00      MTGL
ATOM    501  CG2  ILE    65      39.574 -13.130  29.536  1.00 16.34      MTGL
ATOM    502  CG1  ILE    65      39.173 -10.984  28.322  1.00 18.05      MTGL
ATOM    503  CD1  ILE    65      38.423 -10.321  29.474  1.00 15.44      MTGL
ATOM    504  C    ILE    65      38.989 -12.598  25.760  1.00 16.71      MTGL
ATOM    505  O    ILE    65      37.938 -13.101  25.368  1.00 16.21      MTGL
ATOM    506  N    ALA    66      39.598 -11.609  25.107  1.00 16.15      MTGL
ATOM    507  CA   ALA    66      39.036 -11.087  23.866  1.00 16.93      MTGL
ATOM    508  CB   ALA    66      39.806  -9.854  23.404  1.00 15.85      MTGL
ATOM    509  C    ALA    66      39.106 -12.185  22.802  1.00 17.72      MTGL
ATOM    510  O    ALA    66      38.189 -12.330  21.989  1.00 16.94      MTGL
ATOM    511  N    LYS    67      40.188 -12.965  22.817  1.00 18.09      MTGL
ATOM    512  CA   LYS    67      40.340 -14.059  21.856  1.00 19.65      MTGL
ATOM    513  CB   LYS    67      41.700 -14.748  22.010  1.00 21.06      MTGL
ATOM    514  CG   LYS    67      42.892 -13.953  21.484  1.00 23.60      MTGL
ATOM    515  CD   LYS    67      44.159 -14.795  21.550  1.00 26.88      MTGL
ATOM    516  CE   LYS    67      45.365 -14.050  21.000  1.00 29.59      MTGL
ATOM    517  NZ   LYS    67      45.208 -13.714  19.551  1.00 32.62      MTGL
ATOM    518  C    LYS    67      39.229 -15.085  22.070  1.00 19.44      MTGL
ATOM    519  O    LYS    67      38.667 -15.616  21.109  1.00 19.17      MTGL
ATOM    520  N    ARG    68      38.921 -15.365  23.335  1.00 18.94      MTGL
ATOM    521  CA   ARG    68      37.866 -16.317  23.672  1.00 17.61      MTGL
```

Fig. 1 cont.

| | | | | | | | | | | |
|---|---|---|---|---|---|---|---|---|---|---|
| ATOM | 522 | CB | ARG | 68 | 37.834 | -16.567 | 25.181 | 1.00 | 16.99 | MTGL |
| ATOM | 523 | CG | ARG | 68 | 38.950 | -17.488 | 25.679 | 1.00 | 18.79 | MTGL |
| ATOM | 524 | CD | ARG | 68 | 39.015 | -17.515 | 27.199 | 1.00 | 17.89 | MTGL |
| ATOM | 525 | NE | ARG | 68 | 37.742 | -17.892 | 27.809 | 1.00 | 18.08 | MTGL |
| ATOM | 526 | CZ | ARG | 68 | 37.555 | -18.020 | 29.120 | 1.00 | 18.59 | MTGL |
| ATOM | 527 | NH1 | ARG | 68 | 38.561 | -17.798 | 29.961 | 1.00 | 18.68 | MTGL |
| ATOM | 528 | NH2 | ARG | 68 | 36.371 | -18.381 | 29.595 | 1.00 | 16.96 | MTGL |
| ATOM | 529 | C | ARG | 68 | 36.511 | -15.799 | 23.209 | 1.00 | 17.25 | MTGL |
| ATOM | 530 | O | ARG | 68 | 35.679 | -16.563 | 22.711 | 1.00 | 15.99 | MTGL |
| ATOM | 531 | N | ALA | 69 | 36.285 | -14.503 | 23.395 | 1.00 | 16.95 | MTGL |
| ATOM | 532 | CA | ALA | 69 | 35.030 | -13.886 | 22.982 | 1.00 | 18.21 | MTGL |
| ATOM | 533 | CB | ALA | 69 | 35.001 | -12.411 | 23.393 | 1.00 | 18.02 | MTGL |
| ATOM | 534 | C | ALA | 69 | 34.907 | -14.012 | 21.465 | 1.00 | 18.17 | MTGL |
| ATOM | 535 | O | ALA | 69 | 33.867 | -14.407 | 20.945 | 1.00 | 16.83 | MTGL |
| ATOM | 536 | N | LYS | 70 | 35.984 | -13.675 | 20.764 | 1.00 | 18.35 | MTGL |
| ATOM | 537 | CA | LYS | 70 | 36.011 | -13.764 | 19.312 | 1.00 | 19.84 | MTGL |
| ATOM | 538 | CB | LYS | 70 | 37.402 | -13.390 | 18.795 | 1.00 | 19.40 | MTGL |
| ATOM | 539 | CG | LYS | 70 | 37.548 | -13.420 | 17.284 | 1.00 | 21.56 | MTGL |
| ATOM | 540 | CD | LYS | 70 | 38.992 | -13.123 | 16.892 | 1.00 | 22.53 | MTGL |
| ATOM | 541 | CE | LYS | 70 | 39.180 | -13.123 | 15.383 | 1.00 | 23.66 | MTGL |
| ATOM | 542 | NZ | LYS | 70 | 40.592 | -12.852 | 15.015 | 1.00 | 21.95 | MTGL |
| ATOM | 543 | C | LYS | 70 | 35.648 | -15.186 | 18.861 | 1.00 | 20.29 | MTGL |
| ATOM | 544 | O | LYS | 70 | 34.842 | -15.365 | 17.948 | 1.00 | 19.93 | MTGL |
| ATOM | 545 | N | ALA | 71 | 36.235 | -16.190 | 19.511 | 1.00 | 19.37 | MTGL |
| ATOM | 546 | CA | ALA | 71 | 35.970 | -17.585 | 19.159 | 1.00 | 20.95 | MTGL |
| ATOM | 547 | CB | ALA | 71 | 36.896 | -18.514 | 19.941 | 1.00 | 20.90 | MTGL |
| ATOM | 548 | C | ALA | 71 | 34.514 | -17.975 | 19.405 | 1.00 | 21.38 | MTGL |
| ATOM | 549 | O | ALA | 71 | 34.010 | -18.929 | 18.810 | 1.00 | 22.34 | MTGL |
| ATOM | 550 | N | ALA | 72 | 33.839 | -17.244 | 20.282 | 1.00 | 20.63 | MTGL |
| ATOM | 551 | CA | ALA | 72 | 32.439 | -17.529 | 20.574 | 1.00 | 20.92 | MTGL |
| ATOM | 552 | CB | ALA | 72 | 32.149 | -17.284 | 22.050 | 1.00 | 20.20 | MTGL |
| ATOM | 553 | C | ALA | 72 | 31.523 | -16.659 | 19.710 | 1.00 | 20.68 | MTGL |
| ATOM | 554 | O | ALA | 72 | 30.305 | -16.644 | 19.899 | 1.00 | 20.23 | MTGL |
| ATOM | 555 | N | GLY | 73 | 32.116 | -15.934 | 18.768 | 1.00 | 20.42 | MTGL |
| ATOM | 556 | CA | GLY | 73 | 31.339 | -15.077 | 17.889 | 1.00 | 20.87 | MTGL |
| ATOM | 557 | C | GLY | 73 | 30.874 | -13.774 | 18.523 | 1.00 | 21.42 | MTGL |
| ATOM | 558 | O | GLY | 73 | 29.946 | -13.133 | 18.027 | 1.00 | 21.96 | MTGL |
| ATOM | 559 | N | LEU | 74 | 31.522 | -13.373 | 19.612 | 1.00 | 20.70 | MTGL |
| ATOM | 560 | CA | LEU | 74 | 31.160 | -12.146 | 20.315 | 1.00 | 19.98 | MTGL |
| ATOM | 561 | CB | LEU | 74 | 31.221 | -12.372 | 21.830 | 1.00 | 19.61 | MTGL |
| ATOM | 562 | CG | LEU | 74 | 30.359 | -13.491 | 22.420 | 1.00 | 19.97 | MTGL |
| ATOM | 563 | CD1 | LEU | 74 | 30.692 | -13.659 | 23.898 | 1.00 | 19.32 | MTGL |
| ATOM | 564 | CD2 | LEU | 74 | 28.881 | -13.162 | 22.232 | 1.00 | 18.79 | MTGL |
| ATOM | 565 | C | LEU | 74 | 32.071 | -10.978 | 19.960 | 1.00 | 19.91 | MTGL |
| ATOM | 566 | O | LEU | 74 | 33.292 | -11.133 | 19.882 | 1.00 | 20.26 | MTGL |
| ATOM | 567 | N | GLY | 75 | 31.473 | -9.809 | 19.740 | 1.00 | 19.06 | MTGL |
| ATOM | 568 | CA | GLY | 75 | 32.261 | -8.627 | 19.438 | 1.00 | 18.36 | MTGL |
| ATOM | 569 | C | GLY | 75 | 32.856 | -8.106 | 20.738 | 1.00 | 17.17 | MTGL |
| ATOM | 570 | O | GLY | 75 | 32.380 | -8.457 | 21.821 | 1.00 | 16.83 | MTGL |
| ATOM | 571 | N | VAL | 76 | 33.885 | -7.271 | 20.648 | 1.00 | 16.99 | MTGL |
| ATOM | 572 | CA | VAL | 76 | 34.522 | -6.748 | 21.853 | 1.00 | 17.15 | MTGL |
| ATOM | 573 | CB | VAL | 76 | 35.996 | -7.202 | 21.947 | 1.00 | 18.28 | MTGL |
| ATOM | 574 | CG1 | VAL | 76 | 36.626 | -6.682 | 23.238 | 1.00 | 17.92 | MTGL |
| ATOM | 575 | CG2 | VAL | 76 | 36.074 | -8.726 | 21.896 | 1.00 | 17.32 | MTGL |
| ATOM | 576 | C | VAL | 76 | 34.476 | -5.231 | 21.984 | 1.00 | 17.67 | MTGL |
| ATOM | 577 | O | VAL | 76 | 34.770 | -4.491 | 21.039 | 1.00 | 18.33 | MTGL |
| ATOM | 578 | N | TYR | 77 | 34.108 | -4.785 | 23.177 | 1.00 | 16.77 | MTGL |
| ATOM | 579 | CA | TYR | 77 | 34.013 | -3.366 | 23.517 | 1.00 | 16.63 | MTGL |

Fig. 1 cont.

```
ATOM   580  CB   TYR  77      32.608   -3.102   24.097  1.00 15.27      MTGL
ATOM   581  CG   TYR  77      32.335   -1.799   24.840  1.00 15.55      MTGL
ATOM   582  CD1  TYR  77      33.343   -0.886   25.149  1.00 15.39      MTGL
ATOM   583  CE1  TYR  77      33.068    0.257   25.925  1.00 16.48      MTGL
ATOM   584  CD2  TYR  77      31.046   -1.532   25.312  1.00 16.02      MTGL
ATOM   585  CE2  TYR  77      30.766   -0.414   26.075  1.00 15.87      MTGL
ATOM   586  CZ   TYR  77      31.772    0.475   26.386  1.00 16.20      MTGL
ATOM   587  OH   TYR  77      31.471    1.541   27.200  1.00 15.93      MTGL
ATOM   588  C    TYR  77      35.114   -3.128   24.548  1.00 16.00      MTGL
ATOM   589  O    TYR  77      35.026   -3.604   25.683  1.00 16.53      MTGL
ATOM   590  N    ILE  78      36.163   -2.419   24.142  1.00 16.29      MTGL
ATOM   591  CA   ILE  78      37.280   -2.121   25.044  1.00 17.09      MTGL
ATOM   592  CB   ILE  78      38.611   -2.008   24.261  1.00 17.14      MTGL
ATOM   593  CG2  ILE  78      39.695   -1.387   25.140  1.00 16.04      MTGL
ATOM   594  CG1  ILE  78      39.049   -3.394   23.777  1.00 16.84      MTGL
ATOM   595  CD1  ILE  78      39.424   -4.364   24.905  1.00 17.38      MTGL
ATOM   596  C    ILE  78      37.031   -0.818   25.818  1.00 17.27      MTGL
ATOM   597  O    ILE  78      36.834    0.241   25.227  1.00 17.22      MTGL
ATOM   598  N    ASP  79      37.046   -0.912   27.142  1.00 16.43      MTGL
ATOM   599  CA   ASP  79      36.817    0.234   28.009  1.00 16.05      MTGL
ATOM   600  CB   ASP  79      35.738   -0.127   29.039  1.00 17.34      MTGL
ATOM   601  CG   ASP  79      35.577    0.920   30.133  1.00 19.18      MTGL
ATOM   602  OD1  ASP  79      36.023    2.072   29.952  1.00 19.88      MTGL
ATOM   603  OD2  ASP  79      34.986    0.583   31.181  1.00 20.19      MTGL
ATOM   604  C    ASP  79      38.113    0.657   28.699  1.00 16.01      MTGL
ATOM   605  O    ASP  79      38.479    0.102   29.732  1.00 15.54      MTGL
ATOM   606  N    PHE  80      38.810    1.626   28.105  1.00 15.57      MTGL
ATOM   607  CA   PHE  80      40.065    2.138   28.654  1.00 15.49      MTGL
ATOM   608  CB   PHE  80      40.811    3.005   27.627  1.00 14.72      MTGL
ATOM   609  CG   PHE  80      41.533    2.230   26.566  1.00 14.70      MTGL
ATOM   610  CD1  PHE  80      42.548    1.343   26.899  1.00 14.82      MTGL
ATOM   611  CD2  PHE  80      41.224    2.419   25.222  1.00 15.80      MTGL
ATOM   612  CE1  PHE  80      43.251    0.649   25.912  1.00 15.54      MTGL
ATOM   613  CE2  PHE  80      41.921    1.730   24.221  1.00 16.06      MTGL
ATOM   614  CZ   PHE  80      42.938    0.844   24.568  1.00 14.92      MTGL
ATOM   615  C    PHE  80      39.800    3.009   29.869  1.00 16.16      MTGL
ATOM   616  O    PHE  80      39.126    4.036   29.759  1.00 15.79      MTGL
ATOM   617  N    HIS  81      40.328    2.617   31.025  1.00 15.76      MTGL
ATOM   618  CA   HIS  81      40.140    3.419   32.234  1.00 15.04      MTGL
ATOM   619  CB   HIS  81      40.130    2.533   33.485  1.00 13.87      MTGL
ATOM   620  CG   HIS  81      38.846    1.790   33.686  1.00 14.70      MTGL
ATOM   621  CD2  HIS  81      37.971    1.263   32.795  1.00 13.78      MTGL
ATOM   622  ND1  HIS  81      38.312    1.554   34.933  1.00 13.45      MTGL
ATOM   623  CE1  HIS  81      37.161    0.918   34.804  1.00 15.90      MTGL
ATOM   624  NE2  HIS  81      36.931    0.730   33.516  1.00 14.78      MTGL
ATOM   625  C    HIS  81      41.244    4.466   32.357  1.00 15.46      MTGL
ATOM   626  O    HIS  81      41.113    5.439   33.102  1.00 14.94      MTGL
ATOM   627  N    TYR  82      42.326    4.273   31.609  1.00 15.09      MTGL
ATOM   628  CA   TYR  82      43.452    5.199   31.663  1.00 16.48      MTGL
ATOM   629  CB   TYR  82      43.092    6.520   30.974  1.00 15.74      MTGL
ATOM   630  CG   TYR  82      42.849    6.384   29.476  1.00 15.85      MTGL
ATOM   631  CD1  TYR  82      43.702    5.615   28.680  1.00 15.30      MTGL
ATOM   632  CE1  TYR  82      43.527    5.530   27.307  1.00 16.13      MTGL
ATOM   633  CD2  TYR  82      41.801    7.062   28.852  1.00 15.60      MTGL
ATOM   634  CE2  TYR  82      41.613    6.985   27.465  1.00 16.11      MTGL
ATOM   635  CZ   TYR  82      42.482    6.218   26.705  1.00 17.06      MTGL
ATOM   636  OH   TYR  82      42.331    6.148   25.345  1.00 18.86      MTGL
ATOM   637  C    TYR  82      43.866    5.437   33.122  1.00 17.11      MTGL
```

Fig. 1 cont.

| | | | | | | | | | | |
|---|---|---|---|---|---|---|---|---|---|---|
| ATOM | 638 | O | TYR | 82 | 43.987 | 6.573 | 33.593 | 1.00 | 17.37 | MTGL |
| ATOM | 639 | N | SER | 83 | 44.077 | 4.329 | 33.822 | 1.00 | 17.17 | MTGL |
| ATOM | 640 | CA | SER | 83 | 44.482 | 4.328 | 35.223 | 1.00 | 17.21 | MTGL |
| ATOM | 641 | CB | SER | 83 | 43.288 | 4.679 | 36.115 | 1.00 | 16.41 | MTGL |
| ATOM | 642 | OG | SER | 83 | 43.639 | 4.651 | 37.487 | 1.00 | 16.64 | MTGL |
| ATOM | 643 | C | SER | 83 | 44.948 | 2.904 | 35.518 | 1.00 | 17.88 | MTGL |
| ATOM | 644 | O | SER | 83 | 44.689 | 1.993 | 34.732 | 1.00 | 17.59 | MTGL |
| ATOM | 645 | N | ASP | 84 | 45.646 | 2.706 | 36.630 | 1.00 | 18.00 | MTGL |
| ATOM | 646 | CA | ASP | 84 | 46.106 | 1.369 | 36.984 | 1.00 | 17.91 | MTGL |
| ATOM | 647 | CB | ASP | 84 | 47.378 | 1.415 | 37.840 | 1.00 | 18.31 | MTGL |
| ATOM | 648 | CG | ASP | 84 | 48.570 | 1.993 | 37.105 | 1.00 | 19.40 | MTGL |
| ATOM | 649 | OD1 | ASP | 84 | 48.732 | 1.724 | 35.897 | 1.00 | 18.50 | MTGL |
| ATOM | 650 | OD2 | ASP | 84 | 49.366 | 2.705 | 37.750 | 1.00 | 20.89 | MTGL |
| ATOM | 651 | C | ASP | 84 | 45.017 | 0.665 | 37.785 | 1.00 | 17.16 | MTGL |
| ATOM | 652 | O | ASP | 84 | 45.118 | -0.525 | 38.061 | 1.00 | 16.64 | MTGL |
| ATOM | 653 | N | THR | 85 | 43.978 | 1.406 | 38.152 | 1.00 | 16.98 | MTGL |
| ATOM | 654 | CA | THR | 85 | 42.889 | 0.837 | 38.943 | 1.00 | 17.09 | MTGL |
| ATOM | 655 | CB | THR | 85 | 43.169 | 1.056 | 40.456 | 1.00 | 17.53 | MTGL |
| ATOM | 656 | OG1 | THR | 85 | 42.211 | 0.337 | 41.239 | 1.00 | 20.04 | MTGL |
| ATOM | 657 | CG2 | THR | 85 | 43.107 | 2.549 | 40.805 | 1.00 | 16.84 | MTGL |
| ATOM | 658 | C | THR | 85 | 41.543 | 1.460 | 38.546 | 1.00 | 16.53 | MTGL |
| ATOM | 659 | O | THR | 85 | 41.481 | 2.245 | 37.598 | 1.00 | 16.58 | MTGL |
| ATOM | 660 | N | TRP | 86 | 40.477 | 1.100 | 39.264 | 1.00 | 15.91 | MTGL |
| ATOM | 661 | CA | TRP | 86 | 39.130 | 1.597 | 38.982 | 1.00 | 16.71 | MTGL |
| ATOM | 662 | CB | TRP | 86 | 38.166 | 1.291 | 40.143 | 1.00 | 15.33 | MTGL |
| ATOM | 663 | CG | TRP | 86 | 38.079 | -0.151 | 40.525 | 1.00 | 17.03 | MTGL |
| ATOM | 664 | CD2 | TRP | 86 | 37.311 | -1.165 | 39.871 | 1.00 | 16.85 | MTGL |
| ATOM | 665 | CE2 | TRP | 86 | 37.548 | -2.378 | 40.560 | 1.00 | 17.49 | MTGL |
| ATOM | 666 | CE3 | TRP | 86 | 36.448 | -1.170 | 38.767 | 1.00 | 16.06 | MTGL |
| ATOM | 667 | CD1 | TRP | 86 | 38.731 | -0.768 | 41.555 | 1.00 | 16.85 | MTGL |
| ATOM | 668 | NE1 | TRP | 86 | 38.417 | -2.104 | 41.583 | 1.00 | 17.28 | MTGL |
| ATOM | 669 | CZ2 | TRP | 86 | 36.951 | -3.588 | 40.180 | 1.00 | 16.23 | MTGL |
| ATOM | 670 | CZ3 | TRP | 86 | 35.853 | -2.373 | 38.388 | 1.00 | 17.14 | MTGL |
| ATOM | 671 | CH2 | TRP | 86 | 36.110 | -3.566 | 39.095 | 1.00 | 17.46 | MTGL |
| ATOM | 672 | C | TRP | 86 | 39.044 | 3.093 | 38.703 | 1.00 | 16.71 | MTGL |
| ATOM | 673 | O | TRP | 86 | 39.500 | 3.911 | 39.500 | 1.00 | 16.21 | MTGL |
| ATOM | 674 | N | ALA | 87 | 38.440 | 3.443 | 37.574 | 1.00 | 16.31 | MTGL |
| ATOM | 675 | CA | ALA | 87 | 38.249 | 4.845 | 37.223 | 1.00 | 17.57 | MTGL |
| ATOM | 676 | CB | ALA | 87 | 38.760 | 5.124 | 35.809 | 1.00 | 16.32 | MTGL |
| ATOM | 677 | C | ALA | 87 | 36.753 | 5.119 | 37.297 | 1.00 | 18.11 | MTGL |
| ATOM | 678 | O | ALA | 87 | 35.965 | 4.409 | 36.677 | 1.00 | 18.07 | MTGL |
| ATOM | 679 | N | ASP | 88 | 36.368 | 6.125 | 38.077 | 1.00 | 18.47 | MTGL |
| ATOM | 680 | CA | ASP | 88 | 34.965 | 6.512 | 38.213 | 1.00 | 18.85 | MTGL |
| ATOM | 681 | CB | ASP | 88 | 34.287 | 5.730 | 39.354 | 1.00 | 18.63 | MTGL |
| ATOM | 682 | CG | ASP | 88 | 35.047 | 5.816 | 40.661 | 1.00 | 19.12 | MTGL |
| ATOM | 683 | OD1 | ASP | 88 | 35.352 | 6.940 | 41.109 | 1.00 | 18.34 | MTGL |
| ATOM | 684 | OD2 | ASP | 88 | 35.331 | 4.749 | 41.248 | 1.00 | 19.72 | MTGL |
| ATOM | 685 | C | ASP | 88 | 34.932 | 8.021 | 38.460 | 1.00 | 18.13 | MTGL |
| ATOM | 686 | O | ASP | 88 | 35.980 | 8.656 | 38.505 | 1.00 | 17.65 | MTGL |
| ATOM | 687 | N | PRO | 89 | 33.737 | 8.616 | 38.615 | 1.00 | 18.93 | MTGL |
| ATOM | 688 | CD | PRO | 89 | 32.382 | 8.046 | 38.501 | 1.00 | 19.94 | MTGL |
| ATOM | 689 | CA | PRO | 89 | 33.672 | 10.066 | 38.842 | 1.00 | 19.49 | MTGL |
| ATOM | 690 | CB | PRO | 89 | 32.174 | 10.327 | 39.000 | 1.00 | 19.80 | MTGL |
| ATOM | 691 | CG | PRO | 89 | 31.555 | 9.263 | 38.125 | 1.00 | 19.69 | MTGL |
| ATOM | 692 | C | PRO | 89 | 34.476 | 10.600 | 40.025 | 1.00 | 19.90 | MTGL |
| ATOM | 693 | O | PRO | 89 | 34.833 | 11.778 | 40.048 | 1.00 | 20.62 | MTGL |
| ATOM | 694 | N | ALA | 90 | 34.760 | 9.743 | 40.999 | 1.00 | 18.70 | MTGL |
| ATOM | 695 | CA | ALA | 90 | 35.519 | 10.164 | 42.175 | 1.00 | 19.35 | MTGL |

Fig. 1 cont.

| ATOM | 696 | CB  | ALA | 90 | 34.818 | 9.685  | 43.457 | 1.00 | 17.48 | MTGL |
| ATOM | 697 | C   | ALA | 90 | 36.964 | 9.674  | 42.162 | 1.00 | 18.63 | MTGL |
| ATOM | 698 | O   | ALA | 90 | 37.730 | 9.988  | 43.071 | 1.00 | 19.58 | MTGL |
| ATOM | 699 | N   | HIS | 91 | 37.333 | 8.901  | 41.145 | 1.00 | 17.84 | MTGL |
| ATOM | 700 | CA  | HIS | 91 | 38.698 | 8.391  | 41.039 | 1.00 | 17.68 | MTGL |
| ATOM | 701 | CB  | HIS | 91 | 38.833 | 7.000  | 41.679 | 1.00 | 18.34 | MTGL |
| ATOM | 702 | CG  | HIS | 91 | 38.298 | 6.910  | 43.072 | 1.00 | 20.31 | MTGL |
| ATOM | 703 | CD2 | HIS | 91 | 38.927 | 6.936  | 44.272 | 1.00 | 19.87 | MTGL |
| ATOM | 704 | ND1 | HIS | 91 | 36.953 | 6.784  | 43.344 | 1.00 | 18.50 | MTGL |
| ATOM | 705 | CE1 | HIS | 91 | 36.775 | 6.736  | 44.653 | 1.00 | 20.43 | MTGL |
| ATOM | 706 | NE2 | HIS | 91 | 37.956 | 6.826  | 45.238 | 1.00 | 21.64 | MTGL |
| ATOM | 707 | C   | HIS | 91 | 39.177 | 8.280  | 39.597 | 1.00 | 16.55 | MTGL |
| ATOM | 708 | O   | HIS | 91 | 38.661 | 7.478  | 38.823 | 1.00 | 16.39 | MTGL |
| ATOM | 709 | N   | GLN | 92 | 40.169 | 9.087  | 39.246 | 1.00 | 15.52 | MTGL |
| ATOM | 710 | CA  | GLN | 92 | 40.760 | 9.064  | 37.911 | 1.00 | 15.68 | MTGL |
| ATOM | 711 | CB  | GLN | 92 | 40.281 | 10.255 | 37.072 | 1.00 | 14.49 | MTGL |
| ATOM | 712 | CG  | GLN | 92 | 38.786 | 10.229 | 36.702 | 1.00 | 13.93 | MTGL |
| ATOM | 713 | CD  | GLN | 92 | 38.413 | 9.127  | 35.699 | 1.00 | 14.84 | MTGL |
| ATOM | 714 | OE1 | GLN | 92 | 39.173 | 8.814  | 34.779 | 1.00 | 15.41 | MTGL |
| ATOM | 715 | NE2 | GLN | 92 | 37.221 | 8.559  | 35.861 | 1.00 | 14.23 | MTGL |
| ATOM | 716 | C   | GLN | 92 | 42.254 | 9.166  | 38.190 | 1.00 | 15.81 | MTGL |
| ATOM | 717 | O   | GLN | 92 | 42.925 | 10.108 | 37.782 | 1.00 | 16.26 | MTGL |
| ATOM | 718 | N   | THR | 93 | 42.759 | 8.169  | 38.902 | 1.00 | 16.47 | MTGL |
| ATOM | 719 | CA  | THR | 93 | 44.156 | 8.136  | 39.302 | 1.00 | 17.33 | MTGL |
| ATOM | 720 | CB  | THR | 93 | 44.387 | 7.062  | 40.364 | 1.00 | 17.41 | MTGL |
| ATOM | 721 | OG1 | THR | 93 | 43.433 | 7.239  | 41.417 | 1.00 | 19.90 | MTGL |
| ATOM | 722 | CG2 | THR | 93 | 45.800 | 7.177  | 40.944 | 1.00 | 19.68 | MTGL |
| ATOM | 723 | C   | THR | 93 | 45.136 | 7.925  | 38.165 | 1.00 | 17.55 | MTGL |
| ATOM | 724 | O   | THR | 93 | 45.035 | 6.973  | 37.390 | 1.00 | 17.01 | MTGL |
| ATOM | 725 | N   | MET | 94 | 46.093 | 8.839  | 38.089 | 1.00 | 17.63 | MTGL |
| ATOM | 726 | CA  | MET | 94 | 47.131 | 8.820  | 37.079 | 1.00 | 18.68 | MTGL |
| ATOM | 727 | CB  | MET | 94 | 48.144 | 9.926  | 37.383 | 1.00 | 21.10 | MTGL |
| ATOM | 728 | CG  | MET | 94 | 49.195 | 10.133 | 36.315 | 1.00 | 23.55 | MTGL |
| ATOM | 729 | SD  | MET | 94 | 48.474 | 10.956 | 34.894 | 1.00 | 27.41 | MTGL |
| ATOM | 730 | CE  | MET | 94 | 48.342 | 12.657 | 35.533 | 1.00 | 25.13 | MTGL |
| ATOM | 731 | C   | MET | 94 | 47.854 | 7.476  | 37.064 | 1.00 | 18.43 | MTGL |
| ATOM | 732 | O   | MET | 94 | 48.179 | 6.925  | 38.113 | 1.00 | 18.13 | MTGL |
| ATOM | 733 | N   | PRO | 95 | 48.088 | 6.914  | 35.871 | 1.00 | 17.41 | MTGL |
| ATOM | 734 | CD  | PRO | 95 | 47.534 | 7.255  | 34.551 | 1.00 | 16.67 | MTGL |
| ATOM | 735 | CA  | PRO | 95 | 48.797 | 5.631  | 35.834 | 1.00 | 17.83 | MTGL |
| ATOM | 736 | CB  | PRO | 95 | 48.814 | 5.287  | 34.347 | 1.00 | 17.25 | MTGL |
| ATOM | 737 | CG  | PRO | 95 | 47.544 | 5.914  | 33.843 | 1.00 | 17.35 | MTGL |
| ATOM | 738 | C   | PRO | 95 | 50.202 | 5.903  | 36.371 | 1.00 | 18.71 | MTGL |
| ATOM | 739 | O   | PRO | 95 | 50.784 | 6.952  | 36.084 | 1.00 | 17.30 | MTGL |
| ATOM | 740 | N   | ALA | 96 | 50.746 | 4.978  | 37.152 | 1.00 | 18.59 | MTGL |
| ATOM | 741 | CA  | ALA | 96 | 52.082 | 5.177  | 37.705 | 1.00 | 20.01 | MTGL |
| ATOM | 742 | CB  | ALA | 96 | 52.470 | 3.983  | 38.587 | 1.00 | 19.66 | MTGL |
| ATOM | 743 | C   | ALA | 96 | 53.095 | 5.357  | 36.577 | 1.00 | 20.37 | MTGL |
| ATOM | 744 | O   | ALA | 96 | 53.081 | 4.617  | 35.595 | 1.00 | 20.80 | MTGL |
| ATOM | 745 | N   | GLY | 97 | 53.959 | 6.356  | 36.710 | 1.00 | 20.53 | MTGL |
| ATOM | 746 | CA  | GLY | 97 | 54.967 | 6.595  | 35.693 | 1.00 | 20.43 | MTGL |
| ATOM | 747 | C   | GLY | 97 | 54.611 | 7.644  | 34.654 | 1.00 | 20.83 | MTGL |
| ATOM | 748 | O   | GLY | 97 | 55.491 | 8.144  | 33.959 | 1.00 | 22.30 | MTGL |
| ATOM | 749 | N   | TRP | 98 | 53.332 | 7.982  | 34.537 | 1.00 | 20.23 | MTGL |
| ATOM | 750 | CA  | TRP | 98 | 52.902 | 8.978  | 33.561 | 1.00 | 19.86 | MTGL |
| ATOM | 751 | CB  | TRP | 98 | 51.415 | 8.795  | 33.249 | 1.00 | 18.17 | MTGL |
| ATOM | 752 | CG  | TRP | 98 | 51.106 | 7.576  | 32.421 | 1.00 | 17.34 | MTGL |
| ATOM | 753 | CD2 | TRP | 98 | 49.987 | 7.397  | 31.543 | 1.00 | 16.19 | MTGL |

Fig. 1 cont.

| ATOM | 754 | CE2 | TRP | 98 | 50.082 | 6.093 | 31.006 | 1.00 | 16.95 | MTGL |
| ATOM | 755 | CE3 | TRP | 98 | 48.914 | 8.213 | 31.156 | 1.00 | 15.48 | MTGL |
| ATOM | 756 | CD1 | TRP | 98 | 51.810 | 6.406 | 32.385 | 1.00 | 18.21 | MTGL |
| ATOM | 757 | NE1 | TRP | 98 | 51.202 | 5.511 | 31.538 | 1.00 | 17.45 | MTGL |
| ATOM | 758 | CZ2 | TRP | 98 | 49.140 | 5.580 | 30.103 | 1.00 | 17.12 | MTGL |
| ATOM | 759 | CZ3 | TRP | 98 | 47.974 | 7.704 | 30.257 | 1.00 | 15.71 | MTGL |
| ATOM | 760 | CH2 | TRP | 98 | 48.098 | 6.399 | 29.740 | 1.00 | 16.54 | MTGL |
| ATOM | 761 | C | TRP | 98 | 53.156 | 10.401 | 34.056 | 1.00 | 20.28 | MTGL |
| ATOM | 762 | O | TRP | 98 | 52.958 | 10.706 | 35.230 | 1.00 | 19.92 | MTGL |
| ATOM | 763 | N | PRO | 99 | 53.593 | 11.295 | 33.156 | 1.00 | 21.71 | MTGL |
| ATOM | 764 | CD | PRO | 99 | 53.852 | 11.048 | 31.725 | 1.00 | 22.15 | MTGL |
| ATOM | 765 | CA | PRO | 99 | 53.875 | 12.693 | 33.505 | 1.00 | 22.69 | MTGL |
| ATOM | 766 | CB | PRO | 99 | 54.610 | 13.205 | 32.269 | 1.00 | 22.58 | MTGL |
| ATOM | 767 | CG | PRO | 99 | 53.938 | 12.454 | 31.163 | 1.00 | 22.80 | MTGL |
| ATOM | 768 | C | PRO | 99 | 52.598 | 13.483 | 33.797 | 1.00 | 23.10 | MTGL |
| ATOM | 769 | O | PRO | 99 | 51.530 | 13.156 | 33.277 | 1.00 | 23.44 | MTGL |
| ATOM | 770 | N | SER | 100 | 52.716 | 14.522 | 34.621 | 1.00 | 22.96 | MTGL |
| ATOM | 771 | CA | SER | 100 | 51.572 | 15.353 | 34.995 | 1.00 | 23.06 | MTGL |
| ATOM | 772 | CB | SER | 100 | 51.714 | 15.831 | 36.445 | 1.00 | 24.32 | MTGL |
| ATOM | 773 | OG | SER | 100 | 51.658 | 14.746 | 37.353 | 1.00 | 26.38 | MTGL |
| ATOM | 774 | C | SER | 100 | 51.332 | 16.574 | 34.115 | 1.00 | 22.44 | MTGL |
| ATOM | 775 | O | SER | 100 | 50.202 | 17.051 | 34.032 | 1.00 | 22.25 | MTGL |
| ATOM | 776 | N | ASP | 101 | 52.379 | 17.098 | 33.480 | 1.00 | 22.38 | MTGL |
| ATOM | 777 | CA | ASP | 101 | 52.208 | 18.283 | 32.639 | 1.00 | 23.28 | MTGL |
| ATOM | 778 | CB | ASP | 101 | 53.565 | 18.890 | 32.254 | 1.00 | 24.51 | MTGL |
| ATOM | 779 | CG | ASP | 101 | 54.382 | 17.986 | 31.352 | 1.00 | 25.84 | MTGL |
| ATOM | 780 | OD1 | ASP | 101 | 54.886 | 16.954 | 31.842 | 1.00 | 26.46 | MTGL |
| ATOM | 781 | OD2 | ASP | 101 | 54.515 | 18.310 | 30.152 | 1.00 | 25.84 | MTGL |
| ATOM | 782 | C | ASP | 101 | 51.411 | 17.933 | 31.386 | 1.00 | 22.28 | MTGL |
| ATOM | 783 | O | ASP | 101 | 51.667 | 16.915 | 30.743 | 1.00 | 21.59 | MTGL |
| ATOM | 784 | N | ILE | 102 | 50.452 | 18.787 | 31.042 | 1.00 | 21.77 | MTGL |
| ATOM | 785 | CA | ILE | 102 | 49.584 | 18.548 | 29.890 | 1.00 | 21.42 | MTGL |
| ATOM | 786 | CB | ILE | 102 | 48.623 | 19.738 | 29.663 | 1.00 | 20.48 | MTGL |
| ATOM | 787 | CG2 | ILE | 102 | 49.411 | 20.998 | 29.313 | 1.00 | 20.99 | MTGL |
| ATOM | 788 | CG1 | ILE | 102 | 47.617 | 19.392 | 28.560 | 1.00 | 21.44 | MTGL |
| ATOM | 789 | CD1 | ILE | 102 | 46.730 | 18.200 | 28.879 | 1.00 | 19.62 | MTGL |
| ATOM | 790 | C | ILE | 102 | 50.281 | 18.196 | 28.573 | 1.00 | 21.71 | MTGL |
| ATOM | 791 | O | ILE | 102 | 49.861 | 17.258 | 27.896 | 1.00 | 20.84 | MTGL |
| ATOM | 792 | N | ASP | 103 | 51.336 | 18.918 | 28.201 | 1.00 | 21.01 | MTGL |
| ATOM | 793 | CA | ASP | 103 | 52.012 | 18.608 | 26.945 | 1.00 | 22.44 | MTGL |
| ATOM | 794 | CB | ASP | 103 | 53.219 | 19.523 | 26.716 | 1.00 | 24.91 | MTGL |
| ATOM | 795 | CG | ASP | 103 | 52.821 | 20.942 | 26.370 | 1.00 | 27.06 | MTGL |
| ATOM | 796 | OD1 | ASP | 103 | 51.633 | 21.178 | 26.070 | 1.00 | 27.99 | MTGL |
| ATOM | 797 | OD2 | ASP | 103 | 53.703 | 21.823 | 26.385 | 1.00 | 28.69 | MTGL |
| ATOM | 798 | C | ASP | 103 | 52.478 | 17.160 | 26.886 | 1.00 | 22.61 | MTGL |
| ATOM | 799 | O | ASP | 103 | 52.144 | 16.435 | 25.948 | 1.00 | 23.39 | MTGL |
| ATOM | 800 | N | ASN | 104 | 53.244 | 16.734 | 27.885 | 1.00 | 21.79 | MTGL |
| ATOM | 801 | CA | ASN | 104 | 53.751 | 15.366 | 27.898 | 1.00 | 22.22 | MTGL |
| ATOM | 802 | CB | ASN | 104 | 54.912 | 15.244 | 28.884 | 1.00 | 23.92 | MTGL |
| ATOM | 803 | CG | ASN | 104 | 56.149 | 15.977 | 28.406 | 1.00 | 26.18 | MTGL |
| ATOM | 804 | OD1 | ASN | 104 | 56.715 | 15.643 | 27.364 | 1.00 | 26.60 | MTGL |
| ATOM | 805 | ND2 | ASN | 104 | 56.570 | 16.989 | 29.157 | 1.00 | 26.07 | MTGL |
| ATOM | 806 | C | ASN | 104 | 52.699 | 14.311 | 28.191 | 1.00 | 21.08 | MTGL |
| ATOM | 807 | O | ASN | 104 | 52.774 | 13.210 | 27.655 | 1.00 | 20.89 | MTGL |
| ATOM | 808 | N | LEU | 105 | 51.722 | 14.642 | 29.032 | 1.00 | 20.18 | MTGL |
| ATOM | 809 | CA | LEU | 105 | 50.663 | 13.693 | 29.361 | 1.00 | 19.91 | MTGL |
| ATOM | 810 | CB | LEU | 105 | 49.743 | 14.249 | 30.452 | 1.00 | 17.16 | MTGL |
| ATOM | 811 | CG | LEU | 105 | 48.568 | 13.339 | 30.842 | 1.00 | 18.64 | MTGL |

Fig. 1 cont.

| ATOM | 812 | CD1 | LEU | 105 | 49.089 | 12.019 | 31.413 | 1.00 | 15.72 | MTGL |
|------|-----|-----|-----|-----|--------|--------|--------|------|-------|------|
| ATOM | 813 | CD2 | LEU | 105 | 47.690 | 14.040 | 31.860 | 1.00 | 17.06 | MTGL |
| ATOM | 814 | C   | LEU | 105 | 49.841 | 13.392 | 28.109 | 1.00 | 20.55 | MTGL |
| ATOM | 815 | O   | LEU | 105 | 49.506 | 12.237 | 27.839 | 1.00 | 20.48 | MTGL |
| ATOM | 816 | N   | SER | 106 | 49.521 | 14.435 | 27.346 | 1.00 | 20.24 | MTGL |
| ATOM | 817 | CA  | SER | 106 | 48.746 | 14.264 | 26.124 | 1.00 | 21.47 | MTGL |
| ATOM | 818 | CB  | SER | 106 | 48.514 | 15.610 | 25.437 | 1.00 | 22.23 | MTGL |
| ATOM | 819 | OG  | SER | 106 | 47.695 | 16.447 | 26.235 | 1.00 | 27.30 | MTGL |
| ATOM | 820 | C   | SER | 106 | 49.484 | 13.338 | 25.173 | 1.00 | 20.88 | MTGL |
| ATOM | 821 | O   | SER | 106 | 48.884 | 12.487 | 24.527 | 1.00 | 19.42 | MTGL |
| ATOM | 822 | N   | TRP | 107 | 50.795 | 13.513 | 25.096 | 1.00 | 22.85 | MTGL |
| ATOM | 823 | CA  | TRP | 107 | 51.623 | 12.696 | 24.223 | 1.00 | 24.06 | MTGL |
| ATOM | 824 | CB  | TRP | 107 | 53.033 | 13.282 | 24.164 | 1.00 | 27.94 | MTGL |
| ATOM | 825 | CG  | TRP | 107 | 53.780 | 12.934 | 22.924 | 1.00 | 32.46 | MTGL |
| ATOM | 826 | CD2 | TRP | 107 | 55.136 | 13.276 | 22.621 | 1.00 | 35.03 | MTGL |
| ATOM | 827 | CE2 | TRP | 107 | 55.414 | 12.776 | 21.328 | 1.00 | 36.06 | MTGL |
| ATOM | 828 | CE3 | TRP | 107 | 56.141 | 13.971 | 23.309 | 1.00 | 36.31 | MTGL |
| ATOM | 829 | CD1 | TRP | 107 | 53.303 | 12.249 | 21.839 | 1.00 | 33.32 | MTGL |
| ATOM | 830 | NE1 | TRP | 107 | 54.280 | 12.148 | 20.877 | 1.00 | 35.87 | MTGL |
| ATOM | 831 | CZ2 | TRP | 107 | 56.662 | 12.934 | 20.715 | 1.00 | 36.87 | MTGL |
| ATOM | 832 | CZ3 | TRP | 107 | 57.381 | 14.130 | 22.698 | 1.00 | 37.64 | MTGL |
| ATOM | 833 | CH2 | TRP | 107 | 57.627 | 13.617 | 21.410 | 1.00 | 37.50 | MTGL |
| ATOM | 834 | C   | TRP | 107 | 51.674 | 11.250 | 24.725 | 1.00 | 23.66 | MTGL |
| ATOM | 835 | O   | TRP | 107 | 51.632 | 10.306 | 23.929 | 1.00 | 22.42 | MTGL |
| ATOM | 836 | N   | LYS | 108 | 51.754 | 11.085 | 26.045 | 1.00 | 21.87 | MTGL |
| ATOM | 837 | CA  | LYS | 108 | 51.810 |  9.758 | 26.654 | 1.00 | 21.77 | MTGL |
| ATOM | 838 | CB  | LYS | 108 | 52.012 |  9.870 | 28.167 | 1.00 | 22.68 | MTGL |
| ATOM | 839 | CG  | LYS | 108 | 52.928 |  8.818 | 28.787 | 1.00 | 25.44 | MTGL |
| ATOM | 840 | CD  | LYS | 108 | 52.756 |  7.420 | 28.208 | 1.00 | 25.37 | MTGL |
| ATOM | 841 | CE  | LYS | 108 | 53.657 |  6.436 | 28.948 | 1.00 | 26.82 | MTGL |
| ATOM | 842 | NZ  | LYS | 108 | 53.912 |  5.168 | 28.202 | 1.00 | 25.16 | MTGL |
| ATOM | 843 | C   | LYS | 108 | 50.502 |  9.016 | 26.400 | 1.00 | 21.11 | MTGL |
| ATOM | 844 | O   | LYS | 108 | 50.499 |  7.825 | 26.082 | 1.00 | 20.02 | MTGL |
| ATOM | 845 | N   | LEU | 109 | 49.394 |  9.733 | 26.569 | 1.00 | 20.01 | MTGL |
| ATOM | 846 | CA  | LEU | 109 | 48.069 |  9.165 | 26.378 | 1.00 | 19.28 | MTGL |
| ATOM | 847 | CB  | LEU | 109 | 46.998 | 10.210 | 26.701 | 1.00 | 17.83 | MTGL |
| ATOM | 848 | CG  | LEU | 109 | 45.541 |  9.782 | 26.544 | 1.00 | 18.16 | MTGL |
| ATOM | 849 | CD1 | LEU | 109 | 45.278 |  8.500 | 27.331 | 1.00 | 16.64 | MTGL |
| ATOM | 850 | CD2 | LEU | 109 | 44.639 | 10.912 | 27.023 | 1.00 | 17.12 | MTGL |
| ATOM | 851 | C   | LEU | 109 | 47.922 |  8.689 | 24.941 | 1.00 | 19.15 | MTGL |
| ATOM | 852 | O   | LEU | 109 | 47.356 |  7.630 | 24.681 | 1.00 | 17.95 | MTGL |
| ATOM | 853 | N   | TYR | 110 | 48.439 |  9.485 | 24.013 | 1.00 | 19.31 | MTGL |
| ATOM | 854 | CA  | TYR | 110 | 48.390 |  9.141 | 22.602 | 1.00 | 20.23 | MTGL |
| ATOM | 855 | CB  | TYR | 110 | 48.928 | 10.308 | 21.765 | 1.00 | 20.77 | MTGL |
| ATOM | 856 | CG  | TYR | 110 | 49.112 |  9.988 | 20.301 | 1.00 | 22.28 | MTGL |
| ATOM | 857 | CD1 | TYR | 110 | 50.324 |  9.483 | 19.827 | 1.00 | 22.42 | MTGL |
| ATOM | 858 | CE1 | TYR | 110 | 50.500 |  9.174 | 18.478 | 1.00 | 23.01 | MTGL |
| ATOM | 859 | CD2 | TYR | 110 | 48.072 | 10.179 | 19.388 | 1.00 | 21.90 | MTGL |
| ATOM | 860 | CE2 | TYR | 110 | 48.236 |  9.873 | 18.033 | 1.00 | 22.98 | MTGL |
| ATOM | 861 | CZ  | TYR | 110 | 49.453 |  9.373 | 17.589 | 1.00 | 22.70 | MTGL |
| ATOM | 862 | OH  | TYR | 110 | 49.628 |  9.075 | 16.261 | 1.00 | 22.60 | MTGL |
| ATOM | 863 | C   | TYR | 110 | 49.209 |  7.873 | 22.351 | 1.00 | 20.36 | MTGL |
| ATOM | 864 | O   | TYR | 110 | 48.713 |  6.915 | 21.753 | 1.00 | 19.75 | MTGL |
| ATOM | 865 | N   | ASN | 111 | 50.453 |  7.864 | 22.826 | 1.00 | 19.95 | MTGL |
| ATOM | 866 | CA  | ASN | 111 | 51.333 |  6.712 | 22.650 | 1.00 | 20.79 | MTGL |
| ATOM | 867 | CB  | ASN | 111 | 52.691 |  6.944 | 23.316 | 1.00 | 22.26 | MTGL |
| ATOM | 868 | CG  | ASN | 111 | 53.496 |  8.030 | 22.642 | 1.00 | 26.38 | MTGL |
| ATOM | 869 | OD1 | ASN | 111 | 53.175 |  8.463 | 21.534 | 1.00 | 25.33 | MTGL |

Fig. 1 cont.

| | | | | | | | | | | |
|---|---|---|---|---|---|---|---|---|---|---|
| ATOM | 870 | ND2 | ASN | 111 | 54.556 | 8.463 | 23.317 | 1.00 | 29.11 | MTGL |
| ATOM | 871 | C | ASN | 111 | 50.736 | 5.445 | 23.234 | 1.00 | 20.44 | MTGL |
| ATOM | 872 | O | ASN | 111 | 50.764 | 4.391 | 22.605 | 1.00 | 20.22 | MTGL |
| ATOM | 873 | N | TYR | 112 | 50.218 | 5.551 | 24.452 | 1.00 | 19.27 | MTGL |
| ATOM | 874 | CA | TYR | 112 | 49.622 | 4.406 | 25.123 | 1.00 | 18.94 | MTGL |
| ATOM | 875 | CB | TYR | 112 | 49.131 | 4.801 | 26.517 | 1.00 | 16.74 | MTGL |
| ATOM | 876 | CG | TYR | 112 | 48.211 | 3.770 | 27.137 | 1.00 | 17.22 | MTGL |
| ATOM | 877 | CD1 | TYR | 112 | 48.723 | 2.632 | 27.766 | 1.00 | 15.42 | MTGL |
| ATOM | 878 | CE1 | TYR | 112 | 47.876 | 1.671 | 28.311 | 1.00 | 17.32 | MTGL |
| ATOM | 879 | CD2 | TYR | 112 | 46.827 | 3.916 | 27.065 | 1.00 | 15.87 | MTGL |
| ATOM | 880 | CE2 | TYR | 112 | 45.971 | 2.960 | 27.604 | 1.00 | 17.72 | MTGL |
| ATOM | 881 | CZ | TYR | 112 | 46.500 | 1.844 | 28.225 | 1.00 | 16.39 | MTGL |
| ATOM | 882 | OH | TYR | 112 | 45.653 | 0.907 | 28.766 | 1.00 | 18.06 | MTGL |
| ATOM | 883 | C | TYR | 112 | 48.449 | 3.832 | 24.330 | 1.00 | 18.50 | MTGL |
| ATOM | 884 | O | TYR | 112 | 48.358 | 2.622 | 24.129 | 1.00 | 17.86 | MTGL |
| ATOM | 885 | N | THR | 113 | 47.545 | 4.709 | 23.903 | 1.00 | 18.56 | MTGL |
| ATOM | 886 | CA | THR | 113 | 46.372 | 4.288 | 23.152 | 1.00 | 18.24 | MTGL |
| ATOM | 887 | CB | THR | 113 | 45.408 | 5.474 | 22.930 | 1.00 | 17.98 | MTGL |
| ATOM | 888 | OG1 | THR | 113 | 45.017 | 6.014 | 24.198 | 1.00 | 16.20 | MTGL |
| ATOM | 889 | CG2 | THR | 113 | 44.158 | 5.021 | 22.184 | 1.00 | 17.01 | MTGL |
| ATOM | 890 | C | THR | 113 | 46.765 | 3.682 | 21.805 | 1.00 | 18.67 | MTGL |
| ATOM | 891 | O | THR | 113 | 46.272 | 2.619 | 21.423 | 1.00 | 18.43 | MTGL |
| ATOM | 892 | N | LEU | 114 | 47.655 | 4.360 | 21.090 | 1.00 | 19.14 | MTGL |
| ATOM | 893 | CA | LEU | 114 | 48.114 | 3.873 | 19.797 | 1.00 | 20.50 | MTGL |
| ATOM | 894 | CB | LEU | 114 | 49.133 | 4.848 | 19.197 | 1.00 | 20.12 | MTGL |
| ATOM | 895 | CG | LEU | 114 | 49.864 | 4.396 | 17.929 | 1.00 | 21.74 | MTGL |
| ATOM | 896 | CD1 | LEU | 114 | 48.866 | 4.214 | 16.794 | 1.00 | 21.80 | MTGL |
| ATOM | 897 | CD2 | LEU | 114 | 50.924 | 5.430 | 17.547 | 1.00 | 22.25 | MTGL |
| ATOM | 898 | C | LEU | 114 | 48.753 | 2.498 | 19.984 | 1.00 | 20.96 | MTGL |
| ATOM | 899 | O | LEU | 114 | 48.441 | 1.551 | 19.263 | 1.00 | 21.53 | MTGL |
| ATOM | 900 | N | ASP | 115 | 49.650 | 2.399 | 20.961 | 1.00 | 21.00 | MTGL |
| ATOM | 901 | CA | ASP | 115 | 50.335 | 1.148 | 21.252 | 1.00 | 21.18 | MTGL |
| ATOM | 902 | CB | ASP | 115 | 51.276 | 1.331 | 22.442 | 1.00 | 22.68 | MTGL |
| ATOM | 903 | CG | ASP | 115 | 51.957 | 0.041 | 22.843 | 1.00 | 24.76 | MTGL |
| ATOM | 904 | OD1 | ASP | 115 | 52.826 | -0.429 | 22.078 | 1.00 | 26.71 | MTGL |
| ATOM | 905 | OD2 | ASP | 115 | 51.616 | -0.509 | 23.917 | 1.00 | 25.94 | MTGL |
| ATOM | 906 | C | ASP | 115 | 49.351 | 0.018 | 21.561 | 1.00 | 21.01 | MTGL |
| ATOM | 907 | O | ASP | 115 | 49.461 | -1.078 | 21.012 | 1.00 | 20.38 | MTGL |
| ATOM | 908 | N | ALA | 116 | 48.404 | 0.287 | 22.456 | 1.00 | 19.72 | MTGL |
| ATOM | 909 | CA | ALA | 116 | 47.410 | -0.711 | 22.833 | 1.00 | 19.79 | MTGL |
| ATOM | 910 | CB | ALA | 116 | 46.501 | -0.163 | 23.923 | 1.00 | 19.04 | MTGL |
| ATOM | 911 | C | ALA | 116 | 46.578 | -1.140 | 21.627 | 1.00 | 18.78 | MTGL |
| ATOM | 912 | O | ALA | 116 | 46.302 | -2.323 | 21.448 | 1.00 | 18.71 | MTGL |
| ATOM | 913 | N | ALA | 117 | 46.184 | -0.172 | 20.806 | 1.00 | 18.51 | MTGL |
| ATOM | 914 | CA | ALA | 117 | 45.384 | -0.456 | 19.616 | 1.00 | 19.07 | MTGL |
| ATOM | 915 | CB | ALA | 117 | 45.012 | 0.840 | 18.913 | 1.00 | 17.76 | MTGL |
| ATOM | 916 | C | ALA | 117 | 46.144 | -1.372 | 18.662 | 1.00 | 19.00 | MTGL |
| ATOM | 917 | O | ALA | 117 | 45.588 | -2.344 | 18.157 | 1.00 | 20.94 | MTGL |
| ATOM | 918 | N | ASN | 118 | 47.414 | -1.064 | 18.421 | 1.00 | 19.11 | MTGL |
| ATOM | 919 | CA | ASN | 118 | 48.234 | -1.880 | 17.530 | 1.00 | 20.09 | MTGL |
| ATOM | 920 | CB | ASN | 118 | 49.594 | -1.214 | 17.280 | 1.00 | 19.53 | MTGL |
| ATOM | 921 | CG | ASN | 118 | 49.481 | 0.043 | 16.432 | 1.00 | 21.06 | MTGL |
| ATOM | 922 | OD1 | ASN | 118 | 48.591 | 0.158 | 15.584 | 1.00 | 22.85 | MTGL |
| ATOM | 923 | ND2 | ASN | 118 | 50.394 | 0.984 | 16.644 | 1.00 | 19.62 | MTGL |
| ATOM | 924 | C | ASN | 118 | 48.446 | -3.294 | 18.069 | 1.00 | 20.53 | MTGL |
| ATOM | 925 | O | ASN | 118 | 48.509 | -4.250 | 17.298 | 1.00 | 20.72 | MTGL |
| ATOM | 926 | N | LYS | 119 | 48.570 | -3.427 | 19.389 | 1.00 | 20.26 | MTGL |
| ATOM | 927 | CA | LYS | 119 | 48.755 | -4.745 | 19.992 | 1.00 | 19.69 | MTGL |

Fig. 1 cont.

| | | | | | | | | | | |
|---|---|---|---|---|---|---|---|---|---|---|
| ATOM | 928 | CB | LYS | 119 | 49.134 | -4.616 | 21.468 | 1.00 | 20.25 | MTGL |
| ATOM | 929 | CG | LYS | 119 | 50.589 | -4.225 | 21.668 | 1.00 | 23.15 | MTGL |
| ATOM | 930 | CD | LYS | 119 | 50.933 | -4.015 | 23.131 | 1.00 | 25.43 | MTGL |
| ATOM | 931 | CE | LYS | 119 | 52.378 | -3.533 | 23.273 | 1.00 | 26.95 | MTGL |
| ATOM | 932 | NZ | LYS | 119 | 52.701 | -3.126 | 24.666 | 1.00 | 26.48 | MTGL |
| ATOM | 933 | C | LYS | 119 | 47.482 | -5.570 | 19.843 | 1.00 | 18.61 | MTGL |
| ATOM | 934 | O | LYS | 119 | 47.533 | -6.777 | 19.615 | 1.00 | 16.84 | MTGL |
| ATOM | 935 | N | LEU | 120 | 46.339 | -4.911 | 19.975 | 1.00 | 17.54 | MTGL |
| ATOM | 936 | CA | LEU | 120 | 45.064 | -5.599 | 19.820 | 1.00 | 18.74 | MTGL |
| ATOM | 937 | CB | LEU | 120 | 43.909 | -4.643 | 20.144 | 1.00 | 17.57 | MTGL |
| ATOM | 938 | CG | LEU | 120 | 43.736 | -4.330 | 21.635 | 1.00 | 17.26 | MTGL |
| ATOM | 939 | CD1 | LEU | 120 | 42.836 | -3.117 | 21.830 | 1.00 | 17.85 | MTGL |
| ATOM | 940 | CD2 | LEU | 120 | 43.152 | -5.549 | 22.325 | 1.00 | 16.86 | MTGL |
| ATOM | 941 | C | LEU | 120 | 44.976 | -6.086 | 18.372 | 1.00 | 18.39 | MTGL |
| ATOM | 942 | O | LEU | 120 | 44.660 | -7.243 | 18.116 | 1.00 | 19.13 | MTGL |
| ATOM | 943 | N | GLN | 121 | 45.273 | -5.193 | 17.434 | 1.00 | 19.05 | MTGL |
| ATOM | 944 | CA | GLN | 121 | 45.245 | -5.524 | 16.013 | 1.00 | 20.51 | MTGL |
| ATOM | 945 | CB | GLN | 121 | 45.715 | -4.324 | 15.182 | 1.00 | 20.27 | MTGL |
| ATOM | 946 | CG | GLN | 121 | 45.927 | -4.606 | 13.694 | 1.00 | 19.88 | MTGL |
| ATOM | 947 | CD | GLN | 121 | 44.677 | -5.116 | 12.998 | 1.00 | 20.20 | MTGL |
| ATOM | 948 | OE1 | GLN | 121 | 43.565 | -4.680 | 13.291 | 1.00 | 19.32 | MTGL |
| ATOM | 949 | NE2 | GLN | 121 | 44.859 | -6.035 | 12.055 | 1.00 | 20.98 | MTGL |
| ATOM | 950 | C | GLN | 121 | 46.142 | -6.723 | 15.734 | 1.00 | 20.78 | MTGL |
| ATOM | 951 | O | GLN | 121 | 45.729 | -7.672 | 15.078 | 1.00 | 21.20 | MTGL |
| ATOM | 952 | N | ASN | 122 | 47.369 | -6.676 | 16.242 | 1.00 | 20.58 | MTGL |
| ATOM | 953 | CA | ASN | 122 | 48.322 | -7.762 | 16.037 | 1.00 | 22.39 | MTGL |
| ATOM | 954 | CB | ASN | 122 | 49.685 | -7.371 | 16.611 | 1.00 | 24.20 | MTGL |
| ATOM | 955 | CG | ASN | 122 | 50.350 | -6.260 | 15.817 | 1.00 | 26.36 | MTGL |
| ATOM | 956 | OD1 | ASN | 122 | 51.298 | -5.630 | 16.285 | 1.00 | 29.40 | MTGL |
| ATOM | 957 | ND2 | ASN | 122 | 49.863 | -6.021 | 14.605 | 1.00 | 26.25 | MTGL |
| ATOM | 958 | C | ASN | 122 | 47.859 | -9.082 | 16.646 | 1.00 | 22.40 | MTGL |
| ATOM | 959 | O | ASN | 122 | 48.312 | -10.153 | 16.243 | 1.00 | 23.25 | MTGL |
| ATOM | 960 | N | ALA | 123 | 46.957 | -9.005 | 17.616 | 1.00 | 21.34 | MTGL |
| ATOM | 961 | CA | ALA | 123 | 46.436 | -10.209 | 18.252 | 1.00 | 21.19 | MTGL |
| ATOM | 962 | CB | ALA | 123 | 46.151 | -9.939 | 19.730 | 1.00 | 21.28 | MTGL |
| ATOM | 963 | C | ALA | 123 | 45.163 | -10.669 | 17.545 | 1.00 | 20.31 | MTGL |
| ATOM | 964 | O | ALA | 123 | 44.512 | -11.621 | 17.981 | 1.00 | 21.19 | MTGL |
| ATOM | 965 | N | GLY | 124 | 44.813 | -9.985 | 16.457 | 1.00 | 20.00 | MTGL |
| ATOM | 966 | CA | GLY | 124 | 43.621 | -10.332 | 15.705 | 1.00 | 19.34 | MTGL |
| ATOM | 967 | C | GLY | 124 | 42.338 | -9.853 | 16.367 | 1.00 | 20.32 | MTGL |
| ATOM | 968 | O | GLY | 124 | 41.255 | -10.376 | 16.098 | 1.00 | 19.71 | MTGL |
| ATOM | 969 | N | ILE | 125 | 42.450 | -8.855 | 17.239 | 1.00 | 18.85 | MTGL |
| ATOM | 970 | CA | ILE | 125 | 41.281 | -8.327 | 17.928 | 1.00 | 17.97 | MTGL |
| ATOM | 971 | CB | ILE | 125 | 41.502 | -8.279 | 19.465 | 1.00 | 18.21 | MTGL |
| ATOM | 972 | CG2 | ILE | 125 | 40.264 | -7.709 | 20.149 | 1.00 | 18.39 | MTGL |
| ATOM | 973 | CG1 | ILE | 125 | 41.807 | -9.681 | 20.013 | 1.00 | 16.78 | MTGL |
| ATOM | 974 | CD1 | ILE | 125 | 40.682 | -10.694 | 19.808 | 1.00 | 15.33 | MTGL |
| ATOM | 975 | C | ILE | 125 | 40.936 | -6.908 | 17.460 | 1.00 | 18.72 | MTGL |
| ATOM | 976 | O | ILE | 125 | 41.682 | -5.959 | 17.718 | 1.00 | 18.82 | MTGL |
| ATOM | 977 | N | GLN | 126 | 39.810 | -6.771 | 16.769 | 1.00 | 17.38 | MTGL |
| ATOM | 978 | CA | GLN | 126 | 39.355 | -5.463 | 16.310 | 1.00 | 17.54 | MTGL |
| ATOM | 979 | CB | GLN | 126 | 39.059 | -5.459 | 14.810 | 1.00 | 17.95 | MTGL |
| ATOM | 980 | CG | GLN | 126 | 40.267 | -5.634 | 13.905 | 1.00 | 18.48 | MTGL |
| ATOM | 981 | CD | GLN | 126 | 40.704 | -7.082 | 13.784 | 1.00 | 19.41 | MTGL |
| ATOM | 982 | OE1 | GLN | 126 | 39.874 | -7.991 | 13.722 | 1.00 | 18.45 | MTGL |
| ATOM | 983 | NE2 | GLN | 126 | 42.014 | -7.302 | 13.731 | 1.00 | 18.37 | MTGL |
| ATOM | 984 | C | GLN | 126 | 38.078 | -5.152 | 17.073 | 1.00 | 17.01 | MTGL |
| ATOM | 985 | O | GLN | 126 | 36.990 | -5.578 | 16.686 | 1.00 | 17.42 | MTGL |

Fig. 1 cont.

| | | | | | | | | | | |
|---|---|---|---|---|---|---|---|---|---|---|
| ATOM | 986 | N | PRO | 127 | 38.196 | -4.424 | 18.189 | 1.00 | 17.14 | MTGL |
| ATOM | 987 | CD | PRO | 127 | 39.397 | -3.833 | 18.803 | 1.00 | 16.94 | MTGL |
| ATOM | 988 | CA | PRO | 127 | 36.990 | -4.103 | 18.954 | 1.00 | 17.76 | MTGL |
| ATOM | 989 | CB | PRO | 127 | 37.534 | -3.333 | 20.162 | 1.00 | 17.60 | MTGL |
| ATOM | 990 | CG | PRO | 127 | 38.806 | -2.730 | 19.644 | 1.00 | 20.07 | MTGL |
| ATOM | 991 | C | PRO | 127 | 36.004 | -3.290 | 18.130 | 1.00 | 17.06 | MTGL |
| ATOM | 992 | O | PRO | 127 | 36.400 | -2.472 | 17.303 | 1.00 | 18.03 | MTGL |
| ATOM | 993 | N | THR | 128 | 34.719 | -3.536 | 18.340 | 1.00 | 17.80 | MTGL |
| ATOM | 994 | CA | THR | 128 | 33.688 | -2.803 | 17.620 | 1.00 | 17.59 | MTGL |
| ATOM | 995 | CB | THR | 128 | 32.357 | -3.582 | 17.615 | 1.00 | 18.62 | MTGL |
| ATOM | 996 | OG1 | THR | 128 | 32.035 | -3.994 | 18.951 | 1.00 | 17.44 | MTGL |
| ATOM | 997 | CG2 | THR | 128 | 32.467 | -4.816 | 16.717 | 1.00 | 18.59 | MTGL |
| ATOM | 998 | C | THR | 128 | 33.499 | -1.451 | 18.310 | 1.00 | 17.94 | MTGL |
| ATOM | 999 | O | THR | 128 | 33.086 | -0.476 | 17.683 | 1.00 | 16.71 | MTGL |
| ATOM | 1000 | N | ILE | 129 | 33.834 | -1.397 | 19.600 | 1.00 | 16.54 | MTGL |
| ATOM | 1001 | CA | ILE | 129 | 33.701 | -0.161 | 20.373 | 1.00 | 16.74 | MTGL |
| ATOM | 1002 | CB | ILE | 129 | 32.426 | -0.166 | 21.249 | 1.00 | 17.47 | MTGL |
| ATOM | 1003 | CG2 | ILE | 129 | 32.323 | 1.138 | 22.032 | 1.00 | 16.90 | MTGL |
| ATOM | 1004 | CG1 | ILE | 129 | 31.182 | -0.340 | 20.380 | 1.00 | 18.59 | MTGL |
| ATOM | 1005 | CD1 | ILE | 129 | 29.913 | -0.501 | 21.189 | 1.00 | 18.26 | MTGL |
| ATOM | 1006 | C | ILE | 129 | 34.878 | 0.056 | 21.317 | 1.00 | 16.72 | MTGL |
| ATOM | 1007 | O | ILE | 129 | 35.361 | -0.883 | 21.949 | 1.00 | 16.12 | MTGL |
| ATOM | 1008 | N | VAL | 130 | 35.329 | 1.303 | 21.410 | 1.00 | 16.38 | MTGL |
| ATOM | 1009 | CA | VAL | 130 | 36.413 | 1.666 | 22.313 | 1.00 | 16.43 | MTGL |
| ATOM | 1010 | CB | VAL | 130 | 37.738 | 1.891 | 21.568 | 1.00 | 16.85 | MTGL |
| ATOM | 1011 | CG1 | VAL | 130 | 38.783 | 2.444 | 22.532 | 1.00 | 15.96 | MTGL |
| ATOM | 1012 | CG2 | VAL | 130 | 38.224 | 0.581 | 20.958 | 1.00 | 16.65 | MTGL |
| ATOM | 1013 | C | VAL | 130 | 36.040 | 2.965 | 23.020 | 1.00 | 16.57 | MTGL |
| ATOM | 1014 | O | VAL | 130 | 35.807 | 3.981 | 22.369 | 1.00 | 17.33 | MTGL |
| ATOM | 1015 | N | SER | 131 | 35.955 | 2.931 | 24.347 | 1.00 | 15.26 | MTGL |
| ATOM | 1016 | CA | SER | 131 | 35.640 | 4.142 | 25.088 | 1.00 | 14.32 | MTGL |
| ATOM | 1017 | CB | SER | 131 | 34.741 | 3.840 | 26.296 | 1.00 | 13.74 | MTGL |
| ATOM | 1018 | OG | SER | 131 | 35.427 | 3.100 | 27.299 | 1.00 | 14.55 | MTGL |
| ATOM | 1019 | C | SER | 131 | 36.957 | 4.737 | 25.563 | 1.00 | 13.67 | MTGL |
| ATOM | 1020 | O | SER | 131 | 37.812 | 4.024 | 26.094 | 1.00 | 14.63 | MTGL |
| ATOM | 1021 | N | ILE | 132 | 37.140 | 6.033 | 25.349 | 1.00 | 12.98 | MTGL |
| ATOM | 1022 | CA | ILE | 132 | 38.362 | 6.684 | 25.791 | 1.00 | 13.07 | MTGL |
| ATOM | 1023 | CB | ILE | 132 | 38.793 | 7.796 | 24.811 | 1.00 | 13.05 | MTGL |
| ATOM | 1024 | CG2 | ILE | 132 | 39.419 | 7.169 | 23.573 | 1.00 | 14.24 | MTGL |
| ATOM | 1025 | CG1 | ILE | 132 | 37.591 | 8.649 | 24.397 | 1.00 | 13.32 | MTGL |
| ATOM | 1026 | CD1 | ILE | 132 | 37.960 | 9.760 | 23.429 | 1.00 | 14.06 | MTGL |
| ATOM | 1027 | C | ILE | 132 | 38.103 | 7.234 | 27.188 | 1.00 | 13.33 | MTGL |
| ATOM | 1028 | O | ILE | 132 | 37.800 | 8.415 | 27.372 | 1.00 | 12.93 | MTGL |
| ATOM | 1029 | N | GLY | 133 | 38.206 | 6.339 | 28.170 | 1.00 | 12.78 | MTGL |
| ATOM | 1030 | CA | GLY | 133 | 37.957 | 6.703 | 29.552 | 1.00 | 13.26 | MTGL |
| ATOM | 1031 | C | GLY | 133 | 36.687 | 6.040 | 30.066 | 1.00 | 14.41 | MTGL |
| ATOM | 1032 | O | GLY | 133 | 35.821 | 5.638 | 29.279 | 1.00 | 14.45 | MTGL |
| ATOM | 1033 | N | ASN | 134 | 36.573 | 5.915 | 31.385 | 1.00 | 14.34 | MTGL |
| ATOM | 1034 | CA | ASN | 134 | 35.393 | 5.311 | 31.995 | 1.00 | 14.81 | MTGL |
| ATOM | 1035 | CB | ASN | 134 | 35.797 | 4.063 | 32.780 | 1.00 | 14.03 | MTGL |
| ATOM | 1036 | CG | ASN | 134 | 34.602 | 3.307 | 33.321 | 1.00 | 15.54 | MTGL |
| ATOM | 1037 | OD1 | ASN | 134 | 33.932 | 2.558 | 32.596 | 1.00 | 14.69 | MTGL |
| ATOM | 1038 | ND2 | ASN | 134 | 34.311 | 3.515 | 34.599 | 1.00 | 13.31 | MTGL |
| ATOM | 1039 | C | ASN | 134 | 34.727 | 6.328 | 32.929 | 1.00 | 15.45 | MTGL |
| ATOM | 1040 | O | ASN | 134 | 35.355 | 6.823 | 33.865 | 1.00 | 14.99 | MTGL |
| ATOM | 1041 | N | GLU | 135 | 33.458 | 6.632 | 32.672 | 1.00 | 15.32 | MTGL |
| ATOM | 1042 | CA | GLU | 135 | 32.708 | 7.600 | 33.480 | 1.00 | 16.19 | MTGL |
| ATOM | 1043 | CB | GLU | 135 | 32.225 | 6.948 | 34.780 | 1.00 | 16.84 | MTGL |

Fig. 1 cont.

| ATOM | 1044 | CG  | GLU | 135 | 31.360 | 5.710  | 34.571 | 1.00 | 18.65 | MTGL |
|------|------|-----|-----|-----|--------|--------|--------|------|-------|------|
| ATOM | 1045 | CD  | GLU | 135 | 30.758 | 5.173  | 35.862 | 1.00 | 19.18 | MTGL |
| ATOM | 1046 | OE1 | GLU | 135 | 31.449 | 5.200  | 36.905 | 1.00 | 20.99 | MTGL |
| ATOM | 1047 | OE2 | GLU | 135 | 29.602 | 4.705  | 35.829 | 1.00 | 16.99 | MTGL |
| ATOM | 1048 | C   | GLU | 135 | 33.553 | 8.834  | 33.806 | 1.00 | 16.49 | MTGL |
| ATOM | 1049 | O   | GLU | 135 | 33.777 | 9.153  | 34.974 | 1.00 | 15.93 | MTGL |
| ATOM | 1050 | N   | ILE | 136 | 34.004 | 9.536  | 32.770 | 1.00 | 15.57 | MTGL |
| ATOM | 1051 | CA  | ILE | 136 | 34.846 | 10.712 | 32.957 | 1.00 | 16.13 | MTGL |
| ATOM | 1052 | CB  | ILE | 136 | 35.802 | 10.887 | 31.756 | 1.00 | 16.05 | MTGL |
| ATOM | 1053 | CG2 | ILE | 136 | 36.783 | 9.719  | 31.706 | 1.00 | 16.66 | MTGL |
| ATOM | 1054 | CG1 | ILE | 136 | 35.001 | 10.956 | 30.451 | 1.00 | 16.40 | MTGL |
| ATOM | 1055 | CD1 | ILE | 136 | 35.858 | 11.171 | 29.211 | 1.00 | 14.50 | MTGL |
| ATOM | 1056 | C   | ILE | 136 | 34.060 | 12.006 | 33.168 | 1.00 | 16.79 | MTGL |
| ATOM | 1057 | O   | ILE | 136 | 34.457 | 13.067 | 32.697 | 1.00 | 16.67 | MTGL |
| ATOM | 1058 | N   | ARG | 137 | 32.949 | 11.909 | 33.890 | 1.00 | 17.28 | MTGL |
| ATOM | 1059 | CA  | ARG | 137 | 32.099 | 13.057 | 34.170 | 1.00 | 18.25 | MTGL |
| ATOM | 1060 | CB  | ARG | 137 | 30.884 | 12.612 | 34.976 | 1.00 | 20.33 | MTGL |
| ATOM | 1061 | CG  | ARG | 137 | 29.879 | 13.712 | 35.248 | 1.00 | 22.61 | MTGL |
| ATOM | 1062 | CD  | ARG | 137 | 29.087 | 13.370 | 36.487 | 1.00 | 26.40 | MTGL |
| ATOM | 1063 | NE  | ARG | 137 | 29.837 | 13.668 | 37.696 | 1.00 | 28.06 | MTGL |
| ATOM | 1064 | CZ  | ARG | 137 | 29.643 | 13.076 | 38.869 | 1.00 | 28.40 | MTGL |
| ATOM | 1065 | NH1 | ARG | 137 | 28.726 | 12.132 | 39.006 | 1.00 | 27.39 | MTGL |
| ATOM | 1066 | NH2 | ARG | 137 | 30.355 | 13.459 | 39.918 | 1.00 | 30.54 | MTGL |
| ATOM | 1067 | C   | ARG | 137 | 32.849 | 14.145 | 34.937 | 1.00 | 19.12 | MTGL |
| ATOM | 1068 | O   | ARG | 137 | 32.537 | 15.327 | 34.812 | 1.00 | 19.19 | MTGL |
| ATOM | 1069 | N   | ALA | 138 | 33.832 | 13.744 | 35.738 | 1.00 | 17.89 | MTGL |
| ATOM | 1070 | CA  | ALA | 138 | 34.626 | 14.708 | 36.487 | 1.00 | 18.61 | MTGL |
| ATOM | 1071 | CB  | ALA | 138 | 34.679 | 14.320 | 37.965 | 1.00 | 18.89 | MTGL |
| ATOM | 1072 | C   | ALA | 138 | 36.028 | 14.744 | 35.888 | 1.00 | 18.04 | MTGL |
| ATOM | 1073 | O   | ALA | 138 | 37.003 | 15.050 | 36.573 | 1.00 | 18.75 | MTGL |
| ATOM | 1074 | N   | GLY | 139 | 36.119 | 14.415 | 34.603 | 1.00 | 17.60 | MTGL |
| ATOM | 1075 | CA  | GLY | 139 | 37.401 | 14.424 | 33.920 | 1.00 | 16.74 | MTGL |
| ATOM | 1076 | C   | GLY | 139 | 38.141 | 13.103 | 33.979 | 1.00 | 17.00 | MTGL |
| ATOM | 1077 | O   | GLY | 139 | 37.558 | 12.061 | 34.303 | 1.00 | 15.56 | MTGL |
| ATOM | 1078 | N   | LEU | 140 | 39.430 | 13.150 | 33.653 | 1.00 | 16.36 | MTGL |
| ATOM | 1079 | CA  | LEU | 140 | 40.288 | 11.965 | 33.666 | 1.00 | 16.91 | MTGL |
| ATOM | 1080 | CB  | LEU | 140 | 40.254 | 11.255 | 32.308 | 1.00 | 16.55 | MTGL |
| ATOM | 1081 | CG  | LEU | 140 | 40.965 | 11.954 | 31.137 | 1.00 | 17.14 | MTGL |
| ATOM | 1082 | CD1 | LEU | 140 | 41.157 | 10.962 | 29.985 | 1.00 | 17.61 | MTGL |
| ATOM | 1083 | CD2 | LEU | 140 | 40.158 | 13.157 | 30.673 | 1.00 | 16.51 | MTGL |
| ATOM | 1084 | C   | LEU | 140 | 41.731 | 12.366 | 33.961 | 1.00 | 16.82 | MTGL |
| ATOM | 1085 | O   | LEU | 140 | 42.078 | 13.549 | 33.919 | 1.00 | 16.86 | MTGL |
| ATOM | 1086 | N   | LEU | 141 | 42.566 | 11.373 | 34.254 | 1.00 | 16.21 | MTGL |
| ATOM | 1087 | CA  | LEU | 141 | 43.979 | 11.616 | 34.521 | 1.00 | 16.03 | MTGL |
| ATOM | 1088 | CB  | LEU | 141 | 44.711 | 11.839 | 33.191 | 1.00 | 14.81 | MTGL |
| ATOM | 1089 | CG  | LEU | 141 | 44.626 | 10.646 | 32.220 | 1.00 | 15.72 | MTGL |
| ATOM | 1090 | CD1 | LEU | 141 | 45.076 | 11.054 | 30.818 | 1.00 | 14.73 | MTGL |
| ATOM | 1091 | CD2 | LEU | 141 | 45.494 | 9.501  | 32.752 | 1.00 | 14.97 | MTGL |
| ATOM | 1092 | C   | LEU | 141 | 44.166 | 12.822 | 35.444 | 1.00 | 16.13 | MTGL |
| ATOM | 1093 | O   | LEU | 141 | 44.776 | 13.819 | 35.069 | 1.00 | 15.77 | MTGL |
| ATOM | 1094 | N   | TRP | 142 | 43.631 | 12.715 | 36.655 | 1.00 | 16.15 | MTGL |
| ATOM | 1095 | CA  | TRP | 142 | 43.718 | 13.789 | 37.635 | 1.00 | 16.13 | MTGL |
| ATOM | 1096 | CB  | TRP | 142 | 42.854 | 13.446 | 38.845 | 1.00 | 16.04 | MTGL |
| ATOM | 1097 | CG  | TRP | 142 | 41.387 | 13.408 | 38.559 | 1.00 | 16.68 | MTGL |
| ATOM | 1098 | CD2 | TRP | 142 | 40.345 | 13.114 | 39.494 | 1.00 | 16.86 | MTGL |
| ATOM | 1099 | CE2 | TRP | 142 | 39.117 | 13.217 | 38.800 | 1.00 | 16.85 | MTGL |
| ATOM | 1100 | CE3 | TRP | 142 | 40.330 | 12.779 | 40.855 | 1.00 | 17.53 | MTGL |
| ATOM | 1101 | CD1 | TRP | 142 | 40.769 | 13.669 | 37.365 | 1.00 | 16.02 | MTGL |

Fig. 1 cont.

| | | | | | | | | | |
|---|---|---|---|---|---|---|---|---|---|
| ATOM | 1102 | NE1 | TRP | 142 | 39.404 | 13.557 | 37.503 | 1.00 16.14 | MTGL |
| ATOM | 1103 | CZ2 | TRP | 142 | 37.884 | 12.993 | 39.421 | 1.00 16.71 | MTGL |
| ATOM | 1104 | CZ3 | TRP | 142 | 39.097 | 12.557 | 41.475 | 1.00 17.85 | MTGL |
| ATOM | 1105 | CH2 | TRP | 142 | 37.894 | 12.666 | 40.755 | 1.00 17.70 | MTGL |
| ATOM | 1106 | C | TRP | 142 | 45.151 | 14.036 | 38.092 | 1.00 16.70 | MTGL |
| ATOM | 1107 | O | TRP | 142 | 45.965 | 13.116 | 38.132 | 1.00 15.98 | MTGL |
| ATOM | 1108 | N | PRO | 143 | 45.476 | 15.289 | 38.452 | 1.00 18.10 | MTGL |
| ATOM | 1109 | CD | PRO | 143 | 46.716 | 15.597 | 39.183 | 1.00 18.05 | MTGL |
| ATOM | 1110 | CA | PRO | 143 | 44.586 | 16.458 | 38.444 | 1.00 17.24 | MTGL |
| ATOM | 1111 | CB | PRO | 143 | 45.170 | 17.362 | 39.539 | 1.00 17.56 | MTGL |
| ATOM | 1112 | CG | PRO | 143 | 46.199 | 16.496 | 40.260 | 1.00 19.44 | MTGL |
| ATOM | 1113 | C | PRO | 143 | 44.599 | 17.177 | 37.096 | 1.00 17.09 | MTGL |
| ATOM | 1114 | O | PRO | 143 | 43.804 | 18.092 | 36.864 | 1.00 16.74 | MTGL |
| ATOM | 1115 | N | THR | 144 | 45.509 | 16.767 | 36.219 | 1.00 16.23 | MTGL |
| ATOM | 1116 | CA | THR | 144 | 45.651 | 17.396 | 34.910 | 1.00 17.05 | MTGL |
| ATOM | 1117 | CB | THR | 144 | 46.677 | 16.640 | 34.048 | 1.00 17.49 | MTGL |
| ATOM | 1118 | OG1 | THR | 144 | 47.864 | 16.413 | 34.817 | 1.00 18.41 | MTGL |
| ATOM | 1119 | CG2 | THR | 144 | 47.040 | 17.453 | 32.811 | 1.00 17.61 | MTGL |
| ATOM | 1120 | C | THR | 144 | 44.346 | 17.510 | 34.129 | 1.00 16.98 | MTGL |
| ATOM | 1121 | O | THR | 144 | 44.027 | 18.579 | 33.610 | 1.00 17.37 | MTGL |
| ATOM | 1122 | N | GLY | 145 | 43.594 | 16.414 | 34.052 | 1.00 17.00 | MTGL |
| ATOM | 1123 | CA | GLY | 145 | 42.336 | 16.432 | 33.322 | 1.00 16.55 | MTGL |
| ATOM | 1124 | C | GLY | 145 | 41.111 | 16.472 | 34.219 | 1.00 17.19 | MTGL |
| ATOM | 1125 | O | GLY | 145 | 40.033 | 16.013 | 33.837 | 1.00 15.11 | MTGL |
| ATOM | 1126 | N | ARG | 146 | 41.269 | 17.009 | 35.423 | 1.00 16.86 | MTGL |
| ATOM | 1127 | CA | ARG | 146 | 40.153 | 17.118 | 36.361 | 1.00 18.80 | MTGL |
| ATOM | 1128 | CB | ARG | 146 | 40.707 | 17.308 | 37.784 | 1.00 20.43 | MTGL |
| ATOM | 1129 | CG | ARG | 146 | 39.671 | 17.572 | 38.870 | 1.00 24.77 | MTGL |
| ATOM | 1130 | CD | ARG | 146 | 38.729 | 16.394 | 39.052 | 1.00 27.03 | MTGL |
| ATOM | 1131 | NE | ARG | 146 | 37.715 | 16.623 | 40.081 | 1.00 30.10 | MTGL |
| ATOM | 1132 | CZ | ARG | 146 | 37.922 | 16.516 | 41.391 | 1.00 31.39 | MTGL |
| ATOM | 1133 | NH1 | ARG | 146 | 39.122 | 16.182 | 41.861 | 1.00 31.38 | MTGL |
| ATOM | 1134 | NH2 | ARG | 146 | 36.916 | 16.729 | 42.236 | 1.00 32.17 | MTGL |
| ATOM | 1135 | C | ARG | 146 | 39.261 | 18.308 | 35.961 | 1.00 18.91 | MTGL |
| ATOM | 1136 | O | ARG | 146 | 39.763 | 19.344 | 35.534 | 1.00 17.30 | MTGL |
| ATOM | 1137 | N | THR | 147 | 37.940 | 18.147 | 36.055 | 1.00 18.95 | MTGL |
| ATOM | 1138 | CA | THR | 147 | 37.037 | 19.255 | 35.732 | 1.00 19.02 | MTGL |
| ATOM | 1139 | CB | THR | 147 | 35.550 | 18.826 | 35.731 | 1.00 18.33 | MTGL |
| ATOM | 1140 | OG1 | THR | 147 | 35.278 | 18.044 | 36.890 | 1.00 18.17 | MTGL |
| ATOM | 1141 | CG2 | THR | 147 | 35.217 | 18.016 | 34.490 | 1.00 18.17 | MTGL |
| ATOM | 1142 | C | THR | 147 | 37.278 | 20.271 | 36.858 | 1.00 19.51 | MTGL |
| ATOM | 1143 | O | THR | 147 | 37.539 | 19.861 | 37.983 | 1.00 18.48 | MTGL |
| ATOM | 1144 | N | GLU | 148 | 37.158 | 21.574 | 36.598 | 1.00 19.44 | MTGL |
| ATOM | 1145 | CA | GLU | 148 | 36.771 | 22.124 | 35.317 | 1.00 20.37 | MTGL |
| ATOM | 1146 | CB | GLU | 148 | 35.829 | 23.309 | 35.551 | 1.00 22.32 | MTGL |
| ATOM | 1147 | CG | GLU | 148 | 34.576 | 22.960 | 36.356 | 1.00 26.58 | MTGL |
| ATOM | 1148 | CD | GLU | 148 | 34.081 | 24.123 | 37.217 | 1.00 29.48 | MTGL |
| ATOM | 1149 | OE1 | GLU | 148 | 33.777 | 25.209 | 36.672 | 1.00 30.90 | MTGL |
| ATOM | 1150 | OE2 | GLU | 148 | 33.988 | 23.929 | 38.448 | 1.00 30.75 | MTGL |
| ATOM | 1151 | C | GLU | 148 | 37.858 | 22.540 | 34.312 | 1.00 20.17 | MTGL |
| ATOM | 1152 | O | GLU | 148 | 37.649 | 23.550 | 33.633 | 1.00 20.26 | MTGL |
| ATOM | 1153 | N | ASN | 149 | 39.019 | 21.853 | 34.186 | 0.50 20.18 | MTGL |
| ATOM | 1154 | CA | ASN | 149 | 40.039 | 22.216 | 33.154 | 0.50 20.26 | MTGL |
| ATOM | 1155 | CB | ASN | 149 | 41.436 | 21.616 | 33.436 | 0.50 21.36 | MTGL |
| ATOM | 1156 | CG | ASN | 149 | 42.198 | 22.423 | 34.433 | 0.50 22.41 | MTGL |
| ATOM | 1157 | OD1 | ASN | 149 | 42.651 | 23.520 | 34.132 | 0.50 23.31 | MTGL |
| ATOM | 1158 | ND2 | ASN | 149 | 42.298 | 21.917 | 35.646 | 0.50 23.40 | MTGL |
| ATOM | 1159 | C | ASN | 149 | 39.555 | 21.656 | 31.811 | 0.50 19.48 | MTGL |

Fig. 1 cont.

| | | | | | | | | | | |
|---|---|---|---|---|---|---|---|---|---|---|
| ATOM | 1160 | O | ASN | 149 | 40.152 | 20.702 | 31.289 | 0.50 | 17.94 | MTGL |
| ATOM | 1161 | N | TRP | 150 | 38.480 | 22.230 | 31.261 | 1.00 | 19.00 | MTGL |
| ATOM | 1162 | CA | TRP | 150 | 37.920 | 21.769 | 30.000 | 1.00 | 18.91 | MTGL |
| ATOM | 1163 | CB | TRP | 150 | 36.777 | 22.704 | 29.605 | 1.00 | 18.17 | MTGL |
| ATOM | 1164 | CG | TRP | 150 | 35.710 | 22.781 | 30.629 | 1.00 | 17.82 | MTGL |
| ATOM | 1165 | CD2 | TRP | 150 | 34.895 | 21.702 | 31.094 | 1.00 | 18.44 | MTGL |
| ATOM | 1166 | CE2 | TRP | 150 | 34.013 | 22.232 | 32.060 | 1.00 | 18.24 | MTGL |
| ATOM | 1167 | CE3 | TRP | 150 | 34.824 | 20.335 | 30.787 | 1.00 | 18.25 | MTGL |
| ATOM | 1168 | CD1 | TRP | 150 | 35.301 | 23.895 | 31.310 | 1.00 | 17.99 | MTGL |
| ATOM | 1169 | NE1 | TRP | 150 | 34.282 | 23.571 | 32.170 | 1.00 | 19.19 | MTGL |
| ATOM | 1170 | CZ2 | TRP | 150 | 33.066 | 21.443 | 32.725 | 1.00 | 19.86 | MTGL |
| ATOM | 1171 | CZ3 | TRP | 150 | 33.879 | 19.547 | 31.448 | 1.00 | 19.02 | MTGL |
| ATOM | 1172 | CH2 | TRP | 150 | 33.013 | 20.105 | 32.408 | 1.00 | 19.52 | MTGL |
| ATOM | 1173 | C | TRP | 150 | 38.990 | 21.744 | 28.904 | 1.00 | 19.25 | MTGL |
| ATOM | 1174 | O | TRP | 150 | 39.022 | 20.828 | 28.091 | 1.00 | 19.43 | MTGL |
| ATOM | 1175 | N | ALA | 151 | 39.851 | 22.759 | 28.880 | 1.00 | 17.86 | MTGL |
| ATOM | 1176 | CA | ALA | 151 | 40.897 | 22.822 | 27.864 | 1.00 | 18.96 | MTGL |
| ATOM | 1177 | CB | ALA | 151 | 41.753 | 24.090 | 28.047 | 1.00 | 19.41 | MTGL |
| ATOM | 1178 | C | ALA | 151 | 41.784 | 21.571 | 27.897 | 1.00 | 18.90 | MTGL |
| ATOM | 1179 | O | ALA | 151 | 42.098 | 20.994 | 26.857 | 1.00 | 19.89 | MTGL |
| ATOM | 1180 | N | ASN | 152 | 42.184 | 21.144 | 29.088 | 1.00 | 18.45 | MTGL |
| ATOM | 1181 | CA | ASN | 152 | 43.027 | 19.954 | 29.209 | 1.00 | 18.07 | MTGL |
| ATOM | 1182 | CB | ASN | 152 | 43.584 | 19.830 | 30.635 | 1.00 | 16.97 | MTGL |
| ATOM | 1183 | CG | ASN | 152 | 44.767 | 20.764 | 30.886 | 1.00 | 18.19 | MTGL |
| ATOM | 1184 | OD1 | ASN | 152 | 45.095 | 21.603 | 30.054 | 1.00 | 17.89 | MTGL |
| ATOM | 1185 | ND2 | ASN | 152 | 45.407 | 20.618 | 32.043 | 1.00 | 17.33 | MTGL |
| ATOM | 1186 | C | ASN | 152 | 42.250 | 18.686 | 28.848 | 1.00 | 17.48 | MTGL |
| ATOM | 1187 | O | ASN | 152 | 42.762 | 17.805 | 28.155 | 1.00 | 17.16 | MTGL |
| ATOM | 1188 | N | ILE | 153 | 41.016 | 18.598 | 29.325 | 1.00 | 17.57 | MTGL |
| ATOM | 1189 | CA | ILE | 153 | 40.177 | 17.437 | 29.048 | 1.00 | 18.34 | MTGL |
| ATOM | 1190 | CB | ILE | 153 | 38.801 | 17.573 | 29.741 | 1.00 | 17.84 | MTGL |
| ATOM | 1191 | CG2 | ILE | 153 | 37.836 | 16.486 | 29.243 | 1.00 | 17.51 | MTGL |
| ATOM | 1192 | CG1 | ILE | 153 | 38.987 | 17.468 | 31.255 | 1.00 | 17.49 | MTGL |
| ATOM | 1193 | CD1 | ILE | 153 | 37.761 | 17.837 | 32.060 | 1.00 | 17.26 | MTGL |
| ATOM | 1194 | C | ILE | 153 | 39.974 | 17.246 | 27.548 | 1.00 | 17.82 | MTGL |
| ATOM | 1195 | O | ILE | 153 | 40.174 | 16.150 | 27.027 | 1.00 | 17.52 | MTGL |
| ATOM | 1196 | N | ALA | 154 | 39.596 | 18.318 | 26.858 | 1.00 | 17.93 | MTGL |
| ATOM | 1197 | CA | ALA | 154 | 39.359 | 18.255 | 25.416 | 1.00 | 18.68 | MTGL |
| ATOM | 1198 | CB | ALA | 154 | 38.884 | 19.620 | 24.896 | 1.00 | 17.82 | MTGL |
| ATOM | 1199 | C | ALA | 154 | 40.624 | 17.834 | 24.686 | 1.00 | 18.79 | MTGL |
| ATOM | 1200 | O | ALA | 154 | 40.584 | 17.037 | 23.744 | 1.00 | 17.95 | MTGL |
| ATOM | 1201 | N | ARG | 155 | 41.749 | 18.375 | 25.131 | 1.00 | 18.32 | MTGL |
| ATOM | 1202 | CA | ARG | 155 | 43.025 | 18.064 | 24.512 | 1.00 | 19.09 | MTGL |
| ATOM | 1203 | CB | ARG | 155 | 44.098 | 18.972 | 25.094 | 1.00 | 20.03 | MTGL |
| ATOM | 1204 | CG | ARG | 155 | 45.415 | 18.867 | 24.403 | 1.00 | 23.57 | MTGL |
| ATOM | 1205 | CD | ARG | 155 | 46.295 | 19.990 | 24.873 | 1.00 | 26.84 | MTGL |
| ATOM | 1206 | NE | ARG | 155 | 47.681 | 19.767 | 24.498 | 1.00 | 29.65 | MTGL |
| ATOM | 1207 | CZ | ARG | 155 | 48.686 | 20.513 | 24.931 | 1.00 | 28.58 | MTGL |
| ATOM | 1208 | NH1 | ARG | 155 | 48.443 | 21.525 | 25.753 | 1.00 | 29.23 | MTGL |
| ATOM | 1209 | NH2 | ARG | 155 | 49.922 | 20.244 | 24.540 | 1.00 | 29.12 | MTGL |
| ATOM | 1210 | C | ARG | 155 | 43.402 | 16.598 | 24.721 | 1.00 | 18.37 | MTGL |
| ATOM | 1211 | O | ARG | 155 | 43.848 | 15.916 | 23.792 | 1.00 | 17.92 | MTGL |
| ATOM | 1212 | N | LEU | 156 | 43.217 | 16.115 | 25.944 | 1.00 | 17.77 | MTGL |
| ATOM | 1213 | CA | LEU | 156 | 43.540 | 14.731 | 26.258 | 1.00 | 17.18 | MTGL |
| ATOM | 1214 | CB | LEU | 156 | 43.360 | 14.473 | 27.761 | 1.00 | 16.68 | MTGL |
| ATOM | 1215 | CG | LEU | 156 | 44.375 | 15.158 | 28.689 | 1.00 | 16.04 | MTGL |
| ATOM | 1216 | CD1 | LEU | 156 | 43.921 | 15.032 | 30.139 | 1.00 | 17.64 | MTGL |
| ATOM | 1217 | CD2 | LEU | 156 | 45.745 | 14.532 | 28.504 | 1.00 | 14.11 | MTGL |

Fig. 1 cont.

| | | | | | | | | | | |
|---|---|---|---|---|---|---|---|---|---|---|
| ATOM | 1218 | C | LEU | 156 | 42.660 | 13.777 | 25.447 | 1.00 | 17.29 | MTGL |
| ATOM | 1219 | O | LEU | 156 | 43.152 | 12.794 | 24.886 | 1.00 | 16.71 | MTGL |
| ATOM | 1220 | N | LEU | 157 | 41.363 | 14.071 | 25.377 | 1.00 | 16.48 | MTGL |
| ATOM | 1221 | CA | LEU | 157 | 40.438 | 13.219 | 24.639 | 1.00 | 16.71 | MTGL |
| ATOM | 1222 | CB | LEU | 157 | 38.992 | 13.651 | 24.900 | 1.00 | 15.25 | MTGL |
| ATOM | 1223 | CG | LEU | 157 | 38.509 | 13.425 | 26.339 | 1.00 | 14.15 | MTGL |
| ATOM | 1224 | CD1 | LEU | 157 | 37.080 | 13.903 | 26.505 | 1.00 | 13.65 | MTGL |
| ATOM | 1225 | CD2 | LEU | 157 | 38.599 | 11.944 | 26.676 | 1.00 | 13.61 | MTGL |
| ATOM | 1226 | C | LEU | 157 | 40.744 | 13.230 | 23.146 | 1.00 | 18.12 | MTGL |
| ATOM | 1227 | O | LEU | 157 | 40.549 | 12.224 | 22.456 | 1.00 | 16.85 | MTGL |
| ATOM | 1228 | N | HIS | 158 | 41.231 | 14.366 | 22.652 | 1.00 | 19.80 | MTGL |
| ATOM | 1229 | CA | HIS | 158 | 41.600 | 14.498 | 21.244 | 1.00 | 20.98 | MTGL |
| ATOM | 1230 | CB | HIS | 158 | 42.001 | 15.946 | 20.938 | 1.00 | 22.94 | MTGL |
| ATOM | 1231 | CG | HIS | 158 | 42.458 | 16.170 | 19.528 | 1.00 | 24.32 | MTGL |
| ATOM | 1232 | CD2 | HIS | 158 | 43.695 | 16.367 | 19.013 | 1.00 | 23.88 | MTGL |
| ATOM | 1233 | ND1 | HIS | 158 | 41.586 | 16.230 | 18.460 | 1.00 | 24.92 | MTGL |
| ATOM | 1234 | CE1 | HIS | 158 | 42.266 | 16.460 | 17.350 | 1.00 | 23.22 | MTGL |
| ATOM | 1235 | NE2 | HIS | 158 | 43.548 | 16.547 | 17.658 | 1.00 | 24.57 | MTGL |
| ATOM | 1236 | C | HIS | 158 | 42.783 | 13.567 | 20.973 | 1.00 | 21.01 | MTGL |
| ATOM | 1237 | O | HIS | 158 | 42.809 | 12.851 | 19.971 | 1.00 | 21.78 | MTGL |
| ATOM | 1238 | N | SER | 159 | 43.762 | 13.578 | 21.874 | 1.00 | 20.28 | MTGL |
| ATOM | 1239 | CA | SER | 159 | 44.940 | 12.730 | 21.726 | 1.00 | 20.15 | MTGL |
| ATOM | 1240 | CB | SER | 159 | 45.961 | 13.021 | 22.829 | 1.00 | 21.81 | MTGL |
| ATOM | 1241 | OG | SER | 159 | 46.476 | 14.333 | 22.721 | 1.00 | 24.73 | MTGL |
| ATOM | 1242 | C | SER | 159 | 44.570 | 11.253 | 21.774 | 1.00 | 18.92 | MTGL |
| ATOM | 1243 | O | SER | 159 | 45.095 | 10.453 | 21.004 | 1.00 | 19.31 | MTGL |
| ATOM | 1244 | N | ALA | 160 | 43.675 | 10.894 | 22.687 | 1.00 | 17.87 | MTGL |
| ATOM | 1245 | CA | ALA | 160 | 43.249 | 9.504 | 22.824 | 1.00 | 17.96 | MTGL |
| ATOM | 1246 | CB | ALA | 160 | 42.322 | 9.352 | 24.026 | 1.00 | 18.26 | MTGL |
| ATOM | 1247 | C | ALA | 160 | 42.538 | 9.044 | 21.556 | 1.00 | 18.59 | MTGL |
| ATOM | 1248 | O | ALA | 160 | 42.844 | 7.982 | 21.013 | 1.00 | 17.77 | MTGL |
| ATOM | 1249 | N | ALA | 161 | 41.593 | 9.852 | 21.083 | 1.00 | 18.03 | MTGL |
| ATOM | 1250 | CA | ALA | 161 | 40.846 | 9.519 | 19.875 | 1.00 | 18.84 | MTGL |
| ATOM | 1251 | CB | ALA | 161 | 39.851 | 10.623 | 19.547 | 1.00 | 16.85 | MTGL |
| ATOM | 1252 | C | ALA | 161 | 41.778 | 9.294 | 18.695 | 1.00 | 18.82 | MTGL |
| ATOM | 1253 | O | ALA | 161 | 41.654 | 8.301 | 17.983 | 1.00 | 19.53 | MTGL |
| ATOM | 1254 | N | TRP | 162 | 42.715 | 10.211 | 18.485 | 1.00 | 18.98 | MTGL |
| ATOM | 1255 | CA | TRP | 162 | 43.636 | 10.057 | 17.371 | 1.00 | 19.92 | MTGL |
| ATOM | 1256 | CB | TRP | 162 | 44.330 | 11.386 | 17.064 | 1.00 | 21.12 | MTGL |
| ATOM | 1257 | CG | TRP | 162 | 43.420 | 12.264 | 16.268 | 1.00 | 24.00 | MTGL |
| ATOM | 1258 | CD2 | TRP | 162 | 43.215 | 12.212 | 14.851 | 1.00 | 24.55 | MTGL |
| ATOM | 1259 | CE2 | TRP | 162 | 42.158 | 13.102 | 14.546 | 1.00 | 24.96 | MTGL |
| ATOM | 1260 | CE3 | TRP | 162 | 43.822 | 11.499 | 13.808 | 1.00 | 25.38 | MTGL |
| ATOM | 1261 | CD1 | TRP | 162 | 42.509 | 13.160 | 16.752 | 1.00 | 24.55 | MTGL |
| ATOM | 1262 | NE1 | TRP | 162 | 41.743 | 13.665 | 15.724 | 1.00 | 25.20 | MTGL |
| ATOM | 1263 | CZ2 | TRP | 162 | 41.691 | 13.293 | 13.241 | 1.00 | 24.56 | MTGL |
| ATOM | 1264 | CZ3 | TRP | 162 | 43.355 | 11.689 | 12.507 | 1.00 | 25.72 | MTGL |
| ATOM | 1265 | CH2 | TRP | 162 | 42.302 | 12.581 | 12.238 | 1.00 | 24.73 | MTGL |
| ATOM | 1266 | C | TRP | 162 | 44.643 | 8.927 | 17.556 | 1.00 | 20.10 | MTGL |
| ATOM | 1267 | O | TRP | 162 | 45.263 | 8.483 | 16.596 | 1.00 | 19.99 | MTGL |
| ATOM | 1268 | N | GLY | 163 | 44.803 | 8.458 | 18.786 | 1.00 | 20.69 | MTGL |
| ATOM | 1269 | CA | GLY | 163 | 45.703 | 7.343 | 19.016 | 1.00 | 20.86 | MTGL |
| ATOM | 1270 | C | GLY | 163 | 45.051 | 6.124 | 18.375 | 1.00 | 20.81 | MTGL |
| ATOM | 1271 | O | GLY | 163 | 45.720 | 5.225 | 17.868 | 1.00 | 20.64 | MTGL |
| ATOM | 1272 | N | ILE | 164 | 43.724 | 6.109 | 18.395 | 1.00 | 20.00 | MTGL |
| ATOM | 1273 | CA | ILE | 164 | 42.956 | 5.020 | 17.810 | 1.00 | 19.28 | MTGL |
| ATOM | 1274 | CB | ILE | 164 | 41.515 | 5.020 | 18.347 | 1.00 | 18.69 | MTGL |
| ATOM | 1275 | CG2 | ILE | 164 | 40.670 | 3.977 | 17.601 | 1.00 | 17.15 | MTGL |

Fig. 1 cont.

| ATOM | 1276 | CG1 | ILE | 164 | 41.529 | 4.750 | 19.852 | 1.00 | 18.11 | MTGL |
|------|------|-----|-----|-----|--------|-------|--------|------|-------|------|
| ATOM | 1277 | CD1 | ILE | 164 | 40.155 | 4.779 | 20.489 | 1.00 | 18.52 | MTGL |
| ATOM | 1278 | C | ILE | 164 | 42.913 | 5.181 | 16.291 | 1.00 | 20.20 | MTGL |
| ATOM | 1279 | O | ILE | 164 | 43.125 | 4.219 | 15.548 | 1.00 | 18.00 | MTGL |
| ATOM | 1280 | N | LYS | 165 | 42.645 | 6.405 | 15.839 | 1.00 | 20.30 | MTGL |
| ATOM | 1281 | CA | LYS | 165 | 42.563 | 6.701 | 14.410 | 1.00 | 21.80 | MTGL |
| ATOM | 1282 | CB | LYS | 165 | 42.100 | 8.149 | 14.191 | 1.00 | 21.88 | MTGL |
| ATOM | 1283 | CG | LYS | 165 | 40.670 | 8.436 | 14.647 | 1.00 | 23.28 | MTGL |
| ATOM | 1284 | CD | LYS | 165 | 40.346 | 9.924 | 14.509 | 1.00 | 22.94 | MTGL |
| ATOM | 1285 | CE | LYS | 165 | 38.989 | 10.268 | 15.097 | 1.00 | 24.34 | MTGL |
| ATOM | 1286 | NZ | LYS | 165 | 37.857 | 9.632 | 14.363 | 1.00 | 25.77 | MTGL |
| ATOM | 1287 | C | LYS | 165 | 43.879 | 6.468 | 13.668 | 1.00 | 21.72 | MTGL |
| ATOM | 1288 | O | LYS | 165 | 43.868 | 6.086 | 12.501 | 1.00 | 21.82 | MTGL |
| ATOM | 1289 | N | ASP | 166 | 45.009 | 6.699 | 14.335 | 1.00 | 22.15 | MTGL |
| ATOM | 1290 | CA | ASP | 166 | 46.315 | 6.496 | 13.705 | 1.00 | 21.98 | MTGL |
| ATOM | 1291 | CB | ASP | 166 | 47.373 | 7.438 | 14.299 | 1.00 | 22.61 | MTGL |
| ATOM | 1292 | CG | ASP | 166 | 47.119 | 8.907 | 13.970 | 1.00 | 24.69 | MTGL |
| ATOM | 1293 | OD1 | ASP | 166 | 46.345 | 9.197 | 13.032 | 1.00 | 25.51 | MTGL |
| ATOM | 1294 | OD2 | ASP | 166 | 47.709 | 9.775 | 14.645 | 1.00 | 23.73 | MTGL |
| ATOM | 1295 | C | ASP | 166 | 46.818 | 5.063 | 13.853 | 1.00 | 21.80 | MTGL |
| ATOM | 1296 | O | ASP | 166 | 47.900 | 4.737 | 13.373 | 1.00 | 22.35 | MTGL |
| ATOM | 1297 | N | SER | 167 | 46.043 | 4.208 | 14.511 | 1.00 | 21.58 | MTGL |
| ATOM | 1298 | CA | SER | 167 | 46.460 | 2.822 | 14.722 | 1.00 | 21.57 | MTGL |
| ATOM | 1299 | CB | SER | 167 | 45.724 | 2.229 | 15.927 | 1.00 | 20.98 | MTGL |
| ATOM | 1300 | OG | SER | 167 | 44.368 | 1.952 | 15.620 | 1.00 | 20.07 | MTGL |
| ATOM | 1301 | C | SER | 167 | 46.235 | 1.920 | 13.508 | 1.00 | 21.73 | MTGL |
| ATOM | 1302 | O | SER | 167 | 45.669 | 2.347 | 12.503 | 1.00 | 21.01 | MTGL |
| ATOM | 1303 | N | SER | 168 | 46.676 | 0.668 | 13.619 | 1.00 | 21.44 | MTGL |
| ATOM | 1304 | CA | SER | 168 | 46.520 | -0.304 | 12.539 | 1.00 | 20.71 | MTGL |
| ATOM | 1305 | CB | SER | 168 | 47.711 | -1.264 | 12.519 | 1.00 | 21.31 | MTGL |
| ATOM | 1306 | OG | SER | 168 | 47.836 | -1.921 | 13.768 | 1.00 | 23.08 | MTGL |
| ATOM | 1307 | C | SER | 168 | 45.229 | -1.116 | 12.654 | 1.00 | 20.14 | MTGL |
| ATOM | 1308 | O | SER | 168 | 45.001 | -2.033 | 11.869 | 1.00 | 19.79 | MTGL |
| ATOM | 1309 | N | LEU | 169 | 44.388 | -0.792 | 13.630 | 1.00 | 19.27 | MTGL |
| ATOM | 1310 | CA | LEU | 169 | 43.132 | -1.514 | 13.791 | 1.00 | 19.92 | MTGL |
| ATOM | 1311 | CB | LEU | 169 | 42.306 | -0.921 | 14.935 | 1.00 | 19.48 | MTGL |
| ATOM | 1312 | CG | LEU | 169 | 42.758 | -1.226 | 16.365 | 1.00 | 19.56 | MTGL |
| ATOM | 1313 | CD1 | LEU | 169 | 41.918 | -0.417 | 17.342 | 1.00 | 18.93 | MTGL |
| ATOM | 1314 | CD2 | LEU | 169 | 42.612 | -2.717 | 16.650 | 1.00 | 19.30 | MTGL |
| ATOM | 1315 | C | LEU | 169 | 42.323 | -1.450 | 12.501 | 1.00 | 20.54 | MTGL |
| ATOM | 1316 | O | LEU | 169 | 42.053 | -0.365 | 11.981 | 1.00 | 20.27 | MTGL |
| ATOM | 1317 | N | SER | 170 | 41.940 | -2.614 | 11.987 | 1.00 | 20.36 | MTGL |
| ATOM | 1318 | CA | SER | 170 | 41.159 | -2.678 | 10.760 | 1.00 | 21.47 | MTGL |
| ATOM | 1319 | CB | SER | 170 | 42.088 | -2.784 | 9.545 | 1.00 | 22.54 | MTGL |
| ATOM | 1320 | OG | SER | 170 | 41.344 | -2.749 | 8.341 | 1.00 | 22.78 | MTGL |
| ATOM | 1321 | C | SER | 170 | 40.216 | -3.875 | 10.797 | 1.00 | 21.69 | MTGL |
| ATOM | 1322 | O | SER | 170 | 40.659 | -5.024 | 10.819 | 1.00 | 21.79 | MTGL |
| ATOM | 1323 | N | PRO | 171 | 38.899 | -3.621 | 10.800 | 1.00 | 21.30 | MTGL |
| ATOM | 1324 | CD | PRO | 171 | 37.874 | -4.676 | 10.884 | 1.00 | 21.70 | MTGL |
| ATOM | 1325 | CA | PRO | 171 | 38.277 | -2.294 | 10.764 | 1.00 | 21.48 | MTGL |
| ATOM | 1326 | CB | PRO | 171 | 36.806 | -2.616 | 10.530 | 1.00 | 21.60 | MTGL |
| ATOM | 1327 | CG | PRO | 171 | 36.644 | -3.901 | 11.285 | 1.00 | 22.67 | MTGL |
| ATOM | 1328 | C | PRO | 171 | 38.497 | -1.472 | 12.039 | 1.00 | 21.36 | MTGL |
| ATOM | 1329 | O | PRO | 171 | 38.790 | -2.009 | 13.109 | 1.00 | 20.24 | MTGL |
| ATOM | 1330 | N | LYS | 172 | 38.351 | -0.161 | 11.908 | 1.00 | 20.37 | MTGL |
| ATOM | 1331 | CA | LYS | 172 | 38.525 | 0.749 | 13.032 | 1.00 | 21.42 | MTGL |
| ATOM | 1332 | CB | LYS | 172 | 38.670 | 2.183 | 12.501 | 1.00 | 22.43 | MTGL |
| ATOM | 1333 | CG | LYS | 172 | 39.602 | 3.071 | 13.310 | 1.00 | 25.68 | MTGL |

Fig. 1 cont.

| ATOM | 1334 | CD  | LYS | 172 | 41.052 | 2.616  | 13.220 | 1.00 | 24.85 | MTGL |
|------|------|-----|-----|-----|--------|--------|--------|------|-------|------|
| ATOM | 1335 | CE  | LYS | 172 | 41.659 | 2.946  | 11.878 | 1.00 | 25.80 | MTGL |
| ATOM | 1336 | NZ  | LYS | 172 | 42.984 | 2.294  | 11.703 | 1.00 | 24.26 | MTGL |
| ATOM | 1337 | C   | LYS | 172 | 37.295 | 0.626  | 13.940 | 1.00 | 20.16 | MTGL |
| ATOM | 1338 | O   | LYS | 172 | 36.199 | 0.307  | 13.478 | 1.00 | 19.92 | MTGL |
| ATOM | 1339 | N   | PRO | 173 | 37.465 | 0.848  | 15.248 | 1.00 | 19.30 | MTGL |
| ATOM | 1340 | CD  | PRO | 173 | 38.722 | 1.088  | 15.980 | 1.00 | 19.67 | MTGL |
| ATOM | 1341 | CA  | PRO | 173 | 36.335 | 0.751  | 16.177 | 1.00 | 19.05 | MTGL |
| ATOM | 1342 | CB  | PRO | 173 | 37.018 | 0.437  | 17.497 | 1.00 | 19.14 | MTGL |
| ATOM | 1343 | CG  | PRO | 173 | 38.237 | 1.321  | 17.412 | 1.00 | 18.48 | MTGL |
| ATOM | 1344 | C   | PRO | 173 | 35.565 | 2.066  | 16.270 | 1.00 | 18.59 | MTGL |
| ATOM | 1345 | O   | PRO | 173 | 36.049 | 3.110  | 15.832 | 1.00 | 16.92 | MTGL |
| ATOM | 1346 | N   | LYS | 174 | 34.359 | 2.007  | 16.824 | 1.00 | 17.93 | MTGL |
| ATOM | 1347 | CA  | LYS | 174 | 33.591 | 3.222  | 17.037 | 1.00 | 18.70 | MTGL |
| ATOM | 1348 | CB  | LYS | 174 | 32.109 | 2.901  | 17.240 | 1.00 | 18.25 | MTGL |
| ATOM | 1349 | CG  | LYS | 174 | 31.388 | 2.529  | 15.947 | 1.00 | 19.90 | MTGL |
| ATOM | 1350 | CD  | LYS | 174 | 29.937 | 2.142  | 16.200 | 1.00 | 20.92 | MTGL |
| ATOM | 1351 | CE  | LYS | 174 | 29.230 | 1.784  | 14.892 | 1.00 | 21.51 | MTGL |
| ATOM | 1352 | NZ  | LYS | 174 | 27.839 | 1.317  | 15.135 | 1.00 | 20.89 | MTGL |
| ATOM | 1353 | C   | LYS | 174 | 34.193 | 3.808  | 18.318 | 1.00 | 18.48 | MTGL |
| ATOM | 1354 | O   | LYS | 174 | 34.452 | 3.076  | 19.281 | 1.00 | 18.00 | MTGL |
| ATOM | 1355 | N   | ILE | 175 | 34.448 | 5.112  | 18.320 | 1.00 | 17.76 | MTGL |
| ATOM | 1356 | CA  | ILE | 175 | 35.033 | 5.768  | 19.487 | 1.00 | 17.60 | MTGL |
| ATOM | 1357 | CB  | ILE | 175 | 35.999 | 6.883  | 19.050 | 1.00 | 17.54 | MTGL |
| ATOM | 1358 | CG2 | ILE | 175 | 36.564 | 7.610  | 20.271 | 1.00 | 17.48 | MTGL |
| ATOM | 1359 | CG1 | ILE | 175 | 37.134 | 6.266  | 18.226 | 1.00 | 16.88 | MTGL |
| ATOM | 1360 | CD1 | ILE | 175 | 38.083 | 7.263  | 17.618 | 1.00 | 15.96 | MTGL |
| ATOM | 1361 | C   | ILE | 175 | 33.945 | 6.330  | 20.393 | 1.00 | 17.11 | MTGL |
| ATOM | 1362 | O   | ILE | 175 | 33.102 | 7.122  | 19.962 | 1.00 | 17.92 | MTGL |
| ATOM | 1363 | N   | MET | 176 | 33.966 | 5.914  | 21.653 | 1.00 | 16.13 | MTGL |
| ATOM | 1364 | CA  | MET | 176 | 32.955 | 6.345  | 22.615 | 1.00 | 16.14 | MTGL |
| ATOM | 1365 | CB  | MET | 176 | 32.223 | 5.120  | 23.171 | 1.00 | 16.50 | MTGL |
| ATOM | 1366 | CG  | MET | 176 | 31.333 | 5.410  | 24.379 | 1.00 | 16.70 | MTGL |
| ATOM | 1367 | SD  | MET | 176 | 30.643 | 3.896  | 25.097 | 1.00 | 19.61 | MTGL |
| ATOM | 1368 | CE  | MET | 176 | 29.473 | 3.433  | 23.769 | 1.00 | 15.92 | MTGL |
| ATOM | 1369 | C   | MET | 176 | 33.458 | 7.163  | 23.797 | 1.00 | 16.18 | MTGL |
| ATOM | 1370 | O   | MET | 176 | 34.562 | 6.946  | 24.299 | 1.00 | 15.62 | MTGL |
| ATOM | 1371 | N   | ILE | 177 | 32.628 | 8.109  | 24.227 | 1.00 | 16.05 | MTGL |
| ATOM | 1372 | CA  | ILE | 177 | 32.915 | 8.927  | 25.402 | 1.00 | 16.22 | MTGL |
| ATOM | 1373 | CB  | ILE | 177 | 32.786 | 10.436 | 25.117 | 1.00 | 15.59 | MTGL |
| ATOM | 1374 | CG2 | ILE | 177 | 32.729 | 11.210 | 26.438 | 1.00 | 16.50 | MTGL |
| ATOM | 1375 | CG1 | ILE | 177 | 33.985 | 10.900 | 24.273 | 1.00 | 16.91 | MTGL |
| ATOM | 1376 | CD1 | ILE | 177 | 33.988 | 12.380 | 23.935 | 1.00 | 17.23 | MTGL |
| ATOM | 1377 | C   | ILE | 177 | 31.847 | 8.467  | 26.383 | 1.00 | 15.72 | MTGL |
| ATOM | 1378 | O   | ILE | 177 | 30.660 | 8.467  | 26.062 | 1.00 | 16.21 | MTGL |
| ATOM | 1379 | N   | HIS | 178 | 32.278 | 8.061  | 27.571 | 1.00 | 16.15 | MTGL |
| ATOM | 1380 | CA  | HIS | 178 | 31.376 | 7.518  | 28.581 | 1.00 | 16.02 | MTGL |
| ATOM | 1381 | CB  | HIS | 178 | 31.866 | 6.112  | 28.949 | 1.00 | 14.76 | MTGL |
| ATOM | 1382 | CG  | HIS | 178 | 31.099 | 5.461  | 30.057 | 1.00 | 14.66 | MTGL |
| ATOM | 1383 | CD2 | HIS | 178 | 29.850 | 5.681  | 30.534 | 1.00 | 13.15 | MTGL |
| ATOM | 1384 | ND1 | HIS | 178 | 31.612 | 4.415  | 30.793 | 1.00 | 13.39 | MTGL |
| ATOM | 1385 | CE1 | HIS | 178 | 30.714 | 4.020  | 31.679 | 1.00 | 14.18 | MTGL |
| ATOM | 1386 | NE2 | HIS | 178 | 29.636 | 4.770  | 31.543 | 1.00 | 13.19 | MTGL |
| ATOM | 1387 | C   | HIS | 178 | 31.232 | 8.354  | 29.850 | 1.00 | 16.83 | MTGL |
| ATOM | 1388 | O   | HIS | 178 | 32.210 | 8.605  | 30.553 | 1.00 | 16.59 | MTGL |
| ATOM | 1389 | N   | LEU | 179 | 29.997 | 8.757  | 30.138 | 1.00 | 17.26 | MTGL |
| ATOM | 1390 | CA  | LEU | 179 | 29.670 | 9.539  | 31.329 | 1.00 | 18.11 | MTGL |
| ATOM | 1391 | CB  | LEU | 179 | 29.014 | 10.866 | 30.925 | 1.00 | 18.73 | MTGL |

Fig. 1 cont.

```
ATOM   1392  CG   LEU   179      29.877   12.128   30.808  1.00  20.65       MTGL
ATOM   1393  CD1  LEU   179      31.265   11.812   30.272  1.00  19.45       MTGL
ATOM   1394  CD2  LEU   179      29.150   13.130   29.923  1.00  20.83       MTGL
ATOM   1395  C    LEU   179      28.693    8.732   32.186  1.00  18.96       MTGL
ATOM   1396  O    LEU   179      27.947    7.899   31.668  1.00  19.30       MTGL
ATOM   1397  N    ASP   180      28.693    8.974   33.493  1.00  18.24       MTGL
ATOM   1398  CA   ASP   180      27.780    8.267   34.385  1.00  18.02       MTGL
ATOM   1399  CB   ASP   180      28.377    8.171   35.795  1.00  17.69       MTGL
ATOM   1400  CG   ASP   180      28.398    9.505   36.518  1.00  19.25       MTGL
ATOM   1401  OD1  ASP   180      28.702   10.538   35.884  1.00  19.57       MTGL
ATOM   1402  OD2  ASP   180      28.117    9.512   37.734  1.00  20.92       MTGL
ATOM   1403  C    ASP   180      26.453    9.020   34.430  1.00  18.13       MTGL
ATOM   1404  O    ASP   180      26.268    9.995   33.708  1.00  17.92       MTGL
ATOM   1405  N    ASN   181      25.533    8.546   35.266  1.00  19.02       MTGL
ATOM   1406  CA   ASN   181      24.219    9.165   35.439  1.00  19.13       MTGL
ATOM   1407  CB   ASN   181      24.337   10.360   36.393  1.00  19.61       MTGL
ATOM   1408  CG   ASN   181      24.840    9.959   37.776  1.00  20.81       MTGL
ATOM   1409  OD1  ASN   181      24.561    8.857   38.259  1.00  20.36       MTGL
ATOM   1410  ND2  ASN   181      25.567   10.862   38.427  1.00  21.46       MTGL
ATOM   1411  C    ASN   181      23.541    9.604   34.135  1.00  19.21       MTGL
ATOM   1412  O    ASN   181      23.277   10.791   33.925  1.00  18.32       MTGL
ATOM   1413  N    GLY   182      23.238    8.635   33.276  1.00  18.94       MTGL
ATOM   1414  CA   GLY   182      22.610    8.937   32.003  1.00  18.55       MTGL
ATOM   1415  C    GLY   182      21.309    9.704   32.101  1.00  18.91       MTGL
ATOM   1416  O    GLY   182      20.952   10.428   31.179  1.00  18.95       MTGL
ATOM   1417  N    TRP   183      20.609    9.546   33.219  1.00  19.65       MTGL
ATOM   1418  CA   TRP   183      19.332   10.213   33.459  1.00  19.57       MTGL
ATOM   1419  CB   TRP   183      18.643    9.588   34.671  1.00  20.28       MTGL
ATOM   1420  CG   TRP   183      19.515    9.586   35.904  1.00  21.43       MTGL
ATOM   1421  CD2  TRP   183      19.671   10.653   36.856  1.00  21.48       MTGL
ATOM   1422  CE2  TRP   183      20.614   10.222   37.816  1.00  21.25       MTGL
ATOM   1423  CE3  TRP   183      19.103   11.931   36.989  1.00  21.53       MTGL
ATOM   1424  CD1  TRP   183      20.348    8.585   36.316  1.00  20.88       MTGL
ATOM   1425  NE1  TRP   183      21.011    8.959   37.463  1.00  21.48       MTGL
ATOM   1426  CZ2  TRP   183      21.010   11.024   38.896  1.00  22.46       MTGL
ATOM   1427  CZ3  TRP   183      19.497   12.732   38.065  1.00  21.36       MTGL
ATOM   1428  CH2  TRP   183      20.440   12.272   39.004  1.00  21.87       MTGL
ATOM   1429  C    TRP   183      19.477   11.705   33.724  1.00  20.04       MTGL
ATOM   1430  O    TRP   183      18.506   12.457   33.613  1.00  19.18       MTGL
ATOM   1431  N    ASP   184      20.686   12.126   34.083  1.00  20.76       MTGL
ATOM   1432  CA   ASP   184      20.957   13.522   34.417  1.00  20.14       MTGL
ATOM   1433  CB   ASP   184      22.085   13.581   35.455  1.00  21.31       MTGL
ATOM   1434  CG   ASP   184      22.327   14.986   35.988  1.00  24.62       MTGL
ATOM   1435  OD1  ASP   184      21.643   15.936   35.540  1.00  24.90       MTGL
ATOM   1436  OD2  ASP   184      23.210   15.138   36.859  1.00  25.79       MTGL
ATOM   1437  C    ASP   184      21.312   14.374   33.201  1.00  20.22       MTGL
ATOM   1438  O    ASP   184      22.487   14.584   32.899  1.00  19.35       MTGL
ATOM   1439  N    TRP   185      20.289   14.879   32.518  1.00  19.30       MTGL
ATOM   1440  CA   TRP   185      20.498   15.704   31.333  1.00  19.09       MTGL
ATOM   1441  CB   TRP   185      19.148   16.149   30.753  1.00  18.81       MTGL
ATOM   1442  CG   TRP   185      19.267   17.255   29.746  1.00  18.32       MTGL
ATOM   1443  CD2  TRP   185      20.044   17.245   28.541  1.00  18.10       MTGL
ATOM   1444  CE2  TRP   185      19.889   18.509   27.933  1.00  18.68       MTGL
ATOM   1445  CE3  TRP   185      20.856   16.290   27.917  1.00  18.54       MTGL
ATOM   1446  CD1  TRP   185      18.686   18.491   29.814  1.00  18.71       MTGL
ATOM   1447  NE1  TRP   185      19.057   19.250   28.730  1.00  18.49       MTGL
ATOM   1448  CZ2  TRP   185      20.518   18.845   26.732  1.00  19.18       MTGL
ATOM   1449  CZ3  TRP   185      21.484   16.626   26.722  1.00  18.13       MTGL
```

Fig. 1 cont.

| | | | | | | | | | |
|---|---|---|---|---|---|---|---|---|---|
| ATOM | 1450 | CH2 | TRP | 185 | 21.311 | 17.891 | 26.144 | 1.00 19.60 | MTGL |
| ATOM | 1451 | C | TRP | 185 | 21.360 | 16.931 | 31.626 | 1.00 18.76 | MTGL |
| ATOM | 1452 | O | TRP | 185 | 22.271 | 17.256 | 30.866 | 1.00 17.61 | MTGL |
| ATOM | 1453 | N | GLY | 186 | 21.068 | 17.612 | 32.731 | 1.00 19.33 | MTGL |
| ATOM | 1454 | CA | GLY | 186 | 21.834 | 18.797 | 33.081 | 1.00 19.04 | MTGL |
| ATOM | 1455 | C | GLY | 186 | 23.336 | 18.565 | 33.066 | 1.00 19.17 | MTGL |
| ATOM | 1456 | O | GLY | 186 | 24.098 | 19.353 | 32.505 | 1.00 19.02 | MTGL |
| ATOM | 1457 | N | THR | 187 | 23.772 | 17.473 | 33.677 | 1.00 19.36 | MTGL |
| ATOM | 1458 | CA | THR | 187 | 25.192 | 17.172 | 33.718 | 1.00 20.31 | MTGL |
| ATOM | 1459 | CB | THR | 187 | 25.482 | 16.098 | 34.773 | 1.00 21.41 | MTGL |
| ATOM | 1460 | OG1 | THR | 187 | 25.114 | 16.609 | 36.059 | 1.00 21.37 | MTGL |
| ATOM | 1461 | CG2 | THR | 187 | 26.964 | 15.735 | 34.781 | 1.00 23.08 | MTGL |
| ATOM | 1462 | C | THR | 187 | 25.731 | 16.745 | 32.359 | 1.00 19.27 | MTGL |
| ATOM | 1463 | O | THR | 187 | 26.815 | 17.166 | 31.965 | 1.00 19.21 | MTGL |
| ATOM | 1464 | N | GLN | 188 | 24.980 | 15.916 | 31.637 | 1.00 19.95 | MTGL |
| ATOM | 1465 | CA | GLN | 188 | 25.420 | 15.479 | 30.312 | 1.00 19.24 | MTGL |
| ATOM | 1466 | CB | GLN | 188 | 24.356 | 14.602 | 29.638 | 1.00 19.13 | MTGL |
| ATOM | 1467 | CG | GLN | 188 | 24.033 | 13.278 | 30.329 | 1.00 18.75 | MTGL |
| ATOM | 1468 | CD | GLN | 188 | 25.203 | 12.299 | 30.339 | 1.00 18.38 | MTGL |
| ATOM | 1469 | OE1 | GLN | 188 | 25.874 | 12.099 | 29.328 | 1.00 18.47 | MTGL |
| ATOM | 1470 | NE2 | GLN | 188 | 25.435 | 11.675 | 31.483 | 1.00 16.34 | MTGL |
| ATOM | 1471 | C | GLN | 188 | 25.655 | 16.714 | 29.437 | 1.00 19.43 | MTGL |
| ATOM | 1472 | O | GLN | 188 | 26.695 | 16.850 | 28.792 | 1.00 18.38 | MTGL |
| ATOM | 1473 | N | ASN | 189 | 24.673 | 17.612 | 29.429 | 1.00 20.01 | MTGL |
| ATOM | 1474 | CA | ASN | 189 | 24.733 | 18.830 | 28.625 | 1.00 20.84 | MTGL |
| ATOM | 1475 | CB | ASN | 189 | 23.392 | 19.568 | 28.722 | 1.00 22.61 | MTGL |
| ATOM | 1476 | CG | ASN | 189 | 23.323 | 20.781 | 27.813 | 1.00 24.36 | MTGL |
| ATOM | 1477 | OD1 | ASN | 189 | 23.788 | 20.744 | 26.674 | 1.00 24.74 | MTGL |
| ATOM | 1478 | ND2 | ASN | 189 | 22.725 | 21.860 | 28.310 | 1.00 24.46 | MTGL |
| ATOM | 1479 | C | ASN | 189 | 25.878 | 19.746 | 29.050 | 1.00 21.20 | MTGL |
| ATOM | 1480 | O | ASN | 189 | 26.622 | 20.267 | 28.214 | 1.00 20.76 | MTGL |
| ATOM | 1481 | N | TRP | 190 | 26.015 | 19.935 | 30.356 | 1.00 21.74 | MTGL |
| ATOM | 1482 | CA | TRP | 190 | 27.073 | 20.770 | 30.917 | 1.00 22.16 | MTGL |
| ATOM | 1483 | CB | TRP | 190 | 26.959 | 20.758 | 32.442 | 1.00 23.20 | MTGL |
| ATOM | 1484 | CG | TRP | 190 | 28.143 | 21.315 | 33.192 | 1.00 25.19 | MTGL |
| ATOM | 1485 | CD2 | TRP | 190 | 29.121 | 20.563 | 33.925 | 1.00 25.40 | MTGL |
| ATOM | 1486 | CE2 | TRP | 190 | 30.015 | 21.491 | 34.505 | 1.00 25.48 | MTGL |
| ATOM | 1487 | CE3 | TRP | 190 | 29.336 | 19.194 | 34.137 | 1.00 25.81 | MTGL |
| ATOM | 1488 | CD1 | TRP | 190 | 28.474 | 22.632 | 33.355 | 1.00 24.81 | MTGL |
| ATOM | 1489 | NE1 | TRP | 190 | 29.595 | 22.744 | 34.146 | 1.00 26.35 | MTGL |
| ATOM | 1490 | CZ2 | TRP | 190 | 31.098 | 21.095 | 35.298 | 1.00 26.43 | MTGL |
| ATOM | 1491 | CZ3 | TRP | 190 | 30.420 | 18.800 | 34.925 | 1.00 26.45 | MTGL |
| ATOM | 1492 | CH2 | TRP | 190 | 31.288 | 19.750 | 35.490 | 1.00 25.29 | MTGL |
| ATOM | 1493 | C | TRP | 190 | 28.451 | 20.252 | 30.493 | 1.00 21.86 | MTGL |
| ATOM | 1494 | O | TRP | 190 | 29.322 | 21.023 | 30.081 | 1.00 21.57 | MTGL |
| ATOM | 1495 | N | TRP | 191 | 28.637 | 18.939 | 30.586 | 1.00 20.42 | MTGL |
| ATOM | 1496 | CA | TRP | 191 | 29.915 | 18.325 | 30.245 | 1.00 19.96 | MTGL |
| ATOM | 1497 | CB | TRP | 191 | 29.902 | 16.846 | 30.631 | 1.00 18.89 | MTGL |
| ATOM | 1498 | CG | TRP | 191 | 31.272 | 16.231 | 30.703 | 1.00 18.14 | MTGL |
| ATOM | 1499 | CD2 | TRP | 191 | 32.017 | 15.658 | 29.621 | 1.00 17.74 | MTGL |
| ATOM | 1500 | CE2 | TRP | 191 | 33.244 | 15.201 | 30.154 | 1.00 17.14 | MTGL |
| ATOM | 1501 | CE3 | TRP | 191 | 31.767 | 15.481 | 28.253 | 1.00 17.05 | MTGL |
| ATOM | 1502 | CD1 | TRP | 191 | 32.058 | 16.108 | 31.815 | 1.00 18.47 | MTGL |
| ATOM | 1503 | NE1 | TRP | 191 | 33.241 | 15.489 | 31.494 | 1.00 16.67 | MTGL |
| ATOM | 1504 | CZ2 | TRP | 191 | 34.221 | 14.583 | 29.366 | 1.00 16.52 | MTGL |
| ATOM | 1505 | CZ3 | TRP | 191 | 32.739 | 14.862 | 27.468 | 1.00 15.97 | MTGL |
| ATOM | 1506 | CH2 | TRP | 191 | 33.950 | 14.420 | 28.030 | 1.00 16.29 | MTGL |
| ATOM | 1507 | C | TRP | 191 | 30.293 | 18.455 | 28.770 | 1.00 19.44 | MTGL |

Fig. 1 cont.

| ATOM | 1508 | O | TRP | 191 | 31.342 | 19.019 | 28.436 | 1.00 | 18.48 | MTGL |
|------|------|------|------|------|--------|--------|--------|------|-------|------|
| ATOM | 1509 | N | TYR | 192 | 29.447 | 17.921 | 27.893 | 1.00 | 19.02 | MTGL |
| ATOM | 1510 | CA | TYR | 192 | 29.707 | 17.961 | 26.455 | 1.00 | 18.88 | MTGL |
| ATOM | 1511 | CB | TYR | 192 | 28.629 | 17.174 | 25.702 | 1.00 | 18.06 | MTGL |
| ATOM | 1512 | CG | TYR | 192 | 28.820 | 15.670 | 25.779 | 1.00 | 17.74 | MTGL |
| ATOM | 1513 | CD1 | TYR | 192 | 29.890 | 15.048 | 25.126 | 1.00 | 17.96 | MTGL |
| ATOM | 1514 | CE1 | TYR | 192 | 30.069 | 13.671 | 25.189 | 1.00 | 18.35 | MTGL |
| ATOM | 1515 | CD2 | TYR | 192 | 27.935 | 14.870 | 26.502 | 1.00 | 16.89 | MTGL |
| ATOM | 1516 | CE2 | TYR | 192 | 28.107 | 13.487 | 26.574 | 1.00 | 17.96 | MTGL |
| ATOM | 1517 | CZ | TYR | 192 | 29.172 | 12.895 | 25.917 | 1.00 | 18.14 | MTGL |
| ATOM | 1518 | OH | TYR | 192 | 29.340 | 11.530 | 25.986 | 1.00 | 19.50 | MTGL |
| ATOM | 1519 | C | TYR | 192 | 29.810 | 19.378 | 25.895 | 1.00 | 19.64 | MTGL |
| ATOM | 1520 | O | TYR | 192 | 30.661 | 19.651 | 25.047 | 1.00 | 17.67 | MTGL |
| ATOM | 1521 | N | THR | 193 | 28.956 | 20.280 | 26.373 | 1.00 | 20.13 | MTGL |
| ATOM | 1522 | CA | THR | 193 | 28.988 | 21.658 | 25.904 | 1.00 | 21.63 | MTGL |
| ATOM | 1523 | CB | THR | 193 | 27.884 | 22.504 | 26.569 | 1.00 | 21.95 | MTGL |
| ATOM | 1524 | OG1 | THR | 193 | 26.600 | 21.990 | 26.195 | 1.00 | 23.39 | MTGL |
| ATOM | 1525 | CG2 | THR | 193 | 27.978 | 23.956 | 26.114 | 1.00 | 23.15 | MTGL |
| ATOM | 1526 | C | THR | 193 | 30.346 | 22.306 | 26.189 | 1.00 | 21.54 | MTGL |
| ATOM | 1527 | O | THR | 193 | 30.978 | 22.863 | 25.291 | 1.00 | 21.18 | MTGL |
| ATOM | 1528 | N | ASN | 194 | 30.804 | 22.218 | 27.434 | 1.00 | 21.85 | MTGL |
| ATOM | 1529 | CA | ASN | 194 | 32.084 | 22.816 | 27.800 | 1.00 | 22.13 | MTGL |
| ATOM | 1530 | CB | ASN | 194 | 32.243 | 22.833 | 29.318 | 1.00 | 23.00 | MTGL |
| ATOM | 1531 | CG | ASN | 194 | 31.437 | 23.944 | 29.968 | 1.00 | 24.26 | MTGL |
| ATOM | 1532 | OD1 | ASN | 194 | 31.675 | 25.123 | 29.709 | 1.00 | 25.08 | MTGL |
| ATOM | 1533 | ND2 | ASN | 194 | 30.478 | 23.573 | 30.810 | 1.00 | 23.61 | MTGL |
| ATOM | 1534 | C | ASN | 194 | 33.292 | 22.146 | 27.156 | 1.00 | 21.45 | MTGL |
| ATOM | 1535 | O | ASN | 194 | 34.266 | 22.813 | 26.815 | 1.00 | 21.18 | MTGL |
| ATOM | 1536 | N | VAL | 195 | 33.236 | 20.831 | 26.986 | 1.00 | 21.36 | MTGL |
| ATOM | 1537 | CA | VAL | 195 | 34.346 | 20.123 | 26.362 | 1.00 | 20.65 | MTGL |
| ATOM | 1538 | CB | VAL | 195 | 34.187 | 18.590 | 26.503 | 1.00 | 20.76 | MTGL |
| ATOM | 1539 | CG1 | VAL | 195 | 35.165 | 17.871 | 25.583 | 1.00 | 19.43 | MTGL |
| ATOM | 1540 | CG2 | VAL | 195 | 34.429 | 18.179 | 27.947 | 1.00 | 20.62 | MTGL |
| ATOM | 1541 | C | VAL | 195 | 34.453 | 20.475 | 24.879 | 1.00 | 21.44 | MTGL |
| ATOM | 1542 | O | VAL | 195 | 35.540 | 20.792 | 24.385 | 1.00 | 20.78 | MTGL |
| ATOM | 1543 | N | LEU | 196 | 33.323 | 20.429 | 24.178 | 1.00 | 21.29 | MTGL |
| ATOM | 1544 | CA | LEU | 196 | 33.300 | 20.712 | 22.746 | 1.00 | 23.23 | MTGL |
| ATOM | 1545 | CB | LEU | 196 | 31.953 | 20.285 | 22.150 | 1.00 | 22.71 | MTGL |
| ATOM | 1546 | CG | LEU | 196 | 31.703 | 18.772 | 22.118 | 1.00 | 24.14 | MTGL |
| ATOM | 1547 | CD1 | LEU | 196 | 30.276 | 18.477 | 21.657 | 1.00 | 22.72 | MTGL |
| ATOM | 1548 | CD2 | LEU | 196 | 32.720 | 18.115 | 21.187 | 1.00 | 23.15 | MTGL |
| ATOM | 1549 | C | LEU | 196 | 33.589 | 22.158 | 22.354 | 1.00 | 24.05 | MTGL |
| ATOM | 1550 | O | LEU | 196 | 34.054 | 22.413 | 21.250 | 1.00 | 24.38 | MTGL |
| ATOM | 1551 | N | LYS | 197 | 33.326 | 23.104 | 23.248 | 1.00 | 25.84 | MTGL |
| ATOM | 1552 | CA | LYS | 197 | 33.562 | 24.506 | 22.919 | 1.00 | 27.64 | MTGL |
| ATOM | 1553 | CB | LYS | 197 | 32.753 | 25.413 | 23.850 | 1.00 | 29.58 | MTGL |
| ATOM | 1554 | CG | LYS | 197 | 33.282 | 25.505 | 25.268 | 1.00 | 32.86 | MTGL |
| ATOM | 1555 | CD | LYS | 197 | 32.239 | 26.101 | 26.207 | 1.00 | 35.16 | MTGL |
| ATOM | 1556 | CE | LYS | 197 | 31.742 | 27.456 | 25.726 | 1.00 | 37.48 | MTGL |
| ATOM | 1557 | NZ | LYS | 197 | 30.672 | 28.001 | 26.617 | 1.00 | 39.55 | MTGL |
| ATOM | 1558 | C | LYS | 197 | 35.038 | 24.897 | 22.956 | 1.00 | 27.59 | MTGL |
| ATOM | 1559 | O | LYS | 197 | 35.397 | 26.010 | 22.577 | 1.00 | 27.09 | MTGL |
| ATOM | 1560 | N | GLN | 198 | 35.896 | 23.980 | 23.395 | 1.00 | 27.10 | MTGL |
| ATOM | 1561 | CA | GLN | 198 | 37.323 | 24.271 | 23.459 | 1.00 | 26.85 | MTGL |
| ATOM | 1562 | CB | GLN | 198 | 38.053 | 23.202 | 24.274 | 1.00 | 26.22 | MTGL |
| ATOM | 1563 | CG | GLN | 198 | 37.608 | 23.127 | 25.718 | 1.00 | 24.93 | MTGL |
| ATOM | 1564 | CD | GLN | 198 | 37.637 | 24.480 | 26.400 | 1.00 | 25.72 | MTGL |
| ATOM | 1565 | OE1 | GLN | 198 | 38.667 | 25.152 | 26.432 | 1.00 | 25.49 | MTGL |

Fig. 1 cont.

```
ATOM   1566  NE2 GLN   198      36.501  24.886  26.950  1.00 24.69      MTGL
ATOM   1567  C   GLN   198      37.953  24.381  22.071  1.00 27.46      MTGL
ATOM   1568  O   GLN   198      38.937  25.097  21.885  1.00 27.60      MTGL
ATOM   1569  N   GLY   199      37.401  23.664  21.101  1.00 27.40      MTGL
ATOM   1570  CA  GLY   199      37.941  23.738  19.757  1.00 28.72      MTGL
ATOM   1571  C   GLY   199      39.002  22.713  19.397  1.00 29.03      MTGL
ATOM   1572  O   GLY   199      39.487  22.711  18.269  1.00 30.82      MTGL
ATOM   1573  N   THR   200      39.382  21.852  20.337  1.00 27.35      MTGL
ATOM   1574  CA  THR   200      40.377  20.823  20.041  1.00 26.65      MTGL
ATOM   1575  CB  THR   200      41.335  20.596  21.230  1.00 26.55      MTGL
ATOM   1576  OG1 THR   200      40.579  20.447  22.438  1.00 27.05      MTGL
ATOM   1577  CG2 THR   200      42.297  21.780  21.366  1.00 26.96      MTGL
ATOM   1578  C   THR   200      39.633  19.532  19.705  1.00 25.68      MTGL
ATOM   1579  O   THR   200      39.665  19.072  18.569  1.00 25.00      MTGL
ATOM   1580  N   LEU   201      38.960  18.947  20.690  1.00 25.02      MTGL
ATOM   1581  CA  LEU   201      38.180  17.745  20.428  1.00 24.16      MTGL
ATOM   1582  CB  LEU   201      37.701  17.105  21.734  1.00 23.23      MTGL
ATOM   1583  CG  LEU   201      36.814  15.867  21.556  1.00 23.41      MTGL
ATOM   1584  CD1 LEU   201      37.674  14.680  21.136  1.00 22.70      MTGL
ATOM   1585  CD2 LEU   201      36.099  15.552  22.852  1.00 23.70      MTGL
ATOM   1586  C   LEU   201      36.967  18.221  19.628  1.00 23.81      MTGL
ATOM   1587  O   LEU   201      36.280  19.152  20.041  1.00 22.98      MTGL
ATOM   1588  N   GLU   202      36.710  17.608  18.480  1.00 23.89      MTGL
ATOM   1589  CA  GLU   202      35.554  18.002  17.672  1.00 25.20      MTGL
ATOM   1590  CB  GLU   202      35.962  18.281  16.227  1.00 26.99      MTGL
ATOM   1591  CG  GLU   202      37.142  19.208  16.054  1.00 30.89      MTGL
ATOM   1592  CD  GLU   202      37.380  19.539  14.596  1.00 33.28      MTGL
ATOM   1593  OE1 GLU   202      36.601  20.338  14.034  1.00 35.02      MTGL
ATOM   1594  OE2 GLU   202      38.333  18.989  14.004  1.00 34.29      MTGL
ATOM   1595  C   GLU   202      34.545  16.863  17.667  1.00 24.61      MTGL
ATOM   1596  O   GLU   202      34.886  15.725  17.990  1.00 23.46      MTGL
ATOM   1597  N   LEU   203      33.311  17.169  17.286  1.00 24.45      MTGL
ATOM   1598  CA  LEU   203      32.267  16.157  17.222  1.00 25.47      MTGL
ATOM   1599  CB  LEU   203      30.959  16.768  16.721  1.00 26.23      MTGL
ATOM   1600  CG  LEU   203      30.009  17.289  17.794  1.00 27.61      MTGL
ATOM   1601  CD1 LEU   203      28.830  17.970  17.126  1.00 28.79      MTGL
ATOM   1602  CD2 LEU   203      29.532  16.139  18.672  1.00 27.38      MTGL
ATOM   1603  C   LEU   203      32.666  15.007  16.305  1.00 25.18      MTGL
ATOM   1604  O   LEU   203      32.307  13.857  16.555  1.00 25.60      MTGL
ATOM   1605  N   SER   204      33.411  15.318  15.249  1.00 23.52      MTGL
ATOM   1606  CA  SER   204      33.841  14.295  14.305  1.00 23.46      MTGL
ATOM   1607  CB  SER   204      34.367  14.941  13.016  1.00 24.47      MTGL
ATOM   1608  OG  SER   204      35.559  15.677  13.253  1.00 23.17      MTGL
ATOM   1609  C   SER   204      34.918  13.379  14.877  1.00 22.84      MTGL
ATOM   1610  O   SER   204      35.235  12.353  14.278  1.00 22.80      MTGL
ATOM   1611  N   ASP   205      35.482  13.742  16.027  1.00 21.73      MTGL
ATOM   1612  CA  ASP   205      36.529  12.920  16.626  1.00 21.47      MTGL
ATOM   1613  CB  ASP   205      37.369  13.735  17.616  1.00 21.78      MTGL
ATOM   1614  CG  ASP   205      38.284  14.737  16.925  1.00 23.69      MTGL
ATOM   1615  OD1 ASP   205      38.859  14.388  15.870  1.00 23.46      MTGL
ATOM   1616  OD2 ASP   205      38.442  15.866  17.446  1.00 23.01      MTGL
ATOM   1617  C   ASP   205      36.020  11.653  17.310  1.00 20.42      MTGL
ATOM   1618  O   ASP   205      36.795  10.727  17.545  1.00 20.47      MTGL
ATOM   1619  N   PHE   206      34.736  11.609  17.650  1.00 19.52      MTGL
ATOM   1620  CA  PHE   206      34.183  10.408  18.275  1.00 20.33      MTGL
ATOM   1621  CB  PHE   206      34.060  10.565  19.801  1.00 18.69      MTGL
ATOM   1622  CG  PHE   206      33.098  11.626  20.244  1.00 18.95      MTGL
ATOM   1623  CD1 PHE   206      33.403  12.974  20.083  1.00 18.40      MTGL
```

Fig. 1 cont.

| | | | | | | | | | |
|---|---|---|---|---|---|---|---|---|---|
| ATOM | 1624 | CD2 | PHE | 206 | 31.899 | 11.275 | 20.861 | 1.00 18.16 | MTGL |
| ATOM | 1625 | CE1 | PHE | 206 | 32.529 | 13.959 | 20.534 | 1.00 19.01 | MTGL |
| ATOM | 1626 | CE2 | PHE | 206 | 31.015 | 12.253 | 21.316 | 1.00 19.53 | MTGL |
| ATOM | 1627 | CZ | PHE | 206 | 31.331 | 13.601 | 21.153 | 1.00 18.89 | MTGL |
| ATOM | 1628 | C | PHE | 206 | 32.850 | 10.031 | 17.642 | 1.00 20.83 | MTGL |
| ATOM | 1629 | O | PHE | 206 | 32.267 | 10.825 | 16.901 | 1.00 20.91 | MTGL |
| ATOM | 1630 | N | ASP | 207 | 32.365 | 8.827 | 17.937 | 1.00 20.94 | MTGL |
| ATOM | 1631 | CA | ASP | 207 | 31.134 | 8.331 | 17.322 | 1.00 21.05 | MTGL |
| ATOM | 1632 | CB | ASP | 207 | 31.470 | 7.084 | 16.500 | 1.00 21.79 | MTGL |
| ATOM | 1633 | CG | ASP | 207 | 32.766 | 7.235 | 15.730 | 1.00 22.83 | MTGL |
| ATOM | 1634 | OD1 | ASP | 207 | 32.811 | 8.093 | 14.826 | 1.00 22.13 | MTGL |
| ATOM | 1635 | OD2 | ASP | 207 | 33.739 | 6.506 | 16.036 | 1.00 21.38 | MTGL |
| ATOM | 1636 | C | ASP | 207 | 29.978 | 7.990 | 18.256 | 1.00 20.40 | MTGL |
| ATOM | 1637 | O | ASP | 207 | 28.813 | 8.022 | 17.847 | 1.00 20.09 | MTGL |
| ATOM | 1638 | N | MET | 208 | 30.286 | 7.660 | 19.502 | 1.00 19.17 | MTGL |
| ATOM | 1639 | CA | MET | 208 | 29.236 | 7.281 | 20.431 | 1.00 17.84 | MTGL |
| ATOM | 1640 | CB | MET | 208 | 29.282 | 5.771 | 20.688 | 1.00 17.36 | MTGL |
| ATOM | 1641 | CG | MET | 208 | 29.319 | 4.900 | 19.455 | 1.00 17.72 | MTGL |
| ATOM | 1642 | SD | MET | 208 | 29.434 | 3.141 | 19.906 | 1.00 19.72 | MTGL |
| ATOM | 1643 | CE | MET | 208 | 27.745 | 2.786 | 20.301 | 1.00 18.67 | MTGL |
| ATOM | 1644 | C | MET | 208 | 29.293 | 7.979 | 21.775 | 1.00 17.33 | MTGL |
| ATOM | 1645 | O | MET | 208 | 30.351 | 8.410 | 22.232 | 1.00 16.75 | MTGL |
| ATOM | 1646 | N | MET | 209 | 28.125 | 8.080 | 22.397 | 1.00 16.30 | MTGL |
| ATOM | 1647 | CA | MET | 209 | 27.991 | 8.653 | 23.722 | 1.00 17.25 | MTGL |
| ATOM | 1648 | CB | MET | 209 | 27.037 | 9.852 | 23.730 | 1.00 16.86 | MTGL |
| ATOM | 1649 | CG | MET | 209 | 27.525 | 11.048 | 22.926 | 1.00 17.20 | MTGL |
| ATOM | 1650 | SD | MET | 209 | 26.439 | 12.511 | 23.096 | 1.00 15.98 | MTGL |
| ATOM | 1651 | CE | MET | 209 | 27.636 | 13.808 | 22.762 | 1.00 17.32 | MTGL |
| ATOM | 1652 | C | MET | 209 | 27.405 | 7.529 | 24.557 | 1.00 16.92 | MTGL |
| ATOM | 1653 | O | MET | 209 | 26.311 | 7.033 | 24.273 | 1.00 16.52 | MTGL |
| ATOM | 1654 | N | GLY | 210 | 28.153 | 7.103 | 25.565 | 1.00 16.49 | MTGL |
| ATOM | 1655 | CA | GLY | 210 | 27.675 | 6.038 | 26.423 | 1.00 16.81 | MTGL |
| ATOM | 1656 | C | GLY | 210 | 27.361 | 6.585 | 27.797 | 1.00 16.14 | MTGL |
| ATOM | 1657 | O | GLY | 210 | 27.991 | 7.537 | 28.257 | 1.00 15.66 | MTGL |
| ATOM | 1658 | N | VAL | 211 | 26.370 | 5.998 | 28.450 | 1.00 16.46 | MTGL |
| ATOM | 1659 | CA | VAL | 211 | 25.999 | 6.431 | 29.784 | 1.00 15.55 | MTGL |
| ATOM | 1660 | CB | VAL | 211 | 24.691 | 7.247 | 29.773 | 1.00 15.54 | MTGL |
| ATOM | 1661 | CG1 | VAL | 211 | 24.824 | 8.449 | 28.839 | 1.00 16.27 | MTGL |
| ATOM | 1662 | CG2 | VAL | 211 | 23.525 | 6.354 | 29.353 | 1.00 14.06 | MTGL |
| ATOM | 1663 | C | VAL | 211 | 25.781 | 5.236 | 30.700 | 1.00 16.00 | MTGL |
| ATOM | 1664 | O | VAL | 211 | 25.418 | 4.148 | 30.243 | 1.00 15.69 | MTGL |
| ATOM | 1665 | N | SER | 212 | 26.013 | 5.445 | 31.991 | 1.00 15.22 | MTGL |
| ATOM | 1666 | CA | SER | 212 | 25.766 | 4.414 | 32.983 | 1.00 15.39 | MTGL |
| ATOM | 1667 | CB | SER | 212 | 26.741 | 4.537 | 34.158 | 1.00 15.48 | MTGL |
| ATOM | 1668 | OG | SER | 212 | 28.083 | 4.327 | 33.748 | 1.00 16.02 | MTGL |
| ATOM | 1669 | C | SER | 212 | 24.346 | 4.707 | 33.469 | 1.00 15.93 | MTGL |
| ATOM | 1670 | O | SER | 212 | 23.922 | 5.863 | 33.498 | 1.00 16.20 | MTGL |
| ATOM | 1671 | N | PHE | 213 | 23.599 | 3.670 | 33.821 | 1.00 15.04 | MTGL |
| ATOM | 1672 | CA | PHE | 213 | 22.248 | 3.866 | 34.323 | 1.00 15.18 | MTGL |
| ATOM | 1673 | CB | PHE | 213 | 21.218 | 3.762 | 33.191 | 1.00 14.75 | MTGL |
| ATOM | 1674 | CG | PHE | 213 | 19.801 | 3.982 | 33.647 | 1.00 14.40 | MTGL |
| ATOM | 1675 | CD1 | PHE | 213 | 19.383 | 5.238 | 34.071 | 1.00 15.35 | MTGL |
| ATOM | 1676 | CD2 | PHE | 213 | 18.897 | 2.924 | 33.694 | 1.00 14.80 | MTGL |
| ATOM | 1677 | CE1 | PHE | 213 | 18.079 | 5.441 | 34.542 | 1.00 15.59 | MTGL |
| ATOM | 1678 | CE2 | PHE | 213 | 17.594 | 3.113 | 34.160 | 1.00 15.14 | MTGL |
| ATOM | 1679 | CZ | PHE | 213 | 17.185 | 4.376 | 34.586 | 1.00 15.11 | MTGL |
| ATOM | 1680 | C | PHE | 213 | 21.956 | 2.821 | 35.388 | 1.00 16.01 | MTGL |
| ATOM | 1681 | O | PHE | 213 | 21.757 | 1.646 | 35.078 | 1.00 16.44 | MTGL |

Fig. 1 cont.

| | | | | | | | | | |
|---|---|---|---|---|---|---|---|---|---|
| ATOM | 1682 | N   | TYR | 214 | 21.954 | 3.258  | 36.644 | 1.00 16.44 | MTGL |
| ATOM | 1683 | CA  | TYR | 214 | 21.691 | 2.382  | 37.782 | 1.00 16.37 | MTGL |
| ATOM | 1684 | CB  | TYR | 214 | 22.917 | 2.332  | 38.700 | 1.00 16.76 | MTGL |
| ATOM | 1685 | CG  | TYR | 214 | 24.097 | 1.562  | 38.131 | 1.00 16.18 | MTGL |
| ATOM | 1686 | CD1 | TYR | 214 | 24.114 | 0.168  | 38.139 | 1.00 16.62 | MTGL |
| ATOM | 1687 | CE1 | TYR | 214 | 25.201 | -0.544 | 37.637 | 1.00 17.99 | MTGL |
| ATOM | 1688 | CD2 | TYR | 214 | 25.199 | 2.228  | 37.599 | 1.00 16.40 | MTGL |
| ATOM | 1689 | CE2 | TYR | 214 | 26.295 | 1.524  | 37.093 | 1.00 16.27 | MTGL |
| ATOM | 1690 | CZ  | TYR | 214 | 26.288 | 0.142  | 37.118 | 1.00 16.37 | MTGL |
| ATOM | 1691 | OH  | TYR | 214 | 27.375 | -0.556 | 36.648 | 1.00 17.15 | MTGL |
| ATOM | 1692 | C   | TYR | 214 | 20.479 | 2.904  | 38.554 | 1.00 17.45 | MTGL |
| ATOM | 1693 | O   | TYR | 214 | 20.246 | 4.111  | 38.632 | 1.00 17.08 | MTGL |
| ATOM | 1694 | N   | PRO | 215 | 19.691 | 1.997  | 39.140 | 1.00 17.07 | MTGL |
| ATOM | 1695 | CD  | PRO | 215 | 19.704 | 0.537  | 38.916 | 1.00 17.36 | MTGL |
| ATOM | 1696 | CA  | PRO | 215 | 18.506 | 2.395  | 39.896 | 1.00 17.11 | MTGL |
| ATOM | 1697 | CB  | PRO | 215 | 17.547 | 1.247  | 39.619 | 1.00 17.64 | MTGL |
| ATOM | 1698 | CG  | PRO | 215 | 18.481 | 0.060  | 39.693 | 1.00 17.35 | MTGL |
| ATOM | 1699 | C   | PRO | 215 | 18.728 | 2.576  | 41.395 | 1.00 18.08 | MTGL |
| ATOM | 1700 | O   | PRO | 215 | 17.847 | 3.078  | 42.092 | 1.00 17.47 | MTGL |
| ATOM | 1701 | N   | PHE | 216 | 19.896 | 2.180  | 41.891 | 1.00 18.78 | MTGL |
| ATOM | 1702 | CA  | PHE | 216 | 20.152 | 2.251  | 43.328 | 1.00 19.20 | MTGL |
| ATOM | 1703 | CB  | PHE | 216 | 20.530 | 0.851  | 43.836 | 1.00 17.80 | MTGL |
| ATOM | 1704 | CG  | PHE | 216 | 21.456 | 0.095  | 42.915 | 1.00 18.00 | MTGL |
| ATOM | 1705 | CD1 | PHE | 216 | 22.673 | 0.641  | 42.522 | 1.00 18.05 | MTGL |
| ATOM | 1706 | CD2 | PHE | 216 | 21.117 | -1.172 | 42.456 | 1.00 17.34 | MTGL |
| ATOM | 1707 | CE1 | PHE | 216 | 23.543 | -0.064 | 41.680 | 1.00 17.92 | MTGL |
| ATOM | 1708 | CE2 | PHE | 216 | 21.981 | -1.887 | 41.614 | 1.00 17.55 | MTGL |
| ATOM | 1709 | CZ  | PHE | 216 | 23.194 | -1.331 | 41.228 | 1.00 16.80 | MTGL |
| ATOM | 1710 | C   | PHE | 216 | 21.145 | 3.276  | 43.872 | 1.00 19.84 | MTGL |
| ATOM | 1711 | O   | PHE | 216 | 21.726 | 3.068  | 44.940 | 1.00 21.57 | MTGL |
| ATOM | 1712 | N   | TYR | 217 | 21.346 | 4.379  | 43.161 | 1.00 19.60 | MTGL |
| ATOM | 1713 | CA  | TYR | 217 | 22.251 | 5.419  | 43.647 | 1.00 20.50 | MTGL |
| ATOM | 1714 | CB  | TYR | 217 | 23.468 | 5.575  | 42.732 | 1.00 20.09 | MTGL |
| ATOM | 1715 | CG  | TYR | 217 | 24.398 | 4.382  | 42.724 | 1.00 21.44 | MTGL |
| ATOM | 1716 | CD1 | TYR | 217 | 24.956 | 3.895  | 43.909 | 1.00 21.17 | MTGL |
| ATOM | 1717 | CE1 | TYR | 217 | 25.815 | 2.797  | 43.902 | 1.00 21.86 | MTGL |
| ATOM | 1718 | CD2 | TYR | 217 | 24.721 | 3.739  | 41.529 | 1.00 20.83 | MTGL |
| ATOM | 1719 | CE2 | TYR | 217 | 25.577 | 2.642  | 41.511 | 1.00 21.46 | MTGL |
| ATOM | 1720 | CZ  | TYR | 217 | 26.120 | 2.174  | 42.697 | 1.00 21.33 | MTGL |
| ATOM | 1721 | OH  | TYR | 217 | 26.960 | 1.087  | 42.672 | 1.00 20.10 | MTGL |
| ATOM | 1722 | C   | TYR | 217 | 21.520 | 6.752  | 43.727 | 1.00 21.29 | MTGL |
| ATOM | 1723 | O   | TYR | 217 | 22.127 | 7.778  | 44.026 | 1.00 21.40 | MTGL |
| ATOM | 1724 | N   | SER | 218 | 20.218 | 6.725  | 43.450 | 1.00 21.47 | MTGL |
| ATOM | 1725 | CA  | SER | 218 | 19.387 | 7.926  | 43.475 | 1.00 22.44 | MTGL |
| ATOM | 1726 | CB  | SER | 218 | 20.043 | 9.050  | 42.677 | 1.00 23.02 | MTGL |
| ATOM | 1727 | OG  | SER | 218 | 19.128 | 10.108 | 42.463 | 1.00 23.85 | MTGL |
| ATOM | 1728 | C   | SER | 218 | 18.012 | 7.661  | 42.888 | 1.00 22.12 | MTGL |
| ATOM | 1729 | O   | SER | 218 | 17.888 | 7.058  | 41.821 | 1.00 22.86 | MTGL |
| ATOM | 1730 | N   | SER | 219 | 16.980 | 8.128  | 43.577 | 1.00 21.77 | MTGL |
| ATOM | 1731 | CA  | SER | 219 | 15.615 | 7.938  | 43.111 | 1.00 22.44 | MTGL |
| ATOM | 1732 | CB  | SER | 219 | 14.624 | 8.308  | 44.216 | 1.00 22.46 | MTGL |
| ATOM | 1733 | OG  | SER | 219 | 14.793 | 9.658  | 44.607 | 1.00 22.44 | MTGL |
| ATOM | 1734 | C   | SER | 219 | 15.333 | 8.782  | 41.867 | 1.00 22.56 | MTGL |
| ATOM | 1735 | O   | SER | 219 | 14.282 | 8.646  | 41.247 | 1.00 23.34 | MTGL |
| ATOM | 1736 | N   | SER | 220 | 16.267 | 9.653  | 41.503 | 1.00 22.13 | MTGL |
| ATOM | 1737 | CA  | SER | 220 | 16.088 | 10.488 | 40.319 | 1.00 22.61 | MTGL |
| ATOM | 1738 | CB  | SER | 220 | 17.037 | 11.691 | 40.358 | 1.00 23.25 | MTGL |
| ATOM | 1739 | OG  | SER | 220 | 16.688 | 12.584 | 41.403 | 1.00 25.72 | MTGL |

Fig. 1 cont.

| | | | | | | | | | | |
|---|---|---|---|---|---|---|---|---|---|---|
| ATOM | 1740 | C | SER | 220 | 16.330 | 9.704 | 39.032 | 1.00 | 22.26 | MTGL |
| ATOM | 1741 | O | SER | 220 | 16.025 | 10.187 | 37.942 | 1.00 | 22.75 | MTGL |
| ATOM | 1742 | N | ALA | 221 | 16.872 | 8.495 | 39.160 | 1.00 | 20.89 | MTGL |
| ATOM | 1743 | CA | ALA | 221 | 17.164 | 7.667 | 37.996 | 1.00 | 20.44 | MTGL |
| ATOM | 1744 | CB | ALA | 221 | 18.266 | 6.644 | 38.343 | 1.00 | 19.75 | MTGL |
| ATOM | 1745 | C | ALA | 221 | 15.933 | 6.949 | 37.439 | 1.00 | 20.80 | MTGL |
| ATOM | 1746 | O | ALA | 221 | 15.941 | 5.731 | 37.265 | 1.00 | 20.53 | MTGL |
| ATOM | 1747 | N | THR | 222 | 14.875 | 7.705 | 37.163 | 1.00 | 20.53 | MTGL |
| ATOM | 1748 | CA | THR | 222 | 13.651 | 7.134 | 36.607 | 1.00 | 20.82 | MTGL |
| ATOM | 1749 | CB | THR | 222 | 12.464 | 8.120 | 36.690 | 1.00 | 20.95 | MTGL |
| ATOM | 1750 | OG1 | THR | 222 | 12.792 | 9.310 | 35.966 | 1.00 | 21.38 | MTGL |
| ATOM | 1751 | CG2 | THR | 222 | 12.152 | 8.483 | 38.137 | 1.00 | 21.55 | MTGL |
| ATOM | 1752 | C | THR | 222 | 13.848 | 6.809 | 35.129 | 1.00 | 20.30 | MTGL |
| ATOM | 1753 | O | THR | 222 | 14.754 | 7.334 | 34.479 | 1.00 | 20.05 | MTGL |
| ATOM | 1754 | N | LEU | 223 | 12.990 | 5.947 | 34.598 | 1.00 | 20.97 | MTGL |
| ATOM | 1755 | CA | LEU | 223 | 13.060 | 5.583 | 33.190 | 1.00 | 20.57 | MTGL |
| ATOM | 1756 | CB | LEU | 223 | 12.116 | 4.412 | 32.894 | 1.00 | 21.05 | MTGL |
| ATOM | 1757 | CG | LEU | 223 | 12.455 | 3.097 | 33.612 | 1.00 | 22.20 | MTGL |
| ATOM | 1758 | CD1 | LEU | 223 | 11.415 | 2.039 | 33.276 | 1.00 | 22.93 | MTGL |
| ATOM | 1759 | CD2 | LEU | 223 | 13.841 | 2.629 | 33.195 | 1.00 | 21.13 | MTGL |
| ATOM | 1760 | C | LEU | 223 | 12.674 | 6.800 | 32.346 | 1.00 | 20.76 | MTGL |
| ATOM | 1761 | O | LEU | 223 | 13.214 | 7.009 | 31.258 | 1.00 | 19.94 | MTGL |
| ATOM | 1762 | N | SER | 224 | 11.741 | 7.607 | 32.852 | 1.00 | 20.13 | MTGL |
| ATOM | 1763 | CA | SER | 224 | 11.311 | 8.804 | 32.128 | 1.00 | 20.71 | MTGL |
| ATOM | 1764 | CB | SER | 224 | 10.096 | 9.448 | 32.812 | 1.00 | 21.29 | MTGL |
| ATOM | 1765 | OG | SER | 224 | 10.392 | 9.812 | 34.149 | 1.00 | 26.36 | MTGL |
| ATOM | 1766 | C | SER | 224 | 12.452 | 9.815 | 32.036 | 1.00 | 18.99 | MTGL |
| ATOM | 1767 | O | SER | 224 | 12.641 | 10.450 | 30.999 | 1.00 | 19.23 | MTGL |
| ATOM | 1768 | N | ALA | 225 | 13.214 | 9.967 | 33.115 | 1.00 | 18.09 | MTGL |
| ATOM | 1769 | CA | ALA | 225 | 14.333 | 10.901 | 33.093 | 1.00 | 17.82 | MTGL |
| ATOM | 1770 | CB | ALA | 225 | 14.928 | 11.057 | 34.492 | 1.00 | 17.28 | MTGL |
| ATOM | 1771 | C | ALA | 225 | 15.395 | 10.410 | 32.108 | 1.00 | 17.15 | MTGL |
| ATOM | 1772 | O | ALA | 225 | 16.018 | 11.208 | 31.410 | 1.00 | 18.25 | MTGL |
| ATOM | 1773 | N | LEU | 226 | 15.598 | 9.097 | 32.048 | 1.00 | 16.97 | MTGL |
| ATOM | 1774 | CA | LEU | 226 | 16.580 | 8.534 | 31.122 | 1.00 | 17.41 | MTGL |
| ATOM | 1775 | CB | LEU | 226 | 16.693 | 7.017 | 31.303 | 1.00 | 17.39 | MTGL |
| ATOM | 1776 | CG | LEU | 226 | 17.711 | 6.325 | 30.389 | 1.00 | 17.54 | MTGL |
| ATOM | 1777 | CD1 | LEU | 226 | 19.109 | 6.852 | 30.679 | 1.00 | 17.23 | MTGL |
| ATOM | 1778 | CD2 | LEU | 226 | 17.658 | 4.824 | 30.606 | 1.00 | 17.56 | MTGL |
| ATOM | 1779 | C | LEU | 226 | 16.126 | 8.839 | 29.696 | 1.00 | 17.60 | MTGL |
| ATOM | 1780 | O | LEU | 226 | 16.909 | 9.311 | 28.868 | 1.00 | 17.24 | MTGL |
| ATOM | 1781 | N | LYS | 227 | 14.854 | 8.566 | 29.423 | 1.00 | 17.18 | MTGL |
| ATOM | 1782 | CA | LYS | 227 | 14.277 | 8.811 | 28.105 | 1.00 | 18.16 | MTGL |
| ATOM | 1783 | CB | LYS | 227 | 12.780 | 8.488 | 28.120 | 1.00 | 18.24 | MTGL |
| ATOM | 1784 | CG | LYS | 227 | 12.007 | 8.984 | 26.890 | 1.00 | 18.81 | MTGL |
| ATOM | 1785 | CD | LYS | 227 | 12.540 | 8.394 | 25.590 | 1.00 | 17.63 | MTGL |
| ATOM | 1786 | CE | LYS | 227 | 11.629 | 8.737 | 24.411 | 1.00 | 18.20 | MTGL |
| ATOM | 1787 | NZ | LYS | 227 | 12.191 | 8.269 | 23.111 | 1.00 | 17.92 | MTGL |
| ATOM | 1788 | C | LYS | 227 | 14.476 | 10.258 | 27.668 | 1.00 | 18.40 | MTGL |
| ATOM | 1789 | O | LYS | 227 | 14.978 | 10.526 | 26.576 | 1.00 | 18.56 | MTGL |
| ATOM | 1790 | N | SER | 228 | 14.078 | 11.190 | 28.529 | 1.00 | 18.71 | MTGL |
| ATOM | 1791 | CA | SER | 228 | 14.209 | 12.610 | 28.225 | 1.00 | 18.63 | MTGL |
| ATOM | 1792 | CB | SER | 228 | 13.584 | 13.449 | 29.344 | 1.00 | 19.90 | MTGL |
| ATOM | 1793 | OG | SER | 228 | 13.763 | 14.835 | 29.096 | 1.00 | 20.80 | MTGL |
| ATOM | 1794 | C | SER | 228 | 15.662 | 13.022 | 28.024 | 1.00 | 18.30 | MTGL |
| ATOM | 1795 | O | SER | 228 | 15.973 | 13.778 | 27.106 | 1.00 | 18.71 | MTGL |
| ATOM | 1796 | N | SER | 229 | 16.553 | 12.525 | 28.880 | 1.00 | 17.99 | MTGL |
| ATOM | 1797 | CA | SER | 229 | 17.969 | 12.862 | 28.768 | 1.00 | 18.28 | MTGL |

Fig. 1 cont.

| | | | | | | | | | | |
|---|---|---|---|---|---|---|---|---|---|---|
| ATOM | 1798 | CB | SER | 229 | 18.752 | 12.299 | 29.962 | 1.00 | 18.83 | MTGL |
| ATOM | 1799 | OG | SER | 229 | 20.127 | 12.641 | 29.867 | 1.00 | 17.92 | MTGL |
| ATOM | 1800 | C | SER | 229 | 18.577 | 12.339 | 27.463 | 1.00 | 18.05 | MTGL |
| ATOM | 1801 | O | SER | 229 | 19.251 | 13.076 | 26.744 | 1.00 | 18.70 | MTGL |
| ATOM | 1802 | N | LEU | 230 | 18.338 | 11.070 | 27.149 | 1.00 | 17.87 | MTGL |
| ATOM | 1803 | CA | LEU | 230 | 18.884 | 10.503 | 25.920 | 1.00 | 17.26 | MTGL |
| ATOM | 1804 | CB | LEU | 230 | 18.620 | 8.994 | 25.860 | 1.00 | 16.24 | MTGL |
| ATOM | 1805 | CG | LEU | 230 | 19.265 | 8.162 | 26.976 | 1.00 | 16.12 | MTGL |
| ATOM | 1806 | CD1 | LEU | 230 | 19.069 | 6.676 | 26.671 | 1.00 | 16.29 | MTGL |
| ATOM | 1807 | CD2 | LEU | 230 | 20.749 | 8.473 | 27.084 | 1.00 | 12.97 | MTGL |
| ATOM | 1808 | C | LEU | 230 | 18.299 | 11.204 | 24.689 | 1.00 | 17.08 | MTGL |
| ATOM | 1809 | O | LEU | 230 | 19.014 | 11.458 | 23.721 | 1.00 | 15.52 | MTGL |
| ATOM | 1810 | N | ASP | 231 | 17.006 | 11.525 | 24.728 | 1.00 | 18.20 | MTGL |
| ATOM | 1811 | CA | ASP | 231 | 16.380 | 12.223 | 23.604 | 1.00 | 18.97 | MTGL |
| ATOM | 1812 | CB | ASP | 231 | 14.896 | 12.494 | 23.878 | 1.00 | 20.35 | MTGL |
| ATOM | 1813 | CG | ASP | 231 | 13.985 | 11.337 | 23.455 | 1.00 | 20.69 | MTGL |
| ATOM | 1814 | OD1 | ASP | 231 | 14.460 | 10.361 | 22.838 | 1.00 | 21.48 | MTGL |
| ATOM | 1815 | OD2 | ASP | 231 | 12.775 | 11.418 | 23.738 | 1.00 | 20.71 | MTGL |
| ATOM | 1816 | C | ASP | 231 | 17.102 | 13.553 | 23.393 | 1.00 | 19.05 | MTGL |
| ATOM | 1817 | O | ASP | 231 | 17.423 | 13.927 | 22.265 | 1.00 | 20.05 | MTGL |
| ATOM | 1818 | N | ASN | 232 | 17.369 | 14.260 | 24.486 | 1.00 | 18.97 | MTGL |
| ATOM | 1819 | CA | ASN | 232 | 18.057 | 15.546 | 24.403 | 1.00 | 19.27 | MTGL |
| ATOM | 1820 | CB | ASN | 232 | 18.126 | 16.219 | 25.781 | 1.00 | 19.34 | MTGL |
| ATOM | 1821 | CG | ASN | 232 | 16.775 | 16.752 | 26.238 | 1.00 | 21.88 | MTGL |
| ATOM | 1822 | OD1 | ASN | 232 | 15.911 | 17.054 | 25.420 | 1.00 | 23.78 | MTGL |
| ATOM | 1823 | ND2 | ASN | 232 | 16.595 | 16.882 | 27.545 | 1.00 | 21.09 | MTGL |
| ATOM | 1824 | C | ASN | 232 | 19.459 | 15.397 | 23.834 | 1.00 | 19.42 | MTGL |
| ATOM | 1825 | O | ASN | 232 | 19.887 | 16.205 | 23.003 | 1.00 | 19.51 | MTGL |
| ATOM | 1826 | N | MET | 233 | 20.174 | 14.368 | 24.280 | 1.00 | 19.18 | MTGL |
| ATOM | 1827 | CA | MET | 233 | 21.533 | 14.124 | 23.803 | 1.00 | 19.15 | MTGL |
| ATOM | 1828 | CB | MET | 233 | 22.151 | 12.936 | 24.551 | 1.00 | 18.27 | MTGL |
| ATOM | 1829 | CG | MET | 233 | 22.433 | 13.191 | 26.029 | 1.00 | 19.33 | MTGL |
| ATOM | 1830 | SD | MET | 233 | 22.806 | 11.662 | 26.940 | 1.00 | 19.17 | MTGL |
| ATOM | 1831 | CE | MET | 233 | 24.330 | 11.165 | 26.125 | 1.00 | 17.20 | MTGL |
| ATOM | 1832 | C | MET | 233 | 21.510 | 13.833 | 22.305 | 1.00 | 19.80 | MTGL |
| ATOM | 1833 | O | MET | 233 | 22.356 | 14.314 | 21.547 | 1.00 | 19.41 | MTGL |
| ATOM | 1834 | N | ALA | 234 | 20.529 | 13.043 | 21.885 | 1.00 | 20.01 | MTGL |
| ATOM | 1835 | CA | ALA | 234 | 20.390 | 12.673 | 20.480 | 1.00 | 21.04 | MTGL |
| ATOM | 1836 | CB | ALA | 234 | 19.274 | 11.633 | 20.324 | 1.00 | 19.66 | MTGL |
| ATOM | 1837 | C | ALA | 234 | 20.111 | 13.879 | 19.583 | 1.00 | 21.48 | MTGL |
| ATOM | 1838 | O | ALA | 234 | 20.761 | 14.055 | 18.549 | 1.00 | 20.87 | MTGL |
| ATOM | 1839 | N | LYS | 235 | 19.156 | 14.715 | 19.985 | 1.00 | 22.48 | MTGL |
| ATOM | 1840 | CA | LYS | 235 | 18.804 | 15.881 | 19.176 | 1.00 | 24.12 | MTGL |
| ATOM | 1841 | CB | LYS | 235 | 17.507 | 16.515 | 19.681 | 1.00 | 26.52 | MTGL |
| ATOM | 1842 | CG | LYS | 235 | 17.053 | 17.695 | 18.835 | 1.00 | 33.00 | MTGL |
| ATOM | 1843 | CD | LYS | 235 | 15.744 | 18.274 | 19.331 | 1.00 | 36.39 | MTGL |
| ATOM | 1844 | CE | LYS | 235 | 15.288 | 19.436 | 18.451 | 1.00 | 40.33 | MTGL |
| ATOM | 1845 | NZ | LYS | 235 | 13.979 | 19.997 | 18.912 | 1.00 | 42.05 | MTGL |
| ATOM | 1846 | C | LYS | 235 | 19.900 | 16.937 | 19.145 | 1.00 | 22.78 | MTGL |
| ATOM | 1847 | O | LYS | 235 | 20.041 | 17.660 | 18.169 | 1.00 | 21.57 | MTGL |
| ATOM | 1848 | N | THR | 236 | 20.688 | 17.014 | 20.209 | 1.00 | 23.01 | MTGL |
| ATOM | 1849 | CA | THR | 236 | 21.753 | 18.004 | 20.280 | 1.00 | 22.42 | MTGL |
| ATOM | 1850 | CB | THR | 236 | 22.146 | 18.289 | 21.744 | 1.00 | 22.63 | MTGL |
| ATOM | 1851 | OG1 | THR | 236 | 20.973 | 18.616 | 22.495 | 1.00 | 23.14 | MTGL |
| ATOM | 1852 | CG2 | THR | 236 | 23.118 | 19.459 | 21.818 | 1.00 | 22.49 | MTGL |
| ATOM | 1853 | C | THR | 236 | 23.020 | 17.635 | 19.506 | 1.00 | 22.72 | MTGL |
| ATOM | 1854 | O | THR | 236 | 23.556 | 18.468 | 18.773 | 1.00 | 22.41 | MTGL |
| ATOM | 1855 | N | TRP | 237 | 23.495 | 16.398 | 19.655 | 1.00 | 21.45 | MTGL |

Fig. 1 cont.

| | | | | | | | | | |
|---|---|---|---|---|---|---|---|---|---|
| ATOM | 1856 | CA | TRP | 237 | 24.728 | 15.984 | 18.984 | 1.00 21.17 | MTGL |
| ATOM | 1857 | CB | TRP | 237 | 25.773 | 15.621 | 20.041 | 1.00 21.53 | MTGL |
| ATOM | 1858 | CG | TRP | 237 | 26.103 | 16.796 | 20.916 | 1.00 21.36 | MTGL |
| ATOM | 1859 | CD2 | TRP | 237 | 25.684 | 17.004 | 22.270 | 1.00 20.90 | MTGL |
| ATOM | 1860 | CE2 | TRP | 237 | 26.156 | 18.274 | 22.662 | 1.00 20.29 | MTGL |
| ATOM | 1861 | CE3 | TRP | 237 | 24.957 | 16.237 | 23.191 | 1.00 20.64 | MTGL |
| ATOM | 1862 | CD1 | TRP | 237 | 26.795 | 17.920 | 20.554 | 1.00 21.20 | MTGL |
| ATOM | 1863 | NE1 | TRP | 237 | 26.827 | 18.811 | 21.595 | 1.00 19.36 | MTGL |
| ATOM | 1864 | CZ2 | TRP | 237 | 25.919 | 18.799 | 23.935 | 1.00 20.39 | MTGL |
| ATOM | 1865 | CZ3 | TRP | 237 | 24.724 | 16.760 | 24.458 | 1.00 20.25 | MTGL |
| ATOM | 1866 | CH2 | TRP | 237 | 25.205 | 18.028 | 24.817 | 1.00 20.45 | MTGL |
| ATOM | 1867 | C | TRP | 237 | 24.600 | 14.868 | 17.941 | 1.00 21.19 | MTGL |
| ATOM | 1868 | O | TRP | 237 | 25.561 | 14.555 | 17.238 | 1.00 20.33 | MTGL |
| ATOM | 1869 | N | ASN | 238 | 23.414 | 14.274 | 17.865 | 0.50 21.58 | MTGL |
| ATOM | 1870 | CA | ASN | 238 | 23.119 | 13.212 | 16.908 | 0.50 21.97 | MTGL |
| ATOM | 1871 | CB | ASN | 238 | 22.847 | 13.829 | 15.534 | 0.50 23.20 | MTGL |
| ATOM | 1872 | CG | ASN | 238 | 21.696 | 14.822 | 15.560 | 0.50 24.82 | MTGL |
| ATOM | 1873 | OD1 | ASN | 238 | 20.631 | 14.540 | 16.107 | 0.50 25.88 | MTGL |
| ATOM | 1874 | ND2 | ASN | 238 | 21.904 | 15.989 | 14.960 | 0.50 26.50 | MTGL |
| ATOM | 1875 | C | ASN | 238 | 24.179 | 12.113 | 16.782 | 0.50 21.69 | MTGL |
| ATOM | 1876 | O | ASN | 238 | 24.564 | 11.730 | 15.678 | 0.50 21.51 | MTGL |
| ATOM | 1877 | N | LYS | 239 | 24.644 | 11.607 | 17.919 | 1.00 21.56 | MTGL |
| ATOM | 1878 | CA | LYS | 239 | 25.639 | 10.534 | 17.938 | 1.00 20.81 | MTGL |
| ATOM | 1879 | CB | LYS | 239 | 26.732 | 10.832 | 18.971 | 1.00 21.93 | MTGL |
| ATOM | 1880 | CG | LYS | 239 | 27.684 | 11.957 | 18.598 | 1.00 21.60 | MTGL |
| ATOM | 1881 | CD | LYS | 239 | 28.521 | 11.569 | 17.396 | 1.00 23.06 | MTGL |
| ATOM | 1882 | CE | LYS | 239 | 29.543 | 12.633 | 17.053 | 1.00 23.30 | MTGL |
| ATOM | 1883 | NZ | LYS | 239 | 30.266 | 12.280 | 15.800 | 1.00 22.03 | MTGL |
| ATOM | 1884 | C | LYS | 239 | 24.927 | 9.243 | 18.331 | 1.00 20.23 | MTGL |
| ATOM | 1885 | O | LYS | 239 | 23.814 | 9.287 | 18.856 | 1.00 19.43 | MTGL |
| ATOM | 1886 | N | GLU | 240 | 25.548 | 8.096 | 18.072 | 1.00 19.70 | MTGL |
| ATOM | 1887 | CA | GLU | 240 | 24.933 | 6.835 | 18.467 | 1.00 19.84 | MTGL |
| ATOM | 1888 | CB | GLU | 240 | 25.702 | 5.633 | 17.912 | 1.00 21.53 | MTGL |
| ATOM | 1889 | CG | GLU | 240 | 25.612 | 5.485 | 16.402 | 1.00 24.54 | MTGL |
| ATOM | 1890 | CD | GLU | 240 | 25.950 | 4.081 | 15.930 | 1.00 26.26 | MTGL |
| ATOM | 1891 | OE1 | GLU | 240 | 26.984 | 3.532 | 16.366 | 1.00 27.61 | MTGL |
| ATOM | 1892 | OE2 | GLU | 240 | 25.179 | 3.527 | 15.118 | 1.00 28.35 | MTGL |
| ATOM | 1893 | C | GLU | 240 | 24.972 | 6.823 | 19.985 | 1.00 18.12 | MTGL |
| ATOM | 1894 | O | GLU | 240 | 25.945 | 7.269 | 20.589 | 1.00 16.94 | MTGL |
| ATOM | 1895 | N | ILE | 241 | 23.910 | 6.320 | 20.598 | 1.00 17.17 | MTGL |
| ATOM | 1896 | CA | ILE | 241 | 23.816 | 6.290 | 22.049 | 1.00 17.75 | MTGL |
| ATOM | 1897 | CB | ILE | 241 | 22.639 | 7.161 | 22.509 | 1.00 18.47 | MTGL |
| ATOM | 1898 | CG2 | ILE | 241 | 22.411 | 6.997 | 24.013 | 1.00 19.08 | MTGL |
| ATOM | 1899 | CG1 | ILE | 241 | 22.918 | 8.617 | 22.126 | 1.00 17.74 | MTGL |
| ATOM | 1900 | CD1 | ILE | 241 | 21.732 | 9.539 | 22.297 | 1.00 18.08 | MTGL |
| ATOM | 1901 | C | ILE | 241 | 23.651 | 4.894 | 22.625 | 1.00 17.68 | MTGL |
| ATOM | 1902 | O | ILE | 241 | 23.020 | 4.026 | 22.015 | 1.00 16.98 | MTGL |
| ATOM | 1903 | N | ALA | 242 | 24.219 | 4.683 | 23.809 | 1.00 17.80 | MTGL |
| ATOM | 1904 | CA | ALA | 242 | 24.115 | 3.389 | 24.465 | 1.00 17.48 | MTGL |
| ATOM | 1905 | CB | ALA | 242 | 25.170 | 2.433 | 23.906 | 1.00 16.79 | MTGL |
| ATOM | 1906 | C | ALA | 242 | 24.244 | 3.457 | 25.977 | 1.00 16.97 | MTGL |
| ATOM | 1907 | O | ALA | 242 | 24.966 | 4.291 | 26.520 | 1.00 16.47 | MTGL |
| ATOM | 1908 | N | VAL | 243 | 23.505 | 2.586 | 26.654 | 1.00 16.88 | MTGL |
| ATOM | 1909 | CA | VAL | 243 | 23.594 | 2.478 | 28.098 | 1.00 16.35 | MTGL |
| ATOM | 1910 | CB | VAL | 243 | 22.261 | 2.003 | 28.715 | 1.00 15.54 | MTGL |
| ATOM | 1911 | CG1 | VAL | 243 | 22.470 | 1.580 | 30.159 | 1.00 16.43 | MTGL |
| ATOM | 1912 | CG2 | VAL | 243 | 21.238 | 3.133 | 28.655 | 1.00 15.23 | MTGL |
| ATOM | 1913 | C | VAL | 243 | 24.667 | 1.396 | 28.212 | 1.00 16.01 | MTGL |

Fig. 1 cont.

```
ATOM   1914  O    VAL  243      24.424   0.243  27.856  1.00 16.07      MTGL
ATOM   1915  N    VAL  244      25.860   1.774  28.665  1.00 15.48      MTGL
ATOM   1916  CA   VAL  244      26.971   0.822  28.758  1.00 15.55      MTGL
ATOM   1917  CB   VAL  244      28.292   1.501  28.345  1.00 15.25      MTGL
ATOM   1918  CG1  VAL  244      28.167   2.024  26.922  1.00 15.71      MTGL
ATOM   1919  CG2  VAL  244      28.618   2.646  29.294  1.00 14.98      MTGL
ATOM   1920  C    VAL  244      27.163   0.125  30.097  1.00 15.27      MTGL
ATOM   1921  O    VAL  244      28.052  -0.710  30.244  1.00 16.53      MTGL
ATOM   1922  N    GLU  245      26.326   0.464  31.068  1.00 15.31      MTGL
ATOM   1923  CA   GLU  245      26.387  -0.145  32.391  1.00 15.54      MTGL
ATOM   1924  CB   GLU  245      27.390   0.581  33.301  1.00 15.71      MTGL
ATOM   1925  CG   GLU  245      28.833   0.193  33.105  1.00 17.89      MTGL
ATOM   1926  CD   GLU  245      29.738   0.777  34.177  1.00 19.37      MTGL
ATOM   1927  OE1  GLU  245      29.322   0.824  35.359  1.00 18.55      MTGL
ATOM   1928  OE2  GLU  245      30.867   1.174  33.827  1.00 20.37      MTGL
ATOM   1929  C    GLU  245      25.024  -0.053  33.043  1.00 15.41      MTGL
ATOM   1930  O    GLU  245      24.421   1.014  33.060  1.00 16.55      MTGL
ATOM   1931  N    THR  246      24.533  -1.174  33.563  1.00 15.11      MTGL
ATOM   1932  CA   THR  246      23.266  -1.185  34.280  1.00 14.75      MTGL
ATOM   1933  CB   THR  246      22.053  -1.052  33.322  1.00 15.60      MTGL
ATOM   1934  OG1  THR  246      20.884  -0.721  34.085  1.00 14.95      MTGL
ATOM   1935  CG2  THR  246      21.809  -2.352  32.564  1.00 14.91      MTGL
ATOM   1936  C    THR  246      23.168  -2.467  35.100  1.00 14.67      MTGL
ATOM   1937  O    THR  246      23.853  -3.451  34.807  1.00 15.70      MTGL
ATOM   1938  N    ASN  247      22.331  -2.441  36.134  1.00 14.38      MTGL
ATOM   1939  CA   ASN  247      22.128  -3.579  37.035  1.00 14.91      MTGL
ATOM   1940  CB   ASN  247      23.012  -3.462  38.294  1.00 15.25      MTGL
ATOM   1941  CG   ASN  247      24.397  -4.085  38.150  1.00 16.92      MTGL
ATOM   1942  OD1  ASN  247      25.212  -3.972  39.068  1.00 16.53      MTGL
ATOM   1943  ND2  ASN  247      24.668  -4.746  37.024  1.00 14.82      MTGL
ATOM   1944  C    ASN  247      20.693  -3.554  37.560  1.00 15.99      MTGL
ATOM   1945  O    ASN  247      20.057  -2.496  37.609  1.00 15.64      MTGL
ATOM   1946  N    TRP  248      20.194  -4.723  37.946  1.00 15.53      MTGL
ATOM   1947  CA   TRP  248      18.893  -4.830  38.600  1.00 16.36      MTGL
ATOM   1948  CB   TRP  248      17.732  -5.127  37.657  1.00 14.84      MTGL
ATOM   1949  CG   TRP  248      16.455  -5.135  38.445  1.00 13.73      MTGL
ATOM   1950  CD2  TRP  248      15.743  -3.989  38.940  1.00 14.11      MTGL
ATOM   1951  CE2  TRP  248      14.684  -4.467  39.739  1.00 12.13      MTGL
ATOM   1952  CE3  TRP  248      15.902  -2.603  38.786  1.00 14.57      MTGL
ATOM   1953  CD1  TRP  248      15.812  -6.224  38.949  1.00 13.26      MTGL
ATOM   1954  NE1  TRP  248      14.751  -5.833  39.728  1.00 13.69      MTGL
ATOM   1955  CZ2  TRP  248      13.784  -3.613  40.384  1.00 14.00      MTGL
ATOM   1956  CZ3  TRP  248      15.008  -1.751  39.427  1.00 13.98      MTGL
ATOM   1957  CH2  TRP  248      13.962  -2.260  40.218  1.00 14.50      MTGL
ATOM   1958  C    TRP  248      19.080  -5.972  39.576  1.00 16.41      MTGL
ATOM   1959  O    TRP  248      19.507  -7.060  39.200  1.00 17.70      MTGL
ATOM   1960  N    PRO  249      18.765  -5.739  40.850  1.00 17.62      MTGL
ATOM   1961  CD   PRO  249      18.316  -4.468  41.449  1.00 17.41      MTGL
ATOM   1962  CA   PRO  249      18.933  -6.774  41.868  1.00 17.81      MTGL
ATOM   1963  CB   PRO  249      19.010  -5.961  43.156  1.00 18.08      MTGL
ATOM   1964  CG   PRO  249      18.056  -4.857  42.892  1.00 20.03      MTGL
ATOM   1965  C    PRO  249      17.922  -7.898  41.972  1.00 18.16      MTGL
ATOM   1966  O    PRO  249      16.729  -7.722  41.728  1.00 18.74      MTGL
ATOM   1967  N    ILE  250      18.426  -9.074  42.322  1.00 18.86      MTGL
ATOM   1968  CA   ILE  250      17.561 -10.215  42.549  1.00 20.06      MTGL
ATOM   1969  CB   ILE  250      18.189 -11.544  42.040  1.00 20.52      MTGL
ATOM   1970  CG2  ILE  250      18.230 -11.553  40.518  1.00 19.08      MTGL
ATOM   1971  CG1  ILE  250      19.590 -11.734  42.614  1.00 20.81      MTGL
```

Fig. 1 cont.

| | | | | | | | | | | |
|---|---|---|---|---|---|---|---|---|---|---|
| ATOM | 1972 | CD1 | ILE | 250 | 20.222 | -13.061 | 42.216 | 1.00 | 21.09 | MTGL |
| ATOM | 1973 | C | ILE | 250 | 17.408 | -10.234 | 44.075 | 1.00 | 19.97 | MTGL |
| ATOM | 1974 | O | ILE | 250 | 16.659 | -11.028 | 44.637 | 1.00 | 20.48 | MTGL |
| ATOM | 1975 | N | SER | 251 | 18.127 | -9.327 | 44.735 | 1.00 | 20.21 | MTGL |
| ATOM | 1976 | CA | SER | 251 | 18.072 | -9.206 | 46.188 | 1.00 | 21.30 | MTGL |
| ATOM | 1977 | CB | SER | 251 | 18.878 | -10.331 | 46.843 | 1.00 | 22.63 | MTGL |
| ATOM | 1978 | OG | SER | 251 | 18.757 | -10.273 | 48.253 | 1.00 | 24.04 | MTGL |
| ATOM | 1979 | C | SER | 251 | 18.603 | -7.855 | 46.658 | 1.00 | 21.50 | MTGL |
| ATOM | 1980 | O | SER | 251 | 19.735 | -7.485 | 46.343 | 1.00 | 21.25 | MTGL |
| ATOM | 1981 | N | CYS | 252 | 17.784 | -7.112 | 47.400 | 1.00 | 21.87 | MTGL |
| ATOM | 1982 | CA | CYS | 252 | 18.194 | -5.806 | 47.918 | 1.00 | 23.27 | MTGL |
| ATOM | 1983 | C | CYS | 252 | 17.529 | -5.505 | 49.263 | 1.00 | 24.17 | MTGL |
| ATOM | 1984 | O | CYS | 252 | 16.654 | -4.647 | 49.340 | 1.00 | 24.61 | MTGL |
| ATOM | 1985 | CB | CYS | 252 | 17.840 | -4.684 | 46.927 | 1.00 | 23.57 | MTGL |
| ATOM | 1986 | SG | CYS | 252 | 18.756 | -3.154 | 47.311 | 1.00 | 23.83 | MTGL |
| ATOM | 1987 | N | PRO | 253 | 17.951 | -6.199 | 50.340 | 1.00 | 25.34 | MTGL |
| ATOM | 1988 | CD | PRO | 253 | 18.950 | -7.281 | 50.290 | 1.00 | 26.08 | MTGL |
| ATOM | 1989 | CA | PRO | 253 | 17.428 | -6.052 | 51.707 | 1.00 | 25.93 | MTGL |
| ATOM | 1990 | CB | PRO | 253 | 18.308 | -7.001 | 52.518 | 1.00 | 26.63 | MTGL |
| ATOM | 1991 | CG | PRO | 253 | 18.627 | -8.068 | 51.539 | 1.00 | 27.12 | MTGL |
| ATOM | 1992 | C | PRO | 253 | 17.416 | -4.645 | 52.294 | 1.00 | 26.16 | MTGL |
| ATOM | 1993 | O | PRO | 253 | 16.415 | -4.223 | 52.865 | 1.00 | 26.46 | MTGL |
| ATOM | 1994 | N | ASN | 254 | 18.526 | -3.922 | 52.178 | 1.00 | 26.96 | MTGL |
| ATOM | 1995 | CA | ASN | 254 | 18.574 | -2.560 | 52.713 | 1.00 | 27.76 | MTGL |
| ATOM | 1996 | CB | ASN | 254 | 19.145 | -2.538 | 54.137 | 1.00 | 29.54 | MTGL |
| ATOM | 1997 | CG | ASN | 254 | 20.541 | -3.097 | 54.220 | 1.00 | 31.33 | MTGL |
| ATOM | 1998 | OD1 | ASN | 254 | 20.854 | -4.102 | 53.587 | 1.00 | 34.28 | MTGL |
| ATOM | 1999 | ND2 | ASN | 254 | 21.388 | -2.465 | 55.028 | 1.00 | 30.87 | MTGL |
| ATOM | 2000 | C | ASN | 254 | 19.329 | -1.580 | 51.834 | 1.00 | 26.98 | MTGL |
| ATOM | 2001 | O | ASN | 254 | 20.525 | -1.355 | 51.990 | 1.00 | 26.72 | MTGL |
| ATOM | 2002 | N | PRO | 255 | 18.623 | -0.993 | 50.873 | 1.00 | 26.12 | MTGL |
| ATOM | 2003 | CD | PRO | 255 | 17.274 | -1.385 | 50.443 | 1.00 | 25.65 | MTGL |
| ATOM | 2004 | CA | PRO | 255 | 19.222 | -0.023 | 49.957 | 1.00 | 25.15 | MTGL |
| ATOM | 2005 | CB | PRO | 255 | 18.128 | 0.211 | 48.913 | 1.00 | 25.50 | MTGL |
| ATOM | 2006 | CG | PRO | 255 | 16.895 | -0.262 | 49.550 | 1.00 | 25.88 | MTGL |
| ATOM | 2007 | C | PRO | 255 | 19.638 | 1.279 | 50.637 | 1.00 | 25.08 | MTGL |
| ATOM | 2008 | O | PRO | 255 | 18.993 | 1.735 | 51.586 | 1.00 | 24.66 | MTGL |
| ATOM | 2009 | N | ARG | 256 | 20.717 | 1.869 | 50.128 | 1.00 | 23.54 | MTGL |
| ATOM | 2010 | CA | ARG | 256 | 21.219 | 3.131 | 50.653 | 1.00 | 24.56 | MTGL |
| ATOM | 2011 | CB | ARG | 256 | 22.679 | 3.345 | 50.230 | 1.00 | 26.20 | MTGL |
| ATOM | 2012 | CG | ARG | 256 | 23.290 | 4.673 | 50.685 | 1.00 | 29.88 | MTGL |
| ATOM | 2013 | CD | ARG | 256 | 23.244 | 4.843 | 52.205 | 1.00 | 33.75 | MTGL |
| ATOM | 2014 | NE | ARG | 256 | 24.112 | 3.900 | 52.913 | 1.00 | 36.98 | MTGL |
| ATOM | 2015 | CZ | ARG | 256 | 24.215 | 3.826 | 54.241 | 1.00 | 38.13 | MTGL |
| ATOM | 2016 | NH1 | ARG | 256 | 23.503 | 4.638 | 55.016 | 1.00 | 37.96 | MTGL |
| ATOM | 2017 | NH2 | ARG | 256 | 25.034 | 2.942 | 54.796 | 1.00 | 38.27 | MTGL |
| ATOM | 2018 | C | ARG | 256 | 20.346 | 4.291 | 50.152 | 1.00 | 24.09 | MTGL |
| ATOM | 2019 | O | ARG | 256 | 20.223 | 5.312 | 50.820 | 1.00 | 22.82 | MTGL |
| ATOM | 2020 | N | TYR | 257 | 19.740 | 4.129 | 48.978 | 1.00 | 23.76 | MTGL |
| ATOM | 2021 | CA | TYR | 257 | 18.869 | 5.162 | 48.417 | 1.00 | 24.47 | MTGL |
| ATOM | 2022 | CB | TYR | 257 | 19.506 | 5.829 | 47.197 | 1.00 | 25.66 | MTGL |
| ATOM | 2023 | CG | TYR | 257 | 20.889 | 6.365 | 47.430 | 1.00 | 27.18 | MTGL |
| ATOM | 2024 | CD1 | TYR | 257 | 22.003 | 5.538 | 47.316 | 1.00 | 27.30 | MTGL |
| ATOM | 2025 | CE1 | TYR | 257 | 23.283 | 6.020 | 47.567 | 1.00 | 28.24 | MTGL |
| ATOM | 2026 | CD2 | TYR | 257 | 21.086 | 7.693 | 47.802 | 1.00 | 28.37 | MTGL |
| ATOM | 2027 | CE2 | TYR | 257 | 22.363 | 8.184 | 48.058 | 1.00 | 28.50 | MTGL |
| ATOM | 2028 | CZ | TYR | 257 | 23.455 | 7.341 | 47.940 | 1.00 | 29.46 | MTGL |
| ATOM | 2029 | OH | TYR | 257 | 24.720 | 7.814 | 48.215 | 1.00 | 30.61 | MTGL |

Fig. 1 cont.

```
ATOM   2030  C    TYR   257      17.539    4.578   47.986  1.00 24.30           MTGL
ATOM   2031  O    TYR   257      17.450    3.408   47.619  1.00 24.04           MTGL
ATOM   2032  N    SER   258      16.507    5.411   48.018  1.00 24.57           MTGL
ATOM   2033  CA   SER   258      15.178    4.984   47.607  1.00 24.95           MTGL
ATOM   2034  CB   SER   258      14.162    6.084   47.930  1.00 25.55           MTGL
ATOM   2035  OG   SER   258      14.261    6.471   49.292  1.00 27.69           MTGL
ATOM   2036  C    SER   258      15.230    4.746   46.102  1.00 23.31           MTGL
ATOM   2037  O    SER   258      15.949    5.449   45.392  1.00 23.48           MTGL
ATOM   2038  N    PHE   259      14.488    3.754   45.619  1.00 22.69           MTGL
ATOM   2039  CA   PHE   259      14.459    3.452   44.190  1.00 23.46           MTGL
ATOM   2040  CB   PHE   259      13.961    2.022   43.958  1.00 22.78           MTGL
ATOM   2041  CG   PHE   259      15.051    0.990   43.984  1.00 22.99           MTGL
ATOM   2042  CD1  PHE   259      15.923    0.904   45.066  1.00 24.03           MTGL
ATOM   2043  CD2  PHE   259      15.218    0.112   42.919  1.00 22.03           MTGL
ATOM   2044  CE1  PHE   259      16.945   -0.046   45.089  1.00 24.16           MTGL
ATOM   2045  CE2  PHE   259      16.233   -0.839   42.929  1.00 22.81           MTGL
ATOM   2046  CZ   PHE   259      17.103   -0.918   44.019  1.00 23.26           MTGL
ATOM   2047  C    PHE   259      13.580    4.429   43.411  1.00 23.33           MTGL
ATOM   2048  O    PHE   259      12.681    5.048   43.975  1.00 23.29           MTGL
ATOM   2049  N    PRO   260      13.840    4.581   42.100  1.00 23.87           MTGL
ATOM   2050  CD   PRO   260      14.959    4.002   41.338  1.00 23.34           MTGL
ATOM   2051  CA   PRO   260      13.057    5.492   41.259  1.00 23.83           MTGL
ATOM   2052  CB   PRO   260      13.711    5.346   39.888  1.00 23.96           MTGL
ATOM   2053  CG   PRO   260      15.138    5.012   40.229  1.00 23.75           MTGL
ATOM   2054  C    PRO   260      11.594    5.062   41.255  1.00 24.68           MTGL
ATOM   2055  O    PRO   260      11.287    3.867   41.233  1.00 22.71           MTGL
ATOM   2056  N    SER   261      10.700    6.042   41.274  1.00 24.81           MTGL
ATOM   2057  CA   SER   261       9.267    5.783   41.298  1.00 25.73           MTGL
ATOM   2058  CB   SER   261       8.494    7.107   41.254  1.00 26.69           MTGL
ATOM   2059  OG   SER   261       8.667    7.757   40.003  1.00 27.65           MTGL
ATOM   2060  C    SER   261       8.725    4.862   40.207  1.00 25.31           MTGL
ATOM   2061  O    SER   261       7.853    4.048   40.488  1.00 25.28           MTGL
ATOM   2062  N    ASP   262       9.214    4.979   38.973  1.00 26.49           MTGL
ATOM   2063  CA   ASP   262       8.678    4.131   37.909  1.00 27.78           MTGL
ATOM   2064  CB   ASP   262       8.762    4.824   36.535  1.00 27.44           MTGL
ATOM   2065  CG   ASP   262      10.166    5.267   36.170  1.00 29.75           MTGL
ATOM   2066  OD1  ASP   262      11.138    4.673   36.681  1.00 29.62           MTGL
ATOM   2067  OD2  ASP   262      10.289    6.207   35.349  1.00 29.82           MTGL
ATOM   2068  C    ASP   262       9.259    2.724   37.816  1.00 28.89           MTGL
ATOM   2069  O    ASP   262       9.063    2.037   36.812  1.00 29.03           MTGL
ATOM   2070  N    VAL   263       9.968    2.291   38.857  1.00 29.21           MTGL
ATOM   2071  CA   VAL   263      10.529    0.941   38.878  1.00 29.98           MTGL
ATOM   2072  CB   VAL   263      12.063    0.930   38.613  1.00 29.51           MTGL
ATOM   2073  CG1  VAL   263      12.355    1.468   37.226  1.00 28.86           MTGL
ATOM   2074  CG2  VAL   263      12.788    1.751   39.669  1.00 29.09           MTGL
ATOM   2075  C    VAL   263      10.254    0.257   40.218  1.00 30.76           MTGL
ATOM   2076  O    VAL   263      10.672   -0.879   40.434  1.00 30.49           MTGL
ATOM   2077  N    LYS   264       9.534    0.941   41.108  1.00 31.82           MTGL
ATOM   2078  CA   LYS   264       9.215    0.394   42.432  1.00 33.07           MTGL
ATOM   2079  CB   LYS   264       8.570    1.464   43.317  1.00 34.40           MTGL
ATOM   2080  CG   LYS   264       9.566    2.391   44.002  1.00 36.45           MTGL
ATOM   2081  CD   LYS   264       8.859    3.344   44.961  1.00 38.24           MTGL
ATOM   2082  CE   LYS   264       9.844    4.281   45.655  1.00 40.37           MTGL
ATOM   2083  NZ   LYS   264       9.148    5.291   46.508  1.00 40.59           MTGL
ATOM   2084  C    LYS   264       8.321   -0.842   42.415  1.00 33.40           MTGL
ATOM   2085  O    LYS   264       8.267   -1.595   43.394  1.00 33.28           MTGL
ATOM   2086  N    ASN   265       7.612   -1.049   41.313  1.00 32.77           MTGL
ATOM   2087  CA   ASN   265       6.738   -2.208   41.194  1.00 32.23           MTGL
```

Fig. 1 cont.

```
ATOM   2088  CB  ASN 265       5.587  -1.898  40.236  1.00 34.35      MTGL
ATOM   2089  CG  ASN 265       6.074  -1.544  38.845  1.00 36.81      MTGL
ATOM   2090  OD1 ASN 265       6.837  -0.593  38.667  1.00 37.33      MTGL
ATOM   2091  ND2 ASN 265       5.638  -2.311  37.848  1.00 38.71      MTGL
ATOM   2092  C   ASN 265       7.504  -3.436  40.689  1.00 30.70      MTGL
ATOM   2093  O   ASN 265       6.998  -4.555  40.744  1.00 30.83      MTGL
ATOM   2094  N   ILE 266       8.719  -3.226  40.192  1.00 28.28      MTGL
ATOM   2095  CA  ILE 266       9.517  -4.336  39.687  1.00 25.48      MTGL
ATOM   2096  CB  ILE 266      10.651  -3.848  38.767  1.00 23.96      MTGL
ATOM   2097  CG2 ILE 266      11.449  -5.046  38.257  1.00 23.40      MTGL
ATOM   2098  CG1 ILE 266      10.067  -3.054  37.594  1.00 23.38      MTGL
ATOM   2099  CD1 ILE 266      11.114  -2.516  36.627  1.00 22.30      MTGL
ATOM   2100  C   ILE 266      10.122  -5.094  40.867  1.00 24.88      MTGL
ATOM   2101  O   ILE 266      10.825  -4.520  41.691  1.00 22.68      MTGL
ATOM   2102  N   PRO 267       9.850  -6.404  40.960  1.00 24.25      MTGL
ATOM   2103  CD  PRO 267       9.012  -7.212  40.051  1.00 23.79      MTGL
ATOM   2104  CA  PRO 267      10.374  -7.225  42.052  1.00 23.72      MTGL
ATOM   2105  CB  PRO 267       9.542  -8.497  41.946  1.00 24.48      MTGL
ATOM   2106  CG  PRO 267       9.373  -8.633  40.455  1.00 24.22      MTGL
ATOM   2107  C   PRO 267      11.865  -7.526  41.943  1.00 23.20      MTGL
ATOM   2108  O   PRO 267      12.437  -7.515  40.851  1.00 22.29      MTGL
ATOM   2109  N   PHE 268      12.487  -7.781  43.090  1.00 22.29      MTGL
ATOM   2110  CA  PHE 268      13.898  -8.134  43.119  1.00 22.67      MTGL
ATOM   2111  CB  PHE 268      14.533  -7.757  44.462  1.00 22.68      MTGL
ATOM   2112  CG  PHE 268      14.493  -6.285  44.754  1.00 22.93      MTGL
ATOM   2113  CD1 PHE 268      14.838  -5.360  43.773  1.00 22.68      MTGL
ATOM   2114  CD2 PHE 268      14.115  -5.821  46.008  1.00 23.18      MTGL
ATOM   2115  CE1 PHE 268      14.806  -3.993  44.037  1.00 23.40      MTGL
ATOM   2116  CE2 PHE 268      14.079  -4.454  46.283  1.00 23.36      MTGL
ATOM   2117  CZ  PHE 268      14.425  -3.539  45.298  1.00 23.35      MTGL
ATOM   2118  C   PHE 268      13.925  -9.643  42.921  1.00 21.88      MTGL
ATOM   2119  O   PHE 268      13.780 -10.414  43.873  1.00 21.02      MTGL
ATOM   2120  N   SER 269      14.088 -10.049  41.667  1.00 21.08      MTGL
ATOM   2121  CA  SER 269      14.110 -11.457  41.294  1.00 20.72      MTGL
ATOM   2122  CB  SER 269      12.702 -12.052  41.417  1.00 19.79      MTGL
ATOM   2123  OG  SER 269      11.814 -11.416  40.509  1.00 19.06      MTGL
ATOM   2124  C   SER 269      14.554 -11.546  39.844  1.00 20.32      MTGL
ATOM   2125  O   SER 269      14.670 -10.530  39.161  1.00 19.97      MTGL
ATOM   2126  N   PRO 270      14.814 -12.767  39.354  1.00 21.15      MTGL
ATOM   2127  CD  PRO 270      14.896 -14.054  40.075  1.00 20.43      MTGL
ATOM   2128  CA  PRO 270      15.237 -12.915  37.958  1.00 20.91      MTGL
ATOM   2129  CB  PRO 270      15.407 -14.426  37.809  1.00 20.78      MTGL
ATOM   2130  CG  PRO 270      15.832 -14.852  39.196  1.00 20.58      MTGL
ATOM   2131  C   PRO 270      14.169 -12.348  37.016  1.00 20.97      MTGL
ATOM   2132  O   PRO 270      14.489 -11.688  36.028  1.00 20.64      MTGL
ATOM   2133  N   GLU 271      12.900 -12.605  37.331  1.00 21.15      MTGL
ATOM   2134  CA  GLU 271      11.797 -12.102  36.508  1.00 21.55      MTGL
ATOM   2135  CB  GLU 271      10.446 -12.538  37.082  1.00 22.38      MTGL
ATOM   2136  CG  GLU 271      10.155 -14.036  37.003  1.00 25.49      MTGL
ATOM   2137  CD  GLU 271      11.082 -14.873  37.870  1.00 26.37      MTGL
ATOM   2138  OE1 GLU 271      11.447 -14.415  38.970  1.00 26.39      MTGL
ATOM   2139  OE2 GLU 271      11.433 -15.997  37.457  1.00 27.82      MTGL
ATOM   2140  C   GLU 271      11.861 -10.577  36.476  1.00 20.84      MTGL
ATOM   2141  O   GLU 271      11.640  -9.949  35.434  1.00 20.80      MTGL
ATOM   2142  N   GLY 272      12.166  -9.993  37.631  1.00 19.71      MTGL
ATOM   2143  CA  GLY 272      12.271  -8.550  37.734  1.00 18.93      MTGL
ATOM   2144  C   GLY 272      13.415  -8.008  36.897  1.00 18.95      MTGL
ATOM   2145  O   GLY 272      13.284  -6.941  36.289  1.00 19.13      MTGL
```

Fig. 1 cont.

| | | | | | | | | | | |
|---|---|---|---|---|---|---|---|---|---|---|
| ATOM | 2146 | N | GLN | 273 | 14.534 | -8.734 | 36.859 | 1.00 | 17.61 | MTGL |
| ATOM | 2147 | CA | GLN | 273 | 15.687 | -8.299 | 36.074 | 1.00 | 18.43 | MTGL |
| ATOM | 2148 | CB | GLN | 273 | 16.864 | -9.260 | 36.230 | 1.00 | 17.76 | MTGL |
| ATOM | 2149 | CG | GLN | 273 | 17.467 | -9.345 | 37.610 | 1.00 | 19.26 | MTGL |
| ATOM | 2150 | CD | GLN | 273 | 18.720 | -10.190 | 37.607 | 1.00 | 19.87 | MTGL |
| ATOM | 2151 | OE1 | GLN | 273 | 18.726 | -11.304 | 37.073 | 1.00 | 18.60 | MTGL |
| ATOM | 2152 | NE2 | GLN | 273 | 19.793 | -9.667 | 38.198 | 1.00 | 19.12 | MTGL |
| ATOM | 2153 | C | GLN | 273 | 15.300 | -8.270 | 34.607 | 1.00 | 18.09 | MTGL |
| ATOM | 2154 | O | GLN | 273 | 15.660 | -7.353 | 33.869 | 1.00 | 17.98 | MTGL |
| ATOM | 2155 | N | THR | 274 | 14.579 | -9.305 | 34.193 | 1.00 | 17.84 | MTGL |
| ATOM | 2156 | CA | THR | 274 | 14.131 | -9.433 | 32.815 | 1.00 | 17.91 | MTGL |
| ATOM | 2157 | CB | THR | 274 | 13.293 | -10.712 | 32.637 | 1.00 | 18.13 | MTGL |
| ATOM | 2158 | OG1 | THR | 274 | 14.128 | -11.857 | 32.859 | 1.00 | 19.81 | MTGL |
| ATOM | 2159 | CG2 | THR | 274 | 12.695 | -10.777 | 31.231 | 1.00 | 19.04 | MTGL |
| ATOM | 2160 | C | THR | 274 | 13.293 | -8.219 | 32.428 | 1.00 | 17.34 | MTGL |
| ATOM | 2161 | O | THR | 274 | 13.504 | -7.619 | 31.376 | 1.00 | 16.72 | MTGL |
| ATOM | 2162 | N | THR | 275 | 12.351 | -7.859 | 33.294 | 1.00 | 16.98 | MTGL |
| ATOM | 2163 | CA | THR | 275 | 11.483 | -6.712 | 33.056 | 1.00 | 17.24 | MTGL |
| ATOM | 2164 | CB | THR | 275 | 10.425 | -6.574 | 34.169 | 1.00 | 17.29 | MTGL |
| ATOM | 2165 | OG1 | THR | 275 | 9.587 | -7.735 | 34.181 | 1.00 | 17.49 | MTGL |
| ATOM | 2166 | CG2 | THR | 275 | 9.563 | -5.331 | 33.937 | 1.00 | 16.88 | MTGL |
| ATOM | 2167 | C | THR | 275 | 12.270 | -5.405 | 32.982 | 1.00 | 17.05 | MTGL |
| ATOM | 2168 | O | THR | 275 | 12.090 | -4.618 | 32.052 | 1.00 | 17.86 | MTGL |
| ATOM | 2169 | N | PHE | 276 | 13.139 | -5.174 | 33.963 | 1.00 | 16.71 | MTGL |
| ATOM | 2170 | CA | PHE | 276 | 13.937 | -3.949 | 34.000 | 1.00 | 15.62 | MTGL |
| ATOM | 2171 | CB | PHE | 276 | 14.781 | -3.890 | 35.278 | 1.00 | 15.45 | MTGL |
| ATOM | 2172 | CG | PHE | 276 | 15.621 | -2.646 | 35.389 | 1.00 | 16.62 | MTGL |
| ATOM | 2173 | CD1 | PHE | 276 | 15.048 | -1.437 | 35.777 | 1.00 | 17.56 | MTGL |
| ATOM | 2174 | CD2 | PHE | 276 | 16.976 | -2.675 | 35.077 | 1.00 | 17.00 | MTGL |
| ATOM | 2175 | CE1 | PHE | 276 | 15.817 | -0.272 | 35.860 | 1.00 | 18.40 | MTGL |
| ATOM | 2176 | CE2 | PHE | 276 | 17.757 | -1.518 | 35.155 | 1.00 | 18.28 | MTGL |
| ATOM | 2177 | CZ | PHE | 276 | 17.176 | -0.314 | 35.546 | 1.00 | 17.73 | MTGL |
| ATOM | 2178 | C | PHE | 276 | 14.866 | -3.825 | 32.796 | 1.00 | 16.42 | MTGL |
| ATOM | 2179 | O | PHE | 276 | 14.907 | -2.785 | 32.136 | 1.00 | 17.18 | MTGL |
| ATOM | 2180 | N | ILE | 277 | 15.627 | -4.881 | 32.520 | 1.00 | 15.71 | MTGL |
| ATOM | 2181 | CA | ILE | 277 | 16.558 | -4.864 | 31.399 | 1.00 | 14.72 | MTGL |
| ATOM | 2182 | CB | ILE | 277 | 17.364 | -6.181 | 31.330 | 1.00 | 14.70 | MTGL |
| ATOM | 2183 | CG2 | ILE | 277 | 18.227 | -6.209 | 30.063 | 1.00 | 14.44 | MTGL |
| ATOM | 2184 | CG1 | ILE | 277 | 18.238 | -6.305 | 32.587 | 1.00 | 14.86 | MTGL |
| ATOM | 2185 | CD1 | ILE | 277 | 18.945 | -7.635 | 32.727 | 1.00 | 14.36 | MTGL |
| ATOM | 2186 | C | ILE | 277 | 15.832 | -4.643 | 30.081 | 1.00 | 14.58 | MTGL |
| ATOM | 2187 | O | ILE | 277 | 16.286 | -3.868 | 29.250 | 1.00 | 14.01 | MTGL |
| ATOM | 2188 | N | THR | 278 | 14.708 | -5.330 | 29.890 | 1.00 | 14.56 | MTGL |
| ATOM | 2189 | CA | THR | 278 | 13.930 | -5.182 | 28.663 | 1.00 | 15.56 | MTGL |
| ATOM | 2190 | CB | THR | 278 | 12.724 | -6.159 | 28.635 | 1.00 | 15.82 | MTGL |
| ATOM | 2191 | OG1 | THR | 278 | 13.203 | -7.505 | 28.742 | 1.00 | 16.63 | MTGL |
| ATOM | 2192 | CG2 | THR | 278 | 11.942 | -6.017 | 27.329 | 1.00 | 15.47 | MTGL |
| ATOM | 2193 | C | THR | 278 | 13.411 | -3.747 | 28.530 | 1.00 | 15.31 | MTGL |
| ATOM | 2194 | O | THR | 278 | 13.435 | -3.168 | 27.446 | 1.00 | 16.65 | MTGL |
| ATOM | 2195 | N | ASN | 279 | 12.946 | -3.174 | 29.634 | 1.00 | 15.85 | MTGL |
| ATOM | 2196 | CA | ASN | 279 | 12.430 | -1.808 | 29.609 | 1.00 | 16.36 | MTGL |
| ATOM | 2197 | CB | ASN | 279 | 11.743 | -1.475 | 30.939 | 1.00 | 15.56 | MTGL |
| ATOM | 2198 | CG | ASN | 279 | 10.388 | -2.159 | 31.077 | 1.00 | 17.29 | MTGL |
| ATOM | 2199 | OD1 | ASN | 279 | 9.939 | -2.848 | 30.167 | 1.00 | 15.98 | MTGL |
| ATOM | 2200 | ND2 | ASN | 279 | 9.736 | -1.966 | 32.215 | 1.00 | 17.61 | MTGL |
| ATOM | 2201 | C | ASN | 279 | 13.520 | -0.783 | 29.304 | 1.00 | 16.68 | MTGL |
| ATOM | 2202 | O | ASN | 279 | 13.300 | 0.155 | 28.533 | 1.00 | 16.98 | MTGL |
| ATOM | 2203 | N | VAL | 280 | 14.695 | -0.950 | 29.904 | 1.00 | 16.27 | MTGL |

Fig. 1 cont.

| ATOM | 2204 | CA | VAL | 280 | 15.782 | -0.013 | 29.641 | 1.00 | 15.63 | MTGL |
|------|------|-----|-----|-----|--------|--------|--------|------|-------|------|
| ATOM | 2205 | CB | VAL | 280 | 17.005 | -0.283 | 30.545 | 1.00 | 15.75 | MTGL |
| ATOM | 2206 | CG1 | VAL | 280 | 18.171 | 0.623 | 30.126 | 1.00 | 14.59 | MTGL |
| ATOM | 2207 | CG2 | VAL | 280 | 16.634 | -0.023 | 32.007 | 1.00 | 14.29 | MTGL |
| ATOM | 2208 | C | VAL | 280 | 16.203 | -0.144 | 28.183 | 1.00 | 15.42 | MTGL |
| ATOM | 2209 | O | VAL | 280 | 16.483 | 0.852 | 27.512 | 1.00 | 14.80 | MTGL |
| ATOM | 2210 | N | ALA | 281 | 16.236 | -1.381 | 27.697 | 1.00 | 14.47 | MTGL |
| ATOM | 2211 | CA | ALA | 281 | 16.614 | -1.645 | 26.315 | 1.00 | 15.95 | MTGL |
| ATOM | 2212 | CB | ALA | 281 | 16.573 | -3.147 | 26.035 | 1.00 | 15.85 | MTGL |
| ATOM | 2213 | C | ALA | 281 | 15.662 | -0.922 | 25.369 | 1.00 | 16.21 | MTGL |
| ATOM | 2214 | O | ALA | 281 | 16.087 | -0.290 | 24.403 | 1.00 | 15.33 | MTGL |
| ATOM | 2215 | N | ASN | 282 | 14.369 | -1.018 | 25.653 | 1.00 | 16.95 | MTGL |
| ATOM | 2216 | CA | ASN | 282 | 13.383 | -0.386 | 24.792 | 1.00 | 17.84 | MTGL |
| ATOM | 2217 | CB | ASN | 282 | 12.015 | -1.013 | 25.021 | 1.00 | 19.13 | MTGL |
| ATOM | 2218 | CG | ASN | 282 | 11.924 | -2.398 | 24.400 | 1.00 | 20.19 | MTGL |
| ATOM | 2219 | OD1 | ASN | 282 | 12.393 | -2.605 | 23.289 | 1.00 | 23.04 | MTGL |
| ATOM | 2220 | ND2 | ASN | 282 | 11.328 | -3.341 | 25.108 | 1.00 | 19.74 | MTGL |
| ATOM | 2221 | C | ASN | 282 | 13.337 | 1.124 | 24.910 | 1.00 | 18.52 | MTGL |
| ATOM | 2222 | O | ASN | 282 | 12.841 | 1.806 | 24.011 | 1.00 | 17.57 | MTGL |
| ATOM | 2223 | N | ILE | 283 | 13.851 | 1.651 | 26.015 | 1.00 | 18.29 | MTGL |
| ATOM | 2224 | CA | ILE | 283 | 13.902 | 3.095 | 26.168 | 1.00 | 18.86 | MTGL |
| ATOM | 2225 | CB | ILE | 283 | 14.254 | 3.496 | 27.603 | 1.00 | 19.57 | MTGL |
| ATOM | 2226 | CG2 | ILE | 283 | 14.818 | 4.917 | 27.636 | 1.00 | 20.74 | MTGL |
| ATOM | 2227 | CG1 | ILE | 283 | 13.003 | 3.365 | 28.471 | 1.00 | 21.83 | MTGL |
| ATOM | 2228 | CD1 | ILE | 283 | 13.214 | 3.728 | 29.909 | 1.00 | 25.75 | MTGL |
| ATOM | 2229 | C | ILE | 283 | 14.994 | 3.566 | 25.209 | 1.00 | 17.96 | MTGL |
| ATOM | 2230 | O | ILE | 283 | 14.816 | 4.543 | 24.483 | 1.00 | 17.19 | MTGL |
| ATOM | 2231 | N | VAL | 284 | 16.114 | 2.844 | 25.200 | 1.00 | 17.16 | MTGL |
| ATOM | 2232 | CA | VAL | 284 | 17.236 | 3.164 | 24.321 | 1.00 | 15.86 | MTGL |
| ATOM | 2233 | CB | VAL | 284 | 18.420 | 2.194 | 24.554 | 1.00 | 16.05 | MTGL |
| ATOM | 2234 | CG1 | VAL | 284 | 19.491 | 2.409 | 23.491 | 1.00 | 14.09 | MTGL |
| ATOM | 2235 | CG2 | VAL | 284 | 19.006 | 2.416 | 25.956 | 1.00 | 14.93 | MTGL |
| ATOM | 2236 | C | VAL | 284 | 16.797 | 3.075 | 22.861 | 1.00 | 16.21 | MTGL |
| ATOM | 2237 | O | VAL | 284 | 17.089 | 3.963 | 22.059 | 1.00 | 15.26 | MTGL |
| ATOM | 2238 | N | SER | 285 | 16.086 | 2.004 | 22.519 | 1.00 | 16.71 | MTGL |
| ATOM | 2239 | CA | SER | 285 | 15.618 | 1.813 | 21.145 | 1.00 | 18.87 | MTGL |
| ATOM | 2240 | CB | SER | 285 | 14.977 | 0.429 | 20.979 | 1.00 | 18.71 | MTGL |
| ATOM | 2241 | OG | SER | 285 | 15.954 | -0.595 | 21.082 | 1.00 | 25.57 | MTGL |
| ATOM | 2242 | C | SER | 285 | 14.622 | 2.882 | 20.697 | 1.00 | 18.52 | MTGL |
| ATOM | 2243 | O | SER | 285 | 14.453 | 3.101 | 19.507 | 1.00 | 19.96 | MTGL |
| ATOM | 2244 | N | SER | 286 | 13.964 | 3.544 | 21.644 | 1.00 | 17.61 | MTGL |
| ATOM | 2245 | CA | SER | 286 | 12.993 | 4.574 | 21.295 | 1.00 | 18.49 | MTGL |
| ATOM | 2246 | CB | SER | 286 | 11.970 | 4.754 | 22.421 | 1.00 | 18.70 | MTGL |
| ATOM | 2247 | OG | SER | 286 | 12.505 | 5.533 | 23.483 | 1.00 | 18.21 | MTGL |
| ATOM | 2248 | C | SER | 286 | 13.686 | 5.909 | 21.040 | 1.00 | 18.76 | MTGL |
| ATOM | 2249 | O | SER | 286 | 13.043 | 6.892 | 20.676 | 1.00 | 17.84 | MTGL |
| ATOM | 2250 | N | VAL | 287 | 15.000 | 5.931 | 21.235 | 1.00 | 18.85 | MTGL |
| ATOM | 2251 | CA | VAL | 287 | 15.793 | 7.138 | 21.048 | 1.00 | 17.18 | MTGL |
| ATOM | 2252 | CB | VAL | 287 | 16.866 | 7.267 | 22.158 | 1.00 | 17.69 | MTGL |
| ATOM | 2253 | CG1 | VAL | 287 | 17.764 | 8.477 | 21.890 | 1.00 | 17.29 | MTGL |
| ATOM | 2254 | CG2 | VAL | 287 | 16.189 | 7.399 | 23.512 | 1.00 | 17.29 | MTGL |
| ATOM | 2255 | C | VAL | 287 | 16.493 | 7.144 | 19.702 | 1.00 | 17.44 | MTGL |
| ATOM | 2256 | O | VAL | 287 | 16.979 | 6.112 | 19.241 | 1.00 | 16.36 | MTGL |
| ATOM | 2257 | N | SER | 288 | 16.546 | 8.313 | 19.073 | 1.00 | 18.07 | MTGL |
| ATOM | 2258 | CA | SER | 288 | 17.215 | 8.442 | 17.787 | 1.00 | 18.93 | MTGL |
| ATOM | 2259 | CB | SER | 288 | 17.202 | 9.900 | 17.329 | 1.00 | 19.03 | MTGL |
| ATOM | 2260 | OG | SER | 288 | 17.858 | 10.045 | 16.082 | 1.00 | 21.05 | MTGL |
| ATOM | 2261 | C | SER | 288 | 18.657 | 7.950 | 17.911 | 1.00 | 18.73 | MTGL |

Fig. 1 cont.

| | | | | | | | | | | |
|---|---|---|---|---|---|---|---|---|---|---|
| ATOM | 2262 | O | SER | 288 | 19.444 | 8.498 | 18.682 | 1.00 | 18.95 | MTGL |
| ATOM | 2263 | N | ARG | 289 | 18.984 | 6.915 | 17.145 | 1.00 | 17.81 | MTGL |
| ATOM | 2264 | CA | ARG | 289 | 20.313 | 6.311 | 17.137 | 1.00 | 18.49 | MTGL |
| ATOM | 2265 | CB | ARG | 289 | 21.387 | 7.347 | 16.760 | 1.00 | 20.78 | MTGL |
| ATOM | 2266 | CG | ARG | 289 | 21.128 | 8.067 | 15.429 | 1.00 | 24.72 | MTGL |
| ATOM | 2267 | CD | ARG | 289 | 22.378 | 8.761 | 14.890 | 1.00 | 26.86 | MTGL |
| ATOM | 2268 | NE | ARG | 289 | 23.269 | 7.812 | 14.225 | 1.00 | 31.29 | MTGL |
| ATOM | 2269 | CZ | ARG | 289 | 24.483 | 8.101 | 13.758 | 1.00 | 32.57 | MTGL |
| ATOM | 2270 | NH1 | ARG | 289 | 24.981 | 9.327 | 13.880 | 1.00 | 33.06 | MTGL |
| ATOM | 2271 | NH2 | ARG | 289 | 25.200 | 7.159 | 13.159 | 1.00 | 32.56 | MTGL |
| ATOM | 2272 | C | ARG | 289 | 20.687 | 5.616 | 18.456 | 1.00 | 17.41 | MTGL |
| ATOM | 2273 | O | ARG | 289 | 21.865 | 5.493 | 18.785 | 1.00 | 16.35 | MTGL |
| ATOM | 2274 | N | GLY | 290 | 19.681 | 5.173 | 19.207 | 1.00 | 16.31 | MTGL |
| ATOM | 2275 | CA | GLY | 290 | 19.944 | 4.449 | 20.442 | 1.00 | 16.82 | MTGL |
| ATOM | 2276 | C | GLY | 290 | 20.267 | 3.042 | 19.970 | 1.00 | 17.04 | MTGL |
| ATOM | 2277 | O | GLY | 290 | 19.393 | 2.353 | 19.450 | 1.00 | 16.17 | MTGL |
| ATOM | 2278 | N | VAL | 291 | 21.502 | 2.595 | 20.159 | 1.00 | 17.31 | MTGL |
| ATOM | 2279 | CA | VAL | 291 | 21.893 | 1.290 | 19.644 | 1.00 | 17.47 | MTGL |
| ATOM | 2280 | CB | VAL | 291 | 22.951 | 1.475 | 18.534 | 1.00 | 17.89 | MTGL |
| ATOM | 2281 | CG1 | VAL | 291 | 22.387 | 2.347 | 17.419 | 1.00 | 18.32 | MTGL |
| ATOM | 2282 | CG2 | VAL | 291 | 24.204 | 2.125 | 19.112 | 1.00 | 16.95 | MTGL |
| ATOM | 2283 | C | VAL | 291 | 22.403 | 0.194 | 20.581 | 1.00 | 18.18 | MTGL |
| ATOM | 2284 | O | VAL | 291 | 22.610 | -0.933 | 20.133 | 1.00 | 17.39 | MTGL |
| ATOM | 2285 | N | GLY | 292 | 22.608 | 0.489 | 21.861 | 1.00 | 18.56 | MTGL |
| ATOM | 2286 | CA | GLY | 292 | 23.117 | -0.559 | 22.730 | 1.00 | 17.86 | MTGL |
| ATOM | 2287 | C | GLY | 292 | 22.774 | -0.538 | 24.205 | 1.00 | 18.08 | MTGL |
| ATOM | 2288 | O | GLY | 292 | 22.404 | 0.493 | 24.766 | 1.00 | 17.12 | MTGL |
| ATOM | 2289 | N | LEU | 293 | 22.913 | -1.708 | 24.824 | 1.00 | 18.07 | MTGL |
| ATOM | 2290 | CA | LEU | 293 | 22.653 | -1.902 | 26.246 | 1.00 | 18.28 | MTGL |
| ATOM | 2291 | CB | LEU | 293 | 21.223 | -2.404 | 26.474 | 1.00 | 19.14 | MTGL |
| ATOM | 2292 | CG | LEU | 293 | 20.858 | -2.808 | 27.910 | 1.00 | 22.33 | MTGL |
| ATOM | 2293 | CD1 | LEU | 293 | 21.047 | -1.625 | 28.842 | 1.00 | 23.17 | MTGL |
| ATOM | 2294 | CD2 | LEU | 293 | 19.410 | -3.278 | 27.965 | 1.00 | 23.54 | MTGL |
| ATOM | 2295 | C | LEU | 293 | 23.634 | -2.952 | 26.744 | 1.00 | 17.77 | MTGL |
| ATOM | 2296 | O | LEU | 293 | 23.763 | -4.009 | 26.130 | 1.00 | 17.95 | MTGL |
| ATOM | 2297 | N | PHE | 294 | 24.322 | -2.658 | 27.847 | 1.00 | 16.70 | MTGL |
| ATOM | 2298 | CA | PHE | 294 | 25.288 | -3.586 | 28.431 | 1.00 | 16.53 | MTGL |
| ATOM | 2299 | CB | PHE | 294 | 26.726 | -3.097 | 28.229 | 1.00 | 16.07 | MTGL |
| ATOM | 2300 | CG | PHE | 294 | 27.199 | -3.136 | 26.800 | 1.00 | 16.47 | MTGL |
| ATOM | 2301 | CD1 | PHE | 294 | 26.792 | -2.164 | 25.890 | 1.00 | 16.58 | MTGL |
| ATOM | 2302 | CD2 | PHE | 294 | 28.069 | -4.137 | 26.368 | 1.00 | 15.29 | MTGL |
| ATOM | 2303 | CE1 | PHE | 294 | 27.241 | -2.188 | 24.571 | 1.00 | 16.35 | MTGL |
| ATOM | 2304 | CE2 | PHE | 294 | 28.523 | -4.170 | 25.050 | 1.00 | 15.62 | MTGL |
| ATOM | 2305 | CZ | PHE | 294 | 28.110 | -3.192 | 24.150 | 1.00 | 15.75 | MTGL |
| ATOM | 2306 | C | PHE | 294 | 25.046 | -3.739 | 29.930 | 1.00 | 16.96 | MTGL |
| ATOM | 2307 | O | PHE | 294 | 25.032 | -2.752 | 30.667 | 1.00 | 17.04 | MTGL |
| ATOM | 2308 | N | TYR | 295 | 24.855 | -4.977 | 30.374 | 1.00 | 16.03 | MTGL |
| ATOM | 2309 | CA | TYR | 295 | 24.639 | -5.253 | 31.789 | 1.00 | 15.26 | MTGL |
| ATOM | 2310 | CB | TYR | 295 | 23.905 | -6.582 | 31.963 | 1.00 | 14.47 | MTGL |
| ATOM | 2311 | CG | TYR | 295 | 23.323 | -6.755 | 33.344 | 1.00 | 14.21 | MTGL |
| ATOM | 2312 | CD1 | TYR | 295 | 22.033 | -6.312 | 33.637 | 1.00 | 12.09 | MTGL |
| ATOM | 2313 | CE1 | TYR | 295 | 21.512 | -6.421 | 34.918 | 1.00 | 13.83 | MTGL |
| ATOM | 2314 | CD2 | TYR | 295 | 24.080 | -7.316 | 34.372 | 1.00 | 13.69 | MTGL |
| ATOM | 2315 | CE2 | TYR | 295 | 23.566 | -7.431 | 35.662 | 1.00 | 13.74 | MTGL |
| ATOM | 2316 | CZ | TYR | 295 | 22.284 | -6.979 | 35.930 | 1.00 | 14.39 | MTGL |
| ATOM | 2317 | OH | TYR | 295 | 21.784 | -7.058 | 37.211 | 1.00 | 15.39 | MTGL |
| ATOM | 2318 | C | TYR | 295 | 26.033 | -5.346 | 32.410 | 1.00 | 15.23 | MTGL |
| ATOM | 2319 | O | TYR | 295 | 26.932 | -5.933 | 31.814 | 1.00 | 15.00 | MTGL |

Fig. 1 cont.

```
ATOM   2320  N    TRP   296      26.228  -4.778  33.594  1.00 14.56           MTGL
ATOM   2321  CA   TRP   296      27.559  -4.829  34.195  1.00 15.23           MTGL
ATOM   2322  CB   TRP   296      27.847  -3.541  34.984  1.00 14.28           MTGL
ATOM   2323  CG   TRP   296      29.306  -3.370  35.309  1.00 15.53           MTGL
ATOM   2324  CD2  TRP   296      29.918  -3.408  36.611  1.00 16.19           MTGL
ATOM   2325  CE2  TRP   296      31.309  -3.221  36.424  1.00 15.45           MTGL
ATOM   2326  CE3  TRP   296      29.428  -3.583  37.916  1.00 16.72           MTGL
ATOM   2327  CD1  TRP   296      30.321  -3.168  34.418  1.00 15.37           MTGL
ATOM   2328  NE1  TRP   296      31.526  -3.077  35.079  1.00 15.66           MTGL
ATOM   2329  CZ2  TRP   296      32.219  -3.201  37.495  1.00 15.21           MTGL
ATOM   2330  CZ3  TRP   296      30.334  -3.564  38.985  1.00 16.55           MTGL
ATOM   2331  CH2  TRP   296      31.715  -3.375  38.763  1.00 16.36           MTGL
ATOM   2332  C    TRP   296      27.842  -6.029  35.097  1.00 14.61           MTGL
ATOM   2333  O    TRP   296      27.174  -6.224  36.114  1.00 15.45           MTGL
ATOM   2334  N    GLU   297      28.835  -6.826  34.702  1.00 14.69           MTGL
ATOM   2335  CA   GLU   297      29.298  -7.977  35.479  1.00 14.59           MTGL
ATOM   2336  CB   GLU   297      30.125  -7.465  36.661  1.00 13.64           MTGL
ATOM   2337  CG   GLU   297      31.453  -6.849  36.261  1.00 14.27           MTGL
ATOM   2338  CD   GLU   297      32.506  -7.896  35.947  1.00 13.45           MTGL
ATOM   2339  OE1  GLU   297      32.176  -9.102  35.991  1.00 12.29           MTGL
ATOM   2340  OE2  GLU   297      33.661  -7.510  35.660  1.00 14.90           MTGL
ATOM   2341  C    GLU   297      28.245  -8.952  36.000  1.00 15.16           MTGL
ATOM   2342  O    GLU   297      28.177  -9.219  37.205  1.00 15.61           MTGL
ATOM   2343  N    PRO   298      27.436  -9.529  35.100  1.00 14.59           MTGL
ATOM   2344  CD   PRO   298      27.545  -9.487  33.631  1.00 12.84           MTGL
ATOM   2345  CA   PRO   298      26.395 -10.474  35.517  1.00 14.70           MTGL
ATOM   2346  CB   PRO   298      25.651 -10.750  34.217  1.00 13.52           MTGL
ATOM   2347  CG   PRO   298      26.765 -10.716  33.213  1.00 12.86           MTGL
ATOM   2348  C    PRO   298      26.897 -11.774  36.158  1.00 14.86           MTGL
ATOM   2349  O    PRO   298      26.159 -12.424  36.901  1.00 14.01           MTGL
ATOM   2350  N    ALA   299      28.143 -12.147  35.875  1.00 15.30           MTGL
ATOM   2351  CA   ALA   299      28.689 -13.397  36.396  1.00 16.12           MTGL
ATOM   2352  CB   ALA   299      29.321 -14.184  35.245  1.00 16.45           MTGL
ATOM   2353  C    ALA   299      29.684 -13.297  37.551  1.00 16.40           MTGL
ATOM   2354  O    ALA   299      30.281 -14.303  37.934  1.00 16.31           MTGL
ATOM   2355  N    TRP   300      29.861 -12.104  38.111  1.00 16.53           MTGL
ATOM   2356  CA   TRP   300      30.804 -11.911  39.218  1.00 16.99           MTGL
ATOM   2357  CB   TRP   300      31.205 -10.438  39.300  1.00 15.26           MTGL
ATOM   2358  CG   TRP   300      32.518 -10.195  39.960  1.00 16.30           MTGL
ATOM   2359  CD2  TRP   300      33.248  -8.960  39.982  1.00 14.96           MTGL
ATOM   2360  CE2  TRP   300      34.440  -9.195  40.697  1.00 14.93           MTGL
ATOM   2361  CE3  TRP   300      33.007  -7.679  39.463  1.00 15.40           MTGL
ATOM   2362  CD1  TRP   300      33.274 -11.099  40.648  1.00 14.90           MTGL
ATOM   2363  NE1  TRP   300      34.429 -10.508  41.092  1.00 16.48           MTGL
ATOM   2364  CZ2  TRP   300      35.398  -8.195  40.912  1.00 13.85           MTGL
ATOM   2365  CZ3  TRP   300      33.960  -6.678  39.678  1.00 13.88           MTGL
ATOM   2366  CH2  TRP   300      35.143  -6.949  40.398  1.00 15.26           MTGL
ATOM   2367  C    TRP   300      30.159 -12.347  40.536  1.00 17.14           MTGL
ATOM   2368  O    TRP   300      29.909 -11.522  41.423  1.00 16.66           MTGL
ATOM   2369  N    ILE   301      29.907 -13.645  40.670  1.00 17.69           MTGL
ATOM   2370  CA   ILE   301      29.255 -14.168  41.866  1.00 19.29           MTGL
ATOM   2371  CB   ILE   301      28.893 -15.655  41.695  1.00 20.95           MTGL
ATOM   2372  CG2  ILE   301      27.937 -15.812  40.517  1.00 19.88           MTGL
ATOM   2373  CG1  ILE   301      30.153 -16.496  41.479  1.00 22.04           MTGL
ATOM   2374  CD1  ILE   301      29.858 -17.985  41.366  1.00 23.83           MTGL
ATOM   2375  C    ILE   301      29.973 -13.980  43.205  1.00 19.82           MTGL
ATOM   2376  O    ILE   301      29.325 -14.022  44.249  1.00 19.53           MTGL
ATOM   2377  N    HIS   302      31.287 -13.768  43.189  1.00 19.79           MTGL
```

Fig. 1 cont.

```
ATOM   2378  CA   HIS  302      32.016 -13.555  44.441  1.00 21.73      MTGL
ATOM   2379  CB   HIS  302      33.464 -14.042  44.317  1.00 22.38      MTGL
ATOM   2380  CG   HIS  302      33.603 -15.529  44.396  1.00 24.09      MTGL
ATOM   2381  CD2  HIS  302      33.254 -16.405  45.368  1.00 25.41      MTGL
ATOM   2382  ND1  HIS  302      34.154 -16.282  43.382  1.00 25.82      MTGL
ATOM   2383  CE1  HIS  302      34.137 -17.558  43.724  1.00 26.05      MTGL
ATOM   2384  NE2  HIS  302      33.596 -17.659  44.924  1.00 26.28      MTGL
ATOM   2385  C    HIS  302      32.002 -12.085  44.857  1.00 21.31      MTGL
ATOM   2386  O    HIS  302      32.609 -11.707  45.854  1.00 22.67      MTGL
ATOM   2387  N    ASN  303      31.303 -11.265  44.079  1.00 20.90      MTGL
ATOM   2388  CA   ASN  303      31.183  -9.831  44.337  1.00 20.21      MTGL
ATOM   2389  CB   ASN  303      32.200  -9.074  43.473  1.00 20.27      MTGL
ATOM   2390  CG   ASN  303      32.170  -7.573  43.706  1.00 21.40      MTGL
ATOM   2391  OD1  ASN  303      31.977  -7.118  44.828  1.00 22.04      MTGL
ATOM   2392  ND2  ASN  303      32.380  -6.799  42.643  1.00 19.16      MTGL
ATOM   2393  C    ASN  303      29.752  -9.467  43.946  1.00 20.34      MTGL
ATOM   2394  O    ASN  303      29.508  -8.488  43.233  1.00 18.25      MTGL
ATOM   2395  N    ALA  304      28.820 -10.284  44.432  1.00 19.57      MTGL
ATOM   2396  CA   ALA  304      27.395 -10.180  44.134  1.00 19.48      MTGL
ATOM   2397  CB   ALA  304      26.612 -11.157  45.017  1.00 18.17      MTGL
ATOM   2398  C    ALA  304      26.731  -8.813  44.182  1.00 19.61      MTGL
ATOM   2399  O    ALA  304      25.909  -8.505  43.323  1.00 20.70      MTGL
ATOM   2400  N    ASN  305      27.050  -7.999  45.181  1.00 18.88      MTGL
ATOM   2401  CA   ASN  305      26.424  -6.685  45.271  1.00 19.31      MTGL
ATOM   2402  CB   ASN  305      26.580  -6.114  46.683  1.00 19.61      MTGL
ATOM   2403  CG   ASN  305      28.024  -5.847  47.048  1.00 20.60      MTGL
ATOM   2404  OD1  ASN  305      28.868  -6.747  47.014  1.00 21.53      MTGL
ATOM   2405  ND2  ASN  305      28.318  -4.606  47.403  1.00 21.29      MTGL
ATOM   2406  C    ASN  305      27.018  -5.723  44.240  1.00 19.61      MTGL
ATOM   2407  O    ASN  305      26.522  -4.611  44.041  1.00 19.33      MTGL
ATOM   2408  N    LEU  306      28.088  -6.160  43.587  1.00 18.26      MTGL
ATOM   2409  CA   LEU  306      28.747  -5.359  42.563  1.00 18.47      MTGL
ATOM   2410  CB   LEU  306      27.919  -5.384  41.270  1.00 17.67      MTGL
ATOM   2411  CG   LEU  306      27.771  -6.764  40.612  1.00 18.35      MTGL
ATOM   2412  CD1  LEU  306      26.888  -6.670  39.372  1.00 16.49      MTGL
ATOM   2413  CD2  LEU  306      29.144  -7.300  40.238  1.00 16.40      MTGL
ATOM   2414  C    LEU  306      28.994  -3.915  42.990  1.00 19.28      MTGL
ATOM   2415  O    LEU  306      28.698  -2.981  42.241  1.00 19.04      MTGL
ATOM   2416  N    GLY  307      29.529  -3.740  44.196  1.00 18.62      MTGL
ATOM   2417  CA   GLY  307      29.828  -2.414  44.700  1.00 18.44      MTGL
ATOM   2418  C    GLY  307      28.657  -1.530  45.092  1.00 18.36      MTGL
ATOM   2419  O    GLY  307      28.866  -0.379  45.466  1.00 18.04      MTGL
ATOM   2420  N    SER  308      27.435  -2.047  45.020  1.00 17.93      MTGL
ATOM   2421  CA   SER  308      26.256  -1.256  45.380  1.00 17.81      MTGL
ATOM   2422  CB   SER  308      25.134  -1.480  44.361  1.00 16.84      MTGL
ATOM   2423  OG   SER  308      24.555  -2.759  44.528  1.00 15.76      MTGL
ATOM   2424  C    SER  308      25.756  -1.651  46.762  1.00 18.10      MTGL
ATOM   2425  O    SER  308      26.282  -2.585  47.361  1.00 18.30      MTGL
ATOM   2426  N    SER  309      24.735  -0.947  47.250  1.00 18.76      MTGL
ATOM   2427  CA   SER  309      24.157  -1.220  48.560  1.00 20.76      MTGL
ATOM   2428  CB   SER  309      23.424   0.022  49.092  1.00 21.48      MTGL
ATOM   2429  OG   SER  309      22.304   0.358  48.283  1.00 22.88      MTGL
ATOM   2430  C    SER  309      23.193  -2.404  48.517  1.00 22.16      MTGL
ATOM   2431  O    SER  309      22.754  -2.899  49.560  1.00 23.34      MTGL
ATOM   2432  N    CYS  310      22.852  -2.846  47.312  1.00 22.36      MTGL
ATOM   2433  CA   CYS  310      21.954  -3.987  47.159  1.00 23.23      MTGL
ATOM   2434  C    CYS  310      22.784  -5.265  47.300  1.00 23.23      MTGL
ATOM   2435  O    CYS  310      23.935  -5.300  46.877  1.00 25.45      MTGL
```

Fig. 1 cont.

| | | | | | | | | | |
|---|---|---|---|---|---|---|---|---|---|
| ATOM | 2436 | CB | CYS | 310 | 21.275 | -3.945 | 45.793 | 1.00 23.30 | MTGL |
| ATOM | 2437 | SG | CYS | 310 | 19.871 | -2.792 | 45.648 | 1.00 24.32 | MTGL |
| ATOM | 2438 | N | ALA | 311 | 22.197 | -6.309 | 47.877 | 1.00 21.14 | MTGL |
| ATOM | 2439 | CA | ALA | 311 | 22.903 | -7.564 | 48.110 | 1.00 20.13 | MTGL |
| ATOM | 2440 | CB | ALA | 311 | 22.076 | -8.449 | 49.052 | 1.00 20.15 | MTGL |
| ATOM | 2441 | C | ALA | 311 | 23.335 | -8.383 | 46.894 | 1.00 19.87 | MTGL |
| ATOM | 2442 | O | ALA | 311 | 24.442 | -8.915 | 46.875 | 1.00 18.96 | MTGL |
| ATOM | 2443 | N | ASP | 312 | 22.482 | -8.502 | 45.882 | 1.00 18.99 | MTGL |
| ATOM | 2444 | CA | ASP | 312 | 22.849 | -9.313 | 44.723 | 1.00 19.21 | MTGL |
| ATOM | 2445 | CB | ASP | 312 | 22.346 | -10.747 | 44.931 | 1.00 19.01 | MTGL |
| ATOM | 2446 | CG | ASP | 312 | 22.949 | -11.733 | 43.946 | 1.00 19.92 | MTGL |
| ATOM | 2447 | OD1 | ASP | 312 | 23.450 | -11.305 | 42.884 | 1.00 19.68 | MTGL |
| ATOM | 2448 | OD2 | ASP | 312 | 22.908 | -12.948 | 44.230 | 1.00 20.69 | MTGL |
| ATOM | 2449 | C | ASP | 312 | 22.310 | -8.772 | 43.403 | 1.00 18.27 | MTGL |
| ATOM | 2450 | O | ASP | 312 | 21.098 | -8.692 | 43.205 | 1.00 18.94 | MTGL |
| ATOM | 2451 | N | ASN | 313 | 23.222 | -8.418 | 42.500 | 1.00 17.28 | MTGL |
| ATOM | 2452 | CA | ASN | 313 | 22.855 | -7.892 | 41.187 | 1.00 17.18 | MTGL |
| ATOM | 2453 | CB | ASN | 313 | 23.478 | -6.507 | 40.962 | 1.00 16.90 | MTGL |
| ATOM | 2454 | CG | ASN | 313 | 22.860 | -5.440 | 41.835 | 1.00 17.53 | MTGL |
| ATOM | 2455 | OD1 | ASN | 313 | 21.636 | -5.293 | 41.879 | 1.00 20.07 | MTGL |
| ATOM | 2456 | ND2 | ASN | 313 | 23.704 | -4.677 | 42.529 | 1.00 16.34 | MTGL |
| ATOM | 2457 | C | ASN | 313 | 23.305 | -8.809 | 40.053 | 1.00 17.15 | MTGL |
| ATOM | 2458 | O | ASN | 313 | 23.190 | -8.452 | 38.881 | 1.00 17.24 | MTGL |
| ATOM | 2459 | N | THR | 314 | 23.826 | -9.982 | 40.391 | 1.00 15.74 | MTGL |
| ATOM | 2460 | CA | THR | 314 | 24.289 | -10.903 | 39.365 | 1.00 15.54 | MTGL |
| ATOM | 2461 | CB | THR | 314 | 25.226 | -11.977 | 39.953 | 1.00 15.83 | MTGL |
| ATOM | 2462 | OG1 | THR | 314 | 24.502 | -12.779 | 40.894 | 1.00 16.12 | MTGL |
| ATOM | 2463 | CG2 | THR | 314 | 26.418 | -11.322 | 40.651 | 1.00 14.76 | MTGL |
| ATOM | 2464 | C | THR | 314 | 23.130 | -11.604 | 38.657 | 1.00 16.42 | MTGL |
| ATOM | 2465 | O | THR | 314 | 21.972 | -11.525 | 39.087 | 1.00 15.23 | MTGL |
| ATOM | 2466 | N | MET | 315 | 23.453 | -12.273 | 37.555 | 1.00 16.30 | MTGL |
| ATOM | 2467 | CA | MET | 315 | 22.458 | -13.006 | 36.776 | 1.00 17.57 | MTGL |
| ATOM | 2468 | CB | MET | 315 | 22.390 | -12.447 | 35.350 | 1.00 16.92 | MTGL |
| ATOM | 2469 | CG | MET | 315 | 21.934 | -10.997 | 35.281 | 1.00 16.10 | MTGL |
| ATOM | 2470 | SD | MET | 315 | 21.871 | -10.343 | 33.592 | 1.00 18.97 | MTGL |
| ATOM | 2471 | CE | MET | 315 | 20.232 | -10.916 | 33.083 | 1.00 14.39 | MTGL |
| ATOM | 2472 | C | MET | 315 | 22.820 | -14.492 | 36.753 | 1.00 17.49 | MTGL |
| ATOM | 2473 | O | MET | 315 | 22.404 | -15.234 | 35.871 | 1.00 17.40 | MTGL |
| ATOM | 2474 | N | PHE | 316 | 23.614 | -14.905 | 37.736 | 1.00 17.70 | MTGL |
| ATOM | 2475 | CA | PHE | 316 | 24.050 | -16.291 | 37.879 | 1.00 18.51 | MTGL |
| ATOM | 2476 | CB | PHE | 316 | 25.521 | -16.451 | 37.482 | 1.00 16.98 | MTGL |
| ATOM | 2477 | CG | PHE | 316 | 25.760 | -16.485 | 35.995 | 1.00 17.56 | MTGL |
| ATOM | 2478 | CD1 | PHE | 316 | 25.616 | -15.337 | 35.220 | 1.00 17.13 | MTGL |
| ATOM | 2479 | CD2 | PHE | 316 | 26.124 | -17.671 | 35.370 | 1.00 16.95 | MTGL |
| ATOM | 2480 | CE1 | PHE | 316 | 25.845 | -15.370 | 33.845 | 1.00 17.76 | MTGL |
| ATOM | 2481 | CE2 | PHE | 316 | 26.355 | -17.717 | 33.993 | 1.00 17.39 | MTGL |
| ATOM | 2482 | CZ | PHE | 316 | 26.212 | -16.566 | 33.227 | 1.00 16.28 | MTGL |
| ATOM | 2483 | C | PHE | 316 | 23.891 | -16.679 | 39.344 | 1.00 19.70 | MTGL |
| ATOM | 2484 | O | PHE | 316 | 23.980 | -15.825 | 40.229 | 1.00 19.34 | MTGL |
| ATOM | 2485 | N | SER | 317 | 23.659 | -17.963 | 39.598 | 1.00 19.30 | MTGL |
| ATOM | 2486 | CA | SER | 317 | 23.495 | -18.444 | 40.963 | 1.00 20.50 | MTGL |
| ATOM | 2487 | CB | SER | 317 | 22.894 | -19.853 | 40.972 | 1.00 19.80 | MTGL |
| ATOM | 2488 | OG | SER | 317 | 23.832 | -20.798 | 40.484 | 1.00 18.89 | MTGL |
| ATOM | 2489 | C | SER | 317 | 24.860 | -18.479 | 41.633 | 1.00 20.89 | MTGL |
| ATOM | 2490 | O | SER | 317 | 25.895 | -18.352 | 40.973 | 1.00 19.59 | MTGL |
| ATOM | 2491 | N | GLN | 318 | 24.857 | -18.659 | 42.946 | 1.00 21.68 | MTGL |
| ATOM | 2492 | CA | GLN | 318 | 26.104 | -18.711 | 43.685 | 1.00 22.69 | MTGL |
| ATOM | 2493 | CB | GLN | 318 | 25.813 | -18.649 | 45.186 | 1.00 23.06 | MTGL |

Fig. 1 cont.

```
ATOM   2494  CG   GLN  318      25.363  -17.254  45.625  1.00 24.34           MTGL
ATOM   2495  CD   GLN  318      26.459  -16.209  45.445  1.00 25.12           MTGL
ATOM   2496  OE1  GLN  318      27.473  -16.241  46.142  1.00 27.51           MTGL
ATOM   2497  NE2  GLN  318      26.266  -15.287  44.503  1.00 23.16           MTGL
ATOM   2498  C    GLN  318      26.920  -19.947  43.315  1.00 22.71           MTGL
ATOM   2499  O    GLN  318      28.095  -20.052  43.662  1.00 24.10           MTGL
ATOM   2500  N    SER  319      26.307  -20.875  42.588  1.00 22.97           MTGL
ATOM   2501  CA   SER  319      27.022  -22.074  42.160  1.00 23.61           MTGL
ATOM   2502  CB   SER  319      26.112  -23.306  42.235  1.00 24.83           MTGL
ATOM   2503  OG   SER  319      24.914  -23.111  41.500  1.00 28.30           MTGL
ATOM   2504  C    SER  319      27.553  -21.900  40.737  1.00 23.21           MTGL
ATOM   2505  O    SER  319      28.158  -22.814  40.180  1.00 23.75           MTGL
ATOM   2506  N    GLY  320      27.315  -20.726  40.153  1.00 22.56           MTGL
ATOM   2507  CA   GLY  320      27.798  -20.439  38.811  1.00 22.10           MTGL
ATOM   2508  C    GLY  320      26.851  -20.771  37.670  1.00 22.30           MTGL
ATOM   2509  O    GLY  320      27.262  -20.809  36.504  1.00 22.30           MTGL
ATOM   2510  N    GLN  321      25.582  -21.009  37.984  1.00 21.21           MTGL
ATOM   2511  CA   GLN  321      24.618  -21.337  36.941  1.00 21.36           MTGL
ATOM   2512  CB   GLN  321      23.652  -22.415  37.426  1.00 23.27           MTGL
ATOM   2513  CG   GLN  321      22.649  -22.855  36.371  1.00 24.43           MTGL
ATOM   2514  CD   GLN  321      21.803  -24.021  36.833  1.00 26.48           MTGL
ATOM   2515  OE1  GLN  321      22.320  -25.009  37.347  1.00 27.39           MTGL
ATOM   2516  NE2  GLN  321      20.497  -23.920  36.641  1.00 27.02           MTGL
ATOM   2517  C    GLN  321      23.826  -20.121  36.483  1.00 20.04           MTGL
ATOM   2518  O    GLN  321      23.289  -19.371  37.291  1.00 19.56           MTGL
ATOM   2519  N    ALA  322      23.755  -19.939  35.172  1.00 20.60           MTGL
ATOM   2520  CA   ALA  322      23.028  -18.817  34.596  1.00 20.07           MTGL
ATOM   2521  CB   ALA  322      23.129  -18.864  33.079  1.00 18.41           MTGL
ATOM   2522  C    ALA  322      21.565  -18.855  35.017  1.00 20.05           MTGL
ATOM   2523  O    ALA  322      20.921  -19.901  34.945  1.00 19.07           MTGL
ATOM   2524  N    LEU  323      21.052  -17.713  35.464  0.50 19.28           MTGL
ATOM   2525  CA   LEU  323      19.658  -17.611  35.878  0.50 19.33           MTGL
ATOM   2526  CB   LEU  323      19.470  -16.426  36.830  0.50 18.12           MTGL
ATOM   2527  CG   LEU  323      20.241  -16.493  38.152  0.50 17.16           MTGL
ATOM   2528  CD1  LEU  323      19.944  -15.244  38.979  0.50 16.83           MTGL
ATOM   2529  CD2  LEU  323      19.844  -17.758  38.920  0.50 16.13           MTGL
ATOM   2530  C    LEU  323      18.779  -17.431  34.645  0.50 19.86           MTGL
ATOM   2531  O    LEU  323      19.270  -17.113  33.561  0.50 19.75           MTGL
ATOM   2532  N    SER  324      17.477  -17.630  34.817  1.00 21.01           MTGL
ATOM   2533  CA   SER  324      16.524  -17.511  33.719  1.00 21.34           MTGL
ATOM   2534  CB   SER  324      15.114  -17.827  34.220  1.00 21.65           MTGL
ATOM   2535  OG   SER  324      14.713  -16.887  35.202  1.00 22.41           MTGL
ATOM   2536  C    SER  324      16.529  -16.130  33.075  1.00 21.33           MTGL
ATOM   2537  O    SER  324      16.159  -15.980  31.913  1.00 20.59           MTGL
ATOM   2538  N    SER  325      16.955  -15.123  33.830  1.00 20.04           MTGL
ATOM   2539  CA   SER  325      16.984  -13.759  33.321  1.00 20.07           MTGL
ATOM   2540  CB   SER  325      17.227  -12.780  34.476  1.00 19.69           MTGL
ATOM   2541  OG   SER  325      18.417  -13.106  35.172  1.00 17.73           MTGL
ATOM   2542  C    SER  325      18.012  -13.515  32.213  1.00 20.16           MTGL
ATOM   2543  O    SER  325      17.892  -12.549  31.460  1.00 19.87           MTGL
ATOM   2544  N    LEU  326      19.010  -14.388  32.104  1.00 19.54           MTGL
ATOM   2545  CA   LEU  326      20.048  -14.230  31.085  1.00 19.73           MTGL
ATOM   2546  CB   LEU  326      21.126  -15.314  31.236  1.00 20.49           MTGL
ATOM   2547  CG   LEU  326      22.606  -14.910  31.307  1.00 22.10           MTGL
ATOM   2548  CD1  LEU  326      23.433  -15.966  30.587  1.00 21.95           MTGL
ATOM   2549  CD2  LEU  326      22.848  -13.551  30.678  1.00 22.81           MTGL
ATOM   2550  C    LEU  326      19.519  -14.274  29.646  1.00 19.72           MTGL
ATOM   2551  O    LEU  326      20.094  -13.655  28.754  1.00 19.08           MTGL
```

Fig. 1 cont.

```
ATOM   2552  N    SER  327      18.439  -15.015  29.412  1.00 18.98      MTGL
ATOM   2553  CA   SER  327      17.875  -15.133  28.067  1.00 18.71      MTGL
ATOM   2554  CB   SER  327      16.861  -16.271  28.023  1.00 17.52      MTGL
ATOM   2555  OG   SER  327      15.740  -15.947  28.825  1.00 16.77      MTGL
ATOM   2556  C    SER  327      17.191  -13.851  27.585  1.00 18.81      MTGL
ATOM   2557  O    SER  327      16.698  -13.795  26.459  1.00 18.63      MTGL
ATOM   2558  N    VAL  328      17.140  -12.836  28.440  1.00 18.22      MTGL
ATOM   2559  CA   VAL  328      16.517  -11.573  28.066  1.00 18.51      MTGL
ATOM   2560  CB   VAL  328      16.590  -10.545  29.223  1.00 19.11      MTGL
ATOM   2561  CG1  VAL  328      18.046  -10.177  29.509  1.00 17.14      MTGL
ATOM   2562  CG2  VAL  328      15.777   -9.304  28.868  1.00 19.04      MTGL
ATOM   2563  C    VAL  328      17.210  -10.983  26.839  1.00 19.25      MTGL
ATOM   2564  O    VAL  328      16.589  -10.285  26.039  1.00 18.81      MTGL
ATOM   2565  N    PHE  329      18.498  -11.273  26.685  1.00 20.22      MTGL
ATOM   2566  CA   PHE  329      19.258  -10.752  25.550  1.00 22.10      MTGL
ATOM   2567  CB   PHE  329      20.752  -10.989  25.774  1.00 21.20      MTGL
ATOM   2568  CG   PHE  329      21.307  -10.211  26.929  1.00 21.71      MTGL
ATOM   2569  CD1  PHE  329      21.525   -8.842  26.814  1.00 21.66      MTGL
ATOM   2570  CD2  PHE  329      21.551  -10.831  28.151  1.00 20.67      MTGL
ATOM   2571  CE1  PHE  329      21.979   -8.099  27.901  1.00 22.16      MTGL
ATOM   2572  CE2  PHE  329      22.003  -10.098  29.240  1.00 22.03      MTGL
ATOM   2573  CZ   PHE  329      22.215   -8.728  29.114  1.00 22.57      MTGL
ATOM   2574  C    PHE  329      18.815  -11.340  24.212  1.00 23.27      MTGL
ATOM   2575  O    PHE  329      19.267  -10.904  23.152  1.00 23.56      MTGL
ATOM   2576  N    GLN  330      17.927  -12.326  24.267  1.00 23.16      MTGL
ATOM   2577  CA   GLN  330      17.402  -12.950  23.058  1.00 24.83      MTGL
ATOM   2578  CB   GLN  330      16.994  -14.403  23.333  1.00 25.48      MTGL
ATOM   2579  CG   GLN  330      18.138  -15.371  23.573  1.00 25.89      MTGL
ATOM   2580  CD   GLN  330      17.648  -16.773  23.894  1.00 27.09      MTGL
ATOM   2581  OE1  GLN  330      18.390  -17.748  23.750  1.00 29.08      MTGL
ATOM   2582  NE2  GLN  330      16.400  -16.882  24.343  1.00 24.64      MTGL
ATOM   2583  C    GLN  330      16.157  -12.198  22.596  1.00 25.46      MTGL
ATOM   2584  O    GLN  330      15.651  -12.439  21.502  1.00 25.45      MTGL
ATOM   2585  N    ARG  331      15.669  -11.282  23.426  1.00 25.05      MTGL
ATOM   2586  CA   ARG  331      14.443  -10.573  23.094  1.00 25.37      MTGL
ATOM   2587  CB   ARG  331      13.356  -10.991  24.087  1.00 24.60      MTGL
ATOM   2588  CG   ARG  331      13.223  -12.507  24.246  1.00 25.96      MTGL
ATOM   2589  CD   ARG  331      12.110  -12.882  25.220  1.00 26.44      MTGL
ATOM   2590  NE   ARG  331      12.400  -12.493  26.600  1.00 27.25      MTGL
ATOM   2591  CZ   ARG  331      13.123  -13.218  27.451  1.00 27.98      MTGL
ATOM   2592  NH1  ARG  331      13.637  -14.383  27.073  1.00 26.83      MTGL
ATOM   2593  NH2  ARG  331      13.329  -12.777  28.683  1.00 26.92      MTGL
ATOM   2594  C    ARG  331      14.506   -9.049  23.017  1.00 25.38      MTGL
ATOM   2595  O    ARG  331      13.468   -8.391  23.085  1.00 25.25      MTGL
ATOM   2596  N    ILE  332      15.703   -8.487  22.863  1.00 25.52      MTGL
ATOM   2597  CA   ILE  332      15.847   -7.035  22.779  1.00 26.69      MTGL
ATOM   2598  CB   ILE  332      16.510   -6.459  24.049  1.00 26.08      MTGL
ATOM   2599  CG2  ILE  332      15.646   -6.765  25.269  1.00 25.81      MTGL
ATOM   2600  CG1  ILE  332      17.912   -7.047  24.224  1.00 25.06      MTGL
ATOM   2601  CD1  ILE  332      18.663   -6.506  25.425  1.00 23.51      MTGL
ATOM   2602  C    ILE  332      16.664   -6.599  21.567  1.00 27.88      MTGL
ATOM   2603  O    ILE  332      17.171   -7.485  20.855  1.00 28.65      MTGL
ATOM   2604  OXT  ILE  332      16.787   -5.372  21.344  1.00 30.38      MTGL
END
```

Fig. 1 cont.

```
HEADER                                                                    HIGL
ATOM      1  CB   ALA     1       6.247  74.348 114.849  1.00 27.43       HIGL
ATOM      2  C    ALA     1       7.283  72.458 113.617  1.00 26.21       HIGL
ATOM      3  O    ALA     1       6.683  72.007 112.638  1.00 26.69       HIGL
ATOM      4  N    ALA     1       7.237  74.771 112.633  1.00 26.59       HIGL
ATOM      5  CA   ALA     1       7.343  73.961 113.883  1.00 26.86       HIGL
ATOM      6  N    LEU     2       7.883  71.693 114.524  1.00 24.15       HIGL
ATOM      7  CA   LEU     2       7.971  70.244 114.405  1.00 22.16       HIGL
ATOM      8  CB   LEU     2       8.883  69.700 115.498  1.00 21.06       HIGL
ATOM      9  CG   LEU     2      10.274  70.334 115.565  1.00 20.32       HIGL
ATOM     10  CD1  LEU     2      10.966  69.921 116.848  1.00 19.78       HIGL
ATOM     11  CD2  LEU     2      11.076  69.921 114.346  1.00 20.05       HIGL
ATOM     12  C    LEU     2       6.663  69.471 114.429  1.00 22.53       HIGL
ATOM     13  O    LEU     2       5.748  69.767 115.202  1.00 23.10       HIGL
ATOM     14  N    GLN     3       6.597  68.456 113.576  1.00 21.51       HIGL
ATOM     15  CA   GLN     3       5.430  67.601 113.493  1.00 20.06       HIGL
ATOM     16  CB   GLN     3       5.435  66.837 112.175  1.00 18.80       HIGL
ATOM     17  CG   GLN     3       4.157  66.084 111.909  1.00 19.14       HIGL
ATOM     18  CD   GLN     3       4.246  65.213 110.680  1.00 19.73       HIGL
ATOM     19  OE1  GLN     3       4.884  65.577 109.689  1.00 21.27       HIGL
ATOM     20  NE2  GLN     3       3.594  64.062 110.728  1.00 18.71       HIGL
ATOM     21  C    GLN     3       5.504  66.609 114.644  1.00 19.78       HIGL
ATOM     22  O    GLN     3       4.513  66.342 115.324  1.00 20.14       HIGL
ATOM     23  N    TYR     4       6.696  66.060 114.849  1.00 19.50       HIGL
ATOM     24  CA   TYR     4       6.920  65.083 115.902  1.00 19.32       HIGL
ATOM     25  CB   TYR     4       7.614  63.849 115.328  1.00 18.96       HIGL
ATOM     26  CG   TYR     4       6.913  63.222 114.145  1.00 19.19       HIGL
ATOM     27  CD1  TYR     4       5.639  62.669 114.271  1.00 19.50       HIGL
ATOM     28  CE1  TYR     4       5.019  62.033 113.199  1.00 18.39       HIGL
ATOM     29  CD2  TYR     4       7.546  63.131 112.909  1.00 19.30       HIGL
ATOM     30  CE2  TYR     4       6.935  62.497 111.831  1.00 19.42       HIGL
ATOM     31  CZ   TYR     4       5.672  61.947 111.984  1.00 19.38       HIGL
ATOM     32  OH   TYR     4       5.083  61.288 110.922  1.00 18.91       HIGL
ATOM     33  C    TYR     4       7.790  65.686 117.000  1.00 19.57       HIGL
ATOM     34  O    TYR     4       8.954  66.022 116.776  1.00 19.37       HIGL
ATOM     35  N    LYS     5       7.220  65.845 118.185  1.00 19.13       HIGL
ATOM     36  CA   LYS     5       7.980  66.388 119.293  1.00 19.83       HIGL
ATOM     37  CB   LYS     5       7.666  67.874 119.495  1.00 21.28       HIGL
ATOM     38  CG   LYS     5       6.198  68.219 119.599  1.00 23.14       HIGL
ATOM     39  CD   LYS     5       6.031  69.730 119.695  1.00 25.10       HIGL
ATOM     40  CE   LYS     5       4.563  70.143 119.714  1.00 25.68       HIGL
ATOM     41  NZ   LYS     5       4.438  71.621 119.884  1.00 27.35       HIGL
ATOM     42  C    LYS     5       7.661  65.589 120.539  1.00 19.09       HIGL
ATOM     43  O    LYS     5       6.537  65.616 121.043  1.00 20.34       HIGL
ATOM     44  N    GLY     6       8.653  64.858 121.027  1.00 17.54       HIGL
ATOM     45  CA   GLY     6       8.428  64.050 122.203  1.00 16.41       HIGL
ATOM     46  C    GLY     6       9.685  63.574 122.897  1.00 15.75       HIGL
ATOM     47  O    GLY     6      10.779  64.112 122.698  1.00 15.49       HIGL
ATOM     48  N    VAL     7       9.518  62.548 123.721  1.00 14.73       HIGL
ATOM     49  CA   VAL     7      10.623  61.996 124.470  1.00 14.42       HIGL
ATOM     50  CB   VAL     7      10.518  62.373 125.963  1.00 15.12       HIGL
ATOM     51  CG1  VAL     7      10.337  63.879 126.121  1.00 15.55       HIGL
ATOM     52  CG2  VAL     7       9.361  61.620 126.605  1.00 14.47       HIGL
ATOM     53  C    VAL     7      10.629  60.481 124.392  1.00 13.95       HIGL
ATOM     54  O    VAL     7       9.650  59.863 123.979  1.00 13.25       HIGL
ATOM     55  N    ASP     8      11.753  59.895 124.784  1.00 13.51       HIGL
ATOM     56  CA   ASP     8      11.863  58.452 124.844  1.00 13.71       HIGL
ATOM     57  CB   ASP     8      13.263  57.981 124.473  1.00 13.57       HIGL
ATOM     58  CG   ASP     8      13.354  56.480 124.393  1.00 13.68       HIGL
ATOM     59  OD1  ASP     8      12.912  55.814 125.353  1.00 13.24       HIGL
ATOM     60  OD2  ASP     8      13.861  55.967 123.373  1.00 14.72       HIGL
ATOM     61  C    ASP     8      11.626  58.233 126.324  1.00 13.84       HIGL
ATOM     62  O    ASP     8      12.391  58.735 127.156  1.00 13.94       HIGL
ATOM     63  N    TRP     9      10.562  57.510 126.658  1.00 13.89       HIGL
ATOM     64  CA   TRP     9      10.207  57.280 128.059  1.00 13.87       HIGL
```

Fig. 2

```
ATOM     65  CB   TRP     9       8.822  57.889 128.324  1.00 11.91           HIGL
ATOM     66  CG   TRP     9       7.684  57.044 127.823  1.00 12.26           HIGL
ATOM     67  CD2  TRP     9       6.406  56.867 128.448  1.00 12.11           HIGL
ATOM     68  CE2  TRP     9       5.670  55.963 127.647  1.00 12.19           HIGL
ATOM     69  CE3  TRP     9       5.809  57.383 129.609  1.00 11.70           HIGL
ATOM     70  CD1  TRP     9       7.668  56.268 126.696  1.00 11.92           HIGL
ATOM     71  NE1  TRP     9       6.466  55.614 126.586  1.00 11.76           HIGL
ATOM     72  CZ2  TRP     9       4.365  55.562 127.968  1.00 11.52           HIGL
ATOM     73  CZ3  TRP     9       4.510  56.986 129.930  1.00 11.57           HIGL
ATOM     74  CH2  TRP     9       3.804  56.085 129.111  1.00 11.64           HIGL
ATOM     75  C    TRP     9      10.212  55.798 128.440  1.00 14.10           HIGL
ATOM     76  O    TRP     9       9.551  55.392 129.392  1.00 15.49           HIGL
ATOM     77  N    SER    10      10.984  55.002 127.713  1.00 14.17           HIGL
ATOM     78  CA   SER    10      11.051  53.561 127.939  1.00 14.00           HIGL
ATOM     79  CB   SER    10      12.154  52.958 127.056  1.00 14.22           HIGL
ATOM     80  OG   SER    10      11.946  53.282 125.685  1.00 12.67           HIGL
ATOM     81  C    SER    10      11.232  53.095 129.385  1.00 13.46           HIGL
ATOM     82  O    SER    10      10.652  52.096 129.794  1.00 13.12           HIGL
ATOM     83  N    SER    11      12.021  53.821 130.162  1.00 13.49           HIGL
ATOM     84  CA   SER    11      12.281  53.437 131.542  1.00 13.65           HIGL
ATOM     85  CB   SER    11      13.490  54.200 132.051  1.00 12.96           HIGL
ATOM     86  OG   SER    11      13.175  55.576 132.142  1.00 11.73           HIGL
ATOM     87  C    SER    11      11.134  53.664 132.524  1.00 15.06           HIGL
ATOM     88  O    SER    11      11.192  53.198 133.667  1.00 15.59           HIGL
ATOM     89  N    VAL    12      10.090  54.357 132.089  1.00 15.52           HIGL
ATOM     90  CA   VAL    12       8.987  54.682 132.983  1.00 16.34           HIGL
ATOM     91  CB   VAL    12       7.793  55.248 132.197  1.00 16.01           HIGL
ATOM     92  CG1  VAL    12       7.264  54.205 131.248  1.00 16.29           HIGL
ATOM     93  CG2  VAL    12       6.714  55.720 133.159  1.00 15.28           HIGL
ATOM     94  C    VAL    12       8.485  53.594 133.945  1.00 17.29           HIGL
ATOM     95  O    VAL    12       8.361  53.855 135.143  1.00 18.04           HIGL
ATOM     96  N    MET    13       8.197  52.390 133.457  1.00 17.84           HIGL
ATOM     97  CA   MET    13       7.695  51.346 134.355  1.00 17.96           HIGL
ATOM     98  CB   MET    13       7.044  50.203 133.568  1.00 17.95           HIGL
ATOM     99  CG   MET    13       5.703  50.579 132.968  1.00 19.53           HIGL
ATOM    100  SD   MET    13       4.678  49.147 132.593  1.00 23.13           HIGL
ATOM    101  CE   MET    13       5.559  48.452 131.185  1.00 23.08           HIGL
ATOM    102  C    MET    13       8.756  50.788 135.290  1.00 17.76           HIGL
ATOM    103  O    MET    13       8.456  50.415 136.420  1.00 17.26           HIGL
ATOM    104  N    VAL    14       9.994  50.723 134.817  1.00 17.91           HIGL
ATOM    105  CA   VAL    14      11.082  50.225 135.640  1.00 17.21           HIGL
ATOM    106  CB   VAL    14      12.413  50.169 134.845  1.00 16.85           HIGL
ATOM    107  CG1  VAL    14      13.559  49.837 135.761  1.00 13.37           HIGL
ATOM    108  CG2  VAL    14      12.311  49.128 133.741  1.00 15.66           HIGL
ATOM    109  C    VAL    14      11.212  51.187 136.809  1.00 17.76           HIGL
ATOM    110  O    VAL    14      11.455  50.774 137.945  1.00 18.17           HIGL
ATOM    111  N    GLU    15      11.031  52.473 136.533  1.00 18.10           HIGL
ATOM    112  CA   GLU    15      11.120  53.476 137.586  1.00 19.10           HIGL
ATOM    113  CB   GLU    15      11.207  54.881 136.991  1.00 19.32           HIGL
ATOM    114  CG   GLU    15      12.554  55.178 136.365  1.00 20.08           HIGL
ATOM    115  CD   GLU    15      13.676  55.158 137.383  1.00 21.57           HIGL
ATOM    116  OE1  GLU    15      13.838  54.131 138.076  1.00 22.32           HIGL
ATOM    117  OE2  GLU    15      14.398  56.171 137.492  1.00 22.71           HIGL
ATOM    118  C    GLU    15       9.937  53.387 138.539  1.00 19.39           HIGL
ATOM    119  O    GLU    15      10.107  53.492 139.757  1.00 19.72           HIGL
ATOM    120  N    GLU    16       8.740  53.196 137.992  1.00 19.13           HIGL
ATOM    121  CA   GLU    16       7.562  53.084 138.839  1.00 19.39           HIGL
ATOM    122  CB   GLU    16       6.289  52.932 137.996  1.00 18.72           HIGL
ATOM    123  CG   GLU    16       5.945  54.180 137.193  1.00 19.94           HIGL
ATOM    124  CD   GLU    16       4.840  53.959 136.159  1.00 21.79           HIGL
ATOM    125  OE1  GLU    16       4.817  52.881 135.521  1.00 22.23           HIGL
ATOM    126  OE2  GLU    16       4.003  54.874 135.966  1.00 21.65           HIGL
ATOM    127  C    GLU    16       7.759  51.885 139.761  1.00 19.47           HIGL
ATOM    128  O    GLU    16       7.547  51.989 140.969  1.00 19.63           HIGL
ATOM    129  N    ARG    17       8.190  50.756 139.202  1.00 19.74           HIGL
```

Fig. 2 cont.

| | | | | | | | | | |
|---|---|---|---|---|---|---|---|---|---|
|ATOM|130|CA|ARG|17|8.416|49.562|140.014|1.00 20.25|HIGL|
|ATOM|131|CB|ARG|17|8.911|48.392|139.164|1.00 21.03|HIGL|
|ATOM|132|CG|ARG|17|7.873|47.765|138.257|1.00 23.68|HIGL|
|ATOM|133|CD|ARG|17|8.178|46.286|138.053|1.00 27.08|HIGL|
|ATOM|134|NE|ARG|17|7.410|45.701|136.956|1.00 31.03|HIGL|
|ATOM|135|CZ|ARG|17|7.660|45.919|135.664|1.00 32.87|HIGL|
|ATOM|136|NH1|ARG|17|8.666|46.709|135.299|1.00 32.97|HIGL|
|ATOM|137|NH2|ARG|17|6.902|45.352|134.731|1.00 33.75|HIGL|
|ATOM|138|C|ARG|17|9.445|49.840|141.104|1.00 19.92|HIGL|
|ATOM|139|O|ARG|17|9.443|49.198|142.151|1.00 20.42|HIGL|
|ATOM|140|N|ALA|18|10.325|50.801|140.850|1.00 19.29|HIGL|
|ATOM|141|CA|ALA|18|11.357|51.153|141.811|1.00 17.90|HIGL|
|ATOM|142|CB|ALA|18|12.584|51.698|141.086|1.00 17.12|HIGL|
|ATOM|143|C|ALA|18|10.846|52.168|142.830|1.00 17.59|HIGL|
|ATOM|144|O|ALA|18|11.611|52.653|143.669|1.00 16.93|HIGL|
|ATOM|145|N|GLY|19|9.557|52.494|142.745|1.00 16.98|HIGL|
|ATOM|146|CA|GLY|19|8.963|53.424|143.687|1.00 16.15|HIGL|
|ATOM|147|C|GLY|19|8.935|54.890|143.298|1.00 16.93|HIGL|
|ATOM|148|O|GLY|19|8.543|55.734|144.104|1.00 17.33|HIGL|
|ATOM|149|N|VAL|20|9.333|55.209|142.072|1.00 17.17|HIGL|
|ATOM|150|CA|VAL|20|9.336|56.598|141.626|1.00 17.58|HIGL|
|ATOM|151|CB|VAL|20|10.148|56.764|140.330|1.00 17.22|HIGL|
|ATOM|152|CG1|VAL|20|10.013|58.190|139.814|1.00 16.00|HIGL|
|ATOM|153|CG2|VAL|20|11.609|56.419|140.584|1.00 17.68|HIGL|
|ATOM|154|C|VAL|20|7.945|57.167|141.370|1.00 17.79|HIGL|
|ATOM|155|O|VAL|20|7.084|56.490|140.826|1.00 18.75|HIGL|
|ATOM|156|N|ARG|21|7.740|58.420|141.760|1.00 17.99|HIGL|
|ATOM|157|CA|ARG|21|6.470|59.106|141.537|1.00 18.92|HIGL|
|ATOM|158|CB|ARG|21|5.775|59.399|142.862|1.00 19.66|HIGL|
|ATOM|159|CG|ARG|21|5.367|58.155|143.617|1.00 20.84|HIGL|
|ATOM|160|CD|ARG|21|4.245|57.425|142.917|1.00 21.60|HIGL|
|ATOM|161|NE|ARG|21|3.389|56.783|143.906|1.00 23.75|HIGL|
|ATOM|162|CZ|ARG|21|3.734|55.707|144.598|1.00 23.89|HIGL|
|ATOM|163|NH1|ARG|21|4.920|55.148|144.389|1.00 25.67|HIGL|
|ATOM|164|NH2|ARG|21|2.911|55.215|145.516|1.00 22.10|HIGL|
|ATOM|165|C|ARG|21|6.749|60.412|140.809|1.00 18.45|HIGL|
|ATOM|166|O|ARG|21|7.598|61.198|141.231|1.00 18.88|HIGL|
|ATOM|167|N|TYR|22|6.032|60.640|139.717|1.00 17.66|HIGL|
|ATOM|168|CA|TYR|22|6.221|61.846|138.920|1.00 16.70|HIGL|
|ATOM|169|CB|TYR|22|6.236|61.480|137.438|1.00 15.81|HIGL|
|ATOM|170|CG|TYR|22|7.402|60.608|137.038|1.00 16.16|HIGL|
|ATOM|171|CD1|TYR|22|8.706|61.124|136.998|1.00 14.69|HIGL|
|ATOM|172|CE1|TYR|22|9.790|60.322|136.647|1.00 14.60|HIGL|
|ATOM|173|CD2|TYR|22|7.211|59.260|136.715|1.00 15.58|HIGL|
|ATOM|174|CE2|TYR|22|8.294|58.442|136.361|1.00 16.20|HIGL|
|ATOM|175|CZ|TYR|22|9.582|58.980|136.330|1.00 15.43|HIGL|
|ATOM|176|OH|TYR|22|10.648|58.178|135.994|1.00 12.55|HIGL|
|ATOM|177|C|TYR|22|5.156|62.903|139.166|1.00 17.06|HIGL|
|ATOM|178|O|TYR|22|4.008|62.591|139.482|1.00 17.73|HIGL|
|ATOM|179|N|LYS|23|5.545|64.160|139.011|1.00 17.11|HIGL|
|ATOM|180|CA|LYS|23|4.631|65.279|139.191|1.00 17.49|HIGL|
|ATOM|181|CB|LYS|23|4.813|65.913|140.575|1.00 18.19|HIGL|
|ATOM|182|CG|LYS|23|4.800|64.938|141.748|1.00 19.57|HIGL|
|ATOM|183|CD|LYS|23|6.141|64.239|141.933|1.00 18.82|HIGL|
|ATOM|184|CE|LYS|23|6.061|63.255|143.085|1.00 18.77|HIGL|
|ATOM|185|NZ|LYS|23|7.366|62.602|143.352|1.00 19.04|HIGL|
|ATOM|186|C|LYS|23|4.975|66.318|138.137|1.00 17.45|HIGL|
|ATOM|187|O|LYS|23|6.098|66.342|137.640|1.00 17.10|HIGL|
|ATOM|188|N|ASN|24|4.021|67.171|137.786|1.00 17.71|HIGL|
|ATOM|189|CA|ASN|24|4.315|68.221|136.823|1.00 17.61|HIGL|
|ATOM|190|CB|ASN|24|3.029|68.792|136.210|1.00 17.78|HIGL|
|ATOM|191|CG|ASN|24|1.986|69.174|137.252|1.00 17.86|HIGL|
|ATOM|192|OD1|ASN|24|2.314|69.585|138.368|1.00 18.49|HIGL|
|ATOM|193|ND2|ASN|24|0.717|69.061|136.876|1.00 17.05|HIGL|
|ATOM|194|C|ASN|24|5.081|69.294|137.597|1.00 17.97|HIGL|

Fig. 2 cont.

```
ATOM    195  O    ASN    24       5.481   69.060  138.739  1.00  16.84           HIGL
ATOM    196  N    VAL    25       5.285   70.462  136.994  1.00  19.12           HIGL
ATOM    197  CA   VAL    25       6.033   71.537  137.660  1.00  20.42           HIGL
ATOM    198  CB   VAL    25       6.164   72.813  136.789  1.00  20.47           HIGL
ATOM    199  CG1  VAL    25       7.591   73.345  136.856  1.00  18.59           HIGL
ATOM    200  CG2  VAL    25       5.749   72.534  135.377  1.00  21.79           HIGL
ATOM    201  C    VAL    25       5.399   72.009  138.957  1.00  20.49           HIGL
ATOM    202  O    VAL    25       6.071   72.577  139.812  1.00  19.69           HIGL
ATOM    203  N    ASN    26       4.101   71.782  139.094  1.00  21.96           HIGL
ATOM    204  CA   ASN    26       3.375   72.242  140.271  1.00  22.88           HIGL
ATOM    205  CB   ASN    26       1.979   72.686  139.841  1.00  23.37           HIGL
ATOM    206  CG   ASN    26       2.026   73.861  138.879  1.00  24.96           HIGL
ATOM    207  OD1  ASN    26       1.188   73.986  137.980  1.00  26.06           HIGL
ATOM    208  ND2  ASN    26       3.009   74.739  139.071  1.00  24.54           HIGL
ATOM    209  C    ASN    26       3.295   71.249  141.418  1.00  22.79           HIGL
ATOM    210  O    ASN    26       2.669   71.529  142.441  1.00  23.56           HIGL
ATOM    211  N    GLY    27       3.933   70.095  141.250  1.00  22.15           HIGL
ATOM    212  CA   GLY    27       3.932   69.094  142.299  1.00  20.67           HIGL
ATOM    213  C    GLY    27       2.743   68.157  142.290  1.00  19.93           HIGL
ATOM    214  O    GLY    27       2.574   67.357  143.214  1.00  20.18           HIGL
ATOM    215  N    GLN    28       1.912   68.247  141.258  1.00  19.35           HIGL
ATOM    216  CA   GLN    28       0.748   67.376  141.164  1.00  19.04           HIGL
ATOM    217  CB   GLN    28      -0.314   68.025  140.274  1.00  19.46           HIGL
ATOM    218  CG   GLN    28      -1.579   67.207  140.102  1.00  19.85           HIGL
ATOM    219  CD   GLN    28      -2.666   67.970  139.363  1.00  21.15           HIGL
ATOM    220  OE1  GLN    28      -2.425   68.547  138.299  1.00  21.73           HIGL
ATOM    221  NE2  GLN    28      -3.871   67.971  139.921  1.00  20.85           HIGL
ATOM    222  C    GLN    28       1.164   66.009  140.607  1.00  18.84           HIGL
ATOM    223  O    GLN    28       1.602   65.901  139.464  1.00  18.45           HIGL
ATOM    224  N    GLU    29       1.038   64.973  141.432  1.00  18.66           HIGL
ATOM    225  CA   GLU    29       1.402   63.619  141.042  1.00  18.76           HIGL
ATOM    226  CB   GLU    29       1.487   62.730  142.287  1.00  18.41           HIGL
ATOM    227  CG   GLU    29       1.966   61.316  141.998  1.00  19.70           HIGL
ATOM    228  CD   GLU    29       2.223   60.504  143.252  1.00  21.17           HIGL
ATOM    229  OE1  GLU    29       2.828   61.042  144.204  1.00  22.90           HIGL
ATOM    230  OE2  GLU    29       1.836   59.318  143.285  1.00  21.00           HIGL
ATOM    231  C    GLU    29       0.412   63.005  140.045  1.00  18.74           HIGL
ATOM    232  O    GLU    29      -0.793   63.133  140.205  1.00  20.35           HIGL
ATOM    233  N    LYS    30       0.929   62.357  139.007  1.00  18.03           HIGL
ATOM    234  CA   LYS    30       0.096   61.696  137.997  1.00  18.21           HIGL
ATOM    235  CB   LYS    30      -0.563   62.702  137.038  1.00  18.37           HIGL
ATOM    236  CG   LYS    30      -0.511   64.151  137.467  1.00  19.45           HIGL
ATOM    237  CD   LYS    30      -0.017   65.012  136.323  1.00  19.01           HIGL
ATOM    238  CE   LYS    30      -1.150   65.659  135.558  1.00  19.86           HIGL
ATOM    239  NZ   LYS    30      -1.471   67.014  136.095  1.00  19.22           HIGL
ATOM    240  C    LYS    30       0.999   60.777  137.179  1.00  17.33           HIGL
ATOM    241  O    LYS    30       2.227   60.837  137.297  1.00  18.02           HIGL
ATOM    242  N    PRO    31       0.404   59.905  136.353  1.00  16.17           HIGL
ATOM    243  CD   PRO    31      -1.032   59.580  136.274  1.00  16.56           HIGL
ATOM    244  CA   PRO    31       1.201   58.991  135.525  1.00  15.20           HIGL
ATOM    245  CB   PRO    31       0.147   58.122  134.854  1.00  15.51           HIGL
ATOM    246  CG   PRO    31      -1.001   58.135  135.843  1.00  16.29           HIGL
ATOM    247  C    PRO    31       1.992   59.830  134.521  1.00  15.68           HIGL
ATOM    248  O    PRO    31       1.455   60.782  133.943  1.00  16.00           HIGL
ATOM    249  N    LEU    32       3.258   59.478  134.313  1.00  14.62           HIGL
ATOM    250  CA   LEU    32       4.139   60.224  133.416  1.00  13.57           HIGL
ATOM    251  CB   LEU    32       5.433   59.437  133.198  1.00  12.66           HIGL
ATOM    252  CG   LEU    32       6.592   60.142  132.490  1.00  12.44           HIGL
ATOM    253  CD1  LEU    32       6.934   61.428  133.209  1.00  11.76           HIGL
ATOM    254  CD2  LEU    32       7.805   59.218  132.455  1.00  12.43           HIGL
ATOM    255  C    LEU    32       3.546   60.628  132.062  1.00  13.85           HIGL
ATOM    256  O    LEU    32       3.684   61.781  131.641  1.00  13.20           HIGL
ATOM    257  N    GLU    33       2.881   59.698  131.379  1.00  14.00           HIGL
ATOM    258  CA   GLU    33       2.316   60.020  130.073  1.00  14.95           HIGL
ATOM    259  CB   GLU    33       1.486   58.847  129.510  1.00  15.36           HIGL
```

Fig. 2 cont.

```
ATOM    260  CG   GLU    33      0.259  58.440 130.324  1.00 16.87      HIGL
ATOM    261  CD   GLU    33      0.560  57.350 131.339  1.00 18.43      HIGL
ATOM    262  OE1  GLU    33      1.586  57.459 132.049  1.00 19.77      HIGL
ATOM    263  OE2  GLU    33     -0.234  56.387 131.433  1.00 18.45      HIGL
ATOM    264  C    GLU    33      1.476  61.300 130.102  1.00 15.90      HIGL
ATOM    265  O    GLU    33      1.429  62.032 129.113  1.00 17.16      HIGL
ATOM    266  N    TYR    34      0.824  61.584 131.228  1.00 16.05      HIGL
ATOM    267  CA   TYR    34      0.005  62.787 131.325  1.00 15.44      HIGL
ATOM    268  CB   TYR    34     -1.104  62.593 132.358  1.00 16.32      HIGL
ATOM    269  CG   TYR    34     -2.087  61.551 131.901  1.00 16.99      HIGL
ATOM    270  CD1  TYR    34     -2.063  60.257 132.426  1.00 17.20      HIGL
ATOM    271  CE1  TYR    34     -2.915  59.267 131.937  1.00 17.14      HIGL
ATOM    272  CD2  TYR    34     -2.992  61.832 130.875  1.00 17.08      HIGL
ATOM    273  CE2  TYR    34     -3.845  60.851 130.378  1.00 17.17      HIGL
ATOM    274  CZ   TYR    34     -3.801  59.572 130.913  1.00 17.87      HIGL
ATOM    275  OH   TYR    34     -4.647  58.603 130.425  1.00 19.84      HIGL
ATOM    276  C    TYR    34      0.828  64.030 131.617  1.00 14.61      HIGL
ATOM    277  O    TYR    34      0.512  65.115 131.126  1.00 13.80      HIGL
ATOM    278  N    ILE    35      1.889  63.880 132.399  1.00 14.26      HIGL
ATOM    279  CA   ILE    35      2.763  65.014 132.672  1.00 14.92      HIGL
ATOM    280  CB   ILE    35      3.865  64.662 133.679  1.00 15.08      HIGL
ATOM    281  CG2  ILE    35      4.882  65.794 133.753  1.00 14.72      HIGL
ATOM    282  CG1  ILE    35      3.243  64.398 135.051  1.00 15.03      HIGL
ATOM    283  CD1  ILE    35      4.219  63.877 136.067  1.00 15.01      HIGL
ATOM    284  C    ILE    35      3.424  65.404 131.352  1.00 14.91      HIGL
ATOM    285  O    ILE    35      3.656  66.584 131.092  1.00 15.44      HIGL
ATOM    286  N    LEU    36      3.715  64.403 130.518  1.00 14.83      HIGL
ATOM    287  CA   LEU    36      4.332  64.649 129.215  1.00 14.44      HIGL
ATOM    288  CB   LEU    36      4.765  63.340 128.557  1.00 14.34      HIGL
ATOM    289  CG   LEU    36      5.806  62.491 129.280  1.00 15.12      HIGL
ATOM    290  CD1  LEU    36      6.153  61.306 128.385  1.00 15.81      HIGL
ATOM    291  CD2  LEU    36      7.050  63.320 129.595  1.00 13.46      HIGL
ATOM    292  C    LEU    36      3.385  65.375 128.267  1.00 14.40      HIGL
ATOM    293  O    LEU    36      3.761  66.376 127.659  1.00 13.88      HIGL
ATOM    294  N    ALA    37      2.162  64.864 128.131  1.00 14.45      HIGL
ATOM    295  CA   ALA    37      1.173  65.482 127.247  1.00 15.05      HIGL
ATOM    296  CB   ALA    37     -0.121  64.677 127.269  1.00 14.89      HIGL
ATOM    297  C    ALA    37      0.918  66.915 127.711  1.00 15.47      HIGL
ATOM    298  O    ALA    37      0.757  67.832 126.907  1.00 14.62      HIGL
ATOM    299  N    GLU    38      0.910  67.081 129.028  1.00 16.62      HIGL
ATOM    300  CA   GLU    38      0.693  68.362 129.689  1.00 17.33      HIGL
ATOM    301  CB   GLU    38      0.784  68.145 131.200  1.00 19.24      HIGL
ATOM    302  CG   GLU    38      0.365  69.311 132.054  1.00 21.29      HIGL
ATOM    303  CD   GLU    38      0.550  69.028 133.529  1.00 22.16      HIGL
ATOM    304  OE1  GLU    38      0.222  67.905 133.972  1.00 21.31      HIGL
ATOM    305  OE2  GLU    38      1.018  69.939 134.244  1.00 23.91      HIGL
ATOM    306  C    GLU    38      1.727  69.402 129.262  1.00 16.88      HIGL
ATOM    307  O    GLU    38      1.441  70.597 129.205  1.00 16.84      HIGL
ATOM    308  N    ASN    39      2.934  68.942 128.960  1.00 16.61      HIGL
ATOM    309  CA   ASN    39      4.010  69.841 128.569  1.00 16.17      HIGL
ATOM    310  CB   ASN    39      5.311  69.379 129.218  1.00 16.22      HIGL
ATOM    311  CG   ASN    39      5.441  69.846 130.650  1.00 16.62      HIGL
ATOM    312  OD1  ASN    39      5.928  70.948 130.907  1.00 16.26      HIGL
ATOM    313  ND2  ASN    39      4.991  69.017 131.594  1.00 15.54      HIGL
ATOM    314  C    ASN    39      4.218  70.024 127.067  1.00 16.04      HIGL
ATOM    315  O    ASN    39      5.226  70.597 126.649  1.00 16.85      HIGL
ATOM    316  N    GLY    40      3.279  69.535 126.259  1.00 15.42      HIGL
ATOM    317  CA   GLY    40      3.392  69.694 124.821  1.00 14.77      HIGL
ATOM    318  C    GLY    40      3.895  68.494 124.037  1.00 15.22      HIGL
ATOM    319  O    GLY    40      3.890  68.517 122.810  1.00 15.07      HIGL
ATOM    320  N    VAL    41      4.342  67.451 124.725  1.00 15.28      HIGL
ATOM    321  CA   VAL    41      4.822  66.257 124.038  1.00 15.01      HIGL
ATOM    322  CB   VAL    41      5.357  65.212 125.047  1.00 15.77      HIGL
ATOM    323  CG1  VAL    41      5.682  63.896 124.328  1.00 14.74      HIGL
ATOM    324  CG2  VAL    41      6.596  65.760 125.751  1.00 15.28      HIGL
```

Fig. 2 cont.

```
ATOM    325  C    VAL    41       3.668  65.643 123.259  1.00 14.29      HIGL
ATOM    326  O    VAL    41       2.560  65.558 123.776  1.00 14.34      HIGL
ATOM    327  N    ASN    42       3.913  65.230 122.017  1.00 14.20      HIGL
ATOM    328  CA   ASN    42       2.846  64.611 121.217  1.00 14.11      HIGL
ATOM    329  CB   ASN    42       2.451  65.488 120.008  1.00 13.09      HIGL
ATOM    330  CG   ASN    42       3.588  65.683 119.003  1.00 15.29      HIGL
ATOM    331  OD1  ASN    42       4.632  65.030 119.077  1.00 14.89      HIGL
ATOM    332  ND2  ASN    42       3.376  66.587 118.044  1.00 13.72      HIGL
ATOM    333  C    ASN    42       3.220  63.215 120.734  1.00 13.63      HIGL
ATOM    334  O    ASN    42       2.523  62.628 119.907  1.00 13.90      HIGL
ATOM    335  N    MET    43       4.319  62.683 121.259  1.00 13.09      HIGL
ATOM    336  CA   MET    43       4.776  61.355 120.865  1.00 12.43      HIGL
ATOM    337  CB   MET    43       5.290  61.373 119.421  1.00 12.54      HIGL
ATOM    338  CG   MET    43       5.833  60.029 118.943  1.00 13.16      HIGL
ATOM    339  SD   MET    43       6.153  59.988 117.164  1.00 15.39      HIGL
ATOM    340  CE   MET    43       4.461  60.024 116.523  1.00 14.86      HIGL
ATOM    341  C    MET    43       5.870  60.820 121.774  1.00 11.00      HIGL
ATOM    342  O    MET    43       6.730  61.563 122.229  1.00  9.98      HIGL
ATOM    343  N    VAL    44       5.824  59.522 122.041  1.00 10.40      HIGL
ATOM    344  CA   VAL    44       6.837  58.900 122.872  1.00 10.47      HIGL
ATOM    345  CB   VAL    44       6.218  58.213 124.113  1.00 10.16      HIGL
ATOM    346  CG1  VAL    44       5.663  59.259 125.057  1.00 10.97      HIGL
ATOM    347  CG2  VAL    44       5.120  57.251 123.696  1.00 10.36      HIGL
ATOM    348  C    VAL    44       7.607  57.868 122.051  1.00 10.89      HIGL
ATOM    349  O    VAL    44       7.060  57.241 121.140  1.00  9.61      HIGL
ATOM    350  N    ARG    45       8.889  57.721 122.368  1.00 11.52      HIGL
ATOM    351  CA   ARG    45       9.758  56.765 121.696  1.00 12.77      HIGL
ATOM    352  CB   ARG    45      11.085  57.442 121.351  1.00 14.01      HIGL
ATOM    353  CG   ARG    45      12.129  56.570 120.667  1.00 15.59      HIGL
ATOM    354  CD   ARG    45      13.326  57.430 120.305  1.00 16.97      HIGL
ATOM    355  NE   ARG    45      14.418  56.694 119.679  1.00 17.87      HIGL
ATOM    356  CZ   ARG    45      15.496  56.254 120.320  1.00 17.82      HIGL
ATOM    357  NH1  ARG    45      15.642  56.466 121.620  1.00 17.90      HIGL
ATOM    358  NH2  ARG    45      16.439  55.610 119.653  1.00 18.55      HIGL
ATOM    359  C    ARG    45       9.970  55.628 122.687  1.00 13.22      HIGL
ATOM    360  O    ARG    45      10.244  55.810 123.859  1.00 13.66      HIGL
ATOM    361  N    GLN    46       9.821  54.390 122.232  1.00 13.78      HIGL
ATOM    362  CA   GLN    46       9.996  53.243 123.118  1.00 14.54      HIGL
ATOM    363  CB   GLN    46       8.639  52.573 123.394  1.00 15.20      HIGL
ATOM    364  CG   GLN    46       7.582  53.492 124.043  1.00 16.94      HIGL
ATOM    365  CD   GLN    46       6.298  52.748 124.403  1.00 18.02      HIGL
ATOM    366  OE1  GLN    46       5.361  53.328 124.944  1.00 17.27      HIGL
ATOM    367  NE2  GLN    46       6.257  51.454 124.097  1.00 19.40      HIGL
ATOM    368  C    GLN    46      10.960  52.228 122.512  1.00 14.27      HIGL
ATOM    369  O    GLN    46      10.808  51.829 121.360  1.00 15.12      HIGL
ATOM    370  N    ARG    47      11.962  51.821 123.280  1.00 14.18      HIGL
ATOM    371  CA   ARG    47      12.923  50.847 122.787  1.00 14.34      HIGL
ATOM    372  CB   ARG    47      14.264  51.008 123.510  1.00 14.68      HIGL
ATOM    373  CG   ARG    47      14.172  51.059 125.026  1.00 14.19      HIGL
ATOM    374  CD   ARG    47      15.555  50.900 125.661  1.00 14.01      HIGL
ATOM    375  NE   ARG    47      15.530  51.133 127.101  1.00 13.64      HIGL
ATOM    376  CZ   ARG    47      15.463  52.341 127.651  1.00 13.65      HIGL
ATOM    377  NH1  ARG    47      15.422  53.415 126.872  1.00 12.61      HIGL
ATOM    378  NH2  ARG    47      15.436  52.479 128.969  1.00 12.29      HIGL
ATOM    379  C    ARG    47      12.375  49.434 122.979  1.00 14.38      HIGL
ATOM    380  O    ARG    47      11.742  49.139 123.990  1.00 14.26      HIGL
ATOM    381  N    VAL    48      12.616  48.567 121.999  1.00 14.13      HIGL
ATOM    382  CA   VAL    48      12.136  47.194 122.054  1.00 14.66      HIGL
ATOM    383  CB   VAL    48      11.108  46.931 120.946  1.00 14.30      HIGL
ATOM    384  CG1  VAL    48      10.497  45.549 121.109  1.00 12.51      HIGL
ATOM    385  CG2  VAL    48      10.044  48.001 120.977  1.00 14.44      HIGL
ATOM    386  C    VAL    48      13.266  46.185 121.901  1.00 15.87      HIGL
ATOM    387  O    VAL    48      13.987  46.200 120.903  1.00 16.88      HIGL
ATOM    388  N    TRP    49      13.420  45.319 122.901  1.00 16.25      HIGL
ATOM    389  CA   TRP    49      14.449  44.283 122.881  1.00 16.07      HIGL
```

Fig. 2 cont.

```
ATOM    390  CB   TRP    49      15.243  44.280 124.194  1.00 15.19      HIGL
ATOM    391  CG   TRP    49      16.039  45.533 124.422  1.00 15.37      HIGL
ATOM    392  CD2  TRP    49      16.745  45.898 125.613  1.00 15.05      HIGL
ATOM    393  CE2  TRP    49      17.359  47.146 125.370  1.00 14.69      HIGL
ATOM    394  CE3  TRP    49      16.922  45.290 126.864  1.00 15.17      HIGL
ATOM    395  CD1  TRP    49      16.247  46.550 123.529  1.00 15.47      HIGL
ATOM    396  NE1  TRP    49      17.037  47.521 124.093  1.00 14.49      HIGL
ATOM    397  CZ2  TRP    49      18.138  47.798 126.332  1.00 15.16      HIGL
ATOM    398  CZ3  TRP    49      17.696  45.939 127.819  1.00 14.43      HIGL
ATOM    399  CH2  TRP    49      18.294  47.179 127.547  1.00 14.14      HIGL
ATOM    400  C    TRP    49      13.793  42.924 122.665  1.00 16.51      HIGL
ATOM    401  O    TRP    49      12.657  42.695 123.100  1.00 16.05      HIGL
ATOM    402  N    VAL    50      14.517  42.031 121.990  1.00 16.88      HIGL
ATOM    403  CA   VAL    50      14.031  40.690 121.675  1.00 17.15      HIGL
ATOM    404  CB   VAL    50      15.039  39.953 120.754  1.00 17.71      HIGL
ATOM    405  CG1  VAL    50      14.449  38.639 120.260  1.00 17.30      HIGL
ATOM    406  CG2  VAL    50      15.402  40.841 119.571  1.00 17.23      HIGL
ATOM    407  C    VAL    50      13.763  39.843 122.923  1.00 17.92      HIGL
ATOM    408  O    VAL    50      12.617  39.724 123.362  1.00 18.11      HIGL
ATOM    409  N    ASN    51      14.812  39.258 123.495  1.00 18.58      HIGL
ATOM    410  CA   ASN    51      14.660  38.430 124.690  1.00 18.99      HIGL
ATOM    411  CB   ASN    51      15.126  37.010 124.410  1.00 21.64      HIGL
ATOM    412  CG   ASN    51      14.602  36.480 123.093  1.00 24.95      HIGL
ATOM    413  OD1  ASN    51      13.388  36.364 122.892  1.00 27.18      HIGL
ATOM    414  ND2  ASN    51      15.517  36.156 122.180  1.00 25.56      HIGL
ATOM    415  C    ASN    51      15.443  38.978 125.875  1.00 18.38      HIGL
ATOM    416  O    ASN    51      16.417  38.368 126.319  1.00 17.35      HIGL
ATOM    417  N    PRO    52      15.032  40.144 126.401  1.00 17.80      HIGL
ATOM    418  CD   PRO    52      13.867  40.972 126.053  1.00 17.12      HIGL
ATOM    419  CA   PRO    52      15.747  40.712 127.543  1.00 17.06      HIGL
ATOM    420  CB   PRO    52      14.949  41.971 127.861  1.00 16.91      HIGL
ATOM    421  CG   PRO    52      13.579  41.650 127.364  1.00 17.23      HIGL
ATOM    422  C    PRO    52      15.776  39.716 128.688  1.00 17.60      HIGL
ATOM    423  O    PRO    52      14.828  38.954 128.891  1.00 17.99      HIGL
ATOM    424  N    TRP    53      16.877  39.723 129.428  1.00 17.96      HIGL
ATOM    425  CA   TRP    53      17.068  38.801 130.536  1.00 17.77      HIGL
ATOM    426  CB   TRP    53      18.448  39.013 131.156  1.00 18.06      HIGL
ATOM    427  CG   TRP    53      18.543  40.298 131.917  1.00 18.50      HIGL
ATOM    428  CD2  TRP    53      18.389  40.459 133.328  1.00 18.71      HIGL
ATOM    429  CE2  TRP    53      18.452  41.844 133.600  1.00 17.92      HIGL
ATOM    430  CE3  TRP    53      18.198  39.565 134.390  1.00 18.46      HIGL
ATOM    431  CD1  TRP    53      18.698  41.553 131.404  1.00 18.32      HIGL
ATOM    432  NE1  TRP    53      18.642  42.489 132.409  1.00 17.61      HIGL
ATOM    433  CZ2  TRP    53      18.331  42.357 134.888  1.00 19.23      HIGL
ATOM    434  CZ3  TRP    53      18.077  40.074 135.674  1.00 19.45      HIGL
ATOM    435  CH2  TRP    53      18.143  41.460 135.912  1.00 19.83      HIGL
ATOM    436  C    TRP    53      16.017  38.919 131.631  1.00 17.78      HIGL
ATOM    437  O    TRP    53      15.726  37.944 132.324  1.00 18.33      HIGL
ATOM    438  N    ASP    54      15.447  40.106 131.793  1.00 17.42      HIGL
ATOM    439  CA   ASP    54      14.455  40.307 132.845  1.00 17.12      HIGL
ATOM    440  CB   ASP    54      14.976  41.352 133.830  1.00 16.85      HIGL
ATOM    441  CG   ASP    54      15.139  42.705 133.189  1.00 17.98      HIGL
ATOM    442  OD1  ASP    54      15.083  42.779 131.938  1.00 19.62      HIGL
ATOM    443  OD2  ASP    54      15.325  43.690 133.927  1.00 17.75      HIGL
ATOM    444  C    ASP    54      13.080  40.718 132.320  1.00 16.46      HIGL
ATOM    445  O    ASP    54      12.196  41.080 133.094  1.00 16.77      HIGL
ATOM    446  N    GLY    55      12.907  40.666 131.003  1.00 16.49      HIGL
ATOM    447  CA   GLY    55      11.629  41.019 130.406  1.00 15.10      HIGL
ATOM    448  C    GLY    55      11.396  42.494 130.120  1.00 14.82      HIGL
ATOM    449  O    GLY    55      10.461  42.844 129.401  1.00 14.82      HIGL
ATOM    450  N    ASN    56      12.225  43.375 130.667  1.00 14.46      HIGL
ATOM    451  CA   ASN    56      12.010  44.792 130.418  1.00 14.01      HIGL
ATOM    452  CB   ASN    56      12.784  45.649 131.417  1.00 14.38      HIGL
ATOM    453  CG   ASN    56      12.130  45.660 132.785  1.00 15.79      HIGL
ATOM    454  OD1  ASN    56      10.901  45.606 132.902  1.00 15.70      HIGL
```

Fig. 2 cont.

```
ATOM    455  ND2  ASN    56      12.941  45.743 133.826  1.00 16.95      HIGL
ATOM    456  C    ASN    56      12.341  45.204 128.999  1.00 13.31      HIGL
ATOM    457  O    ASN    56      13.366  44.817 128.442  1.00 12.12      HIGL
ATOM    458  N    TYR    57      11.439  45.991 128.424  1.00 13.34      HIGL
ATOM    459  CA   TYR    57      11.558  46.499 127.065  1.00 13.09      HIGL
ATOM    460  CB   TYR    57      12.968  47.049 126.789  1.00 12.20      HIGL
ATOM    461  CG   TYR    57      13.466  47.989 127.865  1.00 11.14      HIGL
ATOM    462  CD1  TYR    57      12.666  49.030 128.330  1.00 10.28      HIGL
ATOM    463  CE1  TYR    57      13.095  49.859 129.353  1.00  9.79      HIGL
ATOM    464  CD2  TYR    57      14.716  47.808 128.450  1.00 10.12      HIGL
ATOM    465  CE2  TYR    57      15.152  48.630 129.471  1.00  9.28      HIGL
ATOM    466  CZ   TYR    57      14.333  49.654 129.922  1.00  9.42      HIGL
ATOM    467  OH   TYR    57      14.737  50.450 130.973  1.00 10.17      HIGL
ATOM    468  C    TYR    57      11.214  45.426 126.052  1.00 13.71      HIGL
ATOM    469  O    TYR    57      11.460  45.591 124.854  1.00 13.96      HIGL
ATOM    470  N    ASN    58      10.657  44.313 126.515  1.00 13.75      HIGL
ATOM    471  CA   ASN    58      10.276  43.298 125.553  1.00 14.27      HIGL
ATOM    472  CB   ASN    58      10.325  41.874 126.147  1.00 12.09      HIGL
ATOM    473  CG   ASN    58       9.216  41.576 127.140  1.00  9.87      HIGL
ATOM    474  OD1  ASN    58       8.278  42.353 127.323  1.00 11.38      HIGL
ATOM    475  ND2  ASN    58       9.316  40.416 127.777  1.00  5.89      HIGL
ATOM    476  C    ASN    58       8.892  43.669 125.039  1.00 15.29      HIGL
ATOM    477  O    ASN    58       8.301  44.651 125.490  1.00 14.81      HIGL
ATOM    478  N    LEU    59       8.389  42.901 124.085  1.00 17.30      HIGL
ATOM    479  CA   LEU    59       7.096  43.188 123.482  1.00 19.48      HIGL
ATOM    480  CB   LEU    59       6.692  42.037 122.565  1.00 21.08      HIGL
ATOM    481  CG   LEU    59       5.709  42.447 121.470  1.00 23.34      HIGL
ATOM    482  CD1  LEU    59       6.296  43.624 120.673  1.00 23.05      HIGL
ATOM    483  CD2  LEU    59       5.436  41.247 120.561  1.00 23.47      HIGL
ATOM    484  C    LEU    59       5.970  43.488 124.471  1.00 19.90      HIGL
ATOM    485  O    LEU    59       5.367  44.557 124.415  1.00 21.04      HIGL
ATOM    486  N    ASP    60       5.683  42.555 125.372  1.00 20.10      HIGL
ATOM    487  CA   ASP    60       4.619  42.756 126.348  1.00 20.50      HIGL
ATOM    488  CB   ASP    60       4.599  41.613 127.369  1.00 21.74      HIGL
ATOM    489  CG   ASP    60       4.436  40.250 126.720  1.00 23.55      HIGL
ATOM    490  OD1  ASP    60       3.553  40.100 125.844  1.00 23.00      HIGL
ATOM    491  OD2  ASP    60       5.190  39.324 127.094  1.00 24.89      HIGL
ATOM    492  C    ASP    60       4.810  44.078 127.078  1.00 20.77      HIGL
ATOM    493  O    ASP    60       3.869  44.860 127.231  1.00 21.37      HIGL
ATOM    494  N    TYR    61       6.038  44.315 127.529  1.00 20.29      HIGL
ATOM    495  CA   TYR    61       6.393  45.533 128.241  1.00 19.19      HIGL
ATOM    496  CB   TYR    61       7.896  45.526 128.574  1.00 19.77      HIGL
ATOM    497  CG   TYR    61       8.400  46.776 129.274  1.00 19.20      HIGL
ATOM    498  CD1  TYR    61       8.572  47.975 128.580  1.00 19.12      HIGL
ATOM    499  CE1  TYR    61       8.998  49.132 129.229  1.00 19.60      HIGL
ATOM    500  CD2  TYR    61       8.675  46.766 130.638  1.00 19.18      HIGL
ATOM    501  CE2  TYR    61       9.101  47.916 131.297  1.00 20.13      HIGL
ATOM    502  CZ   TYR    61       9.259  49.096 130.589  1.00 20.45      HIGL
ATOM    503  OH   TYR    61       9.663  50.239 131.250  1.00 21.00      HIGL
ATOM    504  C    TYR    61       6.059  46.767 127.414  1.00 19.25      HIGL
ATOM    505  O    TYR    61       5.506  47.738 127.930  1.00 19.40      HIGL
ATOM    506  N    ASN    62       6.390  46.733 126.129  1.00 19.00      HIGL
ATOM    507  CA   ASN    62       6.128  47.878 125.271  1.00 19.77      HIGL
ATOM    508  CB   ASN    62       6.971  47.789 123.999  1.00 20.44      HIGL
ATOM    509  CG   ASN    62       8.403  48.223 124.229  1.00 21.08      HIGL
ATOM    510  OD1  ASN    62       8.685  49.415 124.376  1.00 21.94      HIGL
ATOM    511  ND2  ASN    62       9.315  47.259 124.284  1.00 20.37      HIGL
ATOM    512  C    ASN    62       4.664  48.053 124.925  1.00 19.75      HIGL
ATOM    513  O    ASN    62       4.235  49.156 124.588  1.00 20.46      HIGL
ATOM    514  N    ILE    63       3.892  46.977 125.009  1.00 19.62      HIGL
ATOM    515  CA   ILE    63       2.472  47.073 124.717  1.00 20.26      HIGL
ATOM    516  CB   ILE    63       1.856  45.693 124.478  1.00 20.11      HIGL
ATOM    517  CG2  ILE    63       0.336  45.761 124.598  1.00 19.41      HIGL
ATOM    518  CG1  ILE    63       2.293  45.198 123.101  1.00 20.67      HIGL
ATOM    519  CD1  ILE    63       1.599  43.952 122.648  1.00 23.84      HIGL
```

Fig. 2 cont.

```
ATOM  520  C    ILE  63    1.742  47.775 125.852  1.00 21.15      HIGL
ATOM  521  O    ILE  63    0.807  48.535 125.617  1.00 20.59      HIGL
ATOM  522  N    GLN  64    2.172  47.528 127.086  1.00 22.72      HIGL
ATOM  523  CA   GLN  64    1.547  48.177 128.235  1.00 23.28      HIGL
ATOM  524  CB   GLN  64    2.117  47.626 129.544  1.00 24.62      HIGL
ATOM  525  CG   GLN  64    1.064  47.428 130.630  1.00 27.22      HIGL
ATOM  526  CD   GLN  64    1.641  46.837 131.906  1.00 29.98      HIGL
ATOM  527  OE1  GLN  64    2.314  45.798 131.877  1.00 31.39      HIGL
ATOM  528  NE2  GLN  64    1.380  47.493 133.037  1.00 29.60      HIGL
ATOM  529  C    GLN  64    1.827  49.675 128.130  1.00 22.91      HIGL
ATOM  530  O    GLN  64    0.952  50.501 128.400  1.00 23.24      HIGL
ATOM  531  N    LEU  65    3.045  50.018 127.717  1.00 21.90      HIGL
ATOM  532  CA   LEU  65    3.436  51.415 127.559  1.00 21.80      HIGL
ATOM  533  CB   LEU  65    4.925  51.524 127.241  1.00 21.78      HIGL
ATOM  534  CG   LEU  65    5.863  51.436 128.439  1.00 22.02      HIGL
ATOM  535  CD1  LEU  65    7.300  51.702 128.006  1.00 21.72      HIGL
ATOM  536  CD2  LEU  65    5.424  52.459 129.459  1.00 22.32      HIGL
ATOM  537  C    LEU  65    2.650  52.104 126.458  1.00 21.48      HIGL
ATOM  538  O    LEU  65    2.107  53.191 126.651  1.00 20.27      HIGL
ATOM  539  N    ALA  66    2.604  51.467 125.297  1.00 21.88      HIGL
ATOM  540  CA   ALA  66    1.884  52.017 124.157  1.00 22.71      HIGL
ATOM  541  CB   ALA  66    1.908  51.026 123.006  1.00 21.67      HIGL
ATOM  542  C    ALA  66    0.447  52.340 124.546  1.00 22.91      HIGL
ATOM  543  O    ALA  66   -0.013  53.471 124.395  1.00 23.72      HIGL
ATOM  544  N    ARG  67   -0.256  51.340 125.059  1.00 23.00      HIGL
ATOM  545  CA   ARG  67   -1.635  51.517 125.457  1.00 22.83      HIGL
ATOM  546  CB   ARG  67   -2.121  50.260 126.173  1.00 24.13      HIGL
ATOM  547  CG   ARG  67   -3.621  50.147 126.305  1.00 26.38      HIGL
ATOM  548  CD   ARG  67   -3.993  48.774 126.824  1.00 29.10      HIGL
ATOM  549  NE   ARG  67   -3.810  47.732 125.815  1.00 30.83      HIGL
ATOM  550  CZ   ARG  67   -3.501  46.469 126.098  1.00 32.31      HIGL
ATOM  551  NH1  ARG  67   -3.333  46.096 127.361  1.00 33.65      HIGL
ATOM  552  NH2  ARG  67   -3.369  45.576 125.126  1.00 32.30      HIGL
ATOM  553  C    ARG  67   -1.747  52.749 126.351  1.00 22.02      HIGL
ATOM  554  O    ARG  67   -2.627  53.587 126.158  1.00 22.49      HIGL
ATOM  555  N    ARG  68   -0.843  52.876 127.313  1.00 21.00      HIGL
ATOM  556  CA   ARG  68   -0.860  54.031 128.207  1.00 20.10      HIGL
ATOM  557  CB   ARG  68    0.183  53.867 129.321  1.00 19.58      HIGL
ATOM  558  CG   ARG  68   -0.247  52.927 130.442  1.00 18.60      HIGL
ATOM  559  CD   ARG  68    0.858  52.723 131.475  1.00 17.98      HIGL
ATOM  560  NE   ARG  68    1.319  53.986 132.048  1.00 17.78      HIGL
ATOM  561  CZ   ARG  68    2.210  54.078 133.030  1.00 16.65      HIGL
ATOM  562  NH1  ARG  68    2.735  52.975 133.550  1.00 15.08      HIGL
ATOM  563  NH2  ARG  68    2.574  55.272 133.490  1.00 15.87      HIGL
ATOM  564  C    ARG  68   -0.588  55.322 127.441  1.00 20.06      HIGL
ATOM  565  O    ARG  68   -1.287  56.312 127.613  1.00 19.99      HIGL
ATOM  566  N    ALA  69    0.437  55.306 126.597  1.00 20.75      HIGL
ATOM  567  CA   ALA  69    0.800  56.477 125.808  1.00 21.00      HIGL
ATOM  568  CB   ALA  69    1.979  56.144 124.913  1.00 21.37      HIGL
ATOM  569  C    ALA  69   -0.379  56.960 124.965  1.00 21.40      HIGL
ATOM  570  O    ALA  69   -0.610  58.164 124.829  1.00 20.93      HIGL
ATOM  571  N    LYS  70   -1.114  56.007 124.402  1.00 21.23      HIGL
ATOM  572  CA   LYS  70   -2.273  56.295 123.574  1.00 22.04      HIGL
ATOM  573  CB   LYS  70   -2.770  54.991 122.941  1.00 24.06      HIGL
ATOM  574  CG   LYS  70   -4.006  55.118 122.060  1.00 26.72      HIGL
ATOM  575  CD   LYS  70   -4.553  53.734 121.710  1.00 29.26      HIGL
ATOM  576  CE   LYS  70   -5.785  53.811 120.813  1.00 30.47      HIGL
ATOM  577  NZ   LYS  70   -6.349  52.451 120.547  1.00 31.87      HIGL
ATOM  578  C    LYS  70   -3.394  56.946 124.403  1.00 21.81      HIGL
ATOM  579  O    LYS  70   -4.034  57.901 123.958  1.00 21.40      HIGL
ATOM  580  N    ALA  71   -3.631  56.439 125.609  1.00 20.36      HIGL
ATOM  581  CA   ALA  71   -4.682  57.000 126.448  1.00 19.90      HIGL
ATOM  582  CB   ALA  71   -4.770  56.242 127.767  1.00 19.16      HIGL
ATOM  583  C    ALA  71   -4.432  58.485 126.708  1.00 19.54      HIGL
ATOM  584  O    ALA  71   -5.371  59.259 126.862  1.00 20.19      HIGL
```

Fig. 2 cont.

```
ATOM    585  N   ALA    72      -3.166  58.881 126.754  1.00 18.45           HIGL
ATOM    586  CA  ALA    72      -2.822  60.276 126.987  1.00 17.24           HIGL
ATOM    587  CB  ALA    72      -1.507  60.374 127.753  1.00 16.31           HIGL
ATOM    588  C   ALA    72      -2.722  61.035 125.667  1.00 16.70           HIGL
ATOM    589  O   ALA    72      -2.210  62.147 125.628  1.00 17.88           HIGL
ATOM    590  N   GLY    73      -3.200  60.421 124.589  1.00 15.95           HIGL
ATOM    591  CA  GLY    73      -3.176  61.058 123.284  1.00 15.41           HIGL
ATOM    592  C   GLY    73      -1.809  61.236 122.647  1.00 16.92           HIGL
ATOM    593  O   GLY    73      -1.638  62.056 121.739  1.00 16.80           HIGL
ATOM    594  N   LEU    74      -0.826  60.470 123.107  1.00 16.80           HIGL
ATOM    595  CA  LEU    74       0.516  60.577 122.554  1.00 16.41           HIGL
ATOM    596  CB  LEU    74       1.545  60.366 123.663  1.00 15.23           HIGL
ATOM    597  CG  LEU    74       1.311  61.253 124.884  1.00 14.82           HIGL
ATOM    598  CD1 LEU    74       2.265  60.875 125.994  1.00 13.72           HIGL
ATOM    599  CD2 LEU    74       1.486  62.706 124.492  1.00 14.41           HIGL
ATOM    600  C   LEU    74       0.762  59.577 121.424  1.00 17.36           HIGL
ATOM    601  O   LEU    74       0.319  58.430 121.482  1.00 16.67           HIGL
ATOM    602  N   GLY    75       1.470  60.027 120.392  1.00 18.17           HIGL
ATOM    603  CA  GLY    75       1.785  59.155 119.278  1.00 17.81           HIGL
ATOM    604  C   GLY    75       2.846  58.153 119.695  1.00 18.44           HIGL
ATOM    605  O   GLY    75       3.486  58.299 120.748  1.00 18.86           HIGL
ATOM    606  N   LEU    76       3.058  57.147 118.858  1.00 17.36           HIGL
ATOM    607  CA  LEU    76       4.014  56.103 119.163  1.00 16.84           HIGL
ATOM    608  CB  LEU    76       3.262  54.777 119.306  1.00 16.53           HIGL
ATOM    609  CG  LEU    76       4.075  53.527 119.631  1.00 17.06           HIGL
ATOM    610  CD1 LEU    76       4.742  53.691 120.997  1.00 16.56           HIGL
ATOM    611  CD2 LEU    76       3.161  52.318 119.620  1.00 15.85           HIGL
ATOM    612  C   LEU    76       5.143  55.949 118.139  1.00 16.79           HIGL
ATOM    613  O   LEU    76       4.914  55.918 116.932  1.00 17.69           HIGL
ATOM    614  N   TYR    77       6.364  55.844 118.648  1.00 15.89           HIGL
ATOM    615  CA  TYR    77       7.560  55.664 117.835  1.00 15.08           HIGL
ATOM    616  CB  TYR    77       8.420  56.938 117.927  1.00 14.34           HIGL
ATOM    617  CG  TYR    77       9.866  56.872 117.435  1.00 14.79           HIGL
ATOM    618  CD1 TYR    77      10.428  55.695 116.925  1.00 13.89           HIGL
ATOM    619  CE1 TYR    77      11.774  55.644 116.552  1.00 14.56           HIGL
ATOM    620  CD2 TYR    77      10.693  57.994 117.547  1.00 15.32           HIGL
ATOM    621  CE2 TYR    77      12.039  57.955 117.179  1.00 14.67           HIGL
ATOM    622  CZ  TYR    77      12.577  56.783 116.688  1.00 15.26           HIGL
ATOM    623  OH  TYR    77      13.920  56.753 116.367  1.00 14.00           HIGL
ATOM    624  C   TYR    77       8.261  54.436 118.440  1.00 15.55           HIGL
ATOM    625  O   TYR    77       8.853  54.507 119.530  1.00 15.30           HIGL
ATOM    626  N   ILE    78       8.147  53.306 117.743  1.00 14.24           HIGL
ATOM    627  CA  ILE    78       8.751  52.051 118.183  1.00 14.13           HIGL
ATOM    628  CB  ILE    78       7.970  50.824 117.639  1.00 14.46           HIGL
ATOM    629  CG2 ILE    78       8.742  49.534 117.930  1.00 14.89           HIGL
ATOM    630  CG1 ILE    78       6.575  50.766 118.276  1.00 14.25           HIGL
ATOM    631  CD1 ILE    78       6.567  50.420 119.761  1.00 12.73           HIGL
ATOM    632  C   ILE    78      10.193  51.991 117.701  1.00 13.40           HIGL
ATOM    633  O   ILE    78      10.467  52.112 116.512  1.00 13.27           HIGL
ATOM    634  N   ASN    79      11.104  51.797 118.646  1.00 13.08           HIGL
ATOM    635  CA  ASN    79      12.533  51.753 118.378  1.00 12.27           HIGL
ATOM    636  CB  ASN    79      13.209  52.771 119.304  1.00 12.87           HIGL
ATOM    637  CG  ASN    79      14.714  52.607 119.393  1.00 12.44           HIGL
ATOM    638  OD1 ASN    79      15.291  52.886 120.435  1.00 12.93           HIGL
ATOM    639  ND2 ASN    79      15.353  52.175 118.311  1.00 12.14           HIGL
ATOM    640  C   ASN    79      13.111  50.354 118.587  1.00 12.54           HIGL
ATOM    641  O   ASN    79      13.453  49.979 119.708  1.00 12.54           HIGL
ATOM    642  N   PHE    80      13.209  49.590 117.501  1.00 12.76           HIGL
ATOM    643  CA  PHE    80      13.752  48.232 117.534  1.00 13.01           HIGL
ATOM    644  CB  PHE    80      13.453  47.486 116.228  1.00 12.75           HIGL
ATOM    645  CG  PHE    80      12.076  46.901 116.154  1.00 13.87           HIGL
ATOM    646  CD1 PHE    80      11.636  45.998 117.120  1.00 13.28           HIGL
ATOM    647  CD2 PHE    80      11.218  47.241 115.114  1.00 12.89           HIGL
ATOM    648  CE1 PHE    80      10.363  45.446 117.054  1.00 11.74           HIGL
ATOM    649  CE2 PHE    80       9.943  46.692 115.043  1.00 13.92           HIGL
```

Fig. 2 cont.

```
ATOM    650  CZ   PHE   80       9.517  45.792 116.019  1.00 13.02      HIGL
ATOM    651  C    PHE   80      15.259  48.253 117.690  1.00 13.33      HIGL
ATOM    652  O    PHE   80      15.937  48.944 116.940  1.00 14.29      HIGL
ATOM    653  N    HIS   81      15.784  47.499 118.649  1.00 12.98      HIGL
ATOM    654  CA   HIS   81      17.227  47.426 118.823  1.00 13.87      HIGL
ATOM    655  CB   HIS   81      17.626  47.425 120.304  1.00 13.89      HIGL
ATOM    656  CG   HIS   81      17.633  48.782 120.933  1.00 15.21      HIGL
ATOM    657  CD2  HIS   81      16.749  49.805 120.860  1.00 15.13      HIGL
ATOM    658  ND1  HIS   81      18.639  49.204 121.777  1.00 15.56      HIGL
ATOM    659  CE1  HIS   81      18.375  50.429 122.196  1.00 14.49      HIGL
ATOM    660  NE2  HIS   81      17.234  50.816 121.655  1.00 15.27      HIGL
ATOM    661  C    HIS   81      17.717  46.137 118.176  1.00 13.69      HIGL
ATOM    662  O    HIS   81      18.911  45.971 117.928  1.00 14.21      HIGL
ATOM    663  N    TYR   82      16.784  45.231 117.902  1.00 13.26      HIGL
ATOM    664  CA   TYR   82      17.105  43.939 117.299  1.00 13.09      HIGL
ATOM    665  CB   TYR   82      17.449  44.102 115.819  1.00 13.22      HIGL
ATOM    666  CG   TYR   82      16.277  44.556 114.986  1.00 13.70      HIGL
ATOM    667  CD1  TYR   82      15.014  43.977 115.161  1.00 13.38      HIGL
ATOM    668  CE1  TYR   82      13.939  44.348 114.378  1.00 12.96      HIGL
ATOM    669  CD2  TYR   82      16.429  45.529 114.002  1.00 12.39      HIGL
ATOM    670  CE2  TYR   82      15.359  45.908 113.209  1.00 13.19      HIGL
ATOM    671  CZ   TYR   82      14.114  45.310 113.400  1.00 14.02      HIGL
ATOM    672  OH   TYR   82      13.046  45.652 112.595  1.00 15.86      HIGL
ATOM    673  C    TYR   82      18.257  43.278 118.030  1.00 13.08      HIGL
ATOM    674  O    TYR   82      19.217  42.804 117.421  1.00 12.93      HIGL
ATOM    675  N    SER   83      18.137  43.256 119.352  1.00 13.03      HIGL
ATOM    676  CA   SER   83      19.132  42.668 120.227  1.00 13.56      HIGL
ATOM    677  CB   SER   83      20.266  43.671 120.439  1.00 13.70      HIGL
ATOM    678  OG   SER   83      21.309  43.114 121.210  1.00 15.51      HIGL
ATOM    679  C    SER   83      18.440  42.348 121.557  1.00 14.03      HIGL
ATOM    680  O    SER   83      17.332  42.827 121.805  1.00 13.59      HIGL
ATOM    681  N    ASP   84      19.066  41.532 122.405  1.00 14.12      HIGL
ATOM    682  CA   ASP   84      18.453  41.215 123.694  1.00 14.35      HIGL
ATOM    683  CB   ASP   84      19.025  39.927 124.294  1.00 15.38      HIGL
ATOM    684  CG   ASP   84      18.577  38.682 123.558  1.00 16.47      HIGL
ATOM    685  OD1  ASP   84      17.543  38.736 122.856  1.00 16.36      HIGL
ATOM    686  OD2  ASP   84      19.259  37.643 123.704  1.00 17.16      HIGL
ATOM    687  C    ASP   84      18.760  42.357 124.640  1.00 13.54      HIGL
ATOM    688  O    ASP   84      18.066  42.571 125.629  1.00 12.95      HIGL
ATOM    689  N    THR   85      19.806  43.100 124.308  1.00 12.90      HIGL
ATOM    690  CA   THR   85      20.240  44.199 125.141  1.00 12.85      HIGL
ATOM    691  CB   THR   85      21.471  43.771 125.920  1.00 12.51      HIGL
ATOM    692  OG1  THR   85      21.661  44.642 127.038  1.00 14.10      HIGL
ATOM    693  CG2  THR   85      22.685  43.810 125.013  1.00 12.87      HIGL
ATOM    694  C    THR   85      20.555  45.453 124.314  1.00 12.72      HIGL
ATOM    695  O    THR   85      20.377  45.463 123.095  1.00 12.75      HIGL
ATOM    696  N    TRP   86      21.038  46.495 124.989  1.00 11.76      HIGL
ATOM    697  CA   TRP   86      21.358  47.772 124.354  1.00 10.89      HIGL
ATOM    698  CB   TRP   86      22.198  48.651 125.276  1.00  9.89      HIGL
ATOM    699  CG   TRP   86      21.597  48.938 126.604  1.00 10.03      HIGL
ATOM    700  CD2  TRP   86      20.629  49.947 126.908  1.00  9.39      HIGL
ATOM    701  CE2  TRP   86      20.363  49.865 128.292  1.00  8.31      HIGL
ATOM    702  CE3  TRP   86      19.959  50.913 126.147  1.00  9.93      HIGL
ATOM    703  CD1  TRP   86      21.870  48.302 127.781  1.00  8.33      HIGL
ATOM    704  NE1  TRP   86      21.135  48.852 128.796  1.00  7.98      HIGL
ATOM    705  CZ2  TRP   86      19.457  50.711 128.932  1.00  7.91      HIGL
ATOM    706  CZ3  TRP   86      19.051  51.760 126.788  1.00  9.09      HIGL
ATOM    707  CH2  TRP   86      18.812  51.649 128.166  1.00  9.37      HIGL
ATOM    708  C    TRP   86      22.111  47.668 123.048  1.00 11.73      HIGL
ATOM    709  O    TRP   86      23.216  47.141 123.008  1.00 11.69      HIGL
ATOM    710  N    ALA   87      21.524  48.193 121.980  1.00 12.59      HIGL
ATOM    711  CA   ALA   87      22.189  48.181 120.685  1.00 12.82      HIGL
ATOM    712  CB   ALA   87      21.246  47.706 119.603  1.00 12.18      HIGL
ATOM    713  C    ALA   87      22.665  49.594 120.381  1.00 13.67      HIGL
ATOM    714  O    ALA   87      21.912  50.553 120.532  1.00 13.58      HIGL
```

Fig. 2 cont.

```
ATOM    715  N    ASP  88      23.929  49.710 119.984  1.00 14.42       HIGL
ATOM    716  CA   ASP  88      24.538  50.984 119.628  1.00 14.58       HIGL
ATOM    717  CB   ASP  88      24.990  51.744 120.889  1.00 14.68       HIGL
ATOM    718  CG   ASP  88      25.901  50.925 121.783  1.00 16.21       HIGL
ATOM    719  OD1  ASP  88      26.827  50.268 121.263  1.00 18.18       HIGL
ATOM    720  OD2  ASP  88      25.701  50.949 123.014  1.00 16.03       HIGL
ATOM    721  C    ASP  88      25.721  50.691 118.690  1.00 15.64       HIGL
ATOM    722  O    ASP  88      26.023  49.529 118.416  1.00 15.14       HIGL
ATOM    723  N    PRO  89      26.408  51.734 118.192  1.00 16.24       HIGL
ATOM    724  CD   PRO  89      26.232  53.163 118.505  1.00 16.14       HIGL
ATOM    725  CA   PRO  89      27.545  51.549 117.280  1.00 16.34       HIGL
ATOM    726  CB   PRO  89      28.119  52.954 117.159  1.00 16.73       HIGL
ATOM    727  CG   PRO  89      26.918  53.823 117.343  1.00 17.24       HIGL
ATOM    728  C    PRO  89      28.607  50.541 117.708  1.00 16.16       HIGL
ATOM    729  O    PRO  89      29.283  49.961 116.871  1.00 15.63       HIGL
ATOM    730  N    ALA  90      28.760  50.326 119.006  1.00 16.46       HIGL
ATOM    731  CA   ALA  90      29.773  49.387 119.462  1.00 16.48       HIGL
ATOM    732  CB   ALA  90      30.596  50.003 120.598  1.00 14.72       HIGL
ATOM    733  C    ALA  90      29.191  48.054 119.899  1.00 16.00       HIGL
ATOM    734  O    ALA  90      29.939  47.143 120.241  1.00 17.19       HIGL
ATOM    735  N    HIS  91      27.867  47.933 119.889  1.00 15.05       HIGL
ATOM    736  CA   HIS  91      27.230  46.680 120.288  1.00 14.58       HIGL
ATOM    737  CB   HIS  91      26.897  46.673 121.785  1.00 15.34       HIGL
ATOM    738  CG   HIS  91      27.967  47.242 122.662  1.00 14.94       HIGL
ATOM    739  CD2  HIS  91      28.755  46.663 123.599  1.00 15.42       HIGL
ATOM    740  ND1  HIS  91      28.296  48.582 122.660  1.00 15.37       HIGL
ATOM    741  CE1  HIS  91      29.237  48.803 123.561  1.00 16.41       HIGL
ATOM    742  NE2  HIS  91      29.534  47.654 124.146  1.00 15.75       HIGL
ATOM    743  C    HIS  91      25.939  46.414 119.518  1.00 14.68       HIGL
ATOM    744  O    HIS  91      24.944  47.123 119.679  1.00 14.01       HIGL
ATOM    745  N    GLN  92      25.968  45.385 118.680  1.00 14.89       HIGL
ATOM    746  CA   GLN  92      24.818  44.974 117.885  1.00 14.67       HIGL
ATOM    747  CB   GLN  92      25.000  45.394 116.421  1.00 13.95       HIGL
ATOM    748  CG   GLN  92      24.928  46.904 116.159  1.00 13.75       HIGL
ATOM    749  CD   GLN  92      23.529  47.497 116.368  1.00 13.63       HIGL
ATOM    750  OE1  GLN  92      22.517  46.899 115.985  1.00 12.06       HIGL
ATOM    751  NE2  GLN  92      23.475  48.685 116.958  1.00 11.96       HIGL
ATOM    752  C    GLN  92      24.786  43.451 118.005  1.00 15.14       HIGL
ATOM    753  O    GLN  92      24.994  42.721 117.033  1.00 14.92       HIGL
ATOM    754  N    THR  93      24.530  42.984 119.222  1.00 15.07       HIGL
ATOM    755  CA   THR  93      24.510  41.561 119.520  1.00 14.27       HIGL
ATOM    756  CB   THR  93      24.672  41.329 121.023  1.00 14.39       HIGL
ATOM    757  OG1  THR  93      25.783  42.100 121.497  1.00 13.20       HIGL
ATOM    758  CG2  THR  93      24.906  39.842 121.315  1.00 12.37       HIGL
ATOM    759  C    THR  93      23.259  40.838 119.070  1.00 15.03       HIGL
ATOM    760  O    THR  93      22.169  41.066 119.600  1.00 15.53       HIGL
ATOM    761  N    THR  94      23.428  39.951 118.097  1.00 14.94       HIGL
ATOM    762  CA   THR  94      22.323  39.162 117.576  1.00 15.30       HIGL
ATOM    763  CB   THR  94      22.818  38.169 116.503  1.00 15.55       HIGL
ATOM    764  OG1  THR  94      23.376  38.893 115.399  1.00 15.22       HIGL
ATOM    765  CG2  THR  94      21.677  37.302 116.013  1.00 15.52       HIGL
ATOM    766  C    THR  94      21.720  38.373 118.732  1.00 15.67       HIGL
ATOM    767  O    THR  94      22.447  37.830 119.563  1.00 15.25       HIGL
ATOM    768  N    PRO  95      20.381  38.309 118.806  1.00 16.47       HIGL
ATOM    769  CD   PRO  95      19.409  38.946 117.901  1.00 16.88       HIGL
ATOM    770  CA   PRO  95      19.695  37.573 119.878  1.00 16.79       HIGL
ATOM    771  CB   PRO  95      18.220  37.690 119.490  1.00 16.02       HIGL
ATOM    772  CG   PRO  95      18.161  38.991 118.754  1.00 16.42       HIGL
ATOM    773  C    PRO  95      20.156  36.119 119.896  1.00 17.32       HIGL
ATOM    774  O    PRO  95      20.230  35.480 118.845  1.00 18.48       HIGL
ATOM    775  N    ALA  96      20.472  35.590 121.073  1.00 17.31       HIGL
ATOM    776  CA   ALA  96      20.903  34.196 121.149  1.00 17.43       HIGL
ATOM    777  CB   ALA  96      21.086  33.769 122.598  1.00 17.13       HIGL
ATOM    778  C    ALA  96      19.821  33.356 120.495  1.00 16.72       HIGL
ATOM    779  O    ALA  96      18.636  33.612 120.693  1.00 15.96       HIGL
```

Fig. 2 cont.

```
ATOM    780  N    GLY    97      20.229  32.371 119.700  1.00 17.32      HIGL
ATOM    781  CA   GLY    97      19.263  31.515 119.031  1.00 17.04      HIGL
ATOM    782  C    GLY    97      19.001  31.856 117.573  1.00 17.23      HIGL
ATOM    783  O    GLY    97      18.675  30.976 116.783  1.00 17.90      HIGL
ATOM    784  N    TRP    98      19.135  33.124 117.205  1.00 16.99      HIGL
ATOM    785  CA   TRP    98      18.907  33.524 115.820  1.00 17.97      HIGL
ATOM    786  CB   TRP    98      18.901  35.051 115.726  1.00 18.18      HIGL
ATOM    787  CG   TRP    98      17.627  35.621 116.258  1.00 18.37      HIGL
ATOM    788  CD2  TRP    98      17.022  36.870 115.907  1.00 18.66      HIGL
ATOM    789  CE2  TRP    98      15.824  36.978 116.650  1.00 18.98      HIGL
ATOM    790  CE3  TRP    98      17.372  37.909 115.036  1.00 18.95      HIGL
ATOM    791  CD1  TRP    98      16.798  35.041 117.175  1.00 18.96      HIGL
ATOM    792  NE1  TRP    98      15.714  35.846 117.415  1.00 19.48      HIGL
ATOM    793  CZ2  TRP    98      14.973  38.083 116.550  1.00 18.24      HIGL
ATOM    794  CZ3  TRP    98      16.521  39.011 114.936  1.00 18.88      HIGL
ATOM    795  CH2  TRP    98      15.336  39.085 115.690  1.00 18.43      HIGL
ATOM    796  C    TRP    98      19.939  32.897 114.877  1.00 17.57      HIGL
ATOM    797  O    TRP    98      21.042  32.569 115.285  1.00 17.56      HIGL
ATOM    798  N    PRO    99      19.577  32.707 113.601  1.00 17.79      HIGL
ATOM    799  CD   PRO    99      18.219  32.889 113.063  1.00 17.38      HIGL
ATOM    800  CA   PRO    99      20.459  32.106 112.594  1.00 17.62      HIGL
ATOM    801  CB   PRO    99      19.578  32.055 111.342  1.00 17.40      HIGL
ATOM    802  CG   PRO    99      18.491  33.041 111.616  1.00 18.07      HIGL
ATOM    803  C    PRO    99      21.842  32.693 112.326  1.00 17.38      HIGL
ATOM    804  O    PRO    99      22.147  33.820 112.709  1.00 17.86      HIGL
ATOM    805  N    SER   100      22.670  31.887 111.660  1.00 17.52      HIGL
ATOM    806  CA   SER   100      24.045  32.240 111.323  1.00 16.92      HIGL
ATOM    807  CB   SER   100      24.992  31.142 111.793  1.00 16.67      HIGL
ATOM    808  OG   SER   100      24.564  30.601 113.025  1.00 20.79      HIGL
ATOM    809  C    SER   100      24.283  32.452 109.833  1.00 16.73      HIGL
ATOM    810  O    SER   100      25.419  32.675 109.423  1.00 17.27      HIGL
ATOM    811  N    ASP   101      23.247  32.336 109.012  1.00 16.22      HIGL
ATOM    812  CA   ASP   101      23.422  32.564 107.579  1.00 16.38      HIGL
ATOM    813  CB   ASP   101      23.121  31.303 106.751  1.00 16.22      HIGL
ATOM    814  CG   ASP   101      21.708  30.805 106.929  1.00 15.46      HIGL
ATOM    815  OD1  ASP   101      21.423  30.151 107.950  1.00 16.82      HIGL
ATOM    816  OD2  ASP   101      20.877  31.073 106.047  1.00 16.15      HIGL
ATOM    817  C    ASP   101      22.494  33.707 107.201  1.00 16.52      HIGL
ATOM    818  O    ASP   101      21.387  33.825 107.736  1.00 16.54      HIGL
ATOM    819  N    ILE   102      22.957  34.545 106.280  1.00 15.85      HIGL
ATOM    820  CA   ILE   102      22.220  35.727 105.871  1.00 15.30      HIGL
ATOM    821  CB   ILE   102      22.958  36.484 104.746  1.00 14.62      HIGL
ATOM    822  CG2  ILE   102      22.862  35.709 103.433  1.00 14.59      HIGL
ATOM    823  CG1  ILE   102      22.361  37.884 104.594  1.00 13.26      HIGL
ATOM    824  CD1  ILE   102      22.438  38.731 105.856  1.00 10.57      HIGL
ATOM    825  C    ILE   102      20.779  35.519 105.452  1.00 16.31      HIGL
ATOM    826  O    ILE   102      19.929  36.365 105.739  1.00 17.53      HIGL
ATOM    827  N    ASN   103      20.486  34.409 104.784  1.00 15.84      HIGL
ATOM    828  CA   ASN   103      19.118  34.174 104.347  1.00 15.26      HIGL
ATOM    829  CB   ASN   103      19.056  33.026 103.345  1.00 16.44      HIGL
ATOM    830  CG   ASN   103      17.643  32.754 102.881  1.00 17.90      HIGL
ATOM    831  OD1  ASN   103      17.012  33.606 102.251  1.00 17.31      HIGL
ATOM    832  ND2  ASN   103      17.128  31.568 103.207  1.00 18.73      HIGL
ATOM    833  C    ASN   103      18.195  33.872 105.520  1.00 14.76      HIGL
ATOM    834  O    ASN   103      17.081  34.390 105.592  1.00 14.43      HIGL
ATOM    835  N    ASN   104      18.655  33.029 106.437  1.00 14.10      HIGL
ATOM    836  CA   ASN   104      17.849  32.684 107.598  1.00 13.79      HIGL
ATOM    837  CB   ASN   104      18.391  31.424 108.277  1.00 13.76      HIGL
ATOM    838  CG   ASN   104      17.923  30.149 107.594  1.00 14.35      HIGL
ATOM    839  OD1  ASN   104      16.738  30.006 107.264  1.00 13.83      HIGL
ATOM    840  ND2  ASN   104      18.843  29.212 107.392  1.00 11.49      HIGL
ATOM    841  C    ASN   104      17.766  33.822 108.603  1.00 13.46      HIGL
ATOM    842  O    ASN   104      16.706  34.066 109.169  1.00 13.67      HIGL
ATOM    843  N    LEU   105      18.875  34.522 108.824  1.00 13.84      HIGL
ATOM    844  CA   LEU   105      18.885  35.640 109.762  1.00 14.45      HIGL
```

Fig. 2 cont.

```
ATOM    845  CB   LEU   105      20.282  36.256 109.855  1.00 14.35      HIGL
ATOM    846  CG   LEU   105      20.373  37.492 110.754  1.00 15.28      HIGL
ATOM    847  CD1  LEU   105      19.941  37.133 112.168  1.00 14.98      HIGL
ATOM    848  CD2  LEU   105      21.791  38.025 110.756  1.00 15.43      HIGL
ATOM    849  C    LEU   105      17.891  36.694 109.291  1.00 15.25      HIGL
ATOM    850  O    LEU   105      17.087  37.204 110.074  1.00 14.19      HIGL
ATOM    851  N    ALA   106      17.956  37.009 108.000  1.00 15.85      HIGL
ATOM    852  CA   ALA   106      17.067  37.990 107.399  1.00 17.40      HIGL
ATOM    853  CB   ALA   106      17.417  38.177 105.916  1.00 15.61      HIGL
ATOM    854  C    ALA   106      15.618  37.532 107.548  1.00 18.34      HIGL
ATOM    855  O    ALA   106      14.730  38.326 107.859  1.00 19.25      HIGL
ATOM    856  N    TRP   107      15.390  36.245 107.320  1.00 19.52      HIGL
ATOM    857  CA   TRP   107      14.060  35.663 107.430  1.00 20.70      HIGL
ATOM    858  CB   TRP   107      14.140  34.177 107.104  1.00 22.69      HIGL
ATOM    859  CG   TRP   107      12.847  33.566 106.709  1.00 26.10      HIGL
ATOM    860  CD2  TRP   107      12.607  32.179 106.453  1.00 27.36      HIGL
ATOM    861  CE2  TRP   107      11.256  32.056 106.055  1.00 28.11      HIGL
ATOM    862  CE3  TRP   107      13.404  31.028 106.517  1.00 27.84      HIGL
ATOM    863  CD1  TRP   107      11.665  34.212 106.466  1.00 26.98      HIGL
ATOM    864  NE1  TRP   107      10.705  33.310 106.072  1.00 27.36      HIGL
ATOM    865  CZ2  TRP   107      10.683  30.821 105.720  1.00 28.94      HIGL
ATOM    866  CZ3  TRP   107      12.836  29.804 106.184  1.00 28.94      HIGL
ATOM    867  CH2  TRP   107      11.487  29.711 105.790  1.00 28.79      HIGL
ATOM    868  C    TRP   107      13.567  35.862 108.862  1.00 20.80      HIGL
ATOM    869  O    TRP   107      12.428  36.280 109.097  1.00 19.49      HIGL
ATOM    870  N    LYS   108      14.453  35.567 109.812  1.00 20.81      HIGL
ATOM    871  CA   LYS   108      14.158  35.707 111.231  1.00 20.77      HIGL
ATOM    872  CB   LYS   108      15.358  35.255 112.070  1.00 21.15      HIGL
ATOM    873  CG   LYS   108      15.018  34.250 113.161  1.00 22.88      HIGL
ATOM    874  CD   LYS   108      13.942  34.770 114.100  1.00 23.37      HIGL
ATOM    875  CE   LYS   108      13.525  33.698 115.088  1.00 23.83      HIGL
ATOM    876  NZ   LYS   108      12.322  34.107 115.853  1.00 24.90      HIGL
ATOM    877  C    LYS   108      13.830  37.161 111.554  1.00 19.90      HIGL
ATOM    878  O    LYS   108      12.836  37.450 112.214  1.00 20.08      HIGL
ATOM    879  N    LEU   109      14.674  38.074 111.094  1.00 19.75      HIGL
ATOM    880  CA   LEU   109      14.445  39.488 111.344  1.00 19.93      HIGL
ATOM    881  CB   LEU   109      15.508  40.337 110.654  1.00 17.82      HIGL
ATOM    882  CG   LEU   109      15.390  41.827 110.968  1.00 17.82      HIGL
ATOM    883  CD1  LEU   109      15.672  42.054 112.449  1.00 16.38      HIGL
ATOM    884  CD2  LEU   109      16.368  42.620 110.103  1.00 16.81      HIGL
ATOM    885  C    LEU   109      13.063  39.861 110.822  1.00 20.34      HIGL
ATOM    886  O    LEU   109      12.362  40.679 111.423  1.00 20.28      HIGL
ATOM    887  N    TYR   110      12.679  39.247 109.704  1.00 20.51      HIGL
ATOM    888  CA   TYR   110      11.377  39.489 109.100  1.00 20.92      HIGL
ATOM    889  CB   TYR   110      11.309  38.862 107.704  1.00 21.24      HIGL
ATOM    890  CG   TYR   110       9.918  38.842 107.101  1.00 21.40      HIGL
ATOM    891  CD1  TYR   110       9.064  37.757 107.292  1.00 22.61      HIGL
ATOM    892  CE1  TYR   110       7.771  37.748 106.754  1.00 22.76      HIGL
ATOM    893  CD2  TYR   110       9.445  39.922 106.358  1.00 23.16      HIGL
ATOM    894  CE2  TYR   110       8.155  39.926 105.817  1.00 22.90      HIGL
ATOM    895  CZ   TYR   110       7.325  38.838 106.018  1.00 23.09      HIGL
ATOM    896  OH   TYR   110       6.056  38.849 105.482  1.00 22.70      HIGL
ATOM    897  C    TYR   110      10.249  38.938 109.972  1.00 21.45      HIGL
ATOM    898  O    TYR   110       9.312  39.671 110.303  1.00 22.10      HIGL
ATOM    899  N    ASN   111      10.326  37.659 110.344  1.00 20.73      HIGL
ATOM    900  CA   ASN   111       9.281  37.073 111.182  1.00 20.87      HIGL
ATOM    901  CB   ASN   111       9.589  35.619 111.546  1.00 23.22      HIGL
ATOM    902  CG   ASN   111       9.612  34.699 110.348  1.00 26.49      HIGL
ATOM    903  OD1  ASN   111       9.040  35.005 109.301  1.00 27.21      HIGL
ATOM    904  ND2  ASN   111      10.265  33.552 110.516  1.00 29.16      HIGL
ATOM    905  C    ASN   111       9.147  37.864 112.474  1.00 19.60      HIGL
ATOM    906  O    ASN   111       8.039  38.190 112.905  1.00 19.02      HIGL
ATOM    907  N    TYR   112      10.288  38.169 113.084  1.00 18.21      HIGL
ATOM    908  CA   TYR   112      10.310  38.905 114.337  1.00 16.83      HIGL
ATOM    909  CB   TYR   112      11.751  39.129 114.810  1.00 16.36      HIGL
```

Fig. 2 cont.

```
ATOM    910  CG   TYR   112      11.839  40.071 115.991  1.00 14.95           HIGL
ATOM    911  CD1  TYR   112      11.369  39.691 117.245  1.00 15.11           HIGL
ATOM    912  CE1  TYR   112      11.369  40.581 118.316  1.00 14.94           HIGL
ATOM    913  CD2  TYR   112      12.319  41.366 115.836  1.00 14.45           HIGL
ATOM    914  CE2  TYR   112      12.323  42.264 116.897  1.00 14.83           HIGL
ATOM    915  CZ   TYR   112      11.847  41.866 118.133  1.00 14.96           HIGL
ATOM    916  OH   TYR   112      11.848  42.754 119.182  1.00 15.27           HIGL
ATOM    917  C    TYR   112       9.601  40.243 114.224  1.00 16.36           HIGL
ATOM    918  O    TYR   112       8.686  40.534 114.999  1.00 15.41           HIGL
ATOM    919  N    THR   113      10.034  41.056 113.265  1.00 16.21           HIGL
ATOM    920  CA   THR   113       9.443  42.369 113.058  1.00 15.87           HIGL
ATOM    921  CB   THR   113      10.142  43.125 111.922  1.00 16.16           HIGL
ATOM    922  OG1  THR   113      11.537  43.252 112.221  1.00 15.12           HIGL
ATOM    923  CG2  THR   113       9.537  44.515 111.758  1.00 15.98           HIGL
ATOM    924  C    THR   113       7.973  42.216 112.717  1.00 16.24           HIGL
ATOM    925  O    THR   113       7.124  42.896 113.290  1.00 16.57           HIGL
ATOM    926  N    LEU   114       7.678  41.307 111.790  1.00 16.92           HIGL
ATOM    927  CA   LEU   114       6.304  41.043 111.366  1.00 16.65           HIGL
ATOM    928  CB   LEU   114       6.264  39.849 110.411  1.00 15.97           HIGL
ATOM    929  CG   LEU   114       4.861  39.423 109.964  1.00 16.54           HIGL
ATOM    930  CD1  LEU   114       4.220  40.543 109.154  1.00 15.93           HIGL
ATOM    931  CD2  LEU   114       4.948  38.144 109.146  1.00 14.91           HIGL
ATOM    932  C    LEU   114       5.404  40.754 112.565  1.00 16.56           HIGL
ATOM    933  O    LEU   114       4.420  41.450 112.799  1.00 16.01           HIGL
ATOM    934  N    ASP   115       5.749  39.720 113.320  1.00 16.95           HIGL
ATOM    935  CA   ASP   115       4.967  39.347 114.484  1.00 17.44           HIGL
ATOM    936  CB   ASP   115       5.562  38.104 115.139  1.00 18.68           HIGL
ATOM    937  CG   ASP   115       5.489  36.884 114.235  1.00 20.91           HIGL
ATOM    938  OD1  ASP   115       4.994  37.019 113.095  1.00 20.18           HIGL
ATOM    939  OD2  ASP   115       5.928  35.789 114.658  1.00 22.87           HIGL
ATOM    940  C    ASP   115       4.879  40.481 115.491  1.00 17.05           HIGL
ATOM    941  O    ASP   115       3.813  40.732 116.048  1.00 16.42           HIGL
ATOM    942  N    SER   116       5.990  41.174 115.713  1.00 16.71           HIGL
ATOM    943  CA   SER   116       6.005  42.279 116.660  1.00 17.19           HIGL
ATOM    944  CB   SER   116       7.409  42.869 116.774  1.00 17.37           HIGL
ATOM    945  OG   SER   116       8.307  41.969 117.391  1.00 17.53           HIGL
ATOM    946  C    SER   116       5.023  43.381 116.262  1.00 18.12           HIGL
ATOM    947  O    SER   116       4.231  43.847 117.084  1.00 17.59           HIGL
ATOM    948  N    MET   117       5.080  43.812 115.008  1.00 18.86           HIGL
ATOM    949  CA   MET   117       4.176  44.856 114.552  1.00 19.77           HIGL
ATOM    950  CB   MET   117       4.525  45.262 113.125  1.00 19.25           HIGL
ATOM    951  CG   MET   117       5.862  45.989 113.006  1.00 18.96           HIGL
ATOM    952  SD   MET   117       5.846  47.687 113.654  1.00 20.56           HIGL
ATOM    953  CE   MET   117       6.173  47.395 115.398  1.00 20.80           HIGL
ATOM    954  C    MET   117       2.729  44.384 114.641  1.00 20.69           HIGL
ATOM    955  O    MET   117       1.843  45.134 115.056  1.00 19.86           HIGL
ATOM    956  N    ASN   118       2.488  43.132 114.266  1.00 22.17           HIGL
ATOM    957  CA   ASN   118       1.137  42.589 114.327  1.00 23.55           HIGL
ATOM    958  CB   ASN   118       1.081  41.192 113.704  1.00 22.99           HIGL
ATOM    959  CG   ASN   118       0.966  41.236 112.197  1.00 24.24           HIGL
ATOM    960  OD1  ASN   118       0.231  42.054 111.648  1.00 24.38           HIGL
ATOM    961  ND2  ASN   118       1.680  40.345 111.516  1.00 25.71           HIGL
ATOM    962  C    ASN   118       0.665  42.536 115.772  1.00 24.12           HIGL
ATOM    963  O    ASN   118      -0.532  42.535 116.054  1.00 24.65           HIGL
ATOM    964  N    ARG   119       1.617  42.501 116.691  1.00 25.04           HIGL
ATOM    965  CA   ARG   119       1.289  42.457 118.104  1.00 25.97           HIGL
ATOM    966  CB   ARG   119       2.564  42.289 118.916  1.00 27.25           HIGL
ATOM    967  CG   ARG   119       2.324  41.905 120.343  1.00 30.86           HIGL
ATOM    968  CD   ARG   119       1.727  40.518 120.464  1.00 32.19           HIGL
ATOM    969  NE   ARG   119       1.381  40.252 121.856  1.00 35.20           HIGL
ATOM    970  CZ   ARG   119       2.266  40.036 122.826  1.00 35.79           HIGL
ATOM    971  NH1  ARG   119       3.566  40.038 122.564  1.00 35.68           HIGL
ATOM    972  NH2  ARG   119       1.845  39.846 124.070  1.00 37.32           HIGL
ATOM    973  C    ARG   119       0.572  43.755 118.483  1.00 26.06           HIGL
ATOM    974  O    ARG   119      -0.406  43.744 119.234  1.00 26.17           HIGL
```

Fig. 2 cont.

```
ATOM    975  N    PHE   120       1.058  44.874 117.952  1.00 25.97         HIGL
ATOM    976  CA   PHE   120       0.438  46.166 118.218  1.00 25.91         HIGL
ATOM    977  CB   PHE   120       1.369  47.312 117.811  1.00 24.71         HIGL
ATOM    978  CG   PHE   120       2.516  47.519 118.748  1.00 23.82         HIGL
ATOM    979  CD1  PHE   120       3.748  46.923 118.508  1.00 24.05         HIGL
ATOM    980  CD2  PHE   120       2.356  48.289 119.892  1.00 23.49         HIGL
ATOM    981  CE1  PHE   120       4.806  47.088 119.396  1.00 23.14         HIGL
ATOM    982  CE2  PHE   120       3.407  48.461 120.788  1.00 23.31         HIGL
ATOM    983  CZ   PHE   120       4.632  47.860 120.540  1.00 23.49         HIGL
ATOM    984  C    PHE   120      -0.879  46.283 117.452  1.00 26.35         HIGL
ATOM    985  O    PHE   120      -1.879  46.758 117.988  1.00 26.78         HIGL
ATOM    986  N    ALA   121      -0.870  45.844 116.198  1.00 26.40         HIGL
ATOM    987  CA   ALA   121      -2.058  45.891 115.357  1.00 26.80         HIGL
ATOM    988  CB   ALA   121      -1.755  45.280 114.003  1.00 27.18         HIGL
ATOM    989  C    ALA   121      -3.211  45.143 116.016  1.00 27.34         HIGL
ATOM    990  O    ALA   121      -4.314  45.674 116.152  1.00 27.77         HIGL
ATOM    991  N    ASP   122      -2.948  43.905 116.423  1.00 26.89         HIGL
ATOM    992  CA   ASP   122      -3.965  43.084 117.063  1.00 26.21         HIGL
ATOM    993  CB   ASP   122      -3.436  41.665 117.303  1.00 25.67         HIGL
ATOM    994  CG   ASP   122      -3.074  40.950 116.012  1.00 25.38         HIGL
ATOM    995  OD1  ASP   122      -3.544  41.379 114.929  1.00 24.57         HIGL
ATOM    996  OD2  ASP   122      -2.328  39.950 116.089  1.00 24.15         HIGL
ATOM    997  C    ASP   122      -4.414  43.686 118.389  1.00 26.13         HIGL
ATOM    998  O    ASP   122      -5.549  43.478 118.822  1.00 26.95         HIGL
ATOM    999  N    ALA   123      -3.517  44.427 119.033  1.00 24.90         HIGL
ATOM   1000  CA   ALA   123      -3.821  45.053 120.308  1.00 22.75         HIGL
ATOM   1001  CB   ALA   123      -2.548  45.330 121.058  1.00 23.23         HIGL
ATOM   1002  C    ALA   123      -4.595  46.344 120.102  1.00 22.12         HIGL
ATOM   1003  O    ALA   123      -5.085  46.935 121.058  1.00 22.33         HIGL
ATOM   1004  N    GLY   124      -4.704  46.778 118.850  1.00 21.85         HIGL
ATOM   1005  CA   GLY   124      -5.424  48.002 118.548  1.00 21.93         HIGL
ATOM   1006  C    GLY   124      -4.604  49.253 118.809  1.00 22.90         HIGL
ATOM   1007  O    GLY   124      -5.150  50.350 118.957  1.00 22.21         HIGL
ATOM   1008  N    ILE   125      -3.286  49.078 118.876  1.00 23.51         HIGL
ATOM   1009  CA   ILE   125      -2.352  50.174 119.113  1.00 23.71         HIGL
ATOM   1010  CB   ILE   125      -1.132  49.706 119.949  1.00 24.28         HIGL
ATOM   1011  CG2  ILE   125      -0.171  50.871 120.153  1.00 22.68         HIGL
ATOM   1012  CG1  ILE   125      -1.587  49.094 121.283  1.00 24.08         HIGL
ATOM   1013  CD1  ILE   125      -2.168  50.078 122.258  1.00 24.75         HIGL
ATOM   1014  C    ILE   125      -1.817  50.648 117.765  1.00 24.07         HIGL
ATOM   1015  O    ILE   125      -1.416  49.837 116.939  1.00 24.23         HIGL
ATOM   1016  N    GLN   126      -1.805  51.952 117.533  1.00 24.42         HIGL
ATOM   1017  CA   GLN   126      -1.282  52.451 116.274  1.00 25.40         HIGL
ATOM   1018  CB   GLN   126      -2.112  53.631 115.766  1.00 26.92         HIGL
ATOM   1019  CG   GLN   126      -1.591  54.243 114.464  1.00 29.76         HIGL
ATOM   1020  CD   GLN   126      -1.473  53.223 113.329  1.00 32.33         HIGL
ATOM   1021  OE1  GLN   126      -2.456  52.570 112.953  1.00 33.86         HIGL
ATOM   1022  NE2  GLN   126      -0.267  53.086 112.777  1.00 31.82         HIGL
ATOM   1023  C    GLN   126       0.174  52.883 116.424  1.00 25.09         HIGL
ATOM   1024  O    GLN   126       0.494  53.731 117.260  1.00 25.29         HIGL
ATOM   1025  N    VAL   127       1.046  52.280 115.617  1.00 23.64         HIGL
ATOM   1026  CA   VAL   127       2.465  52.605 115.614  1.00 21.87         HIGL
ATOM   1027  CB   VAL   127       3.329  51.373 115.255  1.00 21.30         HIGL
ATOM   1028  CG1  VAL   127       4.800  51.730 115.338  1.00 20.09         HIGL
ATOM   1029  CG2  VAL   127       3.010  50.217 116.184  1.00 20.69         HIGL
ATOM   1030  C    VAL   127       2.635  53.658 114.526  1.00 21.93         HIGL
ATOM   1031  O    VAL   127       2.268  53.427 113.378  1.00 22.89         HIGL
ATOM   1032  N    ASP   128       3.192  54.809 114.882  1.00 21.66         HIGL
ATOM   1033  CA   ASP   128       3.378  55.896 113.927  1.00 21.09         HIGL
ATOM   1034  CB   ASP   128       3.080  57.211 114.628  1.00 21.65         HIGL
ATOM   1035  CG   ASP   128       1.662  57.260 115.145  1.00 22.08         HIGL
ATOM   1036  OD1  ASP   128       0.744  57.299 114.301  1.00 23.35         HIGL
ATOM   1037  OD2  ASP   128       1.458  57.231 116.380  1.00 22.69         HIGL
ATOM   1038  C    ASP   128       4.746  55.932 113.256  1.00 21.00         HIGL
ATOM   1039  O    ASP   128       4.854  56.276 112.077  1.00 20.64         HIGL
```

Fig. 2 cont.

```
ATOM   1040  N    ILE   129       5.786  55.587 114.010  1.00 19.93      HIGL
ATOM   1041  CA   ILE   129       7.139  55.535 113.472  1.00 18.94      HIGL
ATOM   1042  CB   ILE   129       7.999  56.721 113.927  1.00 17.89      HIGL
ATOM   1043  CG2  ILE   129       9.425  56.533 113.444  1.00 16.07      HIGL
ATOM   1044  CG1  ILE   129       7.440  58.027 113.375  1.00 17.25      HIGL
ATOM   1045  CD1  ILE   129       8.207  59.241 113.843  1.00 16.76      HIGL
ATOM   1046  C    ILE   129       7.808  54.267 113.985  1.00 19.57      HIGL
ATOM   1047  O    ILE   129       7.591  53.867 115.130  1.00 20.12      HIGL
ATOM   1048  N    VAL   130       8.614  53.640 113.133  1.00 19.09      HIGL
ATOM   1049  CA   VAL   130       9.343  52.430 113.497  1.00 18.61      HIGL
ATOM   1050  CB   VAL   130       8.734  51.154 112.868  1.00 19.46      HIGL
ATOM   1051  CG1  VAL   130       9.424  49.923 113.431  1.00 18.88      HIGL
ATOM   1052  CG2  VAL   130       7.255  51.087 113.133  1.00 21.50      HIGL
ATOM   1053  C    VAL   130      10.762  52.531 112.962  1.00 17.57      HIGL
ATOM   1054  O    VAL   130      10.962  52.707 111.759  1.00 17.98      HIGL
ATOM   1055  N    SER   131      11.749  52.439 113.843  1.00 15.84      HIGL
ATOM   1056  CA   SER   131      13.127  52.470 113.377  1.00 14.70      HIGL
ATOM   1057  CB   SER   131      14.038  53.282 114.314  1.00 15.28      HIGL
ATOM   1058  OG   SER   131      14.319  52.589 115.514  1.00 18.11      HIGL
ATOM   1059  C    SER   131      13.565  51.018 113.345  1.00 12.96      HIGL
ATOM   1060  O    SER   131      13.436  50.299 114.335  1.00 11.68      HIGL
ATOM   1061  N    ILE   132      14.039  50.572 112.191  1.00 10.75      HIGL
ATOM   1062  CA   ILE   132      14.492  49.207 112.073  1.00 10.19      HIGL
ATOM   1063  CB   ILE   132      14.319  48.707 110.632  1.00 10.00      HIGL
ATOM   1064  CG2  ILE   132      12.858  48.371 110.380  1.00  9.71      HIGL
ATOM   1065  CG1  ILE   132      14.785  49.781 109.646  1.00 10.09      HIGL
ATOM   1066  CD1  ILE   132      14.716  49.350 108.198  1.00 10.00      HIGL
ATOM   1067  C    ILE   132      15.954  49.155 112.508  1.00 10.16      HIGL
ATOM   1068  O    ILE   132      16.869  49.045 111.693  1.00  9.89      HIGL
ATOM   1069  N    GLY   133      16.160  49.253 113.814  1.00  9.99      HIGL
ATOM   1070  CA   GLY   133      17.500  49.230 114.364  1.00 10.91      HIGL
ATOM   1071  C    GLY   133      17.711  50.461 115.220  1.00 11.73      HIGL
ATOM   1072  O    GLY   133      16.885  51.378 115.193  1.00 11.22      HIGL
ATOM   1073  N    ASN   134      18.804  50.482 115.983  1.00 11.81      HIGL
ATOM   1074  CA   ASN   134      19.119  51.621 116.843  1.00 11.67      HIGL
ATOM   1075  CB   ASN   134      18.878  51.271 118.307  1.00 11.03      HIGL
ATOM   1076  CG   ASN   134      19.010  52.481 119.217  1.00 11.61      HIGL
ATOM   1077  OD1  ASN   134      18.116  53.328 119.269  1.00  9.26      HIGL
ATOM   1078  ND2  ASN   134      20.140  52.579 119.923  1.00 10.03      HIGL
ATOM   1079  C    ASN   134      20.578  52.041 116.673  1.00 12.23      HIGL
ATOM   1080  O    ASN   134      21.488  51.299 117.047  1.00 12.50      HIGL
ATOM   1081  N    GLU   135      20.796  53.237 116.130  1.00 12.34      HIGL
ATOM   1082  CA   GLU   135      22.148  53.745 115.905  1.00 12.34      HIGL
ATOM   1083  CB   GLU   135      22.819  54.137 117.233  1.00 12.86      HIGL
ATOM   1084  CG   GLU   135      22.107  55.229 118.021  1.00 13.57      HIGL
ATOM   1085  CD   GLU   135      22.988  55.855 119.109  1.00 14.70      HIGL
ATOM   1086  OE1  GLU   135      23.605  55.107 119.895  1.00 13.98      HIGL
ATOM   1087  OE2  GLU   135      23.059  57.100 119.186  1.00 14.17      HIGL
ATOM   1088  C    GLU   135      22.980  52.662 115.217  1.00 11.83      HIGL
ATOM   1089  O    GLU   135      24.062  52.307 115.689  1.00 11.40      HIGL
ATOM   1090  N    ILE   136      22.464  52.139 114.107  1.00 11.55      HIGL
ATOM   1091  CA   ILE   136      23.145  51.086 113.366  1.00 12.33      HIGL
ATOM   1092  CB   ILE   136      22.134  50.255 112.537  1.00 11.21      HIGL
ATOM   1093  CG2  ILE   136      21.187  49.523 113.478  1.00 11.90      HIGL
ATOM   1094  CG1  ILE   136      21.346  51.166 111.583  1.00 10.88      HIGL
ATOM   1095  CD1  ILE   136      20.307  50.439 110.712  1.00  5.41      HIGL
ATOM   1096  C    ILE   136      24.272  51.570 112.446  1.00 13.31      HIGL
ATOM   1097  O    ILE   136      24.512  50.981 111.397  1.00 13.57      HIGL
ATOM   1098  N    THR   137      24.978  52.621 112.860  1.00 14.02      HIGL
ATOM   1099  CA   THR   137      26.076  53.177 112.073  1.00 15.42      HIGL
ATOM   1100  CB   THR   137      26.796  54.290 112.828  1.00 15.31      HIGL
ATOM   1101  OG1  THR   137      25.835  55.190 113.390  1.00 15.48      HIGL
ATOM   1102  CG2  THR   137      27.705  55.043 111.887  1.00 13.55      HIGL
ATOM   1103  C    THR   137      27.128  52.139 111.688  1.00 16.83      HIGL
ATOM   1104  O    THR   137      27.690  52.197 110.595  1.00 17.91      HIGL
```

Fig. 2 cont.

| | | | | | | | | | |
|---|---|---|---|---|---|---|---|---|---|
| ATOM | 1105 | N | GLN | 138 | 27.421 | 51.214 | 112.596 | 1.00 17.23 | HIGL |
| ATOM | 1106 | CA | GLN | 138 | 28.396 | 50.166 | 112.308 | 1.00 17.23 | HIGL |
| ATOM | 1107 | CB | GLN | 138 | 29.328 | 49.926 | 113.503 | 1.00 18.55 | HIGL |
| ATOM | 1108 | CG | GLN | 138 | 30.240 | 51.101 | 113.856 | 1.00 22.06 | HIGL |
| ATOM | 1109 | CD | GLN | 138 | 30.963 | 51.687 | 112.642 | 1.00 24.27 | HIGL |
| ATOM | 1110 | OE1 | GLN | 138 | 31.641 | 50.975 | 111.897 | 1.00 24.26 | HIGL |
| ATOM | 1111 | NE2 | GLN | 138 | 30.821 | 52.997 | 112.445 | 1.00 24.87 | HIGL |
| ATOM | 1112 | C | GLN | 138 | 27.633 | 48.886 | 111.985 | 1.00 16.30 | HIGL |
| ATOM | 1113 | O | GLN | 138 | 28.133 | 47.774 | 112.187 | 1.00 15.80 | HIGL |
| ATOM | 1114 | N | GLY | 139 | 26.411 | 49.059 | 111.490 | 1.00 14.43 | HIGL |
| ATOM | 1115 | CA | GLY | 139 | 25.590 | 47.917 | 111.138 | 1.00 14.15 | HIGL |
| ATOM | 1116 | C | GLY | 139 | 24.778 | 47.376 | 112.304 | 1.00 13.48 | HIGL |
| ATOM | 1117 | O | GLY | 139 | 24.703 | 48.001 | 113.363 | 1.00 11.76 | HIGL |
| ATOM | 1118 | N | LEU | 140 | 24.175 | 46.207 | 112.098 | 1.00 12.77 | HIGL |
| ATOM | 1119 | CA | LEU | 140 | 23.353 | 45.562 | 113.114 | 1.00 12.79 | HIGL |
| ATOM | 1120 | CB | LEU | 140 | 21.878 | 45.922 | 112.917 | 1.00 12.46 | HIGL |
| ATOM | 1121 | CG | LEU | 140 | 21.162 | 45.335 | 111.695 | 1.00 12.85 | HIGL |
| ATOM | 1122 | CD1 | LEU | 140 | 19.672 | 45.582 | 111.817 | 1.00 13.35 | HIGL |
| ATOM | 1123 | CD2 | LEU | 140 | 21.687 | 45.954 | 110.416 | 1.00 12.87 | HIGL |
| ATOM | 1124 | C | LEU | 140 | 23.504 | 44.055 | 113.010 | 1.00 13.36 | HIGL |
| ATOM | 1125 | O | LEU | 140 | 24.120 | 43.554 | 112.072 | 1.00 13.25 | HIGL |
| ATOM | 1126 | N | LEU | 141 | 22.937 | 43.342 | 113.980 | 1.00 13.28 | HIGL |
| ATOM | 1127 | CA | LEU | 141 | 22.975 | 41.883 | 114.008 | 1.00 12.60 | HIGL |
| ATOM | 1128 | CB | LEU | 141 | 21.895 | 41.340 | 113.069 | 1.00 10.91 | HIGL |
| ATOM | 1129 | CG | LEU | 141 | 20.481 | 41.627 | 113.587 | 1.00 10.89 | HIGL |
| ATOM | 1130 | CD1 | LEU | 141 | 19.432 | 41.270 | 112.543 | 1.00 9.50 | HIGL |
| ATOM | 1131 | CD2 | LEU | 141 | 20.264 | 40.846 | 114.880 | 1.00 8.29 | HIGL |
| ATOM | 1132 | C | LEU | 141 | 24.337 | 41.284 | 113.656 | 1.00 13.21 | HIGL |
| ATOM | 1133 | O | LEU | 141 | 24.462 | 40.504 | 112.708 | 1.00 14.64 | HIGL |
| ATOM | 1134 | N | TRP | 142 | 25.353 | 41.644 | 114.432 | 1.00 13.26 | HIGL |
| ATOM | 1135 | CA | TRP | 142 | 26.705 | 41.149 | 114.204 | 1.00 13.14 | HIGL |
| ATOM | 1136 | CB | TRP | 142 | 27.686 | 41.859 | 115.130 | 1.00 11.33 | HIGL |
| ATOM | 1137 | CG | TRP | 142 | 27.757 | 43.330 | 114.910 | 1.00 10.90 | HIGL |
| ATOM | 1138 | CD2 | TRP | 142 | 28.488 | 44.272 | 115.695 | 1.00 11.10 | HIGL |
| ATOM | 1139 | CE2 | TRP | 142 | 28.289 | 45.545 | 115.113 | 1.00 11.19 | HIGL |
| ATOM | 1140 | CE3 | TRP | 142 | 29.290 | 44.167 | 116.835 | 1.00 10.40 | HIGL |
| ATOM | 1141 | CD1 | TRP | 142 | 27.158 | 44.046 | 113.911 | 1.00 10.69 | HIGL |
| ATOM | 1142 | NE1 | TRP | 142 | 27.474 | 45.379 | 114.025 | 1.00 10.00 | HIGL |
| ATOM | 1143 | CZ2 | TRP | 142 | 28.869 | 46.705 | 115.635 | 1.00 11.44 | HIGL |
| ATOM | 1144 | CZ3 | TRP | 142 | 29.863 | 45.319 | 117.353 | 1.00 11.67 | HIGL |
| ATOM | 1145 | CH2 | TRP | 142 | 29.650 | 46.573 | 116.750 | 1.00 11.55 | HIGL |
| ATOM | 1146 | C | TRP | 142 | 26.768 | 39.652 | 114.442 | 1.00 13.84 | HIGL |
| ATOM | 1147 | O | TRP | 142 | 26.046 | 39.126 | 115.286 | 1.00 14.95 | HIGL |
| ATOM | 1148 | N | PRO | 143 | 27.680 | 38.952 | 113.751 | 1.00 13.87 | HIGL |
| ATOM | 1149 | CD | PRO | 143 | 27.900 | 37.534 | 114.052 | 1.00 13.74 | HIGL |
| ATOM | 1150 | CA | PRO | 143 | 28.675 | 39.417 | 112.776 | 1.00 14.76 | HIGL |
| ATOM | 1151 | CB | PRO | 143 | 29.669 | 38.253 | 112.701 | 1.00 13.49 | HIGL |
| ATOM | 1152 | CG | PRO | 143 | 29.386 | 37.438 | 113.918 | 1.00 13.80 | HIGL |
| ATOM | 1153 | C | PRO | 143 | 28.174 | 39.778 | 111.381 | 1.00 15.67 | HIGL |
| ATOM | 1154 | O | PRO | 143 | 28.703 | 40.693 | 110.755 | 1.00 16.90 | HIGL |
| ATOM | 1155 | N | LEU | 144 | 27.182 | 39.044 | 110.887 | 1.00 15.74 | HIGL |
| ATOM | 1156 | CA | LEU | 144 | 26.648 | 39.272 | 109.549 | 1.00 16.05 | HIGL |
| ATOM | 1157 | CB | LEU | 144 | 25.366 | 38.459 | 109.358 | 1.00 15.16 | HIGL |
| ATOM | 1158 | CG | LEU | 144 | 25.558 | 36.942 | 109.467 | 1.00 14.79 | HIGL |
| ATOM | 1159 | CD1 | LEU | 144 | 24.214 | 36.248 | 109.414 | 1.00 14.16 | HIGL |
| ATOM | 1160 | CD2 | LEU | 144 | 26.455 | 36.449 | 108.331 | 1.00 14.04 | HIGL |
| ATOM | 1161 | C | LEU | 144 | 26.397 | 40.727 | 109.159 | 1.00 17.32 | HIGL |
| ATOM | 1162 | O | LEU | 144 | 26.911 | 41.191 | 108.144 | 1.00 17.71 | HIGL |
| ATOM | 1163 | N | GLY | 145 | 25.617 | 41.451 | 109.956 | 1.00 17.84 | HIGL |
| ATOM | 1164 | CA | GLY | 145 | 25.325 | 42.835 | 109.617 | 1.00 17.98 | HIGL |
| ATOM | 1165 | C | GLY | 145 | 26.335 | 43.888 | 110.051 | 1.00 18.71 | HIGL |
| ATOM | 1166 | O | GLY | 145 | 26.008 | 45.077 | 110.123 | 1.00 19.15 | HIGL |
| ATOM | 1167 | N | LYS | 146 | 27.560 | 43.477 | 110.341 | 1.00 18.29 | HIGL |
| ATOM | 1168 | CA | LYS | 146 | 28.575 | 44.428 | 110.762 | 1.00 19.30 | HIGL |
| ATOM | 1169 | CB | LYS | 146 | 29.733 | 43.687 | 111.423 | 1.00 18.95 | HIGL |

Fig. 2 cont.

```
ATOM   1170  CG   LYS  146    30.533  44.508 112.414  1.00 18.69    HIGL
ATOM   1171  CD   LYS  146    31.624  43.643 113.039  1.00 20.37    HIGL
ATOM   1172  CE   LYS  146    32.528  44.430 113.984  1.00 20.86    HIGL
ATOM   1173  NZ   LYS  146    31.799  44.955 115.162  1.00 21.63    HIGL
ATOM   1174  C    LYS  146    29.062  45.228 109.550  1.00 20.47    HIGL
ATOM   1175  O    LYS  146    29.211  44.685 108.453  1.00 19.27    HIGL
ATOM   1176  N    THR  147    29.312  46.519 109.752  1.00 21.74    HIGL
ATOM   1177  CA   THR  147    29.746  47.374 108.659  1.00 23.27    HIGL
ATOM   1178  CB   THR  147    30.212  48.734 109.130  1.00 22.61    HIGL
ATOM   1179  OG1  THR  147    30.794  48.619 110.430  1.00 23.56    HIGL
ATOM   1180  CG2  THR  147    29.050  49.703 109.127  1.00 23.05    HIGL
ATOM   1181  C    THR  147    30.817  46.833 107.747  1.00 24.76    HIGL
ATOM   1182  O    THR  147    31.763  46.161 108.173  1.00 24.27    HIGL
ATOM   1183  N    ASN  148    30.631  47.193 106.478  1.00 26.25    HIGL
ATOM   1184  CA   ASN  148    31.456  46.818 105.346  1.00 26.20    HIGL
ATOM   1185  CB   ASN  148    32.917  46.692 105.763  1.00 26.56    HIGL
ATOM   1186  CG   ASN  148    33.560  48.057 105.998  1.00 26.62    HIGL
ATOM   1187  OD1  ASN  148    32.903  48.985 106.472  1.00 26.28    HIGL
ATOM   1188  ND2  ASN  148    34.842  48.183 105.670  1.00 25.69    HIGL
ATOM   1189  C    ASN  148    30.865  45.542 104.762  1.00 26.28    HIGL
ATOM   1190  O    ASN  148    31.279  45.076 103.707  1.00 28.00    HIGL
ATOM   1191  N    ASN  149    29.873  44.998 105.464  1.00 25.38    HIGL
ATOM   1192  CA   ASN  149    29.127  43.826 105.007  1.00 24.20    HIGL
ATOM   1193  CB   ASN  149    28.733  42.927 106.177  1.00 24.04    HIGL
ATOM   1194  CG   ASN  149    29.858  42.016 106.615  1.00 24.57    HIGL
ATOM   1195  OD1  ASN  149    31.033  42.309 106.391  1.00 25.70    HIGL
ATOM   1196  ND2  ASN  149    29.505  40.910 107.260  1.00 23.86    HIGL
ATOM   1197  C    ASN  149    27.877  44.466 104.421  1.00 23.50    HIGL
ATOM   1198  O    ASN  149    26.753  44.011 104.637  1.00 24.05    HIGL
ATOM   1199  N    TRP  150    28.101  45.554 103.698  1.00 21.67    HIGL
ATOM   1200  CA   TRP  150    27.039  46.323 103.079  1.00 20.87    HIGL
ATOM   1201  CB   TRP  150    27.649  47.265 102.045  1.00 19.65    HIGL
ATOM   1202  CG   TRP  150    28.654  48.200 102.653  1.00 19.10    HIGL
ATOM   1203  CD2  TRP  150    28.411  49.153 103.697  1.00 19.28    HIGL
ATOM   1204  CE2  TRP  150    29.631  49.828 103.938  1.00 18.98    HIGL
ATOM   1205  CE3  TRP  150    27.278  49.506 104.452  1.00 18.67    HIGL
ATOM   1206  CD1  TRP  150    29.976  48.329 102.315  1.00 18.26    HIGL
ATOM   1207  NE1  TRP  150    30.567  49.306 103.080  1.00 17.94    HIGL
ATOM   1208  CZ2  TRP  150    29.751  50.837 104.902  1.00 19.36    HIGL
ATOM   1209  CZ3  TRP  150    27.395  50.506 105.409  1.00 19.12    HIGL
ATOM   1210  CH2  TRP  150    28.627  51.162 105.626  1.00 19.64    HIGL
ATOM   1211  C    TRP  150    25.939  45.479 102.451  1.00 20.95    HIGL
ATOM   1212  O    TRP  150    24.757  45.801 102.583  1.00 21.08    HIGL
ATOM   1213  N    TYR  151    26.315  44.400 101.769  1.00 20.56    HIGL
ATOM   1214  CA   TYR  151    25.312  43.551 101.146  1.00 19.67    HIGL
ATOM   1215  CB   TYR  151    25.949  42.403 100.362  1.00 19.65    HIGL
ATOM   1216  CG   TYR  151    24.910  41.515  99.711  1.00 20.60    HIGL
ATOM   1217  CD1  TYR  151    24.183  41.962  98.610  1.00 20.83    HIGL
ATOM   1218  CE1  TYR  151    23.180  41.179  98.036  1.00 20.50    HIGL
ATOM   1219  CD2  TYR  151    24.609  40.249 100.228  1.00 20.51    HIGL
ATOM   1220  CE2  TYR  151    23.601  39.457  99.656  1.00 20.06    HIGL
ATOM   1221  CZ   TYR  151    22.894  39.933  98.559  1.00 20.06    HIGL
ATOM   1222  OH   TYR  151    21.904  39.171  97.972  1.00 19.92    HIGL
ATOM   1223  C    TYR  151    24.389  42.972 102.204  1.00 19.26    HIGL
ATOM   1224  O    TYR  151    23.176  43.114 102.113  1.00 18.33    HIGL
ATOM   1225  N    ASN  152    24.966  42.317 103.209  1.00 19.42    HIGL
ATOM   1226  CA   ASN  152    24.158  41.722 104.267  1.00 19.11    HIGL
ATOM   1227  CB   ASN  152    25.040  41.046 105.326  1.00 19.23    HIGL
ATOM   1228  CG   ASN  152    25.663  39.739 104.835  1.00 20.56    HIGL
ATOM   1229  OD1  ASN  152    25.221  39.154 103.839  1.00 19.15    HIGL
ATOM   1230  ND2  ASN  152    26.687  39.267 105.549  1.00 19.90    HIGL
ATOM   1231  C    ASN  152    23.265  42.756 104.937  1.00 18.86    HIGL
ATOM   1232  O    ASN  152    22.111  42.469 105.248  1.00 19.25    HIGL
ATOM   1233  N    ILE  153    23.792  43.958 105.154  1.00 18.55    HIGL
ATOM   1234  CA   ILE  153    23.024  45.020 105.804  1.00 18.75    HIGL
```

Fig. 2 cont.

```
ATOM   1235  CB   ILE  153      23.891  46.283 106.033  1.00 17.77      HIGL
ATOM   1236  CG2  ILE  153      23.053  47.395 106.623  1.00 16.52      HIGL
ATOM   1237  CG1  ILE  153      25.046  45.949 106.982  1.00 17.36      HIGL
ATOM   1238  CD1  ILE  153      26.068  47.050 107.128  1.00 16.15      HIGL
ATOM   1239  C    ILE  153      21.770  45.414 105.021  1.00 19.29      HIGL
ATOM   1240  O    ILE  153      20.653  45.369 105.557  1.00 18.88      HIGL
ATOM   1241  N    ALA  154      21.950  45.791 103.758  1.00 18.63      HIGL
ATOM   1242  CA   ALA  154      20.814  46.198 102.936  1.00 19.02      HIGL
ATOM   1243  CB   ALA  154      21.280  46.567 101.536  1.00 17.23      HIGL
ATOM   1244  C    ALA  154      19.828  45.043 102.880  1.00 19.18      HIGL
ATOM   1245  O    ALA  154      18.609  45.227 102.823  1.00 19.09      HIGL
ATOM   1246  N    ARG  155      20.393  43.846 102.908  1.00 19.15      HIGL
ATOM   1247  CA   ARG  155      19.646  42.602 102.864  1.00 18.74      HIGL
ATOM   1248  CB   ARG  155      20.661  41.461 102.775  1.00 18.99      HIGL
ATOM   1249  CG   ARG  155      20.110  40.111 102.485  1.00 19.95      HIGL
ATOM   1250  CD   ARG  155      19.495  39.997 101.104  1.00 20.00      HIGL
ATOM   1251  NE   ARG  155      18.768  38.740 101.065  1.00 21.33      HIGL
ATOM   1252  CZ   ARG  155      19.341  37.554 100.901  1.00 22.66      HIGL
ATOM   1253  NH1  ARG  155      20.655  37.462 100.728  1.00 22.62      HIGL
ATOM   1254  NH2  ARG  155      18.607  36.454 100.981  1.00 24.41      HIGL
ATOM   1255  C    ARG  155      18.798  42.509 104.142  1.00 18.62      HIGL
ATOM   1256  O    ARG  155      17.593  42.257 104.105  1.00 18.01      HIGL
ATOM   1257  N    LEU  156      19.432  42.748 105.280  1.00 18.71      HIGL
ATOM   1258  CA   LEU  156      18.725  42.688 106.548  1.00 17.91      HIGL
ATOM   1259  CB   LEU  156      19.720  42.796 107.707  1.00 16.34      HIGL
ATOM   1260  CG   LEU  156      20.507  41.507 107.927  1.00 16.27      HIGL
ATOM   1261  CD1  LEU  156      21.555  41.716 109.000  1.00 15.19      HIGL
ATOM   1262  CD2  LEU  156      19.547  40.384 108.310  1.00 15.70      HIGL
ATOM   1263  C    LEU  156      17.651  43.757 106.680  1.00 17.08      HIGL
ATOM   1264  O    LEU  156      16.531  43.472 107.097  1.00 18.08      HIGL
ATOM   1265  N    LEU  157      17.984  44.987 106.323  1.00 16.61      HIGL
ATOM   1266  CA   LEU  157      17.025  46.069 106.448  1.00 16.27      HIGL
ATOM   1267  CB   LEU  157      17.710  47.405 106.169  1.00 15.39      HIGL
ATOM   1268  CG   LEU  157      18.901  47.674 107.103  1.00 15.27      HIGL
ATOM   1269  CD1  LEU  157      19.582  48.989 106.730  1.00 14.68      HIGL
ATOM   1270  CD2  LEU  157      18.425  47.688 108.546  1.00 13.43      HIGL
ATOM   1271  C    LEU  157      15.819  45.870 105.543  1.00 16.79      HIGL
ATOM   1272  O    LEU  157      14.686  46.120 105.950  1.00 17.48      HIGL
ATOM   1273  N    HIS  158      16.050  45.403 104.321  1.00 17.58      HIGL
ATOM   1274  CA   HIS  158      14.944  45.174 103.401  1.00 17.25      HIGL
ATOM   1275  CB   HIS  158      15.439  44.552 102.099  1.00 17.36      HIGL
ATOM   1276  CG   HIS  158      14.335  44.187 101.159  1.00 18.88      HIGL
ATOM   1277  CD2  HIS  158      13.798  42.986 100.834  1.00 18.45      HIGL
ATOM   1278  ND1  HIS  158      13.587  45.133 100.484  1.00 19.56      HIGL
ATOM   1279  CE1  HIS  158      12.641  44.530  99.790  1.00 18.81      HIGL
ATOM   1280  NE2  HIS  158      12.746  43.225  99.985  1.00 19.02      HIGL
ATOM   1281  C    HIS  158      13.920  44.242 104.051  1.00 17.47      HIGL
ATOM   1282  O    HIS  158      12.723  44.531 104.066  1.00 16.46      HIGL
ATOM   1283  N    SER  159      14.402  43.127 104.592  1.00 17.53      HIGL
ATOM   1284  CA   SER  159      13.535  42.157 105.244  1.00 17.96      HIGL
ATOM   1285  CB   SER  159      14.353  40.973 105.753  1.00 18.70      HIGL
ATOM   1286  OG   SER  159      14.963  40.280 104.684  1.00 20.45      HIGL
ATOM   1287  C    SER  159      12.778  42.782 106.409  1.00 18.11      HIGL
ATOM   1288  O    SER  159      11.577  42.549 106.577  1.00 17.79      HIGL
ATOM   1289  N    ALA  160      13.483  43.573 107.214  1.00 17.67      HIGL
ATOM   1290  CA   ALA  160      12.871  44.231 108.363  1.00 17.44      HIGL
ATOM   1291  CB   ALA  160      13.929  44.922 109.187  1.00 16.81      HIGL
ATOM   1292  C    ALA  160      11.824  45.239 107.918  1.00 17.59      HIGL
ATOM   1293  O    ALA  160      10.737  45.322 108.492  1.00 17.41      HIGL
ATOM   1294  N    ALA  161      12.157  46.012 106.892  1.00 18.14      HIGL
ATOM   1295  CA   ALA  161      11.230  47.011 106.377  1.00 18.38      HIGL
ATOM   1296  CB   ALA  161      11.831  47.714 105.189  1.00 16.08      HIGL
ATOM   1297  C    ALA  161       9.931  46.337 105.974  1.00 19.43      HIGL
ATOM   1298  O    ALA  161       8.844  46.848 106.244  1.00 20.06      HIGL
ATOM   1299  N    TRP  162      10.045  45.176 105.335  1.00 19.98      HIGL
```

Fig. 2 cont.

```
ATOM   1300  CA   TRP  162       8.864  44.463 104.889  1.00 20.45      HIGL
ATOM   1301  CB   TRP  162       9.215  43.511 103.746  1.00 21.00      HIGL
ATOM   1302  CG   TRP  162       9.298  44.267 102.482  1.00 21.58      HIGL
ATOM   1303  CD2  TRP  162       8.222  44.516 101.575  1.00 21.96      HIGL
ATOM   1304  CE2  TRP  162       8.691  45.440 100.612  1.00 21.86      HIGL
ATOM   1305  CE3  TRP  162       6.902  44.056 101.487  1.00 22.03      HIGL
ATOM   1306  CD1  TRP  162      10.354  45.019 102.040  1.00 21.86      HIGL
ATOM   1307  NE1  TRP  162       9.995  45.729 100.919  1.00 21.88      HIGL
ATOM   1308  CZ2  TRP  162       7.884  45.913  99.572  1.00 21.45      HIGL
ATOM   1309  CZ3  TRP  162       6.096  44.530 100.448  1.00 22.27      HIGL
ATOM   1310  CH2  TRP  162       6.594  45.449  99.506  1.00 21.62      HIGL
ATOM   1311  C    TRP  162       8.108  43.746 105.982  1.00 20.46      HIGL
ATOM   1312  O    TRP  162       6.919  43.463 105.829  1.00 21.30      HIGL
ATOM   1313  N    GLY  163       8.783  43.453 107.085  1.00 19.69      HIGL
ATOM   1314  CA   GLY  163       8.089  42.816 108.182  1.00 19.99      HIGL
ATOM   1315  C    GLY  163       7.048  43.833 108.622  1.00 20.35      HIGL
ATOM   1316  O    GLY  163       5.954  43.491 109.075  1.00 20.66      HIGL
ATOM   1317  N    VAL  164       7.398  45.106 108.469  1.00 19.87      HIGL
ATOM   1318  CA   VAL  164       6.504  46.194 108.832  1.00 18.68      HIGL
ATOM   1319  CB   VAL  164       7.266  47.534 108.946  1.00 18.24      HIGL
ATOM   1320  CG1  VAL  164       6.305  48.650 109.336  1.00 17.70      HIGL
ATOM   1321  CG2  VAL  164       8.391  47.409 109.959  1.00 17.30      HIGL
ATOM   1322  C    VAL  164       5.447  46.336 107.748  1.00 18.61      HIGL
ATOM   1323  O    VAL  164       4.254  46.415 108.027  1.00 18.31      HIGL
ATOM   1324  N    LYS  165       5.891  46.356 106.502  1.00 18.63      HIGL
ATOM   1325  CA   LYS  165       4.965  46.516 105.403  1.00 19.93      HIGL
ATOM   1326  CB   LYS  165       5.728  46.615 104.087  1.00 19.36      HIGL
ATOM   1327  CG   LYS  165       6.589  47.869 103.981  1.00 18.36      HIGL
ATOM   1328  CD   LYS  165       7.335  47.923 102.644  1.00 18.25      HIGL
ATOM   1329  CE   LYS  165       8.175  49.182 102.534  1.00 17.76      HIGL
ATOM   1330  NZ   LYS  165       7.317  50.401 102.629  1.00 18.31      HIGL
ATOM   1331  C    LYS  165       3.904  45.428 105.325  1.00 20.82      HIGL
ATOM   1332  O    LYS  165       2.746  45.727 105.049  1.00 21.60      HIGL
ATOM   1333  N    ASP  166       4.283  44.179 105.581  1.00 21.39      HIGL
ATOM   1334  CA   ASP  166       3.327  43.073 105.522  1.00 22.03      HIGL
ATOM   1335  CB   ASP  166       4.039  41.749 105.219  1.00 22.56      HIGL
ATOM   1336  CG   ASP  166       4.642  41.702 103.833  1.00 23.22      HIGL
ATOM   1337  OD1  ASP  166       4.195  42.463 102.951  1.00 23.72      HIGL
ATOM   1338  OD2  ASP  166       5.560  40.879 103.623  1.00 23.83      HIGL
ATOM   1339  C    ASP  166       2.481  42.860 106.782  1.00 22.48      HIGL
ATOM   1340  O    ASP  166       1.724  41.896 106.852  1.00 22.92      HIGL
ATOM   1341  N    SER  167       2.596  43.732 107.777  1.00 22.71      HIGL
ATOM   1342  CA   SER  167       1.825  43.554 109.006  1.00 22.64      HIGL
ATOM   1343  CB   SER  167       2.519  44.259 110.169  1.00 22.61      HIGL
ATOM   1344  OG   SER  167       2.442  45.667 110.023  1.00 23.18      HIGL
ATOM   1345  C    SER  167       0.396  44.081 108.886  1.00 23.16      HIGL
ATOM   1346  O    SER  167       0.040  44.722 107.903  1.00 22.85      HIGL
ATOM   1347  N    ARG  168      -0.418  43.798 109.898  1.00 23.80      HIGL
ATOM   1348  CA   ARG  168      -1.805  44.250 109.933  1.00 23.78      HIGL
ATOM   1349  CB   ARG  168      -2.601  43.465 110.978  1.00 23.09      HIGL
ATOM   1350  CG   ARG  168      -3.597  42.463 110.420  1.00 22.15      HIGL
ATOM   1351  CD   ARG  168      -3.088  41.049 110.571  1.00 21.65      HIGL
ATOM   1352  NE   ARG  168      -2.910  40.664 111.971  1.00 18.91      HIGL
ATOM   1353  CZ   ARG  168      -2.272  39.564 112.348  1.00 18.78      HIGL
ATOM   1354  NH1  ARG  168      -1.763  38.753 111.430  1.00 18.16      HIGL
ATOM   1355  NH2  ARG  168      -2.127  39.278 113.633  1.00 19.17      HIGL
ATOM   1356  C    ARG  168      -1.890  45.734 110.284  1.00 24.65      HIGL
ATOM   1357  O    ARG  168      -2.980  46.299 110.348  1.00 25.72      HIGL
ATOM   1358  N    LEU  169      -0.751  46.366 110.534  1.00 24.93      HIGL
ATOM   1359  CA   LEU  169      -0.767  47.779 110.873  1.00 25.57      HIGL
ATOM   1360  CB   LEU  169       0.642  48.300 111.135  1.00 24.39      HIGL
ATOM   1361  CG   LEU  169       1.239  47.981 112.501  1.00 23.91      HIGL
ATOM   1362  CD1  LEU  169       2.643  48.570 112.579  1.00 23.28      HIGL
ATOM   1363  CD2  LEU  169       0.350  48.545 113.595  1.00 21.07      HIGL
ATOM   1364  C    LEU  169      -1.395  48.596 109.768  1.00 26.78      HIGL
```

Fig. 2 cont.

```
ATOM   1365  O    LEU  169      -1.086  48.421 108.591  1.00 26.61      HIGL
ATOM   1366  N    ASN  170      -2.292  49.485 110.160  1.00 28.98      HIGL
ATOM   1367  CA   ASN  170      -2.962  50.356 109.216  1.00 31.16      HIGL
ATOM   1368  CB   ASN  170      -4.126  49.638 108.536  1.00 34.31      HIGL
ATOM   1369  CG   ASN  170      -4.532  50.301 107.223  1.00 37.73      HIGL
ATOM   1370  OD1  ASN  170      -5.637  50.087 106.717  1.00 39.55      HIGL
ATOM   1371  ND2  ASN  170      -3.628  51.098 106.657  1.00 38.83      HIGL
ATOM   1372  C    ASN  170      -3.482  51.560 109.989  1.00 31.18      HIGL
ATOM   1373  O    ASN  170      -4.227  51.411 110.965  1.00 31.87      HIGL
ATOM   1374  N    PRO  171      -3.044  52.767 109.599  1.00 29.94      HIGL
ATOM   1375  CD   PRO  171      -3.373  54.060 110.227  1.00 29.80      HIGL
ATOM   1376  CA   PRO  171      -2.101  52.949 108.492  1.00 28.18      HIGL
ATOM   1377  CB   PRO  171      -2.094  54.459 108.295  1.00 28.38      HIGL
ATOM   1378  CG   PRO  171      -2.269  54.960 109.698  1.00 29.83      HIGL
ATOM   1379  C    PRO  171      -0.728  52.413 108.889  1.00 26.71      HIGL
ATOM   1380  O    PRO  171      -0.472  52.183 110.068  1.00 25.16      HIGL
ATOM   1381  N    LYS  172       0.139  52.204 107.900  1.00 25.19      HIGL
ATOM   1382  CA   LYS  172       1.482  51.709 108.155  1.00 24.35      HIGL
ATOM   1383  CB   LYS  172       2.119  51.187 106.867  1.00 25.60      HIGL
ATOM   1384  CG   LYS  172       1.274  50.201 106.093  1.00 27.94      HIGL
ATOM   1385  CD   LYS  172       1.253  48.826 106.725  1.00 29.37      HIGL
ATOM   1386  CE   LYS  172       0.451  47.875 105.848  1.00 30.03      HIGL
ATOM   1387  NZ   LYS  172       0.492  46.469 106.329  1.00 30.93      HIGL
ATOM   1388  C    LYS  172       2.332  52.858 108.686  1.00 22.94      HIGL
ATOM   1389  O    LYS  172       2.212  53.992 108.220  1.00 22.83      HIGL
ATOM   1390  N    PRO  173       3.200  52.580 109.671  1.00 21.18      HIGL
ATOM   1391  CD   PRO  173       3.396  51.290 110.354  1.00 21.36      HIGL
ATOM   1392  CA   PRO  173       4.069  53.599 110.254  1.00 20.28      HIGL
ATOM   1393  CB   PRO  173       4.595  52.915 111.508  1.00 20.26      HIGL
ATOM   1394  CG   PRO  173       4.718  51.502 111.059  1.00 20.58      HIGL
ATOM   1395  C    PRO  173       5.197  53.947 109.297  1.00 19.51      HIGL
ATOM   1396  O    PRO  173       5.525  53.172 108.407  1.00 19.40      HIGL
ATOM   1397  N    LYS  174       5.778  55.123 109.482  1.00 18.84      HIGL
ATOM   1398  CA   LYS  174       6.887  55.548 108.655  1.00 18.05      HIGL
ATOM   1399  CB   LYS  174       7.168  57.032 108.875  1.00 18.15      HIGL
ATOM   1400  CG   LYS  174       5.984  57.905 108.527  1.00 18.80      HIGL
ATOM   1401  CD   LYS  174       6.308  59.380 108.602  1.00 19.52      HIGL
ATOM   1402  CE   LYS  174       5.140  60.200 108.085  1.00 18.38      HIGL
ATOM   1403  NZ   LYS  174       5.521  61.622 107.893  1.00 19.70      HIGL
ATOM   1404  C    LYS  174       8.073  54.712 109.097  1.00 17.68      HIGL
ATOM   1405  O    LYS  174       8.348  54.586 110.288  1.00 18.33      HIGL
ATOM   1406  N    ILE  175       8.764  54.119 108.139  1.00 17.03      HIGL
ATOM   1407  CA   ILE  175       9.909  53.291 108.461  1.00 16.37      HIGL
ATOM   1408  CB   ILE  175      10.071  52.178 107.420  1.00 15.88      HIGL
ATOM   1409  CG2  ILE  175      11.276  51.317 107.767  1.00 14.85      HIGL
ATOM   1410  CG1  ILE  175       8.785  51.342 107.387  1.00 14.92      HIGL
ATOM   1411  CD1  ILE  175       8.694  50.358 106.232  1.00 16.47      HIGL
ATOM   1412  C    ILE  175      11.142  54.176 108.517  1.00 15.73      HIGL
ATOM   1413  O    ILE  175      11.417  54.933 107.588  1.00 15.78      HIGL
ATOM   1414  N    MET  176      11.874  54.075 109.620  1.00 14.73      HIGL
ATOM   1415  CA   MET  176      13.054  54.896 109.836  1.00 14.35      HIGL
ATOM   1416  CB   MET  176      12.830  55.786 111.070  1.00 13.52      HIGL
ATOM   1417  CG   MET  176      14.060  56.557 111.518  1.00 13.16      HIGL
ATOM   1418  SD   MET  176      13.928  57.167 113.201  1.00 14.72      HIGL
ATOM   1419  CE   MET  176      12.695  58.477 112.999  1.00 14.08      HIGL
ATOM   1420  C    MET  176      14.358  54.122 110.024  1.00 14.18      HIGL
ATOM   1421  O    MET  176      14.376  53.040 110.603  1.00 14.19      HIGL
ATOM   1422  N    VAL  177      15.444  54.693 109.511  1.00 14.60      HIGL
ATOM   1423  CA   VAL  177      16.777  54.123 109.664  1.00 13.89      HIGL
ATOM   1424  CB   VAL  177      17.532  54.024 108.319  1.00 13.58      HIGL
ATOM   1425  CG1  VAL  177      19.004  53.680 108.573  1.00 12.32      HIGL
ATOM   1426  CG2  VAL  177      16.892  52.940 107.454  1.00 12.15      HIGL
ATOM   1427  C    VAL  177      17.461  55.113 110.597  1.00 13.92      HIGL
ATOM   1428  O    VAL  177      17.503  56.314 110.326  1.00 13.57      HIGL
ATOM   1429  N    HIS  178      17.966  54.595 111.710  1.00 14.28      HIGL
```

Fig. 2 cont.

```
ATOM   1430  CA   HIS  178      18.591  55.407 112.743  1.00 14.37      HIGL
ATOM   1431  CB   HIS  178      17.910  55.083 114.083  1.00 14.38      HIGL
ATOM   1432  CG   HIS  178      18.522  55.762 115.268  1.00 14.85      HIGL
ATOM   1433  CD2  HIS  178      18.456  55.471 116.589  1.00 14.94      HIGL
ATOM   1434  ND1  HIS  178      19.287  56.903 115.163  1.00 15.06      HIGL
ATOM   1435  CE1  HIS  178      19.670  57.285 116.369  1.00 14.39      HIGL
ATOM   1436  NE2  HIS  178      19.179  56.434 117.251  1.00 15.19      HIGL
ATOM   1437  C    HIS  178      20.102  55.235 112.850  1.00 14.74      HIGL
ATOM   1438  O    HIS  178      20.605  54.132 113.072  1.00 14.60      HIGL
ATOM   1439  N    LEU  179      20.812  56.346 112.685  1.00 14.68      HIGL
ATOM   1440  CA   LEU  179      22.269  56.381 112.769  1.00 14.88      HIGL
ATOM   1441  CB   LEU  179      22.866  56.817 111.430  1.00 14.85      HIGL
ATOM   1442  CG   LEU  179      23.217  55.794 110.349  1.00 15.01      HIGL
ATOM   1443  CD1  LEU  179      22.120  54.786 110.177  1.00 15.16      HIGL
ATOM   1444  CD2  LEU  179      23.476  56.536 109.049  1.00 14.52      HIGL
ATOM   1445  C    LEU  179      22.632  57.406 113.830  1.00 14.77      HIGL
ATOM   1446  O    LEU  179      21.867  58.336 114.070  1.00 16.15      HIGL
ATOM   1447  N    ASP  180      23.786  57.244 114.468  1.00 14.56      HIGL
ATOM   1448  CA   ASP  180      24.217  58.200 115.483  1.00 15.13      HIGL
ATOM   1449  CB   ASP  180      25.040  57.491 116.576  1.00 15.21      HIGL
ATOM   1450  CG   ASP  180      26.496  57.238 116.171  1.00 16.64      HIGL
ATOM   1451  OD1  ASP  180      26.744  56.712 115.060  1.00 15.02      HIGL
ATOM   1452  OD2  ASP  180      27.393  57.560 116.987  1.00 16.16      HIGL
ATOM   1453  C    ASP  180      25.039  59.279 114.776  1.00 15.95      HIGL
ATOM   1454  O    ASP  180      25.185  59.233 113.555  1.00 17.25      HIGL
ATOM   1455  N    ASN  181      25.556  60.249 115.525  1.00 15.91      HIGL
ATOM   1456  CA   ASN  181      26.362  61.334 114.960  1.00 15.67      HIGL
ATOM   1457  CB   ASN  181      27.754  60.824 114.594  1.00 16.57      HIGL
ATOM   1458  CG   ASN  181      28.573  60.449 115.807  1.00 17.66      HIGL
ATOM   1459  OD1  ASN  181      28.418  61.031 116.881  1.00 19.18      HIGL
ATOM   1460  ND2  ASN  181      29.464  59.487 115.641  1.00 18.44      HIGL
ATOM   1461  C    ASN  181      25.763  62.034 113.742  1.00 15.63      HIGL
ATOM   1462  O    ASN  181      26.433  62.200 112.731  1.00 15.55      HIGL
ATOM   1463  N    GLY  182      24.508  62.455 113.847  1.00 15.79      HIGL
ATOM   1464  CA   GLY  182      23.853  63.129 112.744  1.00 15.12      HIGL
ATOM   1465  C    GLY  182      24.575  64.373 112.287  1.00 15.79      HIGL
ATOM   1466  O    GLY  182      24.331  64.857 111.184  1.00 16.16      HIGL
ATOM   1467  N    TRP  183      25.459  64.902 113.130  1.00 16.94      HIGL
ATOM   1468  CA   TRP  183      26.227  66.100 112.784  1.00 16.80      HIGL
ATOM   1469  CB   TRP  183      26.854  66.746 114.034  1.00 16.19      HIGL
ATOM   1470  CG   TRP  183      27.735  65.829 114.837  1.00 14.99      HIGL
ATOM   1471  CD2  TRP  183      29.108  65.506 114.577  1.00 14.85      HIGL
ATOM   1472  CE2  TRP  183      29.505  64.558 115.547  1.00 14.72      HIGL
ATOM   1473  CE3  TRP  183      30.041  65.922 113.616  1.00 15.26      HIGL
ATOM   1474  CD1  TRP  183      27.369  65.091 115.919  1.00 15.04      HIGL
ATOM   1475  NE1  TRP  183      28.424  64.324 116.353  1.00 14.56      HIGL
ATOM   1476  CZ2  TRP  183      30.798  64.015 115.586  1.00 13.96      HIGL
ATOM   1477  CZ3  TRP  183      31.332  65.379 113.654  1.00 14.45      HIGL
ATOM   1478  CH2  TRP  183      31.693  64.436 114.634  1.00 13.99      HIGL
ATOM   1479  C    TRP  183      27.333  65.755 111.797  1.00 17.18      HIGL
ATOM   1480  O    TRP  183      27.780  66.606 111.040  1.00 18.90      HIGL
ATOM   1481  N    ASN  184      27.780  64.508 111.807  1.00 17.37      HIGL
ATOM   1482  CA   ASN  184      28.838  64.087 110.901  1.00 18.52      HIGL
ATOM   1483  CB   ASN  184      29.623  62.936 111.514  1.00 18.43      HIGL
ATOM   1484  CG   ASN  184      30.892  62.651 110.760  1.00 18.15      HIGL
ATOM   1485  OD1  ASN  184      30.904  62.652 109.528  1.00 17.65      HIGL
ATOM   1486  ND2  ASN  184      31.972  62.403 111.490  1.00 16.66      HIGL
ATOM   1487  C    ASN  184      28.265  63.647 109.551  1.00 19.20      HIGL
ATOM   1488  O    ASN  184      27.800  62.515 109.406  1.00 19.59      HIGL
ATOM   1489  N    TRP  185      28.318  64.536 108.563  1.00 18.87      HIGL
ATOM   1490  CA   TRP  185      27.780  64.239 107.246  1.00 18.50      HIGL
ATOM   1491  CB   TRP  185      27.752  65.517 106.404  1.00 19.66      HIGL
ATOM   1492  CG   TRP  185      27.658  65.269 104.923  1.00 20.74      HIGL
ATOM   1493  CD2  TRP  185      26.584  64.623 104.224  1.00 21.65      HIGL
ATOM   1494  CE2  TRP  185      26.952  64.564 102.857  1.00 21.97      HIGL
```

Fig. 2 cont.

```
ATOM   1495  CE3  TRP  185      25.349  64.085 104.618  1.00 21.22           HIGL
ATOM   1496  CD1  TRP  185      28.601  65.570 103.982  1.00 20.45           HIGL
ATOM   1497  NE1  TRP  185      28.184  65.151 102.740  1.00 21.70           HIGL
ATOM   1498  CZ2  TRP  185      26.127  63.985 101.880  1.00 21.82           HIGL
ATOM   1499  CZ3  TRP  185      24.526  63.509 103.645  1.00 21.31           HIGL
ATOM   1500  CH2  TRP  185      24.921  63.465 102.292  1.00 21.28           HIGL
ATOM   1501  C    TRP  185      28.510  63.126 106.489  1.00 18.87           HIGL
ATOM   1502  O    TRP  185      27.873  62.328 105.796  1.00 18.21           HIGL
ATOM   1503  N    ASP  186      29.835  63.074 106.606  1.00 18.26           HIGL
ATOM   1504  CA   ASP  186      30.595  62.042 105.918  1.00 18.41           HIGL
ATOM   1505  CB   ASP  186      32.094  62.185 106.181  1.00 19.07           HIGL
ATOM   1506  CG   ASP  186      32.662  63.492 105.644  1.00 19.86           HIGL
ATOM   1507  OD1  ASP  186      32.235  63.922 104.546  1.00 18.31           HIGL
ATOM   1508  OD2  ASP  186      33.539  64.082 106.321  1.00 20.67           HIGL
ATOM   1509  C    ASP  186      30.127  60.669 106.375  1.00 18.79           HIGL
ATOM   1510  O    ASP  186      30.057  59.738 105.569  1.00 19.44           HIGL
ATOM   1511  N    THR  187      29.804  60.541 107.662  1.00 18.54           HIGL
ATOM   1512  CA   THR  187      29.326  59.267 108.185  1.00 18.36           HIGL
ATOM   1513  CB   THR  187      29.144  59.303 109.717  1.00 18.81           HIGL
ATOM   1514  OG1  THR  187      30.334  59.779 110.359  1.00 17.18           HIGL
ATOM   1515  CG2  THR  187      28.841  57.898 110.229  1.00 17.29           HIGL
ATOM   1516  C    THR  187      27.955  58.970 107.554  1.00 18.81           HIGL
ATOM   1517  O    THR  187      27.749  57.924 106.953  1.00 18.82           HIGL
ATOM   1518  N    GLN  188      27.028  59.912 107.690  1.00 18.92           HIGL
ATOM   1519  CA   GLN  188      25.678  59.756 107.123  1.00 18.70           HIGL
ATOM   1520  CB   GLN  188      24.868  61.025 107.278  1.00 18.92           HIGL
ATOM   1521  CG   GLN  188      24.691  61.548 108.719  1.00 20.75           HIGL
ATOM   1522  CD   GLN  188      24.217  60.494 109.715  1.00 21.45           HIGL
ATOM   1523  OE1  GLN  188      23.340  59.658 109.425  1.00 21.55           HIGL
ATOM   1524  NE2  GLN  188      24.775  60.558 110.916  1.00 20.88           HIGL
ATOM   1525  C    GLN  188      25.693  59.419 105.628  1.00 18.27           HIGL
ATOM   1526  O    GLN  188      24.854  58.643 105.144  1.00 19.06           HIGL
ATOM   1527  N    ASN  189      26.652  60.019 104.912  1.00 18.01           HIGL
ATOM   1528  CA   ASN  189      26.837  59.855 103.466  1.00 17.83           HIGL
ATOM   1529  CB   ASN  189      27.713  61.007 102.897  1.00 18.12           HIGL
ATOM   1530  CG   ASN  189      27.816  60.975 101.367  1.00 18.97           HIGL
ATOM   1531  OD1  ASN  189      27.022  60.302 100.708  1.00 18.06           HIGL
ATOM   1532  ND2  ASN  189      28.776  61.718 100.800  1.00 19.12           HIGL
ATOM   1533  C    ASN  189      27.460  58.493 103.165  1.00 17.73           HIGL
ATOM   1534  O    ASN  189      26.935  57.760 102.331  1.00 17.69           HIGL
ATOM   1535  N    TRP  190      28.583  58.180 103.812  1.00 17.17           HIGL
ATOM   1536  CA   TRP  190      29.272  56.895 103.656  1.00 16.53           HIGL
ATOM   1537  CB   TRP  190      30.409  56.855 104.679  1.00 16.92           HIGL
ATOM   1538  CG   TRP  190      30.943  55.516 105.033  1.00 17.78           HIGL
ATOM   1539  CD2  TRP  190      30.714  54.794 106.253  1.00 17.06           HIGL
ATOM   1540  CE2  TRP  190      31.490  53.620 106.192  1.00 18.29           HIGL
ATOM   1541  CE3  TRP  190      29.931  55.028 107.392  1.00 17.68           HIGL
ATOM   1542  CD1  TRP  190      31.811  54.770 104.303  1.00 18.04           HIGL
ATOM   1543  NE1  TRP  190      32.150  53.630 104.991  1.00 18.09           HIGL
ATOM   1544  CZ2  TRP  190      31.511  52.675 107.230  1.00 18.43           HIGL
ATOM   1545  CZ3  TRP  190      29.951  54.083 108.431  1.00 18.02           HIGL
ATOM   1546  CH2  TRP  190      30.738  52.925 108.336  1.00 17.37           HIGL
ATOM   1547  C    TRP  190      28.307  55.715 103.874  1.00 15.60           HIGL
ATOM   1548  O    TRP  190      28.193  54.800 103.053  1.00 16.16           HIGL
ATOM   1549  N    TRP  191      27.609  55.744 104.997  1.00 14.48           HIGL
ATOM   1550  CA   TRP  191      26.674  54.686 105.327  1.00 14.21           HIGL
ATOM   1551  CB   TRP  191      26.028  54.956 106.681  1.00 12.41           HIGL
ATOM   1552  CG   TRP  191      25.437  53.729 107.273  1.00 11.51           HIGL
ATOM   1553  CD2  TRP  191      24.101  53.250 107.097  1.00 10.28           HIGL
ATOM   1554  CE2  TRP  191      23.990  52.044 107.827  1.00 10.64           HIGL
ATOM   1555  CE3  TRP  191      22.986  53.720 106.393  1.00  7.88           HIGL
ATOM   1556  CD1  TRP  191      26.068  52.820 108.074  1.00 12.10           HIGL
ATOM   1557  NE1  TRP  191      25.208  51.805 108.413  1.00 10.86           HIGL
ATOM   1558  CZ2  TRP  191      22.808  51.304 107.876  1.00  9.13           HIGL
ATOM   1559  CZ3  TRP  191      21.818  52.988 106.440  1.00  8.78           HIGL
```

Fig. 2 cont.

| | | | | | | | | | |
|---|---|---|---|---|---|---|---|---|---|
| ATOM | 1560 | CH2 | TRP | 191 | 21.735 | 51.790 | 107.178 | 1.00  9.52 | HIGL |
| ATOM | 1561 | C   | TRP | 191 | 25.566 | 54.471 | 104.292 | 1.00 14.99 | HIGL |
| ATOM | 1562 | O   | TRP | 191 | 25.485 | 53.409 | 103.664 | 1.00 14.62 | HIGL |
| ATOM | 1563 | N   | TYR | 192 | 24.703 | 55.468 | 104.121 | 1.00 15.56 | HIGL |
| ATOM | 1564 | CA  | TYR | 192 | 23.595 | 55.341 | 103.178 | 1.00 16.00 | HIGL |
| ATOM | 1565 | CB  | TYR | 192 | 22.739 | 56.615 | 103.195 | 1.00 15.03 | HIGL |
| ATOM | 1566 | CG  | TYR | 192 | 21.859 | 56.737 | 104.428 | 1.00 14.42 | HIGL |
| ATOM | 1567 | CD1 | TYR | 192 | 20.759 | 55.886 | 104.617 | 1.00 14.00 | HIGL |
| ATOM | 1568 | CE1 | TYR | 192 | 19.954 | 55.987 | 105.746 | 1.00 13.21 | HIGL |
| ATOM | 1569 | CD2 | TYR | 192 | 22.128 | 57.691 | 105.408 | 1.00 13.33 | HIGL |
| ATOM | 1570 | CE2 | TYR | 192 | 21.332 | 57.804 | 106.544 | 1.00 13.35 | HIGL |
| ATOM | 1571 | CZ  | TYR | 192 | 20.244 | 56.950 | 106.709 | 1.00 13.89 | HIGL |
| ATOM | 1572 | OH  | TYR | 192 | 19.442 | 57.073 | 107.826 | 1.00 12.40 | HIGL |
| ATOM | 1573 | C   | TYR | 192 | 24.052 | 55.015 | 101.760 | 1.00 17.04 | HIGL |
| ATOM | 1574 | O   | TYR | 192 | 23.433 | 54.199 | 101.071 | 1.00 17.52 | HIGL |
| ATOM | 1575 | N   | THR | 193 | 25.137 | 55.643 | 101.325 | 1.00 17.90 | HIGL |
| ATOM | 1576 | CA  | THR | 193 | 25.654 | 55.388 |  99.993 | 1.00 18.57 | HIGL |
| ATOM | 1577 | CB  | THR | 193 | 26.949 | 56.186 |  99.738 | 1.00 19.70 | HIGL |
| ATOM | 1578 | OG1 | THR | 193 | 26.634 | 57.582 |  99.645 | 1.00 20.25 | HIGL |
| ATOM | 1579 | CG2 | THR | 193 | 27.629 | 55.716 |  98.441 | 1.00 17.66 | HIGL |
| ATOM | 1580 | C   | THR | 193 | 25.950 | 53.897 |  99.842 | 1.00 18.55 | HIGL |
| ATOM | 1581 | O   | THR | 193 | 25.442 | 53.230 |  98.937 | 1.00 18.73 | HIGL |
| ATOM | 1582 | N   | ASN | 194 | 26.772 | 53.377 | 100.742 | 1.00 17.82 | HIGL |
| ATOM | 1583 | CA  | ASN | 194 | 27.127 | 51.972 | 100.693 | 1.00 18.02 | HIGL |
| ATOM | 1584 | CB  | ASN | 194 | 28.166 | 51.663 | 101.762 | 1.00 17.18 | HIGL |
| ATOM | 1585 | CG  | ASN | 194 | 29.546 | 52.148 | 101.381 | 1.00 16.79 | HIGL |
| ATOM | 1586 | OD1 | ASN | 194 | 30.135 | 51.668 | 100.411 | 1.00 17.28 | HIGL |
| ATOM | 1587 | ND2 | ASN | 194 | 30.073 | 53.102 | 102.137 | 1.00 16.49 | HIGL |
| ATOM | 1588 | C   | ASN | 194 | 25.934 | 51.031 | 100.830 | 1.00 18.35 | HIGL |
| ATOM | 1589 | O   | ASN | 194 | 25.860 | 50.029 | 100.123 | 1.00 20.21 | HIGL |
| ATOM | 1590 | N   | VAL | 195 | 25.003 | 51.345 | 101.724 | 1.00 17.31 | HIGL |
| ATOM | 1591 | CA  | VAL | 195 | 23.838 | 50.495 | 101.908 | 1.00 17.12 | HIGL |
| ATOM | 1592 | CB  | VAL | 195 | 23.052 | 50.887 | 103.185 | 1.00 17.17 | HIGL |
| ATOM | 1593 | CG1 | VAL | 195 | 21.789 | 50.062 | 103.290 | 1.00 16.39 | HIGL |
| ATOM | 1594 | CG2 | VAL | 195 | 23.906 | 50.675 | 104.411 | 1.00 16.35 | HIGL |
| ATOM | 1595 | C   | VAL | 195 | 22.882 | 50.550 | 100.711 | 1.00 17.84 | HIGL |
| ATOM | 1596 | O   | VAL | 195 | 22.414 | 49.514 | 100.223 | 1.00 17.57 | HIGL |
| ATOM | 1597 | N   | LEU | 196 | 22.591 | 51.755 | 100.234 | 1.00 17.80 | HIGL |
| ATOM | 1598 | CA  | LEU | 196 | 21.672 | 51.906 |  99.114 | 1.00 18.71 | HIGL |
| ATOM | 1599 | CB  | LEU | 196 | 21.164 | 53.346 |  99.049 | 1.00 19.05 | HIGL |
| ATOM | 1600 | CG  | LEU | 196 | 20.389 | 53.814 | 100.284 | 1.00 19.84 | HIGL |
| ATOM | 1601 | CD1 | LEU | 196 | 19.935 | 55.255 | 100.071 | 1.00 19.18 | HIGL |
| ATOM | 1602 | CD2 | LEU | 196 | 19.188 | 52.901 | 100.532 | 1.00 18.91 | HIGL |
| ATOM | 1603 | C   | LEU | 196 | 22.219 | 51.490 |  97.745 | 1.00 18.86 | HIGL |
| ATOM | 1604 | O   | LEU | 196 | 21.446 | 51.326 |  96.798 | 1.00 18.34 | HIGL |
| ATOM | 1605 | N   | SER | 197 | 23.537 | 51.316 |  97.631 | 1.00 18.55 | HIGL |
| ATOM | 1606 | CA  | SER | 197 | 24.126 | 50.913 |  96.355 | 1.00 18.26 | HIGL |
| ATOM | 1607 | CB  | SER | 197 | 25.561 | 51.426 |  96.232 | 1.00 17.73 | HIGL |
| ATOM | 1608 | OG  | SER | 197 | 26.436 | 50.722 |  97.091 | 1.00 18.32 | HIGL |
| ATOM | 1609 | C   | SER | 197 | 24.113 | 49.397 |  96.184 | 1.00 18.38 | HIGL |
| ATOM | 1610 | O   | SER | 197 | 24.322 | 48.884 |  95.088 | 1.00 18.24 | HIGL |
| ATOM | 1611 | N   | GLN | 198 | 23.859 | 48.677 |  97.269 | 1.00 18.80 | HIGL |
| ATOM | 1612 | CA  | GLN | 198 | 23.822 | 47.223 |  97.212 | 1.00 18.22 | HIGL |
| ATOM | 1613 | CB  | GLN | 198 | 23.686 | 46.653 |  98.620 | 1.00 19.28 | HIGL |
| ATOM | 1614 | CG  | GLN | 198 | 24.836 | 46.994 |  99.518 | 1.00 19.81 | HIGL |
| ATOM | 1615 | CD  | GLN | 198 | 26.161 | 46.734 |  98.847 | 1.00 21.32 | HIGL |
| ATOM | 1616 | OE1 | GLN | 198 | 26.353 | 45.693 |  98.210 | 1.00 21.68 | HIGL |
| ATOM | 1617 | NE2 | GLN | 198 | 27.091 | 47.679 |  98.984 | 1.00 21.99 | HIGL |
| ATOM | 1618 | C   | GLN | 198 | 22.682 | 46.707 |  96.340 | 1.00 17.65 | HIGL |
| ATOM | 1619 | O   | GLN | 198 | 22.877 | 45.821 |  95.514 | 1.00 17.50 | HIGL |
| ATOM | 1620 | N   | GLY | 199 | 21.486 | 47.253 |  96.536 | 1.00 17.03 | HIGL |
| ATOM | 1621 | CA  | GLY | 199 | 20.347 | 46.821 |  95.745 | 1.00 15.62 | HIGL |
| ATOM | 1622 | C   | GLY | 199 | 19.181 | 46.278 |  96.560 | 1.00 15.72 | HIGL |
| ATOM | 1623 | O   | GLY | 199 | 18.045 | 46.710 |  96.364 | 1.00 15.60 | HIGL |
| ATOM | 1624 | N   | PRO | 200 | 19.422 | 45.336 |  97.488 | 1.00 15.34 | HIGL |

Fig. 2 cont.

```
ATOM   1625  CD   PRO  200      20.704  44.672   97.783  1.00 14.88           HIGL
ATOM   1626  CA   PRO  200      18.350  44.764   98.306  1.00 14.92           HIGL
ATOM   1627  CB   PRO  200      19.104  43.814   99.225  1.00 16.05           HIGL
ATOM   1628  CG   PRO  200      20.245  43.367   98.366  1.00 14.92           HIGL
ATOM   1629  C    PRO  200      17.518  45.794   99.076  1.00 15.90           HIGL
ATOM   1630  O    PRO  200      16.288  45.699   99.112  1.00 14.94           HIGL
ATOM   1631  N    PHE  201      18.178  46.771   99.698  1.00 16.66           HIGL
ATOM   1632  CA   PHE  201      17.457  47.806  100.439  1.00 17.91           HIGL
ATOM   1633  CB   PHE  201      18.296  48.317  101.607  1.00 17.39           HIGL
ATOM   1634  CG   PHE  201      17.523  49.154  102.585  1.00 16.03           HIGL
ATOM   1635  CD1  PHE  201      16.320  48.696  103.108  1.00 15.39           HIGL
ATOM   1636  CD2  PHE  201      18.019  50.376  103.019  1.00 16.33           HIGL
ATOM   1637  CE1  PHE  201      15.627  49.436  104.049  1.00 16.04           HIGL
ATOM   1638  CE2  PHE  201      17.331  51.130  103.967  1.00 16.47           HIGL
ATOM   1639  CZ   PHE  201      16.133  50.658  104.484  1.00 16.02           HIGL
ATOM   1640  C    PHE  201      17.160  48.947   99.481  1.00 19.32           HIGL
ATOM   1641  O    PHE  201      18.052  49.707   99.113  1.00 19.83           HIGL
ATOM   1642  N    GLU  202      15.899  49.066   99.088  1.00 20.88           HIGL
ATOM   1643  CA   GLU  202      15.492  50.079   98.130  1.00 22.59           HIGL
ATOM   1644  CB   GLU  202      14.381  49.527   97.248  1.00 25.23           HIGL
ATOM   1645  CG   GLU  202      14.646  48.127   96.733  1.00 29.70           HIGL
ATOM   1646  CD   GLU  202      13.649  47.709   95.670  1.00 31.92           HIGL
ATOM   1647  OE1  GLU  202      13.642  48.342   94.588  1.00 33.85           HIGL
ATOM   1648  OE2  GLU  202      12.876  46.758   95.916  1.00 32.65           HIGL
ATOM   1649  C    GLU  202      15.033  51.394   98.724  1.00 22.89           HIGL
ATOM   1650  O    GLU  202      14.660  51.473   99.892  1.00 23.53           HIGL
ATOM   1651  N    MET  203      15.046  52.426   97.891  1.00 23.12           HIGL
ATOM   1652  CA   MET  203      14.624  53.748   98.309  1.00 23.40           HIGL
ATOM   1653  CB   MET  203      14.768  54.734   97.153  1.00 24.47           HIGL
ATOM   1654  CG   MET  203      16.202  55.007   96.767  1.00 27.52           HIGL
ATOM   1655  SD   MET  203      17.161  55.583   98.175  1.00 30.04           HIGL
ATOM   1656  CE   MET  203      16.411  57.199   98.411  1.00 29.30           HIGL
ATOM   1657  C    MET  203      13.185  53.748   98.808  1.00 22.78           HIGL
ATOM   1658  O    MET  203      12.835  54.522   99.696  1.00 22.95           HIGL
ATOM   1659  N    SER  204      12.352  52.878   98.251  1.00 21.87           HIGL
ATOM   1660  CA   SER  204      10.956  52.823   98.668  1.00 21.55           HIGL
ATOM   1661  CB   SER  204      10.077  52.307   97.521  1.00 21.02           HIGL
ATOM   1662  OG   SER  204      10.458  51.006   97.107  1.00 20.98           HIGL
ATOM   1663  C    SER  204      10.741  51.961   99.913  1.00 21.58           HIGL
ATOM   1664  O    SER  204       9.610  51.822  100.379  1.00 21.09           HIGL
ATOM   1665  N    ASP  205      11.821  51.388  100.448  1.00 20.89           HIGL
ATOM   1666  CA   ASP  205      11.723  50.545  101.640  1.00 20.32           HIGL
ATOM   1667  CB   ASP  205      12.882  49.539  101.716  1.00 20.48           HIGL
ATOM   1668  CG   ASP  205      12.750  48.411  100.710  1.00 19.95           HIGL
ATOM   1669  OD1  ASP  205      11.607  47.992  100.424  1.00 20.12           HIGL
ATOM   1670  OD2  ASP  205      13.792  47.933  100.220  1.00 19.93           HIGL
ATOM   1671  C    ASP  205      11.681  51.325  102.944  1.00 19.69           HIGL
ATOM   1672  O    ASP  205      11.284  50.780  103.971  1.00 19.83           HIGL
ATOM   1673  N    PHE  206      12.109  52.584  102.927  1.00 19.32           HIGL
ATOM   1674  CA   PHE  206      12.062  53.377  104.149  1.00 19.43           HIGL
ATOM   1675  CB   PHE  206      13.413  53.376  104.877  1.00 19.75           HIGL
ATOM   1676  CG   PHE  206      14.492  54.155  104.194  1.00 20.11           HIGL
ATOM   1677  CD1  PHE  206      14.975  53.768  102.951  1.00 20.98           HIGL
ATOM   1678  CD2  PHE  206      15.090  55.233  104.839  1.00 19.93           HIGL
ATOM   1679  CE1  PHE  206      16.048  54.442  102.364  1.00 20.58           HIGL
ATOM   1680  CE2  PHE  206      16.154  55.908  104.264  1.00 19.23           HIGL
ATOM   1681  CZ   PHE  206      16.636  55.509  103.025  1.00 19.95           HIGL
ATOM   1682  C    PHE  206      11.588  54.791  103.900  1.00 19.04           HIGL
ATOM   1683  O    PHE  206      11.597  55.267  102.773  1.00 19.32           HIGL
ATOM   1684  N    ASP  207      11.173  55.462  104.965  1.00 19.22           HIGL
ATOM   1685  CA   ASP  207      10.636  56.810  104.841  1.00 19.23           HIGL
ATOM   1686  CB   ASP  207       9.175  56.802  105.286  1.00 19.16           HIGL
ATOM   1687  CG   ASP  207       8.407  55.625  104.718  1.00 19.38           HIGL
ATOM   1688  OD1  ASP  207       8.277  55.543  103.480  1.00 20.06           HIGL
ATOM   1689  OD2  ASP  207       7.942  54.778  105.507  1.00 18.36           HIGL
```

Fig. 2 cont.

```
ATOM   1690  C    ASP   207      11.381  57.871 105.629  1.00 18.86           HIGL
ATOM   1691  O    ASP   207      11.381  59.045 105.260  1.00 19.26           HIGL
ATOM   1692  N    MET   208      12.015  57.466 106.716  1.00 18.21           HIGL
ATOM   1693  CA   MET   208      12.714  58.433 107.540  1.00 18.11           HIGL
ATOM   1694  CB   MET   208      12.006  58.596 108.894  1.00 18.41           HIGL
ATOM   1695  CG   MET   208      10.534  58.987 108.820  1.00 20.52           HIGL
ATOM   1696  SD   MET   208       9.808  59.310 110.452  1.00 22.01           HIGL
ATOM   1697  CE   MET   208      10.379  60.977 110.731  1.00 20.87           HIGL
ATOM   1698  C    MET   208      14.161  58.083 107.804  1.00 17.69           HIGL
ATOM   1699  O    MET   208      14.579  56.928 107.707  1.00 17.61           HIGL
ATOM   1700  N    MET   209      14.918  59.119 108.129  1.00 16.92           HIGL
ATOM   1701  CA   MET   209      16.308  58.994 108.488  1.00 16.07           HIGL
ATOM   1702  CB   MET   209      17.213  59.645 107.443  1.00 16.00           HIGL
ATOM   1703  CG   MET   209      17.373  58.828 106.170  1.00 16.81           HIGL
ATOM   1704  SD   MET   209      18.554  59.575 105.009  1.00 19.85           HIGL
ATOM   1705  CE   MET   209      18.496  58.407 103.621  1.00 17.63           HIGL
ATOM   1706  C    MET   209      16.374  59.747 109.809  1.00 16.16           HIGL
ATOM   1707  O    MET   209      16.174  60.969 109.850  1.00 15.45           HIGL
ATOM   1708  N    GLY   210      16.600  59.001 110.891  1.00 15.65           HIGL
ATOM   1709  CA   GLY   210      16.695  59.603 112.210  1.00 14.42           HIGL
ATOM   1710  C    GLY   210      18.150  59.686 112.629  1.00 14.08           HIGL
ATOM   1711  O    GLY   210      18.961  58.883 112.175  1.00 13.68           HIGL
ATOM   1712  N    VAL   211      18.490  60.651 113.484  1.00 13.61           HIGL
ATOM   1713  CA   VAL   211      19.869  60.802 113.936  1.00 13.15           HIGL
ATOM   1714  CB   VAL   211      20.627  61.892 113.141  1.00 12.33           HIGL
ATOM   1715  CG1  VAL   211      20.537  61.611 111.663  1.00 13.18           HIGL
ATOM   1716  CG2  VAL   211      20.067  63.271 113.465  1.00 11.20           HIGL
ATOM   1717  C    VAL   211      19.984  61.175 115.400  1.00 13.77           HIGL
ATOM   1718  O    VAL   211      19.118  61.837 115.958  1.00 13.69           HIGL
ATOM   1719  N    SER   212      21.069  60.741 116.022  1.00 15.09           HIGL
ATOM   1720  CA   SER   212      21.313  61.079 117.411  1.00 15.93           HIGL
ATOM   1721  CB   SER   212      22.016  59.929 118.130  1.00 16.46           HIGL
ATOM   1722  OG   SER   212      21.185  58.781 118.176  1.00 17.21           HIGL
ATOM   1723  C    SER   212      22.208  62.315 117.376  1.00 16.32           HIGL
ATOM   1724  O    SER   212      23.149  62.395 116.582  1.00 16.25           HIGL
ATOM   1725  N    PHE   213      21.890  63.289 118.214  1.00 15.47           HIGL
ATOM   1726  CA   PHE   213      22.666  64.512 118.267  1.00 15.45           HIGL
ATOM   1727  CB   PHE   213      21.923  65.634 117.528  1.00 15.73           HIGL
ATOM   1728  CG   PHE   213      22.673  66.936 117.484  1.00 16.40           HIGL
ATOM   1729  CD1  PHE   213      23.883  67.036 116.799  1.00 16.45           HIGL
ATOM   1730  CD2  PHE   213      22.183  68.057 118.146  1.00 16.56           HIGL
ATOM   1731  CE1  PHE   213      24.596  68.231 116.777  1.00 15.36           HIGL
ATOM   1732  CE2  PHE   213      22.889  69.257 118.130  1.00 16.74           HIGL
ATOM   1733  CZ   PHE   213      24.100  69.340 117.443  1.00 16.06           HIGL
ATOM   1734  C    PHE   213      22.849  64.850 119.738  1.00 14.96           HIGL
ATOM   1735  O    PHE   213      21.888  65.175 120.436  1.00 15.30           HIGL
ATOM   1736  N    TYR   214      24.085  64.742 120.208  1.00 14.20           HIGL
ATOM   1737  CA   TYR   214      24.420  65.016 121.600  1.00 13.58           HIGL
ATOM   1738  CB   TYR   214      24.875  63.736 122.298  1.00 12.69           HIGL
ATOM   1739  CG   TYR   214      23.775  62.742 122.558  1.00 11.90           HIGL
ATOM   1740  CD1  TYR   214      22.902  62.906 123.631  1.00 11.71           HIGL
ATOM   1741  CE1  TYR   214      21.885  61.989 123.874  1.00 11.65           HIGL
ATOM   1742  CD2  TYR   214      23.602  61.635 121.731  1.00 10.99           HIGL
ATOM   1743  CE2  TYR   214      22.591  60.717 121.962  1.00 11.61           HIGL
ATOM   1744  CZ   TYR   214      21.735  60.899 123.035  1.00 11.76           HIGL
ATOM   1745  OH   TYR   214      20.722  59.997 123.259  1.00 12.70           HIGL
ATOM   1746  C    TYR   214      25.541  66.035 121.660  1.00 14.26           HIGL
ATOM   1747  O    TYR   214      26.346  66.141 120.742  1.00 15.11           HIGL
ATOM   1748  N    PRO   215      25.619  66.794 122.755  1.00 14.63           HIGL
ATOM   1749  CD   PRO   215      24.581  67.036 123.775  1.00 14.17           HIGL
ATOM   1750  CA   PRO   215      26.682  67.790 122.847  1.00 14.95           HIGL
ATOM   1751  CB   PRO   215      25.990  68.930 123.572  1.00 14.94           HIGL
ATOM   1752  CG   PRO   215      25.175  68.176 124.596  1.00 14.41           HIGL
ATOM   1753  C    PRO   215      27.924  67.322 123.598  1.00 15.93           HIGL
ATOM   1754  O    PRO   215      28.999  67.898 123.437  1.00 16.94           HIGL
```

Fig. 2 cont.

```
ATOM   1755  N    PHE   216      27.778  66.276 124.405  1.00 16.00           HIGL
ATOM   1756  CA   PHE   216      28.878  65.791 125.231  1.00 16.24           HIGL
ATOM   1757  CB   PHE   216      28.350  65.520 126.644  1.00 16.24           HIGL
ATOM   1758  CG   PHE   216      27.018  64.792 126.677  1.00 16.08           HIGL
ATOM   1759  CD1  PHE   216      26.861  63.555 126.055  1.00 15.04           HIGL
ATOM   1760  CD2  PHE   216      25.924  65.347 127.343  1.00 15.16           HIGL
ATOM   1761  CE1  PHE   216      25.638  62.889 126.095  1.00 15.26           HIGL
ATOM   1762  CE2  PHE   216      24.703  64.686 127.386  1.00 14.85           HIGL
ATOM   1763  CZ   PHE   216      24.560  63.453 126.759  1.00 14.72           HIGL
ATOM   1764  C    PHE   216      29.709  64.595 124.763  1.00 16.64           HIGL
ATOM   1765  O    PHE   216      30.291  63.882 125.580  1.00 16.43           HIGL
ATOM   1766  N    TYR   217      29.789  64.377 123.459  1.00 17.14           HIGL
ATOM   1767  CA   TYR   217      30.582  63.260 122.947  1.00 17.62           HIGL
ATOM   1768  CB   TYR   217      29.675  62.193 122.323  1.00 16.27           HIGL
ATOM   1769  CG   TYR   217      28.847  61.399 123.315  1.00 16.34           HIGL
ATOM   1770  CD1  TYR   217      29.440  60.785 124.421  1.00 16.29           HIGL
ATOM   1771  CE1  TYR   217      28.687  60.024 125.312  1.00 15.97           HIGL
ATOM   1772  CD2  TYR   217      27.477  61.232 123.131  1.00 15.38           HIGL
ATOM   1773  CE2  TYR   217      26.717  60.477 124.016  1.00 14.99           HIGL
ATOM   1774  CZ   TYR   217      27.324  59.875 125.102  1.00 16.23           HIGL
ATOM   1775  OH   TYR   217      26.566  59.120 125.977  1.00 17.30           HIGL
ATOM   1776  C    TYR   217      31.605  63.723 121.909  1.00 18.43           HIGL
ATOM   1777  O    TYR   217      32.308  62.908 121.317  1.00 19.53           HIGL
ATOM   1778  N    SER   218      31.693  65.034 121.703  1.00 18.33           HIGL
ATOM   1779  CA   SER   218      32.616  65.598 120.724  1.00 17.79           HIGL
ATOM   1780  CB   SER   218      32.501  64.839 119.403  1.00 17.69           HIGL
ATOM   1781  OG   SER   218      33.128  65.542 118.347  1.00 18.59           HIGL
ATOM   1782  C    SER   218      32.298  67.070 120.485  1.00 17.69           HIGL
ATOM   1783  O    SER   218      31.141  67.438 120.306  1.00 18.71           HIGL
ATOM   1784  N    ALA   219      33.321  67.912 120.476  1.00 17.22           HIGL
ATOM   1785  CA   ALA   219      33.104  69.337 120.252  1.00 17.23           HIGL
ATOM   1786  CB   ALA   219      34.382  70.118 120.554  1.00 16.44           HIGL
ATOM   1787  C    ALA   219      32.661  69.589 118.816  1.00 16.60           HIGL
ATOM   1788  O    ALA   219      32.258  70.696 118.467  1.00 17.34           HIGL
ATOM   1789  N    SER   220      32.730  68.550 117.991  1.00 16.51           HIGL
ATOM   1790  CA   SER   220      32.355  68.641 116.581  1.00 16.08           HIGL
ATOM   1791  CB   SER   220      32.954  67.466 115.809  1.00 15.86           HIGL
ATOM   1792  OG   SER   220      34.364  67.460 115.917  1.00 16.86           HIGL
ATOM   1793  C    SER   220      30.857  68.682 116.317  1.00 15.46           HIGL
ATOM   1794  O    SER   220      30.432  69.049 115.229  1.00 14.91           HIGL
ATOM   1795  N    ALA   221      30.061  68.300 117.309  1.00 15.99           HIGL
ATOM   1796  CA   ALA   221      28.606  68.279 117.164  1.00 16.78           HIGL
ATOM   1797  CB   ALA   221      27.995  67.427 118.271  1.00 16.23           HIGL
ATOM   1798  C    ALA   221      27.969  69.673 117.164  1.00 17.33           HIGL
ATOM   1799  O    ALA   221      27.074  69.959 117.963  1.00 17.73           HIGL
ATOM   1800  N    THR   222      28.422  70.534 116.260  1.00 17.34           HIGL
ATOM   1801  CA   THR   222      27.889  71.888 116.168  1.00 17.44           HIGL
ATOM   1802  CB   THR   222      28.805  72.788 115.326  1.00 16.76           HIGL
ATOM   1803  OG1  THR   222      28.859  72.290 113.988  1.00 16.54           HIGL
ATOM   1804  CG2  THR   222      30.211  72.801 115.899  1.00 17.46           HIGL
ATOM   1805  C    THR   222      26.505  71.891 115.531  1.00 18.33           HIGL
ATOM   1806  O    THR   222      26.189  71.044 114.692  1.00 19.58           HIGL
ATOM   1807  N    LEU   223      25.675  72.842 115.933  1.00 18.21           HIGL
ATOM   1808  CA   LEU   223      24.338  72.949 115.374  1.00 18.34           HIGL
ATOM   1809  CB   LEU   223      23.611  74.143 115.991  1.00 18.27           HIGL
ATOM   1810  CG   LEU   223      23.370  74.045 117.500  1.00 19.89           HIGL
ATOM   1811  CD1  LEU   223      22.888  75.388 118.034  1.00 19.53           HIGL
ATOM   1812  CD2  LEU   223      22.340  72.943 117.786  1.00 19.06           HIGL
ATOM   1813  C    LEU   223      24.437  73.122 113.860  1.00 18.82           HIGL
ATOM   1814  O    LEU   223      23.605  72.608 113.120  1.00 20.15           HIGL
ATOM   1815  N    ASP   224      25.457  73.846 113.406  1.00 18.59           HIGL
ATOM   1816  CA   ASP   224      25.669  74.086 111.982  1.00 19.10           HIGL
ATOM   1817  CB   ASP   224      26.858  75.026 111.769  1.00 18.84           HIGL
ATOM   1818  CG   ASP   224      26.468  76.494 111.816  1.00 18.91           HIGL
ATOM   1819  OD1  ASP   224      25.286  76.812 112.069  1.00 19.14           HIGL
```

Fig. 2 cont.

| | | | | | | | | | |
|---|---|---|---|---|---|---|---|---|---|
| ATOM | 1820 | OD2 | ASP | 224 | 27.355 | 77.341 | 111.593 | 1.00 19.90 | HIGL |
| ATOM | 1821 | C | ASP | 224 | 25.915 | 72.793 | 111.214 | 1.00 19.58 | HIGL |
| ATOM | 1822 | O | ASP | 224 | 25.341 | 72.583 | 110.146 | 1.00 20.23 | HIGL |
| ATOM | 1823 | N | SER | 225 | 26.785 | 71.939 | 111.750 | 1.00 19.67 | HIGL |
| ATOM | 1824 | CA | SER | 225 | 27.095 | 70.664 | 111.112 | 1.00 19.06 | HIGL |
| ATOM | 1825 | CB | SER | 225 | 28.155 | 69.908 | 111.907 | 1.00 18.84 | HIGL |
| ATOM | 1826 | OG | SER | 225 | 29.403 | 70.567 | 111.840 | 1.00 18.91 | HIGL |
| ATOM | 1827 | C | SER | 225 | 25.838 | 69.811 | 110.997 | 1.00 19.40 | HIGL |
| ATOM | 1828 | O | SER | 225 | 25.601 | 69.186 | 109.968 | 1.00 19.64 | HIGL |
| ATOM | 1829 | N | LEU | 226 | 25.039 | 69.774 | 112.058 | 1.00 19.24 | HIGL |
| ATOM | 1830 | CA | LEU | 226 | 23.799 | 69.009 | 112.026 | 1.00 19.90 | HIGL |
| ATOM | 1831 | CB | LEU | 226 | 23.069 | 69.103 | 113.372 | 1.00 18.41 | HIGL |
| ATOM | 1832 | CG | LEU | 226 | 21.655 | 68.517 | 113.419 | 1.00 18.06 | HIGL |
| ATOM | 1833 | CD1 | LEU | 226 | 21.698 | 67.027 | 113.124 | 1.00 17.29 | HIGL |
| ATOM | 1834 | CD2 | LEU | 226 | 21.042 | 68.768 | 114.786 | 1.00 18.51 | HIGL |
| ATOM | 1835 | C | LEU | 226 | 22.943 | 69.628 | 110.925 | 1.00 20.05 | HIGL |
| ATOM | 1836 | O | LEU | 226 | 22.369 | 68.932 | 110.086 | 1.00 19.89 | HIGL |
| ATOM | 1837 | N | ARG | 227 | 22.883 | 70.951 | 110.941 | 1.00 20.56 | HIGL |
| ATOM | 1838 | CA | ARG | 227 | 22.127 | 71.717 | 109.965 | 1.00 22.15 | HIGL |
| ATOM | 1839 | CB | ARG | 227 | 22.374 | 73.203 | 110.200 | 1.00 23.23 | HIGL |
| ATOM | 1840 | CG | ARG | 227 | 21.847 | 74.113 | 109.125 | 1.00 23.67 | HIGL |
| ATOM | 1841 | CD | ARG | 227 | 20.585 | 74.801 | 109.561 | 1.00 25.35 | HIGL |
| ATOM | 1842 | NE | ARG | 227 | 20.264 | 75.881 | 108.636 | 1.00 27.51 | HIGL |
| ATOM | 1843 | CZ | ARG | 227 | 20.963 | 77.007 | 108.534 | 1.00 27.97 | HIGL |
| ATOM | 1844 | NH1 | ARG | 227 | 22.025 | 77.213 | 109.308 | 1.00 27.24 | HIGL |
| ATOM | 1845 | NH2 | ARG | 227 | 20.609 | 77.919 | 107.639 | 1.00 28.04 | HIGL |
| ATOM | 1846 | C | ARG | 227 | 22.532 | 71.349 | 108.541 | 1.00 22.77 | HIGL |
| ATOM | 1847 | O | ARG | 227 | 21.682 | 71.091 | 107.685 | 1.00 23.17 | HIGL |
| ATOM | 1848 | N | ARG | 228 | 23.835 | 71.337 | 108.292 | 1.00 22.62 | HIGL |
| ATOM | 1849 | CA | ARG | 228 | 24.351 | 71.005 | 106.974 | 1.00 23.23 | HIGL |
| ATOM | 1850 | CB | ARG | 228 | 25.854 | 71.275 | 106.907 | 1.00 25.19 | HIGL |
| ATOM | 1851 | CG | ARG | 228 | 26.497 | 70.808 | 105.611 | 1.00 27.85 | HIGL |
| ATOM | 1852 | CD | ARG | 228 | 27.951 | 71.218 | 105.576 | 1.00 31.64 | HIGL |
| ATOM | 1853 | NE | ARG | 228 | 28.217 | 72.426 | 104.784 | 1.00 34.16 | HIGL |
| ATOM | 1854 | CZ | ARG | 228 | 27.482 | 73.539 | 104.787 | 1.00 34.92 | HIGL |
| ATOM | 1855 | NH1 | ARG | 228 | 26.385 | 73.644 | 105.537 | 1.00 34.00 | HIGL |
| ATOM | 1856 | NH2 | ARG | 228 | 27.869 | 74.572 | 104.049 | 1.00 34.79 | HIGL |
| ATOM | 1857 | C | ARG | 228 | 24.106 | 69.553 | 106.623 | 1.00 21.71 | HIGL |
| ATOM | 1858 | O | ARG | 228 | 23.697 | 69.233 | 105.511 | 1.00 21.40 | HIGL |
| ATOM | 1859 | N | SER | 229 | 24.372 | 68.677 | 107.583 | 1.00 20.74 | HIGL |
| ATOM | 1860 | CA | SER | 229 | 24.209 | 67.248 | 107.385 | 1.00 19.19 | HIGL |
| ATOM | 1861 | CB | SER | 229 | 24.596 | 66.499 | 108.657 | 1.00 17.46 | HIGL |
| ATOM | 1862 | OG | SER | 229 | 24.667 | 65.112 | 108.415 | 1.00 16.03 | HIGL |
| ATOM | 1863 | C | SER | 229 | 22.778 | 66.920 | 106.985 | 1.00 19.19 | HIGL |
| ATOM | 1864 | O | SER | 229 | 22.551 | 66.215 | 106.001 | 1.00 19.76 | HIGL |
| ATOM | 1865 | N | LEU | 230 | 21.816 | 67.443 | 107.738 | 1.00 18.51 | HIGL |
| ATOM | 1866 | CA | LEU | 230 | 20.414 | 67.200 | 107.437 | 1.00 18.83 | HIGL |
| ATOM | 1867 | CB | LEU | 230 | 19.513 | 67.904 | 108.459 | 1.00 18.57 | HIGL |
| ATOM | 1868 | CG | LEU | 230 | 19.748 | 67.471 | 109.906 | 1.00 18.99 | HIGL |
| ATOM | 1869 | CD1 | LEU | 230 | 18.765 | 68.159 | 110.830 | 1.00 18.90 | HIGL |
| ATOM | 1870 | CD2 | LEU | 230 | 19.611 | 65.966 | 110.011 | 1.00 19.09 | HIGL |
| ATOM | 1871 | C | LEU | 230 | 20.072 | 67.653 | 106.025 | 1.00 18.43 | HIGL |
| ATOM | 1872 | O | LEU | 230 | 19.440 | 66.944 | 105.261 | 1.00 18.80 | HIGL |
| ATOM | 1873 | N | ASN | 231 | 20.492 | 68.887 | 105.678 | 1.00 17.99 | HIGL |
| ATOM | 1874 | CA | ASN | 231 | 20.222 | 69.418 | 104.348 | 1.00 18.50 | HIGL |
| ATOM | 1875 | CB | ASN | 231 | 20.775 | 70.832 | 104.203 | 1.00 20.27 | HIGL |
| ATOM | 1876 | CG | ASN | 231 | 19.831 | 71.884 | 104.755 | 1.00 21.88 | HIGL |
| ATOM | 1877 | OD1 | ASN | 231 | 18.703 | 72.029 | 104.276 | 1.00 23.81 | HIGL |
| ATOM | 1878 | ND2 | ASN | 231 | 20.284 | 72.624 | 105.763 | 1.00 21.50 | HIGL |
| ATOM | 1879 | C | ASN | 231 | 20.815 | 68.529 | 103.271 | 1.00 18.28 | HIGL |
| ATOM | 1880 | O | ASN | 231 | 20.164 | 68.262 | 102.256 | 1.00 17.76 | HIGL |
| ATOM | 1881 | N | ASN | 232 | 22.042 | 68.064 | 103.497 | 1.00 17.66 | HIGL |
| ATOM | 1882 | CA | ASN | 232 | 22.703 | 67.190 | 102.534 | 1.00 17.99 | HIGL |
| ATOM | 1883 | CB | ASN | 232 | 24.141 | 66.893 | 102.963 | 1.00 17.29 | HIGL |
| ATOM | 1884 | CG | ASN | 232 | 25.037 | 68.116 | 102.915 | 1.00 16.38 | HIGL |

Fig. 2 cont.

```
ATOM   1885 OD1  ASN    232      24.686  69.141 102.334  1.00 15.50      HIGL
ATOM   1886 ND2  ASN    232      26.213  68.005 103.521  1.00 16.64      HIGL
ATOM   1887 C    ASN    232      21.948  65.872 102.375  1.00 18.25      HIGL
ATOM   1888 O    ASN    232      21.748  65.387 101.259  1.00 17.98      HIGL
ATOM   1889 N    MET    233      21.536  65.298 103.501  1.00 18.52      HIGL
ATOM   1890 CA   MET    233      20.805  64.033 103.507  1.00 18.43      HIGL
ATOM   1891 CB   MET    233      20.538  63.589 104.951  1.00 18.18      HIGL
ATOM   1892 CG   MET    233      21.795  63.269 105.754  1.00 18.25      HIGL
ATOM   1893 SD   MET    233      21.474  63.063 107.531  1.00 19.43      HIGL
ATOM   1894 CE   MET    233      20.199  61.766 107.504  1.00 17.54      HIGL
ATOM   1895 C    MET    233      19.485  64.177 102.758  1.00 18.12      HIGL
ATOM   1896 O    MET    233      19.183  63.394 101.851  1.00 18.23      HIGL
ATOM   1897 N    VAL    234      18.707  65.186 103.146  1.00 17.24      HIGL
ATOM   1898 CA   VAL    234      17.411  65.455 102.530  1.00 16.91      HIGL
ATOM   1899 CB   VAL    234      16.744  66.687 103.179  1.00 15.88      HIGL
ATOM   1900 CG1  VAL    234      15.486  67.056 102.420  1.00 15.35      HIGL
ATOM   1901 CG2  VAL    234      16.413  66.390 104.638  1.00 15.47      HIGL
ATOM   1902 C    VAL    234      17.502  65.678 101.017  1.00 16.63      HIGL
ATOM   1903 O    VAL    234      16.784  65.045 100.245  1.00 16.27      HIGL
ATOM   1904 N    SER    235      18.391  66.575 100.603  1.00 16.80      HIGL
ATOM   1905 CA   SER    235      18.573  66.882  99.190  1.00 17.13      HIGL
ATOM   1906 CB   SER    235      19.578  68.023  99.024  1.00 17.78      HIGL
ATOM   1907 OG   SER    235      19.784  68.317  97.656  1.00 17.56      HIGL
ATOM   1908 C    SER    235      19.049  65.677  98.384  1.00 16.92      HIGL
ATOM   1909 O    SER    235      18.768  65.562  97.190  1.00 17.15      HIGL
ATOM   1910 N    ARG    236      19.759  64.774  99.045  1.00 16.40      HIGL
ATOM   1911 CA   ARG    236      20.290  63.595  98.384  1.00 16.55      HIGL
ATOM   1912 CB   ARG    236      21.568  63.161  99.084  1.00 17.11      HIGL
ATOM   1913 CG   ARG    236      22.156  61.872  98.562  1.00 18.73      HIGL
ATOM   1914 CD   ARG    236      22.995  62.074  97.321  1.00 19.62      HIGL
ATOM   1915 NE   ARG    236      23.973  60.997  97.231  1.00 24.11      HIGL
ATOM   1916 CZ   ARG    236      23.732  59.794  96.710  1.00 25.92      HIGL
ATOM   1917 NH1  ARG    236      22.532  59.505  96.205  1.00 24.62      HIGL
ATOM   1918 NH2  ARG    236      24.691  58.867  96.725  1.00 25.67      HIGL
ATOM   1919 C    ARG    236      19.343  62.400  98.298  1.00 16.75      HIGL
ATOM   1920 O    ARG    236      19.259  61.740  97.259  1.00 15.62      HIGL
ATOM   1921 N    TRP    237      18.637  62.111  99.385  1.00 16.82      HIGL
ATOM   1922 CA   TRP    237      17.745  60.961  99.390  1.00 16.41      HIGL
ATOM   1923 CB   TRP    237      18.224  59.966 100.453  1.00 16.05      HIGL
ATOM   1924 CG   TRP    237      19.505  59.294 100.040  1.00 14.89      HIGL
ATOM   1925 CD2  TRP    237      20.817  59.526 100.571  1.00 14.04      HIGL
ATOM   1926 CE2  TRP    237      21.717  58.738  99.817  1.00 14.30      HIGL
ATOM   1927 CE3  TRP    237      21.322  60.327 101.604  1.00 13.86      HIGL
ATOM   1928 CD1  TRP    237      19.659  58.398  99.023  1.00 15.03      HIGL
ATOM   1929 NE1  TRP    237      20.983  58.060  98.882  1.00 14.90      HIGL
ATOM   1930 CZ2  TRP    237      23.097  58.727 100.061  1.00 13.70      HIGL
ATOM   1931 CZ3  TRP    237      22.695  60.319 101.847  1.00 13.61      HIGL
ATOM   1932 CH2  TRP    237      23.566  59.522 101.074  1.00 14.26      HIGL
ATOM   1933 C    TRP    237      16.266  61.281  99.557  1.00 16.86      HIGL
ATOM   1934 O    TRP    237      15.430  60.383  99.522  1.00 18.12      HIGL
ATOM   1935 N    GLY    238      15.953  62.562  99.732  1.00 16.74      HIGL
ATOM   1936 CA   GLY    238      14.574  62.995  99.869  1.00 16.56      HIGL
ATOM   1937 C    GLY    238      13.714  62.388 100.966  1.00 17.47      HIGL
ATOM   1938 O    GLY    238      12.486  62.346 100.836  1.00 17.51      HIGL
ATOM   1939 N    LYS    239      14.330  61.933 102.053  1.00 16.96      HIGL
ATOM   1940 CA   LYS    239      13.564  61.339 103.146  1.00 16.74      HIGL
ATOM   1941 CB   LYS    239      14.327  60.152 103.724  1.00 16.66      HIGL
ATOM   1942 CG   LYS    239      14.606  59.053 102.730  1.00 17.05      HIGL
ATOM   1943 CD   LYS    239      13.312  58.511 102.175  1.00 15.57      HIGL
ATOM   1944 CE   LYS    239      13.561  57.342 101.262  1.00 14.83      HIGL
ATOM   1945 NZ   LYS    239      12.275  56.925 100.661  1.00 14.06      HIGL
ATOM   1946 C    LYS    239      13.302  62.344 104.261  1.00 16.96      HIGL
ATOM   1947 O    LYS    239      14.036  63.323 104.398  1.00 17.61      HIGL
ATOM   1948 N    GLU    240      12.257  62.118 105.056  1.00 17.26      HIGL
ATOM   1949 CA   GLU    240      11.985  63.016 106.181  1.00 16.82      HIGL
```

Fig. 2 cont.

| ATOM | 1950 | CB  | GLU | 240 | 10.615 | 62.743 | 106.808 | 1.00 | 17.65 | HIGL |
|------|------|-----|-----|-----|--------|--------|---------|------|-------|------|
| ATOM | 1951 | CG  | GLU | 240 | 9.430  | 63.085 | 105.923 | 1.00 | 18.86 | HIGL |
| ATOM | 1952 | CD  | GLU | 240 | 8.116  | 63.080 | 106.690 | 1.00 | 20.65 | HIGL |
| ATOM | 1953 | OE1 | GLU | 240 | 7.818  | 62.067 | 107.353 | 1.00 | 21.31 | HIGL |
| ATOM | 1954 | OE2 | GLU | 240 | 7.381  | 64.091 | 106.634 | 1.00 | 21.43 | HIGL |
| ATOM | 1955 | C   | GLU | 240 | 13.088 | 62.751 | 107.209 | 1.00 | 16.31 | HIGL |
| ATOM | 1956 | O   | GLU | 240 | 13.562 | 61.621 | 107.360 | 1.00 | 15.76 | HIGL |
| ATOM | 1957 | N   | VAL | 241 | 13.493 | 63.793 | 107.917 | 1.00 | 15.69 | HIGL |
| ATOM | 1958 | CA  | VAL | 241 | 14.571 | 63.666 | 108.883 | 1.00 | 15.54 | HIGL |
| ATOM | 1959 | CB  | VAL | 241 | 15.754 | 64.547 | 108.432 | 1.00 | 14.72 | HIGL |
| ATOM | 1960 | CG1 | VAL | 241 | 16.789 | 64.623 | 109.501 | 1.00 | 17.13 | HIGL |
| ATOM | 1961 | CG2 | VAL | 241 | 16.361 | 63.974 | 107.178 | 1.00 | 15.36 | HIGL |
| ATOM | 1962 | C   | VAL | 241 | 14.149 | 64.045 | 110.299 | 1.00 | 15.60 | HIGL |
| ATOM | 1963 | O   | VAL | 241 | 13.161 | 64.758 | 110.495 | 1.00 | 16.76 | HIGL |
| ATOM | 1964 | N   | ALA | 242 | 14.900 | 63.573 | 111.290 | 1.00 | 14.40 | HIGL |
| ATOM | 1965 | CA  | ALA | 242 | 14.577 | 63.888 | 112.673 | 1.00 | 13.72 | HIGL |
| ATOM | 1966 | CB  | ALA | 242 | 13.286 | 63.177 | 113.082 | 1.00 | 12.95 | HIGL |
| ATOM | 1967 | C   | ALA | 242 | 15.681 | 63.519 | 113.645 | 1.00 | 13.47 | HIGL |
| ATOM | 1968 | O   | ALA | 242 | 16.428 | 62.561 | 113.429 | 1.00 | 13.51 | HIGL |
| ATOM | 1969 | N   | VAL | 243 | 15.791 | 64.303 | 114.711 | 1.00 | 13.04 | HIGL |
| ATOM | 1970 | CA  | VAL | 243 | 16.760 | 64.023 | 115.758 | 1.00 | 13.08 | HIGL |
| ATOM | 1971 | CB  | VAL | 243 | 17.192 | 65.294 | 116.497 | 1.00 | 12.64 | HIGL |
| ATOM | 1972 | CG1 | VAL | 243 | 17.918 | 64.924 | 117.771 | 1.00 | 12.23 | HIGL |
| ATOM | 1973 | CG2 | VAL | 243 | 18.088 | 66.125 | 115.604 | 1.00 | 12.08 | HIGL |
| ATOM | 1974 | C   | VAL | 243 | 15.964 | 63.139 | 116.701 | 1.00 | 13.56 | HIGL |
| ATOM | 1975 | O   | VAL | 243 | 15.014 | 63.593 | 117.346 | 1.00 | 13.37 | HIGL |
| ATOM | 1976 | N   | VAL | 244 | 16.328 | 61.866 | 116.754 | 1.00 | 14.00 | HIGL |
| ATOM | 1977 | CA  | VAL | 244 | 15.608 | 60.927 | 117.593 | 1.00 | 14.42 | HIGL |
| ATOM | 1978 | CB  | VAL | 244 | 15.476 | 59.569 | 116.877 | 1.00 | 13.73 | HIGL |
| ATOM | 1979 | CG1 | VAL | 244 | 14.782 | 59.774 | 115.548 | 1.00 | 13.75 | HIGL |
| ATOM | 1980 | CG2 | VAL | 244 | 16.831 | 58.955 | 116.653 | 1.00 | 12.09 | HIGL |
| ATOM | 1981 | C   | VAL | 244 | 16.242 | 60.742 | 118.965 | 1.00 | 15.18 | HIGL |
| ATOM | 1982 | O   | VAL | 244 | 15.748 | 59.965 | 119.783 | 1.00 | 14.93 | HIGL |
| ATOM | 1983 | N   | GLU | 245 | 17.320 | 61.479 | 119.218 | 1.00 | 15.57 | HIGL |
| ATOM | 1984 | CA  | GLU | 245 | 18.023 | 61.397 | 120.490 | 1.00 | 16.66 | HIGL |
| ATOM | 1985 | CB  | GLU | 245 | 18.933 | 60.176 | 120.517 | 1.00 | 17.90 | HIGL |
| ATOM | 1986 | CG  | GLU | 245 | 18.295 | 58.883 | 120.921 | 1.00 | 19.86 | HIGL |
| ATOM | 1987 | CD  | GLU | 245 | 19.325 | 57.778 | 121.021 | 1.00 | 21.19 | HIGL |
| ATOM | 1988 | OE1 | GLU | 245 | 20.395 | 58.018 | 121.624 | 1.00 | 22.19 | HIGL |
| ATOM | 1989 | OE2 | GLU | 245 | 19.071 | 56.673 | 120.502 | 1.00 | 22.22 | HIGL |
| ATOM | 1990 | C   | GLU | 245 | 18.892 | 62.616 | 120.780 | 1.00 | 17.25 | HIGL |
| ATOM | 1991 | O   | GLU | 245 | 19.756 | 62.984 | 119.979 | 1.00 | 17.63 | HIGL |
| ATOM | 1992 | N   | THR | 246 | 18.675 | 63.226 | 121.938 | 1.00 | 16.70 | HIGL |
| ATOM | 1993 | CA  | THR | 246 | 19.468 | 64.372 | 122.350 | 1.00 | 16.24 | HIGL |
| ATOM | 1994 | CB  | THR | 246 | 19.133 | 65.632 | 121.534 | 1.00 | 16.24 | HIGL |
| ATOM | 1995 | OG1 | THR | 246 | 20.097 | 66.649 | 121.831 | 1.00 | 16.02 | HIGL |
| ATOM | 1996 | CG2 | THR | 246 | 17.737 | 66.146 | 121.872 | 1.00 | 14.97 | HIGL |
| ATOM | 1997 | C   | THR | 246 | 19.221 | 64.650 | 123.824 | 1.00 | 16.42 | HIGL |
| ATOM | 1998 | O   | THR | 246 | 18.165 | 64.315 | 124.356 | 1.00 | 16.91 | HIGL |
| ATOM | 1999 | N   | ASN | 247 | 20.206 | 65.256 | 124.475 | 1.00 | 16.16 | HIGL |
| ATOM | 2000 | CA  | ASN | 247 | 20.125 | 65.586 | 125.891 | 1.00 | 16.42 | HIGL |
| ATOM | 2001 | CB  | ASN | 247 | 20.753 | 64.482 | 126.754 | 1.00 | 18.32 | HIGL |
| ATOM | 2002 | CG  | ASN | 247 | 19.876 | 63.247 | 126.900 | 1.00 | 19.99 | HIGL |
| ATOM | 2003 | OD1 | ASN | 247 | 20.357 | 62.190 | 127.311 | 1.00 | 20.70 | HIGL |
| ATOM | 2004 | ND2 | ASN | 247 | 18.593 | 63.374 | 126.587 | 1.00 | 19.85 | HIGL |
| ATOM | 2005 | C   | ASN | 247 | 20.931 | 66.850 | 126.139 | 1.00 | 16.21 | HIGL |
| ATOM | 2006 | O   | ASN | 247 | 21.769 | 67.235 | 125.329 | 1.00 | 16.56 | HIGL |
| ATOM | 2007 | N   | TRP | 248 | 20.664 | 67.491 | 127.267 | 1.00 | 15.12 | HIGL |
| ATOM | 2008 | CA  | TRP | 248 | 21.407 | 68.666 | 127.680 | 1.00 | 14.40 | HIGL |
| ATOM | 2009 | CB  | TRP | 248 | 20.750 | 69.965 | 127.235 | 1.00 | 14.05 | HIGL |
| ATOM | 2010 | CG  | TRP | 248 | 21.582 | 71.144 | 127.642 | 1.00 | 13.41 | HIGL |
| ATOM | 2011 | CD2 | TRP | 248 | 22.789 | 71.592 | 127.020 | 1.00 | 12.55 | HIGL |
| ATOM | 2012 | CE2 | TRP | 248 | 23.279 | 72.674 | 127.787 | 1.00 | 13.08 | HIGL |
| ATOM | 2013 | CE3 | TRP | 248 | 23.508 | 71.183 | 125.890 | 1.00 | 12.85 | HIGL |
| ATOM | 2014 | CD1 | TRP | 248 | 21.391 | 71.950 | 128.728 | 1.00 | 13.60 | HIGL |

Fig. 2 cont.

```
ATOM   2015  NE1  TRP  248    22.408  72.870 128.824  1.00 12.73       HIGL
ATOM   2016  CZ2  TRP  248    24.457  73.352 127.458  1.00 12.54       HIGL
ATOM   2017  CZ3  TRP  248    24.679  71.857 125.564  1.00 11.70       HIGL
ATOM   2018  CH2  TRP  248    25.141  72.929 126.347  1.00 12.92       HIGL
ATOM   2019  C    TRP  248    21.404  68.570 129.188  1.00 14.62       HIGL
ATOM   2020  O    TRP  248    20.351  68.434 129.802  1.00 15.22       HIGL
ATOM   2021  N    PRO  249    22.585  68.633 129.808  1.00 14.33       HIGL
ATOM   2022  CD   PRO  249    23.925  68.623 129.197  1.00 14.04       HIGL
ATOM   2023  CA   PRO  249    22.673  68.532 131.260  1.00 14.94       HIGL
ATOM   2024  CB   PRO  249    24.099  68.041 131.468  1.00 14.74       HIGL
ATOM   2025  CG   PRO  249    24.836  68.752 130.390  1.00 13.70       HIGL
ATOM   2026  C    PRO  249    22.381  69.783 132.066  1.00 15.82       HIGL
ATOM   2027  O    PRO  249    22.594  70.895 131.604  1.00 16.63       HIGL
ATOM   2028  N    THR  250    21.882  69.578 133.282  1.00 17.24       HIGL
ATOM   2029  CA   THR  250    21.603  70.672 134.207  1.00 17.83       HIGL
ATOM   2030  CB   THR  250    20.308  70.451 134.975  1.00 16.40       HIGL
ATOM   2031  OG1  THR  250    20.478  69.353 135.875  1.00 16.53       HIGL
ATOM   2032  CG2  THR  250    19.174  70.153 134.014  1.00 17.51       HIGL
ATOM   2033  C    THR  250    22.758  70.645 135.206  1.00 18.49       HIGL
ATOM   2034  O    THR  250    22.875  71.509 136.078  1.00 19.82       HIGL
ATOM   2035  N    SER  251    23.601  69.627 135.057  1.00 18.20       HIGL
ATOM   2036  CA   SER  251    24.769  69.426 135.897  1.00 17.27       HIGL
ATOM   2037  CB   SER  251    24.373  68.700 137.181  1.00 16.80       HIGL
ATOM   2038  OG   SER  251    25.486  68.537 138.046  1.00 16.67       HIGL
ATOM   2039  C    SER  251    25.769  68.579 135.122  1.00 17.65       HIGL
ATOM   2040  O    SER  251    25.444  67.476 134.682  1.00 17.82       HIGL
ATOM   2041  N    CYS  252    26.975  69.099 134.936  1.00 17.77       HIGL
ATOM   2042  CA   CYS  252    28.012  68.359 134.218  1.00 19.00       HIGL
ATOM   2043  C    CYS  252    29.375  68.791 134.751  1.00 18.46       HIGL
ATOM   2044  O    CYS  252    30.142  69.460 134.069  1.00 18.37       HIGL
ATOM   2045  CB   CYS  252    27.940  68.611 132.703  1.00 19.48       HIGL
ATOM   2046  SG   CYS  252    28.860  67.349 131.755  1.00 21.91       HIGL
ATOM   2047  N    PRO  253    29.687  68.402 135.992  1.00 18.43       HIGL
ATOM   2048  CD   PRO  253    28.822  67.630 136.898  1.00 17.81       HIGL
ATOM   2049  CA   PRO  253    30.950  68.739 136.650  1.00 18.32       HIGL
ATOM   2050  CB   PRO  253    30.789  68.130 138.038  1.00 17.88       HIGL
ATOM   2051  CG   PRO  253    29.313  68.078 138.228  1.00 18.40       HIGL
ATOM   2052  C    PRO  253    32.191  68.204 135.952  1.00 18.83       HIGL
ATOM   2053  O    PRO  253    33.213  68.887 135.900  1.00 18.49       HIGL
ATOM   2054  N    TYR  254    32.102  66.989 135.414  1.00 19.26       HIGL
ATOM   2055  CA   TYR  254    33.256  66.378 134.766  1.00 19.93       HIGL
ATOM   2056  CB   TYR  254    33.782  65.223 135.616  1.00 19.85       HIGL
ATOM   2057  CG   TYR  254    33.909  65.574 137.076  1.00 19.85       HIGL
ATOM   2058  CD1  TYR  254    32.816  65.468 137.934  1.00 18.49       HIGL
ATOM   2059  CE1  TYR  254    32.915  65.836 139.268  1.00 18.20       HIGL
ATOM   2060  CD2  TYR  254    35.112  66.060 137.594  1.00 19.80       HIGL
ATOM   2061  CE2  TYR  254    35.218  66.434 138.930  1.00 18.50       HIGL
ATOM   2062  CZ   TYR  254    34.115  66.319 139.755  1.00 18.08       HIGL
ATOM   2063  OH   TYR  254    34.207  66.697 141.065  1.00 18.79       HIGL
ATOM   2064  C    TYR  254    33.031  65.873 133.357  1.00 21.05       HIGL
ATOM   2065  O    TYR  254    32.995  64.667 133.128  1.00 22.11       HIGL
ATOM   2066  N    PRO  255    32.898  66.789 132.387  1.00 21.11       HIGL
ATOM   2067  CD   PRO  255    33.042  68.251 132.488  1.00 20.35       HIGL
ATOM   2068  CA   PRO  255    32.684  66.391 130.999  1.00 21.28       HIGL
ATOM   2069  CB   PRO  255    32.472  67.724 130.299  1.00 21.29       HIGL
ATOM   2070  CG   PRO  255    33.369  68.632 131.075  1.00 20.00       HIGL
ATOM   2071  C    PRO  255    33.910  65.667 130.469  1.00 22.18       HIGL
ATOM   2072  O    PRO  255    35.034  66.059 130.767  1.00 22.28       HIGL
ATOM   2073  N    ARG  256    33.698  64.613 129.686  1.00 23.41       HIGL
ATOM   2074  CA   ARG  256    34.817  63.872 129.118  1.00 24.09       HIGL
ATOM   2075  CB   ARG  256    34.386  62.462 128.702  1.00 25.18       HIGL
ATOM   2076  CG   ARG  256    35.537  61.602 128.198  1.00 28.36       HIGL
ATOM   2077  CD   ARG  256    35.062  60.254 127.676  1.00 31.88       HIGL
ATOM   2078  NE   ARG  256    36.176  59.403 127.254  1.00 35.40       HIGL
ATOM   2079  CZ   ARG  256    36.043  58.228 126.636  1.00 36.69       HIGL
```

Fig. 2 cont.

```
ATOM   2080  NH1  ARG  256      34.837  57.744 126.353  1.00 36.99           HIGL
ATOM   2081  NH2  ARG  256      37.122  57.528 126.305  1.00 37.44           HIGL
ATOM   2082  C    ARG  256      35.354  64.625 127.905  1.00 23.61           HIGL
ATOM   2083  O    ARG  256      36.538  64.553 127.593  1.00 23.73           HIGL
ATOM   2084  N    TYR  257      34.481  65.357 127.226  1.00 22.94           HIGL
ATOM   2085  CA   TYR  257      34.893  66.107 126.054  1.00 23.27           HIGL
ATOM   2086  CB   TYR  257      34.287  65.502 124.788  1.00 23.86           HIGL
ATOM   2087  CG   TYR  257      34.485  64.018 124.653  1.00 24.59           HIGL
ATOM   2088  CD1  TYR  257      33.570  63.124 125.204  1.00 25.20           HIGL
ATOM   2089  CE1  TYR  257      33.742  61.747 125.077  1.00 26.62           HIGL
ATOM   2090  CD2  TYR  257      35.585  63.502 123.970  1.00 24.88           HIGL
ATOM   2091  CE2  TYR  257      35.771  62.128 123.838  1.00 26.37           HIGL
ATOM   2092  CZ   TYR  257      34.843  61.255 124.395  1.00 27.15           HIGL
ATOM   2093  OH   TYR  257      35.018  59.895 124.276  1.00 27.95           HIGL
ATOM   2094  C    TYR  257      34.480  67.567 126.127  1.00 23.40           HIGL
ATOM   2095  O    TYR  257      33.530  67.929 126.813  1.00 23.44           HIGL
ATOM   2096  N    GLN  258      35.204  68.406 125.404  1.00 23.33           HIGL
ATOM   2097  CA   GLN  258      34.886  69.816 125.367  1.00 23.32           HIGL
ATOM   2098  CB   GLN  258      35.998  70.566 124.641  1.00 25.30           HIGL
ATOM   2099  CG   GLN  258      35.814  72.063 124.549  1.00 29.69           HIGL
ATOM   2100  CD   GLN  258      37.146  72.781 124.380  1.00 33.22           HIGL
ATOM   2101  OE1  GLN  258      37.199  73.936 123.943  1.00 34.85           HIGL
ATOM   2102  NE2  GLN  258      38.234  72.099 124.741  1.00 33.71           HIGL
ATOM   2103  C    GLN  258      33.573  69.922 124.608  1.00 21.85           HIGL
ATOM   2104  O    GLN  258      33.359  69.209 123.632  1.00 21.62           HIGL
ATOM   2105  N    PHE  259      32.680  70.784 125.067  1.00 20.74           HIGL
ATOM   2106  CA   PHE  259      31.405  70.954 124.390  1.00 20.36           HIGL
ATOM   2107  CB   PHE  259      30.415  71.652 125.318  1.00 20.17           HIGL
ATOM   2108  CG   PHE  259      29.691  70.718 126.243  1.00 20.50           HIGL
ATOM   2109  CD1  PHE  259      30.383  69.756 126.969  1.00 20.48           HIGL
ATOM   2110  CD2  PHE  259      28.310  70.803 126.391  1.00 19.48           HIGL
ATOM   2111  CE1  PHE  259      29.707  68.887 127.830  1.00 21.21           HIGL
ATOM   2112  CE2  PHE  259      27.629  69.943 127.246  1.00 19.74           HIGL
ATOM   2113  CZ   PHE  259      28.328  68.982 127.968  1.00 20.03           HIGL
ATOM   2114  C    PHE  259      31.578  71.769 123.110  1.00 20.28           HIGL
ATOM   2115  O    PHE  259      32.557  72.486 122.953  1.00 19.93           HIGL
ATOM   2116  N    PRO  260      30.637  71.651 122.165  1.00 20.85           HIGL
ATOM   2117  CD   PRO  260      29.527  70.687 122.073  1.00 20.21           HIGL
ATOM   2118  CA   PRO  260      30.766  72.427 120.924  1.00 21.17           HIGL
ATOM   2119  CB   PRO  260      29.506  72.048 120.156  1.00 21.01           HIGL
ATOM   2120  CG   PRO  260      29.291  70.617 120.584  1.00 20.56           HIGL
ATOM   2121  C    PRO  260      30.837  73.928 121.239  1.00 21.74           HIGL
ATOM   2122  O    PRO  260      30.163  74.414 122.150  1.00 21.19           HIGL
ATOM   2123  N    ALA  261      31.657  74.654 120.487  1.00 21.93           HIGL
ATOM   2124  CA   ALA  261      31.830  76.089 120.697  1.00 22.38           HIGL
ATOM   2125  CB   ALA  261      32.836  76.636 119.697  1.00 21.76           HIGL
ATOM   2126  C    ALA  261      30.540  76.901 120.621  1.00 22.55           HIGL
ATOM   2127  O    ALA  261      30.411  77.929 121.290  1.00 23.31           HIGL
ATOM   2128  N    ASP  262      29.586  76.449 119.814  1.00 22.59           HIGL
ATOM   2129  CA   ASP  262      28.331  77.173 119.674  1.00 23.66           HIGL
ATOM   2130  CB   ASP  262      27.570  76.715 118.426  1.00 24.06           HIGL
ATOM   2131  CG   ASP  262      27.368  75.206 118.369  1.00 25.82           HIGL
ATOM   2132  OD1  ASP  262      27.333  74.550 119.435  1.00 26.18           HIGL
ATOM   2133  OD2  ASP  262      27.224  74.677 117.243  1.00 26.76           HIGL
ATOM   2134  C    ASP  262      27.401  77.095 120.878  1.00 24.22           HIGL
ATOM   2135  O    ASP  262      26.449  77.866 120.965  1.00 24.88           HIGL
ATOM   2136  N    VAL  263      27.661  76.174 121.802  1.00 25.01           HIGL
ATOM   2137  CA   VAL  263      26.803  76.042 122.976  1.00 26.27           HIGL
ATOM   2138  CB   VAL  263      26.062  74.680 122.990  1.00 25.93           HIGL
ATOM   2139  CG1  VAL  263      25.179  74.554 121.757  1.00 24.73           HIGL
ATOM   2140  CG2  VAL  263      27.056  73.540 123.063  1.00 25.19           HIGL
ATOM   2141  C    VAL  263      27.525  76.211 124.309  1.00 27.53           HIGL
ATOM   2142  O    VAL  263      26.931  76.014 125.365  1.00 27.35           HIGL
ATOM   2143  N    ARG  264      28.799  76.590 124.257  1.00 29.44           HIGL
ATOM   2144  CA   ARG  264      29.595  76.782 125.466  1.00 31.50           HIGL
```

Fig. 2 cont.

```
ATOM   2145  CB   ARG   264      31.066  76.969 125.092  1.00 32.75           HIGL
ATOM   2146  CG   ARG   264      31.645  75.755 124.389  1.00 35.35           HIGL
ATOM   2147  CD   ARG   264      33.075  75.968 123.917  1.00 37.11           HIGL
ATOM   2148  NE   ARG   264      33.550  74.810 123.161  1.00 38.51           HIGL
ATOM   2149  CZ   ARG   264      34.738  74.727 122.571  1.00 38.26           HIGL
ATOM   2150  NH1  ARG   264      35.590  75.742 122.646  1.00 38.84           HIGL
ATOM   2151  NH2  ARG   264      35.072  73.629 121.903  1.00 37.21           HIGL
ATOM   2152  C    ARG   264      29.110  77.968 126.294  1.00 31.82           HIGL
ATOM   2153  O    ARG   264      29.649  78.256 127.360  1.00 32.57           HIGL
ATOM   2154  N    ASN   265      28.086  78.648 125.796  1.00 31.94           HIGL
ATOM   2155  CA   ASN   265      27.508  79.801 126.480  1.00 31.74           HIGL
ATOM   2156  CB   ASN   265      27.189  80.893 125.464  1.00 33.87           HIGL
ATOM   2157  CG   ASN   265      26.419  80.357 124.264  1.00 35.62           HIGL
ATOM   2158  OD1  ASN   265      25.213  80.600 124.115  1.00 36.81           HIGL
ATOM   2159  ND2  ASN   265      27.113  79.608 123.407  1.00 35.24           HIGL
ATOM   2160  C    ASN   265      26.227  79.376 127.175  1.00 30.26           HIGL
ATOM   2161  O    ASN   265      25.738  80.064 128.067  1.00 31.10           HIGL
ATOM   2162  N    VAL   266      25.685  78.240 126.746  1.00 28.31           HIGL
ATOM   2163  CA   VAL   266      24.455  77.701 127.307  1.00 25.56           HIGL
ATOM   2164  CB   VAL   266      23.844  76.635 126.374  1.00 25.88           HIGL
ATOM   2165  CG1  VAL   266      22.547  76.096 126.970  1.00 25.25           HIGL
ATOM   2166  CG2  VAL   266      23.594  77.241 124.992  1.00 24.06           HIGL
ATOM   2167  C    VAL   266      24.755  77.087 128.668  1.00 23.91           HIGL
ATOM   2168  O    VAL   266      25.624  76.228 128.798  1.00 23.76           HIGL
ATOM   2169  N    PRO   267      24.038  77.534 129.706  1.00 21.98           HIGL
ATOM   2170  CD   PRO   267      23.034  78.615 129.662  1.00 20.37           HIGL
ATOM   2171  CA   PRO   267      24.216  77.047 131.075  1.00 20.98           HIGL
ATOM   2172  CB   PRO   267      23.483  78.099 131.899  1.00 20.76           HIGL
ATOM   2173  CG   PRO   267      22.349  78.475 130.996  1.00 20.01           HIGL
ATOM   2174  C    PRO   267      23.670  75.655 131.340  1.00 20.67           HIGL
ATOM   2175  O    PRO   267      22.759  75.190 130.652  1.00 20.51           HIGL
ATOM   2176  N    PHE   268      24.239  74.985 132.338  1.00 20.18           HIGL
ATOM   2177  CA   PHE   268      23.755  73.668 132.713  1.00 19.81           HIGL
ATOM   2178  CB   PHE   268      24.863  72.819 133.338  1.00 19.33           HIGL
ATOM   2179  CG   PHE   268      26.001  72.540 132.405  1.00 18.57           HIGL
ATOM   2180  CD1  PHE   268      25.755  72.175 131.079  1.00 18.00           HIGL
ATOM   2181  CD2  PHE   268      27.320  72.663 132.837  1.00 17.98           HIGL
ATOM   2182  CE1  PHE   268      26.802  71.941 130.196  1.00 17.94           HIGL
ATOM   2183  CE2  PHE   268      28.382  72.431 131.961  1.00 17.83           HIGL
ATOM   2184  CZ   PHE   268      28.121  72.070 130.635  1.00 18.17           HIGL
ATOM   2185  C    PHE   268      22.667  73.953 133.727  1.00 19.80           HIGL
ATOM   2186  O    PHE   268      22.942  74.140 134.916  1.00 19.98           HIGL
ATOM   2187  N    SER   269      21.434  74.020 133.234  1.00 18.90           HIGL
ATOM   2188  CA   SER   269      20.281  74.310 134.066  1.00 18.82           HIGL
ATOM   2189  CB   SER   269      20.339  75.752 134.567  1.00 19.28           HIGL
ATOM   2190  OG   SER   269      20.163  76.667 133.494  1.00 20.35           HIGL
ATOM   2191  C    SER   269      19.021  74.133 133.243  1.00 18.90           HIGL
ATOM   2192  O    SER   269      19.080  73.972 132.022  1.00 19.79           HIGL
ATOM   2193  N    ALA   270      17.880  74.169 133.917  1.00 17.92           HIGL
ATOM   2194  CA   ALA   270      16.604  74.030 133.245  1.00 17.69           HIGL
ATOM   2195  CB   ALA   270      15.478  74.256 134.230  1.00 17.34           HIGL
ATOM   2196  C    ALA   270      16.526  75.050 132.111  1.00 18.21           HIGL
ATOM   2197  O    ALA   270      16.018  74.752 131.028  1.00 19.17           HIGL
ATOM   2198  N    ALA   271      17.033  76.254 132.359  1.00 17.66           HIGL
ATOM   2199  CA   ALA   271      17.008  77.307 131.346  1.00 16.71           HIGL
ATOM   2200  CB   ALA   271      17.545  78.605 131.926  1.00 16.21           HIGL
ATOM   2201  C    ALA   271      17.838  76.886 130.145  1.00 16.17           HIGL
ATOM   2202  O    ALA   271      17.407  77.035 129.006  1.00 15.94           HIGL
ATOM   2203  N    GLY   272      19.024  76.348 130.415  1.00 16.09           HIGL
ATOM   2204  CA   GLY   272      19.906  75.900 129.353  1.00 16.02           HIGL
ATOM   2205  C    GLY   272      19.321  74.768 128.528  1.00 16.50           HIGL
ATOM   2206  O    GLY   272      19.527  74.700 127.316  1.00 16.42           HIGL
ATOM   2207  N    GLN   273      18.593  73.867 129.177  1.00 16.88           HIGL
ATOM   2208  CA   GLN   273      17.985  72.762 128.454  1.00 17.26           HIGL
ATOM   2209  CB   GLN   273      17.267  71.809 129.414  1.00 16.57           HIGL
```

Fig. 2 cont.

```
ATOM   2210 CG   GLN   273      18.186  71.041 130.354  1.00 16.40      HIGL
ATOM   2211 CD   GLN   273      17.438  70.007 131.175  1.00 15.47      HIGL
ATOM   2212 OE1  GLN   273      16.479  70.330 131.868  1.00 15.89      HIGL
ATOM   2213 NE2  GLN   273      17.877  68.758 131.101  1.00 15.09      HIGL
ATOM   2214 C    GLN   273      16.986  73.323 127.452  1.00 18.10      HIGL
ATOM   2215 O    GLN   273      16.955  72.903 126.297  1.00 19.02      HIGL
ATOM   2216 N    THR   274      16.172  74.275 127.901  1.00 18.71      HIGL
ATOM   2217 CA   THR   274      15.161  74.899 127.058  1.00 19.11      HIGL
ATOM   2218 CB   THR   274      14.419  76.016 127.826  1.00 20.20      HIGL
ATOM   2219 OG1  THR   274      13.856  75.469 129.026  1.00 21.70      HIGL
ATOM   2220 CG2  THR   274      13.293  76.603 126.978  1.00 20.14      HIGL
ATOM   2221 C    THR   274      15.840  75.498 125.842  1.00 19.34      HIGL
ATOM   2222 O    THR   274      15.485  75.213 124.700  1.00 18.39      HIGL
ATOM   2223 N    GLN   275      16.838  76.325 126.115  1.00 20.37      HIGL
ATOM   2224 CA   GLN   275      17.613  76.999 125.087  1.00 21.17      HIGL
ATOM   2225 CB   GLN   275      18.747  77.761 125.766  1.00 22.42      HIGL
ATOM   2226 CG   GLN   275      19.418  78.828 124.942  1.00 25.01      HIGL
ATOM   2227 CD   GLN   275      20.454  79.578 125.759  1.00 28.13      HIGL
ATOM   2228 OE1  GLN   275      20.205  79.943 126.918  1.00 28.91      HIGL
ATOM   2229 NE2  GLN   275      21.621  79.817 125.166  1.00 29.71      HIGL
ATOM   2230 C    GLN   275      18.180  75.997 124.077  1.00 21.54      HIGL
ATOM   2231 O    GLN   275      18.022  76.167 122.866  1.00 21.25      HIGL
ATOM   2232 N    TYR   276      18.831  74.948 124.579  1.00 20.83      HIGL
ATOM   2233 CA   TYR   276      19.431  73.941 123.712  1.00 20.67      HIGL
ATOM   2234 CB   TYR   276      20.283  72.961 124.528  1.00 19.62      HIGL
ATOM   2235 CG   TYR   276      20.995  71.923 123.681  1.00 18.90      HIGL
ATOM   2236 CD1  TYR   276      22.193  72.222 123.020  1.00 18.90      HIGL
ATOM   2237 CE1  TYR   276      22.854  71.260 122.245  1.00 18.33      HIGL
ATOM   2238 CD2  TYR   276      20.471  70.641 123.540  1.00 18.85      HIGL
ATOM   2239 CE2  TYR   276      21.114  69.677 122.769  1.00 18.77      HIGL
ATOM   2240 CZ   TYR   276      22.304  69.986 122.127  1.00 19.64      HIGL
ATOM   2241 OH   TYR   276      22.938  69.006 121.391  1.00 19.63      HIGL
ATOM   2242 C    TYR   276      18.406  73.150 122.907  1.00 20.77      HIGL
ATOM   2243 O    TYR   276      18.547  72.992 121.695  1.00 20.48      HIGL
ATOM   2244 N    ILE   277      17.386  72.639 123.584  1.00 21.04      HIGL
ATOM   2245 CA   ILE   277      16.361  71.857 122.912  1.00 21.46      HIGL
ATOM   2246 CB   ILE   277      15.303  71.345 123.913  1.00 21.68      HIGL
ATOM   2247 CG2  ILE   277      14.172  70.635 123.167  1.00 21.01      HIGL
ATOM   2248 CG1  ILE   277      15.965  70.393 124.912  1.00 20.42      HIGL
ATOM   2249 CD1  ILE   277      15.058  69.950 126.033  1.00 21.50      HIGL
ATOM   2250 C    ILE   277      15.685  72.690 121.841  1.00 21.85      HIGL
ATOM   2251 O    ILE   277      15.334  72.185 120.780  1.00 21.88      HIGL
ATOM   2252 N    GLN   278      15.520  73.975 122.114  1.00 22.68      HIGL
ATOM   2253 CA   GLN   278      14.881  74.863 121.159  1.00 23.40      HIGL
ATOM   2254 CB   GLN   278      14.468  76.164 121.856  1.00 25.27      HIGL
ATOM   2255 CG   GLN   278      13.664  77.127 120.993  1.00 28.71      HIGL
ATOM   2256 CD   GLN   278      12.524  77.786 121.759  1.00 31.37      HIGL
ATOM   2257 OE1  GLN   278      12.699  78.244 122.900  1.00 32.36      HIGL
ATOM   2258 NE2  GLN   278      11.347  77.845 121.132  1.00 31.74      HIGL
ATOM   2259 C    GLN   278      15.789  75.145 119.963  1.00 22.37      HIGL
ATOM   2260 O    GLN   278      15.319  75.205 118.829  1.00 22.41      HIGL
ATOM   2261 N    SER   279      17.085  75.311 120.213  1.00 21.36      HIGL
ATOM   2262 CA   SER   279      18.042  75.563 119.137  1.00 20.77      HIGL
ATOM   2263 CB   SER   279      19.445  75.775 119.697  1.00 20.20      HIGL
ATOM   2264 OG   SER   279      19.492  76.892 120.554  1.00 21.57      HIGL
ATOM   2265 C    SER   279      18.083  74.372 118.185  1.00 20.98      HIGL
ATOM   2266 O    SER   279      18.103  74.536 116.962  1.00 21.23      HIGL
ATOM   2267 N    VAL   280      18.102  73.172 118.762  1.00 20.27      HIGL
ATOM   2268 CA   VAL   280      18.141  71.945 117.983  1.00 19.59      HIGL
ATOM   2269 CB   VAL   280      18.294  70.721 118.905  1.00 18.93      HIGL
ATOM   2270 CG1  VAL   280      18.277  69.436 118.088  1.00 18.16      HIGL
ATOM   2271 CG2  VAL   280      19.586  70.837 119.686  1.00 17.85      HIGL
ATOM   2272 C    VAL   280      16.865  71.821 117.161  1.00 19.71      HIGL
ATOM   2273 O    VAL   280      16.895  71.371 116.015  1.00 19.74      HIGL
ATOM   2274 N    ALA   281      15.744  72.229 117.746  1.00 19.63      HIGL
```

Fig. 2 cont.

| | | | | | | | | | | |
|---|---|---|---|---|---|---|---|---|---|---|
| ATOM | 2275 | CA | ALA | 281 | 14.467 | 72.176 | 117.044 | 1.00 | 19.86 | HIGL |
| ATOM | 2276 | CB | ALA | 281 | 13.324 | 72.570 | 117.982 | 1.00 | 19.49 | HIGL |
| ATOM | 2277 | C | ALA | 281 | 14.519 | 73.123 | 115.847 | 1.00 | 19.99 | HIGL |
| ATOM | 2278 | O | ALA | 281 | 14.070 | 72.782 | 114.751 | 1.00 | 19.99 | HIGL |
| ATOM | 2279 | N | ASN | 282 | 15.080 | 74.309 | 116.056 | 1.00 | 20.40 | HIGL |
| ATOM | 2280 | CA | ASN | 282 | 15.189 | 75.283 | 114.979 | 1.00 | 21.01 | HIGL |
| ATOM | 2281 | CB | ASN | 282 | 15.867 | 76.562 | 115.463 | 1.00 | 22.58 | HIGL |
| ATOM | 2282 | CG | ASN | 282 | 15.081 | 77.253 | 116.555 | 1.00 | 25.95 | HIGL |
| ATOM | 2283 | OD1 | ASN | 282 | 13.850 | 77.335 | 116.489 | 1.00 | 27.58 | HIGL |
| ATOM | 2284 | ND2 | ASN | 282 | 15.786 | 77.765 | 117.567 | 1.00 | 25.99 | HIGL |
| ATOM | 2285 | C | ASN | 282 | 15.976 | 74.709 | 113.818 | 1.00 | 20.44 | HIGL |
| ATOM | 2286 | O | ASN | 282 | 15.608 | 74.915 | 112.662 | 1.00 | 21.36 | HIGL |
| ATOM | 2287 | N | VAL | 283 | 17.058 | 73.995 | 114.118 | 1.00 | 18.69 | HIGL |
| ATOM | 2288 | CA | VAL | 283 | 17.868 | 73.396 | 113.064 | 1.00 | 18.11 | HIGL |
| ATOM | 2289 | CB | VAL | 283 | 19.105 | 72.668 | 113.639 | 1.00 | 17.40 | HIGL |
| ATOM | 2290 | CG1 | VAL | 283 | 19.738 | 71.771 | 112.581 | 1.00 | 15.51 | HIGL |
| ATOM | 2291 | CG2 | VAL | 283 | 20.117 | 73.692 | 114.128 | 1.00 | 15.34 | HIGL |
| ATOM | 2292 | C | VAL | 283 | 17.028 | 72.418 | 112.256 | 1.00 | 18.82 | HIGL |
| ATOM | 2293 | O | VAL | 283 | 16.972 | 72.504 | 111.034 | 1.00 | 19.69 | HIGL |
| ATOM | 2294 | N | VAL | 284 | 16.365 | 71.497 | 112.942 | 1.00 | 19.82 | HIGL |
| ATOM | 2295 | CA | VAL | 284 | 15.518 | 70.514 | 112.277 | 1.00 | 20.48 | HIGL |
| ATOM | 2296 | CB | VAL | 284 | 14.874 | 69.570 | 113.304 | 1.00 | 19.52 | HIGL |
| ATOM | 2297 | CG1 | VAL | 284 | 14.015 | 68.549 | 112.595 | 1.00 | 17.63 | HIGL |
| ATOM | 2298 | CG2 | VAL | 284 | 15.956 | 68.896 | 114.132 | 1.00 | 18.42 | HIGL |
| ATOM | 2299 | C | VAL | 284 | 14.405 | 71.185 | 111.452 | 1.00 | 21.90 | HIGL |
| ATOM | 2300 | O | VAL | 284 | 14.205 | 70.863 | 110.279 | 1.00 | 22.17 | HIGL |
| ATOM | 2301 | N | SER | 285 | 13.685 | 72.117 | 112.068 | 1.00 | 22.19 | HIGL |
| ATOM | 2302 | CA | SER | 285 | 12.609 | 72.820 | 111.380 | 1.00 | 22.67 | HIGL |
| ATOM | 2303 | CB | SER | 285 | 11.936 | 73.817 | 112.317 | 1.00 | 22.73 | HIGL |
| ATOM | 2304 | OG | SER | 285 | 11.369 | 73.153 | 113.426 | 1.00 | 26.28 | HIGL |
| ATOM | 2305 | C | SER | 285 | 13.112 | 73.571 | 110.160 | 1.00 | 23.02 | HIGL |
| ATOM | 2306 | O | SER | 285 | 12.447 | 73.585 | 109.126 | 1.00 | 23.75 | HIGL |
| ATOM | 2307 | N | SER | 286 | 14.279 | 74.203 | 110.282 | 1.00 | 23.31 | HIGL |
| ATOM | 2308 | CA | SER | 286 | 14.848 | 74.975 | 109.177 | 1.00 | 23.26 | HIGL |
| ATOM | 2309 | CB | SER | 286 | 16.231 | 75.524 | 109.545 | 1.00 | 22.79 | HIGL |
| ATOM | 2310 | OG | SER | 286 | 17.224 | 74.513 | 109.479 | 1.00 | 22.57 | HIGL |
| ATOM | 2311 | C | SER | 286 | 14.969 | 74.104 | 107.937 | 1.00 | 23.61 | HIGL |
| ATOM | 2312 | O | SER | 286 | 14.824 | 74.586 | 106.812 | 1.00 | 24.61 | HIGL |
| ATOM | 2313 | N | VAL | 287 | 15.227 | 72.817 | 108.150 | 1.00 | 22.94 | HIGL |
| ATOM | 2314 | CA | VAL | 287 | 15.371 | 71.876 | 107.051 | 1.00 | 22.39 | HIGL |
| ATOM | 2315 | CB | VAL | 287 | 16.126 | 70.596 | 107.494 | 1.00 | 21.12 | HIGL |
| ATOM | 2316 | CG1 | VAL | 287 | 16.217 | 69.617 | 106.341 | 1.00 | 19.58 | HIGL |
| ATOM | 2317 | CG2 | VAL | 287 | 17.500 | 70.952 | 107.989 | 1.00 | 19.96 | HIGL |
| ATOM | 2318 | C | VAL | 287 | 14.020 | 71.452 | 106.510 | 1.00 | 22.70 | HIGL |
| ATOM | 2319 | O | VAL | 287 | 13.129 | 71.075 | 107.266 | 1.00 | 22.82 | HIGL |
| ATOM | 2320 | N | SER | 288 | 13.857 | 71.530 | 105.197 | 1.00 | 23.99 | HIGL |
| ATOM | 2321 | CA | SER | 288 | 12.609 | 71.083 | 104.598 | 1.00 | 25.42 | HIGL |
| ATOM | 2322 | CB | SER | 288 | 12.661 | 71.204 | 103.077 | 1.00 | 25.83 | HIGL |
| ATOM | 2323 | OG | SER | 288 | 13.511 | 70.204 | 102.537 | 1.00 | 26.10 | HIGL |
| ATOM | 2324 | C | SER | 288 | 12.606 | 69.606 | 104.969 | 1.00 | 25.73 | HIGL |
| ATOM | 2325 | O | SER | 288 | 13.655 | 68.951 | 104.917 | 1.00 | 27.44 | HIGL |
| ATOM | 2326 | N | LYS | 289 | 11.456 | 69.073 | 105.342 | 1.00 | 24.12 | HIGL |
| ATOM | 2327 | CA | LYS | 289 | 11.400 | 67.668 | 105.716 | 1.00 | 23.58 | HIGL |
| ATOM | 2328 | CB | LYS | 289 | 12.074 | 66.790 | 104.657 | 1.00 | 23.46 | HIGL |
| ATOM | 2329 | CG | LYS | 289 | 11.229 | 66.659 | 103.407 | 1.00 | 24.42 | HIGL |
| ATOM | 2330 | CD | LYS | 289 | 11.870 | 65.809 | 102.341 | 1.00 | 24.82 | HIGL |
| ATOM | 2331 | CE | LYS | 289 | 10.907 | 65.640 | 101.180 | 1.00 | 25.59 | HIGL |
| ATOM | 2332 | NZ | LYS | 289 | 9.680 | 64.915 | 101.624 | 1.00 | 27.30 | HIGL |
| ATOM | 2333 | C | LYS | 289 | 12.010 | 67.422 | 107.085 | 1.00 | 22.49 | HIGL |
| ATOM | 2334 | O | LYS | 289 | 12.135 | 66.281 | 107.524 | 1.00 | 22.48 | HIGL |
| ATOM | 2335 | N | GLY | 290 | 12.415 | 68.498 | 107.749 | 1.00 | 21.72 | HIGL |
| ATOM | 2336 | CA | GLY | 290 | 12.913 | 68.353 | 109.102 | 1.00 | 21.35 | HIGL |
| ATOM | 2337 | C | GLY | 290 | 11.587 | 68.203 | 109.830 | 1.00 | 20.86 | HIGL |
| ATOM | 2338 | O | GLY | 290 | 10.805 | 69.154 | 109.888 | 1.00 | 21.50 | HIGL |
| ATOM | 2339 | N | VAL | 291 | 11.305 | 67.029 | 110.379 | 1.00 | 19.98 | HIGL |

Fig. 2 cont.

```
ATOM  2340 CA  VAL 291   10.008 66.845 111.013 1.00 19.00      HIGL
ATOM  2341 CB  VAL 291    9.168 65.836 110.206 1.00 18.98      HIGL
ATOM  2342 CG1 VAL 291    9.040 66.301 108.764 1.00 18.95      HIGL
ATOM  2343 CG2 VAL 291    9.816 64.471 110.258 1.00 19.17      HIGL
ATOM  2344 C   VAL 291    9.927 66.441 112.479 1.00 18.36      HIGL
ATOM  2345 O   VAL 291    8.834 66.482 113.055 1.00 18.16      HIGL
ATOM  2346 N   GLY 292   11.043 66.061 113.098 1.00 16.75      HIGL
ATOM  2347 CA  GLY 292   10.943 65.657 114.489 1.00 15.82      HIGL
ATOM  2348 C   GLY 292   12.114 65.858 115.421 1.00 15.38      HIGL
ATOM  2349 O   GLY 292   13.248 66.043 114.990 1.00 15.70      HIGL
ATOM  2350 N   LEU 293   11.822 65.825 116.719 1.00 15.28      HIGL
ATOM  2351 CA  LEU 293   12.842 65.963 117.757 1.00 14.98      HIGL
ATOM  2352 CB  LEU 293   13.059 67.436 118.131 1.00 14.38      HIGL
ATOM  2353 CG  LEU 293   14.200 67.697 119.131 1.00 14.97      HIGL
ATOM  2354 CD1 LEU 293   14.507 69.175 119.180 1.00 16.01      HIGL
ATOM  2355 CD2 LEU 293   13.824 67.197 120.524 1.00 15.85      HIGL
ATOM  2356 C   LEU 293   12.450 65.168 119.006 1.00 14.59      HIGL
ATOM  2357 O   LEU 293   11.367 65.356 119.559 1.00 14.50      HIGL
ATOM  2358 N   PHE 294   13.334 64.281 119.454 1.00 14.69      HIGL
ATOM  2359 CA  PHE 294   13.047 63.487 120.644 1.00 14.76      HIGL
ATOM  2360 CB  PHE 294   12.807 62.023 120.288 1.00 13.63      HIGL
ATOM  2361 CG  PHE 294   11.566 61.788 119.496 1.00 14.32      HIGL
ATOM  2362 CD1 PHE 294   11.557 61.983 118.116 1.00 14.42      HIGL
ATOM  2363 CD2 PHE 294   10.394 61.372 120.127 1.00 14.49      HIGL
ATOM  2364 CE1 PHE 294   10.395 61.763 117.372 1.00 14.13      HIGL
ATOM  2365 CE2 PHE 294    9.225 61.149 119.397 1.00 14.10      HIGL
ATOM  2366 CZ  PHE 294    9.224 61.344 118.017 1.00 14.44      HIGL
ATOM  2367 C   PHE 294   14.152 63.552 121.684 1.00 14.75      HIGL
ATOM  2368 O   PHE 294   15.312 63.249 121.394 1.00 15.47      HIGL
ATOM  2369 N   TYR 295   13.778 63.947 122.897 1.00 14.13      HIGL
ATOM  2370 CA  TYR 295   14.716 64.024 124.006 1.00 13.77      HIGL
ATOM  2371 CB  TYR 295   14.199 64.993 125.065 1.00 13.42      HIGL
ATOM  2372 CG  TYR 295   15.267 65.439 126.031 1.00 12.18      HIGL
ATOM  2373 CD1 TYR 295   15.972 66.628 125.825 1.00 11.42      HIGL
ATOM  2374 CE1 TYR 295   16.991 67.020 126.696 1.00 11.09      HIGL
ATOM  2375 CD2 TYR 295   15.602 64.656 127.131 1.00 10.29      HIGL
ATOM  2376 CE2 TYR 295   16.612 65.040 128.004 1.00 10.79      HIGL
ATOM  2377 CZ  TYR 295   17.304 66.217 127.782 1.00 10.57      HIGL
ATOM  2378 OH  TYR 295   18.317 66.569 128.640 1.00  9.73      HIGL
ATOM  2379 C   TYR 295   14.783 62.609 124.586 1.00 13.63      HIGL
ATOM  2380 O   TYR 295   13.747 61.970 124.793 1.00 13.59      HIGL
ATOM  2381 N   TRP 296   15.990 62.120 124.854 1.00 12.80      HIGL
ATOM  2382 CA  TRP 296   16.138 60.764 125.369 1.00 12.83      HIGL
ATOM  2383 CB  TRP 296   17.412 60.119 124.809 1.00 13.03      HIGL
ATOM  2384 CG  TRP 296   17.448 58.640 125.023 1.00 13.14      HIGL
ATOM  2385 CD2 TRP 296   18.316 57.918 125.900 1.00 13.55      HIGL
ATOM  2386 CE2 TRP 296   17.949 56.555 125.825 1.00 13.63      HIGL
ATOM  2387 CE3 TRP 296   19.369 58.289 126.747 1.00 14.63      HIGL
ATOM  2388 CD1 TRP 296   16.615 57.711 124.460 1.00 14.08      HIGL
ATOM  2389 NE1 TRP 296   16.909 56.456 124.939 1.00 13.47      HIGL
ATOM  2390 CZ2 TRP 296   18.596 55.562 126.567 1.00 13.78      HIGL
ATOM  2391 CZ3 TRP 296   20.017 57.297 127.487 1.00 13.79      HIGL
ATOM  2392 CH2 TRP 296   19.624 55.953 127.390 1.00 14.10      HIGL
ATOM  2393 C   TRP 296   16.135 60.615 126.887 1.00 12.44      HIGL
ATOM  2394 O   TRP 296   16.964 61.202 127.582 1.00 11.79      HIGL
ATOM  2395 N   GLU 297   15.190 59.811 127.376 1.00 12.90      HIGL
ATOM  2396 CA  GLU 297   15.029 59.502 128.797 1.00 12.94      HIGL
ATOM  2397 CB  GLU 297   16.061 58.455 129.199 1.00 13.78      HIGL
ATOM  2398 CG  GLU 297   15.780 57.087 128.595 1.00 14.60      HIGL
ATOM  2399 CD  GLU 297   14.616 56.394 129.271 1.00 14.61      HIGL
ATOM  2400 OE1 GLU 297   13.947 57.031 130.112 1.00 13.68      HIGL
ATOM  2401 OE2 GLU 297   14.370 55.211 128.962 1.00 15.38      HIGL
ATOM  2402 C   GLU 297   15.089 60.687 129.749 1.00 13.20      HIGL
ATOM  2403 O   GLU 297   15.911 60.728 130.665 1.00 11.51      HIGL
ATOM  2404 N   PRO 298   14.185 61.659 129.563 1.00 14.35      HIGL
```

Fig. 2 cont.

```
ATOM   2405  CD    PRO  298      13.050  61.665 128.618  1.00 14.17      HIGL
ATOM   2406  CA    PRO  298      14.150  62.846 130.416  1.00 14.61      HIGL
ATOM   2407  CB    PRO  298      13.123  63.733 129.719  1.00 14.43      HIGL
ATOM   2408  CG    PRO  298      12.143  62.727 129.206  1.00 14.48      HIGL
ATOM   2409  C     PRO  298      13.750  62.555 131.857  1.00 14.61      HIGL
ATOM   2410  O     PRO  298      14.058  63.339 132.754  1.00 15.09      HIGL
ATOM   2411  N     ALA  299      13.082  61.427 132.080  1.00 14.64      HIGL
ATOM   2412  CA    ALA  299      12.601  61.093 133.419  1.00 15.80      HIGL
ATOM   2413  CB    ALA  299      11.089  60.869 133.372  1.00 15.02      HIGL
ATOM   2414  C     ALA  299      13.264  59.930 134.140  1.00 16.15      HIGL
ATOM   2415  O     ALA  299      12.746  59.459 135.148  1.00 15.99      HIGL
ATOM   2416  N     TRP  300      14.410  59.479 133.646  1.00 17.81      HIGL
ATOM   2417  CA    TRP  300      15.115  58.361 134.269  1.00 18.35      HIGL
ATOM   2418  CB    TRP  300      16.003  57.672 133.238  1.00 17.62      HIGL
ATOM   2419  CG    TRP  300      16.304  56.260 133.577  1.00 17.58      HIGL
ATOM   2420  CD2   TRP  300      16.887  55.281 132.714  1.00 18.60      HIGL
ATOM   2421  CE2   TRP  300      17.067  54.105 133.479  1.00 19.31      HIGL
ATOM   2422  CE3   TRP  300      17.281  55.283 131.369  1.00 17.87      HIGL
ATOM   2423  CD1   TRP  300      16.151  55.659 134.790  1.00 18.39      HIGL
ATOM   2424  NE1   TRP  300      16.608  54.365 134.743  1.00 18.74      HIGL
ATOM   2425  CZ2   TRP  300      17.630  52.938 132.942  1.00 19.15      HIGL
ATOM   2426  CZ3   TRP  300      17.843  54.123 130.835  1.00 18.15      HIGL
ATOM   2427  CH2   TRP  300      18.011  52.969 131.621  1.00 18.86      HIGL
ATOM   2428  C     TRP  300      15.967  58.852 135.441  1.00 19.00      HIGL
ATOM   2429  O     TRP  300      17.197  58.757 135.418  1.00 19.92      HIGL
ATOM   2430  N     ILE  301      15.299  59.358 136.473  1.00 18.81      HIGL
ATOM   2431  CA    ILE  301      15.975  59.908 137.637  1.00 18.49      HIGL
ATOM   2432  CB    ILE  301      14.955  60.382 138.686  1.00 18.53      HIGL
ATOM   2433  CG2   ILE  301      14.008  61.385 138.058  1.00 17.80      HIGL
ATOM   2434  CG1   ILE  301      14.161  59.196 139.226  1.00 20.04      HIGL
ATOM   2435  CD1   ILE  301      13.109  59.586 140.250  1.00 21.03      HIGL
ATOM   2436  C     ILE  301      17.002  59.006 138.311  1.00 18.58      HIGL
ATOM   2437  O     ILE  301      17.991  59.499 138.851  1.00 18.75      HIGL
ATOM   2438  N     HIS  302      16.786  57.696 138.286  1.00 18.55      HIGL
ATOM   2439  CA    HIS  302      17.741  56.781 138.907  1.00 18.79      HIGL
ATOM   2440  CB    HIS  302      17.041  55.490 139.329  1.00 18.93      HIGL
ATOM   2441  CG    HIS  302      16.222  55.629 140.573  1.00 18.69      HIGL
ATOM   2442  CD2   HIS  302      16.287  56.523 141.587  1.00 17.82      HIGL
ATOM   2443  ND1   HIS  302      15.191  54.769 140.884  1.00 18.89      HIGL
ATOM   2444  CE1   HIS  302      14.653  55.129 142.036  1.00 17.89      HIGL
ATOM   2445  NE2   HIS  302      15.300  56.191 142.483  1.00 17.70      HIGL
ATOM   2446  C     HIS  302      18.925  56.453 137.997  1.00 19.20      HIGL
ATOM   2447  O     HIS  302      19.703  55.542 138.289  1.00 19.21      HIGL
ATOM   2448  N     ASN  303      19.057  57.203 136.904  1.00 19.05      HIGL
ATOM   2449  CA    ASN  303      20.140  57.013 135.944  1.00 19.03      HIGL
ATOM   2450  CB    ASN  303      19.737  55.956 134.909  1.00 19.73      HIGL
ATOM   2451  CG    ASN  303      20.845  55.653 133.920  1.00 20.38      HIGL
ATOM   2452  OD1   ASN  303      22.026  55.600 134.286  1.00 20.50      HIGL
ATOM   2453  ND2   ASN  303      20.474  55.436 132.662  1.00 19.58      HIGL
ATOM   2454  C     ASN  303      20.425  58.352 135.265  1.00 19.33      HIGL
ATOM   2455  O     ASN  303      20.706  58.413 134.068  1.00 19.13      HIGL
ATOM   2456  N     ALA  304      20.360  59.414 136.071  1.00 19.41      HIGL
ATOM   2457  CA    ALA  304      20.562  60.804 135.654  1.00 18.77      HIGL
ATOM   2458  CB    ALA  304      20.840  61.662 136.876  1.00 17.04      HIGL
ATOM   2459  C     ALA  304      21.603  61.102 134.584  1.00 18.84      HIGL
ATOM   2460  O     ALA  304      21.340  61.883 133.671  1.00 19.33      HIGL
ATOM   2461  N     ASN  305      22.784  60.508 134.692  1.00 19.13      HIGL
ATOM   2462  CA    ASN  305      23.826  60.761 133.704  1.00 18.89      HIGL
ATOM   2463  CB    ASN  305      25.162  60.163 134.158  1.00 20.60      HIGL
ATOM   2464  CG    ASN  305      25.115  58.665 134.292  1.00 21.86      HIGL
ATOM   2465  OD1   ASN  305      24.345  58.119 135.085  1.00 23.48      HIGL
ATOM   2466  ND2   ASN  305      25.945  57.984 133.516  1.00 23.52      HIGL
ATOM   2467  C     ASN  305      23.448  60.207 132.343  1.00 18.26      HIGL
ATOM   2468  O     ASN  305      23.993  60.628 131.331  1.00 19.25      HIGL
ATOM   2469  N     LEU  306      22.507  59.269 132.323  1.00 17.83      HIGL
```

Fig. 2 cont.

```
ATOM   2470  CA   LEU   306      22.035  58.657 131.080  1.00 17.26           HIGL
ATOM   2471  CB   LEU   306      21.217  59.670 130.270  1.00 16.18           HIGL
ATOM   2472  CG   LEU   306      19.907  60.128 130.937  1.00 16.97           HIGL
ATOM   2473  CD1  LEU   306      19.284  61.278 130.161  1.00 15.17           HIGL
ATOM   2474  CD2  LEU   306      18.937  58.954 131.024  1.00 16.01           HIGL
ATOM   2475  C    LEU   306      23.156  58.076 130.216  1.00 17.50           HIGL
ATOM   2476  O    LEU   306      23.137  58.195 128.988  1.00 17.52           HIGL
ATOM   2477  N    GLY   307      24.131  57.450 130.870  1.00 17.26           HIGL
ATOM   2478  CA   GLY   307      25.235  56.836 130.159  1.00 16.70           HIGL
ATOM   2479  C    GLY   307      26.294  57.773 129.616  1.00 16.64           HIGL
ATOM   2480  O    GLY   307      27.191  57.333 128.901  1.00 16.25           HIGL
ATOM   2481  N    SER   308      26.204  59.056 129.950  1.00 16.62           HIGL
ATOM   2482  CA   SER   308      27.181  60.032 129.471  1.00 17.50           HIGL
ATOM   2483  CB   SER   308      26.477  61.300 128.987  1.00 17.40           HIGL
ATOM   2484  OG   SER   308      26.026  62.065 130.091  1.00 18.14           HIGL
ATOM   2485  C    SER   308      28.159  60.402 130.582  1.00 17.77           HIGL
ATOM   2486  O    SER   308      28.059  59.905 131.712  1.00 18.46           HIGL
ATOM   2487  N    SER   309      29.104  61.278 130.265  1.00 17.09           HIGL
ATOM   2488  CA   SER   309      30.074  61.693 131.263  1.00 17.48           HIGL
ATOM   2489  CB   SER   309      31.384  62.138 130.599  1.00 15.98           HIGL
ATOM   2490  OG   SER   309      31.196  63.287 129.794  1.00 15.84           HIGL
ATOM   2491  C    SER   309      29.485  62.818 132.118  1.00 17.77           HIGL
ATOM   2492  O    SER   309      30.100  63.268 133.084  1.00 17.93           HIGL
ATOM   2493  N    CYS   310      28.289  63.273 131.763  1.00 18.10           HIGL
ATOM   2494  CA   CYS   310      27.641  64.323 132.541  1.00 18.95           HIGL
ATOM   2495  C    CYS   310      26.881  63.668 133.695  1.00 18.10           HIGL
ATOM   2496  O    CYS   310      26.437  62.528 133.583  1.00 18.94           HIGL
ATOM   2497  CB   CYS   310      26.686  65.139 131.670  1.00 19.41           HIGL
ATOM   2498  SG   CYS   310      27.452  66.412 130.600  1.00 24.23           HIGL
ATOM   2499  N    ALA   311      26.733  64.392 134.798  1.00 16.72           HIGL
ATOM   2500  CA   ALA   311      26.061  63.873 135.986  1.00 15.09           HIGL
ATOM   2501  CB   ALA   311      26.451  64.713 137.187  1.00 13.34           HIGL
ATOM   2502  C    ALA   311      24.539  63.768 135.917  1.00 14.53           HIGL
ATOM   2503  O    ALA   311      23.959  62.805 136.416  1.00 14.36           HIGL
ATOM   2504  N    ASP   312      23.893  64.755 135.308  1.00 14.02           HIGL
ATOM   2505  CA   ASP   312      22.437  64.767 135.233  1.00 14.14           HIGL
ATOM   2506  CB   ASP   312      21.888  65.569 136.414  1.00 13.88           HIGL
ATOM   2507  CG   ASP   312      20.417  65.338 136.647  1.00 15.05           HIGL
ATOM   2508  OD1  ASP   312      19.703  64.943 135.692  1.00 16.00           HIGL
ATOM   2509  OD2  ASP   312      19.973  65.562 137.795  1.00 14.74           HIGL
ATOM   2510  C    ASP   312      21.910  65.376 133.932  1.00 14.14           HIGL
ATOM   2511  O    ASP   312      22.085  66.571 133.690  1.00 13.77           HIGL
ATOM   2512  N    ASN   313      21.260  64.555 133.108  1.00 14.50           HIGL
ATOM   2513  CA   ASN   313      20.684  65.016 131.845  1.00 15.03           HIGL
ATOM   2514  CB   ASN   313      21.177  64.160 130.672  1.00 16.08           HIGL
ATOM   2515  CG   ASN   313      22.633  64.403 130.337  1.00 18.13           HIGL
ATOM   2516  OD1  ASN   313      23.069  65.544 130.228  1.00 19.71           HIGL
ATOM   2517  ND2  ASN   313      23.391  63.326 130.159  1.00 17.96           HIGL
ATOM   2518  C    ASN   313      19.159  64.947 131.889  1.00 14.73           HIGL
ATOM   2519  O    ASN   313      18.491  65.155 130.881  1.00 14.78           HIGL
ATOM   2520  N    THR   314      18.608  64.649 133.057  1.00 15.17           HIGL
ATOM   2521  CA   THR   314      17.160  64.535 133.207  1.00 16.32           HIGL
ATOM   2522  CB   THR   314      16.794  63.799 134.499  1.00 16.08           HIGL
ATOM   2523  OG1  THR   314      17.198  64.596 135.619  1.00 16.57           HIGL
ATOM   2524  CG2  THR   314      17.497  62.452 134.563  1.00 15.34           HIGL
ATOM   2525  C    THR   314      16.444  65.878 133.237  1.00 16.22           HIGL
ATOM   2526  O    THR   314      17.033  66.908 133.551  1.00 17.07           HIGL
ATOM   2527  N    MET   315      15.161  65.851 132.911  1.00 16.05           HIGL
ATOM   2528  CA   MET   315      14.352  67.055 132.929  1.00 17.30           HIGL
ATOM   2529  CB   MET   315      13.588  67.205 131.613  1.00 17.97           HIGL
ATOM   2530  CG   MET   315      14.505  67.282 130.405  1.00 18.13           HIGL
ATOM   2531  SD   MET   315      13.637  67.606 128.894  1.00 18.76           HIGL
ATOM   2532  CE   MET   315      13.387  69.339 129.091  1.00 19.34           HIGL
ATOM   2533  C    MET   315      13.393  66.933 134.104  1.00 18.03           HIGL
ATOM   2534  O    MET   315      12.283  67.467 134.103  1.00 17.72           HIGL
```

Fig. 2 cont.

```
ATOM   2535  N    PHE  316      13.844  66.195 135.108  1.00 18.72           HIGL
ATOM   2536  CA   PHE  316      13.075  66.002 136.316  1.00 19.71           HIGL
ATOM   2537  CB   PHE  316      12.431  64.619 136.349  1.00 20.13           HIGL
ATOM   2538  CG   PHE  316      11.179  64.517 135.541  1.00 20.75           HIGL
ATOM   2539  CD1  PHE  316      11.232  64.450 134.153  1.00 21.09           HIGL
ATOM   2540  CD2  PHE  316       9.942  64.492 136.167  1.00 19.49           HIGL
ATOM   2541  CE1  PHE  316      10.065  64.359 133.402  1.00 20.74           HIGL
ATOM   2542  CE2  PHE  316       8.776  64.401 135.429  1.00 19.68           HIGL
ATOM   2543  CZ   PHE  316       8.836  64.335 134.041  1.00 20.74           HIGL
ATOM   2544  C    PHE  316      13.926  66.175 137.561  1.00 20.14           HIGL
ATOM   2545  O    PHE  316      15.155  66.134 137.528  1.00 21.09           HIGL
ATOM   2546  N    THR  317      13.232  66.386 138.662  1.00 20.18           HIGL
ATOM   2547  CA   THR  317      13.836  66.550 139.960  1.00 20.01           HIGL
ATOM   2548  CB   THR  317      12.783  67.140 140.933  1.00 19.47           HIGL
ATOM   2549  OG1  THR  317      13.102  68.508 141.196  1.00 20.10           HIGL
ATOM   2550  CG2  THR  317      12.710  66.363 142.215  1.00 18.19           HIGL
ATOM   2551  C    THR  317      14.271  65.161 140.408  1.00 20.33           HIGL
ATOM   2552  O    THR  317      13.739  64.155 139.939  1.00 20.58           HIGL
ATOM   2553  N    PRO  318      15.265  65.087 141.299  1.00 20.32           HIGL
ATOM   2554  CD   PRO  318      16.162  66.175 141.728  1.00 20.23           HIGL
ATOM   2555  CA   PRO  318      15.740  63.793 141.791  1.00 19.64           HIGL
ATOM   2556  CB   PRO  318      16.859  64.187 142.743  1.00 19.58           HIGL
ATOM   2557  CG   PRO  318      17.416  65.425 142.093  1.00 19.55           HIGL
ATOM   2558  C    PRO  318      14.615  63.044 142.498  1.00 19.76           HIGL
ATOM   2559  O    PRO  318      14.709  61.841 142.739  1.00 19.67           HIGL
ATOM   2560  N    SER  319      13.551  63.772 142.827  1.00 19.98           HIGL
ATOM   2561  CA   SER  319      12.403  63.195 143.504  1.00 20.20           HIGL
ATOM   2562  CB   SER  319      11.887  64.147 144.578  1.00 20.64           HIGL
ATOM   2563  OG   SER  319      11.025  65.119 144.016  1.00 23.02           HIGL
ATOM   2564  C    SER  319      11.291  62.889 142.504  1.00 20.42           HIGL
ATOM   2565  O    SER  319      10.263  62.305 142.861  1.00 20.64           HIGL
ATOM   2566  N    GLY  320      11.489  63.298 141.254  1.00 20.38           HIGL
ATOM   2567  CA   GLY  320      10.505  63.006 140.225  1.00 19.64           HIGL
ATOM   2568  C    GLY  320       9.585  64.119 139.765  1.00 19.52           HIGL
ATOM   2569  O    GLY  320       8.657  63.862 138.996  1.00 19.02           HIGL
ATOM   2570  N    GLN  321       9.833  65.347 140.213  1.00 18.90           HIGL
ATOM   2571  CA   GLN  321       8.991  66.475 139.824  1.00 19.06           HIGL
ATOM   2572  CB   GLN  321       8.940  67.520 140.948  1.00 20.13           HIGL
ATOM   2573  CG   GLN  321       8.219  68.811 140.564  1.00 22.26           HIGL
ATOM   2574  CD   GLN  321       7.946  69.703 141.762  1.00 23.01           HIGL
ATOM   2575  OE1  GLN  321       7.346  69.264 142.748  1.00 25.05           HIGL
ATOM   2576  NE2  GLN  321       8.377  70.958 141.682  1.00 20.98           HIGL
ATOM   2577  C    GLN  321       9.477  67.129 138.540  1.00 18.11           HIGL
ATOM   2578  O    GLN  321      10.639  67.520 138.428  1.00 17.69           HIGL
ATOM   2579  N    ALA  322       8.578  67.263 137.574  1.00 17.71           HIGL
ATOM   2580  CA   ALA  322       8.938  67.857 136.293  1.00 17.37           HIGL
ATOM   2581  CB   ALA  322       7.725  67.942 135.387  1.00 16.48           HIGL
ATOM   2582  C    ALA  322       9.546  69.231 136.466  1.00 17.45           HIGL
ATOM   2583  O    ALA  322       9.078  70.041 137.268  1.00 19.09           HIGL
ATOM   2584  N    LEU  323      10.601  69.476 135.706  1.00 17.15           HIGL
ATOM   2585  CA   LEU  323      11.305  70.743 135.720  1.00 16.94           HIGL
ATOM   2586  CB   LEU  323      12.755  70.512 135.299  1.00 16.28           HIGL
ATOM   2587  CG   LEU  323      13.901  70.773 136.279  1.00 15.82           HIGL
ATOM   2588  CD1  LEU  323      13.500  70.423 137.707  1.00 14.61           HIGL
ATOM   2589  CD2  LEU  323      15.113  69.964 135.823  1.00 14.44           HIGL
ATOM   2590  C    LEU  323      10.603  71.677 134.731  1.00 17.93           HIGL
ATOM   2591  O    LEU  323       9.883  71.225 133.838  1.00 16.70           HIGL
ATOM   2592  N    SER  324      10.811  72.980 134.893  1.00 18.92           HIGL
ATOM   2593  CA   SER  324      10.186  73.966 134.018  1.00 19.03           HIGL
ATOM   2594  CB   SER  324      10.663  75.370 134.383  1.00 19.54           HIGL
ATOM   2595  OG   SER  324      12.069  75.478 134.241  1.00 20.56           HIGL
ATOM   2596  C    SER  324      10.496  73.707 132.555  1.00 19.19           HIGL
ATOM   2597  O    SER  324       9.628  73.843 131.697  1.00 20.39           HIGL
ATOM   2598  N    SER  325      11.743  73.338 132.282  1.00 19.12           HIGL
ATOM   2599  CA   SER  325      12.217  73.073 130.927  1.00 18.61           HIGL
```

Fig. 2 cont.

```
ATOM   2600  CB   SER  325     13.681  72.639 130.980  1.00 18.82      HIGL
ATOM   2601  OG   SER  325     13.838  71.516 131.828  1.00 18.06      HIGL
ATOM   2602  C    SER  325     11.414  72.047 130.132  1.00 18.61      HIGL
ATOM   2603  O    SER  325     11.458  72.036 128.905  1.00 18.45      HIGL
ATOM   2604  N    LEU  326     10.680  71.184 130.820  1.00 19.28      HIGL
ATOM   2605  CA   LEU  326      9.893  70.167 130.132  1.00 19.85      HIGL
ATOM   2606  CB   LEU  326      9.212  69.243 131.145  1.00 20.13      HIGL
ATOM   2607  CG   LEU  326      9.112  67.733 130.862  1.00 22.13      HIGL
ATOM   2608  CD1  LEU  326      7.849  67.179 131.542  1.00 20.56      HIGL
ATOM   2609  CD2  LEU  326      9.063  67.453 129.364  1.00 21.71      HIGL
ATOM   2610  C    LEU  326      8.822  70.787 129.230  1.00 20.36      HIGL
ATOM   2611  O    LEU  326      8.415  70.187 128.233  1.00 19.41      HIGL
ATOM   2612  N    SER  327      8.363  71.986 129.580  1.00 20.97      HIGL
ATOM   2613  CA   SER  327      7.317  72.642 128.803  1.00 21.71      HIGL
ATOM   2614  CB   SER  327      6.595  73.684 129.653  1.00 21.54      HIGL
ATOM   2615  OG   SER  327      7.439  74.785 129.921  1.00 23.10      HIGL
ATOM   2616  C    SER  327      7.829  73.301 127.533  1.00 22.18      HIGL
ATOM   2617  O    SER  327      7.100  74.056 126.887  1.00 23.13      HIGL
ATOM   2618  N    VAL  328      9.080  73.032 127.180  1.00 21.90      HIGL
ATOM   2619  CA   VAL  328      9.651  73.588 125.959  1.00 22.31      HIGL
ATOM   2620  CB   VAL  328     11.188  73.333 125.873  1.00 22.21      HIGL
ATOM   2621  CG1  VAL  328     11.483  71.843 125.809  1.00 21.74      HIGL
ATOM   2622  CG2  VAL  328     11.759  74.026 124.657  1.00 21.78      HIGL
ATOM   2623  C    VAL  328      8.958  72.917 124.764  1.00 22.65      HIGL
ATOM   2624  O    VAL  328      8.973  73.429 123.645  1.00 22.63      HIGL
ATOM   2625  N    PHE  329      8.338  71.771 125.013  1.00 22.73      HIGL
ATOM   2626  CA   PHE  329      7.654  71.048 123.959  1.00 23.91      HIGL
ATOM   2627  CB   PHE  329      7.268  69.658 124.454  1.00 23.67      HIGL
ATOM   2628  CG   PHE  329      8.440  68.723 124.557  1.00 24.39      HIGL
ATOM   2629  CD1  PHE  329      9.067  68.252 123.409  1.00 24.10      HIGL
ATOM   2630  CD2  PHE  329      8.949  68.349 125.796  1.00 23.95      HIGL
ATOM   2631  CE1  PHE  329     10.185  67.424 123.491  1.00 24.86      HIGL
ATOM   2632  CE2  PHE  329     10.063  67.524 125.887  1.00 24.79      HIGL
ATOM   2633  CZ   PHE  329     10.686  67.060 124.729  1.00 24.99      HIGL
ATOM   2634  C    PHE  329      6.446  71.806 123.420  1.00 24.94      HIGL
ATOM   2635  O    PHE  329      5.885  71.438 122.384  1.00 24.54      HIGL
ATOM   2636  N    HIS  330      6.053  72.867 124.123  1.00 25.53      HIGL
ATOM   2637  CA   HIS  330      4.944  73.706 123.677  1.00 25.92      HIGL
ATOM   2638  CB   HIS  330      4.376  74.554 124.828  1.00 25.05      HIGL
ATOM   2639  CG   HIS  330      3.507  73.795 125.786  1.00 23.98      HIGL
ATOM   2640  CD2  HIS  330      3.511  73.739 127.139  1.00 23.72      HIGL
ATOM   2641  ND1  HIS  330      2.451  73.010 125.377  1.00 23.63      HIGL
ATOM   2642  CE1  HIS  330      1.843  72.503 126.434  1.00 22.96      HIGL
ATOM   2643  NE2  HIS  330      2.467  72.931 127.517  1.00 23.30      HIGL
ATOM   2644  C    HIS  330      5.488  74.650 122.601  1.00 26.65      HIGL
ATOM   2645  O    HIS  330      4.891  74.806 121.540  1.00 27.30      HIGL
ATOM   2646  N    ARG  331      6.632  75.267 122.888  1.00 27.80      HIGL
ATOM   2647  CA   ARG  331      7.273  76.214 121.976  1.00 28.68      HIGL
ATOM   2648  CB   ARG  331      8.405  76.953 122.698  1.00 31.32      HIGL
ATOM   2649  CG   ARG  331      7.935  78.120 123.555  1.00 35.13      HIGL
ATOM   2650  CD   ARG  331      9.101  78.976 124.057  1.00 37.60      HIGL
ATOM   2651  NE   ARG  331      9.862  78.322 125.116  1.00 39.32      HIGL
ATOM   2652  CZ   ARG  331      9.311  77.800 126.208  1.00 41.08      HIGL
ATOM   2653  NH1  ARG  331      7.994  77.854 126.382  1.00 41.70      HIGL
ATOM   2654  NH2  ARG  331     10.075  77.233 127.133  1.00 41.35      HIGL
ATOM   2655  C    ARG  331      7.821  75.668 120.661  1.00 28.01      HIGL
ATOM   2656  O    ARG  331      8.119  76.440 119.753  1.00 28.33      HIGL
ATOM   2657  N    ILE  332      7.966  74.355 120.545  1.00 27.15      HIGL
ATOM   2658  CA   ILE  332      8.503  73.790 119.313  1.00 25.82      HIGL
ATOM   2659  CB   ILE  332      9.717  72.876 119.596  1.00 24.07      HIGL
ATOM   2660  CG2  ILE  332     10.747  73.636 120.419  1.00 22.61      HIGL
ATOM   2661  CG1  ILE  332      9.262  71.611 120.331  1.00 23.55      HIGL
ATOM   2662  CD1  ILE  332     10.328  70.559 120.487  1.00 21.73      HIGL
ATOM   2663  C    ILE  332      7.463  72.999 118.534  1.00 26.35      HIGL
ATOM   2664  O    ILE  332      7.659  72.716 117.351  1.00 27.46      HIGL
END
```

Fig. 2 cont.

```
HEADER                                                               AAGL
ATOM      1  CB  ALA     1      30.233  36.166 100.975  1.00 33.89   AAGL
ATOM      2  C   ALA     1      30.173  35.826 103.455  1.00 33.23   AAGL
ATOM      3  O   ALA     1      30.978  35.045 103.960  1.00 32.69   AAGL
ATOM      4  N   ALA     1      32.066  36.993 102.404  1.00 32.99   AAGL
ATOM      5  CA  ALA     1      30.595  36.767 102.330  1.00 33.73   AAGL
ATOM      6  N   LEU     2      28.909  35.906 103.856  1.00 31.18   AAGL
ATOM      7  CA  LEU     2      28.412  35.052 104.926  1.00 29.30   AAGL
ATOM      8  CB  LEU     2      27.023  35.510 105.362  1.00 29.79   AAGL
ATOM      9  CG  LEU     2      26.868  36.944 105.864  1.00 30.10   AAGL
ATOM     10  CD1 LEU     2      25.382  37.292 105.912  1.00 32.47   AAGL
ATOM     11  CD2 LEU     2      27.511  37.098 107.236  1.00 30.25   AAGL
ATOM     12  C   LEU     2      28.340  33.612 104.451  1.00 28.19   AAGL
ATOM     13  O   LEU     2      28.258  33.351 103.250  1.00 28.93   AAGL
ATOM     14  N   THR     3      28.370  32.679 105.396  1.00 27.70   AAGL
ATOM     15  CA  THR     3      28.304  31.267 105.071  1.00 27.25   AAGL
ATOM     16  CB  THR     3      28.401  30.410 106.349  1.00 28.42   AAGL
ATOM     17  OG1 THR     3      29.650  30.681 107.001  1.00 28.17   AAGL
ATOM     18  CG2 THR     3      28.327  28.920 106.010  1.00 27.90   AAGL
ATOM     19  C   THR     3      27.000  30.971 104.343  1.00 26.98   AAGL
ATOM     20  O   THR     3      26.965  30.159 103.416  1.00 26.10   AAGL
ATOM     21  N   TYR     4      25.931  31.650 104.756  1.00 26.84   AAGL
ATOM     22  CA  TYR     4      24.623  31.465 104.137  1.00 24.81   AAGL
ATOM     23  CB  TYR     4      23.665  30.721 105.079  1.00 25.74   AAGL
ATOM     24  CG  TYR     4      24.137  29.377 105.602  1.00 25.74   AAGL
ATOM     25  CD1 TYR     4      24.318  28.288 104.746  1.00 26.33   AAGL
ATOM     26  CE1 TYR     4      24.692  27.034 105.247  1.00 27.71   AAGL
ATOM     27  CD2 TYR     4      24.349  29.182 106.965  1.00 25.74   AAGL
ATOM     28  CE2 TYR     4      24.724  27.940 107.473  1.00 26.87   AAGL
ATOM     29  CZ  TYR     4      24.891  26.870 106.609  1.00 26.22   AAGL
ATOM     30  OH  TYR     4      25.248  25.646 107.118  1.00 29.24   AAGL
ATOM     31  C   TYR     4      23.977  32.803 103.787  1.00 24.69   AAGL
ATOM     32  O   TYR     4      23.914  33.712 104.619  1.00 24.65   AAGL
ATOM     33  N   ARG     5      23.515  32.919 102.549  1.00 23.45   AAGL
ATOM     34  CA  ARG     5      22.801  34.103 102.069  1.00 25.24   AAGL
ATOM     35  CB  ARG     5      23.551  34.823 100.939  1.00 29.22   AAGL
ATOM     36  CG  ARG     5      24.781  35.609 101.366  1.00 29.88   AAGL
ATOM     37  CD  ARG     5      26.042  34.797 101.168  1.00 29.48   AAGL
ATOM     38  NE  ARG     5      26.159  34.336  99.792  1.00 29.78   AAGL
ATOM     39  CZ  ARG     5      27.061  33.454  99.373  1.00 27.81   AAGL
ATOM     40  NH1 ARG     5      27.934  32.940 100.225  1.00 27.49   AAGL
ATOM     41  NH2 ARG     5      27.068  33.068  98.104  1.00 29.30   AAGL
ATOM     42  C   ARG     5      21.554  33.439 101.507  1.00 25.34   AAGL
ATOM     43  O   ARG     5      21.547  32.962 100.371  1.00 23.77   AAGL
ATOM     44  N   GLY     6      20.502  33.381 102.308  1.00 24.34   AAGL
ATOM     45  CA  GLY     6      19.321  32.694 101.837  1.00 21.41   AAGL
ATOM     46  C   GLY     6      18.031  33.457 101.755  1.00 22.93   AAGL
ATOM     47  O   GLY     6      17.957  34.649 102.053  1.00 21.36   AAGL
ATOM     48  N   ALA     7      17.008  32.727 101.330  1.00 21.72   AAGL
ATOM     49  CA  ALA     7      15.669  33.248 101.182  1.00 22.02   AAGL
ATOM     50  CB  ALA     7      15.481  33.797  99.780  1.00 22.89   AAGL
ATOM     51  C   ALA     7      14.689  32.110 101.422  1.00 21.79   AAGL
ATOM     52  O   ALA     7      14.973  30.956 101.101  1.00 23.27   AAGL
ATOM     53  N   ASP     8      13.548  32.435 102.014  1.00 20.87   AAGL
ATOM     54  CA  ASP     8      12.501  31.448 102.247  1.00 21.47   AAGL
ATOM     55  CB  ASP     8      11.854  31.650 103.625  1.00 20.38   AAGL
ATOM     56  CG  ASP     8      10.772  30.617 103.923  1.00 20.93   AAGL
ATOM     57  OD1 ASP     8       9.920  30.363 103.044  1.00 20.43   AAGL
ATOM     58  OD2 ASP     8      10.768  30.069 105.048  1.00 19.51   AAGL
ATOM     59  C   ASP     8      11.482  31.736 101.153  1.00 19.96   AAGL
ATOM     60  O   ASP     8      10.773  32.738 101.205  1.00 21.04   AAGL
ATOM     61  N   ILE     9      11.424  30.870 100.149  1.00 20.91   AAGL
ATOM     62  CA  ILE     9      10.490  31.065  99.049  1.00 21.73   AAGL
ATOM     63  CB  ILE     9      11.234  31.102  97.689  1.00 21.80   AAGL
ATOM     64  CG2 ILE     9      12.174  32.300  97.648  1.00 23.18   AAGL
ATOM     65  CG1 ILE     9      12.015  29.807  97.479  1.00 22.70   AAGL
```

Fig. 3

```
ATOM     66  CD1 ILE     9      12.626  29.683  96.085  1.00 25.10           AAGL
ATOM     67  C   ILE     9       9.452  29.945  99.038  1.00 23.69           AAGL
ATOM     68  O   ILE     9       9.018  29.490  97.984  1.00 22.97           AAGL
ATOM     69  N   SER    10       9.059  29.511 100.232  1.00 22.26           AAGL
ATOM     70  CA  SER    10       8.080  28.441 100.377  1.00 22.83           AAGL
ATOM     71  CB  SER    10       7.658  28.325 101.840  1.00 20.03           AAGL
ATOM     72  OG  SER    10       8.782  28.078 102.658  1.00 21.43           AAGL
ATOM     73  C   SER    10       6.833  28.617  99.508  1.00 22.20           AAGL
ATOM     74  O   SER    10       6.286  27.649  98.995  1.00 24.50           AAGL
ATOM     75  N   SER    11       6.388  29.855  99.347  1.00 23.05           AAGL
ATOM     76  CA  SER    11       5.198  30.148  98.563  1.00 24.59           AAGL
ATOM     77  CB  SER    11       4.784  31.598  98.792  1.00 26.58           AAGL
ATOM     78  OG  SER    11       5.775  32.473  98.275  1.00 26.05           AAGL
ATOM     79  C   SER    11       5.347  29.935  97.057  1.00 25.49           AAGL
ATOM     80  O   SER    11       4.351  29.913  96.338  1.00 25.69           AAGL
ATOM     81  N   LEU    12       6.578  29.781  96.583  1.00 26.51           AAGL
ATOM     82  CA  LEU    12       6.817  29.637  95.149  1.00 25.87           AAGL
ATOM     83  CB  LEU    12       8.237  29.143  94.884  1.00 26.84           AAGL
ATOM     84  CG  LEU    12       8.609  29.025  93.398  1.00 26.26           AAGL
ATOM     85  CD1 LEU    12       8.307  30.324  92.665  1.00 26.19           AAGL
ATOM     86  CD2 LEU    12      10.078  28.685  93.273  1.00 28.47           AAGL
ATOM     87  C   LEU    12       5.844  28.768  94.362  1.00 28.42           AAGL
ATOM     88  O   LEU    12       5.181  29.257  93.447  1.00 28.84           AAGL
ATOM     89  N   LEU    13       5.758  27.487  94.701  1.00 28.60           AAGL
ATOM     90  CA  LEU    13       4.879  26.590  93.963  1.00 30.83           AAGL
ATOM     91  CB  LEU    13       4.997  25.164  94.514  1.00 30.59           AAGL
ATOM     92  CG  LEU    13       6.443  24.657  94.640  1.00 29.90           AAGL
ATOM     93  CD1 LEU    13       6.441  23.200  95.044  1.00 30.84           AAGL
ATOM     94  CD2 LEU    13       7.179  24.821  93.315  1.00 31.95           AAGL
ATOM     95  C   LEU    13       3.430  27.062  93.967  1.00 31.99           AAGL
ATOM     96  O   LEU    13       2.703  26.844  93.001  1.00 33.62           AAGL
ATOM     97  N   LEU    14       3.008  27.725  95.038  1.00 33.18           AAGL
ATOM     98  CA  LEU    14       1.639  28.226  95.106  1.00 33.64           AAGL
ATOM     99  CB  LEU    14       1.289  28.683  96.523  1.00 34.87           AAGL
ATOM    100  CG  LEU    14       0.959  27.561  97.502  1.00 35.78           AAGL
ATOM    101  CD1 LEU    14       0.492  28.145  98.828  1.00 36.41           AAGL
ATOM    102  CD2 LEU    14      -0.137  26.693  96.895  1.00 37.20           AAGL
ATOM    103  C   LEU    14       1.423  29.385  94.141  1.00 34.86           AAGL
ATOM    104  O   LEU    14       0.352  29.522  93.551  1.00 33.97           AAGL
ATOM    105  N   LEU    15       2.443  30.218  93.978  1.00 34.48           AAGL
ATOM    106  CA  LEU    15       2.344  31.359  93.080  1.00 35.10           AAGL
ATOM    107  CB  LEU    15       3.428  32.390  93.415  1.00 35.52           AAGL
ATOM    108  CG  LEU    15       3.232  33.227  94.696  1.00 37.21           AAGL
ATOM    109  CD1 LEU    15       2.912  32.357  95.879  1.00 37.69           AAGL
ATOM    110  CD2 LEU    15       4.496  34.018  94.975  1.00 35.91           AAGL
ATOM    111  C   LEU    15       2.458  30.904  91.624  1.00 35.48           AAGL
ATOM    112  O   LEU    15       1.647  31.306  90.782  1.00 35.67           AAGL
ATOM    113  N   GLU    16       3.449  30.065  91.329  1.00 35.68           AAGL
ATOM    114  CA  GLU    16       3.619  29.561  89.966  1.00 37.14           AAGL
ATOM    115  CB  GLU    16       4.747  28.527  89.890  1.00 35.01           AAGL
ATOM    116  CG  GLU    16       6.159  29.083  90.020  1.00 34.68           AAGL
ATOM    117  CD  GLU    16       7.214  27.993  89.905  1.00 35.45           AAGL
ATOM    118  OE1 GLU    16       6.928  26.849  90.317  1.00 35.57           AAGL
ATOM    119  OE2 GLU    16       8.336  28.271  89.419  1.00 35.12           AAGL
ATOM    120  C   GLU    16       2.317  28.913  89.527  1.00 39.70           AAGL
ATOM    121  O   GLU    16       1.846  29.139  88.411  1.00 40.81           AAGL
ATOM    122  N   ASP    17       1.727  28.112  90.411  1.00 41.41           AAGL
ATOM    123  CA  ASP    17       0.470  27.444  90.099  1.00 44.13           AAGL
ATOM    124  CB  ASP    17       0.029  26.557  91.262  1.00 44.94           AAGL
ATOM    125  CG  ASP    17       0.510  25.127  91.117  1.00 47.20           AAGL
ATOM    126  OD1 ASP    17       0.423  24.359  92.103  1.00 47.97           AAGL
ATOM    127  OD2 ASP    17       0.959  24.757  90.006  1.00 50.11           AAGL
ATOM    128  C   ASP    17      -0.625  28.447  89.771  1.00 45.54           AAGL
ATOM    129  O   ASP    17      -1.458  28.195  88.896  1.00 47.39           AAGL
ATOM    130  N   GLU    18      -0.629  29.581  90.471  1.00 45.43           AAGL
ATOM    131  CA  GLU    18      -1.625  30.617  90.234  1.00 47.08           AAGL
```

Fig. 3 cont.

```
ATOM    132  CB  GLU    18    -1.762  31.537  91.458  1.00 49.00     AAGL
ATOM    133  CG  GLU    18    -2.526  30.900  92.622  1.00 52.65     AAGL
ATOM    134  CD  GLU    18    -2.530  31.755  93.890  1.00 55.02     AAGL
ATOM    135  OE1 GLU    18    -3.112  31.305  94.911  1.00 55.65     AAGL
ATOM    136  OE2 GLU    18    -1.953  32.870  93.870  1.00 56.34     AAGL
ATOM    137  C   GLU    18    -1.267  31.432  88.994  1.00 46.48     AAGL
ATOM    138  O   GLU    18    -1.845  32.492  88.743  1.00 46.57     AAGL
ATOM    139  N   GLY    19    -0.307  30.929  88.223  1.00 45.75     AAGL
ATOM    140  CA  GLY    19     0.091  31.609  87.006  1.00 45.53     AAGL
ATOM    141  C   GLY    19     1.245  32.588  87.113  1.00 45.29     AAGL
ATOM    142  O   GLY    19     1.636  33.185  86.113  1.00 44.87     AAGL
ATOM    143  N   TYR    20     1.802  32.758  88.309  1.00 44.55     AAGL
ATOM    144  CA  TYR    20     2.911  33.685  88.497  1.00 44.04     AAGL
ATOM    145  CB  TYR    20     3.098  33.987  89.985  1.00 46.33     AAGL
ATOM    146  CG  TYR    20     2.199  35.092  90.475  1.00 46.92     AAGL
ATOM    147  CD1 TYR    20     1.174  34.837  91.384  1.00 47.92     AAGL
ATOM    148  CE1 TYR    20     0.317  35.856  91.804  1.00 48.81     AAGL
ATOM    149  CD2 TYR    20     2.351  36.388  89.995  1.00 48.25     AAGL
ATOM    150  CE2 TYR    20     1.509  37.406  90.399  1.00 48.75     AAGL
ATOM    151  CZ  TYR    20     0.494  37.135  91.301  1.00 49.08     AAGL
ATOM    152  OH  TYR    20    -0.350  38.146  91.676  1.00 50.05     AAGL
ATOM    153  C   TYR    20     4.243  33.232  87.916  1.00 42.70     AAGL
ATOM    154  O   TYR    20     4.541  32.043  87.857  1.00 41.19     AAGL
ATOM    155  N   SER    21     5.040  34.211  87.494  1.00 42.54     AAGL
ATOM    156  CA  SER    21     6.360  33.981  86.918  1.00 42.59     AAGL
ATOM    157  CB  SER    21     6.255  33.775  85.402  1.00 43.78     AAGL
ATOM    158  OG  SER    21     5.527  34.835  84.790  1.00 44.41     AAGL
ATOM    159  C   SER    21     7.191  35.224  87.221  1.00 41.81     AAGL
ATOM    160  O   SER    21     6.639  36.307  87.421  1.00 42.15     AAGL
ATOM    161  N   TYR    22     8.510  35.075  87.260  1.00 40.81     AAGL
ATOM    162  CA  TYR    22     9.382  36.205  87.558  1.00 40.63     AAGL
ATOM    163  CB  TYR    22    10.143  35.955  88.855  1.00 39.48     AAGL
ATOM    164  CG  TYR    22     9.248  35.579  90.010  1.00 37.92     AAGL
ATOM    165  CD1 TYR    22     8.820  34.261  90.186  1.00 35.93     AAGL
ATOM    166  CE1 TYR    22     7.987  33.913  91.246  1.00 35.62     AAGL
ATOM    167  CD2 TYR    22     8.820  36.540  90.921  1.00 37.21     AAGL
ATOM    168  CE2 TYR    22     7.982  36.204  91.982  1.00 35.75     AAGL
ATOM    169  CZ  TYR    22     7.574  34.897  92.140  1.00 36.41     AAGL
ATOM    170  OH  TYR    22     6.761  34.573  93.196  1.00 34.78     AAGL
ATOM    171  C   TYR    22    10.385  36.498  86.455  1.00 41.14     AAGL
ATOM    172  O   TYR    22    10.607  35.672  85.568  1.00 40.90     AAGL
ATOM    173  N   LYS    23    10.990  37.684  86.532  1.00 40.98     AAGL
ATOM    174  CA  LYS    23    11.987  38.131  85.565  1.00 41.42     AAGL
ATOM    175  CB  LYS    23    11.430  39.257  84.690  1.00 44.58     AAGL
ATOM    176  CG  LYS    23    10.779  38.781  83.398  1.00 49.11     AAGL
ATOM    177  CD  LYS    23     9.379  38.262  83.633  1.00 51.49     AAGL
ATOM    178  CE  LYS    23     8.453  39.401  84.042  1.00 52.49     AAGL
ATOM    179  NZ  LYS    23     8.461  40.487  83.021  1.00 51.35     AAGL
ATOM    180  C   LYS    23    13.248  38.634  86.243  1.00 40.33     AAGL
ATOM    181  O   LYS    23    13.184  39.363  87.241  1.00 39.11     AAGL
ATOM    182  N   ASN    24    14.396  38.246  85.693  1.00 38.79     AAGL
ATOM    183  CA  ASN    24    15.682  38.672  86.226  1.00 40.03     AAGL
ATOM    184  CB  ASN    24    16.807  37.935  85.509  1.00 42.29     AAGL
ATOM    185  CG  ASN    24    16.738  38.104  84.004  1.00 42.84     AAGL
ATOM    186  OD1 ASN    24    16.732  39.224  83.497  1.00 43.55     AAGL
ATOM    187  ND2 ASN    24    16.675  36.993  83.282  1.00 45.13     AAGL
ATOM    188  C   ASN    24    15.840  40.178  86.018  1.00 40.98     AAGL
ATOM    189  O   ASN    24    14.938  40.837  85.494  1.00 38.96     AAGL
ATOM    190  N   LEU    25    16.987  40.720  86.423  1.00 42.28     AAGL
ATOM    191  CA  LEU    25    17.246  42.149  86.283  1.00 44.49     AAGL
ATOM    192  CB  LEU    25    18.528  42.543  87.032  1.00 44.66     AAGL
ATOM    193  CG  LEU    25    18.549  42.643  88.563  1.00 45.79     AAGL
ATOM    194  CD1 LEU    25    17.376  43.494  89.037  1.00 45.23     AAGL
ATOM    195  CD2 LEU    25    18.493  41.252  89.189  1.00 46.13     AAGL
ATOM    196  C   LEU    25    17.345  42.614  84.824  1.00 45.76     AAGL
ATOM    197  O   LEU    25    17.454  43.814  84.562  1.00 46.23     AAGL
```

Fig. 3 cont.

```
ATOM    198  N    ASN   26      17.311  41.675  83.880  1.00 46.41      AAGL
ATOM    199  CA   ASN   26      17.365  42.021  82.455  1.00 47.05      AAGL
ATOM    200  CB   ASN   26      18.288  41.066  81.676  1.00 47.42      AAGL
ATOM    201  CG   ASN   26      19.747  41.198  82.074  1.00 49.18      AAGL
ATOM    202  OD1  ASN   26      20.207  42.276  82.459  1.00 49.93      AAGL
ATOM    203  ND2  ASN   26      20.492  40.100  81.961  1.00 49.97      AAGL
ATOM    204  C    ASN   26      15.966  41.947  81.848  1.00 47.00      AAGL
ATOM    205  O    ASN   26      15.796  42.082  80.634  1.00 47.34      AAGL
ATOM    206  N    GLY   27      14.961  41.712  82.684  1.00 45.83      AAGL
ATOM    207  CA   GLY   27      13.602  41.628  82.176  1.00 45.48      AAGL
ATOM    208  C    GLY   27      13.343  40.327  81.436  1.00 45.43      AAGL
ATOM    209  O    GLY   27      12.388  40.225  80.669  1.00 46.84      AAGL
ATOM    210  N    GLN   28      14.198  39.332  81.648  1.00 45.03      AAGL
ATOM    211  CA   GLN   28      14.023  38.037  81.002  1.00 44.89      AAGL
ATOM    212  CB   GLN   28      15.385  37.428  80.633  1.00 46.09      AAGL
ATOM    213  CG   GLN   28      16.346  38.371  79.909  1.00 48.72      AAGL
ATOM    214  CD   GLN   28      17.649  37.684  79.531  1.00 49.91      AAGL
ATOM    215  OE1  GLN   28      17.674  36.802  78.668  1.00 51.23      AAGL
ATOM    216  NE2  GLN   28      18.740  38.075  80.187  1.00 51.05      AAGL
ATOM    217  C    GLN   28      13.312  37.093  81.980  1.00 43.57      AAGL
ATOM    218  O    GLN   28      13.800  36.871  83.088  1.00 40.72      AAGL
ATOM    219  N    THR   29      12.166  36.542  81.580  1.00 42.64      AAGL
ATOM    220  CA   THR   29      11.441  35.610  82.445  1.00 42.01      AAGL
ATOM    221  CB   THR   29      10.201  35.022  81.746  1.00 42.12      AAGL
ATOM    222  OG1  THR   29       9.191  36.030  81.626  1.00 42.02      AAGL
ATOM    223  CG2  THR   29       9.639  33.857  82.552  1.00 41.97      AAGL
ATOM    224  C    THR   29      12.393  34.472  82.787  1.00 41.90      AAGL
ATOM    225  O    THR   29      13.233  34.095  81.966  1.00 41.33      AAGL
ATOM    226  N    GLN   30      12.261  33.909  83.984  1.00 40.58      AAGL
ATOM    227  CA   GLN   30      13.158  32.835  84.392  1.00 39.49      AAGL
ATOM    228  CB   GLN   30      14.585  33.383  84.396  1.00 40.50      AAGL
ATOM    229  CG   GLN   30      15.604  32.528  85.100  1.00 43.69      AAGL
ATOM    230  CD   GLN   30      17.014  33.031  84.892  1.00 46.36      AAGL
ATOM    231  OE1  GLN   30      17.325  34.200  85.159  1.00 45.16      AAGL
ATOM    232  NE2  GLN   30      17.888  32.145  84.409  1.00 47.79      AAGL
ATOM    233  C    GLN   30      12.790  32.268  85.763  1.00 38.44      AAGL
ATOM    234  O    GLN   30      12.368  33.004  86.656  1.00 38.87      AAGL
ATOM    235  N    ALA   31      12.946  30.958  85.929  1.00 36.80      AAGL
ATOM    236  CA   ALA   31      12.617  30.314  87.202  1.00 34.49      AAGL
ATOM    237  CB   ALA   31      13.079  28.855  87.186  1.00 34.38      AAGL
ATOM    238  C    ALA   31      13.261  31.059  88.371  1.00 32.91      AAGL
ATOM    239  O    ALA   31      14.474  31.278  88.392  1.00 32.07      AAGL
ATOM    240  N    LEU   32      12.441  31.432  89.352  1.00 33.31      AAGL
ATOM    241  CA   LEU   32      12.914  32.180  90.522  1.00 29.54      AAGL
ATOM    242  CB   LEU   32      11.809  32.294  91.574  1.00 28.70      AAGL
ATOM    243  CG   LEU   32      12.229  33.100  92.815  1.00 26.84      AAGL
ATOM    244  CD1  LEU   32      12.430  34.545  92.422  1.00 26.55      AAGL
ATOM    245  CD2  LEU   32      11.173  32.985  93.916  1.00 26.84      AAGL
ATOM    246  C    LEU   32      14.160  31.618  91.192  1.00 30.30      AAGL
ATOM    247  O    LEU   32      15.068  32.375  91.545  1.00 29.24      AAGL
ATOM    248  N    GLU   33      14.205  30.304  91.387  1.00 29.20      AAGL
ATOM    249  CA   GLU   33      15.360  29.698  92.036  1.00 29.33      AAGL
ATOM    250  CB   GLU   33      15.164  28.184  92.223  1.00 30.11      AAGL
ATOM    251  CG   GLU   33      15.225  27.380  90.934  1.00 32.96      AAGL
ATOM    252  CD   GLU   33      13.872  27.167  90.294  1.00 32.82      AAGL
ATOM    253  OE1  GLU   33      12.979  28.030  90.451  1.00 32.32      AAGL
ATOM    254  OE2  GLU   33      13.706  26.126  89.609  1.00 34.46      AAGL
ATOM    255  C    GLU   33      16.641  29.949  91.242  1.00 30.20      AAGL
ATOM    256  O    GLU   33      17.708  30.125  91.828  1.00 30.32      AAGL
ATOM    257  N    THR   34      16.544  29.967  89.912  1.00 31.16      AAGL
ATOM    258  CA   THR   34      17.734  30.197  89.102  1.00 32.16      AAGL
ATOM    259  CB   THR   34      17.545  29.703  87.636  1.00 34.39      AAGL
ATOM    260  OG1  THR   34      16.690  30.598  86.916  1.00 39.01      AAGL
ATOM    261  CG2  THR   34      16.915  28.315  87.628  1.00 33.29      AAGL
ATOM    262  C    THR   34      18.100  31.677  89.120  1.00 30.19      AAGL
ATOM    263  O    THR   34      19.269  32.027  89.031  1.00 32.36      AAGL
```

Fig. 3 cont.

```
ATOM    264  N    ILE   35      17.101  32.542  89.254  1.00 29.48      AAGL
ATOM    265  CA   ILE   35      17.343  33.982  89.318  1.00 29.20      AAGL
ATOM    266  CB   ILE   35      16.030  34.783  89.364  1.00 29.36      AAGL
ATOM    267  CG2  ILE   35      16.329  36.253  89.647  1.00 32.47      AAGL
ATOM    268  CG1  ILE   35      15.265  34.620  88.052  1.00 30.39      AAGL
ATOM    269  CD1  ILE   35      13.998  35.456  87.981  1.00 32.09      AAGL
ATOM    270  C    ILE   35      18.103  34.276  90.605  1.00 29.48      AAGL
ATOM    271  O    ILE   35      19.039  35.068  90.627  1.00 28.30      AAGL
ATOM    272  N    LEU   36      17.676  33.631  91.684  1.00 28.93      AAGL
ATOM    273  CA   LEU   36      18.297  33.809  92.989  1.00 27.40      AAGL
ATOM    274  CB   LEU   36      17.420  33.142  94.050  1.00 29.01      AAGL
ATOM    275  CG   LEU   36      16.067  33.824  94.220  1.00 29.41      AAGL
ATOM    276  CD1  LEU   36      15.139  32.993  95.105  1.00 32.23      AAGL
ATOM    277  CD2  LEU   36      16.318  35.198  94.831  1.00 29.88      AAGL
ATOM    278  C    LEU   36      19.693  33.220  93.036  1.00 26.84      AAGL
ATOM    279  O    LEU   36      20.630  33.840  93.542  1.00 26.88      AAGL
ATOM    280  N    ALA   37      19.829  32.005  92.515  1.00 28.77      AAGL
ATOM    281  CA   ALA   37      21.118  31.325  92.509  1.00 30.25      AAGL
ATOM    282  CB   ALA   37      20.988  29.971  91.805  1.00 29.94      AAGL
ATOM    283  C    ALA   37      22.185  32.180  91.827  1.00 29.84      AAGL
ATOM    284  O    ALA   37      23.274  32.373  92.365  1.00 30.61      AAGL
ATOM    285  N    ASP   38      21.856  32.706  90.652  1.00 30.68      AAGL
ATOM    286  CA   ASP   38      22.798  33.524  89.894  1.00 31.88      AAGL
ATOM    287  CB   ASP   38      22.240  33.843  88.508  1.00 32.57      AAGL
ATOM    288  CG   ASP   38      22.007  32.603  87.673  1.00 36.25      AAGL
ATOM    289  OD1  ASP   38      22.749  31.610  87.859  1.00 36.97      AAGL
ATOM    290  OD2  ASP   38      21.085  32.621  86.830  1.00 37.38      AAGL
ATOM    291  C    ASP   38      23.127  34.824  90.601  1.00 31.89      AAGL
ATOM    292  O    ASP   38      24.174  35.423  90.353  1.00 33.41      AAGL
ATOM    293  N    ALA   39      22.226  35.265  91.476  1.00 31.50      AAGL
ATOM    294  CA   ALA   39      22.433  36.503  92.207  1.00 29.58      AAGL
ATOM    295  CB   ALA   39      21.088  37.099  92.626  1.00 29.62      AAGL
ATOM    296  C    ALA   39      23.319  36.300  93.423  1.00 29.11      AAGL
ATOM    297  O    ALA   39      23.739  37.268  94.053  1.00 28.08      AAGL
ATOM    298  N    GLY   40      23.603  35.047  93.769  1.00 28.38      AAGL
ATOM    299  CA   GLY   40      24.462  34.804  94.915  1.00 28.68      AAGL
ATOM    300  C    GLY   40      23.804  34.079  96.077  1.00 27.30      AAGL
ATOM    301  O    GLY   40      24.489  33.628  96.994  1.00 28.21      AAGL
ATOM    302  N    ILE   41      22.480  33.973  96.046  1.00 27.82      AAGL
ATOM    303  CA   ILE   41      21.754  33.271  97.105  1.00 28.31      AAGL
ATOM    304  CB   ILE   41      20.231  33.267  96.841  1.00 28.86      AAGL
ATOM    305  CG2  ILE   41      19.502  32.678  98.047  1.00 26.11      AAGL
ATOM    306  CG1  ILE   41      19.741  34.680  96.490  1.00 32.71      AAGL
ATOM    307  CD1  ILE   41      20.041  35.739  97.526  1.00 34.86      AAGL
ATOM    308  C    ILE   41      22.262  31.830  97.055  1.00 29.05      AAGL
ATOM    309  O    ILE   41      22.275  31.223  95.982  1.00 28.58      AAGL
ATOM    310  N    ASN   42      22.694  31.283  98.192  1.00 27.24      AAGL
ATOM    311  CA   ASN   42      23.209  29.921  98.192  1.00 27.38      AAGL
ATOM    312  CB   ASN   42      24.715  29.897  98.547  1.00 26.67      AAGL
ATOM    313  CG   ASN   42      25.014  30.267  99.999  1.00 29.27      AAGL
ATOM    314  OD1  ASN   42      26.177  30.238 100.422  1.00 30.70      AAGL
ATOM    315  ND2  ASN   42      23.984  30.620 100.767  1.00 28.35      AAGL
ATOM    316  C    ASN   42      22.449  28.945  99.077  1.00 27.09      AAGL
ATOM    317  O    ASN   42      22.873  27.801  99.244  1.00 25.65      AAGL
ATOM    318  N    SER   43      21.324  29.390  99.633  1.00 25.87      AAGL
ATOM    319  CA   SER   43      20.525  28.520 100.481  1.00 25.56      AAGL
ATOM    320  CB   SER   43      21.049  28.551 101.913  1.00 26.01      AAGL
ATOM    321  OG   SER   43      20.497  27.483 102.665  1.00 25.97      AAGL
ATOM    322  C    SER   43      19.051  28.914 100.462  1.00 25.21      AAGL
ATOM    323  O    SER   43      18.714  30.096 100.411  1.00 22.67      AAGL
ATOM    324  N    ILE   44      18.177  27.910 100.494  1.00 24.04      AAGL
ATOM    325  CA   ILE   44      16.737  28.146 100.475  1.00 23.25      AAGL
ATOM    326  CB   ILE   44      16.105  27.603  99.166  1.00 25.17      AAGL
ATOM    327  CG2  ILE   44      14.599  27.796  99.185  1.00 23.06      AAGL
ATOM    328  CG1  ILE   44      16.698  28.333  97.953  1.00 25.29      AAGL
ATOM    329  CD1  ILE   44      16.327  29.795  97.867  1.00 26.67      AAGL
```

Fig. 3 cont.

```
ATOM    330  C    ILE   44      16.057  27.481 101.677  1.00 23.88      AAGL
ATOM    331  O    ILE   44      16.273  26.305 101.953  1.00 22.19      AAGL
ATOM    332  N    ARG   45      15.244  28.262 102.384  1.00 21.15      AAGL
ATOM    333  CA   ARG   45      14.512  27.796 103.558  1.00 20.84      AAGL
ATOM    334  CB   ARG   45      14.497  28.905 104.607  1.00 19.60      AAGL
ATOM    335  CG   ARG   45      13.815  28.594 105.927  1.00 22.30      AAGL
ATOM    336  CD   ARG   45      13.941  29.840 106.803  1.00 22.44      AAGL
ATOM    337  NE   ARG   45      13.442  29.713 108.172  1.00 21.57      AAGL
ATOM    338  CZ   ARG   45      12.253  30.147 108.580  1.00 21.21      AAGL
ATOM    339  NH1  ARG   45      11.420  30.721 107.726  1.00 19.38      AAGL
ATOM    340  NH2  ARG   45      11.924  30.071 109.864  1.00 18.87      AAGL
ATOM    341  C    ARG   45      13.091  27.456 103.120  1.00 18.60      AAGL
ATOM    342  O    ARG   45      12.471  28.214 102.376  1.00 19.88      AAGL
ATOM    343  N    GLN   46      12.582  26.314 103.574  1.00 19.69      AAGL
ATOM    344  CA   GLN   46      11.235  25.881 103.212  1.00 18.26      AAGL
ATOM    345  CB   GLN   46      11.311  24.701 102.234  1.00 19.90      AAGL
ATOM    346  CG   GLN   46      12.070  25.027 100.949  1.00 19.68      AAGL
ATOM    347  CD   GLN   46      12.093  23.880  99.946  1.00 23.43      AAGL
ATOM    348  OE1  GLN   46      12.705  23.992  98.882  1.00 26.77      AAGL
ATOM    349  NE2  GLN   46      11.429  22.777 100.278  1.00 21.73      AAGL
ATOM    350  C    GLN   46      10.432  25.467 104.445  1.00 17.71      AAGL
ATOM    351  O    GLN   46      10.896  24.649 105.238  1.00 18.22      AAGL
ATOM    352  N    ARG   47       9.233  26.023 104.601  1.00 18.28      AAGL
ATOM    353  CA   ARG   47       8.409  25.670 105.751  1.00 18.38      AAGL
ATOM    354  CB   ARG   47       7.414  26.792 106.095  1.00 18.50      AAGL
ATOM    355  CG   ARG   47       6.542  27.319 104.954  1.00 21.41      AAGL
ATOM    356  CD   ARG   47       5.455  28.254 105.503  1.00 20.07      AAGL
ATOM    357  NE   ARG   47       4.735  28.978 104.453  1.00 18.68      AAGL
ATOM    358  CZ   ARG   47       5.228  30.016 103.783  1.00 19.34      AAGL
ATOM    359  NH1  ARG   47       6.448  30.472 104.054  1.00 20.84      AAGL
ATOM    360  NH2  ARG   47       4.513  30.582 102.819  1.00 19.53      AAGL
ATOM    361  C    ARG   47       7.677  24.365 105.472  1.00 18.74      AAGL
ATOM    362  O    ARG   47       7.101  24.183 104.403  1.00 18.19      AAGL
ATOM    363  N    VAL   48       7.710  23.458 106.445  1.00 19.24      AAGL
ATOM    364  CA   VAL   48       7.074  22.155 106.301  1.00 20.17      AAGL
ATOM    365  CB   VAL   48       8.109  21.023 106.490  1.00 20.89      AAGL
ATOM    366  CG1  VAL   48       7.488  19.677 106.130  1.00 20.76      AAGL
ATOM    367  CG2  VAL   48       9.350  21.301 105.644  1.00 21.80      AAGL
ATOM    368  C    VAL   48       5.947  21.932 107.311  1.00 20.72      AAGL
ATOM    369  O    VAL   48       6.166  22.027 108.517  1.00 19.48      AAGL
ATOM    370  N    TRP   49       4.748  21.647 106.805  1.00 18.93      AAGL
ATOM    371  CA   TRP   49       3.590  21.371 107.646  1.00 19.06      AAGL
ATOM    372  CB   TRP   49       2.382  22.168 107.167  1.00 19.85      AAGL
ATOM    373  CG   TRP   49       2.525  23.645 107.414  1.00 19.05      AAGL
ATOM    374  CD2  TRP   49       1.608  24.673 107.024  1.00 18.82      AAGL
ATOM    375  CE2  TRP   49       2.125  25.897 107.504  1.00 19.73      AAGL
ATOM    376  CE3  TRP   49       0.396  24.678 106.316  1.00 20.02      AAGL
ATOM    377  CD1  TRP   49       3.535  24.271 108.090  1.00 17.67      AAGL
ATOM    378  NE1  TRP   49       3.300  25.620 108.149  1.00 18.03      AAGL
ATOM    379  CZ2  TRP   49       1.475  27.117 107.301  1.00 20.25      AAGL
ATOM    380  CZ3  TRP   49      -0.253  25.899 106.112  1.00 22.82      AAGL
ATOM    381  CH2  TRP   49       0.291  27.100 106.606  1.00 22.06      AAGL
ATOM    382  C    TRP   49       3.306  19.873 107.587  1.00 19.52      AAGL
ATOM    383  O    TRP   49       3.553  19.231 106.563  1.00 19.96      AAGL
ATOM    384  N    VAL   50       2.778  19.322 108.677  1.00 18.80      AAGL
ATOM    385  CA   VAL   50       2.522  17.886 108.756  1.00 20.11      AAGL
ATOM    386  CB   VAL   50       2.398  17.443 110.231  1.00 18.82      AAGL
ATOM    387  CG1  VAL   50       2.120  15.954 110.316  1.00 21.34      AAGL
ATOM    388  CG2  VAL   50       3.695  17.768 110.966  1.00 21.13      AAGL
ATOM    389  C    VAL   50       1.340  17.362 107.947  1.00 22.22      AAGL
ATOM    390  O    VAL   50       1.538  16.629 106.973  1.00 23.75      AAGL
ATOM    391  N    ASN   51       0.119  17.721 108.329  1.00 22.74      AAGL
ATOM    392  CA   ASN   51      -1.044  17.251 107.585  1.00 25.51      AAGL
ATOM    393  CB   ASN   51      -1.765  16.133 108.354  1.00 26.96      AAGL
ATOM    394  CG   ASN   51      -0.879  14.932 108.619  0.50 27.07      AAGL
ATOM    395  OD1  ASN   51      -0.265  14.387 107.707  0.50 29.27      AAGL
```

Fig. 3 cont.

```
ATOM  396  ND2  ASN  51    -0.821  14.505  109.878  0.50  28.87    AAGL
ATOM  397  C    ASN  51    -2.055  18.350  107.238  1.00  26.72    AAGL
ATOM  398  O    ASN  51    -3.204  18.305  107.668  1.00  27.90    AAGL
ATOM  399  N    PRO  52    -1.638  19.358  106.459  1.00  26.25    AAGL
ATOM  400  CD   PRO  52    -0.337  19.594  105.814  1.00  25.34    AAGL
ATOM  401  CA   PRO  52    -2.599  20.410  106.113  1.00  26.62    AAGL
ATOM  402  CB   PRO  52    -1.735  21.431  105.389  1.00  25.68    AAGL
ATOM  403  CG   PRO  52    -0.697  20.582  104.735  1.00  25.47    AAGL
ATOM  404  C    PRO  52    -3.690  19.816  105.215  1.00  28.63    AAGL
ATOM  405  O    PRO  52    -3.391  19.112  104.254  1.00  27.01    AAGL
ATOM  406  N    SER  53    -4.949  20.086  105.543  1.00  29.82    AAGL
ATOM  407  CA   SER  53    -6.062  19.554  104.760  1.00  33.18    AAGL
ATOM  408  CB   SER  53    -7.394  20.100  105.281  1.00  35.65    AAGL
ATOM  409  OG   SER  53    -7.728  19.496  106.515  1.00  38.67    AAGL
ATOM  410  C    SER  53    -5.948  19.859  103.274  1.00  32.30    AAGL
ATOM  411  O    SER  53    -6.284  19.019  102.434  1.00  32.67    AAGL
ATOM  412  N    ASP  54    -5.469  21.053  102.949  1.00  31.58    AAGL
ATOM  413  CA   ASP  54    -5.343  21.444  101.555  1.00  31.37    AAGL
ATOM  414  CB   ASP  54    -5.736  22.922  101.389  1.00  33.51    AAGL
ATOM  415  CG   ASP  54    -4.616  23.878  101.754  1.00  35.96    AAGL
ATOM  416  OD1  ASP  54    -3.796  23.537  102.630  1.00  35.79    AAGL
ATOM  417  OD2  ASP  54    -4.569  24.986  101.166  1.00  38.48    AAGL
ATOM  418  C    ASP  54    -3.974  21.164  100.937  1.00  30.51    AAGL
ATOM  419  O    ASP  54    -3.715  21.572   99.812  1.00  30.89    AAGL
ATOM  420  N    GLY  55    -3.110  20.460  101.670  1.00  31.08    AAGL
ATOM  421  CA   GLY  55    -1.790  20.102  101.161  1.00  29.00    AAGL
ATOM  422  C    GLY  55    -0.684  21.149  101.119  1.00  28.85    AAGL
ATOM  423  O    GLY  55     0.475  20.829  100.834  1.00  27.57    AAGL
ATOM  424  N    SER  56    -1.028  22.399  101.398  1.00  29.06    AAGL
ATOM  425  CA   SER  56    -0.036  23.468  101.362  1.00  29.25    AAGL
ATOM  426  CB   SER  56    -0.685  24.799  101.747  1.00  33.01    AAGL
ATOM  427  OG   SER  56    -1.603  25.222  100.746  1.00  35.28    AAGL
ATOM  428  C    SER  56     1.163  23.211  102.266  1.00  27.16    AAGL
ATOM  429  O    SER  56     1.013  22.944  103.462  1.00  26.75    AAGL
ATOM  430  N    TYR  57     2.350  23.282  101.673  1.00  24.25    AAGL
ATOM  431  CA   TYR  57     3.611  23.102  102.379  1.00  23.39    AAGL
ATOM  432  CB   TYR  57     3.773  24.192  103.455  1.00  21.44    AAGL
ATOM  433  CG   TYR  57     3.411  25.586  102.983  1.00  18.93    AAGL
ATOM  434  CD1  TYR  57     4.090  26.183  101.927  1.00  20.85    AAGL
ATOM  435  CE1  TYR  57     3.733  27.448  101.457  1.00  20.55    AAGL
ATOM  436  CD2  TYR  57     2.363  26.291  103.575  1.00  20.42    AAGL
ATOM  437  CE2  TYR  57     1.992  27.555  103.119  1.00  23.25    AAGL
ATOM  438  CZ   TYR  57     2.687  28.130  102.049  1.00  22.03    AAGL
ATOM  439  OH   TYR  57     2.323  29.367  101.572  1.00  24.57    AAGL
ATOM  440  C    TYR  57     3.809  21.736  103.024  1.00  24.63    AAGL
ATOM  441  O    TYR  57     4.583  21.619  103.972  1.00  22.67    AAGL
ATOM  442  N    ASP  58     3.121  20.701  102.540  1.00  25.81    AAGL
ATOM  443  CA   ASP  58     3.319  19.376  103.128  1.00  27.04    AAGL
ATOM  444  CB   ASP  58     2.084  18.473  102.946  1.00  27.80    AAGL
ATOM  445  CG   ASP  58     1.763  18.160  101.491  1.00  32.21    AAGL
ATOM  446  OD1  ASP  58     2.652  18.279  100.623  1.00  30.26    AAGL
ATOM  447  OD2  ASP  58     0.597  17.768  101.228  1.00  32.38    AAGL
ATOM  448  C    ASP  58     4.574  18.724  102.542  1.00  28.05    AAGL
ATOM  449  O    ASP  58     5.320  19.367  101.793  1.00  27.53    AAGL
ATOM  450  N    LEU  59     4.820  17.462  102.883  1.00  26.92    AAGL
ATOM  451  CA   LEU  59     6.018  16.786  102.403  1.00  28.31    AAGL
ATOM  452  CB   LEU  59     6.116  15.377  103.001  1.00  30.14    AAGL
ATOM  453  CG   LEU  59     7.435  14.620  102.784  1.00  29.84    AAGL
ATOM  454  CD1  LEU  59     8.609  15.430  103.323  1.00  31.61    AAGL
ATOM  455  CD2  LEU  59     7.355  13.265  103.479  1.00  31.80    AAGL
ATOM  456  C    LEU  59     6.145  16.714  100.885  1.00  26.89    AAGL
ATOM  457  O    LEU  59     7.220  16.952  100.342  1.00  24.30    AAGL
ATOM  458  N    ASP  60     5.061  16.401  100.188  1.00  28.43    AAGL
ATOM  459  CA   ASP  60     5.145  16.315   98.736  1.00  29.43    AAGL
ATOM  460  CB   ASP  60     3.850  15.740   98.149  1.00  32.44    AAGL
ATOM  461  CG   ASP  60     3.557  14.332   98.651  1.00  37.53    AAGL
```

Fig. 3 cont.

```
ATOM    462  OD1 ASP    60       4.518  13.547  98.833  1.00 40.66      AAGL
ATOM    463  OD2 ASP    60       2.365  14.000  98.858  1.00 42.65      AAGL
ATOM    464  C   ASP    60       5.439  17.689  98.137  1.00 30.40      AAGL
ATOM    465  O   ASP    60       6.266  17.816  97.237  1.00 28.80      AAGL
ATOM    466  N   TYR    61       4.761  18.710  98.651  1.00 28.48      AAGL
ATOM    467  CA  TYR    61       4.944  20.088  98.203  1.00 25.60      AAGL
ATOM    468  CB  TYR    61       4.100  21.031  99.080  1.00 25.21      AAGL
ATOM    469  CG  TYR    61       4.182  22.508  98.723  1.00 25.14      AAGL
ATOM    470  CD1 TYR    61       5.283  23.286  99.095  1.00 23.80      AAGL
ATOM    471  CE1 TYR    61       5.360  24.639  98.759  1.00 24.64      AAGL
ATOM    472  CD2 TYR    61       3.154  23.125  98.006  1.00 25.32      AAGL
ATOM    473  CE2 TYR    61       3.220  24.481  97.664  1.00 26.31      AAGL
ATOM    474  CZ  TYR    61       4.327  25.231  98.043  1.00 25.45      AAGL
ATOM    475  OH  TYR    61       4.403  26.565  97.687  1.00 24.80      AAGL
ATOM    476  C   TYR    61       6.422  20.444  98.330  1.00 26.83      AAGL
ATOM    477  O   TYR    61       7.039  20.948  97.393  1.00 25.72      AAGL
ATOM    478  N   ASN    62       6.992  20.159  99.493  1.00 24.55      AAGL
ATOM    479  CA  ASN    62       8.388  20.458  99.733  1.00 25.46      AAGL
ATOM    480  CB  ASN    62       8.695  20.315 101.225  1.00 25.35      AAGL
ATOM    481  CG  ASN    62       8.316  21.568 102.009  1.00 25.66      AAGL
ATOM    482  OD1 ASN    62       9.047  22.556 101.998  1.00 23.45      AAGL
ATOM    483  ND2 ASN    62       7.159  21.539 102.666  1.00 21.77      AAGL
ATOM    484  C   ASN    62       9.355  19.629  98.899  1.00 25.81      AAGL
ATOM    485  O   ASN    62      10.450  20.090  98.596  1.00 23.79      AAGL
ATOM    486  N   LEU    63       8.969  18.411  98.528  1.00 25.79      AAGL
ATOM    487  CA  LEU    63       9.856  17.589  97.708  1.00 27.44      AAGL
ATOM    488  CB  LEU    63       9.320  16.153  97.581  1.00 29.01      AAGL
ATOM    489  CG  LEU    63       9.673  15.225  98.743  1.00 31.95      AAGL
ATOM    490  CD1 LEU    63       9.041  13.851  98.508  1.00 32.91      AAGL
ATOM    491  CD2 LEU    63      11.199  15.114  98.872  1.00 32.19      AAGL
ATOM    492  C   LEU    63      10.001  18.207  96.322  1.00 27.90      AAGL
ATOM    493  O   LEU    63      11.102  18.275  95.772  1.00 29.37      AAGL
ATOM    494  N   GLU    64       8.882  18.662  95.768  1.00 28.38      AAGL
ATOM    495  CA  GLU    64       8.859  19.280  94.447  1.00 30.60      AAGL
ATOM    496  CB  GLU    64       7.414  19.642  94.078  1.00 32.03      AAGL
ATOM    497  CG  GLU    64       7.198  20.124  92.639  1.00 36.66      AAGL
ATOM    498  CD  GLU    64       5.747  20.468  92.364  1.00 38.83      AAGL
ATOM    499  OE1 GLU    64       4.874  19.637  92.688  1.00 41.75      AAGL
ATOM    500  OE2 GLU    64       5.464  21.565  91.822  1.00 41.60      AAGL
ATOM    501  C   GLU    64       9.727  20.536  94.454  1.00 29.58      AAGL
ATOM    502  O   GLU    64      10.525  20.769  93.541  1.00 27.18      AAGL
ATOM    503  N   LEU    65       9.578  21.343  95.497  1.00 27.01      AAGL
ATOM    504  CA  LEU    65      10.344  22.576  95.611  1.00 25.95      AAGL
ATOM    505  CB  LEU    65       9.754  23.455  96.721  1.00 27.05      AAGL
ATOM    506  CG  LEU    65      10.420  24.806  97.018  1.00 25.59      AAGL
ATOM    507  CD1 LEU    65      10.528  25.628  95.760  1.00 24.36      AAGL
ATOM    508  CD2 LEU    65       9.600  25.544  98.074  1.00 25.15      AAGL
ATOM    509  C   LEU    65      11.824  22.329  95.877  1.00 26.00      AAGL
ATOM    510  O   LEU    65      12.677  23.029  95.329  1.00 27.12      AAGL
ATOM    511  N   ALA    66      12.131  21.330  96.699  1.00 23.38      AAGL
ATOM    512  CA  ALA    66      13.517  21.025  97.038  1.00 25.19      AAGL
ATOM    513  CB  ALA    66      13.572  20.017  98.203  1.00 25.90      AAGL
ATOM    514  C   ALA    66      14.278  20.481  95.833  1.00 27.46      AAGL
ATOM    515  O   ALA    66      15.479  20.714  95.697  1.00 28.22      AAGL
ATOM    516  N   LYS    67      13.578  19.752  94.969  1.00 28.70      AAGL
ATOM    517  CA  LYS    67      14.201  19.188  93.768  1.00 32.17      AAGL
ATOM    518  CB  LYS    67      13.164  18.444  92.924  1.00 32.68      AAGL
ATOM    519  CG  LYS    67      12.902  17.003  93.358  1.00 36.34      AAGL
ATOM    520  CD  LYS    67      11.676  16.443  92.655  1.00 38.14      AAGL
ATOM    521  CE  LYS    67      11.447  14.989  93.012  1.00 41.38      AAGL
ATOM    522  NZ  LYS    67      10.184  14.468  92.407  1.00 43.11      AAGL
ATOM    523  C   LYS    67      14.813  20.303  92.931  1.00 32.63      AAGL
ATOM    524  O   LYS    67      15.943  20.192  92.453  1.00 32.89      AAGL
ATOM    525  N   ARG    68      14.053  21.376  92.763  1.00 31.49      AAGL
ATOM    526  CA  ARG    68      14.497  22.523  91.988  1.00 31.44      AAGL
ATOM    527  CB  ARG    68      13.300  23.419  91.683  1.00 31.14      AAGL
```

Fig. 3 cont.

```
ATOM    528  CG   ARG    68      12.313  22.760  90.730  1.00 33.54      AAGL
ATOM    529  CD   ARG    68      11.016  23.518  90.619  1.00 32.13      AAGL
ATOM    530  NE   ARG    68      11.222  24.924  90.303  1.00 31.17      AAGL
ATOM    531  CZ   ARG    68      10.238  25.763  90.002  1.00 32.92      AAGL
ATOM    532  NH1  ARG    68       8.985  25.327  89.970  1.00 33.31      AAGL
ATOM    533  NH2  ARG    68      10.498  27.040  89.755  1.00 31.47      AAGL
ATOM    534  C    ARG    68      15.595  23.311  92.691  1.00 31.54      AAGL
ATOM    535  O    ARG    68      16.459  23.905  92.040  1.00 31.76      AAGL
ATOM    536  N    VAL    69      15.570  23.319  94.021  1.00 28.62      AAGL
ATOM    537  CA   VAL    69      16.584  24.025  94.794  1.00 27.79      AAGL
ATOM    538  CB   VAL    69      16.204  24.061  96.281  1.00 24.83      AAGL
ATOM    539  CG1  VAL    69      17.294  24.735  97.092  1.00 27.63      AAGL
ATOM    540  CG2  VAL    69      14.886  24.781  96.442  1.00 26.08      AAGL
ATOM    541  C    VAL    69      17.934  23.325  94.635  1.00 29.09      AAGL
ATOM    542  O    VAL    69      18.968  23.970  94.458  1.00 28.64      AAGL
ATOM    543  N    LYS    70      17.908  21.998  94.711  1.00 29.15      AAGL
ATOM    544  CA   LYS    70      19.108  21.187  94.561  1.00 31.30      AAGL
ATOM    545  CB   LYS    70      18.756  19.707  94.743  1.00 34.31      AAGL
ATOM    546  CG   LYS    70      19.889  18.752  94.422  1.00 36.20      AAGL
ATOM    547  CD   LYS    70      19.399  17.319  94.271  1.00 40.57      AAGL
ATOM    548  CE   LYS    70      18.290  17.224  93.229  1.00 41.78      AAGL
ATOM    549  NZ   LYS    70      18.666  17.932  91.966  1.00 42.36      AAGL
ATOM    550  C    LYS    70      19.693  21.403  93.159  1.00 31.39      AAGL
ATOM    551  O    LYS    70      20.903  21.592  92.997  1.00 31.53      AAGL
ATOM    552  N    ALA    71      18.813  21.386  92.165  1.00 30.10      AAGL
ATOM    553  CA   ALA    71      19.196  21.564  90.771  1.00 31.78      AAGL
ATOM    554  CB   ALA    71      17.957  21.525  89.879  1.00 30.31      AAGL
ATOM    555  C    ALA    71      19.949  22.870  90.570  1.00 33.02      AAGL
ATOM    556  O    ALA    71      20.975  22.900  89.888  1.00 32.79      AAGL
ATOM    557  N    ALA    72      19.442  23.940  91.179  1.00 32.06      AAGL
ATOM    558  CA   ALA    72      20.054  25.257  91.071  1.00 30.23      AAGL
ATOM    559  CB   ALA    72      19.048  26.323  91.463  1.00 31.29      AAGL
ATOM    560  C    ALA    72      21.316  25.389  91.915  1.00 29.83      AAGL
ATOM    561  O    ALA    72      21.908  26.463  91.990  1.00 29.82      AAGL
ATOM    562  N    GLY    73      21.714  24.298  92.561  1.00 28.89      AAGL
ATOM    563  CA   GLY    73      22.926  24.304  93.360  1.00 30.91      AAGL
ATOM    564  C    GLY    73      22.909  25.064  94.675  1.00 32.00      AAGL
ATOM    565  O    GLY    73      23.939  25.589  95.111  1.00 30.50      AAGL
ATOM    566  N    MET    74      21.748  25.121  95.316  1.00 31.23      AAGL
ATOM    567  CA   MET    74      21.641  25.814  96.593  1.00 31.02      AAGL
ATOM    568  CB   MET    74      20.500  26.840  96.537  1.00 29.51      AAGL
ATOM    569  CG   MET    74      20.676  27.893  95.434  1.00 29.42      AAGL
ATOM    570  SD   MET    74      19.481  29.259  95.503  1.00 28.77      AAGL
ATOM    571  CE   MET    74      18.129  28.654  94.532  1.00 26.24      AAGL
ATOM    572  C    MET    74      21.388  24.768  97.681  1.00 29.72      AAGL
ATOM    573  O    MET    74      20.893  23.682  97.385  1.00 30.60      AAGL
ATOM    574  N    SER    75      21.750  25.075  98.925  1.00 28.06      AAGL
ATOM    575  CA   SER    75      21.534  24.125 100.011  1.00 25.93      AAGL
ATOM    576  CB   SER    75      22.454  24.426 101.202  1.00 25.27      AAGL
ATOM    577  OG   SER    75      22.281  25.752 101.671  1.00 24.77      AAGL
ATOM    578  C    SER    75      20.075  24.203 100.439  1.00 27.57      AAGL
ATOM    579  O    SER    75      19.343  25.089  99.997  1.00 26.04      AAGL
ATOM    580  N    LEU    76      19.655  23.268 101.286  1.00 25.74      AAGL
ATOM    581  CA   LEU    76      18.273  23.227 101.747  1.00 27.05      AAGL
ATOM    582  CB   LEU    76      17.602  21.941 101.268  1.00 28.62      AAGL
ATOM    583  CG   LEU    76      16.130  21.726 101.615  1.00 31.64      AAGL
ATOM    584  CD1  LEU    76      15.268  22.677 100.772  1.00 29.51      AAGL
ATOM    585  CD2  LEU    76      15.748  20.268 101.346  1.00 32.16      AAGL
ATOM    586  C    LEU    76      18.177  23.309 103.264  1.00 24.07      AAGL
ATOM    587  O    LEU    76      18.890  22.619 103.985  1.00 24.81      AAGL
ATOM    588  N    TYR    77      17.293  24.179 103.732  1.00 24.59      AAGL
ATOM    589  CA   TYR    77      17.044  24.375 105.162  1.00 21.21      AAGL
ATOM    590  CB   TYR    77      17.441  25.812 105.550  1.00 21.04      AAGL
ATOM    591  CG   TYR    77      16.903  26.417 106.849  1.00 22.71      AAGL
ATOM    592  CD1  TYR    77      16.207  25.664 107.800  1.00 20.07      AAGL
ATOM    593  CE1  TYR    77      15.681  26.276 108.959  1.00 21.30      AAGL
```

Fig. 3 cont.

```
ATOM    594  CD2 TYR    77      17.069  27.784 107.091  1.00 20.07           AAGL
ATOM    595  CE2 TYR    77      16.558  28.394 108.232  1.00 22.16           AAGL
ATOM    596  CZ  TYR    77      15.863  27.646 109.159  1.00 22.47           AAGL
ATOM    597  OH  TYR    77      15.331  28.312 110.248  1.00 21.22           AAGL
ATOM    598  C   TYR    77      15.553  24.121 105.318  1.00 19.67           AAGL
ATOM    599  O   TYR    77      14.730  24.875 104.804  1.00 21.16           AAGL
ATOM    600  N   LEU    78      15.217  23.021 105.989  1.00 19.73           AAGL
ATOM    601  CA  LEU    78      13.826  22.662 106.216  1.00 20.07           AAGL
ATOM    602  CB  LEU    78      13.645  21.140 106.164  1.00 20.48           AAGL
ATOM    603  CG  LEU    78      13.793  20.485 104.784  1.00 24.57           AAGL
ATOM    604  CD1 LEU    78      13.633  18.969 104.898  1.00 25.27           AAGL
ATOM    605  CD2 LEU    78      12.750  21.067 103.833  1.00 23.90           AAGL
ATOM    606  C   LEU    78      13.379  23.199 107.568  1.00 17.57           AAGL
ATOM    607  O   LEU    78      13.980  22.891 108.599  1.00 18.99           AAGL
ATOM    608  N   ASP    79      12.332  24.018 107.534  1.00 18.03           AAGL
ATOM    609  CA  ASP    79      11.754  24.642 108.721  1.00 18.85           AAGL
ATOM    610  CB  ASP    79      11.386  26.098 108.389  1.00 19.55           AAGL
ATOM    611  CG  ASP    79      10.593  26.785 109.493  1.00 25.39           AAGL
ATOM    612  OD1 ASP    79      10.682  26.370 110.662  1.00 22.47           AAGL
ATOM    613  OD2 ASP    79       9.885  27.761 109.180  1.00 27.84           AAGL
ATOM    614  C   ASP    79      10.514  23.848 109.116  1.00 16.61           AAGL
ATOM    615  O   ASP    79       9.427  24.105 108.608  1.00 16.77           AAGL
ATOM    616  N   LEU    80      10.686  22.881 110.014  1.00 16.76           AAGL
ATOM    617  CA  LEU    80       9.573  22.051 110.452  1.00 17.99           AAGL
ATOM    618  CB  LEU    80      10.077  20.777 111.132  1.00 18.64           AAGL
ATOM    619  CG  LEU    80      11.103  19.918 110.385  1.00 19.36           AAGL
ATOM    620  CD1 LEU    80      11.345  18.636 111.166  1.00 20.62           AAGL
ATOM    621  CD2 LEU    80      10.603  19.605 108.986  1.00 18.29           AAGL
ATOM    622  C   LEU    80       8.708  22.802 111.441  1.00 18.46           AAGL
ATOM    623  O   LEU    80       9.162  23.121 112.529  1.00 20.06           AAGL
ATOM    624  N   HIS    81       7.464  23.086 111.071  1.00 17.32           AAGL
ATOM    625  CA  HIS    81       6.572  23.780 111.987  1.00 16.30           AAGL
ATOM    626  CB  HIS    81       5.475  24.525 111.223  1.00 15.62           AAGL
ATOM    627  CG  HIS    81       5.939  25.810 110.612  1.00 19.94           AAGL
ATOM    628  CD2 HIS    81       7.137  26.167 110.093  1.00 19.51           AAGL
ATOM    629  ND1 HIS    81       5.129  26.921 110.507  1.00 20.10           AAGL
ATOM    630  CE1 HIS    81       5.811  27.909 109.952  1.00 20.61           AAGL
ATOM    631  NE2 HIS    81       7.031  27.477 109.693  1.00 20.38           AAGL
ATOM    632  C   HIS    81       5.939  22.811 112.984  1.00 17.32           AAGL
ATOM    633  O   HIS    81       5.368  23.240 113.987  1.00 18.88           AAGL
ATOM    634  N   LEU    82       6.045  21.513 112.709  1.00 16.02           AAGL
ATOM    635  CA  LEU    82       5.484  20.480 113.588  1.00 17.14           AAGL
ATOM    636  CB  LEU    82       6.339  20.342 114.850  1.00 16.85           AAGL
ATOM    637  CG  LEU    82       7.813  20.007 114.595  1.00 20.75           AAGL
ATOM    638  CD1 LEU    82       8.537  19.890 115.923  1.00 18.12           AAGL
ATOM    639  CD2 LEU    82       7.935  18.712 113.812  1.00 18.95           AAGL
ATOM    640  C   LEU    82       4.048  20.826 113.965  1.00 18.59           AAGL
ATOM    641  O   LEU    82       3.664  20.829 115.146  1.00 18.40           AAGL
ATOM    642  N   SER    83       3.268  21.109 112.930  1.00 16.93           AAGL
ATOM    643  CA  SER    83       1.868  21.475 113.052  1.00 16.95           AAGL
ATOM    644  CB  SER    83       1.757  22.914 113.569  1.00 17.01           AAGL
ATOM    645  OG  SER    83       0.415  23.351 113.629  1.00 17.93           AAGL
ATOM    646  C   SER    83       1.276  21.367 111.649  1.00 18.89           AAGL
ATOM    647  O   SER    83       2.011  21.239 110.664  1.00 19.84           AAGL
ATOM    648  N   ASP    84      -0.046  21.404 111.561  1.00 19.63           AAGL
ATOM    649  CA  ASP    84      -0.715  21.317 110.275  1.00 20.59           AAGL
ATOM    650  CB  ASP    84      -2.107  20.695 110.421  1.00 22.19           AAGL
ATOM    651  CG  ASP    84      -2.062  19.246 110.817  1.00 21.52           AAGL
ATOM    652  OD1 ASP    84      -1.025  18.597 110.572  1.00 23.10           AAGL
ATOM    653  OD2 ASP    84      -3.079  18.755 111.360  1.00 23.55           AAGL
ATOM    654  C   ASP    84      -0.866  22.706 109.689  1.00 21.71           AAGL
ATOM    655  O   ASP    84      -1.340  22.854 108.563  1.00 21.81           AAGL
ATOM    656  N   THR    85      -0.461  23.717 110.453  1.00 21.01           AAGL
ATOM    657  CA  THR    85      -0.573  25.102 110.012  1.00 19.92           AAGL
ATOM    658  CB  THR    85      -1.971  25.670 110.370  1.00 22.17           AAGL
ATOM    659  OG1 THR    85      -2.144  26.952 109.763  1.00 22.62           AAGL
```

Fig. 3 cont.

```
ATOM    660  CG2 THR    85      -2.134  25.800 111.874  1.00 23.94      AAGL
ATOM    661  C   THR    85       0.527  25.958 110.646  1.00 19.33      AAGL
ATOM    662  O   THR    85       1.429  25.425 111.298  1.00 18.85      AAGL
ATOM    663  N   TRP    86       0.454  27.276 110.450  1.00 18.81      AAGL
ATOM    664  CA  TRP    86       1.455  28.199 110.988  1.00 17.88      AAGL
ATOM    665  CB  TRP    86       1.011  29.654 110.800  1.00 17.85      AAGL
ATOM    666  CG  TRP    86       0.672  30.016 109.399  1.00 18.75      AAGL
ATOM    667  CD2 TRP    86       1.587  30.427 108.382  1.00 18.96      AAGL
ATOM    668  CE2 TRP    86       0.832  30.649 107.209  1.00 21.98      AAGL
ATOM    669  CE3 TRP    86       2.975  30.628 108.345  1.00 18.78      AAGL
ATOM    670  CD1 TRP    86      -0.563  30.004 108.826  1.00 21.00      AAGL
ATOM    671  NE1 TRP    86      -0.478  30.386 107.508  1.00 21.68      AAGL
ATOM    672  CZ2 TRP    86       1.418  31.065 106.007  1.00 19.73      AAGL
ATOM    673  CZ3 TRP    86       3.556  31.041 107.151  1.00 20.30      AAGL
ATOM    674  CH2 TRP    86       2.775  31.255 105.998  1.00 18.40      AAGL
ATOM    675  C   TRP    86       1.757  27.994 112.467  1.00 18.54      AAGL
ATOM    676  O   TRP    86       0.847  27.998 113.302  1.00 17.68      AAGL
ATOM    677  N   ALA    87       3.035  27.830 112.793  1.00 15.65      AAGL
ATOM    678  CA  ALA    87       3.440  27.669 114.182  1.00 19.55      AAGL
ATOM    679  CB  ALA    87       4.263  26.393 114.355  1.00 17.55      AAGL
ATOM    680  C   ALA    87       4.266  28.880 114.613  1.00 17.89      AAGL
ATOM    681  O   ALA    87       5.179  29.303 113.896  1.00 18.09      AAGL
ATOM    682  N   ASP    88       3.933  29.441 115.772  1.00 18.18      AAGL
ATOM    683  CA  ASP    88       4.655  30.585 116.325  1.00 18.94      AAGL
ATOM    684  CB  ASP    88       4.276  31.885 115.604  1.00 21.76      AAGL
ATOM    685  CG  ASP    88       2.798  32.205 115.699  1.00 26.60      AAGL
ATOM    686  OD1 ASP    88       2.221  32.074 116.789  1.00 24.49      AAGL
ATOM    687  OD2 ASP    88       2.216  32.599 114.673  1.00 30.64      AAGL
ATOM    688  C   ASP    88       4.349  30.674 117.826  1.00 20.25      AAGL
ATOM    689  O   ASP    88       3.617  29.838 118.354  1.00 18.36      AAGL
ATOM    690  N   PRO    89       4.900  31.681 118.528  1.00 19.03      AAGL
ATOM    691  CD  PRO    89       5.879  32.685 118.078  1.00 20.41      AAGL
ATOM    692  CA  PRO    89       4.656  31.813 119.969  1.00 19.78      AAGL
ATOM    693  CB  PRO    89       5.435  33.071 120.339  1.00 22.34      AAGL
ATOM    694  CG  PRO    89       6.561  33.059 119.354  1.00 20.37      AAGL
ATOM    695  C   PRO    89       3.206  31.882 120.421  1.00 21.51      AAGL
ATOM    696  O   PRO    89       2.909  31.593 121.578  1.00 22.07      AAGL
ATOM    697  N   SER    90       2.297  32.251 119.527  1.00 20.56      AAGL
ATOM    698  CA  SER    90       0.904  32.335 119.924  1.00 21.51      AAGL
ATOM    699  CB  SER    90       0.283  33.644 119.425  1.00 24.67      AAGL
ATOM    700  OG  SER    90       0.139  33.643 118.023  1.00 29.17      AAGL
ATOM    701  C   SER    90       0.086  31.138 119.451  1.00 21.66      AAGL
ATOM    702  O   SER    90      -1.094  31.018 119.792  1.00 18.80      AAGL
ATOM    703  N   ASP    91       0.710  30.249 118.674  1.00 19.99      AAGL
ATOM    704  CA  ASP    91       0.025  29.052 118.188  1.00 21.82      AAGL
ATOM    705  CB  ASP    91      -0.839  29.374 116.961  1.00 26.37      AAGL
ATOM    706  CG  ASP    91      -2.057  30.208 117.305  0.50 27.60      AAGL
ATOM    707  OD1 ASP    91      -2.904  29.743 118.104  0.50 29.99      AAGL
ATOM    708  OD2 ASP    91      -2.168  31.328 116.770  0.50 29.72      AAGL
ATOM    709  C   ASP    91       0.974  27.912 117.816  1.00 19.33      AAGL
ATOM    710  O   ASP    91       1.713  27.997 116.834  1.00 20.80      AAGL
ATOM    711  N   GLN    92       0.945  26.851 118.614  1.00 16.40      AAGL
ATOM    712  CA  GLN    92       1.751  25.653 118.369  1.00 17.43      AAGL
ATOM    713  CB  GLN    92       2.820  25.482 119.449  1.00 16.72      AAGL
ATOM    714  CG  GLN    92       3.897  26.562 119.457  1.00 15.88      AAGL
ATOM    715  CD  GLN    92       4.894  26.427 118.319  1.00 16.69      AAGL
ATOM    716  OE1 GLN    92       5.078  25.345 117.770  1.00 18.84      AAGL
ATOM    717  NE2 GLN    92       5.550  27.524 117.970  1.00 15.00      AAGL
ATOM    718  C   GLN    92       0.782  24.472 118.403  1.00 17.98      AAGL
ATOM    719  O   GLN    92       0.855  23.615 119.284  1.00 18.87      AAGL
ATOM    720  N   THR    93      -0.140  24.444 117.450  1.00 18.32      AAGL
ATOM    721  CA  THR    93      -1.137  23.378 117.396  1.00 19.90      AAGL
ATOM    722  CB  THR    93      -2.303  23.732 116.451  1.00 21.83      AAGL
ATOM    723  OG1 THR    93      -2.845  25.001 116.824  1.00 23.30      AAGL
ATOM    724  CG2 THR    93      -3.415  22.691 116.564  1.00 23.34      AAGL
ATOM    725  C   THR    93      -0.553  22.052 116.946  1.00 19.51      AAGL
```

Fig. 3 cont.

```
ATOM    726  O    THR   93       0.000  21.935 115.856  1.00 19.99      AAGL
ATOM    727  N    THR   94      -0.685  21.050 117.802  1.00 19.55      AAGL
ATOM    728  CA   THR   94      -0.181  19.716 117.510  1.00 20.32      AAGL
ATOM    729  CB   THR   94      -0.463  18.775 118.699  1.00 20.34      AAGL
ATOM    730  OG1  THR   94       0.320  19.190 119.824  1.00 20.72      AAGL
ATOM    731  CG2  THR   94      -0.141  17.334 118.348  1.00 20.41      AAGL
ATOM    732  C    THR   94      -0.866  19.171 116.261  1.00 19.20      AAGL
ATOM    733  O    THR   94      -2.060  19.367 116.071  1.00 19.04      AAGL
ATOM    734  N    PRO   95      -0.111  18.495 115.381  1.00 19.53      AAGL
ATOM    735  CD   PRO   95       1.352  18.315 115.386  1.00 17.38      AAGL
ATOM    736  CA   PRO   95      -0.703  17.937 114.160  1.00 20.73      AAGL
ATOM    737  CB   PRO   95       0.424  17.086 113.590  1.00 16.98      AAGL
ATOM    738  CG   PRO   95       1.638  17.872 113.952  1.00 20.07      AAGL
ATOM    739  C    PRO   95      -1.939  17.091 114.452  1.00 22.21      AAGL
ATOM    740  O    PRO   95      -2.002  16.399 115.468  1.00 19.37      AAGL
ATOM    741  N    SER   96      -2.926  17.163 113.569  1.00 23.26      AAGL
ATOM    742  CA   SER   96      -4.125  16.353 113.740  1.00 27.34      AAGL
ATOM    743  CB   SER   96      -5.153  16.695 112.656  1.00 29.38      AAGL
ATOM    744  OG   SER   96      -4.577  16.561 111.365  1.00 34.62      AAGL
ATOM    745  C    SER   96      -3.635  14.911 113.590  1.00 28.07      AAGL
ATOM    746  O    SER   96      -2.863  14.602 112.685  1.00 29.54      AAGL
ATOM    747  N    GLY   97      -4.064  14.029 114.482  1.00 28.91      AAGL
ATOM    748  CA   GLY   97      -3.607  12.655 114.390  1.00 28.58      AAGL
ATOM    749  C    GLY   97      -2.478  12.365 115.365  1.00 27.25      AAGL
ATOM    750  O    GLY   97      -2.214  11.202 115.679  1.00 28.56      AAGL
ATOM    751  N    TRP   98      -1.786  13.408 115.819  1.00 23.62      AAGL
ATOM    752  CA   TRP   98      -0.715  13.227 116.801  1.00 20.63      AAGL
ATOM    753  CB   TRP   98       0.396  14.250 116.590  1.00 20.68      AAGL
ATOM    754  CG   TRP   98       1.253  13.995 115.382  1.00 20.26      AAGL
ATOM    755  CD2  TRP   98       2.561  14.517 115.148  1.00 19.57      AAGL
ATOM    756  CE2  TRP   98       2.945  14.123 113.845  1.00 20.94      AAGL
ATOM    757  CE3  TRP   98       3.449  15.288 115.913  1.00 19.61      AAGL
ATOM    758  CD1  TRP   98       0.905  13.311 114.246  1.00 21.24      AAGL
ATOM    759  NE1  TRP   98       1.918  13.386 113.318  1.00 21.31      AAGL
ATOM    760  CZ2  TRP   98       4.178  14.475 113.290  1.00 20.47      AAGL
ATOM    761  CZ3  TRP   98       4.675  15.638 115.362  1.00 20.55      AAGL
ATOM    762  CH2  TRP   98       5.028  15.230 114.058  1.00 21.24      AAGL
ATOM    763  C    TRP   98      -1.348  13.397 118.190  1.00 21.31      AAGL
ATOM    764  O    TRP   98      -2.422  13.973 118.312  1.00 21.68      AAGL
ATOM    765  N    SER   99      -0.675  12.910 119.227  1.00 22.27      AAGL
ATOM    766  CA   SER   99      -1.210  12.951 120.591  1.00 20.04      AAGL
ATOM    767  CB   SER   99      -0.531  11.870 121.446  1.00 21.78      AAGL
ATOM    768  OG   SER   99      -1.115  11.794 122.746  1.00 19.99      AAGL
ATOM    769  C    SER   99      -1.172  14.262 121.377  1.00 20.81      AAGL
ATOM    770  O    SER   99      -0.174  14.974 121.391  1.00 20.17      AAGL
ATOM    771  N    THR  100      -2.284  14.555 122.039  1.00 21.47      AAGL
ATOM    772  CA   THR  100      -2.401  15.730 122.896  1.00 22.60      AAGL
ATOM    773  CB   THR  100      -3.564  16.655 122.455  1.00 22.41      AAGL
ATOM    774  OG1  THR  100      -4.759  15.882 122.308  1.00 23.06      AAGL
ATOM    775  CG2  THR  100      -3.248  17.339 121.128  1.00 22.11      AAGL
ATOM    776  C    THR  100      -2.706  15.190 124.294  1.00 23.80      AAGL
ATOM    777  O    THR  100      -3.150  15.930 125.174  1.00 23.03      AAGL
ATOM    778  N    THR  101      -2.448  13.895 124.488  1.00 24.54      AAGL
ATOM    779  CA   THR  101      -2.737  13.228 125.755  1.00 23.47      AAGL
ATOM    780  CB   THR  101      -4.055  12.440 125.638  1.00 24.48      AAGL
ATOM    781  OG1  THR  101      -3.897  11.412 124.652  1.00 25.27      AAGL
ATOM    782  CG2  THR  101      -5.198  13.356 125.213  1.00 25.93      AAGL
ATOM    783  C    THR  101      -1.679  12.256 126.301  1.00 25.35      AAGL
ATOM    784  O    THR  101      -1.794  11.802 127.437  1.00 25.05      AAGL
ATOM    785  N    ASP  102      -0.657  11.932 125.513  1.00 23.02      AAGL
ATOM    786  CA   ASP  102       0.366  10.989 125.968  1.00 24.03      AAGL
ATOM    787  CB   ASP  102       0.013   9.579 125.488  1.00 25.87      AAGL
ATOM    788  CG   ASP  102       0.934   8.515 126.052  1.00 29.80      AAGL
ATOM    789  OD1  ASP  102       2.163   8.600 125.864  1.00 30.75      AAGL
ATOM    790  OD2  ASP  102       0.425   7.571 126.683  1.00 35.27      AAGL
ATOM    791  C    ASP  102       1.746  11.370 125.446  1.00 24.10      AAGL
ATOM    792  O    ASP  102       2.005  11.269 124.245  1.00 24.23      AAGL
```

Fig. 3 cont.

```
ATOM    793  N   LEU  103      2.640  11.791 126.338  1.00 23.33      AAGL
ATOM    794  CA  LEU  103      3.974  12.189 125.898  1.00 23.77      AAGL
ATOM    795  CB  LEU  103      4.801  12.749 127.056  1.00 24.26      AAGL
ATOM    796  CG  LEU  103      6.113  13.383 126.579  1.00 23.41      AAGL
ATOM    797  CD1 LEU  103      5.800  14.627 125.765  1.00 23.25      AAGL
ATOM    798  CD2 LEU  103      7.005  13.729 127.764  1.00 24.01      AAGL
ATOM    799  C   LEU  103      4.744  11.046 125.257  1.00 24.93      AAGL
ATOM    800  O   LEU  103      5.522  11.259 124.326  1.00 22.87      AAGL
ATOM    801  N   GLY  104      4.535   9.837 125.765  1.00 24.55      AAGL
ATOM    802  CA  GLY  104      5.229   8.689 125.213  1.00 25.67      AAGL
ATOM    803  C   GLY  104      4.863   8.514 123.757  1.00 24.34      AAGL
ATOM    804  O   GLY  104      5.727   8.334 122.899  1.00 25.72      AAGL
ATOM    805  N   THR  105      3.571   8.571 123.475  1.00 23.33      AAGL
ATOM    806  CA  THR  105      3.084   8.425 122.115  1.00 24.93      AAGL
ATOM    807  CB  THR  105      1.546   8.360 122.095  1.00 25.14      AAGL
ATOM    808  OG1 THR  105      1.109   7.236 122.870  1.00 28.55      AAGL
ATOM    809  CG2 THR  105      1.029   8.211 120.684  1.00 27.78      AAGL
ATOM    810  C   THR  105      3.561   9.596 121.260  1.00 23.97      AAGL
ATOM    811  O   THR  105      4.008   9.412 120.132  1.00 24.40      AAGL
ATOM    812  N   LEU  106      3.485  10.802 121.812  1.00 22.92      AAGL
ATOM    813  CA  LEU  106      3.898  12.000 121.085  1.00 21.38      AAGL
ATOM    814  CB  LEU  106      3.568  13.254 121.896  1.00 19.99      AAGL
ATOM    815  CG  LEU  106      3.895  14.579 121.196  1.00 18.13      AAGL
ATOM    816  CD1 LEU  106      3.066  14.714 119.923  1.00 16.54      AAGL
ATOM    817  CD2 LEU  106      3.613  15.735 122.141  1.00 15.43      AAGL
ATOM    818  C   LEU  106      5.382  11.995 120.729  1.00 23.00      AAGL
ATOM    819  O   LEU  106      5.755  12.330 119.601  1.00 22.17      AAGL
ATOM    820  N   LYS  107      6.230  11.627 121.684  1.00 23.39      AAGL
ATOM    821  CA  LYS  107      7.662  11.578 121.420  1.00 24.69      AAGL
ATOM    822  CB  LYS  107      8.446  11.129 122.660  1.00 25.78      AAGL
ATOM    823  CG  LYS  107      8.496  12.144 123.789  1.00 27.94      AAGL
ATOM    824  CD  LYS  107      9.574  11.781 124.801  1.00 31.83      AAGL
ATOM    825  CE  LYS  107      9.360  10.393 125.384  1.00 36.44      AAGL
ATOM    826  NZ  LYS  107     10.431  10.009 126.355  1.00 39.34      AAGL
ATOM    827  C   LYS  107      7.942  10.609 120.278  1.00 24.60      AAGL
ATOM    828  O   LYS  107      8.829  10.852 119.461  1.00 24.29      AAGL
ATOM    829  N   TRP  108      7.183   9.518 120.220  1.00 24.58      AAGL
ATOM    830  CA  TRP  108      7.372   8.526 119.165  1.00 26.57      AAGL
ATOM    831  CB  TRP  108      6.616   7.231 119.487  1.00 30.79      AAGL
ATOM    832  CG  TRP  108      7.429   6.243 120.257  1.00 37.55      AAGL
ATOM    833  CD2 TRP  108      8.617   5.579 119.806  1.00 41.19      AAGL
ATOM    834  CE2 TRP  108      9.055   4.744 120.861  1.00 41.70      AAGL
ATOM    835  CE3 TRP  108      9.356   5.610 118.611  1.00 40.79      AAGL
ATOM    836  CD1 TRP  108      7.199   5.797 121.530  1.00 39.67      AAGL
ATOM    837  NE1 TRP  108      8.173   4.898 121.899  1.00 41.76      AAGL
ATOM    838  CZ2 TRP  108     10.202   3.942 120.760  1.00 42.41      AAGL
ATOM    839  CZ3 TRP  108     10.498   4.814 118.510  1.00 42.96      AAGL
ATOM    840  CH2 TRP  108     10.908   3.992 119.582  1.00 43.14      AAGL
ATOM    841  C   TRP  108      6.925   9.040 117.807  1.00 25.36      AAGL
ATOM    842  O   TRP  108      7.585   8.785 116.801  1.00 25.01      AAGL
ATOM    843  N   GLN  109      5.808   9.763 117.782  1.00 22.63      AAGL
ATOM    844  CA  GLN  109      5.277  10.304 116.539  1.00 22.94      AAGL
ATOM    845  CB  GLN  109      3.884  10.886 116.784  1.00 22.73      AAGL
ATOM    846  CG  GLN  109      2.863   9.838 117.229  1.00 24.36      AAGL
ATOM    847  CD  GLN  109      1.555  10.447 117.706  1.00 25.79      AAGL
ATOM    848  OE1 GLN  109      1.551  11.462 118.410  1.00 25.25      AAGL
ATOM    849  NE2 GLN  109      0.434   9.821 117.340  1.00 24.06      AAGL
ATOM    850  C   GLN  109      6.212  11.362 115.958  1.00 22.81      AAGL
ATOM    851  O   GLN  109      6.416  11.418 114.747  1.00 23.48      AAGL
ATOM    852  N   LEU  110      6.796  12.181 116.826  1.00 23.23      AAGL
ATOM    853  CA  LEU  110      7.716  13.223 116.389  1.00 23.80      AAGL
ATOM    854  CB  LEU  110      8.031  14.188 117.539  1.00 24.37      AAGL
ATOM    855  CG  LEU  110      9.119  15.231 117.255  1.00 22.16      AAGL
ATOM    856  CD1 LEU  110      8.792  15.973 115.960  1.00 22.25      AAGL
ATOM    857  CD2 LEU  110      9.230  16.199 118.420  1.00 23.11      AAGL
ATOM    858  C   LEU  110      9.005  12.596 115.870  1.00 25.82      AAGL
ATOM    859  O   LEU  110      9.523  13.010 114.835  1.00 24.35      AAGL
```

Fig. 3 cont.

```
ATOM    860  N    TYR   111       9.524  11.608 116.594  1.00 25.68      AAGL
ATOM    861  CA   TYR   111      10.746  10.915 116.179  1.00 24.78      AAGL
ATOM    862  CB   TYR   111      11.151   9.869 117.230  1.00 25.83      AAGL
ATOM    863  CG   TYR   111      12.199   8.874 116.767  1.00 27.35      AAGL
ATOM    864  CD1  TYR   111      11.848   7.774 115.986  1.00 29.55      AAGL
ATOM    865  CE1  TYR   111      12.810   6.866 115.544  1.00 31.93      AAGL
ATOM    866  CD2  TYR   111      13.541   9.043 117.099  1.00 28.41      AAGL
ATOM    867  CE2  TYR   111      14.514   8.143 116.661  1.00 32.12      AAGL
ATOM    868  CZ   TYR   111      14.143   7.060 115.882  1.00 31.55      AAGL
ATOM    869  OH   TYR   111      15.104   6.183 115.423  1.00 34.00      AAGL
ATOM    870  C    TYR   111      10.505  10.246 114.832  1.00 24.33      AAGL
ATOM    871  O    TYR   111      11.307  10.383 113.901  1.00 26.25      AAGL
ATOM    872  N    ASN   112       9.398   9.521 114.731  1.00 23.20      AAGL
ATOM    873  CA   ASN   112       9.042   8.842 113.492  1.00 24.57      AAGL
ATOM    874  CB   ASN   112       7.750   8.041 113.688  1.00 27.15      AAGL
ATOM    875  CG   ASN   112       7.963   6.757 114.473  0.50 25.91      AAGL
ATOM    876  OD1  ASN   112       7.010   6.023 114.752  0.50 29.07      AAGL
ATOM    877  ND2  ASN   112       9.209   6.475 114.825  0.50 26.44      AAGL
ATOM    878  C    ASN   112       8.865   9.865 112.364  1.00 26.29      AAGL
ATOM    879  O    ASN   112       9.227   9.607 111.211  1.00 23.16      AAGL
ATOM    880  N    TYR   113       8.317  11.028 112.702  1.00 23.87      AAGL
ATOM    881  CA   TYR   113       8.097  12.075 111.711  1.00 23.73      AAGL
ATOM    882  CB   TYR   113       7.328  13.239 112.315  1.00 23.08      AAGL
ATOM    883  CG   TYR   113       7.148  14.387 111.341  1.00 22.30      AAGL
ATOM    884  CD1  TYR   113       6.290  14.271 110.243  1.00 20.43      AAGL
ATOM    885  CE1  TYR   113       6.134  15.327 109.335  1.00 21.15      AAGL
ATOM    886  CD2  TYR   113       7.847  15.584 111.510  1.00 20.85      AAGL
ATOM    887  CE2  TYR   113       7.699  16.642 110.612  1.00 18.32      AAGL
ATOM    888  CZ   TYR   113       6.846  16.512 109.533  1.00 19.02      AAGL
ATOM    889  OH   TYR   113       6.706  17.562 108.654  1.00 18.05      AAGL
ATOM    890  C    TYR   113       9.391  12.613 111.111  1.00 23.40      AAGL
ATOM    891  O    TYR   113       9.561  12.611 109.891  1.00 24.13      AAGL
ATOM    892  N    THR   114      10.300  13.085 111.957  1.00 22.35      AAGL
ATOM    893  CA   THR   114      11.552  13.623 111.441  1.00 23.52      AAGL
ATOM    894  CB   THR   114      12.413  14.260 112.569  1.00 22.78      AAGL
ATOM    895  OG1  THR   114      12.714  13.292 113.578  1.00 23.02      AAGL
ATOM    896  CG2  THR   114      11.662  15.433 113.210  1.00 22.56      AAGL
ATOM    897  C    THR   114      12.339  12.530 110.711  1.00 24.38      AAGL
ATOM    898  O    THR   114      12.954  12.783 109.673  1.00 23.70      AAGL
ATOM    899  N    LEU   115      12.309  11.315 111.250  1.00 26.01      AAGL
ATOM    900  CA   LEU   115      12.995  10.189 110.618  1.00 26.48      AAGL
ATOM    901  CB   LEU   115      12.785   8.909 111.443  1.00 27.61      AAGL
ATOM    902  CG   LEU   115      13.278   7.573 110.853  1.00 28.64      AAGL
ATOM    903  CD1  LEU   115      14.787   7.644 110.546  1.00 29.41      AAGL
ATOM    904  CD2  LEU   115      12.991   6.434 111.836  1.00 31.02      AAGL
ATOM    905  C    LEU   115      12.432  10.002 109.208  1.00 27.33      AAGL
ATOM    906  O    LEU   115      13.180   9.902 108.236  1.00 29.69      AAGL
ATOM    907  N    GLU   116      11.106   9.979 109.102  1.00 27.14      AAGL
ATOM    908  CA   GLU   116      10.428   9.800 107.825  1.00 28.85      AAGL
ATOM    909  CB   GLU   116       8.919   9.674 108.057  1.00 33.11      AAGL
ATOM    910  CG   GLU   116       8.111   9.374 106.803  1.00 40.59      AAGL
ATOM    911  CD   GLU   116       8.196   7.914 106.368  1.00 44.26      AAGL
ATOM    912  OE1  GLU   116       7.696   7.603 105.266  1.00 47.23      AAGL
ATOM    913  OE2  GLU   116       8.744   7.073 107.118  1.00 47.05      AAGL
ATOM    914  C    GLU   116      10.707  10.952 106.853  1.00 28.50      AAGL
ATOM    915  O    GLU   116      10.936  10.730 105.667  1.00 28.60      AAGL
ATOM    916  N    VAL   117      10.671  12.184 107.354  1.00 25.75      AAGL
ATOM    917  CA   VAL   117      10.933  13.345 106.507  1.00 25.01      AAGL
ATOM    918  CB   VAL   117      10.841  14.657 107.303  1.00 25.08      AAGL
ATOM    919  CG1  VAL   117      11.393  15.810 106.473  1.00 24.84      AAGL
ATOM    920  CG2  VAL   117       9.390  14.924 107.685  1.00 25.17      AAGL
ATOM    921  C    VAL   117      12.321  13.256 105.894  1.00 25.14      AAGL
ATOM    922  O    VAL   117      12.488  13.445 104.684  1.00 26.07      AAGL
ATOM    923  N    CYS   118      13.313  12.982 106.734  1.00 22.94      AAGL
ATOM    924  CA   CYS   118      14.684  12.868 106.261  1.00 24.56      AAGL
ATOM    925  CB   CYS   118      15.644  12.710 107.446  1.00 24.73      AAGL
ATOM    926  SG   CYS   118      15.852  14.220 108.485  1.00 26.92      AAGL
```

Fig. 3 cont.

```
ATOM    927  C   CYS   118      14.810  11.682 105.289  1.00 25.33           AAGL
ATOM    928  O   CYS   118      15.417  11.813 104.228  1.00 25.49           AAGL
ATOM    929  N   ASN   119      14.224  10.537 105.638  1.00 25.35           AAGL
ATOM    930  CA  ASN   119      14.296   9.372 104.753  1.00 28.13           AAGL
ATOM    931  CB  ASN   119      13.618   8.156 105.382  1.00 28.39           AAGL
ATOM    932  CG  ASN   119      14.446   7.539 106.477  1.00 28.84           AAGL
ATOM    933  OD1 ASN   119      15.607   7.906 106.681  1.00 28.82           AAGL
ATOM    934  ND2 ASN   119      13.858   6.592 107.191  1.00 31.56           AAGL
ATOM    935  C   ASN   119      13.685   9.618 103.381  1.00 28.08           AAGL
ATOM    936  O   ASN   119      14.199   9.129 102.376  1.00 31.49           AAGL
ATOM    937  N   THR   120      12.594  10.372 103.326  1.00 28.01           AAGL
ATOM    938  CA  THR   120      11.952  10.641 102.046  1.00 27.89           AAGL
ATOM    939  CB  THR   120      10.596  11.321 102.231  1.00 30.29           AAGL
ATOM    940  OG1 THR   120       9.752  10.480 103.034  1.00 31.43           AAGL
ATOM    941  CG2 THR   120       9.926  11.536 100.873  1.00 30.28           AAGL
ATOM    942  C   THR   120      12.838  11.495 101.147  1.00 28.78           AAGL
ATOM    943  O   THR   120      12.869  11.290  99.933  1.00 29.09           AAGL
ATOM    944  N   PHE   121      13.557  12.452 101.728  1.00 28.45           AAGL
ATOM    945  CA  PHE   121      14.463  13.269 100.930  1.00 28.19           AAGL
ATOM    946  CB  PHE   121      14.985  14.461 101.741  1.00 29.04           AAGL
ATOM    947  CG  PHE   121      14.023  15.616 101.789  1.00 27.88           AAGL
ATOM    948  CD1 PHE   121      12.847  15.529 102.530  1.00 28.91           AAGL
ATOM    949  CD2 PHE   121      14.242  16.753 101.018  1.00 28.77           AAGL
ATOM    950  CE1 PHE   121      11.905  16.549 102.496  1.00 26.83           AAGL
ATOM    951  CE2 PHE   121      13.301  17.780 100.979  1.00 29.21           AAGL
ATOM    952  CZ  PHE   121      12.130  17.676 101.719  1.00 29.40           AAGL
ATOM    953  C   PHE   121      15.622  12.391 100.454  1.00 28.62           AAGL
ATOM    954  O   PHE   121      16.064  12.485  99.308  1.00 29.15           AAGL
ATOM    955  N   ALA   122      16.102  11.519 101.332  1.00 28.34           AAGL
ATOM    956  CA  ALA   122      17.187  10.622 100.964  1.00 29.64           AAGL
ATOM    957  CB  ALA   122      17.599   9.768 102.158  1.00 27.49           AAGL
ATOM    958  C   ALA   122      16.748   9.731  99.795  1.00 29.44           AAGL
ATOM    959  O   ALA   122      17.538   9.447  98.890  1.00 30.54           AAGL
ATOM    960  N   GLU   123      15.492   9.295  99.801  1.00 27.94           AAGL
ATOM    961  CA  GLU   123      15.004   8.448  98.720  1.00 28.60           AAGL
ATOM    962  CB  GLU   123      13.654   7.837  99.085  1.00 30.65           AAGL
ATOM    963  CG  GLU   123      13.693   7.161 100.439  1.00 35.94           AAGL
ATOM    964  CD  GLU   123      12.401   6.467 100.813  1.00 38.73           AAGL
ATOM    965  OE1 GLU   123      11.315   6.915 100.376  1.00 39.11           AAGL
ATOM    966  OE2 GLU   123      12.485   5.476 101.570  1.00 39.90           AAGL
ATOM    967  C   GLU   123      14.899   9.237  97.420  1.00 28.83           AAGL
ATOM    968  O   GLU   123      14.826   8.658  96.338  1.00 25.94           AAGL
ATOM    969  N   ASN   124      14.893  10.561  97.535  1.00 27.22           AAGL
ATOM    970  CA  ASN   124      14.825  11.434  96.366  1.00 26.84           AAGL
ATOM    971  CB  ASN   124      13.786  12.537  96.579  1.00 27.25           AAGL
ATOM    972  CG  ASN   124      12.367  12.067  96.302  1.00 28.47           AAGL
ATOM    973  OD1 ASN   124      11.888  12.130  95.168  1.00 28.23           AAGL
ATOM    974  ND2 ASN   124      11.691  11.580  97.336  1.00 30.75           AAGL
ATOM    975  C   ASN   124      16.186  12.063  96.085  1.00 26.40           AAGL
ATOM    976  O   ASN   124      16.290  13.015  95.315  1.00 25.52           AAGL
ATOM    977  N   ASP   125      17.223  11.538  96.726  1.00 26.35           AAGL
ATOM    978  CA  ASP   125      18.580  12.039  96.532  1.00 29.66           AAGL
ATOM    979  CB  ASP   125      19.066  11.654  95.131  1.00 31.58           AAGL
ATOM    980  CG  ASP   125      20.550  11.898  94.939  1.00 34.86           AAGL
ATOM    981  OD1 ASP   125      21.314  11.723  95.912  1.00 36.55           AAGL
ATOM    982  OD2 ASP   125      20.958  12.254  93.813  1.00 35.76           AAGL
ATOM    983  C   ASP   125      18.715  13.555  96.738  1.00 30.52           AAGL
ATOM    984  O   ASP   125      19.286  14.265  95.906  1.00 28.80           AAGL
ATOM    985  N   ILE  126      18.181  14.042  97.853  1.00 30.01           AAGL
ATOM    986  CA  ILE  126      18.270  15.458  98.200  1.00 30.54           AAGL
ATOM    987  CB  ILE  126      16.886  16.127  98.234  1.00 30.36           AAGL
ATOM    988  CG2 ILE  126      17.014  17.532  98.817  1.00 31.24           AAGL
ATOM    989  CG1 ILE  126      16.294  16.182  96.823  1.00 29.46           AAGL
ATOM    990  CD1 ILE  126      14.803  16.480  96.798  1.00 32.42           AAGL
ATOM    991  C   ILE  126      18.894  15.566  99.590  1.00 32.08           AAGL
ATOM    992  O   ILE  126      18.381  14.988 100.550  1.00 33.29           AAGL
ATOM    993  N   ASP  127      20.004  16.292  99.689  1.00 30.97           AAGL
```

Fig. 3 cont.

```
ATOM    994  CA   ASP  127      20.701  16.475 100.960  1.00 32.32      AAGL
ATOM    995  CB   ASP  127      22.181  16.777 100.719  1.00 36.39      AAGL
ATOM    996  CG   ASP  127      22.849  15.758  99.822  1.00 40.70      AAGL
ATOM    997  OD1  ASP  127      23.019  14.591 100.244  1.00 43.54      AAGL
ATOM    998  OD2  ASP  127      23.201  16.126  98.680  1.00 45.38      AAGL
ATOM    999  C    ASP  127      20.082  17.655 101.687  1.00 31.14      AAGL
ATOM   1000  O    ASP  127      19.643  18.616 101.053  1.00 30.94      AAGL
ATOM   1001  N    ILE  128      20.063  17.587 103.012  1.00 29.03      AAGL
ATOM   1002  CA   ILE  128      19.505  18.659 103.825  1.00 27.70      AAGL
ATOM   1003  CB   ILE  128      18.442  18.112 104.806  1.00 27.94      AAGL
ATOM   1004  CG2  ILE  128      17.866  19.250 105.645  1.00 25.95      AAGL
ATOM   1005  CG1  ILE  128      17.333  17.408 104.017  1.00 27.55      AAGL
ATOM   1006  CD1  ILE  128      16.289  16.716 104.883  1.00 29.46      AAGL
ATOM   1007  C    ILE  128      20.630  19.317 104.611  1.00 25.60      AAGL
ATOM   1008  O    ILE  128      21.370  18.645 105.328  1.00 28.07      AAGL
ATOM   1009  N    GLU  129      20.766  20.632 104.465  1.00 24.98      AAGL
ATOM   1010  CA   GLU  129      21.818  21.380 105.156  1.00 24.49      AAGL
ATOM   1011  CB   GLU  129      22.107  22.671 104.382  1.00 27.35      AAGL
ATOM   1012  CG   GLU  129      23.218  23.552 104.946  1.00 30.16      AAGL
ATOM   1013  CD   GLU  129      24.601  22.996 104.682  1.00 32.15      AAGL
ATOM   1014  OE1  GLU  129      24.720  22.097 103.821  1.00 32.40      AAGL
ATOM   1015  OE2  GLU  129      25.563  23.469 105.326  1.00 31.39      AAGL
ATOM   1016  C    GLU  129      21.418  21.713 106.593  1.00 24.14      AAGL
ATOM   1017  O    GLU  129      22.210  21.561 107.531  1.00 23.23      AAGL
ATOM   1018  N    ILE  130      20.184  22.174 106.761  1.00 22.11      AAGL
ATOM   1019  CA   ILE  130      19.696  22.535 108.083  1.00 20.15      AAGL
ATOM   1020  CB   ILE  130      19.719  24.065 108.301  1.00 21.07      AAGL
ATOM   1021  CG2  ILE  130      19.096  24.406 109.636  1.00 22.31      AAGL
ATOM   1022  CG1  ILE  130      21.147  24.601 108.233  1.00 20.04      AAGL
ATOM   1023  CD1  ILE  130      21.215  26.109 108.266  1.00 21.74      AAGL
ATOM   1024  C    ILE  130      18.256  22.091 108.265  1.00 20.32      AAGL
ATOM   1025  O    ILE  130      17.464  22.096 107.328  1.00 18.94      AAGL
ATOM   1026  N    ILE  131      17.920  21.696 109.480  1.00 21.44      AAGL
ATOM   1027  CA   ILE  131      16.551  21.316 109.759  1.00 22.36      AAGL
ATOM   1028  CB   ILE  131      16.324  19.791 109.544  1.00 23.90      AAGL
ATOM   1029  CG2  ILE  131      17.138  18.979 110.541  1.00 28.54      AAGL
ATOM   1030  CG1  ILE  131      14.826  19.488 109.629  1.00 26.48      AAGL
ATOM   1031  CD1  ILE  131      14.427  18.156 109.005  1.00 28.03      AAGL
ATOM   1032  C    ILE  131      16.253  21.765 111.185  1.00 21.53      AAGL
ATOM   1033  O    ILE  131      16.978  21.430 112.119  1.00 20.84      AAGL
ATOM   1034  N    SER  132      15.217  22.587 111.335  1.00 20.93      AAGL
ATOM   1035  CA   SER  132      14.859  23.089 112.654  1.00 19.31      AAGL
ATOM   1036  CB   SER  132      14.444  24.562 112.578  1.00 18.01      AAGL
ATOM   1037  OG   SER  132      13.232  24.709 111.869  1.00 21.72      AAGL
ATOM   1038  C    SER  132      13.720  22.261 113.221  1.00 19.27      AAGL
ATOM   1039  O    SER  132      12.766  21.930 112.520  1.00 19.32      AAGL
ATOM   1040  N    ILE  133      13.842  21.901 114.491  1.00 19.77      AAGL
ATOM   1041  CA   ILE  133      12.806  21.122 115.143  1.00 20.58      AAGL
ATOM   1042  CB   ILE  133      13.367  20.295 116.317  1.00 21.64      AAGL
ATOM   1043  CG2  ILE  133      12.297  19.334 116.823  1.00 18.97      AAGL
ATOM   1044  CG1  ILE  133      14.644  19.559 115.890  1.00 21.37      AAGL
ATOM   1045  CD1  ILE  133      14.515  18.774 114.605  1.00 25.39      AAGL
ATOM   1046  C    ILE  133      11.815  22.142 115.689  1.00 20.75      AAGL
ATOM   1047  O    ILE  133      11.890  22.529 116.850  1.00 21.44      AAGL
ATOM   1048  N    GLY  134      10.904  22.581 114.833  1.00 19.14      AAGL
ATOM   1049  CA   GLY  134       9.919  23.560 115.241  1.00 18.88      AAGL
ATOM   1050  C    GLY  134      10.240  24.936 114.690  1.00 18.31      AAGL
ATOM   1051  O    GLY  134      11.344  25.181 114.199  1.00 19.16      AAGL
ATOM   1052  N    ASN  135       9.268  25.835 114.769  1.00 16.66      AAGL
ATOM   1053  CA   ASN  135       9.427  27.201 114.289  1.00 16.54      AAGL
ATOM   1054  CB   ASN  135       8.507  27.457 113.097  1.00 15.67      AAGL
ATOM   1055  CG   ASN  135       8.666  28.854 112.532  1.00 20.06      AAGL
ATOM   1056  OD1  ASN  135       9.590  29.120 111.759  1.00 19.47      AAGL
ATOM   1057  ND2  ASN  135       7.773  29.762 112.932  1.00 14.55      AAGL
ATOM   1058  C    ASN  135       9.044  28.146 115.420  1.00 17.93      AAGL
ATOM   1059  O    ASN  135       7.940  28.063 115.935  1.00 16.64      AAGL
ATOM   1060  N    GLU  136       9.967  29.030 115.793  1.00 16.85      AAGL
```

Fig. 3 cont.

```
ATOM   1061  CA   GLU   136       9.760  30.001 116.865  1.00 17.43      AAGL
ATOM   1062  CB   GLU   136       8.892  31.169 116.371  1.00 18.10      AAGL
ATOM   1063  CG   GLU   136       9.517  31.970 115.228  1.00 17.17      AAGL
ATOM   1064  CD   GLU   136       8.747  33.240 114.867  1.00 18.85      AAGL
ATOM   1065  OE1  GLU   136       7.592  33.416 115.314  1.00 19.27      AAGL
ATOM   1066  OE2  GLU   136       9.305  34.071 114.120  1.00 18.05      AAGL
ATOM   1067  C    GLU   136       9.116  29.338 118.080  1.00 17.00      AAGL
ATOM   1068  O    GLU   136       8.013  29.697 118.478  1.00 18.88      AAGL
ATOM   1069  N    ILE   137       9.819  28.379 118.674  1.00 16.48      AAGL
ATOM   1070  CA   ILE   137       9.283  27.657 119.828  1.00 16.33      AAGL
ATOM   1071  CB   ILE   137       9.753  26.185 119.830  1.00 17.11      AAGL
ATOM   1072  CG2  ILE   137       9.204  25.457 118.615  1.00 18.25      AAGL
ATOM   1073  CG1  ILE   137      11.276  26.119 119.848  1.00 18.08      AAGL
ATOM   1074  CD1  ILE   137      11.822  24.717 120.029  1.00 19.03      AAGL
ATOM   1075  C    ILE   137       9.600  28.266 121.200  1.00 16.65      AAGL
ATOM   1076  O    ILE   137       9.770  27.540 122.178  1.00 18.23      AAGL
ATOM   1077  N    ARG   138       9.668  29.591 121.271  1.00 15.75      AAGL
ATOM   1078  CA   ARG   138       9.948  30.265 122.537  1.00 19.97      AAGL
ATOM   1079  CB   ARG   138      10.069  31.776 122.327  1.00 21.48      AAGL
ATOM   1080  CG   ARG   138      10.434  32.559 123.586  1.00 23.19      AAGL
ATOM   1081  CD   ARG   138      10.971  33.946 123.230  1.00 25.82      AAGL
ATOM   1082  NE   ARG   138      10.007  34.726 122.454  1.00 29.47      AAGL
ATOM   1083  CZ   ARG   138       8.900  35.263 122.956  1.00 29.69      AAGL
ATOM   1084  NH1  ARG   138       8.610  35.110 124.243  1.00 32.98      AAGL
ATOM   1085  NH2  ARG   138       8.075  35.939 122.168  1.00 29.53      AAGL
ATOM   1086  C    ARG   138       8.852  29.971 123.557  1.00 20.72      AAGL
ATOM   1087  O    ARG   138       9.112  29.926 124.755  1.00 22.83      AAGL
ATOM   1088  N    ALA   139       7.624  29.788 123.081  1.00 19.30      AAGL
ATOM   1089  CA   ALA   139       6.513  29.470 123.969  1.00 19.27      AAGL
ATOM   1090  CB   ALA   139       5.268  30.275 123.586  1.00 21.29      AAGL
ATOM   1091  C    ALA   139       6.227  27.971 123.893  1.00 20.13      AAGL
ATOM   1092  O    ALA   139       5.102  27.517 124.135  1.00 19.76      AAGL
ATOM   1093  N    GLY   140       7.264  27.207 123.565  1.00 16.96      AAGL
ATOM   1094  CA   GLY   140       7.124  25.769 123.465  1.00 17.78      AAGL
ATOM   1095  C    GLY   140       6.640  25.305 122.102  1.00 18.69      AAGL
ATOM   1096  O    GLY   140       6.669  26.058 121.119  1.00 15.87      AAGL
ATOM   1097  N    LEU   141       6.185  24.058 122.051  1.00 18.79      AAGL
ATOM   1098  CA   LEU   141       5.689  23.458 120.815  1.00 18.06      AAGL
ATOM   1099  CB   LEU   141       6.855  22.900 119.999  1.00 17.19      AAGL
ATOM   1100  CG   LEU   141       7.477  21.595 120.523  1.00 18.49      AAGL
ATOM   1101  CD1  LEU   141       8.404  21.018 119.457  1.00 17.04      AAGL
ATOM   1102  CD2  LEU   141       8.231  21.842 121.827  1.00 17.24      AAGL
ATOM   1103  C    LEU   141       4.741  22.310 121.145  1.00 17.11      AAGL
ATOM   1104  O    LEU   141       4.632  21.901 122.295  1.00 19.24      AAGL
ATOM   1105  N    LEU   142       4.063  21.795 120.126  1.00 15.85      AAGL
ATOM   1106  CA   LEU   142       3.162  20.664 120.293  1.00 16.79      AAGL
ATOM   1107  CB   LEU   142       3.981  19.370 120.301  1.00 17.91      AAGL
ATOM   1108  CG   LEU   142       4.783  19.127 119.017  1.00 18.45      AAGL
ATOM   1109  CD1  LEU   142       5.725  17.947 119.195  1.00 16.19      AAGL
ATOM   1110  CD2  LEU   142       3.827  18.888 117.861  1.00 18.62      AAGL
ATOM   1111  C    LEU   142       2.319  20.766 121.562  1.00 18.08      AAGL
ATOM   1112  O    LEU   142       2.374  19.909 122.440  1.00 18.47      AAGL
ATOM   1113  N    TRP   143       1.539  21.830 121.652  1.00 18.54      AAGL
ATOM   1114  CA   TRP   143       0.684  22.038 122.810  1.00 18.96      AAGL
ATOM   1115  CB   TRP   143       0.063  23.431 122.763  1.00 17.05      AAGL
ATOM   1116  CG   TRP   143       1.061  24.544 122.780  1.00 15.57      AAGL
ATOM   1117  CD2  TRP   143       0.807  25.920 122.475  1.00 16.04      AAGL
ATOM   1118  CE2  TRP   143       2.014  26.621 122.675  1.00 15.69      AAGL
ATOM   1119  CE3  TRP   143      -0.324  26.629 122.053  1.00 17.45      AAGL
ATOM   1120  CD1  TRP   143       2.375  24.468 123.139  1.00 15.44      AAGL
ATOM   1121  NE1  TRP   143       2.954  25.711 123.081  1.00 14.73      AAGL
ATOM   1122  CZ2  TRP   143       2.120  27.998 122.467  1.00 18.72      AAGL
ATOM   1123  CZ3  TRP   143      -0.215  28.000 121.848  1.00 20.29      AAGL
ATOM   1124  CH2  TRP   143       0.995  28.666 122.055  1.00 18.09      AAGL
ATOM   1125  C    TRP   143      -0.420  20.989 122.830  1.00 17.60      AAGL
ATOM   1126  O    TRP   143      -0.860  20.526 121.787  1.00 19.46      AAGL
ATOM   1127  N    PRO   144      -0.928  20.646 124.022  1.00 19.35      AAGL
```

Fig. 3 cont.

```
ATOM   1128  CD   PRO  144   -2.116  19.777  124.132  1.00  18.54      AAGL
ATOM   1129  CA   PRO  144   -0.549  21.167  125.340  1.00  18.49      AAGL
ATOM   1130  CB   PRO  144   -1.796  20.898  126.169  1.00  18.97      AAGL
ATOM   1131  CG   PRO  144   -2.228  19.560  125.628  1.00  20.05      AAGL
ATOM   1132  C    PRO  144    0.687  20.546  125.990  1.00  17.18      AAGL
ATOM   1133  O    PRO  144    1.303  21.162  126.855  1.00  17.80      AAGL
ATOM   1134  N    LEU  145    1.043  19.329  125.592  1.00  16.38      AAGL
ATOM   1135  CA   LEU  145    2.184  18.655  126.206  1.00  18.03      AAGL
ATOM   1136  CB   LEU  145    2.401  17.277  125.567  1.00  19.70      AAGL
ATOM   1137  CG   LEU  145    1.382  16.208  125.988  1.00  21.47      AAGL
ATOM   1138  CD1  LEU  145    1.529  14.966  125.133  1.00  24.17      AAGL
ATOM   1139  CD2  LEU  145    1.584  15.871  127.450  1.00  22.76      AAGL
ATOM   1140  C    LEU  145    3.482  19.449  126.189  1.00  18.55      AAGL
ATOM   1141  O    LEU  145    4.291  19.335  127.113  1.00  18.42      AAGL
ATOM   1142  N    GLY  146    3.671  20.262  125.152  1.00  18.88      AAGL
ATOM   1143  CA   GLY  146    4.884  21.050  125.045  1.00  18.53      AAGL
ATOM   1144  C    GLY  146    4.759  22.511  125.444  1.00  19.09      AAGL
ATOM   1145  O    GLY  146    5.509  23.351  124.948  1.00  17.40      AAGL
ATOM   1146  N    GLU  147    3.811  22.827  126.326  1.00  18.92      AAGL
ATOM   1147  CA   GLU  147    3.647  24.207  126.792  1.00  18.48      AAGL
ATOM   1148  CB   GLU  147    2.298  24.382  127.499  1.00  17.73      AAGL
ATOM   1149  CG   GLU  147    1.111  24.296  126.565  1.00  18.17      AAGL
ATOM   1150  CD   GLU  147    0.452  25.642  126.328  1.00  21.87      AAGL
ATOM   1151  OE1  GLU  147    1.137  26.684  126.464  1.00  24.40      AAGL
ATOM   1152  OE2  GLU  147   -0.751  25.655  125.997  1.00  22.11      AAGL
ATOM   1153  C    GLU  147    4.789  24.512  127.759  1.00  19.00      AAGL
ATOM   1154  O    GLU  147    5.421  23.589  128.287  1.00  20.89      AAGL
ATOM   1155  N    THR  148    5.046  25.797  128.003  1.00  18.85      AAGL
ATOM   1156  CA   THR  148    6.137  26.194  128.887  1.00  21.19      AAGL
ATOM   1157  CB   THR  148    6.486  27.705  128.746  1.00  21.41      AAGL
ATOM   1158  OG1  THR  148    5.307  28.498  128.908  1.00  23.59      AAGL
ATOM   1159  CG2  THR  148    7.095  27.987  127.379  1.00  21.18      AAGL
ATOM   1160  C    THR  148    5.889  25.868  130.354  1.00  21.42      AAGL
ATOM   1161  O    THR  148    6.711  26.180  131.207  1.00  21.58      AAGL
ATOM   1162  N    SER  149    4.753  25.251  130.656  1.00  20.92      AAGL
ATOM   1163  CA   SER  149    4.487  24.852  132.027  1.00  22.49      AAGL
ATOM   1164  CB   SER  149    2.990  24.593  132.228  1.00  20.24      AAGL
ATOM   1165  OG   SER  149    2.442  23.871  131.142  1.00  21.26      AAGL
ATOM   1166  C    SER  149    5.314  23.582  132.275  1.00  23.11      AAGL
ATOM   1167  O    SER  149    5.420  23.093  133.397  1.00  23.52      AAGL
ATOM   1168  N    SER  150    5.914  23.062  131.205  1.00  22.32      AAGL
ATOM   1169  CA   SER  150    6.749  21.868  131.299  1.00  22.70      AAGL
ATOM   1170  CB   SER  150    5.925  20.609  131.003  1.00  23.28      AAGL
ATOM   1171  OG   SER  150    6.735  19.445  131.058  1.00  24.36      AAGL
ATOM   1172  C    SER  150    7.946  21.937  130.345  1.00  22.43      AAGL
ATOM   1173  O    SER  150    7.909  21.386  129.246  1.00  22.55      AAGL
ATOM   1174  N    TYR  151    9.007  22.619  130.766  1.00  22.50      AAGL
ATOM   1175  CA   TYR  151   10.195  22.714  129.932  1.00  23.76      AAGL
ATOM   1176  CB   TYR  151   11.192  23.730  130.511  1.00  23.66      AAGL
ATOM   1177  CG   TYR  151   10.861  25.169  130.153  1.00  25.07      AAGL
ATOM   1178  CD1  TYR  151   10.054  25.950  130.978  1.00  22.33      AAGL
ATOM   1179  CE1  TYR  151    9.719  27.270  130.628  1.00  22.71      AAGL
ATOM   1180  CD2  TYR  151   11.329  25.740  128.965  1.00  24.38      AAGL
ATOM   1181  CE2  TYR  151   10.997  27.057  128.610  1.00  23.11      AAGL
ATOM   1182  CZ   TYR  151   10.195  27.812  129.446  1.00  22.47      AAGL
ATOM   1183  OH   TYR  151    9.881  29.113  129.116  1.00  23.02      AAGL
ATOM   1184  C    TYR  151   10.827  21.327  129.804  1.00  24.63      AAGL
ATOM   1185  O    TYR  151   11.627  21.070  128.903  1.00  23.36      AAGL
ATOM   1186  N    SER  152   10.441  20.427  130.703  1.00  25.50      AAGL
ATOM   1187  CA   SER  152   10.942  19.064  130.670  1.00  24.95      AAGL
ATOM   1188  CB   SER  152   10.539  18.325  131.945  1.00  25.80      AAGL
ATOM   1189  OG   SER  152   11.051  17.010  131.928  1.00  31.90      AAGL
ATOM   1190  C    SER  152   10.364  18.358  129.442  1.00  23.88      AAGL
ATOM   1191  O    SER  152   11.081  17.695  128.696  1.00  24.71      AAGL
ATOM   1192  N    ASN  153    9.059  18.502  129.229  1.00  24.00      AAGL
ATOM   1193  CA   ASN  153    8.414  17.885  128.075  1.00  22.02      AAGL
ATOM   1194  CB   ASN  153    6.901  18.108  128.132  1.00  21.03      AAGL
```

Fig. 3 cont.

```
ATOM   1195  CG  ASN  153      6.225  17.239 129.168  1.00 22.68      AAGL
ATOM   1196  OD1 ASN  153      6.888  16.579 129.971  1.00 21.72      AAGL
ATOM   1197  ND2 ASN  153      4.897  17.235 129.159  1.00 19.51      AAGL
ATOM   1198  C   ASN  153      8.970  18.486 126.782  1.00 21.57      AAGL
ATOM   1199  O   ASN  153      9.178  17.782 125.792  1.00 19.66      AAGL
ATOM   1200  N   ILE  154      9.192  19.797 126.798  1.00 20.58      AAGL
ATOM   1201  CA  ILE  154      9.733  20.490 125.636  1.00 21.12      AAGL
ATOM   1202  CB  ILE  154      9.922  21.988 125.909  1.00 21.27      AAGL
ATOM   1203  CG2 ILE  154     10.721  22.626 124.771  1.00 20.30      AAGL
ATOM   1204  CG1 ILE  154      8.563  22.666 126.092  1.00 20.35      AAGL
ATOM   1205  CD1 ILE  154      8.664  24.125 126.509  1.00 21.33      AAGL
ATOM   1206  C   ILE  154     11.097  19.901 125.304  1.00 22.17      AAGL
ATOM   1207  O   ILE  154     11.395  19.610 124.147  1.00 19.83      AAGL
ATOM   1208  N   GLY  155     11.920  19.735 126.337  1.00 23.65      AAGL
ATOM   1209  CA  GLY  155     13.246  19.181 126.147  1.00 24.02      AAGL
ATOM   1210  C   GLY  155     13.201  17.756 125.635  1.00 23.51      AAGL
ATOM   1211  O   GLY  155     13.968  17.384 124.745  1.00 23.80      AAGL
ATOM   1212  N   ALA  156     12.300  16.952 126.191  1.00 24.34      AAGL
ATOM   1213  CA  ALA  156     12.169  15.560 125.774  1.00 23.36      AAGL
ATOM   1214  CB  ALA  156     11.203  14.826 126.700  1.00 25.00      AAGL
ATOM   1215  C   ALA  156     11.701  15.457 124.324  1.00 23.25      AAGL
ATOM   1216  O   ALA  156     12.121  14.571 123.589  1.00 22.33      AAGL
ATOM   1217  N   LEU  157     10.831  16.371 123.911  1.00 22.39      AAGL
ATOM   1218  CA  LEU  157     10.340  16.376 122.538  1.00 21.31      AAGL
ATOM   1219  CB  LEU  157      9.161  17.343 122.408  1.00 20.00      AAGL
ATOM   1220  CG  LEU  157      7.868  16.843 123.059  1.00 22.93      AAGL
ATOM   1221  CD1 LEU  157      6.894  17.994 123.274  1.00 22.57      AAGL
ATOM   1222  CD2 LEU  157      7.260  15.751 122.164  1.00 21.07      AAGL
ATOM   1223  C   LEU  157     11.443  16.772 121.564  1.00 21.89      AAGL
ATOM   1224  O   LEU  157     11.616  16.146 120.518  1.00 20.81      AAGL
ATOM   1225  N   LEU  158     12.195  17.813 121.905  1.00 21.14      AAGL
ATOM   1226  CA  LEU  158     13.267  18.257 121.021  1.00 22.43      AAGL
ATOM   1227  CB  LEU  158     13.903  19.540 121.569  1.00 22.22      AAGL
ATOM   1228  CG  LEU  158     12.982  20.775 121.562  1.00 21.62      AAGL
ATOM   1229  CD1 LEU  158     13.640  21.917 122.316  1.00 21.34      AAGL
ATOM   1230  CD2 LEU  158     12.683  21.193 120.131  1.00 21.57      AAGL
ATOM   1231  C   LEU  158     14.299  17.133 120.880  1.00 24.78      AAGL
ATOM   1232  O   LEU  158     14.807  16.880 119.794  1.00 23.68      AAGL
ATOM   1233  N   HIS  159     14.584  16.457 121.990  1.00 24.81      AAGL
ATOM   1234  CA  HIS  159     15.518  15.332 122.009  1.00 26.46      AAGL
ATOM   1235  CB  HIS  159     15.566  14.738 123.423  1.00 27.84      AAGL
ATOM   1236  CG  HIS  159     16.473  13.553 123.563  1.00 30.73      AAGL
ATOM   1237  CD2 HIS  159     16.204  12.248 123.812  1.00 32.59      AAGL
ATOM   1238  ND1 HIS  159     17.845  13.651 123.482  1.00 31.02      AAGL
ATOM   1239  CE1 HIS  159     18.383  12.460 123.676  1.00 32.44      AAGL
ATOM   1240  NE2 HIS  159     17.409  11.592 123.880  1.00 33.23      AAGL
ATOM   1241  C   HIS  159     15.029  14.270 121.017  1.00 26.31      AAGL
ATOM   1242  O   HIS  159     15.796  13.772 120.190  1.00 26.14      AAGL
ATOM   1243  N   SER  160     13.749  13.922 121.110  1.00 25.57      AAGL
ATOM   1244  CA  SER  160     13.149  12.927 120.220  1.00 26.09      AAGL
ATOM   1245  CB  SER  160     11.679  12.695 120.590  1.00 26.91      AAGL
ATOM   1246  OG  SER  160     11.555  12.082 121.857  1.00 28.98      AAGL
ATOM   1247  C   SER  160     13.225  13.333 118.745  1.00 25.22      AAGL
ATOM   1248  O   SER  160     13.564  12.516 117.885  1.00 26.49      AAGL
ATOM   1249  N   GLY  161     12.890  14.586 118.452  1.00 22.94      AAGL
ATOM   1250  CA  GLY  161     12.934  15.051 117.078  1.00 22.94      AAGL
ATOM   1251  C   GLY  161     14.359  15.017 116.556  1.00 23.15      AAGL
ATOM   1252  O   GLY  161     14.631  14.541 115.450  1.00 23.15      AAGL
ATOM   1253  N   ALA  162     15.277  15.519 117.368  1.00 24.30      AAGL
ATOM   1254  CA  ALA  162     16.683  15.548 117.002  1.00 26.37      AAGL
ATOM   1255  CB  ALA  162     17.510  16.073 118.164  1.00 24.96      AAGL
ATOM   1256  C   ALA  162     17.172  14.160 116.598  1.00 27.69      AAGL
ATOM   1257  O   ALA  162     17.801  13.995 115.546  1.00 27.54      AAGL
ATOM   1258  N   TRP  163     16.876  13.159 117.423  1.00 27.38      AAGL
ATOM   1259  CA  TRP  163     17.320  11.806 117.124  1.00 26.93      AAGL
ATOM   1260  CB  TRP  163     17.222  10.929 118.368  1.00 28.85      AAGL
ATOM   1261  CG  TRP  163     18.386  11.181 119.245  1.00 31.71      AAGL
```

Fig. 3 cont.

```
ATOM   1262  CD2 TRP   163      19.668  10.565 119.134  1.00 32.43      AAGL
ATOM   1263  CE2 TRP   163      20.516  11.194 120.068  1.00 31.66      AAGL
ATOM   1264  CE3 TRP   163      20.185   9.541 118.329  1.00 32.40      AAGL
ATOM   1265  CD1 TRP   163      18.497  12.130 120.217  1.00 31.49      AAGL
ATOM   1266  NE1 TRP   163      19.776  12.149 120.715  1.00 32.86      AAGL
ATOM   1267  CZ2 TRP   163      21.858  10.836 120.223  1.00 32.68      AAGL
ATOM   1268  CZ3 TRP   163      21.522   9.184 118.479  1.00 32.50      AAGL
ATOM   1269  CH2 TRP   163      22.342   9.832 119.421  1.00 32.64      AAGL
ATOM   1270  C   TRP   163      16.636  11.144 115.952  1.00 27.25      AAGL
ATOM   1271  O   TRP   163      17.177  10.205 115.372  1.00 28.73      AAGL
ATOM   1272  N   GLY   164      15.448  11.613 115.598  1.00 25.57      AAGL
ATOM   1273  CA  GLY   164      14.782  11.045 114.445  1.00 24.90      AAGL
ATOM   1274  C   GLY   164      15.651  11.409 113.253  1.00 26.22      AAGL
ATOM   1275  O   GLY   164      15.831  10.618 112.326  1.00 26.72      AAGL
ATOM   1276  N   VAL   165      16.206  12.618 113.290  1.00 25.62      AAGL
ATOM   1277  CA  VAL   165      17.078  13.087 112.219  1.00 26.48      AAGL
ATOM   1278  CB  VAL   165      17.379  14.598 112.356  1.00 26.61      AAGL
ATOM   1279  CG1 VAL   165      18.398  15.026 111.293  1.00 23.67      AAGL
ATOM   1280  CG2 VAL   165      16.090  15.397 112.216  1.00 25.11      AAGL
ATOM   1281  C   VAL   165      18.406  12.328 112.251  1.00 27.69      AAGL
ATOM   1282  O   VAL   165      18.850  11.788 111.233  1.00 29.75      AAGL
ATOM   1283  N   LYS   166      19.037  12.295 113.420  1.00 27.66      AAGL
ATOM   1284  CA  LYS   166      20.313  11.607 113.581  1.00 29.81      AAGL
ATOM   1285  CB  LYS   166      20.770  11.661 115.045  1.00 29.36      AAGL
ATOM   1286  CG  LYS   166      21.062  13.060 115.590  1.00 30.72      AAGL
ATOM   1287  CD  LYS   166      21.442  12.982 117.065  1.00 33.25      AAGL
ATOM   1288  CE  LYS   166      21.674  14.358 117.677  1.00 33.72      AAGL
ATOM   1289  NZ  LYS   166      22.883  15.036 117.122  1.00 33.70      AAGL
ATOM   1290  C   LYS   166      20.229  10.144 113.136  1.00 31.30      AAGL
ATOM   1291  O   LYS   166      21.206   9.594 112.622  1.00 31.56      AAGL
ATOM   1292  N   ASP   167      19.065   9.519 113.319  1.00 30.83      AAGL
ATOM   1293  CA  ASP   167      18.893   8.116 112.944  1.00 32.56      AAGL
ATOM   1294  CB  ASP   167      17.863   7.442 113.854  1.00 31.71      AAGL
ATOM   1295  CG  ASP   167      18.387   7.187 115.245  1.00 33.01      AAGL
ATOM   1296  OD1 ASP   167      19.620   7.148 115.425  1.00 33.60      AAGL
ATOM   1297  OD2 ASP   167      17.558   7.006 116.160  1.00 32.14      AAGL
ATOM   1298  C   ASP   167      18.481   7.858 111.494  1.00 33.63      AAGL
ATOM   1299  O   ASP   167      18.347   6.696 111.082  1.00 32.89      AAGL
ATOM   1300  N   SER   168      18.280   8.925 110.724  1.00 31.74      AAGL
ATOM   1301  CA  SER   168      17.846   8.786 109.341  1.00 31.90      AAGL
ATOM   1302  CB  SER   168      17.279  10.111 108.823  1.00 29.91      AAGL
ATOM   1303  OG  SER   168      18.301  11.074 108.654  1.00 30.10      AAGL
ATOM   1304  C   SER   168      18.922   8.294 108.378  1.00 32.86      AAGL
ATOM   1305  O   SER   168      20.114   8.248 108.704  1.00 31.48      AAGL
ATOM   1306  N   ASN   169      18.470   7.950 107.179  1.00 34.44      AAGL
ATOM   1307  CA  ASN   169      19.328   7.430 106.123  1.00 37.26      AAGL
ATOM   1308  CB  ASN   169      18.493   6.545 105.195  1.00 38.60      AAGL
ATOM   1309  CG  ASN   169      17.848   5.377 105.925  1.00 37.67      AAGL
ATOM   1310  OD1 ASN   169      16.833   4.841 105.482  1.00 40.60      AAGL
ATOM   1311  ND2 ASN   169      18.440   4.971 107.044  1.00 39.67      AAGL
ATOM   1312  C   ASN   169      20.043   8.508 105.308  1.00 38.79      AAGL
ATOM   1313  O   ASN   169      20.725   8.194 104.324  1.00 39.86      AAGL
ATOM   1314  N   LEU   170      19.891   9.773 105.695  1.00 38.43      AAGL
ATOM   1315  CA  LEU   170      20.562  10.849 104.966  1.00 39.07      AAGL
ATOM   1316  CB  LEU   170      20.133  12.222 105.502  1.00 36.50      AAGL
ATOM   1317  CG  LEU   170      18.784  12.783 105.053  1.00 35.65      AAGL
ATOM   1318  CD1 LEU   170      18.533  14.122 105.733  1.00 36.42      AAGL
ATOM   1319  CD2 LEU   170      18.775  12.960 103.548  1.00 35.41      AAGL
ATOM   1320  C   LEU   170      22.068  10.672 105.146  1.00 40.51      AAGL
ATOM   1321  O   LEU   170      22.580  10.787 106.257  1.00 41.18      AAGL
ATOM   1322  N   ALA   171      22.770  10.392 104.050  1.00 43.25      AAGL
ATOM   1323  CA  ALA   171      24.219  10.180 104.078  1.00 44.92      AAGL
ATOM   1324  CB  ALA   171      24.796  10.430 102.700  1.00 45.32      AAGL
ATOM   1325  C   ALA   171      24.913  11.063 105.117  1.00 45.99      AAGL
ATOM   1326  O   ALA   171      25.671  10.568 105.962  1.00 47.05      AAGL
ATOM   1327  N   THR   172      24.668  12.370 105.044  1.00 46.11      AAGL
ATOM   1328  CA  THR   172      25.246  13.316 105.998  1.00 45.78      AAGL
```

Fig. 3 cont.

```
ATOM   1329  CB  THR  172      25.856  14.549 105.320  1.00 46.89      AAGL
ATOM   1330  OG1 THR  172      26.551  14.167 104.132  1.00 48.14      AAGL
ATOM   1331  CG2 THR  172      26.822  15.224 106.269  1.00 46.74      AAGL
ATOM   1332  C   THR  172      24.117  13.844 106.868  1.00 44.10      AAGL
ATOM   1333  O   THR  172      23.086  14.272 106.351  1.00 44.98      AAGL
ATOM   1334  N   THR  173      24.311  13.835 108.179  1.00 42.61      AAGL
ATOM   1335  CA  THR  173      23.283  14.319 109.088  1.00 39.37      AAGL
ATOM   1336  CB  THR  173      23.621  13.926 110.530  1.00 39.69      AAGL
ATOM   1337  OG1 THR  173      23.691  12.497 110.620  1.00 40.97      AAGL
ATOM   1338  CG2 THR  173      22.555  14.436 111.494  1.00 40.31      AAGL
ATOM   1339  C   THR  173      23.140  15.837 108.969  1.00 36.34      AAGL
ATOM   1340  O   THR  173      24.118  16.581 109.083  1.00 35.72      AAGL
ATOM   1341  N   PRO  174      21.916  16.319 108.702  1.00 33.51      AAGL
ATOM   1342  CD  PRO  174      20.709  15.592 108.274  1.00 33.11      AAGL
ATOM   1343  CA  PRO  174      21.728  17.766 108.580  1.00 30.76      AAGL
ATOM   1344  CB  PRO  174      20.252  17.891 108.223  1.00 31.41      AAGL
ATOM   1345  CG  PRO  174      19.989  16.624 107.452  1.00 33.06      AAGL
ATOM   1346  C   PRO  174      22.056  18.475 109.883  1.00 27.61      AAGL
ATOM   1347  O   PRO  174      22.074  17.865 110.945  1.00 26.79      AAGL
ATOM   1348  N   LYS  175      22.332  19.767 109.800  1.00 28.61      AAGL
ATOM   1349  CA  LYS  175      22.614  20.541 111.001  1.00 27.46      AAGL
ATOM   1350  CB  LYS  175      23.167  21.917 110.636  1.00 30.67      AAGL
ATOM   1351  CG  LYS  175      24.679  22.002 110.611  1.00 35.14      AAGL
ATOM   1352  CD  LYS  175      25.286  20.926 109.751  1.00 39.94      AAGL
ATOM   1353  CE  LYS  175      26.804  21.046 109.733  1.00 42.54      AAGL
ATOM   1354  NZ  LYS  175      27.396  20.867 111.091  1.00 43.56      AAGL
ATOM   1355  C   LYS  175      21.267  20.693 111.695  1.00 26.21      AAGL
ATOM   1356  O   LYS  175      20.297  21.096 111.068  1.00 25.54      AAGL
ATOM   1357  N   ILE  176      21.209  20.350 112.975  1.00 24.86      AAGL
ATOM   1358  CA  ILE  176      19.968  20.443 113.728  1.00 24.97      AAGL
ATOM   1359  CB  ILE  176      19.899  19.320 114.779  1.00 25.45      AAGL
ATOM   1360  CG2 ILE  176      18.689  19.515 115.676  1.00 25.15      AAGL
ATOM   1361  CG1 ILE  176      19.847  17.964 114.061  1.00 25.46      AAGL
ATOM   1362  CD1 ILE  176      20.148  16.775 114.941  1.00 26.04      AAGL
ATOM   1363  C   ILE  176      19.866  21.807 114.395  1.00 23.30      AAGL
ATOM   1364  O   ILE  176      20.752  22.208 115.136  1.00 24.10      AAGL
ATOM   1365  N   MET  177      18.769  22.507 114.127  1.00 23.38      AAGL
ATOM   1366  CA  MET  177      18.557  23.847 114.656  1.00 22.20      AAGL
ATOM   1367  CB  MET  177      18.401  24.837 113.488  1.00 20.47      AAGL
ATOM   1368  CG  MET  177      17.934  26.249 113.903  1.00 21.58      AAGL
ATOM   1369  SD  MET  177      17.586  27.336 112.488  1.00 22.93      AAGL
ATOM   1370  CE  MET  177      19.288  27.706 111.969  1.00 22.76      AAGL
ATOM   1371  C   MET  177      17.352  24.013 115.576  1.00 21.82      AAGL
ATOM   1372  O   MET  177      16.343  23.326 115.425  1.00 21.31      AAGL
ATOM   1373  N   ILE  178      17.485  24.927 116.534  1.00 20.60      AAGL
ATOM   1374  CA  ILE  178      16.395  25.294 117.433  1.00 21.53      AAGL
ATOM   1375  CB  ILE  178      16.750  25.134 118.932  1.00 22.17      AAGL
ATOM   1376  CG2 ILE  178      15.678  25.810 119.798  1.00 22.88      AAGL
ATOM   1377  CG1 ILE  178      16.830  23.647 119.286  1.00 23.39      AAGL
ATOM   1378  CD1 ILE  178      17.014  23.363 120.767  1.00 25.76      AAGL
ATOM   1379  C   ILE  178      16.204  26.766 117.088  1.00 19.40      AAGL
ATOM   1380  O   ILE  178      17.156  27.555 117.127  1.00 19.88      AAGL
ATOM   1381  N   HIS  179      14.971  27.125 116.751  1.00 18.62      AAGL
ATOM   1382  CA  HIS  179      14.632  28.475 116.312  1.00 18.14      AAGL
ATOM   1383  CB  HIS  179      14.054  28.356 114.899  1.00 17.60      AAGL
ATOM   1384  CG  HIS  179      13.454  29.617 114.363  1.00 18.42      AAGL
ATOM   1385  CD2 HIS  179      13.731  30.919 114.609  1.00 17.14      AAGL
ATOM   1386  ND1 HIS  179      12.438  29.611 113.432  1.00 18.37      AAGL
ATOM   1387  CE1 HIS  179      12.114  30.855 113.129  1.00 16.27      AAGL
ATOM   1388  NE2 HIS  179      12.883  31.668 113.830  1.00 17.92      AAGL
ATOM   1389  C   HIS  179      13.658  29.235 117.227  1.00 20.10      AAGL
ATOM   1390  O   HIS  179      12.541  28.780 117.470  1.00 20.46      AAGL
ATOM   1391  N   LEU  180      14.090  30.394 117.716  1.00 18.07      AAGL
ATOM   1392  CA  LEU  180      13.258  31.237 118.574  1.00 19.85      AAGL
ATOM   1393  CB  LEU  180      13.930  31.480 119.928  1.00 20.54      AAGL
ATOM   1394  CG  LEU  180      14.253  30.306 120.854  1.00 24.61      AAGL
ATOM   1395  CD1 LEU  180      14.701  30.866 122.208  1.00 23.57      AAGL
```

Fig. 3 cont.

```
ATOM   1396  CD2 LEU   180      13.038  29.405 121.029  1.00 22.59         AAGL
ATOM   1397  C   LEU   180      13.027  32.588 117.905  1.00 20.35         AAGL
ATOM   1398  O   LEU   180      13.838  33.032 117.099  1.00 20.34         AAGL
ATOM   1399  N   ASP   181      11.918  33.237 118.240  1.00 19.30         AAGL
ATOM   1400  CA  ASP   181      11.623  34.548 117.688  1.00 19.90         AAGL
ATOM   1401  CB  ASP   181      10.112  34.796 117.680  1.00 21.15         AAGL
ATOM   1402  CG  ASP   181       9.522  34.825 119.070  1.00 22.95         AAGL
ATOM   1403  OD1 ASP   181       9.910  33.973 119.900  1.00 22.67         AAGL
ATOM   1404  OD2 ASP   181       8.664  35.697 119.336  1.00 25.18         AAGL
ATOM   1405  C   ASP   181      12.315  35.580 118.576  1.00 21.86         AAGL
ATOM   1406  O   ASP   181      13.020  35.218 119.524  1.00 23.76         AAGL
ATOM   1407  N   ASP   182      12.107  36.856 118.271  1.00 22.19         AAGL
ATOM   1408  CA  ASP   182      12.718  37.948 119.034  1.00 22.68         AAGL
ATOM   1409  CB  ASP   182      12.013  38.129 120.381  1.00 24.73         AAGL
ATOM   1410  CG  ASP   182      10.589  38.605 120.234  1.00 26.20         AAGL
ATOM   1411  OD1 ASP   182      10.226  39.052 119.134  1.00 30.46         AAGL
ATOM   1412  OD2 ASP   182       9.829  38.539 121.226  1.00 30.54         AAGL
ATOM   1413  C   ASP   182      14.205  37.719 119.282  1.00 21.94         AAGL
ATOM   1414  O   ASP   182      14.645  37.656 120.432  1.00 22.68         AAGL
ATOM   1415  N   GLY   183      14.975  37.610 118.203  1.00 21.90         AAGL
ATOM   1416  CA  GLY   183      16.403  37.388 118.334  1.00 20.97         AAGL
ATOM   1417  C   GLY   183      17.158  38.524 119.003  1.00 21.01         AAGL
ATOM   1418  O   GLY   183      18.279  38.340 119.478  1.00 24.20         AAGL
ATOM   1419  N   TRP   184      16.550  39.701 119.045  1.00 23.43         AAGL
ATOM   1420  CA  TRP   184      17.191  40.859 119.655  1.00 25.63         AAGL
ATOM   1421  CB  TRP   184      16.514  42.141 119.173  1.00 24.89         AAGL
ATOM   1422  CG  TRP   184      15.045  42.120 119.376  1.00 27.09         AAGL
ATOM   1423  CD2 TRP   184      14.346  42.467 120.576  1.00 28.81         AAGL
ATOM   1424  CE2 TRP   184      12.971  42.248 120.336  1.00 28.20         AAGL
ATOM   1425  CE3 TRP   184      14.750  42.944 121.833  1.00 30.34         AAGL
ATOM   1426  CD1 TRP   184      14.098  41.717 118.481  1.00 27.72         AAGL
ATOM   1427  NE1 TRP   184      12.847  41.792 119.049  1.00 27.27         AAGL
ATOM   1428  CZ2 TRP   184      11.994  42.487 121.308  1.00 32.25         AAGL
ATOM   1429  CZ3 TRP   184      13.776  43.184 122.802  1.00 33.25         AAGL
ATOM   1430  CH2 TRP   184      12.414  42.954 122.533  1.00 30.56         AAGL
ATOM   1431  C   TRP   184      17.155  40.816 121.184  1.00 27.12         AAGL
ATOM   1432  O   TRP   184      17.869  41.563 121.850  1.00 26.68         AAGL
ATOM   1433  N   SER   185      16.332  39.935 121.742  1.00 26.77         AAGL
ATOM   1434  CA  SER   185      16.207  39.846 123.190  1.00 28.56         AAGL
ATOM   1435  CB  SER   185      14.739  39.648 123.558  1.00 28.06         AAGL
ATOM   1436  OG  SER   185      14.594  39.465 124.949  1.00 31.97         AAGL
ATOM   1437  C   SER   185      17.055  38.761 123.858  1.00 27.96         AAGL
ATOM   1438  O   SER   185      16.660  37.600 123.919  1.00 29.29         AAGL
ATOM   1439  N   TRP   186      18.218  39.142 124.374  1.00 27.87         AAGL
ATOM   1440  CA  TRP   186      19.091  38.176 125.032  1.00 27.87         AAGL
ATOM   1441  CB  TRP   186      20.380  38.853 125.511  1.00 29.10         AAGL
ATOM   1442  CG  TRP   186      21.165  38.036 126.509  1.00 27.39         AAGL
ATOM   1443  CD2 TRP   186      21.670  36.705 126.335  1.00 29.36         AAGL
ATOM   1444  CE2 TRP   186      22.338  36.352 127.531  1.00 30.06         AAGL
ATOM   1445  CE3 TRP   186      21.625  35.774 125.285  1.00 30.04         AAGL
ATOM   1446  CD1 TRP   186      21.534  38.422 127.765  1.00 29.38         AAGL
ATOM   1447  NE1 TRP   186      22.239  37.417 128.386  1.00 28.39         AAGL
ATOM   1448  CZ2 TRP   186      22.957  35.108 127.705  1.00 30.53         AAGL
ATOM   1449  CZ3 TRP   186      22.240  34.540 125.459  1.00 30.87         AAGL
ATOM   1450  CH2 TRP   186      22.898  34.218 126.662  1.00 31.05         AAGL
ATOM   1451  C   TRP   186      18.418  37.486 126.217  1.00 28.13         AAGL
ATOM   1452  O   TRP   186      18.620  36.291 126.445  1.00 27.04         AAGL
ATOM   1453  N   ASP   187      17.628  38.232 126.979  1.00 28.09         AAGL
ATOM   1454  CA  ASP   187      16.961  37.643 128.131  1.00 29.42         AAGL
ATOM   1455  CB  ASP   187      16.156  38.704 128.887  1.00 32.15         AAGL
ATOM   1456  CG  ASP   187      17.028  39.817 129.450  1.00 37.52         AAGL
ATOM   1457  OD1 ASP   187      18.255  39.612 129.611  1.00 39.29         AAGL
ATOM   1458  OD2 ASP   187      16.476  40.896 129.748  1.00 41.44         AAGL
ATOM   1459  C   ASP   187      16.035  36.488 127.724  1.00 28.91         AAGL
ATOM   1460  O   ASP   187      16.033  35.431 128.357  1.00 27.77         AAGL
ATOM   1461  N   GLN   188      15.250  36.691 126.668  1.00 27.43         AAGL
ATOM   1462  CA  GLN   188      14.326  35.657 126.215  1.00 27.67         AAGL
```

Fig. 3 cont.

```
ATOM   1463  CB  GLN   188      13.357  36.220 125.170  1.00 28.11      AAGL
ATOM   1464  CG  GLN   188      12.222  37.066 125.735  1.00 31.74      AAGL
ATOM   1465  CD  GLN   188      11.247  36.258 126.588  1.00 36.22      AAGL
ATOM   1466  OE1 GLN   188      10.921  35.103 126.274  1.00 36.68      AAGL
ATOM   1467  NE2 GLN   188      10.760  36.867 127.660  1.00 37.18      AAGL
ATOM   1468  C   GLN   188      15.061  34.456 125.641  1.00 26.39      AAGL
ATOM   1469  O   GLN   188      14.710  33.318 125.934  1.00 26.19      AAGL
ATOM   1470  N   GLN   189      16.086  34.712 124.829  1.00 25.52      AAGL
ATOM   1471  CA  GLN   189      16.864  33.633 124.225  1.00 24.65      AAGL
ATOM   1472  CB  GLN   189      17.997  34.191 123.351  1.00 24.63      AAGL
ATOM   1473  CG  GLN   189      17.576  34.991 122.126  1.00 24.46      AAGL
ATOM   1474  CD  GLN   189      16.736  34.191 121.149  1.00 21.93      AAGL
ATOM   1475  OE1 GLN   189      17.097  33.084 120.760  1.00 20.15      AAGL
ATOM   1476  NE2 GLN   189      15.613  34.759 120.739  1.00 23.53      AAGL
ATOM   1477  C   GLN   189      17.484  32.759 125.308  1.00 25.42      AAGL
ATOM   1478  O   GLN   189      17.314  31.544 125.324  1.00 23.58      AAGL
ATOM   1479  N   ASN   190      18.199  33.405 126.219  1.00 25.59      AAGL
ATOM   1480  CA  ASN   190      18.892  32.725 127.293  1.00 26.28      AAGL
ATOM   1481  CB  ASN   190      19.745  33.736 128.056  1.00 28.08      AAGL
ATOM   1482  CG  ASN   190      20.593  33.091 129.135  1.00 29.88      AAGL
ATOM   1483  OD1 ASN   190      21.204  32.041 128.922  1.00 29.87      AAGL
ATOM   1484  ND2 ASN   190      20.649  33.727 130.295  1.00 33.02      AAGL
ATOM   1485  C   ASN   190      17.978  31.970 128.250  1.00 26.80      AAGL
ATOM   1486  O   ASN   190      18.300  30.866 128.675  1.00 27.29      AAGL
ATOM   1487  N   TYR   191      16.838  32.554 128.590  1.00 27.59      AAGL
ATOM   1488  CA  TYR   191      15.931  31.878 129.504  1.00 27.82      AAGL
ATOM   1489  CB  TYR   191      14.735  32.767 129.832  1.00 28.23      AAGL
ATOM   1490  CG  TYR   191      13.815  32.132 130.844  1.00 30.08      AAGL
ATOM   1491  CD1 TYR   191      12.775  31.294 130.446  1.00 32.24      AAGL
ATOM   1492  CE1 TYR   191      11.975  30.641 131.385  1.00 33.28      AAGL
ATOM   1493  CD2 TYR   191      14.032  32.308 132.210  1.00 31.47      AAGL
ATOM   1494  CE2 TYR   191      13.240  31.662 133.157  1.00 31.82      AAGL
ATOM   1495  CZ  TYR   191      12.219  30.830 132.739  1.00 34.47      AAGL
ATOM   1496  OH  TYR   191      11.458  30.168 133.679  1.00 36.38      AAGL
ATOM   1497  C   TYR   191      15.443  30.551 128.929  1.00 27.27      AAGL
ATOM   1498  O   TYR   191      15.392  29.537 129.631  1.00 25.68      AAGL
ATOM   1499  N   PHE   192      15.079  30.557 127.651  1.00 25.48      AAGL
ATOM   1500  CA  PHE   192      14.605  29.341 127.016  1.00 26.24      AAGL
ATOM   1501  CB  PHE   192      14.260  29.593 125.541  1.00 24.60      AAGL
ATOM   1502  CG  PHE   192      13.854  28.351 124.799  1.00 22.89      AAGL
ATOM   1503  CD1 PHE   192      12.541  27.893 124.848  1.00 23.14      AAGL
ATOM   1504  CD2 PHE   192      14.795  27.607 124.098  1.00 22.70      AAGL
ATOM   1505  CE1 PHE   192      12.169  26.706 124.208  1.00 22.64      AAGL
ATOM   1506  CE2 PHE   192      14.439  26.417 123.455  1.00 22.68      AAGL
ATOM   1507  CZ  PHE   192      13.125  25.965 123.510  1.00 23.16      AAGL
ATOM   1508  C   PHE   192      15.651  28.237 127.095  1.00 26.50      AAGL
ATOM   1509  O   PHE   192      15.386  27.154 127.612  1.00 25.06      AAGL
ATOM   1510  N   TYR   193      16.847  28.513 126.577  1.00 26.97      AAGL
ATOM   1511  CA  TYR   193      17.898  27.510 126.570  1.00 28.47      AAGL
ATOM   1512  CB  TYR   193      19.066  27.991 125.704  1.00 25.93      AAGL
ATOM   1513  CG  TYR   193      18.675  28.113 124.243  1.00 26.36      AAGL
ATOM   1514  CD1 TYR   193      18.344  26.979 123.498  1.00 24.37      AAGL
ATOM   1515  CE1 TYR   193      17.905  27.084 122.178  1.00 23.29      AAGL
ATOM   1516  CD2 TYR   193      18.561  29.357 123.632  1.00 26.34      AAGL
ATOM   1517  CE2 TYR   193      18.121  29.474 122.307  1.00 24.57      AAGL
ATOM   1518  CZ  TYR   193      17.797  28.331 121.592  1.00 23.44      AAGL
ATOM   1519  OH  TYR   193      17.370  28.431 120.290  1.00 24.47      AAGL
ATOM   1520  C   TYR   193      18.384  27.087 127.952  1.00 28.72      AAGL
ATOM   1521  O   TYR   193      18.542  25.892 128.212  1.00 29.46      AAGL
ATOM   1522  N   GLU   194      18.610  28.046 128.844  1.00 30.56      AAGL
ATOM   1523  CA  GLU   194      19.081  27.684 130.177  1.00 32.74      AAGL
ATOM   1524  CB  GLU   194      19.344  28.921 131.048  1.00 36.66      AAGL
ATOM   1525  CG  GLU   194      20.119  28.543 132.325  1.00 42.88      AAGL
ATOM   1526  CD  GLU   194      20.271  29.668 133.327  1.00 46.55      AAGL
ATOM   1527  OE1 GLU   194      21.086  29.502 134.275  1.00 48.27      AAGL
ATOM   1528  OE2 GLU   194      19.580  30.704 133.194  1.00 47.67      AAGL
ATOM   1529  C   GLU   194      18.056  26.802 130.875  1.00 31.54      AAGL
```

Fig. 3 cont.

```
ATOM   1530  O    GLU  194      18.396  25.764 131.445  1.00 31.58      AAGL
ATOM   1531  N    THR  195      16.795  27.212 130.823  1.00 30.56      AAGL
ATOM   1532  CA   THR  195      15.731  26.453 131.468  1.00 28.40      AAGL
ATOM   1533  CB   THR  195      14.408  27.226 131.402  1.00 27.94      AAGL
ATOM   1534  OG1  THR  195      14.611  28.545 131.929  1.00 25.50      AAGL
ATOM   1535  CG2  THR  195      13.330  26.516 132.211  1.00 26.24      AAGL
ATOM   1536  C    THR  195      15.535  25.054 130.868  1.00 28.06      AAGL
ATOM   1537  O    THR  195      15.427  24.071 131.599  1.00 26.71      AAGL
ATOM   1538  N    VAL  196      15.486  24.961 129.545  1.00 27.08      AAGL
ATOM   1539  CA   VAL  196      15.301  23.666 128.902  1.00 27.16      AAGL
ATOM   1540  CB   VAL  196      15.035  23.838 127.369  1.00 29.10      AAGL
ATOM   1541  CG1  VAL  196      16.227  24.510 126.700  1.00 30.65      AAGL
ATOM   1542  CG2  VAL  196      14.748  22.487 126.727  1.00 31.18      AAGL
ATOM   1543  C    VAL  196      16.502  22.736 129.137  1.00 26.59      AAGL
ATOM   1544  O    VAL  196      16.330  21.563 129.449  1.00 25.06      AAGL
ATOM   1545  N    LEU  197      17.716  23.266 129.015  1.00 26.11      AAGL
ATOM   1546  CA   LEU  197      18.911  22.451 129.214  1.00 28.97      AAGL
ATOM   1547  CB   LEU  197      20.161  23.207 128.735  1.00 29.84      AAGL
ATOM   1548  CG   LEU  197      20.233  23.474 127.220  1.00 30.49      AAGL
ATOM   1549  CD1  LEU  197      21.377  24.445 126.927  1.00 32.56      AAGL
ATOM   1550  CD2  LEU  197      20.413  22.176 126.464  1.00 30.05      AAGL
ATOM   1551  C    LEU  197      19.069  22.032 130.674  1.00 28.89      AAGL
ATOM   1552  O    LEU  197      19.632  20.976 130.971  1.00 30.68      AAGL
ATOM   1553  N    ALA  198      18.550  22.844 131.586  1.00 29.81      AAGL
ATOM   1554  CA   ALA  198      18.646  22.530 133.008  1.00 30.14      AAGL
ATOM   1555  CB   ALA  198      18.110  23.688 133.831  1.00 29.46      AAGL
ATOM   1556  C    ALA  198      17.913  21.237 133.387  1.00 31.06      AAGL
ATOM   1557  O    ALA  198      18.223  20.624 134.411  1.00 30.62      AAGL
ATOM   1558  N    THR  199      16.951  20.814 132.569  1.00 30.12      AAGL
ATOM   1559  CA   THR  199      16.192  19.599 132.868  1.00 29.04      AAGL
ATOM   1560  CB   THR  199      14.831  19.569 132.137  1.00 30.14      AAGL
ATOM   1561  OG1  THR  199      15.051  19.375 130.735  1.00 28.92      AAGL
ATOM   1562  CG2  THR  199      14.058  20.876 132.351  1.00 28.52      AAGL
ATOM   1563  C    THR  199      16.926  18.308 132.497  1.00 30.21      AAGL
ATOM   1564  O    THR  199      16.602  17.237 133.006  1.00 31.94      AAGL
ATOM   1565  N    GLY  200      17.907  18.406 131.613  1.00 29.95      AAGL
ATOM   1566  CA   GLY  200      18.626  17.219 131.194  1.00 30.95      AAGL
ATOM   1567  C    GLY  200      17.868  16.428 130.143  1.00 31.30      AAGL
ATOM   1568  O    GLY  200      18.376  15.436 129.625  1.00 31.90      AAGL
ATOM   1569  N    GLU  201      16.647  16.850 129.823  1.00 31.18      AAGL
ATOM   1570  CA   GLU  201      15.856  16.145 128.813  1.00 30.31      AAGL
ATOM   1571  CB   GLU  201      14.385  16.557 128.881  1.00 29.74      AAGL
ATOM   1572  CG   GLU  201      13.640  16.062 130.110  1.00 32.87      AAGL
ATOM   1573  CD   GLU  201      13.710  14.555 130.285  1.00 33.76      AAGL
ATOM   1574  OE1  GLU  201      13.838  13.833 129.274  1.00 34.18      AAGL
ATOM   1575  OE2  GLU  201      13.617  14.086 131.443  1.00 34.63      AAGL
ATOM   1576  C    GLU  201      16.399  16.440 127.423  1.00 28.94      AAGL
ATOM   1577  O    GLU  201      16.271  15.625 126.511  1.00 27.79      AAGL
ATOM   1578  N    LEU  202      16.988  17.623 127.272  1.00 28.10      AAGL
ATOM   1579  CA   LEU  202      17.587  18.033 126.009  1.00 28.10      AAGL
ATOM   1580  CB   LEU  202      17.029  19.376 125.548  1.00 28.75      AAGL
ATOM   1581  CG   LEU  202      17.766  19.987 124.350  1.00 27.26      AAGL
ATOM   1582  CD1  LEU  202      17.461  19.196 123.090  1.00 27.62      AAGL
ATOM   1583  CD2  LEU  202      17.337  21.430 124.178  1.00 29.02      AAGL
ATOM   1584  C    LEU  202      19.088  18.170 126.240  1.00 28.79      AAGL
ATOM   1585  O    LEU  202      19.518  18.888 127.141  1.00 29.33      AAGL
ATOM   1586  N    LEU  203      19.875  17.473 125.433  1.00 29.74      AAGL
ATOM   1587  CA   LEU  203      21.326  17.524 125.557  1.00 32.35      AAGL
ATOM   1588  CB   LEU  203      21.920  16.146 125.271  1.00 33.32      AAGL
ATOM   1589  CG   LEU  203      21.643  15.084 126.328  1.00 33.68      AAGL
ATOM   1590  CD1  LEU  203      22.436  13.828 125.998  1.00 38.12      AAGL
ATOM   1591  CD2  LEU  203      22.053  15.615 127.694  1.00 37.93      AAGL
ATOM   1592  C    LEU  203      21.934  18.541 124.603  1.00 32.26      AAGL
ATOM   1593  O    LEU  203      21.475  18.694 123.474  1.00 33.19      AAGL
ATOM   1594  N    SER  204      22.975  19.231 125.055  1.00 33.40      AAGL
ATOM   1595  CA   SER  204      23.634  20.215 124.213  1.00 34.27      AAGL
ATOM   1596  CB   SER  204      24.824  20.826 124.947  1.00 34.70      AAGL
```

Fig. 3 cont.

```
ATOM   1597  OG   SER  204      25.380  21.894 124.194  1.00 36.69           AAGL
ATOM   1598  C    SER  204      24.103  19.529 122.934  1.00 34.03           AAGL
ATOM   1599  O    SER  204      24.163  20.145 121.871  1.00 35.28           AAGL
ATOM   1600  N    THR  205      24.438  18.248 123.043  1.00 32.63           AAGL
ATOM   1601  CA   THR  205      24.890  17.491 121.880  1.00 33.11           AAGL
ATOM   1602  CB   THR  205      25.650  16.204 122.302  1.00 33.97           AAGL
ATOM   1603  OG1  THR  205      24.875  15.458 123.256  1.00 35.21           AAGL
ATOM   1604  CG2  THR  205      26.989  16.572 122.919  1.00 34.51           AAGL
ATOM   1605  C    THR  205      23.737  17.111 120.951  1.00 32.07           AAGL
ATOM   1606  O    THR  205      23.960  16.584 119.865  1.00 32.54           AAGL
ATOM   1607  N    ASP  206      22.504  17.389 121.367  1.00 30.83           AAGL
ATOM   1608  CA   ASP  206      21.352  17.054 120.536  1.00 29.51           AAGL
ATOM   1609  CB   ASP  206      20.060  17.033 121.351  1.00 28.56           AAGL
ATOM   1610  CG   ASP  206      19.996  15.871 122.315  1.00 31.99           AAGL
ATOM   1611  OD1  ASP  206      20.539  14.791 121.990  1.00 30.07           AAGL
ATOM   1612  OD2  ASP  206      19.385  16.037 123.390  1.00 30.30           AAGL
ATOM   1613  C    ASP  206      21.151  17.986 119.352  1.00 28.75           AAGL
ATOM   1614  O    ASP  206      20.514  17.597 118.376  1.00 29.56           AAGL
ATOM   1615  N    PHE  207      21.653  19.217 119.437  1.00 27.57           AAGL
ATOM   1616  CA   PHE  207      21.496  20.147 118.321  1.00 27.18           AAGL
ATOM   1617  CB   PHE  207      20.315  21.106 118.567  1.00 24.79           AAGL
ATOM   1618  CG   PHE  207      20.541  22.115 119.651  1.00 24.63           AAGL
ATOM   1619  CD1  PHE  207      20.643  21.728 120.981  1.00 26.07           AAGL
ATOM   1620  CD2  PHE  207      20.613  23.473 119.341  1.00 26.18           AAGL
ATOM   1621  CE1  PHE  207      20.811  22.677 121.986  1.00 23.87           AAGL
ATOM   1622  CE2  PHE  207      20.782  24.433 120.340  1.00 24.35           AAGL
ATOM   1623  CZ   PHE  207      20.880  24.032 121.661  1.00 26.22           AAGL
ATOM   1624  C    PHE  207      22.767  20.917 117.974  1.00 27.60           AAGL
ATOM   1625  O    PHE  207      23.700  20.987 118.772  1.00 28.27           AAGL
ATOM   1626  N    ASP  208      22.784  21.503 116.780  1.00 28.39           AAGL
ATOM   1627  CA   ASP  208      23.958  22.209 116.278  1.00 28.84           AAGL
ATOM   1628  CB   ASP  208      24.329  21.618 114.918  1.00 28.97           AAGL
ATOM   1629  CG   ASP  208      24.337  20.102 114.930  1.00 29.39           AAGL
ATOM   1630  OD1  ASP  208      25.139  19.521 115.686  1.00 30.72           AAGL
ATOM   1631  OD2  ASP  208      23.537  19.494 114.187  1.00 30.15           AAGL
ATOM   1632  C    ASP  208      23.910  23.737 116.143  1.00 28.85           AAGL
ATOM   1633  O    ASP  208      24.866  24.418 116.520  1.00 28.49           AAGL
ATOM   1634  N    TYR  209      22.817  24.263 115.595  1.00 26.19           AAGL
ATOM   1635  CA   TYR  209      22.674  25.704 115.368  1.00 25.08           AAGL
ATOM   1636  CB   TYR  209      22.353  26.001 113.896  1.00 26.01           AAGL
ATOM   1637  CG   TYR  209      23.397  25.677 112.854  1.00 23.51           AAGL
ATOM   1638  CD1  TYR  209      24.728  25.427 113.191  1.00 27.73           AAGL
ATOM   1639  CE1  TYR  209      25.693  25.222 112.194  1.00 27.06           AAGL
ATOM   1640  CD2  TYR  209      23.056  25.705 111.506  1.00 26.41           AAGL
ATOM   1641  CE2  TYR  209      24.007  25.503 110.505  1.00 29.44           AAGL
ATOM   1642  CZ   TYR  209      25.318  25.267 110.856  1.00 25.86           AAGL
ATOM   1643  OH   TYR  209      26.244  25.103 109.853  1.00 26.38           AAGL
ATOM   1644  C    TYR  209      21.578  26.398 116.163  1.00 23.78           AAGL
ATOM   1645  O    TYR  209      20.611  25.774 116.589  1.00 23.59           AAGL
ATOM   1646  N    PHE  210      21.745  27.711 116.315  1.00 25.60           AAGL
ATOM   1647  CA   PHE  210      20.775  28.584 116.969  1.00 24.58           AAGL
ATOM   1648  CB   PHE  210      21.441  29.576 117.918  1.00 25.18           AAGL
ATOM   1649  CG   PHE  210      21.826  29.004 119.234  1.00 26.35           AAGL
ATOM   1650  CD1  PHE  210      20.895  28.309 120.004  1.00 26.01           AAGL
ATOM   1651  CD2  PHE  210      23.104  29.214 119.741  1.00 26.73           AAGL
ATOM   1652  CE1  PHE  210      21.234  27.836 121.269  1.00 28.08           AAGL
ATOM   1653  CE2  PHE  210      23.453  28.746 121.000  1.00 29.00           AAGL
ATOM   1654  CZ   PHE  210      22.519  28.057 121.768  1.00 28.84           AAGL
ATOM   1655  C    PHE  210      20.167  29.402 115.842  1.00 25.37           AAGL
ATOM   1656  O    PHE  210      20.894  29.932 115.005  1.00 26.01           AAGL
ATOM   1657  N    GLY  211      18.845  29.514 115.817  1.00 22.48           AAGL
ATOM   1658  CA   GLY  211      18.214  30.313 114.784  1.00 21.15           AAGL
ATOM   1659  C    GLY  211      17.305  31.333 115.441  1.00 20.32           AAGL
ATOM   1660  O    GLY  211      16.631  31.007 116.412  1.00 22.35           AAGL
ATOM   1661  N    VAL  212      17.285  32.560 114.931  1.00 20.60           AAGL
ATOM   1662  CA   VAL  212      16.428  33.595 115.501  1.00 19.19           AAGL
ATOM   1663  CB   VAL  212      17.206  34.592 116.400  1.00 20.57           AAGL
```

Fig. 3 cont.

| | | | | | | | | | |
|---|---|---|---|---|---|---|---|---|---|
| ATOM | 1664 | CG1 | VAL | 212 | 17.920 | 33.859 | 117.512 | 1.00 21.04 | AAGL |
| ATOM | 1665 | CG2 | VAL | 212 | 18.169 | 35.419 | 115.554 | 1.00 22.31 | AAGL |
| ATOM | 1666 | C | VAL | 212 | 15.781 | 34.426 | 114.410 | 1.00 19.78 | AAGL |
| ATOM | 1667 | O | VAL | 212 | 16.358 | 34.616 | 113.339 | 1.00 19.10 | AAGL |
| ATOM | 1668 | N | SER | 213 | 14.581 | 34.914 | 114.692 | 1.00 18.35 | AAGL |
| ATOM | 1669 | CA | SER | 213 | 13.869 | 35.775 | 113.758 | 1.00 19.01 | AAGL |
| ATOM | 1670 | CB | SER | 213 | 12.353 | 35.630 | 113.933 | 1.00 18.11 | AAGL |
| ATOM | 1671 | OG | SER | 213 | 11.934 | 34.305 | 113.696 | 1.00 17.61 | AAGL |
| ATOM | 1672 | C | SER | 213 | 14.277 | 37.187 | 114.148 | 1.00 18.11 | AAGL |
| ATOM | 1673 | O | SER | 213 | 14.506 | 37.461 | 115.323 | 1.00 21.77 | AAGL |
| ATOM | 1674 | N | TYR | 214 | 14.384 | 38.081 | 113.174 | 1.00 17.30 | AAGL |
| ATOM | 1675 | CA | TYR | 214 | 14.744 | 39.458 | 113.478 | 1.00 17.43 | AAGL |
| ATOM | 1676 | CB | TYR | 214 | 16.252 | 39.688 | 113.352 | 1.00 19.55 | AAGL |
| ATOM | 1677 | CG | TYR | 214 | 16.647 | 41.122 | 113.624 | 1.00 18.83 | AAGL |
| ATOM | 1678 | CD1 | TYR | 214 | 16.558 | 41.661 | 114.911 | 1.00 22.19 | AAGL |
| ATOM | 1679 | CE1 | TYR | 214 | 16.872 | 43.004 | 115.158 | 1.00 22.03 | AAGL |
| ATOM | 1680 | CD2 | TYR | 214 | 17.063 | 41.959 | 112.590 | 1.00 23.69 | AAGL |
| ATOM | 1681 | CE2 | TYR | 214 | 17.381 | 43.307 | 112.828 | 1.00 22.60 | AAGL |
| ATOM | 1682 | CZ | TYR | 214 | 17.279 | 43.816 | 114.113 | 1.00 22.17 | AAGL |
| ATOM | 1683 | OH | TYR | 214 | 17.561 | 45.141 | 114.346 | 1.00 24.19 | AAGL |
| ATOM | 1684 | C | TYR | 214 | 14.013 | 40.386 | 112.534 | 1.00 18.48 | AAGL |
| ATOM | 1685 | O | TYR | 214 | 14.361 | 40.488 | 111.358 | 1.00 18.33 | AAGL |
| ATOM | 1686 | N | TYR | 215 | 12.990 | 41.048 | 113.067 | 1.00 18.28 | AAGL |
| ATOM | 1687 | CA | TYR | 215 | 12.171 | 41.979 | 112.311 | 1.00 16.96 | AAGL |
| ATOM | 1688 | CB | TYR | 215 | 10.717 | 41.506 | 112.321 | 1.00 16.58 | AAGL |
| ATOM | 1689 | CG | TYR | 215 | 10.497 | 40.277 | 111.465 | 1.00 16.72 | AAGL |
| ATOM | 1690 | CD1 | TYR | 215 | 10.456 | 40.377 | 110.075 | 1.00 19.62 | AAGL |
| ATOM | 1691 | CE1 | TYR | 215 | 10.264 | 39.252 | 109.274 | 1.00 18.54 | AAGL |
| ATOM | 1692 | CD2 | TYR | 215 | 10.346 | 39.013 | 112.038 | 1.00 16.88 | AAGL |
| ATOM | 1693 | CE2 | TYR | 215 | 10.156 | 37.875 | 111.245 | 1.00 17.19 | AAGL |
| ATOM | 1694 | CZ | TYR | 215 | 10.111 | 38.007 | 109.862 | 1.00 16.90 | AAGL |
| ATOM | 1695 | OH | TYR | 215 | 9.868 | 36.910 | 109.064 | 1.00 17.46 | AAGL |
| ATOM | 1696 | C | TYR | 215 | 12.297 | 43.374 | 112.920 | 1.00 19.56 | AAGL |
| ATOM | 1697 | O | TYR | 215 | 12.487 | 43.523 | 114.124 | 1.00 19.95 | AAGL |
| ATOM | 1698 | N | PRO | 216 | 12.184 | 44.418 | 112.087 | 1.00 20.63 | AAGL |
| ATOM | 1699 | CD | PRO | 216 | 12.160 | 44.396 | 110.613 | 1.00 20.25 | AAGL |
| ATOM | 1700 | CA | PRO | 216 | 12.308 | 45.788 | 112.589 | 1.00 20.50 | AAGL |
| ATOM | 1701 | CB | PRO | 216 | 13.033 | 46.476 | 111.450 | 1.00 22.26 | AAGL |
| ATOM | 1702 | CG | PRO | 216 | 12.318 | 45.881 | 110.243 | 1.00 20.29 | AAGL |
| ATOM | 1703 | C | PRO | 216 | 11.005 | 46.503 | 112.922 | 1.00 21.80 | AAGL |
| ATOM | 1704 | O | PRO | 216 | 11.021 | 47.552 | 113.569 | 1.00 23.06 | AAGL |
| ATOM | 1705 | N | PHE | 217 | 9.885 | 45.934 | 112.495 | 1.00 20.15 | AAGL |
| ATOM | 1706 | CA | PHE | 217 | 8.599 | 46.580 | 112.682 | 1.00 19.12 | AAGL |
| ATOM | 1707 | CB | PHE | 217 | 7.940 | 46.729 | 111.308 | 1.00 21.27 | AAGL |
| ATOM | 1708 | CG | PHE | 217 | 8.166 | 45.548 | 110.390 | 1.00 22.97 | AAGL |
| ATOM | 1709 | CD1 | PHE | 217 | 7.783 | 44.263 | 110.773 | 1.00 22.42 | AAGL |
| ATOM | 1710 | CD2 | PHE | 217 | 8.733 | 45.730 | 109.129 | 1.00 24.02 | AAGL |
| ATOM | 1711 | CE1 | PHE | 217 | 7.953 | 43.177 | 109.912 | 1.00 22.58 | AAGL |
| ATOM | 1712 | CE2 | PHE | 217 | 8.910 | 44.651 | 108.260 | 1.00 22.45 | AAGL |
| ATOM | 1713 | CZ | PHE | 217 | 8.518 | 43.372 | 108.652 | 1.00 22.51 | AAGL |
| ATOM | 1714 | C | PHE | 217 | 7.586 | 46.016 | 113.671 | 1.00 20.44 | AAGL |
| ATOM | 1715 | O | PHE | 217 | 6.391 | 46.271 | 113.523 | 1.00 21.67 | AAGL |
| ATOM | 1716 | N | TYR | 218 | 8.040 | 45.270 | 114.676 | 1.00 22.47 | AAGL |
| ATOM | 1717 | CA | TYR | 218 | 7.130 | 44.715 | 115.688 | 1.00 23.80 | AAGL |
| ATOM | 1718 | CB | TYR | 218 | 7.155 | 43.177 | 115.681 | 1.00 24.44 | AAGL |
| ATOM | 1719 | CG | TYR | 218 | 6.583 | 42.525 | 114.439 | 1.00 21.12 | AAGL |
| ATOM | 1720 | CD1 | TYR | 218 | 5.331 | 42.891 | 113.952 | 1.00 22.80 | AAGL |
| ATOM | 1721 | CE1 | TYR | 218 | 4.789 | 42.281 | 112.815 | 1.00 25.22 | AAGL |
| ATOM | 1722 | CD2 | TYR | 218 | 7.286 | 41.528 | 113.763 | 1.00 23.62 | AAGL |
| ATOM | 1723 | CE2 | TYR | 218 | 6.753 | 40.910 | 112.625 | 1.00 23.28 | AAGL |
| ATOM | 1724 | CZ | TYR | 218 | 5.504 | 41.294 | 112.159 | 1.00 24.22 | AAGL |
| ATOM | 1725 | OH | TYR | 218 | 4.970 | 40.698 | 111.038 | 1.00 24.13 | AAGL |
| ATOM | 1726 | C | TYR | 218 | 7.493 | 45.201 | 117.089 | 1.00 26.28 | AAGL |
| ATOM | 1727 | O | TYR | 218 | 6.956 | 44.707 | 118.087 | 1.00 28.68 | AAGL |
| ATOM | 1728 | N | SER | 219 | 8.407 | 46.163 | 117.165 | 1.00 27.77 | AAGL |
| ATOM | 1729 | CA | SER | 219 | 8.854 | 46.712 | 118.447 | 1.00 28.32 | AAGL |
| ATOM | 1730 | CB | SER | 219 | 9.124 | 45.592 | 119.457 | 1.00 29.25 | AAGL |

Fig. 3 cont.

```
ATOM   1731  OG   SER   219       9.908  46.078 120.538  1.00 31.84      AAGL
ATOM   1732  C    SER   219      10.119  47.549 118.303  1.00 28.53      AAGL
ATOM   1733  O    SER   219      11.107  47.110 117.716  1.00 26.20      AAGL
ATOM   1734  N    ALA   220      10.090  48.750 118.870  1.00 29.00      AAGL
ATOM   1735  CA   ALA   220      11.235  49.647 118.816  1.00 28.92      AAGL
ATOM   1736  CB   ALA   220      10.851  51.003 119.371  1.00 28.98      AAGL
ATOM   1737  C    ALA   220      12.440  49.104 119.572  1.00 29.06      AAGL
ATOM   1738  O    ALA   220      13.520  49.683 119.507  1.00 30.49      AAGL
ATOM   1739  N    SER   221      12.260  48.003 120.293  1.00 29.58      AAGL
ATOM   1740  CA   SER   221      13.358  47.404 121.046  1.00 29.31      AAGL
ATOM   1741  CB   SER   221      12.815  46.522 122.169  1.00 29.65      AAGL
ATOM   1742  OG   SER   221      12.148  47.295 123.152  1.00 33.54      AAGL
ATOM   1743  C    SER   221      14.278  46.565 120.160  1.00 27.63      AAGL
ATOM   1744  O    SER   221      15.375  46.201 120.570  1.00 27.79      AAGL
ATOM   1745  N    ALA   222      13.828  46.264 118.948  1.00 26.73      AAGL
ATOM   1746  CA   ALA   222      14.598  45.445 118.017  1.00 25.72      AAGL
ATOM   1747  CB   ALA   222      13.662  44.864 116.953  1.00 24.78      AAGL
ATOM   1748  C    ALA   222      15.764  46.187 117.347  1.00 26.39      AAGL
ATOM   1749  O    ALA   222      15.889  46.189 116.117  1.00 24.72      AAGL
ATOM   1750  N    THR   223      16.619  46.809 118.157  1.00 25.12      AAGL
ATOM   1751  CA   THR   223      17.771  47.536 117.632  1.00 26.47      AAGL
ATOM   1752  CB   THR   223      18.360  48.498 118.678  1.00 26.69      AAGL
ATOM   1753  OG1  THR   223      18.793  47.749 119.822  1.00 28.21      AAGL
ATOM   1754  CG2  THR   223      17.321  49.520 119.104  1.00 25.83      AAGL
ATOM   1755  C    THR   223      18.877  46.573 117.223  1.00 25.83      AAGL
ATOM   1756  O    THR   223      18.982  45.465 117.751  1.00 28.38      AAGL
ATOM   1757  N    LEU   224      19.703  47.000 116.278  1.00 26.34      AAGL
ATOM   1758  CA   LEU   224      20.807  46.177 115.817  1.00 27.64      AAGL
ATOM   1759  CB   LEU   224      21.516  46.857 114.647  1.00 30.65      AAGL
ATOM   1760  CG   LEU   224      20.769  46.842 113.311  1.00 31.90      AAGL
ATOM   1761  CD1  LEU   224      21.565  47.603 112.257  1.00 32.52      AAGL
ATOM   1762  CD2  LEU   224      20.558  45.406 112.873  1.00 32.19      AAGL
ATOM   1763  C    LEU   224      21.781  45.958 116.967  1.00 28.76      AAGL
ATOM   1764  O    LEU   224      22.495  44.956 117.011  1.00 30.90      AAGL
ATOM   1765  N    ALA   225      21.796  46.902 117.903  1.00 29.40      AAGL
ATOM   1766  CA   ALA   225      22.663  46.833 119.070  1.00 29.81      AAGL
ATOM   1767  CB   ALA   225      22.632  48.163 119.812  1.00 31.20      AAGL
ATOM   1768  C    ALA   225      22.252  45.701 120.013  1.00 30.35      AAGL
ATOM   1769  O    ALA   225      23.105  45.003 120.560  1.00 29.58      AAGL
ATOM   1770  N    SER   226      20.948  45.526 120.215  1.00 30.66      AAGL
ATOM   1771  CA   SER   226      20.472  44.454 121.090  1.00 30.00      AAGL
ATOM   1772  CB   SER   226      18.995  44.642 121.423  1.00 30.27      AAGL
ATOM   1773  OG   SER   226      18.851  45.426 122.592  1.00 34.03      AAGL
ATOM   1774  C    SER   226      20.685  43.096 120.437  1.00 27.61      AAGL
ATOM   1775  O    SER   226      21.003  42.114 121.113  1.00 27.38      AAGL
ATOM   1776  N    LEU   227      20.510  43.053 119.119  1.00 26.75      AAGL
ATOM   1777  CA   LEU   227      20.691  41.828 118.359  1.00 27.51      AAGL
ATOM   1778  CB   LEU   227      20.337  42.060 116.884  1.00 25.07      AAGL
ATOM   1779  CG   LEU   227      20.555  40.857 115.967  1.00 24.78      AAGL
ATOM   1780  CD1  LEU   227      19.578  39.755 116.340  1.00 24.45      AAGL
ATOM   1781  CD2  LEU   227      20.374  41.268 114.514  1.00 23.51      AAGL
ATOM   1782  C    LEU   227      22.148  41.407 118.465  1.00 28.41      AAGL
ATOM   1783  O    LEU   227      22.456  40.253 118.726  1.00 28.87      AAGL
ATOM   1784  N    LYS   228      23.037  42.372 118.256  1.00 30.45      AAGL
ATOM   1785  CA   LYS   228      24.474  42.132 118.316  1.00 31.96      AAGL
ATOM   1786  CB   LYS   228      25.201  43.469 118.150  1.00 36.24      AAGL
ATOM   1787  CG   LYS   228      26.700  43.390 117.906  1.00 41.65      AAGL
ATOM   1788  CD   LYS   228      27.242  44.757 117.477  1.00 43.74      AAGL
ATOM   1789  CE   LYS   228      26.876  45.827 118.489  1.00 46.64      AAGL
ATOM   1790  NZ   LYS   228      27.322  47.191 118.075  1.00 47.80      AAGL
ATOM   1791  C    LYS   228      24.820  41.485 119.653  1.00 30.16      AAGL
ATOM   1792  O    LYS   228      25.538  40.484 119.710  1.00 31.36      AAGL
ATOM   1793  N    THR   229      24.299  42.056 120.732  1.00 29.71      AAGL
ATOM   1794  CA   THR   229      24.553  41.532 122.063  1.00 30.66      AAGL
ATOM   1795  CB   THR   229      23.981  42.452 123.142  1.00 31.91      AAGL
ATOM   1796  OG1  THR   229      24.783  43.637 123.232  1.00 35.38      AAGL
ATOM   1797  CG2  THR   229      23.978  41.748 124.483  1.00 34.76      AAGL
```

Fig. 3 cont.

```
ATOM   1798  C    THR  229    23.973  40.145 122.282  1.00 30.52      AAGL
ATOM   1799  O    THR  229    24.615  39.290 122.883  1.00 30.20      AAGL
ATOM   1800  N    SER  230    22.753  39.932 121.795  1.00 29.88      AAGL
ATOM   1801  CA   SER  230    22.077  38.646 121.948  1.00 27.75      AAGL
ATOM   1802  CB   SER  230    20.626  38.766 121.470  1.00 27.43      AAGL
ATOM   1803  OG   SER  230    19.947  37.532 121.612  1.00 28.20      AAGL
ATOM   1804  C    SER  230    22.790  37.534 121.178  1.00 27.11      AAGL
ATOM   1805  O    SER  230    22.994  36.436 121.698  1.00 27.65      AAGL
ATOM   1806  N    LEU  231    23.157  37.814 119.935  1.00 27.30      AAGL
ATOM   1807  CA   LEU  231    23.859  36.829 119.122  1.00 28.25      AAGL
ATOM   1808  CB   LEU  231    24.037  37.341 117.687  1.00 28.04      AAGL
ATOM   1809  CG   LEU  231    22.767  37.430 116.832  1.00 28.82      AAGL
ATOM   1810  CD1  LEU  231    23.091  38.027 115.468  1.00 29.62      AAGL
ATOM   1811  CD2  LEU  231    22.171  36.034 116.670  1.00 25.68      AAGL
ATOM   1812  C    LEU  231    25.228  36.541 119.733  1.00 29.07      AAGL
ATOM   1813  O    LEU  231    25.685  35.399 119.743  1.00 27.21      AAGL
ATOM   1814  N    ALA  232    25.874  37.585 120.244  1.00 30.00      AAGL
ATOM   1815  CA   ALA  232    27.198  37.449 120.849  1.00 31.64      AAGL
ATOM   1816  CB   ALA  232    27.733  38.828 121.257  1.00 30.69      AAGL
ATOM   1817  C    ALA  232    27.142  36.535 122.063  1.00 31.96      AAGL
ATOM   1818  O    ALA  232    27.980  35.645 122.229  1.00 32.99      AAGL
ATOM   1819  N    ASN  233    26.146  36.757 122.913  1.00 31.75      AAGL
ATOM   1820  CA   ASN  233    25.989  35.960 124.118  1.00 33.65      AAGL
ATOM   1821  CB   ASN  233    25.010  36.646 125.071  1.00 33.95      AAGL
ATOM   1822  CG   ASN  233    25.507  38.010 125.528  1.00 37.26      AAGL
ATOM   1823  OD1  ASN  233    26.712  38.267 125.547  1.00 37.11      AAGL
ATOM   1824  ND2  ASN  233    24.582  38.884 125.912  1.00 37.35      AAGL
ATOM   1825  C    ASN  233    25.558  34.513 123.866  1.00 33.38      AAGL
ATOM   1826  O    ASN  233    25.932  33.616 124.621  1.00 34.08      AAGL
ATOM   1827  N    LEU  234    24.780  34.280 122.812  1.00 32.11      AAGL
ATOM   1828  CA   LEU  234    24.331  32.927 122.498  1.00 31.75      AAGL
ATOM   1829  CB   LEU  234    23.387  32.935 121.286  1.00 29.34      AAGL
ATOM   1830  CG   LEU  234    21.875  33.038 121.527  1.00 28.94      AAGL
ATOM   1831  CD1  LEU  234    21.151  33.301 120.209  1.00 28.45      AAGL
ATOM   1832  CD2  LEU  234    21.373  31.739 122.157  1.00 29.20      AAGL
ATOM   1833  C    LEU  234    25.529  32.036 122.200  1.00 31.64      AAGL
ATOM   1834  O    LEU  234    25.651  30.937 122.737  1.00 31.64      AAGL
ATOM   1835  N    GLN  235    26.413  32.530 121.340  1.00 31.31      AAGL
ATOM   1836  CA   GLN  235    27.601  31.797 120.944  1.00 34.83      AAGL
ATOM   1837  CB   GLN  235    28.302  32.560 119.810  1.00 34.48      AAGL
ATOM   1838  CG   GLN  235    29.283  31.756 118.991  1.00 36.34      AAGL
ATOM   1839  CD   GLN  235    30.545  31.410 119.747  1.00 38.22      AAGL
ATOM   1840  OE1  GLN  235    31.065  32.224 120.511  1.00 38.29      AAGL
ATOM   1841  NE2  GLN  235    31.059  30.204 119.521  1.00 38.94      AAGL
ATOM   1842  C    GLN  235    28.557  31.597 122.122  1.00 35.64      AAGL
ATOM   1843  O    GLN  235    29.063  30.500 122.335  1.00 34.97      AAGL
ATOM   1844  N    SER  236    28.776  32.659 122.894  1.00 36.91      AAGL
ATOM   1845  CA   SER  236    29.694  32.626 124.034  1.00 39.04      AAGL
ATOM   1846  CB   SER  236    29.942  34.056 124.552  1.00 39.04      AAGL
ATOM   1847  OG   SER  236    28.764  34.620 125.122  1.00 40.94      AAGL
ATOM   1848  C    SER  236    29.221  31.750 125.191  1.00 39.31      AAGL
ATOM   1849  O    SER  236    30.027  31.118 125.885  1.00 40.12      AAGL
ATOM   1850  N    THR  237    27.913  31.703 125.394  1.00 38.31      AAGL
ATOM   1851  CA   THR  237    27.353  30.930 126.489  1.00 37.56      AAGL
ATOM   1852  CB   THR  237    26.002  31.514 126.918  1.00 36.05      AAGL
ATOM   1853  OG1  THR  237    26.183  32.883 127.291  1.00 35.25      AAGL
ATOM   1854  CG2  THR  237    25.432  30.738 128.101  1.00 36.50      AAGL
ATOM   1855  C    THR  237    27.169  29.459 126.181  1.00 36.88      AAGL
ATOM   1856  O    THR  237    27.503  28.606 127.003  1.00 37.95      AAGL
ATOM   1857  N    TYR  238    26.653  29.158 124.992  1.00 35.86      AAGL
ATOM   1858  CA   TYR  238    26.391  27.777 124.594  1.00 34.18      AAGL
ATOM   1859  CB   TYR  238    24.955  27.684 124.059  1.00 33.21      AAGL
ATOM   1860  CG   TYR  238    23.924  28.178 125.056  1.00 32.37      AAGL
ATOM   1861  CD1  TYR  238    23.513  27.376 126.125  1.00 31.26      AAGL
ATOM   1862  CE1  TYR  238    22.630  27.860 127.093  1.00 32.64      AAGL
ATOM   1863  CD2  TYR  238    23.416  29.473 124.976  1.00 31.04      AAGL
ATOM   1864  CE2  TYR  238    22.531  29.961 125.935  1.00 32.31      AAGL
```

Fig. 3 cont.

```
ATOM   1865  CZ   TYR   238      22.146  29.150 126.992  1.00 32.31           AAGL
ATOM   1866  OH   TYR   238      21.291  29.646 127.951  1.00 34.51           AAGL
ATOM   1867  C    TYR   238      27.377  27.210 123.570  1.00 34.17           AAGL
ATOM   1868  O    TYR   238      27.327  26.023 123.245  1.00 32.44           AAGL
ATOM   1869  N    ASP   239      28.263  28.060 123.060  1.00 34.59           AAGL
ATOM   1870  CA   ASP   239      29.267  27.645 122.080  1.00 35.46           AAGL
ATOM   1871  CB   ASP   239      30.292  26.716 122.754  1.00 38.30           AAGL
ATOM   1872  CG   ASP   239      31.412  26.290 121.819  1.00 39.89           AAGL
ATOM   1873  OD1  ASP   239      31.811  27.088 120.939  1.00 40.54           AAGL
ATOM   1874  OD2  ASP   239      31.911  25.155 121.975  1.00 41.25           AAGL
ATOM   1875  C    ASP   239      28.688  26.982 120.829  1.00 34.34           AAGL
ATOM   1876  O    ASP   239      29.098  25.885 120.451  1.00 34.85           AAGL
ATOM   1877  N    LYS   240      27.735  27.656 120.190  1.00 32.57           AAGL
ATOM   1878  CA   LYS   240      27.121  27.155 118.963  1.00 31.63           AAGL
ATOM   1879  CB   LYS   240      25.746  26.525 119.234  1.00 30.18           AAGL
ATOM   1880  CG   LYS   240      25.764  25.264 120.104  1.00 33.39           AAGL
ATOM   1881  CD   LYS   240      24.367  24.648 120.218  1.00 31.95           AAGL
ATOM   1882  CE   LYS   240      24.318  23.502 121.247  1.00 32.26           AAGL
ATOM   1883  NZ   LYS   240      25.241  22.379 120.930  1.00 29.98           AAGL
ATOM   1884  C    LYS   240      26.953  28.315 117.990  1.00 29.66           AAGL
ATOM   1885  O    LYS   240      26.779  29.460 118.400  1.00 30.38           AAGL
ATOM   1886  N    PRO   241      27.010  28.036 116.679  1.00 29.06           AAGL
ATOM   1887  CD   PRO   241      27.422  26.781 116.028  1.00 29.36           AAGL
ATOM   1888  CA   PRO   241      26.850  29.106 115.691  1.00 27.35           AAGL
ATOM   1889  CB   PRO   241      27.136  28.403 114.371  1.00 27.28           AAGL
ATOM   1890  CG   PRO   241      28.058  27.285 114.768  1.00 29.28           AAGL
ATOM   1891  C    PRO   241      25.434  29.693 115.732  1.00 28.09           AAGL
ATOM   1892  O    PRO   241      24.491  29.048 116.201  1.00 27.43           AAGL
ATOM   1893  N    VAL   242      25.294  30.911 115.225  1.00 27.44           AAGL
ATOM   1894  CA   VAL   242      24.005  31.588 115.192  1.00 27.37           AAGL
ATOM   1895  CB   VAL   242      24.047  32.871 116.015  1.00 24.62           AAGL
ATOM   1896  CG1  VAL   242      24.156  32.531 117.479  1.00 27.77           AAGL
ATOM   1897  CG2  VAL   242      25.242  33.719 115.588  1.00 27.66           AAGL
ATOM   1898  C    VAL   242      23.614  31.929 113.763  1.00 26.08           AAGL
ATOM   1899  O    VAL   242      24.468  32.140 112.903  1.00 27.26           AAGL
ATOM   1900  N    VAL   243      22.313  31.990 113.512  1.00 25.38           AAGL
ATOM   1901  CA   VAL   243      21.806  32.287 112.179  1.00 22.94           AAGL
ATOM   1902  CB   VAL   243      21.431  30.973 111.419  1.00 24.38           AAGL
ATOM   1903  CG1  VAL   243      20.994  31.285 109.996  1.00 23.02           AAGL
ATOM   1904  CG2  VAL   243      22.612  30.009 111.409  1.00 25.53           AAGL
ATOM   1905  C    VAL   243      20.541  33.129 112.289  1.00 22.55           AAGL
ATOM   1906  O    VAL   243      19.691  32.836 113.115  1.00 21.01           AAGL
ATOM   1907  N    VAL   244      20.432  34.188 111.487  1.00 21.40           AAGL
ATOM   1908  CA   VAL   244      19.213  34.995 111.483  1.00 21.25           AAGL
ATOM   1909  CB   VAL   244      19.469  36.463 111.094  1.00 21.49           AAGL
ATOM   1910  CG1  VAL   244      18.139  37.170 110.884  1.00 22.74           AAGL
ATOM   1911  CG2  VAL   244      20.263  37.163 112.188  1.00 20.20           AAGL
ATOM   1912  C    VAL   244      18.414  34.309 110.387  1.00 19.60           AAGL
ATOM   1913  O    VAL   244      18.720  34.446 109.205  1.00 20.42           AAGL
ATOM   1914  N    VAL   245      17.395  33.557 110.780  1.00 17.97           AAGL
ATOM   1915  CA   VAL   245      16.635  32.788 109.807  1.00 17.90           AAGL
ATOM   1916  CB   VAL   245      16.234  31.431 110.413  1.00 18.93           AAGL
ATOM   1917  CG1  VAL   245      17.485  30.699 110.871  1.00 18.12           AAGL
ATOM   1918  CG2  VAL   245      15.274  31.637 111.578  1.00 17.48           AAGL
ATOM   1919  C    VAL   245      15.415  33.450 109.192  1.00 17.32           AAGL
ATOM   1920  O    VAL   245      14.783  32.882 108.308  1.00 17.57           AAGL
ATOM   1921  N    GLU   246      15.085  34.644 109.666  1.00 17.88           AAGL
ATOM   1922  CA   GLU   246      13.949  35.392 109.143  1.00 18.02           AAGL
ATOM   1923  CB   GLU   246      12.657  35.023 109.875  1.00 22.04           AAGL
ATOM   1924  CG   GLU   246      11.917  33.816 109.352  1.00 22.72           AAGL
ATOM   1925  CD   GLU   246      10.611  33.589 110.102  1.00 24.03           AAGL
ATOM   1926  OE1  GLU   246       9.882  34.579 110.340  1.00 20.71           AAGL
ATOM   1927  OE2  GLU   246      10.311  32.422 110.438  1.00 22.70           AAGL
ATOM   1928  C    GLU   246      14.163  36.882 109.327  1.00 18.20           AAGL
ATOM   1929  O    GLU   246      14.547  37.316 110.404  1.00 19.12           AAGL
ATOM   1930  N    THR   247      13.912  37.658 108.281  1.00 17.83           AAGL
ATOM   1931  CA   THR   247      14.024  39.114 108.372  1.00 19.34           AAGL
```

Fig. 3 cont.

```
ATOM   1932  CB   THR  247    15.505  39.584 108.487  1.00 21.29      AAGL
ATOM   1933  OG1  THR  247    15.532  40.968 108.857  1.00 22.65      AAGL
ATOM   1934  CG2  THR  247    16.238  39.409 107.172  1.00 20.07      AAGL
ATOM   1935  C    THR  247    13.356  39.774 107.167  1.00 18.87      AAGL
ATOM   1936  O    THR  247    13.167  39.141 106.134  1.00 19.64      AAGL
ATOM   1937  N    ASN  248    12.980  41.039 107.326  1.00 17.13      AAGL
ATOM   1938  CA   ASN  248    12.312  41.816 106.281  1.00 18.39      AAGL
ATOM   1939  CB   ASN  248    10.793  41.800 106.466  1.00 19.04      AAGL
ATOM   1940  CG   ASN  248    10.095  40.616 105.836  1.00 20.07      AAGL
ATOM   1941  OD1  ASN  248     8.889  40.475 106.007  1.00 23.76      AAGL
ATOM   1942  ND2  ASN  248    10.820  39.775 105.113  1.00 20.10      AAGL
ATOM   1943  C    ASN  248    12.685  43.291 106.427  1.00 18.69      AAGL
ATOM   1944  O    ASN  248    13.135  43.725 107.483  1.00 17.33      AAGL
ATOM   1945  N    TRP  249    12.466  44.046 105.355  1.00 19.91      AAGL
ATOM   1946  CA   TRP  249    12.630  45.503 105.355  1.00 21.18      AAGL
ATOM   1947  CB   TRP  249    14.065  45.981 105.129  1.00 21.42      AAGL
ATOM   1948  CG   TRP  249    14.117  47.491 105.288  1.00 19.99      AAGL
ATOM   1949  CD2  TRP  249    14.261  48.225 106.517  1.00 19.73      AAGL
ATOM   1950  CE2  TRP  249    14.108  49.599 106.208  1.00 19.65      AAGL
ATOM   1951  CE3  TRP  249    14.499  47.853 107.847  1.00 19.37      AAGL
ATOM   1952  CD1  TRP  249    13.895  48.431 104.313  1.00 20.84      AAGL
ATOM   1953  NE1  TRP  249    13.887  49.693 104.861  1.00 19.99      AAGL
ATOM   1954  CZ2  TRP  249    14.185  50.604 107.187  1.00 20.08      AAGL
ATOM   1955  CZ3  TRP  249    14.575  48.853 108.820  1.00 21.35      AAGL
ATOM   1956  CH2  TRP  249    14.418  50.214 108.481  1.00 21.66      AAGL
ATOM   1957  C    TRP  249    11.722  46.003 104.241  1.00 20.70      AAGL
ATOM   1958  O    TRP  249    11.800  45.539 103.102  1.00 22.36      AAGL
ATOM   1959  N    PRO  250    10.838  46.957 104.559  1.00 22.00      AAGL
ATOM   1960  CD   PRO  250    10.686  47.625 105.865  1.00 21.04      AAGL
ATOM   1961  CA   PRO  250     9.894  47.508 103.587  1.00 21.27      AAGL
ATOM   1962  CB   PRO  250     8.876  48.210 104.477  1.00 22.31      AAGL
ATOM   1963  CG   PRO  250     9.744  48.783 105.538  1.00 22.64      AAGL
ATOM   1964  C    PRO  250    10.402  48.435 102.507  1.00 23.33      AAGL
ATOM   1965  O    PRO  250    11.270  49.268 102.743  1.00 21.79      AAGL
ATOM   1966  N    VAL  251     9.844  48.282 101.311  1.00 23.27      AAGL
ATOM   1967  CA   VAL  251    10.185  49.165 100.212  1.00 24.85      AAGL
ATOM   1968  CB   VAL  251    10.171  48.437  98.854  1.00 24.44      AAGL
ATOM   1969  CG1  VAL  251    11.335  47.476  98.787  1.00 24.31      AAGL
ATOM   1970  CG2  VAL  251     8.865  47.699  98.657  1.00 28.76      AAGL
ATOM   1971  C    VAL  251     9.095  50.227 100.278  1.00 26.42      AAGL
ATOM   1972  O    VAL  251     9.177  51.281  99.646  1.00 24.68      AAGL
ATOM   1973  N    SER  252     8.075  49.934 101.083  1.00 27.57      AAGL
ATOM   1974  CA   SER  252     6.962  50.851 101.298  1.00 27.22      AAGL
ATOM   1975  CB   SER  252     5.942  50.722 100.164  1.00 28.72      AAGL
ATOM   1976  OG   SER  252     4.895  51.662 100.327  1.00 28.82      AAGL
ATOM   1977  C    SER  252     6.289  50.558 102.642  1.00 28.31      AAGL
ATOM   1978  O    SER  252     5.858  49.434 102.886  1.00 26.39      AAGL
ATOM   1979  N    CYS  253     6.232  51.559 103.518  1.00 27.82      AAGL
ATOM   1980  CA   CYS  253     5.594  51.413 104.824  1.00 27.19      AAGL
ATOM   1981  C    CYS  253     4.932  52.738 105.201  1.00 28.86      AAGL
ATOM   1982  O    CYS  253     5.411  53.436 106.091  1.00 27.40      AAGL
ATOM   1983  CB   CYS  253     6.611  51.031 105.913  1.00 27.78      AAGL
ATOM   1984  SG   CYS  253     5.803  50.369 107.406  1.00 28.15      AAGL
ATOM   1985  N    PRO  254     3.812  53.089 104.528  1.00 30.47      AAGL
ATOM   1986  CD   PRO  254     3.166  52.222 103.525  1.00 30.66      AAGL
ATOM   1987  CA   PRO  254     3.022  54.314 104.725  1.00 32.44      AAGL
ATOM   1988  CB   PRO  254     1.739  54.023 103.951  1.00 32.43      AAGL
ATOM   1989  CG   PRO  254     2.206  53.171 102.837  1.00 33.11      AAGL
ATOM   1990  C    PRO  254     2.739  54.660 106.181  1.00 34.76      AAGL
ATOM   1991  O    PRO  254     2.780  55.828 106.570  1.00 35.87      AAGL
ATOM   1992  N    ASN  255     2.429  53.653 106.987  1.00 35.37      AAGL
ATOM   1993  CA   ASN  255     2.161  53.912 108.392  1.00 36.89      AAGL
ATOM   1994  CB   ASN  255     0.755  54.457 108.575  1.00 37.41      AAGL
ATOM   1995  CG   ASN  255     0.410  54.682 110.030  1.00 38.46      AAGL
ATOM   1996  OD1  ASN  255     1.254  55.124 110.832  1.00 35.39      AAGL
ATOM   1997  ND2  ASN  255    -0.833  54.389 110.387  1.00 34.81      AAGL
ATOM   1998  C    ASN  255     2.354  52.691 109.263  1.00 35.87      AAGL
```

Fig. 3 cont.

```
ATOM   1999  O    ASN   255     1.471  51.841 109.375  1.00 36.70      AAGL
ATOM   2000  N    PRO   256     3.520  52.601 109.910  1.00 35.76      AAGL
ATOM   2001  CD   PRO   256     4.640  53.550 109.780  1.00 35.85      AAGL
ATOM   2002  CA   PRO   256     3.878  51.493 110.791  1.00 34.93      AAGL
ATOM   2003  CB   PRO   256     5.387  51.654 110.927  1.00 35.60      AAGL
ATOM   2004  CG   PRO   256     5.558  53.122 110.901  1.00 36.37      AAGL
ATOM   2005  C    PRO   256     3.158  51.543 112.140  1.00 34.50      AAGL
ATOM   2006  O    PRO   256     3.041  52.604 112.752  1.00 33.71      AAGL
ATOM   2007  N    ALA   257     2.683  50.393 112.603  1.00 32.93      AAGL
ATOM   2008  CA   ALA   257     1.988  50.327 113.880  1.00 31.85      AAGL
ATOM   2009  CB   ALA   257     1.371  48.946 114.079  1.00 31.01      AAGL
ATOM   2010  C    ALA   257     2.970  50.621 115.000  1.00 32.12      AAGL
ATOM   2011  O    ALA   257     2.591  51.139 116.046  1.00 31.82      AAGL
ATOM   2012  N    TYR   258     4.237  50.291 114.771  1.00 31.15      AAGL
ATOM   2013  CA   TYR   258     5.279  50.504 115.761  1.00 32.72      AAGL
ATOM   2014  CB   TYR   258     5.892  49.168 116.169  1.00 35.88      AAGL
ATOM   2015  CG   TYR   258     4.954  48.226 116.880  1.00 38.05      AAGL
ATOM   2016  CD1  TYR   258     4.136  47.341 116.170  1.00 37.62      AAGL
ATOM   2017  CE1  TYR   258     3.276  46.468 116.840  1.00 40.53      AAGL
ATOM   2018  CD2  TYR   258     4.889  48.216 118.267  1.00 39.82      AAGL
ATOM   2019  CE2  TYR   258     4.039  47.357 118.943  1.00 41.64      AAGL
ATOM   2020  CZ   TYR   258     3.236  46.489 118.232  1.00 42.48      AAGL
ATOM   2021  OH   TYR   258     2.386  45.659 118.934  1.00 45.83      AAGL
ATOM   2022  C    TYR   258     6.414  51.411 115.293  1.00 32.44      AAGL
ATOM   2023  O    TYR   258     6.736  51.468 114.108  1.00 31.27      AAGL
ATOM   2024  N    ALA   259     7.021  52.121 116.237  1.00 30.79      AAGL
ATOM   2025  CA   ALA   259     8.147  52.983 115.919  1.00 31.35      AAGL
ATOM   2026  CB   ALA   259     8.479  53.864 117.118  1.00 33.39      AAGL
ATOM   2027  C    ALA   259     9.315  52.046 115.607  1.00 29.93      AAGL
ATOM   2028  O    ALA   259     9.458  51.004 116.242  1.00 29.16      AAGL
ATOM   2029  N    PHE   260    10.137  52.392 114.623  1.00 29.81      AAGL
ATOM   2030  CA   PHE   260    11.281  51.548 114.285  1.00 29.03      AAGL
ATOM   2031  CB   PHE   260    11.772  51.871 112.867  1.00 28.71      AAGL
ATOM   2032  CG   PHE   260    11.007  51.157 111.776  1.00 29.00      AAGL
ATOM   2033  CD1  PHE   260     9.622  51.242 111.704  1.00 29.61      AAGL
ATOM   2034  CD2  PHE   260    11.676  50.379 110.840  1.00 28.02      AAGL
ATOM   2035  CE1  PHE   260     8.915  50.558 110.720  1.00 30.59      AAGL
ATOM   2036  CE2  PHE   260    10.979  49.694 109.854  1.00 29.46      AAGL
ATOM   2037  CZ   PHE   260     9.594  49.783 109.796  1.00 29.30      AAGL
ATOM   2038  C    PHE   260    12.409  51.765 115.300  1.00 29.23      AAGL
ATOM   2039  O    PHE   260    12.464  52.806 115.957  1.00 29.38      AAGL
ATOM   2040  N    PRO   261    13.302  50.771 115.466  1.00 29.34      AAGL
ATOM   2041  CD   PRO   261    13.247  49.414 114.891  1.00 29.47      AAGL
ATOM   2042  CA   PRO   261    14.418  50.891 116.409  1.00 29.63      AAGL
ATOM   2043  CB   PRO   261    15.194  49.599 116.186  1.00 28.18      AAGL
ATOM   2044  CG   PRO   261    14.096  48.617 115.852  1.00 28.51      AAGL
ATOM   2045  C    PRO   261    15.240  52.137 116.063  1.00 29.95      AAGL
ATOM   2046  O    PRO   261    15.312  52.539 114.897  1.00 30.37      AAGL
ATOM   2047  N    SER   262    15.846  52.736 117.082  1.00 32.41      AAGL
ATOM   2048  CA   SER   262    16.637  53.951 116.922  1.00 31.88      AAGL
ATOM   2049  CB   SER   262    17.167  54.396 118.291  1.00 33.67      AAGL
ATOM   2050  OG   SER   262    17.708  53.295 119.003  1.00 37.49      AAGL
ATOM   2051  C    SER   262    17.785  53.858 115.918  1.00 32.30      AAGL
ATOM   2052  O    SER   262    17.967  54.773 115.107  1.00 32.95      AAGL
ATOM   2053  N    ASP   263    18.565  52.778 115.955  1.00 31.17      AAGL
ATOM   2054  CA   ASP   263    19.660  52.663 115.000  1.00 31.60      AAGL
ATOM   2055  CB   ASP   263    20.768  51.724 115.512  1.00 31.48      AAGL
ATOM   2056  CG   ASP   263    20.241  50.418 116.090  1.00 31.74      AAGL
ATOM   2057  OD1  ASP   263    19.111  49.994 115.748  1.00 30.33      AAGL
ATOM   2058  OD2  ASP   263    20.987  49.796 116.887  1.00 30.41      AAGL
ATOM   2059  C    ASP   263    19.210  52.227 113.604  1.00 31.45      AAGL
ATOM   2060  O    ASP   263    20.036  51.858 112.768  1.00 32.04      AAGL
ATOM   2061  N    LEU   264    17.905  52.296 113.344  1.00 30.59      AAGL
ATOM   2062  CA   LEU   264    17.363  51.920 112.038  1.00 28.75      AAGL
ATOM   2063  CB   LEU   264    16.621  50.575 112.123  1.00 27.83      AAGL
ATOM   2064  CG   LEU   264    17.375  49.323 112.570  1.00 24.26      AAGL
ATOM   2065  CD1  LEU   264    16.389  48.179 112.752  1.00 25.96      AAGL
```

Fig. 3 cont.

```
ATOM   2066  CD2 LEU   264     18.429  48.955 111.552  1.00 27.53      AAGL
ATOM   2067  C   LEU   264     16.391  52.971 111.512  1.00 28.95      AAGL
ATOM   2068  O   LEU   264     15.941  52.893 110.374  1.00 27.43      AAGL
ATOM   2069  N   SER   265     16.074  53.965 112.331  1.00 30.75      AAGL
ATOM   2070  CA  SER   265     15.120  54.986 111.925  1.00 32.24      AAGL
ATOM   2071  CB  SER   265     14.662  55.779 113.154  1.00 33.67      AAGL
ATOM   2072  OG  SER   265     15.763  56.287 113.892  1.00 34.70      AAGL
ATOM   2073  C   SER   265     15.572  55.941 110.815  1.00 33.25      AAGL
ATOM   2074  O   SER   265     14.776  56.742 110.328  1.00 34.94      AAGL
ATOM   2075  N   SER   266     16.832  55.859 110.399  1.00 33.96      AAGL
ATOM   2076  CA  SER   266     17.305  56.745 109.339  1.00 33.28      AAGL
ATOM   2077  CB  SER   266     18.765  57.133 109.576  1.00 34.74      AAGL
ATOM   2078  OG  SER   266     19.652  56.107 109.142  1.00 40.32      AAGL
ATOM   2079  C   SER   266     17.176  56.085 107.964  1.00 31.87      AAGL
ATOM   2080  O   SER   266     17.236  56.754 106.931  1.00 30.82      AAGL
ATOM   2081  N   ILE   267     16.982  54.773 107.956  1.00 28.10      AAGL
ATOM   2082  CA  ILE   267     16.874  54.025 106.713  1.00 26.55      AAGL
ATOM   2083  CB  ILE   267     17.067  52.523 106.983  1.00 25.69      AAGL
ATOM   2084  CG2 ILE   267     17.120  51.757 105.666  1.00 26.74      AAGL
ATOM   2085  CG1 ILE   267     18.349  52.323 107.801  1.00 28.70      AAGL
ATOM   2086  CD1 ILE   267     18.606  50.889 108.250  1.00 27.91      AAGL
ATOM   2087  C   ILE   267     15.537  54.267 106.024  1.00 25.54      AAGL
ATOM   2088  O   ILE   267     14.482  54.060 106.604  1.00 24.26      AAGL
ATOM   2089  N   PRO   268     15.567  54.734 104.767  1.00 25.09      AAGL
ATOM   2090  CD  PRO   268     16.725  55.097 103.932  1.00 26.35      AAGL
ATOM   2091  CA  PRO   268     14.312  54.986 104.058  1.00 25.07      AAGL
ATOM   2092  CB  PRO   268     14.767  55.792 102.844  1.00 26.89      AAGL
ATOM   2093  CG  PRO   268     16.108  55.205 102.560  1.00 26.87      AAGL
ATOM   2094  C   PRO   268     13.602  53.694 103.662  1.00 24.21      AAGL
ATOM   2095  O   PRO   268     14.208  52.622 103.644  1.00 23.10      AAGL
ATOM   2096  N   PHE   269     12.313  53.806 103.362  1.00 23.20      AAGL
ATOM   2097  CA  PHE   269     11.525  52.664 102.931  1.00 23.46      AAGL
ATOM   2098  CB  PHE   269     10.091  52.765 103.446  1.00 24.32      AAGL
ATOM   2099  CG  PHE   269      9.994  52.861 104.942  1.00 24.64      AAGL
ATOM   2100  CD1 PHE   269     10.819  52.093 105.758  1.00 25.88      AAGL
ATOM   2101  CD2 PHE   269      9.070  53.706 105.535  1.00 25.95      AAGL
ATOM   2102  CE1 PHE   269     10.722  52.168 107.151  1.00 26.08      AAGL
ATOM   2103  CE2 PHE   269      8.965  53.788 106.925  1.00 23.79      AAGL
ATOM   2104  CZ  PHE   269      9.793  53.016 107.732  1.00 23.02      AAGL
ATOM   2105  C   PHE   269     11.548  52.698 101.413  1.00 23.22      AAGL
ATOM   2106  O   PHE   269     10.778  53.420 100.774  1.00 23.95      AAGL
ATOM   2107  N   SER   270     12.462  51.916 100.848  1.00 23.29      AAGL
ATOM   2108  CA  SER   270     12.649  51.848  99.410  1.00 24.41      AAGL
ATOM   2109  CB  SER   270     13.282  53.140  98.924  1.00 24.90      AAGL
ATOM   2110  OG  SER   270     14.547  53.300  99.540  1.00 25.23      AAGL
ATOM   2111  C   SER   270     13.596  50.702  99.125  1.00 22.81      AAGL
ATOM   2112  O   SER   270     14.147  50.105 100.055  1.00 25.01      AAGL
ATOM   2113  N   VAL   271     13.791  50.392  97.845  1.00 23.71      AAGL
ATOM   2114  CA  VAL   271     14.702  49.316  97.477  1.00 22.85      AAGL
ATOM   2115  CB  VAL   271     14.846  49.170  95.948  1.00 24.85      AAGL
ATOM   2116  CG1 VAL   271     15.953  48.172  95.630  1.00 23.46      AAGL
ATOM   2117  CG2 VAL   271     13.534  48.698  95.338  1.00 22.67      AAGL
ATOM   2118  C   VAL   271     16.065  49.649  98.056  1.00 24.60      AAGL
ATOM   2119  O   VAL   271     16.744  48.787  98.613  1.00 24.45      AAGL
ATOM   2120  N   ALA   272     16.453  50.914  97.932  1.00 25.33      AAGL
ATOM   2121  CA  ALA   272     17.740  51.373  98.442  1.00 24.59      AAGL
ATOM   2122  CB  ALA   272     17.946  52.858  98.104  1.00 26.33      AAGL
ATOM   2123  C   ALA   272     17.814  51.162  99.951  1.00 21.83      AAGL
ATOM   2124  O   ALA   272     18.839  50.732 100.479  1.00 21.37      AAGL
ATOM   2125  N   GLY   273     16.722  51.463 100.646  1.00 22.29      AAGL
ATOM   2126  CA  GLY   273     16.710  51.284 102.086  1.00 22.02      AAGL
ATOM   2127  C   GLY   273     16.808  49.814 102.448  1.00 21.98      AAGL
ATOM   2128  O   GLY   273     17.427  49.442 103.443  1.00 22.94      AAGL
ATOM   2129  N   GLN   274     16.192  48.973 101.623  1.00 23.13      AAGL
ATOM   2130  CA  GLN   274     16.210  47.534 101.837  1.00 23.82      AAGL
ATOM   2131  CB  GLN   274     15.354  46.862 100.770  1.00 26.47      AAGL
ATOM   2132  CG  GLN   274     14.976  45.429 101.049  1.00 28.49      AAGL
```

Fig. 3 cont.

```
ATOM   2133  CD   GLN  274     13.969  44.926 100.034  1.00 29.11      AAGL
ATOM   2134  OE1  GLN  274     14.273  44.819  98.846  1.00 26.58      AAGL
ATOM   2135  NE2  GLN  274     12.760  44.630 100.491  1.00 22.87      AAGL
ATOM   2136  C    GLN  274     17.655  47.047 101.741  1.00 24.42      AAGL
ATOM   2137  O    GLN  274     18.090  46.184 102.500  1.00 23.54      AAGL
ATOM   2138  N    GLN  275     18.405  47.621 100.807  1.00 22.92      AAGL
ATOM   2139  CA   GLN  275     19.802  47.240 100.627  1.00 22.23      AAGL
ATOM   2140  CB   GLN  275     20.347  47.863  99.349  1.00 25.17      AAGL
ATOM   2141  CG   GLN  275     19.668  47.370  98.089  1.00 25.16      AAGL
ATOM   2142  CD   GLN  275     20.162  48.099  96.862  1.00 29.65      AAGL
ATOM   2143  OE1  GLN  275     19.879  49.283  96.677  1.00 33.06      AAGL
ATOM   2144  NE2  GLN  275     20.915  47.403  96.021  1.00 30.34      AAGL
ATOM   2145  C    GLN  275     20.658  47.679 101.807  1.00 22.46      AAGL
ATOM   2146  O    GLN  275     21.492  46.924 102.289  1.00 23.14      AAGL
ATOM   2147  N    GLU  276     20.444  48.906 102.268  1.00 23.39      AAGL
ATOM   2148  CA   GLU  276     21.203  49.448 103.386  1.00 22.93      AAGL
ATOM   2149  CB   GLU  276     20.821  50.917 103.615  1.00 26.77      AAGL
ATOM   2150  CG   GLU  276     21.393  51.518 104.891  1.00 31.09      AAGL
ATOM   2151  CD   GLU  276     21.007  52.982 105.081  1.00 33.52      AAGL
ATOM   2152  OE1  GLU  276     19.968  53.402 104.533  1.00 35.95      AAGL
ATOM   2153  OE2  GLU  276     21.734  53.704 105.791  1.00 34.45      AAGL
ATOM   2154  C    GLU  276     20.948  48.620 104.643  1.00 23.86      AAGL
ATOM   2155  O    GLU  276     21.870  48.302 105.385  1.00 22.86      AAGL
ATOM   2156  N    PHE  277     19.692  48.261 104.876  1.00 22.41      AAGL
ATOM   2157  CA   PHE  277     19.355  47.458 106.042  1.00 21.05      AAGL
ATOM   2158  CB   PHE  277     17.844  47.222 106.120  1.00 20.89      AAGL
ATOM   2159  CG   PHE  277     17.447  46.219 107.171  1.00 19.02      AAGL
ATOM   2160  CD1  PHE  277     17.541  46.533 108.518  1.00 21.55      AAGL
ATOM   2161  CD2  PHE  277     17.003  44.946 106.805  1.00 22.72      AAGL
ATOM   2162  CE1  PHE  277     17.200  45.594 109.498  1.00 23.87      AAGL
ATOM   2163  CE2  PHE  277     16.660  43.998 107.781  1.00 21.01      AAGL
ATOM   2164  CZ   PHE  277     16.759  44.323 109.122  1.00 22.10      AAGL
ATOM   2165  C    PHE  277     20.051  46.102 105.989  1.00 20.46      AAGL
ATOM   2166  O    PHE  277     20.676  45.674 106.952  1.00 20.12      AAGL
ATOM   2167  N    LEU  278     19.928  45.421 104.856  1.00 20.92      AAGL
ATOM   2168  CA   LEU  278     20.541  44.107 104.716  1.00 23.04      AAGL
ATOM   2169  CB   LEU  278     20.225  43.512 103.340  1.00 24.67      AAGL
ATOM   2170  CG   LEU  278     18.764  43.076 103.160  1.00 24.46      AAGL
ATOM   2171  CD1  LEU  278     18.548  42.589 101.741  1.00 26.14      AAGL
ATOM   2172  CD2  LEU  278     18.427  41.964 104.161  1.00 26.55      AAGL
ATOM   2173  C    LEU  278     22.040  44.144 104.947  1.00 23.23      AAGL
ATOM   2174  O    LEU  278     22.593  43.273 105.615  1.00 20.93      AAGL
ATOM   2175  N    GLU  279     22.707  45.155 104.404  1.00 24.22      AAGL
ATOM   2176  CA   GLU  279     24.141  45.244 104.601  1.00 25.09      AAGL
ATOM   2177  CB   GLU  279     24.735  46.309 103.682  1.00 26.59      AAGL
ATOM   2178  CG   GLU  279     24.418  46.045 102.213  1.00 32.07      AAGL
ATOM   2179  CD   GLU  279     25.419  46.691 101.274  1.00 37.00      AAGL
ATOM   2180  OE1  GLU  279     25.859  47.815 101.576  1.00 39.68      AAGL
ATOM   2181  OE2  GLU  279     25.756  46.078 100.235  1.00 40.09      AAGL
ATOM   2182  C    GLU  279     24.460  45.537 106.062  1.00 23.19      AAGL
ATOM   2183  O    GLU  279     25.409  44.984 106.614  1.00 23.97      AAGL
ATOM   2184  N    LYS  280     23.669  46.391 106.701  1.00 24.51      AAGL
ATOM   2185  CA   LYS  280     23.922  46.688 108.105  1.00 24.24      AAGL
ATOM   2186  CB   LYS  280     23.076  47.879 108.566  1.00 25.42      AAGL
ATOM   2187  CG   LYS  280     23.535  49.186 107.912  1.00 30.50      AAGL
ATOM   2188  CD   LYS  280     22.847  50.429 108.463  1.00 35.06      AAGL
ATOM   2189  CE   LYS  280     23.561  51.683 107.932  1.00 38.33      AAGL
ATOM   2190  NZ   LYS  280     23.003  52.962 108.460  1.00 39.58      AAGL
ATOM   2191  C    LYS  280     23.665  45.458 108.975  1.00 24.77      AAGL
ATOM   2192  O    LYS  280     24.382  45.219 109.949  1.00 21.68      AAGL
ATOM   2193  N    LEU  281     22.655  44.669 108.614  1.00 23.74      AAGL
ATOM   2194  CA   LEU  281     22.351  43.449 109.365  1.00 23.71      AAGL
ATOM   2195  CB   LEU  281     21.023  42.844 108.891  1.00 21.53      AAGL
ATOM   2196  CG   LEU  281     20.603  41.484 109.478  1.00 21.28      AAGL
ATOM   2197  CD1  LEU  281     20.583  41.533 110.996  1.00 19.24      AAGL
ATOM   2198  CD2  LEU  281     19.226  41.109 108.937  1.00 19.79      AAGL
ATOM   2199  C    LEU  281     23.482  42.429 109.172  1.00 22.36      AAGL
```

Fig. 3 cont.

| | | | | | | | | | |
|---|---|---|---|---|---|---|---|---|---|
| ATOM | 2200 | O | LEU | 281 | 23.940 | 41.803 | 110.125 | 1.00 24.16 | AAGL |
| ATOM | 2201 | N | ALA | 282 | 23.921 | 42.267 | 107.928 | 1.00 23.73 | AAGL |
| ATOM | 2202 | CA | ALA | 282 | 24.998 | 41.339 | 107.611 | 1.00 23.94 | AAGL |
| ATOM | 2203 | CB | ALA | 282 | 25.272 | 41.356 | 106.120 | 1.00 23.77 | AAGL |
| ATOM | 2204 | C | ALA | 282 | 26.264 | 41.713 | 108.382 | 1.00 24.05 | AAGL |
| ATOM | 2205 | O | ALA | 282 | 27.060 | 40.848 | 108.741 | 1.00 25.21 | AAGL |
| ATOM | 2206 | N | ALA | 283 | 26.441 | 43.005 | 108.643 | 1.00 25.21 | AAGL |
| ATOM | 2207 | CA | ALA | 283 | 27.614 | 43.477 | 109.372 | 1.00 25.75 | AAGL |
| ATOM | 2208 | CB | ALA | 283 | 27.616 | 45.005 | 109.424 | 1.00 26.48 | AAGL |
| ATOM | 2209 | C | ALA | 283 | 27.635 | 42.898 | 110.786 | 1.00 26.18 | AAGL |
| ATOM | 2210 | O | ALA | 283 | 28.658 | 42.387 | 111.248 | 1.00 25.57 | AAGL |
| ATOM | 2211 | N | VAL | 284 | 26.493 | 42.963 | 111.466 | 1.00 25.74 | AAGL |
| ATOM | 2212 | CA | VAL | 284 | 26.383 | 42.438 | 112.824 | 1.00 25.11 | AAGL |
| ATOM | 2213 | CB | VAL | 284 | 24.972 | 42.711 | 113.414 | 1.00 24.63 | AAGL |
| ATOM | 2214 | CG1 | VAL | 284 | 24.806 | 41.992 | 114.744 | 1.00 24.88 | AAGL |
| ATOM | 2215 | CG2 | VAL | 284 | 24.779 | 44.220 | 113.606 | 1.00 27.53 | AAGL |
| ATOM | 2216 | C | VAL | 284 | 26.658 | 40.941 | 112.857 | 1.00 23.65 | AAGL |
| ATOM | 2217 | O | VAL | 284 | 27.416 | 40.456 | 113.694 | 1.00 23.12 | AAGL |
| ATOM | 2218 | N | VAL | 285 | 26.052 | 40.209 | 111.930 | 1.00 25.11 | AAGL |
| ATOM | 2219 | CA | VAL | 285 | 26.236 | 38.769 | 111.881 | 1.00 23.69 | AAGL |
| ATOM | 2220 | CB | VAL | 285 | 25.302 | 38.135 | 110.839 | 1.00 24.54 | AAGL |
| ATOM | 2221 | CG1 | VAL | 285 | 25.490 | 36.626 | 110.822 | 1.00 25.86 | AAGL |
| ATOM | 2222 | CG2 | VAL | 285 | 23.855 | 38.490 | 111.171 | 1.00 26.53 | AAGL |
| ATOM | 2223 | C | VAL | 285 | 27.679 | 38.406 | 111.559 | 1.00 26.05 | AAGL |
| ATOM | 2224 | O | VAL | 285 | 28.256 | 37.514 | 112.179 | 1.00 25.09 | AAGL |
| ATOM | 2225 | N | GLU | 286 | 28.259 | 39.101 | 110.587 | 1.00 24.87 | AAGL |
| ATOM | 2226 | CA | GLU | 286 | 29.639 | 38.847 | 110.201 | 1.00 26.91 | AAGL |
| ATOM | 2227 | CB | GLU | 286 | 30.041 | 39.737 | 109.025 | 1.00 29.06 | AAGL |
| ATOM | 2228 | CG | GLU | 286 | 31.518 | 39.586 | 108.629 | 1.00 32.60 | AAGL |
| ATOM | 2229 | CD | GLU | 286 | 31.812 | 38.250 | 107.971 | 1.00 35.44 | AAGL |
| ATOM | 2230 | OE1 | GLU | 286 | 31.578 | 38.120 | 106.751 | 1.00 36.64 | AAGL |
| ATOM | 2231 | OE2 | GLU | 286 | 32.264 | 37.322 | 108.672 | 1.00 35.13 | AAGL |
| ATOM | 2232 | C | GLU | 286 | 30.587 | 39.110 | 111.367 | 1.00 26.68 | AAGL |
| ATOM | 2233 | O | GLU | 286 | 31.528 | 38.354 | 111.590 | 1.00 27.24 | AAGL |
| ATOM | 2234 | N | ALA | 287 | 30.343 | 40.181 | 112.111 | 1.00 25.24 | AAGL |
| ATOM | 2235 | CA | ALA | 287 | 31.211 | 40.522 | 113.230 | 1.00 27.43 | AAGL |
| ATOM | 2236 | CB | ALA | 287 | 31.032 | 41.990 | 113.600 | 1.00 27.81 | AAGL |
| ATOM | 2237 | C | ALA | 287 | 31.003 | 39.650 | 114.465 | 1.00 29.71 | AAGL |
| ATOM | 2238 | O | ALA | 287 | 31.726 | 39.795 | 115.451 | 1.00 31.32 | AAGL |
| ATOM | 2239 | N | THR | 288 | 30.024 | 38.749 | 114.415 | 1.00 28.83 | AAGL |
| ATOM | 2240 | CA | THR | 288 | 29.744 | 37.871 | 115.549 | 1.00 29.55 | AAGL |
| ATOM | 2241 | CB | THR | 288 | 28.242 | 37.499 | 115.618 | 1.00 28.36 | AAGL |
| ATOM | 2242 | OG1 | THR | 288 | 27.444 | 38.680 | 115.459 | 1.00 29.45 | AAGL |
| ATOM | 2243 | CG2 | THR | 288 | 27.921 | 36.854 | 116.962 | 1.00 31.36 | AAGL |
| ATOM | 2244 | C | THR | 288 | 30.533 | 36.577 | 115.393 | 1.00 27.55 | AAGL |
| ATOM | 2245 | O | THR | 288 | 30.708 | 36.094 | 114.280 | 1.00 27.21 | AAGL |
| ATOM | 2246 | N | THR | 289 | 31.006 | 36.015 | 116.504 | 1.00 30.08 | AAGL |
| ATOM | 2247 | CA | THR | 289 | 31.757 | 34.770 | 116.437 | 1.00 31.68 | AAGL |
| ATOM | 2248 | CB | THR | 289 | 32.352 | 34.384 | 117.806 | 1.00 34.06 | AAGL |
| ATOM | 2249 | OG1 | THR | 289 | 33.186 | 35.449 | 118.291 | 1.00 35.86 | AAGL |
| ATOM | 2250 | CG2 | THR | 289 | 33.186 | 33.128 | 117.673 | 1.00 34.89 | AAGL |
| ATOM | 2251 | C | THR | 289 | 30.817 | 33.659 | 115.964 | 1.00 33.04 | AAGL |
| ATOM | 2252 | O | THR | 289 | 29.842 | 33.332 | 116.632 | 1.00 34.14 | AAGL |
| ATOM | 2253 | N | ASP | 290 | 31.120 | 33.085 | 114.807 | 1.00 33.28 | AAGL |
| ATOM | 2254 | CA | ASP | 290 | 30.298 | 32.030 | 114.211 | 1.00 32.82 | AAGL |
| ATOM | 2255 | CB | ASP | 290 | 30.183 | 30.812 | 115.137 | 1.00 33.97 | AAGL |
| ATOM | 2256 | CG | ASP | 290 | 31.397 | 29.900 | 115.054 | 1.00 38.26 | AAGL |
| ATOM | 2257 | OD1 | ASP | 290 | 32.093 | 29.921 | 114.006 | 1.00 38.79 | AAGL |
| ATOM | 2258 | OD2 | ASP | 290 | 31.651 | 29.152 | 116.024 | 1.00 38.34 | AAGL |
| ATOM | 2259 | C | ASP | 290 | 28.903 | 32.495 | 113.793 | 1.00 30.86 | AAGL |
| ATOM | 2260 | O | ASP | 290 | 27.909 | 31.781 | 113.979 | 1.00 31.04 | AAGL |
| ATOM | 2261 | N | GLY | 291 | 28.841 | 33.705 | 113.246 | 1.00 30.92 | AAGL |
| ATOM | 2262 | CA | GLY | 291 | 27.590 | 34.240 | 112.740 | 1.00 28.36 | AAGL |
| ATOM | 2263 | C | GLY | 291 | 27.579 | 33.689 | 111.331 | 1.00 28.69 | AAGL |
| ATOM | 2264 | O | GLY | 291 | 28.358 | 34.133 | 110.487 | 1.00 29.95 | AAGL |
| ATOM | 2265 | N | LEU | 292 | 26.702 | 32.726 | 111.065 | 1.00 25.52 | AAGL |
| ATOM | 2266 | CA | LEU | 292 | 26.662 | 32.072 | 109.767 | 1.00 25.89 | AAGL |

Fig. 3 cont.

```
ATOM   2267  CB   LEU   292      26.184  30.632 109.940  1.00 25.46      AAGL
ATOM   2268  CG   LEU   292      27.072  29.798 110.858  1.00 26.52      AAGL
ATOM   2269  CD1  LEU   292      26.632  28.354 110.807  1.00 26.92      AAGL
ATOM   2270  CD2  LEU   292      28.526  29.929 110.418  1.00 27.08      AAGL
ATOM   2271  C    LEU   292      25.908  32.700 108.613  1.00 25.35      AAGL
ATOM   2272  O    LEU   292      26.298  32.528 107.459  1.00 25.52      AAGL
ATOM   2273  N    GLY   293      24.824  33.413 108.887  1.00 25.75      AAGL
ATOM   2274  CA   GLY   293      24.118  33.990 107.769  1.00 22.89      AAGL
ATOM   2275  C    GLY   293      22.785  34.642 108.043  1.00 23.42      AAGL
ATOM   2276  O    GLY   293      22.366  34.828 109.187  1.00 21.61      AAGL
ATOM   2277  N    VAL   294      22.123  34.984 106.950  1.00 21.14      AAGL
ATOM   2278  CA   VAL   294      20.841  35.647 107.003  1.00 22.60      AAGL
ATOM   2279  CB   VAL   294      21.013  37.164 106.775  1.00 24.33      AAGL
ATOM   2280  CG1  VAL   294      19.657  37.818 106.538  1.00 25.68      AAGL
ATOM   2281  CG2  VAL   294      21.719  37.789 107.969  1.00 23.35      AAGL
ATOM   2282  C    VAL   294      19.926  35.094 105.932  1.00 23.50      AAGL
ATOM   2283  O    VAL   294      20.351  34.867 104.799  1.00 22.80      AAGL
ATOM   2284  N    TYR   295      18.668  34.871 106.293  1.00 21.62      AAGL
ATOM   2285  CA   TYR   295      17.684  34.387 105.338  1.00 20.32      AAGL
ATOM   2286  CB   TYR   295      17.105  33.035 105.761  1.00 20.96      AAGL
ATOM   2287  CG   TYR   295      18.040  31.862 105.606  1.00 21.66      AAGL
ATOM   2288  CD1  TYR   295      19.124  31.692 106.461  1.00 20.77      AAGL
ATOM   2289  CE1  TYR   295      19.974  30.584 106.337  1.00 22.52      AAGL
ATOM   2290  CD2  TYR   295      17.820  30.904 104.617  1.00 21.20      AAGL
ATOM   2291  CE2  TYR   295      18.658  29.798 104.481  1.00 22.01      AAGL
ATOM   2292  CZ   TYR   295      19.732  29.640 105.341  1.00 22.76      AAGL
ATOM   2293  OH   TYR   295      20.564  28.543 105.211  1.00 23.00      AAGL
ATOM   2294  C    TYR   295      16.554  35.399 105.295  1.00 21.79      AAGL
ATOM   2295  O    TYR   295      15.933  35.672 106.325  1.00 20.79      AAGL
ATOM   2296  N    TYR   296      16.296  35.966 104.118  1.00 20.08      AAGL
ATOM   2297  CA   TYR   296      15.212  36.927 103.975  1.00 19.64      AAGL
ATOM   2298  CB   TYR   296      15.328  37.704 102.666  1.00 20.69      AAGL
ATOM   2299  CG   TYR   296      14.503  38.972 102.656  1.00 19.70      AAGL
ATOM   2300  CD1  TYR   296      15.005  40.152 103.194  1.00 21.48      AAGL
ATOM   2301  CE1  TYR   296      14.236  41.310 103.232  1.00 21.48      AAGL
ATOM   2302  CD2  TYR   296      13.203  38.980 102.147  1.00 19.37      AAGL
ATOM   2303  CE2  TYR   296      12.423  40.138 102.182  1.00 21.23      AAGL
ATOM   2304  CZ   TYR   296      12.948  41.295 102.729  1.00 20.28      AAGL
ATOM   2305  OH   TYR   296      12.177  42.427 102.797  1.00 19.16      AAGL
ATOM   2306  C    TYR   296      13.947  36.090 103.939  1.00 20.23      AAGL
ATOM   2307  O    TYR   296      13.945  35.010 103.359  1.00 22.11      AAGL
ATOM   2308  N    TRP   297      12.868  36.578 104.538  1.00 17.43      AAGL
ATOM   2309  CA   TRP   297      11.641  35.795 104.553  1.00 17.69      AAGL
ATOM   2310  CB   TRP   297      10.942  35.894 105.920  1.00 19.08      AAGL
ATOM   2311  CG   TRP   297       9.854  34.864 106.075  1.00 19.30      AAGL
ATOM   2312  CD2  TRP   297       8.440  35.098 106.104  1.00 19.62      AAGL
ATOM   2313  CE2  TRP   297       7.808  33.837 106.201  1.00 20.98      AAGL
ATOM   2314  CE3  TRP   297       7.644  36.250 106.057  1.00 21.65      AAGL
ATOM   2315  CD1  TRP   297      10.018  33.511 106.155  1.00 21.34      AAGL
ATOM   2316  NE1  TRP   297       8.793  32.885 106.231  1.00 21.42      AAGL
ATOM   2317  CZ2  TRP   297       6.418  33.696 106.251  1.00 19.44      AAGL
ATOM   2318  CZ3  TRP   297       6.257  36.109 106.106  1.00 24.11      AAGL
ATOM   2319  CH2  TRP   297       5.661  34.836 106.201  1.00 22.67      AAGL
ATOM   2320  C    TRP   297      10.647  36.175 103.464  1.00 18.74      AAGL
ATOM   2321  O    TRP   297      10.158  37.305 103.428  1.00 17.76      AAGL
ATOM   2322  N    GLU   298      10.357  35.214 102.584  1.00 18.51      AAGL
ATOM   2323  CA   GLU   298       9.391  35.390 101.505  1.00 18.03      AAGL
ATOM   2324  CB   GLU   298       7.976  35.340 102.084  1.00 19.76      AAGL
ATOM   2325  CG   GLU   298       7.562  33.964 102.582  1.00 19.56      AAGL
ATOM   2326  CD   GLU   298       7.283  32.996 101.447  1.00 20.53      AAGL
ATOM   2327  OE1  GLU   298       7.320  33.422 100.274  1.00 21.41      AAGL
ATOM   2328  OE2  GLU   298       7.016  31.811 101.733  1.00 22.59      AAGL
ATOM   2329  C    GLU   298       9.553  36.664 100.668  1.00 20.54      AAGL
ATOM   2330  O    GLU   298       8.636  37.482 100.569  1.00 21.31      AAGL
ATOM   2331  N    PRO   299      10.715  36.832 100.025  1.00 21.16      AAGL
ATOM   2332  CD   PRO   299      11.893  35.949 100.046  1.00 20.70      AAGL
ATOM   2333  CA   PRO   299      10.964  38.022  99.203  1.00 21.46      AAGL
```

Fig. 3 cont.

```
ATOM   2334  CB  PRO 299      12.455  37.913  98.897  1.00 22.49           AAGL
ATOM   2335  CG  PRO 299      12.658  36.429  98.826  1.00 23.37           AAGL
ATOM   2336  C   PRO 299      10.133  38.131  97.924  1.00 21.34           AAGL
ATOM   2337  O   PRO 299      10.051  39.203  97.329  1.00 25.08           AAGL
ATOM   2338  N   ALA 300       9.515  37.031  97.507  1.00 21.73           AAGL
ATOM   2339  CA  ALA 300       8.751  37.021  96.264  1.00 23.94           AAGL
ATOM   2340  CB  ALA 300       9.418  36.071  95.272  1.00 23.80           AAGL
ATOM   2341  C   ALA 300       7.280  36.663  96.386  1.00 23.97           AAGL
ATOM   2342  O   ALA 300       6.663  36.277  95.394  1.00 24.57           AAGL
ATOM   2343  N   TRP 301       6.707  36.802  97.579  1.00 25.04           AAGL
ATOM   2344  CA  TRP 301       5.301  36.454  97.775  1.00 24.04           AAGL
ATOM   2345  CB  TRP 301       5.007  36.244  99.266  1.00 25.15           AAGL
ATOM   2346  CG  TRP 301       3.744  35.459  99.531  1.00 23.59           AAGL
ATOM   2347  CD2 TRP 301       3.394  34.781 100.744  1.00 23.73           AAGL
ATOM   2348  CE2 TRP 301       2.119  34.200 100.548  1.00 23.63           AAGL
ATOM   2349  CE3 TRP 301       4.033  34.607 101.980  1.00 24.03           AAGL
ATOM   2350  CD1 TRP 301       2.697  35.267  98.673  1.00 23.60           AAGL
ATOM   2351  NE1 TRP 301       1.717  34.513  99.278  1.00 24.88           AAGL
ATOM   2352  CZ2 TRP 301       1.470  33.458 101.544  1.00 22.63           AAGL
ATOM   2353  CZ3 TRP 301       3.387  33.871 102.969  1.00 22.92           AAGL
ATOM   2354  CH2 TRP 301       2.119  33.306 102.741  1.00 21.62           AAGL
ATOM   2355  C   TRP 301       4.322  37.485  97.213  1.00 25.72           AAGL
ATOM   2356  O   TRP 301       3.682  38.220  97.968  1.00 24.12           AAGL
ATOM   2357  N   ILE 302       4.192  37.532  95.889  1.00 26.27           AAGL
ATOM   2358  CA  ILE 302       3.273  38.475  95.256  1.00 26.33           AAGL
ATOM   2359  CB  ILE 302       3.257  38.317  93.722  1.00 28.94           AAGL
ATOM   2360  CG2 ILE 302       2.804  39.615  93.081  1.00 30.12           AAGL
ATOM   2361  CG1 ILE 302       4.653  37.963  93.215  1.00 32.05           AAGL
ATOM   2362  CD1 ILE 302       5.671  39.038  93.462  1.00 33.22           AAGL
ATOM   2363  C   ILE 302       1.872  38.180  95.770  1.00 24.91           AAGL
ATOM   2364  O   ILE 302       1.467  37.017  95.840  1.00 26.39           AAGL
ATOM   2365  N   GLY 303       1.134  39.223  96.133  1.00 25.25           AAGL
ATOM   2366  CA  GLY 303      -0.210  39.018  96.646  1.00 27.25           AAGL
ATOM   2367  C   GLY 303      -0.298  39.086  98.159  1.00 26.83           AAGL
ATOM   2368  O   GLY 303      -1.394  39.110  98.728  1.00 27.53           AAGL
ATOM   2369  N   ASN 304       0.861  39.090  98.812  1.00 25.82           AAGL
ATOM   2370  CA  ASN 304       0.958  39.182 100.267  1.00 23.80           AAGL
ATOM   2371  CB  ASN 304       1.113  37.783 100.887  1.00 22.97           AAGL
ATOM   2372  CG  ASN 304       1.131  37.811 102.413  1.00 23.62           AAGL
ATOM   2373  OD1 ASN 304       0.494  38.663 103.038  1.00 25.26           AAGL
ATOM   2374  ND2 ASN 304       1.841  36.864 103.017  1.00 20.66           AAGL
ATOM   2375  C   ASN 304       2.200  40.031 100.539  1.00 22.75           AAGL
ATOM   2376  O   ASN 304       3.030  39.704 101.382  1.00 21.47           AAGL
ATOM   2377  N   ALA 305       2.306  41.139  99.812  1.00 23.77           AAGL
ATOM   2378  CA  ALA 305       3.454  42.028  99.926  1.00 23.13           AAGL
ATOM   2379  CB  ALA 305       3.281  43.211  98.980  1.00 25.11           AAGL
ATOM   2380  C   ALA 305       3.770  42.520 101.335  1.00 22.70           AAGL
ATOM   2381  O   ALA 305       4.928  42.784 101.650  1.00 23.39           AAGL
ATOM   2382  N   GLY 306       2.753  42.632 102.182  1.00 23.04           AAGL
ATOM   2383  CA  GLY 306       2.970  43.093 103.543  1.00 21.61           AAGL
ATOM   2384  C   GLY 306       3.592  42.023 104.421  1.00 20.83           AAGL
ATOM   2385  O   GLY 306       4.185  42.323 105.461  1.00 20.31           AAGL
ATOM   2386  N   LEU 307       3.445  40.771 103.997  1.00 20.88           AAGL
ATOM   2387  CA  LEU 307       3.980  39.615 104.710  1.00 19.63           AAGL
ATOM   2388  CB  LEU 307       5.511  39.575 104.599  1.00 19.26           AAGL
ATOM   2389  CG  LEU 307       6.089  39.333 103.198  1.00 17.07           AAGL
ATOM   2390  CD1 LEU 307       7.602  39.293 103.292  1.00 21.74           AAGL
ATOM   2391  CD2 LEU 307       5.568  38.012 102.625  1.00 18.50           AAGL
ATOM   2392  C   LEU 307       3.580  39.543 106.178  1.00 20.69           AAGL
ATOM   2393  O   LEU 307       4.377  39.131 107.018  1.00 20.75           AAGL
ATOM   2394  N   GLY 308       2.352  39.955 106.484  1.00 19.76           AAGL
ATOM   2395  CA  GLY 308       1.870  39.898 107.854  1.00 22.38           AAGL
ATOM   2396  C   GLY 308       2.188  41.068 108.769  1.00 23.64           AAGL
ATOM   2397  O   GLY 308       1.785  41.072 109.938  1.00 23.65           AAGL
ATOM   2398  N   SER 309       2.907  42.060 108.252  1.00 23.88           AAGL
ATOM   2399  CA  SER 309       3.275  43.227 109.045  1.00 22.50           AAGL
ATOM   2400  CB  SER 309       4.693  43.684 108.695  1.00 22.00           AAGL
```

Fig. 3 cont.

```
ATOM   2401  OG  SER  309     4.719  44.264 107.407  1.00 20.09      AAGL
ATOM   2402  C   SER  309     2.312  44.385 108.790  1.00 23.02      AAGL
ATOM   2403  O   SER  309     1.388  44.271 107.983  1.00 23.42      AAGL
ATOM   2404  N   SER  310     2.539  45.494 109.486  1.00 20.79      AAGL
ATOM   2405  CA  SER  310     1.707  46.684 109.316  1.00 23.22      AAGL
ATOM   2406  CB  SER  310     1.715  47.535 110.592  1.00 22.59      AAGL
ATOM   2407  OG  SER  310     3.022  48.003 110.903  1.00 24.03      AAGL
ATOM   2408  C   SER  310     2.234  47.512 108.138  1.00 23.44      AAGL
ATOM   2409  O   SER  310     1.658  48.545 107.773  1.00 23.68      AAGL
ATOM   2410  N   CYS  311     3.340  47.069 107.548  1.00 21.68      AAGL
ATOM   2411  CA  CYS  311     3.892  47.788 106.413  1.00 23.63      AAGL
ATOM   2412  C   CYS  311     3.210  47.381 105.123  1.00 24.17      AAGL
ATOM   2413  O   CYS  311     2.591  46.321 105.044  1.00 26.98      AAGL
ATOM   2414  CB  CYS  311     5.387  47.545 106.289  1.00 25.30      AAGL
ATOM   2415  SG  CYS  311     6.407  48.425 107.501  1.00 27.01      AAGL
ATOM   2416  N   ALA  312     3.343  48.219 104.104  1.00 23.57      AAGL
ATOM   2417  CA  ALA  312     2.707  47.954 102.821  1.00 25.20      AAGL
ATOM   2418  CB  ALA  312     2.516  49.266 102.053  1.00 25.76      AAGL
ATOM   2419  C   ALA  312     3.400  46.950 101.919  1.00 25.50      AAGL
ATOM   2420  O   ALA  312     2.741  46.128 101.288  1.00 24.61      AAGL
ATOM   2421  N   ASP  313     4.726  47.003 101.858  1.00 25.50      AAGL
ATOM   2422  CA  ASP  313     5.444  46.122 100.949  1.00 25.55      AAGL
ATOM   2423  CB  ASP  313     5.560  46.827  99.596  1.00 28.83      AAGL
ATOM   2424  CG  ASP  313     5.870  45.886  98.471  1.00 31.63      AAGL
ATOM   2425  OD1 ASP  313     6.652  44.940  98.680  1.00 29.42      AAGL
ATOM   2426  OD2 ASP  313     5.337  46.107  97.358  1.00 37.09      AAGL
ATOM   2427  C   ASP  313     6.836  45.752 101.440  1.00 25.26      AAGL
ATOM   2428  O   ASP  313     7.698  46.620 101.575  1.00 25.34      AAGL
ATOM   2429  N   ASN  314     7.049  44.460 101.685  1.00 22.30      AAGL
ATOM   2430  CA  ASN  314     8.335  43.956 102.157  1.00 21.78      AAGL
ATOM   2431  CB  ASN  314     8.156  43.167 103.458  1.00 23.69      AAGL
ATOM   2432  CG  ASN  314     7.832  44.056 104.640  1.00 25.29      AAGL
ATOM   2433  OD1 ASN  314     8.520  45.039 104.883  1.00 28.43      AAGL
ATOM   2434  ND2 ASN  314     6.787  43.716 105.382  1.00 24.92      AAGL
ATOM   2435  C   ASN  314     8.999  43.053 101.127  1.00 22.83      AAGL
ATOM   2436  O   ASN  314    10.043  42.469 101.393  1.00 21.72      AAGL
ATOM   2437  N   LEU  315     8.388  42.942  99.955  1.00 22.78      AAGL
ATOM   2438  CA  LEU  315     8.919  42.086  98.907  1.00 22.99      AAGL
ATOM   2439  CB  LEU  315     7.879  41.913  97.796  1.00 22.49      AAGL
ATOM   2440  CG  LEU  315     6.491  41.421  98.219  1.00 22.62      AAGL
ATOM   2441  CD1 LEU  315     5.599  41.214  96.991  1.00 25.48      AAGL
ATOM   2442  CD2 LEU  315     6.638  40.117  98.978  1.00 23.90      AAGL
ATOM   2443  C   LEU  315    10.219  42.604  98.310  1.00 24.65      AAGL
ATOM   2444  O   LEU  315    10.608  43.756  98.523  1.00 24.23      AAGL
ATOM   2445  N   MET  316    10.898  41.728  97.576  1.00 25.62      AAGL
ATOM   2446  CA  MET  316    12.135  42.088  96.901  1.00 28.28      AAGL
ATOM   2447  CB  MET  316    13.280  41.159  97.321  1.00 26.81      AAGL
ATOM   2448  CG  MET  316    13.718  41.299  98.777  1.00 27.89      AAGL
ATOM   2449  SD  MET  316    15.182  40.302  99.187  1.00 29.46      AAGL
ATOM   2450  CE  MET  316    16.470  41.485  98.890  1.00 29.41      AAGL
ATOM   2451  C   MET  316    11.889  41.977  95.393  1.00 29.33      AAGL
ATOM   2452  O   MET  316    12.824  41.939  94.599  1.00 29.21      AAGL
ATOM   2453  N   VAL  317    10.616  41.910  95.015  1.00 30.78      AAGL
ATOM   2454  CA  VAL  317    10.217  41.820  93.614  1.00 32.20      AAGL
ATOM   2455  CB  VAL  317     9.681  40.416  93.263  1.00 31.88      AAGL
ATOM   2456  CG1 VAL  317    10.763  39.374  93.477  1.00 33.90      AAGL
ATOM   2457  CG2 VAL  317     8.479  40.100  94.128  1.00 36.43      AAGL
ATOM   2458  C   VAL  317     9.113  42.836  93.346  1.00 33.46      AAGL
ATOM   2459  O   VAL  317     8.342  43.169  94.246  1.00 30.98      AAGL
ATOM   2460  N   ASP  318     9.041  43.333  92.113  1.00 33.99      AAGL
ATOM   2461  CA  ASP  318     8.015  44.309  91.760  1.00 38.16      AAGL
ATOM   2462  CB  ASP  318     8.405  45.073  90.493  1.00 39.54      AAGL
ATOM   2463  CG  ASP  318     7.502  46.252  90.240  1.00 38.96      AAGL
ATOM   2464  OD1 ASP  318     6.267  46.066  90.216  1.00 40.93      AAGL
ATOM   2465  OD2 ASP  318     8.022  47.370  90.058  1.00 42.03      AAGL
ATOM   2466  C   ASP  318     6.671  43.621  91.547  1.00 41.03      AAGL
ATOM   2467  O   ASP  318     6.512  42.800  90.642  1.00 41.02      AAGL
```

Fig. 3 cont.

```
ATOM   2468  N    TYR   319       5.695   43.985   92.373  1.00 43.91      AAGL
ATOM   2469  CA   TYR   319       4.370   43.388   92.312  1.00 46.99      AAGL
ATOM   2470  CB   TYR   319       3.555   43.811   93.548  1.00 48.59      AAGL
ATOM   2471  CG   TYR   319       3.003   45.224   93.516  1.00 48.66      AAGL
ATOM   2472  CD1  TYR   319       1.702   45.475   93.080  1.00 49.01      AAGL
ATOM   2473  CE1  TYR   319       1.180   46.778   93.066  1.00 49.49      AAGL
ATOM   2474  CD2  TYR   319       3.772   46.305   93.937  1.00 49.12      AAGL
ATOM   2475  CE2  TYR   319       3.264   47.610   93.929  1.00 49.13      AAGL
ATOM   2476  CZ   TYR   319       1.967   47.836   93.493  1.00 49.15      AAGL
ATOM   2477  OH   TYR   319       1.457   49.115   93.495  1.00 48.83      AAGL
ATOM   2478  C    TYR   319       3.602   43.705   91.034  1.00 49.01      AAGL
ATOM   2479  O    TYR   319       2.479   43.221   90.840  1.00 51.46      AAGL
ATOM   2480  N    THR   320       4.178   44.522   90.158  1.00 48.98      AAGL
ATOM   2481  CA   THR   320       3.491   44.827   88.909  1.00 48.98      AAGL
ATOM   2482  CB   THR   320       3.383   46.349   88.642  1.00 48.87      AAGL
ATOM   2483  OG1  THR   320       4.681   46.899   88.371  1.00 48.24      AAGL
ATOM   2484  CG2  THR   320       2.770   47.054   89.829  1.00 48.99      AAGL
ATOM   2485  C    THR   320       4.206   44.184   87.730  1.00 49.75      AAGL
ATOM   2486  O    THR   320       3.572   43.536   86.896  1.00 50.61      AAGL
ATOM   2487  N    THR   321       5.524   44.349   87.671  1.00 49.77      AAGL
ATOM   2488  CA   THR   321       6.316   43.798   86.575  1.00 50.22      AAGL
ATOM   2489  CB   THR   321       7.561   44.673   86.297  1.00 50.80      AAGL
ATOM   2490  OG1  THR   321       8.505   44.522   87.368  1.00 51.66      AAGL
ATOM   2491  CG2  THR   321       7.168   46.144   86.193  1.00 51.57      AAGL
ATOM   2492  C    THR   321       6.805   42.371   86.807  1.00 50.00      AAGL
ATOM   2493  O    THR   321       7.360   41.743   85.905  1.00 50.77      AAGL
ATOM   2494  N    ASP   322       6.617   41.859   88.016  1.00 49.25      AAGL
ATOM   2495  CA   ASP   322       7.082   40.515   88.345  1.00 47.20      AAGL
ATOM   2496  CB   ASP   322       6.534   39.471   87.354  1.00 50.64      AAGL
ATOM   2497  CG   ASP   322       5.010   39.462   87.262  1.00 52.01      AAGL
ATOM   2498  OD1  ASP   322       4.313   39.445   88.309  1.00 52.82      AAGL
ATOM   2499  OD2  ASP   322       4.502   39.442   86.113  1.00 55.12      AAGL
ATOM   2500  C    ASP   322       8.616   40.486   88.288  1.00 44.47      AAGL
ATOM   2501  O    ASP   322       9.231   39.416   88.385  1.00 44.83      AAGL
ATOM   2502  N    GLU   323       9.236   41.652   88.124  1.00 41.39      AAGL
ATOM   2503  CA   GLU   323      10.696   41.745   88.049  1.00 39.30      AAGL
ATOM   2504  CB   GLU   323      11.093   42.894   87.127  1.00 41.31      AAGL
ATOM   2505  CG   GLU   323      12.586   43.108   86.977  1.00 44.75      AAGL
ATOM   2506  CD   GLU   323      12.911   44.040   85.812  1.00 47.16      AAGL
ATOM   2507  OE1  GLU   323      14.099   44.371   85.612  1.00 47.71      AAGL
ATOM   2508  OE2  GLU   323      11.971   44.438   85.091  1.00 47.99      AAGL
ATOM   2509  C    GLU   323      11.346   41.939   89.420  1.00 36.82      AAGL
ATOM   2510  O    GLU   323      10.898   42.761   90.220  1.00 35.46      AAGL
ATOM   2511  N    VAL   324      12.410   41.182   89.675  1.00 35.31      AAGL
ATOM   2512  CA   VAL   324      13.120   41.257   90.948  1.00 32.93      AAGL
ATOM   2513  CB   VAL   324      14.154   40.103   91.099  1.00 33.31      AAGL
ATOM   2514  CG1  VAL   324      13.487   38.770   90.827  1.00 32.75      AAGL
ATOM   2515  CG2  VAL   324      15.341   40.316   90.153  1.00 32.38      AAGL
ATOM   2516  C    VAL   324      13.864   42.573   91.090  1.00 33.56      AAGL
ATOM   2517  O    VAL   324      14.329   43.153   90.093  1.00 33.29      AAGL
ATOM   2518  N    TYR   325      13.974   43.045   92.328  1.00 30.85      AAGL
ATOM   2519  CA   TYR   325      14.683   44.282   92.608  1.00 31.59      AAGL
ATOM   2520  CB   TYR   325      14.228   44.910   93.929  1.00 30.31      AAGL
ATOM   2521  CG   TYR   325      12.794   45.387   93.972  1.00 31.58      AAGL
ATOM   2522  CD1  TYR   325      12.225   46.079   92.901  1.00 31.55      AAGL
ATOM   2523  CE1  TYR   325      10.908   46.548   92.970  1.00 33.68      AAGL
ATOM   2524  CD2  TYR   325      12.015   45.177   95.112  1.00 30.63      AAGL
ATOM   2525  CE2  TYR   325      10.714   45.639   95.192  1.00 30.81      AAGL
ATOM   2526  CZ   TYR   325      10.164   46.323   94.127  1.00 33.10      AAGL
ATOM   2527  OH   TYR   325       8.878   46.780   94.231  1.00 32.89      AAGL
ATOM   2528  C    TYR   325      16.169   44.003   92.714  1.00 31.02      AAGL
ATOM   2529  O    TYR   325      16.602   42.859   92.908  1.00 28.70      AAGL
ATOM   2530  N    GLU   326      16.946   45.070   92.599  1.00 31.64      AAGL
ATOM   2531  CA   GLU   326      18.398   45.010   92.684  1.00 31.11      AAGL
ATOM   2532  CB   GLU   326      18.949   46.406   92.388  1.00 34.73      AAGL
ATOM   2533  CG   GLU   326      20.432   46.588   92.571  1.00 39.05      AAGL
ATOM   2534  CD   GLU   326      20.851   47.994   92.209  1.00 41.46      AAGL
```

Fig. 3 cont.

```
ATOM   2535  OE1 GLU  326      20.682  48.359  91.021  1.00 42.66           AAGL
ATOM   2536  OE2 GLU  326      21.334  48.731  93.106  1.00 40.82           AAGL
ATOM   2537  C   GLU  326      18.848  44.538  94.065  1.00 29.10           AAGL
ATOM   2538  O   GLU  326      19.996  44.136  94.253  1.00 27.19           AAGL
ATOM   2539  N   SER  327      17.939  44.581  95.035  1.00 27.41           AAGL
ATOM   2540  CA  SER  327      18.265  44.147  96.387  1.00 25.31           AAGL
ATOM   2541  CB  SER  327      17.127  44.519  97.347  1.00 23.59           AAGL
ATOM   2542  OG  SER  327      15.870  44.218  96.776  1.00 25.25           AAGL
ATOM   2543  C   SER  327      18.574  42.650  96.458  1.00 24.17           AAGL
ATOM   2544  O   SER  327      19.243  42.195  97.383  1.00 25.88           AAGL
ATOM   2545  N   ILE  328      18.107  41.880  95.479  1.00 27.45           AAGL
ATOM   2546  CA  ILE  328      18.395  40.446  95.466  1.00 28.86           AAGL
ATOM   2547  CB  ILE  328      17.692  39.728  94.295  1.00 31.12           AAGL
ATOM   2548  CG2 ILE  328      18.120  38.277  94.250  1.00 35.58           AAGL
ATOM   2549  CG1 ILE  328      16.175  39.823  94.448  1.00 33.48           AAGL
ATOM   2550  CD1 ILE  328      15.647  39.194  95.727  1.00 36.80           AAGL
ATOM   2551  C   ILE  328      19.904  40.248  95.317  1.00 29.16           AAGL
ATOM   2552  O   ILE  328      20.486  39.324  95.897  1.00 27.50           AAGL
ATOM   2553  N   GLU  329      20.536  41.124  94.538  1.00 30.01           AAGL
ATOM   2554  CA  GLU  329      21.978  41.045  94.328  1.00 30.96           AAGL
ATOM   2555  CB  GLU  329      22.435  42.017  93.229  1.00 33.99           AAGL
ATOM   2556  CG  GLU  329      21.773  41.813  91.866  1.00 37.96           AAGL
ATOM   2557  CD  GLU  329      22.520  42.542  90.746  1.00 42.17           AAGL
ATOM   2558  OE1 GLU  329      22.731  43.773  90.863  1.00 42.73           AAGL
ATOM   2559  OE2 GLU  329      22.898  41.883  89.746  1.00 42.99           AAGL
ATOM   2560  C   GLU  329      22.682  41.386  95.627  1.00 29.64           AAGL
ATOM   2561  O   GLU  329      23.693  40.771  95.988  1.00 29.09           AAGL
ATOM   2562  N   THR  330      22.142  42.368  96.340  1.00 28.03           AAGL
ATOM   2563  CA  THR  330      22.720  42.776  97.611  1.00 26.58           AAGL
ATOM   2564  CB  THR  330      21.958  43.986  98.200  1.00 27.90           AAGL
ATOM   2565  OG1 THR  330      22.099  45.110  97.323  1.00 26.78           AAGL
ATOM   2566  CG2 THR  330      22.495  44.345  99.574  1.00 27.91           AAGL
ATOM   2567  C   THR  330      22.671  41.608  98.606  1.00 26.92           AAGL
ATOM   2568  O   THR  330      23.654  41.325  99.301  1.00 25.31           AAGL
ATOM   2569  N   LEU  331      21.529  40.930  98.667  1.00 25.72           AAGL
ATOM   2570  CA  LEU  331      21.368  39.791  99.571  1.00 24.97           AAGL
ATOM   2571  CB  LEU  331      19.923  39.282  99.532  1.00 24.19           AAGL
ATOM   2572  CG  LEU  331      19.567  37.968 100.247  1.00 23.31           AAGL
ATOM   2573  CD1 LEU  331      19.873  38.051 101.736  1.00 25.91           AAGL
ATOM   2574  CD2 LEU  331      18.082  37.674 100.034  1.00 23.20           AAGL
ATOM   2575  C   LEU  331      22.319  38.674  99.158  1.00 25.90           AAGL
ATOM   2576  O   LEU  331      22.971  38.054 100.001  1.00 25.54           AAGL
ATOM   2577  N   GLY  332      22.390  38.427  97.853  1.00 26.10           AAGL
ATOM   2578  CA  GLY  332      23.262  37.386  97.337  1.00 28.89           AAGL
ATOM   2579  C   GLY  332      24.738  37.631  97.594  1.00 31.12           AAGL
ATOM   2580  O   GLY  332      25.526  36.682  97.614  1.00 30.65           AAGL
ATOM   2581  N   GLU  333      25.120  38.890  97.805  1.00 31.60           AAGL
ATOM   2582  CA  GLU  333      26.524  39.229  98.044  1.00 33.74           AAGL
ATOM   2583  CB  GLU  333      26.949  40.400  97.148  1.00 34.97           AAGL
ATOM   2584  CG  GLU  333      26.639  40.205  95.673  1.00 37.79           AAGL
ATOM   2585  CD  GLU  333      26.846  41.471  94.846  1.00 41.19           AAGL
ATOM   2586  OE1 GLU  333      26.164  41.621  93.807  1.00 40.67           AAGL
ATOM   2587  OE2 GLU  333      27.694  42.309  95.225  1.00 44.05           AAGL
ATOM   2588  C   GLU  333      26.844  39.586  99.490  1.00 35.01           AAGL
ATOM   2589  O   GLU  333      27.924  40.109  99.776  1.00 33.69           AAGL
ATOM   2590  N   LEU  334      25.925  39.319 100.410  1.00 34.35           AAGL
ATOM   2591  CA  LEU  334      26.193  39.655 101.805  1.00 33.87           AAGL
ATOM   2592  CB  LEU  334      24.963  39.371 102.672  1.00 33.01           AAGL
ATOM   2593  CG  LEU  334      23.721  40.228 102.407  1.00 32.82           AAGL
ATOM   2594  CD1 LEU  334      22.611  39.797 103.347  1.00 28.38           AAGL
ATOM   2595  CD2 LEU  334      24.044  41.711 102.607  1.00 30.26           AAGL
ATOM   2596  C   LEU  334      27.396  38.881 102.344  1.00 35.69           AAGL
ATOM   2597  O   LEU  334      27.475  37.650 102.129  1.00 36.26           AAGL
ATOM   2598  OXT LEU  334      28.249  39.520 102.989  1.00 35.77           AAGL
END
```

Fig. 3 cont.

```
HEADER                                                                     BLGL
ATOM      1   C    GLY    11      35.975  14.251  23.684  1.00 48.49       BLGL
ATOM      2   O    GLY    11      36.590  13.193  23.517  1.00 48.50       BLGL
ATOM      3   N    GLY    11      36.372  16.222  25.216  1.00 48.08       BLGL
ATOM      4   CA   GLY    11      36.733  15.548  23.933  1.00 47.57       BLGL
ATOM      5   N    LEU    12      34.642  14.326  23.653  1.00 48.44       BLGL
ATOM      6   CA   LEU    12      33.796  13.147  23.416  1.00 45.49       BLGL
ATOM      7   CB   LEU    12      32.592  13.139  24.371  1.00 43.64       BLGL
ATOM      8   CG   LEU    12      31.626  11.961  24.199  1.00 41.45       BLGL
ATOM      9   CD1  LEU    12      32.074  10.803  25.085  1.00 36.51       BLGL
ATOM     10   CD2  LEU    12      30.203  12.400  24.550  1.00 41.11       BLGL
ATOM     11   C    LEU    12      33.272  13.109  21.979  1.00 44.11       BLGL
ATOM     12   O    LEU    12      32.688  14.086  21.502  1.00 45.18       BLGL
ATOM     13   N    TYR    13      33.487  11.986  21.295  1.00 42.63       BLGL
ATOM     14   CA   TYR    13      33.004  11.817  19.928  1.00 41.19       BLGL
ATOM     15   CB   TYR    13      34.083  11.206  19.042  1.00 45.36       BLGL
ATOM     16   CG   TYR    13      33.594  10.996  17.624  1.00 52.03       BLGL
ATOM     17   CD1  TYR    13      33.232   9.727  17.167  1.00 53.91       BLGL
ATOM     18   CE1  TYR    13      32.703   9.545  15.872  1.00 55.69       BLGL
ATOM     19   CD2  TYR    13      33.420  12.083  16.756  1.00 53.77       BLGL
ATOM     20   CE2  TYR    13      32.890  11.914  15.466  1.00 54.66       BLGL
ATOM     21   CZ   TYR    13      32.534  10.644  15.031  1.00 56.09       BLGL
ATOM     22   OH   TYR    13      32.009  10.473  13.764  1.00 56.62       BLGL
ATOM     23   C    TYR    13      31.755  10.932  19.837  1.00 38.22       BLGL
ATOM     24   O    TYR    13      31.686   9.887  20.471  1.00 38.74       BLGL
ATOM     25   N    VAL    14      30.776  11.355  19.039  1.00 34.88       BLGL
ATOM     26   CA   VAL    14      29.537  10.604  18.845  1.00 31.50       BLGL
ATOM     27   CB   VAL    14      28.418  11.094  19.777  1.00 30.78       BLGL
ATOM     28   CG1  VAL    14      27.102  10.405  19.427  1.00 30.71       BLGL
ATOM     29   CG2  VAL    14      28.790  10.812  21.203  1.00 30.70       BLGL
ATOM     30   C    VAL    14      29.069  10.798  17.420  1.00 30.74       BLGL
ATOM     31   O    VAL    14      28.776  11.917  17.007  1.00 31.52       BLGL
ATOM     32   N    GLU    15      28.994   9.710  16.669  1.00 30.21       BLGL
ATOM     33   CA   GLU    15      28.555   9.788  15.288  1.00 30.31       BLGL
ATOM     34   CB   GLU    15      29.002   8.546  14.534  1.00 33.96       BLGL
ATOM     35   CG   GLU    15      28.509   8.486  13.113  1.00 43.05       BLGL
ATOM     36   CD   GLU    15      28.927   7.202  12.424  1.00 49.32       BLGL
ATOM     37   OE1  GLU    15      28.886   6.140  13.087  1.00 51.29       BLGL
ATOM     38   OE2  GLU    15      29.285   7.251  11.223  1.00 54.28       BLGL
ATOM     39   C    GLU    15      27.045   9.931  15.206  1.00 28.83       BLGL
ATOM     40   O    GLU    15      26.303   9.161  15.816  1.00 26.88       BLGL
ATOM     41   N    LYS    16      26.596  10.923  14.445  1.00 29.24       BLGL
ATOM     42   CA   LYS    16      25.173  11.173  14.280  1.00 30.57       BLGL
ATOM     43   CB   LYS    16      24.933  12.207  13.174  1.00 32.52       BLGL
ATOM     44   CG   LYS    16      23.454  12.496  12.948  1.00 38.94       BLGL
ATOM     45   CD   LYS    16      23.141  12.889  11.510  1.00 43.38       BLGL
ATOM     46   CE   LYS    16      23.632  14.282  11.176  1.00 46.85       BLGL
ATOM     47   NZ   LYS    16      23.276  14.648   9.776  1.00 50.40       BLGL
ATOM     48   C    LYS    16      24.399   9.902  13.938  1.00 29.87       BLGL
ATOM     49   O    LYS    16      24.836   9.090  13.121  1.00 28.75       BLGL
ATOM     50   N    VAL    17      23.249   9.733  14.575  1.00 29.36       BLGL
ATOM     51   CA   VAL    17      22.394   8.591  14.306  1.00 29.25       BLGL
ATOM     52   CB   VAL    17      21.437   8.328  15.476  1.00 28.63       BLGL
ATOM     53   CG1  VAL    17      20.469   7.201  15.127  1.00 28.74       BLGL
ATOM     54   CG2  VAL    17      22.236   7.982  16.702  1.00 30.70       BLGL
ATOM     55   C    VAL    17      21.582   8.940  13.064  1.00 30.63       BLGL
ATOM     56   O    VAL    17      20.794   9.891  13.064  1.00 30.98       BLGL
ATOM     57   N    SER    18      21.782   8.172  12.005  1.00 30.58       BLGL
ATOM     58   CA   SER    18      21.083   8.422  10.758  1.00 33.73       BLGL
ATOM     59   CB   SER    18      21.787   7.675   9.628  1.00 36.18       BLGL
ATOM     60   OG   SER    18      21.984   6.324   9.990  1.00 38.96       BLGL
ATOM     61   C    SER    18      19.611   8.032  10.800  1.00 32.04       BLGL
ATOM     62   O    SER    18      19.264   6.933  11.231  1.00 31.91       BLGL
ATOM     63   N    GLY    19      18.755   8.950  10.359  1.00 31.92       BLGL
ATOM     64   CA   GLY    19      17.328   8.697  10.327  1.00 30.75       BLGL
ATOM     65   C    GLY    19      16.601   8.894  11.638  1.00 30.09       BLGL
```

Fig. 4

```
ATOM     66  O   GLY    19      15.395   8.684  11.705  1.00 32.49      BLGL
ATOM     67  N   LEU    20      17.314   9.295  12.681  1.00 28.46      BLGL
ATOM     68  CA  LEU    20      16.672   9.498  13.967  1.00 28.28      BLGL
ATOM     69  CB  LEU    20      17.706   9.910  15.013  1.00 29.28      BLGL
ATOM     70  CG  LEU    20      17.141   9.983  16.436  1.00 29.10      BLGL
ATOM     71  CD1 LEU    20      16.756   8.586  16.904  1.00 27.36      BLGL
ATOM     72  CD2 LEU    20      18.165  10.598  17.359  1.00 29.58      BLGL
ATOM     73  C   LEU    20      15.565  10.548  13.890  1.00 25.87      BLGL
ATOM     74  O   LEU    20      15.821  11.686  13.535  1.00 24.28      BLGL
ATOM     75  N   ARG    21      14.342  10.147  14.226  1.00 28.07      BLGL
ATOM     76  CA  ARG    21      13.176  11.030  14.213  1.00 30.64      BLGL
ATOM     77  CB  ARG    21      11.912  10.211  14.476  1.00 31.64      BLGL
ATOM     78  CG  ARG    21      11.955   9.430  15.792  1.00 35.81      BLGL
ATOM     79  CD  ARG    21      10.892   8.339  15.840  1.00 36.79      BLGL
ATOM     80  NE  ARG    21       9.536   8.877  15.850  1.00 37.50      BLGL
ATOM     81  CZ  ARG    21       8.445   8.133  15.699  1.00 38.47      BLGL
ATOM     82  NH1 ARG    21       8.567   6.826  15.525  1.00 37.04      BLGL
ATOM     83  NH2 ARG    21       7.235   8.688  15.731  1.00 39.56      BLGL
ATOM     84  C   ARG    21      13.316  12.114  15.277  1.00 32.05      BLGL
ATOM     85  O   ARG    21      13.840  11.862  16.354  1.00 31.41      BLGL
ATOM     86  N   LYS    22      12.832  13.315  14.978  1.00 35.57      BLGL
ATOM     87  CA  LYS    22      12.927  14.428  15.916  1.00 37.84      BLGL
ATOM     88  CB  LYS    22      12.378  15.713  15.291  1.00 42.04      BLGL
ATOM     89  CG  LYS    22      13.278  16.381  14.265  1.00 47.84      BLGL
ATOM     90  CD  LYS    22      12.908  17.872  14.150  1.00 51.73      BLGL
ATOM     91  CE  LYS    22      13.460  18.518  12.882  1.00 52.80      BLGL
ATOM     92  NZ  LYS    22      12.732  18.062  11.661  1.00 52.64      BLGL
ATOM     93  C   LYS    22      12.225  14.227  17.253  1.00 36.42      BLGL
ATOM     94  O   LYS    22      12.672  14.762  18.264  1.00 37.54      BLGL
ATOM     95  N   ASP    23      11.128  13.476  17.262  1.00 34.94      BLGL
ATOM     96  CA  ASP    23      10.370  13.264  18.495  1.00 33.91      BLGL
ATOM     97  CB  ASP    23       8.869  13.257  18.181  1.00 34.54      BLGL
ATOM     98  CG  ASP    23       8.465  12.096  17.303  1.00 34.79      BLGL
ATOM     99  OD1 ASP    23       9.242  11.739  16.392  1.00 33.67      BLGL
ATOM    100  OD2 ASP    23       7.365  11.547  17.521  1.00 39.44      BLGL
ATOM    101  C   ASP    23      10.754  11.989  19.238  1.00 31.78      BLGL
ATOM    102  O   ASP    23      10.001  11.495  20.083  1.00 31.40      BLGL
ATOM    103  N   PHE    24      11.932  11.467  18.921  1.00 28.21      BLGL
ATOM    104  CA  PHE    24      12.423  10.256  19.551  1.00 25.65      BLGL
ATOM    105  CB  PHE    24      13.788   9.904  18.967  1.00 25.73      BLGL
ATOM    106  CG  PHE    24      14.281   8.538  19.337  1.00 25.81      BLGL
ATOM    107  CD1 PHE    24      15.134   8.359  20.422  1.00 25.77      BLGL
ATOM    108  CD2 PHE    24      13.930   7.431  18.573  1.00 25.98      BLGL
ATOM    109  CE1 PHE    24      15.642   7.093  20.739  1.00 25.74      BLGL
ATOM    110  CE2 PHE    24      14.431   6.161  18.881  1.00 27.08      BLGL
ATOM    111  CZ  PHE    24      15.292   5.992  19.967  1.00 24.69      BLGL
ATOM    112  C   PHE    24      12.517  10.473  21.055  1.00 22.99      BLGL
ATOM    113  O   PHE    24      12.961  11.520  21.519  1.00 23.30      BLGL
ATOM    114  N   ILE    25      12.077   9.474  21.804  1.00 19.49      BLGL
ATOM    115  CA  ILE    25      12.096   9.514  23.254  1.00 17.47      BLGL
ATOM    116  CB  ILE    25      11.137   8.465  23.820  1.00 15.37      BLGL
ATOM    117  CG2 ILE    25      11.388   8.253  25.306  1.00 13.70      BLGL
ATOM    118  CG1 ILE    25       9.706   8.883  23.524  1.00 13.77      BLGL
ATOM    119  CD1 ILE    25       8.696   7.834  23.915  1.00 18.01      BLGL
ATOM    120  C   ILE    25      13.487   9.227  23.799  1.00 17.49      BLGL
ATOM    121  O   ILE    25      14.091   8.211  23.465  1.00 16.53      BLGL
ATOM    122  N   LYS    26      13.985  10.128  24.637  1.00 16.78      BLGL
ATOM    123  CA  LYS    26      15.294   9.962  25.259  1.00 18.11      BLGL
ATOM    124  CB  LYS    26      16.213  11.096  24.825  1.00 19.07      BLGL
ATOM    125  CG  LYS    26      16.276  11.237  23.314  1.00 21.25      BLGL
ATOM    126  CD  LYS    26      16.943  12.520  22.899  1.00 23.74      BLGL
ATOM    127  CE  LYS    26      16.949  12.669  21.387  1.00 24.53      BLGL
ATOM    128  NZ  LYS    26      17.505  13.994  20.995  1.00 26.16      BLGL
ATOM    129  C   LYS    26      15.032  10.015  26.754  1.00 17.62      BLGL
ATOM    130  O   LYS    26      14.990  11.089  27.340  1.00 18.88      BLGL
ATOM    131  N   GLY    27      14.845   8.850  27.367  1.00 15.97      BLGL
```

Fig. 4 cont.

```
ATOM    132  CA   GLY    27      14.540   8.822  28.783  1.00 14.87      BLGL
ATOM    133  C    GLY    27      15.553   8.183  29.706  1.00 15.36      BLGL
ATOM    134  O    GLY    27      16.490   7.523  29.278  1.00 14.26      BLGL
ATOM    135  N    VAL    28      15.364   8.413  30.997  1.00 15.73      BLGL
ATOM    136  CA   VAL    28      16.233   7.847  32.002  1.00 15.81      BLGL
ATOM    137  CB   VAL    28      17.285   8.866  32.505  1.00 15.33      BLGL
ATOM    138  CG1  VAL    28      18.189   9.289  31.359  1.00 15.90      BLGL
ATOM    139  CG2  VAL    28      16.604  10.073  33.113  1.00 15.60      BLGL
ATOM    140  C    VAL    28      15.367   7.411  33.164  1.00 17.23      BLGL
ATOM    141  O    VAL    28      14.294   7.967  33.405  1.00 16.45      BLGL
ATOM    142  N    ASP    29      15.817   6.380  33.860  1.00 17.41      BLGL
ATOM    143  CA   ASP    29      15.098   5.902  35.023  1.00 18.06      BLGL
ATOM    144  CB   ASP    29      14.855   4.391  34.925  1.00 16.28      BLGL
ATOM    145  CG   ASP    29      14.123   3.832  36.138  1.00 18.27      BLGL
ATOM    146  OD1  ASP    29      13.426   2.801  35.978  1.00 15.84      BLGL
ATOM    147  OD2  ASP    29      14.258   4.409  37.246  1.00 14.09      BLGL
ATOM    148  C    ASP    29      16.006   6.248  36.201  1.00 17.72      BLGL
ATOM    149  O    ASP    29      17.075   5.670  36.362  1.00 18.18      BLGL
ATOM    150  N    VAL    30      15.592   7.228  36.994  1.00 17.06      BLGL
ATOM    151  CA   VAL    30      16.360   7.653  38.158  1.00 14.73      BLGL
ATOM    152  CB   VAL    30      16.740   9.151  38.051  1.00 13.70      BLGL
ATOM    153  CG1  VAL    30      17.688   9.354  36.880  1.00 12.16      BLGL
ATOM    154  CG2  VAL    30      15.485  10.017  37.872  1.00  9.08      BLGL
ATOM    155  C    VAL    30      15.551   7.422  39.426  1.00 14.73      BLGL
ATOM    156  O    VAL    30      15.491   8.275  40.302  1.00 16.61      BLGL
ATOM    157  N    SER    31      14.931   6.252  39.515  1.00 16.06      BLGL
ATOM    158  CA   SER    31      14.090   5.899  40.660  1.00 19.01      BLGL
ATOM    159  CB   SER    31      13.540   4.481  40.481  1.00 17.38      BLGL
ATOM    160  OG   SER    31      12.719   4.395  39.331  1.00 19.20      BLGL
ATOM    161  C    SER    31      14.769   6.007  42.030  1.00 19.31      BLGL
ATOM    162  O    SER    31      14.120   6.282  43.041  1.00 19.82      BLGL
ATOM    163  N    SER    32      16.075   5.797  42.059  1.00 18.54      BLGL
ATOM    164  CA   SER    32      16.826   5.845  43.301  1.00 19.36      BLGL
ATOM    165  CB   SER    32      18.121   5.055  43.133  1.00 18.42      BLGL
ATOM    166  OG   SER    32      18.909   5.611  42.088  1.00 16.54      BLGL
ATOM    167  C    SER    32      17.161   7.259  43.775  1.00 21.13      BLGL
ATOM    168  O    SER    32      17.612   7.442  44.902  1.00 20.54      BLGL
ATOM    169  N    ILE    33      16.931   8.256  42.925  1.00 21.96      BLGL
ATOM    170  CA   ILE    33      17.256   9.644  43.263  1.00 22.33      BLGL
ATOM    171  CB   ILE    33      16.752  10.622  42.161  1.00 21.13      BLGL
ATOM    172  CG2  ILE    33      15.234  10.621  42.095  1.00 19.56      BLGL
ATOM    173  CG1  ILE    33      17.283  12.027  42.439  1.00 20.03      BLGL
ATOM    174  CD1  ILE    33      18.794  12.117  42.425  1.00 17.45      BLGL
ATOM    175  C    ILE    33      16.796  10.152  44.636  1.00 23.71      BLGL
ATOM    176  O    ILE    33      17.549  10.858  45.309  1.00 25.43      BLGL
ATOM    177  N    ILE    34      15.581   9.797  45.059  1.00 24.35      BLGL
ATOM    178  CA   ILE    34      15.066  10.235  46.362  1.00 23.98      BLGL
ATOM    179  CB   ILE    34      13.539   9.951  46.486  1.00 23.20      BLGL
ATOM    180  CG2  ILE    34      13.170   9.637  47.922  1.00 24.75      BLGL
ATOM    181  CG1  ILE    34      12.735  11.183  46.063  1.00 20.84      BLGL
ATOM    182  CD1  ILE    34      13.078  11.696  44.729  1.00 21.81      BLGL
ATOM    183  C    ILE    34      15.815   9.598  47.550  1.00 24.38      BLGL
ATOM    184  O    ILE    34      16.186  10.290  48.502  1.00 25.31      BLGL
ATOM    185  N    ALA    35      16.041   8.290  47.500  1.00 22.66      BLGL
ATOM    186  CA   ALA    35      16.761   7.622  48.579  1.00 22.83      BLGL
ATOM    187  CB   ALA    35      16.803   6.117  48.344  1.00 20.64      BLGL
ATOM    188  C    ALA    35      18.178   8.165  48.681  1.00 23.42      BLGL
ATOM    189  O    ALA    35      18.687   8.377  49.776  1.00 25.98      BLGL
ATOM    190  N    LEU    36      18.813   8.382  47.536  1.00 23.28      BLGL
ATOM    191  CA   LEU    36      20.173   8.900  47.508  1.00 25.90      BLGL
ATOM    192  CB   LEU    36      20.726   8.908  46.073  1.00 26.42      BLGL
ATOM    193  CG   LEU    36      21.093   7.571  45.421  1.00 25.94      BLGL
ATOM    194  CD1  LEU    36      21.783   7.836  44.105  1.00 29.58      BLGL
ATOM    195  CD2  LEU    36      22.017   6.778  46.323  1.00 28.67      BLGL
ATOM    196  C    LEU    36      20.237  10.308  48.089  1.00 26.59      BLGL
ATOM    197  O    LEU    36      21.140  10.637  48.863  1.00 25.84      BLGL
```

Fig. 4 cont.

```
ATOM    198  N    GLU   37      19.282  11.144  47.708  1.00  26.12      BLGL
ATOM    199  CA   GLU   37      19.259  12.501  48.214  1.00  28.35      BLGL
ATOM    200  CB   GLU   37      18.092  13.264  47.594  1.00  26.08      BLGL
ATOM    201  CG   GLU   37      18.409  13.814  46.220  1.00  29.12      BLGL
ATOM    202  CD   GLU   37      17.238  14.542  45.612  1.00  30.50      BLGL
ATOM    203  OE1  GLU   37      17.422  15.243  44.593  1.00  26.60      BLGL
ATOM    204  OE2  GLU   37      16.128  14.400  46.163  1.00  35.60      BLGL
ATOM    205  C    GLU   37      19.170  12.526  49.739  1.00  28.90      BLGL
ATOM    206  O    GLU   37      19.828  13.334  50.393  1.00  30.03      BLGL
ATOM    207  N    GLU   38      18.366  11.633  50.301  1.00  29.70      BLGL
ATOM    208  CA   GLU   38      18.212  11.570  51.746  1.00  31.72      BLGL
ATOM    209  CB   GLU   38      17.037  10.677  52.125  1.00  31.95      BLGL
ATOM    210  CG   GLU   38      15.752  11.052  51.450  1.00  37.83      BLGL
ATOM    211  CD   GLU   38      14.562  10.379  52.094  1.00  40.58      BLGL
ATOM    212  OE1  GLU   38      14.609   9.150  52.302  1.00  39.84      BLGL
ATOM    213  OE2  GLU   38      13.578  11.086  52.390  1.00  45.75      BLGL
ATOM    214  C    GLU   38      19.467  11.026  52.415  1.00  32.56      BLGL
ATOM    215  O    GLU   38      19.641  11.156  53.627  1.00  36.26      BLGL
ATOM    216  N    SER   39      20.335  10.402  51.632  1.00  30.07      BLGL
ATOM    217  CA   SER   39      21.553   9.842  52.176  1.00  27.49      BLGL
ATOM    218  CB   SER   39      21.939   8.602  51.379  1.00  29.09      BLGL
ATOM    219  OG   SER   39      20.872   7.667  51.376  1.00  24.83      BLGL
ATOM    220  C    SER   39      22.660  10.882  52.133  1.00  28.20      BLGL
ATOM    221  O    SER   39      23.791  10.624  52.547  1.00  29.82      BLGL
ATOM    222  N    GLY   40      22.327  12.063  51.626  1.00  28.31      BLGL
ATOM    223  CA   GLY   40      23.303  13.135  51.558  1.00  29.30      BLGL
ATOM    224  C    GLY   40      23.975  13.332  50.214  1.00  29.65      BLGL
ATOM    225  O    GLY   40      24.717  14.296  50.031  1.00  31.52      BLGL
ATOM    226  N    VAL   41      23.730  12.428  49.272  1.00  28.29      BLGL
ATOM    227  CA   VAL   41      24.333  12.540  47.948  1.00  27.33      BLGL
ATOM    228  CB   VAL   41      24.014  11.299  47.075  1.00  26.80      BLGL
ATOM    229  CG1  VAL   41      24.634  11.458  45.699  1.00  24.11      BLGL
ATOM    230  CG2  VAL   41      24.531  10.034  47.754  1.00  25.53      BLGL
ATOM    231  C    VAL   41      23.816  13.788  47.242  1.00  27.51      BLGL
ATOM    232  O    VAL   41      22.630  14.107  47.315  1.00  27.71      BLGL
ATOM    233  N    ALA   42      24.716  14.496  46.568  1.00  28.05      BLGL
ATOM    234  CA   ALA   42      24.364  15.713  45.840  1.00  27.62      BLGL
ATOM    235  CB   ALA   42      24.952  16.935  46.538  1.00  26.85      BLGL
ATOM    236  C    ALA   42      24.898  15.624  44.415  1.00  28.00      BLGL
ATOM    237  O    ALA   42      25.918  14.986  44.158  1.00  29.09      BLGL
ATOM    238  N    PHE   43      24.205  16.267  43.489  1.00  27.56      BLGL
ATOM    239  CA   PHE   43      24.625  16.244  42.101  1.00  30.30      BLGL
ATOM    240  CB   PHE   43      23.529  15.626  41.223  1.00  29.43      BLGL
ATOM    241  CG   PHE   43      23.281  14.176  41.513  1.00  29.78      BLGL
ATOM    242  CD1  PHE   43      22.538  13.791  42.630  1.00  26.98      BLGL
ATOM    243  CD2  PHE   43      23.855  13.188  40.714  1.00  28.78      BLGL
ATOM    244  CE1  PHE   43      22.373  12.442  42.957  1.00  25.96      BLGL
ATOM    245  CE2  PHE   43      23.698  11.835  41.031  1.00  28.67      BLGL
ATOM    246  CZ   PHE   43      22.954  11.461  42.160  1.00  26.33      BLGL
ATOM    247  C    PHE   43      24.954  17.651  41.632  1.00  32.38      BLGL
ATOM    248  O    PHE   43      24.351  18.622  42.096  1.00  33.12      BLGL
ATOM    249  N    TYR   44      25.915  17.759  40.719  1.00  32.89      BLGL
ATOM    250  CA   TYR   44      26.326  19.054  40.203  1.00  34.23      BLGL
ATOM    251  CB   TYR   44      27.807  19.289  40.482  1.00  33.04      BLGL
ATOM    252  CG   TYR   44      28.165  19.083  41.926  1.00  33.71      BLGL
ATOM    253  CD1  TYR   44      28.177  17.809  42.481  1.00  32.43      BLGL
ATOM    254  CE1  TYR   44      28.453  17.617  43.820  1.00  35.78      BLGL
ATOM    255  CD2  TYR   44      28.444  20.167  42.752  1.00  34.36      BLGL
ATOM    256  CE2  TYR   44      28.721  19.986  44.099  1.00  34.85      BLGL
ATOM    257  CZ   TYR   44      28.722  18.708  44.627  1.00  35.70      BLGL
ATOM    258  OH   TYR   44      28.974  18.515  45.966  1.00  37.37      BLGL
ATOM    259  C    TYR   44      26.085  19.114  38.717  1.00  35.88      BLGL
ATOM    260  O    TYR   44      25.531  18.189  38.134  1.00  36.33      BLGL
ATOM    261  N    ASN   45      26.509  20.211  38.106  1.00  39.58      BLGL
ATOM    262  CA   ASN   45      26.350  20.391  36.672  1.00  43.09      BLGL
ATOM    263  CB   ASN   45      25.429  21.581  36.391  1.00  45.50      BLGL
```

Fig. 4 cont.

```
ATOM    264  CG   ASN    45      26.156  22.912  36.452  1.00  47.10           BLGL
ATOM    265  OD1  ASN    45      26.932  23.180  37.373  1.00  44.32           BLGL
ATOM    266  ND2  ASN    45      25.897  23.760  35.464  1.00  49.84           BLGL
ATOM    267  C    ASN    45      27.721  20.618  36.038  1.00  43.53           BLGL
ATOM    268  O    ASN    45      28.746  20.564  36.718  1.00  41.75           BLGL
ATOM    269  N    GLU    46      27.733  20.861  34.735  1.00  47.02           BLGL
ATOM    270  CA   GLU    46      28.979  21.090  34.011  1.00  51.61           BLGL
ATOM    271  CB   GLU    46      28.673  21.715  32.656  1.00  55.53           BLGL
ATOM    272  CG   GLU    46      27.635  20.976  31.820  1.00  59.75           BLGL
ATOM    273  CD   GLU    46      28.162  19.673  31.261  1.00  62.26           BLGL
ATOM    274  OE1  GLU    46      29.304  19.665  30.749  1.00  62.58           BLGL
ATOM    275  OE2  GLU    46      27.429  18.665  31.320  1.00  63.83           BLGL
ATOM    276  C    GLU    46      29.917  22.027  34.782  1.00  52.77           BLGL
ATOM    277  O    GLU    46      31.035  21.648  35.144  1.00  52.27           BLGL
ATOM    278  N    SER    47      29.440  23.248  35.029  1.00  53.78           BLGL
ATOM    279  CA   SER    47      30.197  24.288  35.723  1.00  54.29           BLGL
ATOM    280  CB   SER    47      29.312  25.518  35.940  1.00  56.24           BLGL
ATOM    281  OG   SER    47      28.822  26.029  34.707  1.00  57.54           BLGL
ATOM    282  C    SER    47      30.779  23.857  37.058  1.00  54.34           BLGL
ATOM    283  O    SER    47      31.720  24.477  37.552  1.00  56.28           BLGL
ATOM    284  N    GLY    48      30.215  22.812  37.651  1.00  53.12           BLGL
ATOM    285  CA   GLY    48      30.724  22.344  38.926  1.00  52.44           BLGL
ATOM    286  C    GLY    48      29.883  22.783  40.109  1.00  52.32           BLGL
ATOM    287  O    GLY    48      30.200  22.455  41.258  1.00  51.88           BLGL
ATOM    288  N    LYS    49      28.807  23.518  39.832  1.00  51.68           BLGL
ATOM    289  CA   LYS    49      27.919  24.009  40.882  1.00  50.92           BLGL
ATOM    290  CB   LYS    49      27.338  25.368  40.477  1.00  52.51           BLGL
ATOM    291  CG   LYS    49      26.440  25.314  39.255  1.00  54.74           BLGL
ATOM    292  CD   LYS    49      26.139  26.704  38.706  1.00  58.30           BLGL
ATOM    293  CE   LYS    49      25.326  27.551  39.672  1.00  59.50           BLGL
ATOM    294  NZ   LYS    49      25.039  28.909  39.112  1.00  61.13           BLGL
ATOM    295  C    LYS    49      26.779  23.039  41.204  1.00  49.26           BLGL
ATOM    296  O    LYS    49      26.215  22.391  40.320  1.00  50.56           BLGL
ATOM    297  N    LYS    50      26.444  22.953  42.483  1.00  46.67           BLGL
ATOM    298  CA   LYS    50      25.377  22.082  42.955  1.00  44.89           BLGL
ATOM    299  CB   LYS    50      25.229  22.272  44.465  1.00  44.47           BLGL
ATOM    300  CG   LYS    50      24.483  21.182  45.190  1.00  47.37           BLGL
ATOM    301  CD   LYS    50      24.732  21.290  46.692  1.00  50.81           BLGL
ATOM    302  CE   LYS    50      23.926  20.260  47.478  1.00  53.40           BLGL
ATOM    303  NZ   LYS    50      24.326  20.203  48.917  1.00  55.24           BLGL
ATOM    304  C    LYS    50      24.088  22.473  42.221  1.00  43.33           BLGL
ATOM    305  O    LYS    50      23.726  23.647  42.187  1.00  43.90           BLGL
ATOM    306  N    GLN    51      23.400  21.497  41.631  1.00  41.68           BLGL
ATOM    307  CA   GLN    51      22.167  21.765  40.884  1.00  38.41           BLGL
ATOM    308  CB   GLN    51      22.531  22.164  39.449  1.00  38.23           BLGL
ATOM    309  CG   GLN    51      21.352  22.358  38.507  1.00  38.66           BLGL
ATOM    310  CD   GLN    51      21.797  22.731  37.099  1.00  38.67           BLGL
ATOM    311  OE1  GLN    51      22.206  23.862  36.846  1.00  38.64           BLGL
ATOM    312  NE2  GLN    51      21.730  21.771  36.181  1.00  38.86           BLGL
ATOM    313  C    GLN    51      21.241  20.548  40.867  1.00  35.96           BLGL
ATOM    314  O    GLN    51      21.714  19.417  40.893  1.00  35.98           BLGL
ATOM    315  N    ASP    52      19.928  20.778  40.827  1.00  34.78           BLGL
ATOM    316  CA   ASP    52      18.955  19.677  40.797  1.00  34.16           BLGL
ATOM    317  CB   ASP    52      17.522  20.215  40.657  1.00  35.75           BLGL
ATOM    318  CG   ASP    52      16.475  19.100  40.603  1.00  36.25           BLGL
ATOM    319  OD1  ASP    52      15.271  19.396  40.465  1.00  35.18           BLGL
ATOM    320  OD2  ASP    52      16.857  17.919  40.703  1.00  41.59           BLGL
ATOM    321  C    ASP    52      19.269  18.760  39.610  1.00  33.33           BLGL
ATOM    322  O    ASP    52      19.475  19.231  38.483  1.00  33.59           BLGL
ATOM    323  N    ILE    53      19.294  17.454  39.856  1.00  29.47           BLGL
ATOM    324  CA   ILE    53      19.620  16.512  38.797  1.00  26.79           BLGL
ATOM    325  CB   ILE    53      19.692  15.059  39.336  1.00  25.32           BLGL
ATOM    326  CG2  ILE    53      18.304  14.567  39.715  1.00  24.80           BLGL
ATOM    327  CG1  ILE    53      20.326  14.147  38.277  1.00  25.86           BLGL
ATOM    328  CD1  ILE    53      20.638  12.753  38.777  1.00  25.81           BLGL
ATOM    329  C    ILE    53      18.644  16.588  37.631  1.00  25.41           BLGL
```

Fig. 4 cont.

```
ATOM    330  O   ILE    53      19.042  16.436  36.475  1.00 23.70      BLGL
ATOM    331  N   PHE    54      17.372  16.836  37.926  1.00 23.59      BLGL
ATOM    332  CA  PHE    54      16.380  16.930  36.868  1.00 25.83      BLGL
ATOM    333  CB  PHE    54      14.972  17.002  37.456  1.00 23.83      BLGL
ATOM    334  CG  PHE    54      14.526  15.723  38.072  1.00 22.74      BLGL
ATOM    335  CD1 PHE    54      14.799  15.449  39.402  1.00 25.01      BLGL
ATOM    336  CD2 PHE    54      13.885  14.760  37.306  1.00 21.32      BLGL
ATOM    337  CE1 PHE    54      14.443  14.229  39.961  1.00 27.14      BLGL
ATOM    338  CE2 PHE    54      13.525  13.537  37.856  1.00 23.72      BLGL
ATOM    339  CZ  PHE    54      13.803  13.268  39.184  1.00 24.12      BLGL
ATOM    340  C   PHE    54      16.641  18.121  35.953  1.00 27.75      BLGL
ATOM    341  O   PHE    54      16.378  18.064  34.753  1.00 27.66      BLGL
ATOM    342  N   ASN    55      17.167  19.197  36.522  1.00 30.60      BLGL
ATOM    343  CA  ASN    55      17.485  20.385  35.740  1.00 32.40      BLGL
ATOM    344  CB  ASN    55      17.927  21.528  36.665  1.00 38.72      BLGL
ATOM    345  CG  ASN    55      18.157  22.835  35.919  1.00 43.16      BLGL
ATOM    346  OD1 ASN    55      18.775  23.767  36.444  1.00 46.30      BLGL
ATOM    347  ND2 ASN    55      17.657  22.912  34.692  1.00 47.38      BLGL
ATOM    348  C   ASN    55      18.631  19.996  34.808  1.00 30.86      BLGL
ATOM    349  O   ASN    55      18.624  20.327  33.623  1.00 29.18      BLGL
ATOM    350  N   THR    56      19.608  19.281  35.363  1.00 28.42      BLGL
ATOM    351  CA  THR    56      20.765  18.824  34.606  1.00 26.82      BLGL
ATOM    352  CB  THR    56      21.769  18.101  35.514  1.00 27.58      BLGL
ATOM    353  OG1 THR    56      22.198  18.988  36.558  1.00 29.47      BLGL
ATOM    354  CG2 THR    56      22.969  17.642  34.714  1.00 22.45      BLGL
ATOM    355  C   THR    56      20.353  17.870  33.489  1.00 27.22      BLGL
ATOM    356  O   THR    56      20.851  17.952  32.366  1.00 27.23      BLGL
ATOM    357  N   LEU    57      19.441  16.961  33.805  1.00 27.52      BLGL
ATOM    358  CA  LEU    57      18.950  15.997  32.830  1.00 27.42      BLGL
ATOM    359  CB  LEU    57      17.978  15.033  33.508  1.00 26.87      BLGL
ATOM    360  CG  LEU    57      18.453  13.617  33.847  1.00 26.41      BLGL
ATOM    361  CD1 LEU    57      19.941  13.572  34.078  1.00 23.65      BLGL
ATOM    362  CD2 LEU    57      17.691  13.138  35.074  1.00 25.32      BLGL
ATOM    363  C   LEU    57      18.257  16.686  31.662  1.00 28.88      BLGL
ATOM    364  O   LEU    57      18.430  16.288  30.515  1.00 29.93      BLGL
ATOM    365  N   LYS    58      17.474  17.718  31.959  1.00 30.47      BLGL
ATOM    366  CA  LYS    58      16.757  18.455  30.926  1.00 30.56      BLGL
ATOM    367  CB  LYS    58      15.836  19.507  31.561  1.00 32.82      BLGL
ATOM    368  CG  LYS    58      15.038  20.330  30.551  1.00 33.72      BLGL
ATOM    369  CD  LYS    58      14.129  19.438  29.710  1.00 36.45      BLGL
ATOM    370  CE  LYS    58      13.279  20.253  28.732  1.00 38.35      BLGL
ATOM    371  NZ  LYS    58      12.233  19.436  28.049  1.00 36.51      BLGL
ATOM    372  C   LYS    58      17.726  19.135  29.969  1.00 30.23      BLGL
ATOM    373  O   LYS    58      17.564  19.064  28.753  1.00 31.14      BLGL
ATOM    374  N   GLU    59      18.734  19.793  30.522  1.00 30.65      BLGL
ATOM    375  CA  GLU    59      19.722  20.483  29.709  1.00 31.60      BLGL
ATOM    376  CB  GLU    59      20.668  21.275  30.610  1.00 35.74      BLGL
ATOM    377  CG  GLU    59      19.971  22.381  31.397  1.00 42.93      BLGL
ATOM    378  CD  GLU    59      20.839  22.960  32.511  1.00 48.75      BLGL
ATOM    379  OE1 GLU    59      20.327  23.818  33.264  1.00 51.01      BLGL
ATOM    380  OE2 GLU    59      22.026  22.558  32.638  1.00 51.49      BLGL
ATOM    381  C   GLU    59      20.511  19.493  28.862  1.00 30.47      BLGL
ATOM    382  O   GLU    59      21.086  19.859  27.838  1.00 30.17      BLGL
ATOM    383  N   ALA    60      20.531  18.235  29.293  1.00 29.36      BLGL
ATOM    384  CA  ALA    60      21.253  17.186  28.582  1.00 28.02      BLGL
ATOM    385  CB  ALA    60      21.611  16.065  29.543  1.00 29.83      BLGL
ATOM    386  C   ALA    60      20.461  16.623  27.406  1.00 27.47      BLGL
ATOM    387  O   ALA    60      20.975  15.807  26.643  1.00 26.82      BLGL
ATOM    388  N   GLY    61      19.208  17.048  27.269  1.00 27.12      BLGL
ATOM    389  CA  GLY    61      18.387  16.574  26.167  1.00 25.98      BLGL
ATOM    390  C   GLY    61      17.379  15.484  26.500  1.00 24.46      BLGL
ATOM    391  O   GLY    61      16.678  14.995  25.613  1.00 22.97      BLGL
ATOM    392  N   VAL    62      17.307  15.101  27.773  1.00 23.85      BLGL
ATOM    393  CA  VAL    62      16.373  14.075  28.223  1.00 22.41      BLGL
ATOM    394  CB  VAL    62      16.738  13.577  29.651  1.00 22.60      BLGL
ATOM    395  CG1 VAL    62      15.754  12.514  30.107  1.00 22.01      BLGL
```

Fig. 4 cont.

```
ATOM    396  CG2 VAL    62      18.146  13.018  29.664  1.00 20.65          BLGL
ATOM    397  C   VAL    62      14.958  14.658  28.230  1.00 22.28          BLGL
ATOM    398  O   VAL    62      14.743  15.783  28.686  1.00 24.37          BLGL
ATOM    399  N   ASN    63      13.997  13.896  27.721  1.00 20.64          BLGL
ATOM    400  CA  ASN    63      12.615  14.356  27.660  1.00 21.22          BLGL
ATOM    401  CB  ASN    63      12.203  14.546  26.204  1.00 20.41          BLGL
ATOM    402  CG  ASN    63      12.528  13.337  25.349  1.00 20.90          BLGL
ATOM    403  OD1 ASN    63      12.248  12.195  25.723  1.00 22.33          BLGL
ATOM    404  ND2 ASN    63      13.112  13.581  24.189  1.00 20.98          BLGL
ATOM    405  C   ASN    63      11.641  13.396  28.330  1.00 21.56          BLGL
ATOM    406  O   ASN    63      10.426  13.606  28.304  1.00 24.89          BLGL
ATOM    407  N   TYR    64      12.171  12.346  28.939  1.00 19.85          BLGL
ATOM    408  CA  TYR    64      11.323  11.360  29.578  1.00 18.37          BLGL
ATOM    409  CB  TYR    64      11.054  10.226  28.590  1.00 18.15          BLGL
ATOM    410  CG  TYR    64       9.601  10.025  28.244  1.00 18.02          BLGL
ATOM    411  CD1 TYR    64       8.724   9.446  29.155  1.00 16.59          BLGL
ATOM    412  CE1 TYR    64       7.397   9.210  28.821  1.00 17.75          BLGL
ATOM    413  CD2 TYR    64       9.109  10.375  26.985  1.00 20.14          BLGL
ATOM    414  CE2 TYR    64       7.781  10.145  26.640  1.00 17.07          BLGL
ATOM    415  CZ  TYR    64       6.935   9.560  27.562  1.00 18.10          BLGL
ATOM    416  OH  TYR    64       5.634   9.301  27.223  1.00 19.97          BLGL
ATOM    417  C   TYR    64      11.963  10.804  30.839  1.00 17.64          BLGL
ATOM    418  O   TYR    64      13.181  10.683  30.927  1.00 17.84          BLGL
ATOM    419  N   VAL    65      11.137  10.470  31.819  1.00 15.63          BLGL
ATOM    420  CA  VAL    65      11.644   9.905  33.050  1.00 16.50          BLGL
ATOM    421  CB  VAL    65      11.567  10.909  34.215  1.00 15.92          BLGL
ATOM    422  CG1 VAL    65      11.909  10.207  35.522  1.00 14.90          BLGL
ATOM    423  CG2 VAL    65      12.536  12.055  33.975  1.00 14.25          BLGL
ATOM    424  C   VAL    65      10.847   8.668  33.414  1.00 15.70          BLGL
ATOM    425  O   VAL    65       9.621   8.691  33.388  1.00 16.30          BLGL
ATOM    426  N   ARG    66      11.548   7.587  33.740  1.00 15.28          BLGL
ATOM    427  CA  ARG    66      10.898   6.343  34.126  1.00 14.69          BLGL
ATOM    428  CB  ARG    66      11.520   5.145  33.396  1.00 12.92          BLGL
ATOM    429  CG  ARG    66      10.676   3.897  33.521  1.00 16.36          BLGL
ATOM    430  CD  ARG    66      11.131   2.751  32.621  1.00 17.95          BLGL
ATOM    431  NE  ARG    66      11.997   1.835  33.347  1.00 21.82          BLGL
ATOM    432  CZ  ARG    66      11.882   0.514  33.336  1.00 20.23          BLGL
ATOM    433  NH1 ARG    66      10.933  -0.072  32.628  1.00 20.47          BLGL
ATOM    434  NH2 ARG    66      12.720  -0.218  34.050  1.00 22.65          BLGL
ATOM    435  C   ARG    66      11.049   6.155  35.627  1.00 15.52          BLGL
ATOM    436  O   ARG    66      12.097   6.461  36.194  1.00 19.23          BLGL
ATOM    437  N   VAL    67      10.003   5.663  36.277  1.00 14.45          BLGL
ATOM    438  CA  VAL    67      10.065   5.437  37.709  1.00 14.29          BLGL
ATOM    439  CB  VAL    67       9.387   6.591  38.500  1.00 14.34          BLGL
ATOM    440  CG1 VAL    67       8.010   6.866  37.946  1.00 15.07          BLGL
ATOM    441  CG2 VAL    67       9.279   6.226  39.974  1.00 14.76          BLGL
ATOM    442  C   VAL    67       9.380   4.134  38.050  1.00 13.80          BLGL
ATOM    443  O   VAL    67       8.243   3.902  37.652  1.00 16.06          BLGL
ATOM    444  N   ARG    68      10.084   3.274  38.772  1.00 12.24          BLGL
ATOM    445  CA  ARG    68       9.512   2.007  39.170  1.00 13.36          BLGL
ATOM    446  CB  ARG    68      10.613   0.987  39.505  1.00 15.94          BLGL
ATOM    447  CG  ARG    68      11.653   1.445  40.530  1.00 16.59          BLGL
ATOM    448  CD  ARG    68      12.582   0.299  40.946  1.00 17.71          BLGL
ATOM    449  NE  ARG    68      13.727   0.787  41.717  1.00 20.66          BLGL
ATOM    450  CZ  ARG    68      14.806   1.365  41.187  1.00 19.69          BLGL
ATOM    451  NH1 ARG    68      15.791   1.788  41.964  1.00 18.60          BLGL
ATOM    452  NH2 ARG    68      14.912   1.502  39.876  1.00 19.53          BLGL
ATOM    453  C   ARG    68       8.621   2.250  40.383  1.00 16.28          BLGL
ATOM    454  O   ARG    68       8.875   3.152  41.185  1.00 13.92          BLGL
ATOM    455  N   ILE    69       7.567   1.449  40.506  1.00 16.59          BLGL
ATOM    456  CA  ILE    69       6.649   1.582  41.619  1.00 17.08          BLGL
ATOM    457  CB  ILE    69       5.331   2.254  41.176  1.00 17.80          BLGL
ATOM    458  CG2 ILE    69       4.442   2.505  42.392  1.00 16.20          BLGL
ATOM    459  CG1 ILE    69       5.634   3.577  40.463  1.00 18.54          BLGL
ATOM    460  CD1 ILE    69       4.420   4.258  39.861  1.00 16.60          BLGL
ATOM    461  C   ILE    69       6.326   0.224  42.227  1.00 19.49          BLGL
```

Fig. 4 cont.

```
ATOM    462  O    ILE   69      5.851  -0.684  41.537  1.00 21.07      BLGL
ATOM    463  N    TRP   70      6.613   0.088  43.518  1.00 19.80      BLGL
ATOM    464  CA   TRP   70      6.329  -1.132  44.261  1.00 20.02      BLGL
ATOM    465  CB   TRP   70      7.534  -1.548  45.108  1.00 20.03      BLGL
ATOM    466  CG   TRP   70      8.693  -2.052  44.299  1.00 20.74      BLGL
ATOM    467  CD2  TRP   70     10.078  -1.707  44.460  1.00 20.58      BLGL
ATOM    468  CE2  TRP   70     10.807  -2.445  43.496  1.00 20.35      BLGL
ATOM    469  CE3  TRP   70     10.774  -0.847  45.322  1.00 19.46      BLGL
ATOM    470  CD1  TRP   70      8.643  -2.958  43.278  1.00 20.51      BLGL
ATOM    471  NE1  TRP   70      9.906  -3.198  42.791  1.00 18.08      BLGL
ATOM    472  CZ2  TRP   70     12.200  -2.350  43.372  1.00 17.40      BLGL
ATOM    473  CZ3  TRP   70     12.162  -0.752  45.197  1.00 18.53      BLGL
ATOM    474  CH2  TRP   70     12.856  -1.501  44.227  1.00 17.88      BLGL
ATOM    475  C    TRP   70      5.145  -0.805  45.164  1.00 21.18      BLGL
ATOM    476  O    TRP   70      5.010   0.328  45.626  1.00 20.39      BLGL
ATOM    477  N    ASN   71      4.279  -1.782  45.405  1.00 21.89      BLGL
ATOM    478  CA   ASN   71      3.105  -1.553  46.238  1.00 23.11      BLGL
ATOM    479  CB   ASN   71      2.204  -2.787  46.234  1.00 21.89      BLGL
ATOM    480  CG   ASN   71      1.600  -3.059  44.875  1.00 24.42      BLGL
ATOM    481  OD1  ASN   71      2.312  -3.325  43.907  1.00 24.93      BLGL
ATOM    482  ND2  ASN   71      0.277  -2.986  44.792  1.00 24.52      BLGL
ATOM    483  C    ASN   71      3.454  -1.182  47.673  1.00 23.89      BLGL
ATOM    484  O    ASN   71      3.114  -0.093  48.150  1.00 23.65      BLGL
ATOM    485  N    ASP   72      4.139  -2.094  48.356  1.00 25.19      BLGL
ATOM    486  CA   ASP   72      4.531  -1.888  49.747  1.00 24.90      BLGL
ATOM    487  CB   ASP   72      3.576  -2.642  50.669  1.00 24.77      BLGL
ATOM    488  CG   ASP   72      3.706  -2.214  52.105  1.00 25.24      BLGL
ATOM    489  OD1  ASP   72      3.494  -3.063  52.990  1.00 26.84      BLGL
ATOM    490  OD2  ASP   72      4.006  -1.026  52.346  1.00 24.35      BLGL
ATOM    491  C    ASP   72      5.953  -2.384  49.997  1.00 24.58      BLGL
ATOM    492  O    ASP   72      6.151  -3.472  50.538  1.00 25.47      BLGL
ATOM    493  N    PRO   73      6.962  -1.586  49.619  1.00 24.27      BLGL
ATOM    494  CD   PRO   73      6.856  -0.281  48.940  1.00 23.33      BLGL
ATOM    495  CA   PRO   73      8.366  -1.962  49.805  1.00 24.32      BLGL
ATOM    496  CB   PRO   73      9.091  -1.009  48.866  1.00 24.01      BLGL
ATOM    497  CG   PRO   73      8.272   0.237  49.001  1.00 23.40      BLGL
ATOM    498  C    PRO   73      8.863  -1.840  51.248  1.00 27.14      BLGL
ATOM    499  O    PRO   73      9.987  -1.395  51.491  1.00 28.54      BLGL
ATOM    500  N    TYR   74      8.033  -2.233  52.208  1.00 27.12      BLGL
ATOM    501  CA   TYR   74      8.429  -2.147  53.609  1.00 26.57      BLGL
ATOM    502  CB   TYR   74      7.838  -0.889  54.256  1.00 25.70      BLGL
ATOM    503  CG   TYR   74      8.022   0.386  53.463  1.00 21.92      BLGL
ATOM    504  CD1  TYR   74      7.148   0.721  52.427  1.00 22.26      BLGL
ATOM    505  CE1  TYR   74      7.304   1.909  51.707  1.00 21.83      BLGL
ATOM    506  CD2  TYR   74      9.057   1.265  53.758  1.00 18.92      BLGL
ATOM    507  CE2  TYR   74      9.223   2.448  53.049  1.00 19.47      BLGL
ATOM    508  CZ   TYR   74      8.345   2.766  52.026  1.00 21.06      BLGL
ATOM    509  OH   TYR   74      8.503   3.939  51.323  1.00 21.16      BLGL
ATOM    510  C    TYR   74      7.970  -3.371  54.395  1.00 26.69      BLGL
ATOM    511  O    TYR   74      7.119  -4.131  53.928  1.00 26.70      BLGL
ATOM    512  N    ASP   75      8.547  -3.568  55.579  1.00 25.47      BLGL
ATOM    513  CA   ASP   75      8.151  -4.687  56.422  1.00 25.66      BLGL
ATOM    514  CB   ASP   75      9.348  -5.260  57.201  1.00 26.96      BLGL
ATOM    515  CG   ASP   75      9.948  -4.282  58.207  1.00 26.69      BLGL
ATOM    516  OD1  ASP   75     10.931  -4.668  58.867  1.00 25.84      BLGL
ATOM    517  OD2  ASP   75      9.455  -3.146  58.350  1.00 28.52      BLGL
ATOM    518  C    ASP   75      7.060  -4.208  57.367  1.00 26.20      BLGL
ATOM    519  O    ASP   75      6.634  -3.063  57.286  1.00 27.42      BLGL
ATOM    520  N    ALA   76      6.602  -5.078  58.255  1.00 27.05      BLGL
ATOM    521  CA   ALA   76      5.535  -4.722  59.184  1.00 28.91      BLGL
ATOM    522  CB   ALA   76      5.304  -5.869  60.153  1.00 29.44      BLGL
ATOM    523  C    ALA   76      5.793  -3.438  59.964  1.00 29.89      BLGL
ATOM    524  O    ALA   76      4.873  -2.666  60.241  1.00 31.61      BLGL
ATOM    525  N    ASN   77      7.051  -3.213  60.307  1.00 29.94      BLGL
ATOM    526  CA   ASN   77      7.445  -2.059  61.091  1.00 30.08      BLGL
ATOM    527  CB   ASN   77      8.619  -2.460  61.970  1.00 30.88      BLGL
```

Fig. 4 cont.

```
ATOM    528  CG   ASN    77       8.337  -3.728  62.740  1.00 31.46           BLGL
ATOM    529  OD1  ASN    77       9.085  -4.700  62.659  1.00 35.40           BLGL
ATOM    530  ND2  ASN    77       7.241  -3.729  63.485  1.00 29.08           BLGL
ATOM    531  C    ASN    77       7.768  -0.802  60.294  1.00 30.14           BLGL
ATOM    532  O    ASN    77       8.048   0.249  60.874  1.00 31.47           BLGL
ATOM    533  N    GLY    78       7.742  -0.906  58.971  1.00 29.60           BLGL
ATOM    534  CA   GLY    78       7.998   0.260  58.146  1.00 30.47           BLGL
ATOM    535  C    GLY    78       9.422   0.434  57.665  1.00 30.69           BLGL
ATOM    536  O    GLY    78       9.803   1.524  57.243  1.00 31.23           BLGL
ATOM    537  N    ASN    79      10.212  -0.631  57.735  1.00 30.64           BLGL
ATOM    538  CA   ASN    79      11.599  -0.586  57.285  1.00 31.66           BLGL
ATOM    539  CB   ASN    79      12.437  -1.618  58.043  1.00 32.77           BLGL
ATOM    540  CG   ASN    79      12.478  -1.356  59.539  1.00 32.28           BLGL
ATOM    541  OD1  ASN    79      12.875  -0.277  59.981  1.00 31.97           BLGL
ATOM    542  ND2  ASN    79      12.074  -2.346  60.325  1.00 29.86           BLGL
ATOM    543  C    ASN    79      11.652  -0.888  55.788  1.00 31.40           BLGL
ATOM    544  O    ASN    79      11.253  -1.971  55.352  1.00 31.55           BLGL
ATOM    545  N    GLY    80      12.146   0.072  55.013  1.00 30.48           BLGL
ATOM    546  CA   GLY    80      12.224  -0.092  53.573  1.00 28.01           BLGL
ATOM    547  C    GLY    80      13.066  -1.265  53.132  1.00 26.92           BLGL
ATOM    548  O    GLY    80      14.104  -1.544  53.737  1.00 28.09           BLGL
ATOM    549  N    TYR    81      12.611  -1.958  52.089  1.00 25.24           BLGL
ATOM    550  CA   TYR    81      13.330  -3.110  51.539  1.00 24.70           BLGL
ATOM    551  CB   TYR    81      12.446  -3.891  50.559  1.00 26.19           BLGL
ATOM    552  CG   TYR    81      11.309  -4.704  51.155  1.00 28.51           BLGL
ATOM    553  CD1  TYR    81      10.337  -5.264  50.324  1.00 30.98           BLGL
ATOM    554  CE1  TYR    81       9.285  -6.014  50.836  1.00 33.39           BLGL
ATOM    555  CD2  TYR    81      11.202  -4.919  52.525  1.00 27.25           BLGL
ATOM    556  CE2  TYR    81      10.151  -5.673  53.053  1.00 30.71           BLGL
ATOM    557  CZ   TYR    81       9.191  -6.218  52.201  1.00 32.59           BLGL
ATOM    558  OH   TYR    81       8.134  -6.955  52.701  1.00 29.32           BLGL
ATOM    559  C    TYR    81      14.581  -2.643  50.791  1.00 23.17           BLGL
ATOM    560  O    TYR    81      15.424  -3.449  50.411  1.00 22.30           BLGL
ATOM    561  N    GLY    82      14.692  -1.337  50.575  1.00 22.25           BLGL
ATOM    562  CA   GLY    82      15.840  -0.812  49.863  1.00 22.06           BLGL
ATOM    563  C    GLY    82      15.544  -0.631  48.388  1.00 23.07           BLGL
ATOM    564  O    GLY    82      14.392  -0.466  47.994  1.00 22.83           BLGL
ATOM    565  N    GLY    83      16.582  -0.660  47.561  1.00 23.84           BLGL
ATOM    566  CA   GLY    83      16.384  -0.485  46.133  1.00 23.31           BLGL
ATOM    567  C    GLY    83      15.731   0.843  45.796  1.00 23.19           BLGL
ATOM    568  O    GLY    83      15.219   1.024  44.693  1.00 23.86           BLGL
ATOM    569  N    GLY    84      15.740   1.772  46.748  1.00 22.55           BLGL
ATOM    570  CA   GLY    84      15.142   3.075  46.514  1.00 18.60           BLGL
ATOM    571  C    GLY    84      13.832   3.262  47.243  1.00 18.25           BLGL
ATOM    572  O    GLY    84      13.282   4.354  47.254  1.00 19.59           BLGL
ATOM    573  N    ASN    85      13.339   2.199  47.867  1.00 18.82           BLGL
ATOM    574  CA   ASN    85      12.070   2.246  48.591  1.00 22.71           BLGL
ATOM    575  CB   ASN    85      12.217   3.011  49.914  1.00 22.20           BLGL
ATOM    576  CG   ASN    85      13.143   2.319  50.902  1.00 24.42           BLGL
ATOM    577  OD1  ASN    85      13.320   1.102  50.869  1.00 25.77           BLGL
ATOM    578  ND2  ASN    85      13.721   3.098  51.806  1.00 25.80           BLGL
ATOM    579  C    ASN    85      11.004   2.929  47.729  1.00 23.49           BLGL
ATOM    580  O    ASN    85      10.235   3.761  48.214  1.00 23.21           BLGL
ATOM    581  N    ASN    86      10.950   2.566  46.452  1.00 23.70           BLGL
ATOM    582  CA   ASN    86      10.001   3.196  45.546  1.00 24.44           BLGL
ATOM    583  CB   ASN    86      10.447   3.008  44.106  1.00 21.35           BLGL
ATOM    584  CG   ASN    86      11.781   3.627  43.847  1.00 21.48           BLGL
ATOM    585  OD1  ASN    86      12.811   2.972  43.976  1.00 22.65           BLGL
ATOM    586  ND2  ASN    86      11.781   4.908  43.500  1.00 20.47           BLGL
ATOM    587  C    ASN    86       8.546   2.785  45.679  1.00 25.13           BLGL
ATOM    588  O    ASN    86       8.159   1.666  45.357  1.00 23.77           BLGL
ATOM    589  N    ASP    87       7.742   3.723  46.155  1.00 25.52           BLGL
ATOM    590  CA   ASP    87       6.323   3.500  46.323  1.00 26.02           BLGL
ATOM    591  CB   ASP    87       5.954   3.547  47.803  1.00 25.67           BLGL
ATOM    592  CG   ASP    87       6.584   4.724  48.524  1.00 30.07           BLGL
ATOM    593  OD1  ASP    87       6.994   5.705  47.851  1.00 29.90           BLGL
```

Fig. 4 cont.

```
ATOM    594  OD2 ASP    87       6.656   4.668  49.771  1.00 31.21      BLGL
ATOM    595  C   ASP    87       5.625   4.613  45.566  1.00 25.13      BLGL
ATOM    596  O   ASP    87       6.276   5.396  44.877  1.00 25.07      BLGL
ATOM    597  N   LEU    88       4.307   4.693  45.694  1.00 25.05      BLGL
ATOM    598  CA  LEU    88       3.566   5.732  44.996  1.00 27.31      BLGL
ATOM    599  CB  LEU    88       2.059   5.528  45.183  1.00 25.49      BLGL
ATOM    600  CG  LEU    88       1.163   6.603  44.564  1.00 23.47      BLGL
ATOM    601  CD1 LEU    88       1.378   6.668  43.059  1.00 23.31      BLGL
ATOM    602  CD2 LEU    88      -0.283   6.294  44.880  1.00 23.48      BLGL
ATOM    603  C   LEU    88       3.956   7.146  45.440  1.00 28.05      BLGL
ATOM    604  O   LEU    88       3.942   8.072  44.633  1.00 28.88      BLGL
ATOM    605  N   GLU    89       4.310   7.312  46.713  1.00 28.47      BLGL
ATOM    606  CA  GLU    89       4.679   8.627  47.223  1.00 31.19      BLGL
ATOM    607  CB  GLU    89       4.884   8.596  48.743  1.00 38.35      BLGL
ATOM    608  CG  GLU    89       4.732   7.224  49.404  1.00 49.47      BLGL
ATOM    609  CD  GLU    89       3.309   6.673  49.355  1.00 54.88      BLGL
ATOM    610  OE1 GLU    89       3.095   5.617  48.709  1.00 55.88      BLGL
ATOM    611  OE2 GLU    89       2.413   7.297  49.968  1.00 58.86      BLGL
ATOM    612  C   GLU    89       5.931   9.157  46.547  1.00 28.83      BLGL
ATOM    613  O   GLU    89       5.958  10.293  46.083  1.00 29.30      BLGL
ATOM    614  N   LYS    90       6.970   8.337  46.486  1.00 27.00      BLGL
ATOM    615  CA  LYS    90       8.202   8.758  45.833  1.00 25.31      BLGL
ATOM    616  CB  LYS    90       9.308   7.731  46.074  1.00 24.21      BLGL
ATOM    617  CG  LYS    90       9.730   7.618  47.526  1.00 23.42      BLGL
ATOM    618  CD  LYS    90      11.003   6.815  47.664  1.00 23.39      BLGL
ATOM    619  CE  LYS    90      11.521   6.845  49.092  1.00 22.77      BLGL
ATOM    620  NZ  LYS    90      10.589   6.181  50.039  1.00 24.27      BLGL
ATOM    621  C   LYS    90       7.966   8.940  44.333  1.00 24.86      BLGL
ATOM    622  O   LYS    90       8.604   9.779  43.696  1.00 23.88      BLGL
ATOM    623  N   ALA    91       7.043   8.157  43.776  1.00 22.89      BLGL
ATOM    624  CA  ALA    91       6.727   8.252  42.362  1.00 23.29      BLGL
ATOM    625  CB  ALA    91       5.709   7.175  41.972  1.00 21.21      BLGL
ATOM    626  C   ALA    91       6.172   9.644  42.060  1.00 23.82      BLGL
ATOM    627  O   ALA    91       6.501  10.244  41.042  1.00 24.10      BLGL
ATOM    628  N   ILE    92       5.335  10.154  42.956  1.00 24.44      BLGL
ATOM    629  CA  ILE    92       4.743  11.471  42.782  1.00 25.65      BLGL
ATOM    630  CB  ILE    92       3.549  11.651  43.748  1.00 26.69      BLGL
ATOM    631  CG2 ILE    92       2.943  13.041  43.600  1.00 25.04      BLGL
ATOM    632  CG1 ILE    92       2.484  10.602  43.418  1.00 27.42      BLGL
ATOM    633  CD1 ILE    92       1.341  10.553  44.385  1.00 25.99      BLGL
ATOM    634  C   ILE    92       5.794  12.568  42.992  1.00 25.95      BLGL
ATOM    635  O   ILE    92       5.800  13.575  42.286  1.00 26.66      BLGL
ATOM    636  N   GLN    93       6.687  12.367  43.956  1.00 25.21      BLGL
ATOM    637  CA  GLN    93       7.746  13.332  44.206  1.00 25.19      BLGL
ATOM    638  CB  GLN    93       8.623  12.886  45.369  1.00 27.76      BLGL
ATOM    639  CG  GLN    93       8.285  13.505  46.705  1.00 33.90      BLGL
ATOM    640  CD  GLN    93       9.215  13.020  47.818  1.00 38.24      BLGL
ATOM    641  OE1 GLN    93       9.088  11.890  48.303  1.00 35.85      BLGL
ATOM    642  NE2 GLN    93      10.165  13.873  48.216  1.00 40.86      BLGL
ATOM    643  C   GLN    93       8.595  13.427  42.949  1.00 24.82      BLGL
ATOM    644  O   GLN    93       8.870  14.514  42.454  1.00 27.29      BLGL
ATOM    645  N   ILE    94       9.008  12.276  42.434  1.00 23.84      BLGL
ATOM    646  CA  ILE    94       9.818  12.225  41.223  1.00 21.73      BLGL
ATOM    647  CB  ILE    94      10.263  10.772  40.929  1.00 20.65      BLGL
ATOM    648  CG2 ILE    94      10.936  10.687  39.568  1.00 19.77      BLGL
ATOM    649  CG1 ILE    94      11.202  10.293  42.043  1.00 18.55      BLGL
ATOM    650  CD1 ILE    94      11.644   8.866  41.914  1.00 12.93      BLGL
ATOM    651  C   ILE    94       9.027  12.770  40.038  1.00 21.61      BLGL
ATOM    652  O   ILE    94       9.545  13.553  39.232  1.00 19.49      BLGL
ATOM    653  N   GLY    95       7.764  12.362  39.955  1.00 22.02      BLGL
ATOM    654  CA  GLY    95       6.897  12.798  38.876  1.00 23.64      BLGL
ATOM    655  C   GLY    95       6.787  14.302  38.771  1.00 24.52      BLGL
ATOM    656  O   GLY    95       6.932  14.870  37.683  1.00 24.81      BLGL
ATOM    657  N   LYS    96       6.526  14.947  39.907  1.00 26.80      BLGL
ATOM    658  CA  LYS    96       6.401  16.403  39.971  1.00 26.56      BLGL
ATOM    659  CB  LYS    96       6.095  16.844  41.401  1.00 26.83      BLGL
```

Fig. 4 cont.

```
ATOM    660  CG  LYS  96    4.653  16.630  41.818  1.00 30.58    BLGL
ATOM    661  CD  LYS  96    4.413  17.224  43.192  1.00 34.86    BLGL
ATOM    662  CE  LYS  96    2.939  17.256  43.541  1.00 38.91    BLGL
ATOM    663  NZ  LYS  96    2.712  17.810  44.909  1.00 42.19    BLGL
ATOM    664  C   LYS  96    7.663  17.106  39.474  1.00 26.13    BLGL
ATOM    665  O   LYS  96    7.592  18.041  38.676  1.00 25.77    BLGL
ATOM    666  N   ARG  97    8.818  16.649  39.946  1.00 26.45    BLGL
ATOM    667  CA  ARG  97   10.089  17.232  39.533  1.00 25.62    BLGL
ATOM    668  CB  ARG  97   11.229  16.598  40.335  1.00 26.14    BLGL
ATOM    669  CG  ARG  97   11.105  16.909  41.824  1.00 28.26    BLGL
ATOM    670  CD  ARG  97   12.157  16.228  42.687  1.00 28.70    BLGL
ATOM    671  NE  ARG  97   13.514  16.674  42.385  1.00 30.96    BLGL
ATOM    672  CZ  ARG  97   14.593  16.211  43.007  1.00 29.36    BLGL
ATOM    673  NH1 ARG  97   14.460  15.297  43.959  1.00 26.96    BLGL
ATOM    674  NH2 ARG  97   15.799  16.650  42.671  1.00 26.20    BLGL
ATOM    675  C   ARG  97   10.310  17.060  38.032  1.00 24.94    BLGL
ATOM    676  O   ARG  97   10.778  17.973  37.354  1.00 24.07    BLGL
ATOM    677  N   ALA  98    9.959  15.890  37.510  1.00 24.88    BLGL
ATOM    678  CA  ALA  98   10.104  15.626  36.084  1.00 24.73    BLGL
ATOM    679  CB  ALA  98    9.673  14.198  35.771  1.00 26.89    BLGL
ATOM    680  C   ALA  98    9.265  16.620  35.277  1.00 24.32    BLGL
ATOM    681  O   ALA  98    9.715  17.145  34.256  1.00 21.35    BLGL
ATOM    682  N   ASN  99    8.041  16.875  35.727  1.00 25.11    BLGL
ATOM    683  CA  ASN  99    7.196  17.830  35.019  1.00 27.26    BLGL
ATOM    684  CB  ASN  99    5.802  17.871  35.601  1.00 29.92    BLGL
ATOM    685  CG  ASN  99    5.039  16.631  35.330  1.00 36.77    BLGL
ATOM    686  OD1 ASN  99    3.817  16.649  35.364  1.00 43.97    BLGL
ATOM    687  ND2 ASN  99    5.743  15.529  35.063  1.00 38.67    BLGL
ATOM    688  C   ASN  99    7.766  19.229  35.096  1.00 26.84    BLGL
ATOM    689  O   ASN  99    7.850  19.919  34.090  1.00 29.38    BLGL
ATOM    690  N   ALA 100    8.143  19.652  36.298  1.00 23.90    BLGL
ATOM    691  CA  ALA 100    8.689  20.982  36.481  1.00 23.21    BLGL
ATOM    692  CB  ALA 100    9.214  21.137  37.894  1.00 20.39    BLGL
ATOM    693  C   ALA 100    9.800  21.244  35.470  1.00 25.29    BLGL
ATOM    694  O   ALA 100   10.088  22.394  35.141  1.00 26.23    BLGL
ATOM    695  N   ASN 101   10.409  20.174  34.963  1.00 25.14    BLGL
ATOM    696  CA  ASN 101   11.492  20.307  33.998  1.00 25.17    BLGL
ATOM    697  CB  ASN 101   12.696  19.515  34.483  1.00 24.95    BLGL
ATOM    698  CG  ASN 101   13.280  20.091  35.747  1.00 25.85    BLGL
ATOM    699  OD1 ASN 101   13.914  21.145  35.719  1.00 29.40    BLGL
ATOM    700  ND2 ASN 101   13.054  19.422  36.868  1.00 24.97    BLGL
ATOM    701  C   ASN 101   11.118  19.898  32.582  1.00 25.90    BLGL
ATOM    702  O   ASN 101   11.978  19.563  31.772  1.00 27.14    BLGL
ATOM    703  N   GLY 102    9.824  19.932  32.290  1.00 25.80    BLGL
ATOM    704  CA  GLY 102    9.345  19.598  30.962  1.00 24.78    BLGL
ATOM    705  C   GLY 102    9.671  18.215  30.447  1.00 25.83    BLGL
ATOM    706  O   GLY 102   10.048  18.061  29.289  1.00 27.54    BLGL
ATOM    707  N   MET 103    9.525  17.205  31.297  1.00 26.80    BLGL
ATOM    708  CA  MET 103    9.793  15.827  30.899  1.00 26.04    BLGL
ATOM    709  CB  MET 103   11.006  15.283  31.662  1.00 26.48    BLGL
ATOM    710  CG  MET 103   12.265  16.110  31.451  1.00 29.27    BLGL
ATOM    711  SD  MET 103   13.767  15.380  32.124  1.00 31.74    BLGL
ATOM    712  CE  MET 103   13.716  16.017  33.804  1.00 31.73    BLGL
ATOM    713  C   MET 103    8.559  14.978  31.191  1.00 25.31    BLGL
ATOM    714  O   MET 103    7.892  15.179  32.206  1.00 24.54    BLGL
ATOM    715  N   LYS 104    8.243  14.044  30.294  1.00 24.62    BLGL
ATOM    716  CA  LYS 104    7.082  13.174  30.484  1.00 24.42    BLGL
ATOM    717  CB  LYS 104    6.668  12.527  29.167  1.00 28.12    BLGL
ATOM    718  CG  LYS 104    6.265  13.483  28.062  1.00 32.81    BLGL
ATOM    719  CD  LYS 104    4.800  13.820  28.149  1.00 35.64    BLGL
ATOM    720  CE  LYS 104    4.294  14.402  26.843  1.00 37.37    BLGL
ATOM    721  NZ  LYS 104    2.807  14.485  26.870  1.00 40.79    BLGL
ATOM    722  C   LYS 104    7.452  12.075  31.466  1.00 22.98    BLGL
ATOM    723  O   LYS 104    8.632  11.840  31.720  1.00 23.51    BLGL
ATOM    724  N   LEU 105    6.450  11.398  32.014  1.00 21.49    BLGL
ATOM    725  CA  LEU 105    6.705  10.313  32.955  1.00 19.77    BLGL
```

Fig. 4 cont.

```
ATOM    726  CB  LEU   105       5.975   10.559   34.279  1.00 18.76      BLGL
ATOM    727  CG  LEU   105       6.334    9.548   35.381  1.00 19.18      BLGL
ATOM    728  CD1 LEU   105       7.586   10.007   36.100  1.00 16.56      BLGL
ATOM    729  CD2 LEU   105       5.195    9.412   36.364  1.00 21.13      BLGL
ATOM    730  C   LEU   105       6.280    8.941   32.418  1.00 19.86      BLGL
ATOM    731  O   LEU   105       5.285    8.812   31.701  1.00 16.96      BLGL
ATOM    732  N   LEU   106       7.059    7.920   32.758  1.00 19.88      BLGL
ATOM    733  CA  LEU   106       6.738    6.551   32.381  1.00 19.92      BLGL
ATOM    734  CB  LEU   106       7.889    5.878   31.637  1.00 17.61      BLGL
ATOM    735  CG  LEU   106       7.550    4.607   30.838  1.00 21.29      BLGL
ATOM    736  CD1 LEU   106       8.845    3.872   30.511  1.00 18.25      BLGL
ATOM    737  CD2 LEU   106       6.627    3.689   31.604  1.00 17.96      BLGL
ATOM    738  C   LEU   106       6.567    5.877   33.730  1.00 19.81      BLGL
ATOM    739  O   LEU   106       7.546    5.660   34.437  1.00 19.58      BLGL
ATOM    740  N   ALA   107       5.327    5.581   34.102  1.00 20.44      BLGL
ATOM    741  CA  ALA   107       5.052    4.922   35.373  1.00 20.99      BLGL
ATOM    742  CB  ALA   107       3.634    5.240   35.826  1.00 21.52      BLGL
ATOM    743  C   ALA   107       5.224    3.418   35.177  1.00 21.97      BLGL
ATOM    744  O   ALA   107       4.493    2.796   34.406  1.00 23.04      BLGL
ATOM    745  N   ASP   108       6.192    2.828   35.867  1.00 21.22      BLGL
ATOM    746  CA  ASP   108       6.438    1.400   35.726  1.00 20.00      BLGL
ATOM    747  CB  ASP   108       7.932    1.175   35.463  1.00 17.66      BLGL
ATOM    748  CG  ASP   108       8.327   -0.289   35.455  1.00 17.79      BLGL
ATOM    749  OD1 ASP   108       7.448   -1.173   35.519  1.00 16.92      BLGL
ATOM    750  OD2 ASP   108       9.542   -0.562   35.385  1.00 18.27      BLGL
ATOM    751  C   ASP   108       5.966    0.625   36.953  1.00 21.24      BLGL
ATOM    752  O   ASP   108       6.635    0.614   37.984  1.00 25.51      BLGL
ATOM    753  N   PHE   109       4.801   -0.010   36.840  1.00 19.98      BLGL
ATOM    754  CA  PHE   109       4.256   -0.792   37.939  1.00 20.05      BLGL
ATOM    755  CB  PHE   109       2.739   -0.903   37.850  1.00 20.06      BLGL
ATOM    756  CG  PHE   109       2.033    0.386   38.066  1.00 21.36      BLGL
ATOM    757  CD1 PHE   109       1.751    1.225   36.995  1.00 21.28      BLGL
ATOM    758  CD2 PHE   109       1.665    0.777   39.349  1.00 21.79      BLGL
ATOM    759  CE1 PHE   109       1.110    2.442   37.194  1.00 24.40      BLGL
ATOM    760  CE2 PHE   109       1.026    1.989   39.564  1.00 23.03      BLGL
ATOM    761  CZ  PHE   109       0.745    2.828   38.482  1.00 23.74      BLGL
ATOM    762  C   PHE   109       4.822   -2.190   37.949  1.00 19.77      BLGL
ATOM    763  O   PHE   109       4.680   -2.932   36.978  1.00 18.81      BLGL
ATOM    764  N   HIS   110       5.464   -2.547   39.054  1.00 19.76      BLGL
ATOM    765  CA  HIS   110       6.023   -3.875   39.188  1.00 20.72      BLGL
ATOM    766  CB  HIS   110       7.207   -3.876   40.157  1.00 20.31      BLGL
ATOM    767  CG  HIS   110       8.497   -3.439   39.540  1.00 20.23      BLGL
ATOM    768  CD2 HIS   110       8.779   -2.456   38.653  1.00 19.83      BLGL
ATOM    769  ND1 HIS   110       9.703   -4.034   39.845  1.00 21.63      BLGL
ATOM    770  CE1 HIS   110      10.671   -3.437   39.174  1.00 20.13      BLGL
ATOM    771  NE2 HIS   110      10.137   -2.475   38.442  1.00 20.13      BLGL
ATOM    772  C   HIS   110       4.948   -4.823   39.695  1.00 20.55      BLGL
ATOM    773  O   HIS   110       5.056   -6.036   39.536  1.00 20.58      BLGL
ATOM    774  N   TYR   111       3.900   -4.267   40.291  1.00 21.08      BLGL
ATOM    775  CA  TYR   111       2.827   -5.093   40.830  1.00 23.38      BLGL
ATOM    776  CB  TYR   111       2.039   -5.759   39.695  1.00 22.62      BLGL
ATOM    777  CG  TYR   111       1.274   -4.758   38.858  1.00 23.84      BLGL
ATOM    778  CD1 TYR   111       1.551   -4.593   37.501  1.00 22.76      BLGL
ATOM    779  CE1 TYR   111       0.878   -3.641   36.742  1.00 23.56      BLGL
ATOM    780  CD2 TYR   111       0.297   -3.945   39.437  1.00 24.23      BLGL
ATOM    781  CE2 TYR   111      -0.378   -2.991   38.688  1.00 23.70      BLGL
ATOM    782  CZ  TYR   111      -0.082   -2.844   37.344  1.00 23.27      BLGL
ATOM    783  OH  TYR   111      -0.738   -1.887   36.609  1.00 24.35      BLGL
ATOM    784  C   TYR   111       3.439   -6.137   41.754  1.00 22.90      BLGL
ATOM    785  O   TYR   111       3.094   -7.317   41.718  1.00 22.52      BLGL
ATOM    786  N   SER   112       4.372   -5.668   42.574  1.00 22.56      BLGL
ATOM    787  CA  SER   112       5.071   -6.493   43.544  1.00 22.63      BLGL
ATOM    788  CB  SER   112       6.249   -7.201   42.892  1.00 22.37      BLGL
ATOM    789  OG  SER   112       7.002   -7.894   43.866  1.00 23.73      BLGL
ATOM    790  C   SER   112       5.585   -5.542   44.601  1.00 23.27      BLGL
ATOM    791  O   SER   112       5.631   -4.333   44.368  1.00 24.65      BLGL
```

Fig. 4 cont.

```
ATOM    792  N   ASP 113      5.968  -6.069  45.760  1.00 22.31      BLGL
ATOM    793  CA  ASP 113      6.486  -5.208  46.815  1.00 22.28      BLGL
ATOM    794  CB  ASP 113      6.202  -5.795  48.199  1.00 22.82      BLGL
ATOM    795  CG  ASP 113      4.732  -5.719  48.577  1.00 25.54      BLGL
ATOM    796  OD1 ASP 113      4.032  -4.825  48.056  1.00 23.47      BLGL
ATOM    797  OD2 ASP 113      4.281  -6.544  49.406  1.00 24.91      BLGL
ATOM    798  C   ASP 113      7.982  -4.969  46.651  1.00 21.86      BLGL
ATOM    799  O   ASP 113      8.548  -4.101  47.309  1.00 21.62      BLGL
ATOM    800  N   PHE 114      8.622  -5.738  45.775  1.00 20.23      BLGL
ATOM    801  CA  PHE 114     10.046  -5.563  45.547  1.00 20.78      BLGL
ATOM    802  CB  PHE 114     10.853  -6.387  46.549  1.00 21.28      BLGL
ATOM    803  CG  PHE 114     12.221  -5.822  46.838  1.00 24.03      BLGL
ATOM    804  CD1 PHE 114     12.420  -4.441  46.919  1.00 24.35      BLGL
ATOM    805  CD2 PHE 114     13.308  -6.666  47.064  1.00 24.49      BLGL
ATOM    806  CE1 PHE 114     13.684  -3.909  47.224  1.00 22.80      BLGL
ATOM    807  CE2 PHE 114     14.575  -6.144  47.372  1.00 20.26      BLGL
ATOM    808  CZ  PHE 114     14.761  -4.767  47.451  1.00 20.45      BLGL
ATOM    809  C   PHE 114     10.392  -5.952  44.122  1.00 21.41      BLGL
ATOM    810  O   PHE 114      9.507  -6.328  43.361  1.00 21.59      BLGL
ATOM    811  N   TRP 115     11.675  -5.856  43.768  1.00 20.29      BLGL
ATOM    812  CA  TRP 115     12.152  -6.160  42.418  1.00 19.28      BLGL
ATOM    813  CB  TRP 115     13.634  -6.577  42.445  1.00 20.57      BLGL
ATOM    814  CG  TRP 115     14.575  -5.534  42.963  1.00 21.03      BLGL
ATOM    815  CD2 TRP 115     14.942  -4.315  42.311  1.00 20.71      BLGL
ATOM    816  CE2 TRP 115     15.786  -3.607  43.198  1.00 21.97      BLGL
ATOM    817  CE3 TRP 115     14.637  -3.747  41.066  1.00 20.82      BLGL
ATOM    818  CD1 TRP 115     15.202  -5.523  44.177  1.00 19.55      BLGL
ATOM    819  NE1 TRP 115     15.929  -4.371  44.328  1.00 18.99      BLGL
ATOM    820  CZ2 TRP 115     16.329  -2.350  42.878  1.00 22.16      BLGL
ATOM    821  CZ3 TRP 115     15.177  -2.499  40.746  1.00 21.59      BLGL
ATOM    822  CH2 TRP 115     16.013  -1.815  41.653  1.00 22.47      BLGL
ATOM    823  C   TRP 115     11.361  -7.231  41.665  1.00 18.82      BLGL
ATOM    824  O   TRP 115     11.090  -8.308  42.193  1.00 17.18      BLGL
ATOM    825  N   ALA 116     10.995  -6.925  40.426  1.00 17.42      BLGL
ATOM    826  CA  ALA 116     10.277  -7.874  39.589  1.00 19.55      BLGL
ATOM    827  CB  ALA 116      8.914  -7.326  39.223  1.00 18.74      BLGL
ATOM    828  C   ALA 116     11.110  -8.105  38.331  1.00 22.25      BLGL
ATOM    829  O   ALA 116     11.457  -7.157  37.631  1.00 25.39      BLGL
ATOM    830  N   ASP 117     11.450  -9.358  38.051  1.00 21.71      BLGL
ATOM    831  CA  ASP 117     12.243  -9.672  36.872  1.00 22.29      BLGL
ATOM    832  CB  ASP 117     13.736  -9.620  37.209  1.00 22.60      BLGL
ATOM    833  CG  ASP 117     14.124 -10.578  38.309  1.00 26.69      BLGL
ATOM    834  OD1 ASP 117     13.662 -11.738  38.294  1.00 29.56      BLGL
ATOM    835  OD2 ASP 117     14.907 -10.171  39.190  1.00 30.52      BLGL
ATOM    836  C   ASP 117     11.843 -11.045  36.346  1.00 22.91      BLGL
ATOM    837  O   ASP 117     10.840 -11.601  36.784  1.00 24.06      BLGL
ATOM    838  N   PRO 118     12.617 -11.619  35.409  1.00 22.06      BLGL
ATOM    839  CD  PRO 118     13.734 -11.056  34.639  1.00 20.93      BLGL
ATOM    840  CA  PRO 118     12.252 -12.935  34.880  1.00 24.27      BLGL
ATOM    841  CB  PRO 118     13.301 -13.176  33.802  1.00 22.87      BLGL
ATOM    842  CG  PRO 118     13.629 -11.821  33.353  1.00 24.48      BLGL
ATOM    843  C   PRO 118     12.202 -14.077  35.884  1.00 26.00      BLGL
ATOM    844  O   PRO 118     11.667 -15.140  35.580  1.00 29.05      BLGL
ATOM    845  N   ALA 119     12.755 -13.868  37.071  1.00 28.00      BLGL
ATOM    846  CA  ALA 119     12.762 -14.917  38.086  1.00 28.48      BLGL
ATOM    847  CB  ALA 119     14.186 -15.188  38.543  1.00 27.97      BLGL
ATOM    848  C   ALA 119     11.899 -14.568  39.283  1.00 28.36      BLGL
ATOM    849  O   ALA 119     11.407 -15.447  39.981  1.00 30.80      BLGL
ATOM    850  N   LYS 120     11.719 -13.279  39.524  1.00 29.14      BLGL
ATOM    851  CA  LYS 120     10.920 -12.842  40.654  1.00 29.76      BLGL
ATOM    852  CB  LYS 120     11.793 -12.032  41.617  1.00 31.32      BLGL
ATOM    853  CG  LYS 120     12.940 -12.838  42.213  1.00 38.25      BLGL
ATOM    854  CD  LYS 120     13.897 -12.000  43.074  1.00 40.66      BLGL
ATOM    855  CE  LYS 120     14.801 -11.115  42.222  1.00 44.93      BLGL
ATOM    856  NZ  LYS 120     15.827 -10.373  43.027  1.00 46.70      BLGL
ATOM    857  C   LYS 120      9.708 -12.020  40.224  1.00 28.61      BLGL
```

Fig. 4 cont.

```
ATOM    858  O    LYS  120      9.841 -10.912  39.702  1.00 28.45      BLGL
ATOM    859  N    GLN  121      8.525 -12.589  40.425  1.00 26.27      BLGL
ATOM    860  CA   GLN  121      7.273 -11.913  40.108  1.00 25.49      BLGL
ATOM    861  CB   GLN  121      6.673 -12.457  38.805  1.00 24.33      BLGL
ATOM    862  CG   GLN  121      7.392 -12.034  37.525  1.00 20.53      BLGL
ATOM    863  CD   GLN  121      7.376 -10.528  37.291  1.00 18.36      BLGL
ATOM    864  OE1  GLN  121      6.425  -9.838  37.659  1.00 15.80      BLGL
ATOM    865  NE2  GLN  121      8.424 -10.017  36.655  1.00 17.37      BLGL
ATOM    866  C    GLN  121      6.328 -12.176  41.281  1.00 25.36      BLGL
ATOM    867  O    GLN  121      5.176 -12.571  41.099  1.00 26.22      BLGL
ATOM    868  N    LYS  122      6.843 -11.970  42.489  1.00 25.47      BLGL
ATOM    869  CA   LYS  122      6.091 -12.188  43.716  1.00 25.96      BLGL
ATOM    870  CB   LYS  122      7.031 -12.079  44.924  1.00 27.22      BLGL
ATOM    871  CG   LYS  122      6.394 -12.412  46.260  1.00 29.39      BLGL
ATOM    872  CD   LYS  122      6.870 -13.759  46.785  1.00 32.32      BLGL
ATOM    873  CE   LYS  122      7.832 -13.609  47.961  1.00 31.56      BLGL
ATOM    874  NZ   LYS  122      7.187 -12.997  49.160  1.00 32.62      BLGL
ATOM    875  C    LYS  122      4.968 -11.162  43.833  1.00 26.53      BLGL
ATOM    876  O    LYS  122      5.151  -9.988  43.504  1.00 28.15      BLGL
ATOM    877  N    ALA  123      3.804 -11.603  44.298  1.00 25.34      BLGL
ATOM    878  CA   ALA  123      2.669 -10.700  44.449  1.00 24.78      BLGL
ATOM    879  CB   ALA  123      1.377 -11.491  44.559  1.00 24.09      BLGL
ATOM    880  C    ALA  123      2.830  -9.820  45.675  1.00 23.46      BLGL
ATOM    881  O    ALA  123      3.519 -10.177  46.622  1.00 23.28      BLGL
ATOM    882  N    PRO  124      2.212  -8.636  45.660  1.00 23.79      BLGL
ATOM    883  CD   PRO  124      1.484  -7.998  44.548  1.00 21.21      BLGL
ATOM    884  CA   PRO  124      2.310  -7.738  46.811  1.00 22.77      BLGL
ATOM    885  CB   PRO  124      1.392  -6.588  46.419  1.00 21.28      BLGL
ATOM    886  CG   PRO  124      1.521  -6.547  44.927  1.00 19.51      BLGL
ATOM    887  C    PRO  124      1.791  -8.491  48.037  1.00 23.09      BLGL
ATOM    888  O    PRO  124      0.883  -9.312  47.922  1.00 22.17      BLGL
ATOM    889  N    LYS  125      2.360  -8.228  49.205  1.00 25.24      BLGL
ATOM    890  CA   LYS  125      1.910  -8.916  50.411  1.00 25.84      BLGL
ATOM    891  CB   LYS  125      2.612  -8.350  51.656  1.00 23.65      BLGL
ATOM    892  CG   LYS  125      4.109  -8.642  51.733  1.00 21.46      BLGL
ATOM    893  CD   LYS  125      4.750  -8.067  52.990  1.00 15.25      BLGL
ATOM    894  CE   LYS  125      4.683  -6.554  53.029  1.00 20.47      BLGL
ATOM    895  NZ   LYS  125      5.440  -5.911  51.912  1.00 22.44      BLGL
ATOM    896  C    LYS  125      0.391  -8.807  50.570  1.00 27.21      BLGL
ATOM    897  O    LYS  125     -0.264  -9.763  50.976  1.00 27.46      BLGL
ATOM    898  N    ALA  126     -0.170  -7.651  50.232  1.00 27.45      BLGL
ATOM    899  CA   ALA  126     -1.608  -7.438  50.360  1.00 28.44      BLGL
ATOM    900  CB   ALA  126     -1.942  -5.996  50.042  1.00 27.50      BLGL
ATOM    901  C    ALA  126     -2.445  -8.367  49.487  1.00 30.46      BLGL
ATOM    902  O    ALA  126     -3.578  -8.700  49.835  1.00 32.72      BLGL
ATOM    903  N    TRP  127     -1.893  -8.780  48.352  1.00 31.67      BLGL
ATOM    904  CA   TRP  127     -2.608  -9.663  47.436  1.00 32.34      BLGL
ATOM    905  CB   TRP  127     -2.274  -9.301  45.983  1.00 29.98      BLGL
ATOM    906  CG   TRP  127     -2.525  -7.864  45.623  1.00 26.78      BLGL
ATOM    907  CD2  TRP  127     -2.176  -7.215  44.392  1.00 25.87      BLGL
ATOM    908  CE2  TRP  127     -2.582  -5.869  44.499  1.00 24.64      BLGL
ATOM    909  CE3  TRP  127     -1.558  -7.643  43.207  1.00 25.70      BLGL
ATOM    910  CD1  TRP  127     -3.116  -6.913  46.400  1.00 25.22      BLGL
ATOM    911  NE1  TRP  127     -3.153  -5.712  45.735  1.00 25.00      BLGL
ATOM    912  CZ2  TRP  127     -2.390  -4.942  43.469  1.00 23.42      BLGL
ATOM    913  CZ3  TRP  127     -1.367  -6.723  42.183  1.00 24.22      BLGL
ATOM    914  CH2  TRP  127     -1.781  -5.387  42.323  1.00 24.78      BLGL
ATOM    915  C    TRP  127     -2.220 -11.113  47.694  1.00 34.48      BLGL
ATOM    916  O    TRP  127     -2.786 -12.039  47.101  1.00 34.45      BLGL
ATOM    917  N    ALA  128     -1.244 -11.284  48.585  1.00 37.15      BLGL
ATOM    918  CA   ALA  128     -0.704 -12.589  48.971  1.00 38.47      BLGL
ATOM    919  CB   ALA  128     -0.198 -12.528  50.396  1.00 40.00      BLGL
ATOM    920  C    ALA  128     -1.663 -13.759  48.817  1.00 39.10      BLGL
ATOM    921  O    ALA  128     -1.406 -14.671  48.032  1.00 38.72      BLGL
ATOM    922  N    ASN  129     -2.754 -13.751  49.574  1.00 40.50      BLGL
ATOM    923  CA   ASN  129     -3.716 -14.836  49.473  1.00 44.45      BLGL
```

Fig. 4 cont.

```
ATOM    924  CB  ASN   129      -3.794 -15.632  50.788  1.00 47.42      BLGL
ATOM    925  CG  ASN   129      -3.746 -14.751  52.018  1.00 50.55      BLGL
ATOM    926  OD1 ASN   129      -3.975 -13.545  51.941  1.00 54.24      BLGL
ATOM    927  ND2 ASN   129      -3.460 -15.356  53.168  1.00 50.85      BLGL
ATOM    928  C   ASN   129      -5.107 -14.380  49.047  1.00 44.76      BLGL
ATOM    929  O   ASN   129      -6.070 -14.460  49.813  1.00 45.16      BLGL
ATOM    930  N   LEU   130      -5.194 -13.901  47.810  1.00 44.30      BLGL
ATOM    931  CA  LEU   130      -6.452 -13.456  47.230  1.00 43.76      BLGL
ATOM    932  CB  LEU   130      -6.341 -12.018  46.731  1.00 44.19      BLGL
ATOM    933  CG  LEU   130      -6.396 -10.901  47.767  1.00 44.74      BLGL
ATOM    934  CD1 LEU   130      -6.258  -9.564  47.071  1.00 45.24      BLGL
ATOM    935  CD2 LEU   130      -7.712 -10.970  48.515  1.00 45.37      BLGL
ATOM    936  C   LEU   130      -6.727 -14.363  46.049  1.00 43.61      BLGL
ATOM    937  O   LEU   130      -5.801 -14.769  45.351  1.00 43.36      BLGL
ATOM    938  N   ASN   131      -7.991 -14.695  45.823  1.00 44.12      BLGL
ATOM    939  CA  ASN   131      -8.318 -15.549  44.690  1.00 44.97      BLGL
ATOM    940  CB  ASN   131      -9.757 -16.078  44.801  1.00 47.76      BLGL
ATOM    941  CG  ASN   131     -10.794 -14.976  44.772  1.00 51.05      BLGL
ATOM    942  OD1 ASN   131     -10.669 -13.968  45.465  1.00 55.52      BLGL
ATOM    943  ND2 ASN   131     -11.835 -15.170  43.977  1.00 52.37      BLGL
ATOM    944  C   ASN   131      -8.133 -14.706  43.436  1.00 43.17      BLGL
ATOM    945  O   ASN   131      -8.381 -13.502  43.451  1.00 42.05      BLGL
ATOM    946  N   PHE   132      -7.682 -15.338  42.360  1.00 42.47      BLGL
ATOM    947  CA  PHE   132      -7.440 -14.638  41.107  1.00 42.04      BLGL
ATOM    948  CB  PHE   132      -7.430 -15.619  39.940  1.00 42.05      BLGL
ATOM    949  CG  PHE   132      -7.126 -14.971  38.633  1.00 42.75      BLGL
ATOM    950  CD1 PHE   132      -5.870 -14.426  38.396  1.00 42.49      BLGL
ATOM    951  CD2 PHE   132      -8.103 -14.855  37.656  1.00 43.76      BLGL
ATOM    952  CE1 PHE   132      -5.594 -13.769  37.204  1.00 42.79      BLGL
ATOM    953  CE2 PHE   132      -7.834 -14.197  36.455  1.00 44.60      BLGL
ATOM    954  CZ  PHE   132      -6.579 -13.655  36.232  1.00 43.31      BLGL
ATOM    955  C   PHE   132      -8.439 -13.523  40.808  1.00 41.68      BLGL
ATOM    956  O   PHE   132      -8.050 -12.415  40.445  1.00 41.50      BLGL
ATOM    957  N   GLU   133      -9.725 -13.815  40.951  1.00 42.52      BLGL
ATOM    958  CA  GLU   133     -10.759 -12.821  40.691  1.00 42.35      BLGL
ATOM    959  CB  GLU   133     -12.138 -13.409  40.985  1.00 46.23      BLGL
ATOM    960  CG  GLU   133     -12.591 -14.433  39.967  1.00 53.21      BLGL
ATOM    961  CD  GLU   133     -12.550 -13.879  38.553  1.00 57.33      BLGL
ATOM    962  OE1 GLU   133     -13.059 -12.757  38.347  1.00 58.31      BLGL
ATOM    963  OE2 GLU   133     -12.015 -14.564  37.652  1.00 61.34      BLGL
ATOM    964  C   GLU   133     -10.573 -11.542  41.500  1.00 40.12      BLGL
ATOM    965  O   GLU   133     -10.654 -10.443  40.951  1.00 38.25      BLGL
ATOM    966  N   ASP   134     -10.326 -11.691  42.800  1.00 38.18      BLGL
ATOM    967  CA  ASP   134     -10.133 -10.547  43.684  1.00 37.03      BLGL
ATOM    968  CB  ASP   134     -10.203 -10.994  45.142  1.00 39.68      BLGL
ATOM    969  CG  ASP   134     -11.625 -11.128  45.640  1.00 40.58      BLGL
ATOM    970  OD1 ASP   134     -11.816 -11.683  46.744  1.00 40.76      BLGL
ATOM    971  OD2 ASP   134     -12.546 -10.666  44.930  1.00 42.41      BLGL
ATOM    972  C   ASP   134      -8.816  -9.822  43.434  1.00 34.44      BLGL
ATOM    973  O   ASP   134      -8.710  -8.611  43.633  1.00 33.65      BLGL
ATOM    974  N   LYS   135      -7.810 -10.570  43.003  1.00 32.43      BLGL
ATOM    975  CA  LYS   135      -6.510  -9.989  42.717  1.00 30.17      BLGL
ATOM    976  CB  LYS   135      -5.468 -11.092  42.537  1.00 28.01      BLGL
ATOM    977  CG  LYS   135      -4.058 -10.568  42.377  1.00 25.79      BLGL
ATOM    978  CD  LYS   135      -3.090 -11.647  41.928  1.00 24.80      BLGL
ATOM    979  CE  LYS   135      -2.994 -12.773  42.922  1.00 24.10      BLGL
ATOM    980  NZ  LYS   135      -1.961 -13.742  42.491  1.00 24.21      BLGL
ATOM    981  C   LYS   135      -6.615  -9.147  41.443  1.00 29.06      BLGL
ATOM    982  O   LYS   135      -6.092  -8.032  41.384  1.00 29.12      BLGL
ATOM    983  N   LYS   136      -7.303  -9.682  40.436  1.00 28.19      BLGL
ATOM    984  CA  LYS   136      -7.492  -8.986  39.166  1.00 26.63      BLGL
ATOM    985  CB  LYS   136      -8.364  -9.819  38.220  1.00 28.55      BLGL
ATOM    986  CG  LYS   136      -8.455  -9.248  36.811  1.00 33.70      BLGL
ATOM    987  CD  LYS   136      -9.739  -9.661  36.093  1.00 40.26      BLGL
ATOM    988  CE  LYS   136      -9.825 -11.171  35.873  1.00 44.05      BLGL
ATOM    989  NZ  LYS   136     -11.113 -11.590  35.228  1.00 44.46      BLGL
```

Fig. 4 cont.

```
ATOM    990  C    LYS  136     -8.149  -7.627  39.408  1.00 24.62      BLGL
ATOM    991  O    LYS  136     -7.714  -6.611  38.868  1.00 24.91      BLGL
ATOM    992  N    THR  137     -9.197  -7.607  40.221  1.00 23.73      BLGL
ATOM    993  CA   THR  137     -9.874  -6.356  40.519  1.00 24.53      BLGL
ATOM    994  CB   THR  137    -11.262  -6.603  41.168  1.00 26.21      BLGL
ATOM    995  OG1  THR  137    -11.679  -5.422  41.855  1.00 28.27      BLGL
ATOM    996  CG2  THR  137    -11.220  -7.759  42.134  1.00 27.71      BLGL
ATOM    997  C    THR  137     -9.017  -5.451  41.412  1.00 24.00      BLGL
ATOM    998  O    THR  137     -9.108  -4.221  41.334  1.00 23.13      BLGL
ATOM    999  N    ALA  138     -8.174  -6.054  42.248  1.00 22.08      BLGL
ATOM   1000  CA   ALA  138     -7.289  -5.277  43.115  1.00 23.30      BLGL
ATOM   1001  CB   ALA  138     -6.612  -6.182  44.128  1.00 19.73      BLGL
ATOM   1002  C    ALA  138     -6.228  -4.570  42.265  1.00 23.73      BLGL
ATOM   1003  O    ALA  138     -5.896  -3.401  42.497  1.00 23.84      BLGL
ATOM   1004  N    LEU  139     -5.700  -5.288  41.280  1.00 21.33      BLGL
ATOM   1005  CA   LEU  139     -4.690  -4.729  40.402  1.00 22.61      BLGL
ATOM   1006  CB   LEU  139     -4.144  -5.806  39.460  1.00 21.44      BLGL
ATOM   1007  CG   LEU  139     -2.895  -5.411  38.656  1.00 21.68      BLGL
ATOM   1008  CD1  LEU  139     -2.111  -6.664  38.340  1.00 22.58      BLGL
ATOM   1009  CD2  LEU  139     -3.265  -4.658  37.383  1.00 17.55      BLGL
ATOM   1010  C    LEU  139     -5.280  -3.576  39.603  1.00 23.36      BLGL
ATOM   1011  O    LEU  139     -4.629  -2.550  39.401  1.00 23.02      BLGL
ATOM   1012  N    TYR  140     -6.513  -3.747  39.141  1.00 24.62      BLGL
ATOM   1013  CA   TYR  140     -7.176  -2.697  38.381  1.00 25.60      BLGL
ATOM   1014  CB   TYR  140     -8.514  -3.206  37.833  1.00 23.98      BLGL
ATOM   1015  CG   TYR  140     -9.494  -2.109  37.498  1.00 22.17      BLGL
ATOM   1016  CD1  TYR  140    -10.389  -1.634  38.452  1.00 25.15      BLGL
ATOM   1017  CE1  TYR  140    -11.259  -0.580  38.167  1.00 25.77      BLGL
ATOM   1018  CD2  TYR  140     -9.492  -1.508  36.247  1.00 22.26      BLGL
ATOM   1019  CE2  TYR  140    -10.353  -0.457  35.950  1.00 24.44      BLGL
ATOM   1020  CZ   TYR  140    -11.235   0.003  36.911  1.00 25.75      BLGL
ATOM   1021  OH   TYR  140    -12.096   1.036  36.615  1.00 25.22      BLGL
ATOM   1022  C    TYR  140     -7.393  -1.468  39.272  1.00 27.76      BLGL
ATOM   1023  O    TYR  140     -7.167  -0.335  38.845  1.00 26.59      BLGL
ATOM   1024  N    GLN  141     -7.828  -1.698  40.508  1.00 29.36      BLGL
ATOM   1025  CA   GLN  141     -8.061  -0.605  41.446  1.00 31.47      BLGL
ATOM   1026  CB   GLN  141     -8.645  -1.134  42.758  1.00 34.45      BLGL
ATOM   1027  CG   GLN  141    -10.105  -1.525  42.664  1.00 44.36      BLGL
ATOM   1028  CD   GLN  141    -11.015  -0.331  42.408  1.00 49.85      BLGL
ATOM   1029  OE1  GLN  141    -12.161  -0.487  41.957  1.00 52.06      BLGL
ATOM   1030  NE2  GLN  141    -10.515   0.870  42.707  1.00 49.83      BLGL
ATOM   1031  C    GLN  141     -6.782   0.154  41.751  1.00 29.93      BLGL
ATOM   1032  O    GLN  141     -6.751   1.387  41.698  1.00 28.20      BLGL
ATOM   1033  N    TYR  142     -5.730  -0.593  42.079  1.00 27.46      BLGL
ATOM   1034  CA   TYR  142     -4.445  -0.002  42.413  1.00 25.44      BLGL
ATOM   1035  CB   TYR  142     -3.426  -1.105  42.694  1.00 26.98      BLGL
ATOM   1036  CG   TYR  142     -2.025  -0.585  42.928  1.00 26.89      BLGL
ATOM   1037  CD1  TYR  142     -1.752   0.281  43.979  1.00 25.19      BLGL
ATOM   1038  CE1  TYR  142     -0.473   0.768  44.189  1.00 28.95      BLGL
ATOM   1039  CD2  TYR  142     -0.979  -0.950  42.088  1.00 27.59      BLGL
ATOM   1040  CE2  TYR  142      0.305  -0.468  42.287  1.00 29.43      BLGL
ATOM   1041  CZ   TYR  142      0.553   0.390  43.341  1.00 30.68      BLGL
ATOM   1042  OH   TYR  142      1.829   0.862  43.554  1.00 32.86      BLGL
ATOM   1043  C    TYR  142     -3.922   0.912  41.311  1.00 24.17      BLGL
ATOM   1044  O    TYR  142     -3.466   2.026  41.572  1.00 22.37      BLGL
ATOM   1045  N    THR  143     -3.988   0.432  40.076  1.00 23.95      BLGL
ATOM   1046  CA   THR  143     -3.518   1.205  38.941  1.00 24.20      BLGL
ATOM   1047  CB   THR  143     -3.626   0.397  37.649  1.00 22.46      BLGL
ATOM   1048  OG1  THR  143     -3.000  -0.875  37.838  1.00 19.33      BLGL
ATOM   1049  CG2  THR  143     -2.948   1.129  36.508  1.00 20.23      BLGL
ATOM   1050  C    THR  143     -4.361   2.459  38.803  1.00 25.95      BLGL
ATOM   1051  O    THR  143     -3.836   3.568  38.689  1.00 27.54      BLGL
ATOM   1052  N    LYS  144     -5.673   2.263  38.821  1.00 27.01      BLGL
ATOM   1053  CA   LYS  144     -6.636   3.346  38.690  1.00 28.79      BLGL
ATOM   1054  CB   LYS  144     -8.053   2.779  38.818  1.00 30.43      BLGL
ATOM   1055  CG   LYS  144     -9.167   3.787  38.626  1.00 32.32      BLGL
```

Fig. 4 cont.

```
ATOM   1056  CD   LYS  144    -9.391   4.123  37.167  1.00 35.17      BLGL
ATOM   1057  CE   LYS  144   -10.603   5.033  37.010  1.00 36.95      BLGL
ATOM   1058  NZ   LYS  144   -11.835   4.435  37.605  1.00 37.88      BLGL
ATOM   1059  C    LYS  144    -6.401   4.421  39.748  1.00 28.67      BLGL
ATOM   1060  O    LYS  144    -6.322   5.606  39.433  1.00 29.09      BLGL
ATOM   1061  N    GLN  145    -6.287   4.010  41.004  1.00 28.65      BLGL
ATOM   1062  CA   GLN  145    -6.062   4.969  42.075  1.00 31.28      BLGL
ATOM   1063  CB   GLN  145    -6.116   4.281  43.440  1.00 35.75      BLGL
ATOM   1064  CG   GLN  145    -7.463   3.632  43.756  1.00 45.00      BLGL
ATOM   1065  CD   GLN  145    -8.638   4.586  43.565  1.00 50.27      BLGL
ATOM   1066  OE1  GLN  145    -8.697   5.651  44.189  1.00 53.13      BLGL
ATOM   1067  NE2  GLN  145    -9.580   4.206  42.699  1.00 51.05      BLGL
ATOM   1068  C    GLN  145    -4.720   5.666  41.905  1.00 30.73      BLGL
ATOM   1069  O    GLN  145    -4.653   6.895  41.883  1.00 31.69      BLGL
ATOM   1070  N    SER  146    -3.655   4.880  41.778  1.00 28.68      BLGL
ATOM   1071  CA   SER  146    -2.315   5.429  41.614  1.00 27.00      BLGL
ATOM   1072  CB   SER  146    -1.326   4.319  41.276  1.00 26.10      BLGL
ATOM   1073  OG   SER  146    -1.175   3.432  42.363  1.00 25.05      BLGL
ATOM   1074  C    SER  146    -2.258   6.485  40.529  1.00 26.20      BLGL
ATOM   1075  O    SER  146    -1.733   7.576  40.739  1.00 24.18      BLGL
ATOM   1076  N    LEU  147    -2.793   6.148  39.363  1.00 26.95      BLGL
ATOM   1077  CA   LEU  147    -2.798   7.069  38.240  1.00 28.50      BLGL
ATOM   1078  CB   LEU  147    -3.399   6.386  37.004  1.00 29.76      BLGL
ATOM   1079  CG   LEU  147    -2.403   5.891  35.949  1.00 29.50      BLGL
ATOM   1080  CD1  LEU  147    -1.214   5.237  36.616  1.00 31.84      BLGL
ATOM   1081  CD2  LEU  147    -3.098   4.918  35.010  1.00 31.26      BLGL
ATOM   1082  C    LEU  147    -3.554   8.352  38.563  1.00 28.49      BLGL
ATOM   1083  O    LEU  147    -3.059   9.448  38.291  1.00 26.93      BLGL
ATOM   1084  N    LYS  148    -4.740   8.227  39.156  1.00 29.43      BLGL
ATOM   1085  CA   LYS  148    -5.520   9.412  39.485  1.00 32.08      BLGL
ATOM   1086  CB   LYS  148    -6.897   9.041  40.039  1.00 35.85      BLGL
ATOM   1087  CG   LYS  148    -7.879  10.208  39.955  1.00 44.89      BLGL
ATOM   1088  CD   LYS  148    -9.276   9.854  40.430  1.00 48.80      BLGL
ATOM   1089  CE   LYS  148    -9.319   9.641  41.939  1.00 53.72      BLGL
ATOM   1090  NZ   LYS  148    -8.537   8.451  42.388  1.00 55.41      BLGL
ATOM   1091  C    LYS  148    -4.772  10.277  40.488  1.00 30.09      BLGL
ATOM   1092  O    LYS  148    -4.833  11.502  40.419  1.00 30.55      BLGL
ATOM   1093  N    ALA  149    -4.063   9.636  41.412  1.00 27.72      BLGL
ATOM   1094  CA   ALA  149    -3.279  10.352  42.411  1.00 27.90      BLGL
ATOM   1095  CB   ALA  149    -2.623   9.367  43.368  1.00 26.54      BLGL
ATOM   1096  C    ALA  149    -2.208  11.196  41.720  1.00 28.02      BLGL
ATOM   1097  O    ALA  149    -1.981  12.357  42.075  1.00 27.39      BLGL
ATOM   1098  N    MET  150    -1.547  10.607  40.729  1.00 27.66      BLGL
ATOM   1099  CA   MET  150    -0.511  11.319  39.996  1.00 28.87      BLGL
ATOM   1100  CB   MET  150     0.228  10.357  39.063  1.00 28.84      BLGL
ATOM   1101  CG   MET  150     1.084   9.358  39.828  1.00 31.73      BLGL
ATOM   1102  SD   MET  150     2.122   8.307  38.803  1.00 34.53      BLGL
ATOM   1103  CE   MET  150     1.218   6.808  38.827  1.00 36.46      BLGL
ATOM   1104  C    MET  150    -1.101  12.491  39.219  1.00 28.60      BLGL
ATOM   1105  O    MET  150    -0.518  13.575  39.167  1.00 25.71      BLGL
ATOM   1106  N    LYS  151    -2.269  12.274  38.626  1.00 30.33      BLGL
ATOM   1107  CA   LYS  151    -2.939  13.327  37.871  1.00 31.72      BLGL
ATOM   1108  CB   LYS  151    -4.229  12.793  37.254  1.00 32.47      BLGL
ATOM   1109  CG   LYS  151    -4.036  12.005  35.980  1.00 35.00      BLGL
ATOM   1110  CD   LYS  151    -3.833  12.927  34.789  1.00 38.64      BLGL
ATOM   1111  CE   LYS  151    -3.939  12.159  33.477  1.00 40.97      BLGL
ATOM   1112  NZ   LYS  151    -3.816  13.050  32.295  1.00 40.80      BLGL
ATOM   1113  C    LYS  151    -3.261  14.501  38.787  1.00 31.68      BLGL
ATOM   1114  O    LYS  151    -3.008  15.655  38.442  1.00 32.97      BLGL
ATOM   1115  N    ALA  152    -3.823  14.199  39.953  1.00 31.23      BLGL
ATOM   1116  CA   ALA  152    -4.176  15.228  40.921  1.00 30.30      BLGL
ATOM   1117  CB   ALA  152    -4.759  14.590  42.185  1.00 29.61      BLGL
ATOM   1118  C    ALA  152    -2.952  16.057  41.273  1.00 29.37      BLGL
ATOM   1119  O    ALA  152    -3.066  17.247  41.544  1.00 30.53      BLGL
ATOM   1120  N    ALA  153    -1.783  15.425  41.272  1.00 29.04      BLGL
ATOM   1121  CA   ALA  153    -0.543  16.124  41.596  1.00 29.10      BLGL
```

Fig. 4 cont.

```
ATOM   1122  CB   ALA  153      0.517  15.134  42.032  1.00 30.13      BLGL
ATOM   1123  C    ALA  153     -0.056  16.910  40.391  1.00 29.10      BLGL
ATOM   1124  O    ALA  153      0.990  17.561  40.435  1.00 29.45      BLGL
ATOM   1125  N    GLY  154     -0.824  16.835  39.310  1.00 28.65      BLGL
ATOM   1126  CA   GLY  154     -0.482  17.557  38.101  1.00 26.76      BLGL
ATOM   1127  C    GLY  154      0.711  17.017  37.340  1.00 26.93      BLGL
ATOM   1128  O    GLY  154      1.406  17.770  36.661  1.00 25.28      BLGL
ATOM   1129  N    ILE  155      0.948  15.713  37.444  1.00 27.10      BLGL
ATOM   1130  CA   ILE  155      2.064  15.080  36.745  1.00 25.61      BLGL
ATOM   1131  CB   ILE  155      2.532  13.809  37.496  1.00 24.73      BLGL
ATOM   1132  CG2  ILE  155      3.661  13.118  36.724  1.00 23.73      BLGL
ATOM   1133  CG1  ILE  155      2.985  14.196  38.907  1.00 22.31      BLGL
ATOM   1134  CD1  ILE  155      3.188  13.018  39.842  1.00 21.74      BLGL
ATOM   1135  C    ILE  155      1.672  14.723  35.306  1.00 24.09      BLGL
ATOM   1136  O    ILE  155      0.568  14.240  35.056  1.00 25.01      BLGL
ATOM   1137  N    ASP  156      2.581  14.975  34.369  1.00 21.70      BLGL
ATOM   1138  CA   ASP  156      2.354  14.695  32.959  1.00 23.92      BLGL
ATOM   1139  CB   ASP  156      3.172  15.657  32.089  1.00 26.46      BLGL
ATOM   1140  CG   ASP  156      2.889  15.486  30.602  1.00 30.77      BLGL
ATOM   1141  OD1  ASP  156      3.579  16.140  29.792  1.00 33.81      BLGL
ATOM   1142  OD2  ASP  156      1.976  14.706  30.239  1.00 32.30      BLGL
ATOM   1143  C    ASP  156      2.757  13.261  32.644  1.00 23.58      BLGL
ATOM   1144  O    ASP  156      3.904  12.986  32.319  1.00 26.10      BLGL
ATOM   1145  N    ILE  157      1.805  12.348  32.750  1.00 22.55      BLGL
ATOM   1146  CA   ILE  157      2.062  10.945  32.484  1.00 21.98      BLGL
ATOM   1147  CB   ILE  157      1.070  10.058  33.254  1.00 22.84      BLGL
ATOM   1148  CG2  ILE  157      1.368   8.595  32.990  1.00 18.93      BLGL
ATOM   1149  CG1  ILE  157      1.137  10.385  34.744  1.00 23.81      BLGL
ATOM   1150  CD1  ILE  157     -0.082   9.922  35.514  1.00 26.52      BLGL
ATOM   1151  C    ILE  157      1.894  10.675  30.997  1.00 20.48      BLGL
ATOM   1152  O    ILE  157      0.819  10.885  30.443  1.00 22.51      BLGL
ATOM   1153  N    GLY  158      2.950  10.207  30.349  1.00 18.57      BLGL
ATOM   1154  CA   GLY  158      2.847   9.927  28.935  1.00 16.55      BLGL
ATOM   1155  C    GLY  158      2.758   8.445  28.632  1.00 17.26      BLGL
ATOM   1156  O    GLY  158      2.227   8.042  27.599  1.00 17.93      BLGL
ATOM   1157  N    MET  159      3.245   7.622  29.550  1.00 18.71      BLGL
ATOM   1158  CA   MET  159      3.260   6.186  29.322  1.00 19.00      BLGL
ATOM   1159  CB   MET  159      4.559   5.834  28.588  1.00 17.91      BLGL
ATOM   1160  CG   MET  159      4.563   4.506  27.872  1.00 24.08      BLGL
ATOM   1161  SD   MET  159      6.139   4.187  27.000  1.00 30.17      BLGL
ATOM   1162  CE   MET  159      6.095   5.442  25.740  1.00 26.74      BLGL
ATOM   1163  C    MET  159      3.156   5.395  30.630  1.00 19.17      BLGL
ATOM   1164  O    MET  159      3.573   5.855  31.696  1.00 16.99      BLGL
ATOM   1165  N    VAL  160      2.579   4.204  30.543  1.00 18.21      BLGL
ATOM   1166  CA   VAL  160      2.450   3.345  31.707  1.00 17.42      BLGL
ATOM   1167  CB   VAL  160      1.002   3.285  32.245  1.00 17.75      BLGL
ATOM   1168  CG1  VAL  160      0.920   2.287  33.384  1.00 16.21      BLGL
ATOM   1169  CG2  VAL  160      0.570   4.654  32.739  1.00 18.60      BLGL
ATOM   1170  C    VAL  160      2.891   1.944  31.332  1.00 17.12      BLGL
ATOM   1171  O    VAL  160      2.516   1.406  30.292  1.00 17.78      BLGL
ATOM   1172  N    GLN  161      3.704   1.360  32.192  1.00 17.31      BLGL
ATOM   1173  CA   GLN  161      4.211   0.028  31.963  1.00 17.58      BLGL
ATOM   1174  CB   GLN  161      5.709   0.018  32.272  1.00 17.55      BLGL
ATOM   1175  CG   GLN  161      6.446  -1.213  31.826  1.00 16.31      BLGL
ATOM   1176  CD   GLN  161      7.935  -1.106  32.056  1.00 16.53      BLGL
ATOM   1177  OE1  GLN  161      8.570  -0.132  31.641  1.00 17.05      BLGL
ATOM   1178  NE2  GLN  161      8.508  -2.114  32.707  1.00 12.70      BLGL
ATOM   1179  C    GLN  161      3.439  -0.903  32.893  1.00 16.74      BLGL
ATOM   1180  O    GLN  161      3.455  -0.719  34.106  1.00 17.03      BLGL
ATOM   1181  N    VAL  162      2.736  -1.882  32.330  1.00 14.93      BLGL
ATOM   1182  CA   VAL  162      1.975  -2.818  33.153  1.00 14.33      BLGL
ATOM   1183  CB   VAL  162      0.648  -3.209  32.455  1.00 14.98      BLGL
ATOM   1184  CG1  VAL  162     -0.143  -4.195  33.304  1.00 12.90      BLGL
ATOM   1185  CG2  VAL  162     -0.176  -1.964  32.213  1.00 12.73      BLGL
ATOM   1186  C    VAL  162      2.840  -4.051  33.411  1.00 15.01      BLGL
ATOM   1187  O    VAL  162      2.763  -5.046  32.691  1.00 15.57      BLGL
```

Fig. 4 cont.

| ATOM | 1188 | N   | GLY | 163 |  3.674 |  -3.965 | 34.444 | 1.00 | 13.93 | BLGL |
| ATOM | 1189 | CA  | GLY | 163 |  4.568 |  -5.062 | 34.765 | 1.00 | 16.33 | BLGL |
| ATOM | 1190 | C   | GLY | 163 |  6.001 |  -4.755 | 34.350 | 1.00 | 17.03 | BLGL |
| ATOM | 1191 | O   | GLY | 163 |  6.239 |  -3.875 | 33.521 | 1.00 | 17.31 | BLGL |
| ATOM | 1192 | N   | ASN | 164 |  6.958 |  -5.485 | 34.917 | 1.00 | 17.42 | BLGL |
| ATOM | 1193 | CA  | ASN | 164 |  8.374 |  -5.274 | 34.628 | 1.00 | 16.23 | BLGL |
| ATOM | 1194 | CB  | ASN | 164 |  9.035 |  -4.629 | 35.845 | 1.00 | 13.47 | BLGL |
| ATOM | 1195 | CG  | ASN | 164 | 10.413 |  -4.117 | 35.556 | 1.00 | 11.45 | BLGL |
| ATOM | 1196 | OD1 | ASN | 164 | 10.581 |  -3.019 | 35.026 | 1.00 | 13.59 | BLGL |
| ATOM | 1197 | ND2 | ASN | 164 | 11.416 |  -4.912 | 35.889 | 1.00 | 11.01 | BLGL |
| ATOM | 1198 | C   | ASN | 164 |  9.051 |  -6.614 | 34.315 | 1.00 | 17.48 | BLGL |
| ATOM | 1199 | O   | ASN | 164 |  9.131 |  -7.490 | 35.175 | 1.00 | 19.59 | BLGL |
| ATOM | 1200 | N   | GLU | 165 |  9.537 |  -6.765 | 33.085 | 1.00 | 17.58 | BLGL |
| ATOM | 1201 | CA  | GLU | 165 | 10.197 |  -7.998 | 32.643 | 1.00 | 17.54 | BLGL |
| ATOM | 1202 | CB  | GLU | 165 | 11.605 |  -8.093 | 33.244 | 1.00 | 16.33 | BLGL |
| ATOM | 1203 | CG  | GLU | 165 | 12.467 |  -6.875 | 32.940 | 1.00 | 17.40 | BLGL |
| ATOM | 1204 | CD  | GLU | 165 | 13.938 |  -7.095 | 33.223 | 1.00 | 17.97 | BLGL |
| ATOM | 1205 | OE1 | GLU | 165 | 14.260 |  -7.739 | 34.236 | 1.00 | 20.07 | BLGL |
| ATOM | 1206 | OE2 | GLU | 165 | 14.783 |  -6.613 | 32.442 | 1.00 | 15.79 | BLGL |
| ATOM | 1207 | C   | GLU | 165 |  9.372 |  -9.248 | 32.982 | 1.00 | 16.57 | BLGL |
| ATOM | 1208 | O   | GLU | 165 |  9.875 | -10.221 | 33.534 | 1.00 | 14.22 | BLGL |
| ATOM | 1209 | N   | THR | 166 |  8.094 |  -9.196 | 32.618 | 1.00 | 16.92 | BLGL |
| ATOM | 1210 | CA  | THR | 166 |  7.146 | -10.267 | 32.860 | 1.00 | 15.12 | BLGL |
| ATOM | 1211 | CB  | THR | 166 |  5.723 |  -9.713 | 32.782 | 1.00 | 17.38 | BLGL |
| ATOM | 1212 | OG1 | THR | 166 |  5.514 |  -9.130 | 31.490 | 1.00 | 16.95 | BLGL |
| ATOM | 1213 | CG2 | THR | 166 |  5.511 |  -8.629 | 33.850 | 1.00 | 17.63 | BLGL |
| ATOM | 1214 | C   | THR | 166 |  7.304 | -11.411 | 31.860 | 1.00 | 15.92 | BLGL |
| ATOM | 1215 | O   | THR | 166 |  6.380 | -11.741 | 31.131 | 1.00 | 13.18 | BLGL |
| ATOM | 1216 | N   | ASN | 167 |  8.488 | -12.013 | 31.835 | 1.00 | 18.90 | BLGL |
| ATOM | 1217 | CA  | ASN | 167 |  8.775 | -13.122 | 30.933 | 1.00 | 19.84 | BLGL |
| ATOM | 1218 | CB  | ASN | 167 | 10.277 | -13.399 | 30.885 | 1.00 | 19.56 | BLGL |
| ATOM | 1219 | CG  | ASN | 167 | 11.014 | -12.455 | 29.974 | 1.00 | 19.68 | BLGL |
| ATOM | 1220 | OD1 | ASN | 167 | 10.597 | -11.320 | 29.774 | 1.00 | 21.70 | BLGL |
| ATOM | 1221 | ND2 | ASN | 167 | 12.132 | -12.912 | 29.429 | 1.00 | 19.90 | BLGL |
| ATOM | 1222 | C   | ASN | 167 |  8.074 | -14.397 | 31.343 | 1.00 | 20.80 | BLGL |
| ATOM | 1223 | O   | ASN | 167 |  7.670 | -15.175 | 30.489 | 1.00 | 22.87 | BLGL |
| ATOM | 1224 | N   | GLY | 168 |  7.936 | -14.615 | 32.647 | 1.00 | 22.03 | BLGL |
| ATOM | 1225 | CA  | GLY | 168 |  7.302 | -15.833 | 33.114 | 1.00 | 24.61 | BLGL |
| ATOM | 1226 | C   | GLY | 168 |  6.216 | -15.699 | 34.164 | 1.00 | 26.99 | BLGL |
| ATOM | 1227 | O   | GLY | 168 |  5.663 | -16.702 | 34.620 | 1.00 | 28.98 | BLGL |
| ATOM | 1228 | N   | GLY | 169 |  5.898 | -14.478 | 34.562 | 1.00 | 26.63 | BLGL |
| ATOM | 1229 | CA  | GLY | 169 |  4.865 | -14.319 | 35.558 | 1.00 | 25.86 | BLGL |
| ATOM | 1230 | C   | GLY | 169 |  4.516 | -12.878 | 35.831 | 1.00 | 27.02 | BLGL |
| ATOM | 1231 | O   | GLY | 169 |  5.166 | -11.959 | 35.334 | 1.00 | 28.44 | BLGL |
| ATOM | 1232 | N   | LEU | 170 |  3.467 | -12.691 | 36.622 | 1.00 | 26.37 | BLGL |
| ATOM | 1233 | CA  | LEU | 170 |  2.996 | -11.371 | 37.005 | 1.00 | 23.73 | BLGL |
| ATOM | 1234 | CB  | LEU | 170 |  2.164 | -10.751 | 35.875 | 1.00 | 20.57 | BLGL |
| ATOM | 1235 | CG  | LEU | 170 |  1.474 |  -9.415 | 36.185 | 1.00 | 21.09 | BLGL |
| ATOM | 1236 | CD1 | LEU | 170 |  2.470 |  -8.395 | 36.723 | 1.00 | 21.42 | BLGL |
| ATOM | 1237 | CD2 | LEU | 170 |  0.811 |  -8.894 | 34.934 | 1.00 | 20.49 | BLGL |
| ATOM | 1238 | C   | LEU | 170 |  2.158 | -11.504 | 38.272 | 1.00 | 23.90 | BLGL |
| ATOM | 1239 | O   | LEU | 170 |  1.222 | -12.305 | 38.326 | 1.00 | 22.71 | BLGL |
| ATOM | 1240 | N   | ALA | 171 |  2.522 | -10.731 | 39.292 | 1.00 | 23.01 | BLGL |
| ATOM | 1241 | CA  | ALA | 171 |  1.816 | -10.724 | 40.567 | 1.00 | 22.14 | BLGL |
| ATOM | 1242 | CB  | ALA | 171 |  0.544 |  -9.911 | 40.433 | 1.00 | 22.04 | BLGL |
| ATOM | 1243 | C   | ALA | 171 |  1.488 | -12.114 | 41.109 | 1.00 | 23.55 | BLGL |
| ATOM | 1244 | O   | ALA | 171 |  0.354 | -12.382 | 41.512 | 1.00 | 23.66 | BLGL |
| ATOM | 1245 | N   | GLY | 172 |  2.479 | -12.996 | 41.122 | 1.00 | 22.96 | BLGL |
| ATOM | 1246 | CA  | GLY | 172 |  2.259 | -14.337 | 41.632 | 1.00 | 25.97 | BLGL |
| ATOM | 1247 | C   | GLY | 172 |  1.592 | -15.299 | 40.666 | 1.00 | 27.36 | BLGL |
| ATOM | 1248 | O   | GLY | 172 |  1.412 | -16.474 | 40.980 | 1.00 | 27.94 | BLGL |
| ATOM | 1249 | N   | GLU | 173 |  1.225 | -14.808 | 39.490 | 1.00 | 28.30 | BLGL |
| ATOM | 1250 | CA  | GLU | 173 |  0.584 | -15.643 | 38.487 | 1.00 | 29.90 | BLGL |
| ATOM | 1251 | CB  | GLU | 173 | -0.540 | -14.858 | 37.815 | 1.00 | 30.87 | BLGL |
| ATOM | 1252 | CG  | GLU | 173 | -1.888 | -15.557 | 37.824 | 1.00 | 33.63 | BLGL |
| ATOM | 1253 | CD  | GLU | 173 | -2.308 | -16.014 | 39.208 | 1.00 | 34.41 | BLGL |

Fig. 4 cont.

```
ATOM   1254  OE1 GLU   173      -2.334 -15.181  40.139  1.00 34.20        BLGL
ATOM   1255  OE2 GLU   173      -2.618 -17.214  39.359  1.00 34.57        BLGL
ATOM   1256  C   GLU   173       1.619 -16.084  37.450  1.00 30.77        BLGL
ATOM   1257  O   GLU   173       2.481 -15.302  37.053  1.00 31.69        BLGL
ATOM   1258  N   THR   174       1.539 -17.338  37.017  1.00 30.71        BLGL
ATOM   1259  CA  THR   174       2.484 -17.864  36.038  1.00 30.81        BLGL
ATOM   1260  CB  THR   174       3.366 -18.975  36.661  1.00 30.70        BLGL
ATOM   1261  OG1 THR   174       2.533 -20.027  37.167  1.00 33.92        BLGL
ATOM   1262  CG2 THR   174       4.201 -18.416  37.792  1.00 29.44        BLGL
ATOM   1263  C   THR   174       1.801 -18.426  34.792  1.00 31.23        BLGL
ATOM   1264  O   THR   174       2.470 -18.868  33.857  1.00 31.14        BLGL
ATOM   1265  N   ASP   175       0.473 -18.409  34.779  1.00 31.31        BLGL
ATOM   1266  CA  ASP   175      -0.276 -18.923  33.640  1.00 31.53        BLGL
ATOM   1267  CB  ASP   175      -1.565 -19.589  34.120  1.00 35.17        BLGL
ATOM   1268  CG  ASP   175      -2.447 -20.030  32.972  1.00 38.71        BLGL
ATOM   1269  OD1 ASP   175      -1.925 -20.654  32.023  1.00 39.79        BLGL
ATOM   1270  OD2 ASP   175      -3.665 -19.758  33.022  1.00 42.47        BLGL
ATOM   1271  C   ASP   175      -0.605 -17.796  32.674  1.00 30.63        BLGL
ATOM   1272  O   ASP   175      -1.363 -16.890  33.016  1.00 30.64        BLGL
ATOM   1273  N   TRP   176      -0.055 -17.861  31.463  1.00 27.62        BLGL
ATOM   1274  CA  TRP   176      -0.281 -16.806  30.480  1.00 27.93        BLGL
ATOM   1275  CB  TRP   176       0.403 -17.147  29.157  1.00 24.63        BLGL
ATOM   1276  CG  TRP   176       1.882 -16.910  29.193  1.00 26.55        BLGL
ATOM   1277  CD2 TRP   176       2.557 -15.666  28.966  1.00 27.36        BLGL
ATOM   1278  CE2 TRP   176       3.940 -15.900  29.148  1.00 27.27        BLGL
ATOM   1279  CE3 TRP   176       2.128 -14.375  28.625  1.00 27.01        BLGL
ATOM   1280  CD1 TRP   176       2.855 -17.820  29.498  1.00 26.56        BLGL
ATOM   1281  NE1 TRP   176       4.094 -17.222  29.473  1.00 26.37        BLGL
ATOM   1282  CZ2 TRP   176       4.899 -14.887  29.004  1.00 25.56        BLGL
ATOM   1283  CZ3 TRP   176       3.085 -13.365  28.482  1.00 25.94        BLGL
ATOM   1284  CH2 TRP   176       4.453 -13.631  28.671  1.00 25.57        BLGL
ATOM   1285  C   TRP   176      -1.739 -16.427  30.234  1.00 29.80        BLGL
ATOM   1286  O   TRP   176      -2.033 -15.289  29.857  1.00 30.42        BLGL
ATOM   1287  N   ALA   177      -2.656 -17.368  30.441  1.00 31.37        BLGL
ATOM   1288  CA  ALA   177      -4.073 -17.077  30.249  1.00 30.31        BLGL
ATOM   1289  CB  ALA   177      -4.889 -18.354  30.339  1.00 30.40        BLGL
ATOM   1290  C   ALA   177      -4.500 -16.104  31.342  1.00 31.32        BLGL
ATOM   1291  O   ALA   177      -5.199 -15.124  31.085  1.00 31.10        BLGL
ATOM   1292  N   LYS   178      -4.070 -16.379  32.569  1.00 30.35        BLGL
ATOM   1293  CA  LYS   178      -4.401 -15.507  33.680  1.00 31.58        BLGL
ATOM   1294  CB  LYS   178      -4.181 -16.235  35.008  1.00 33.69        BLGL
ATOM   1295  CG  LYS   178      -5.114 -17.410  35.234  1.00 37.35        BLGL
ATOM   1296  CD  LYS   178      -4.994 -17.911  36.664  1.00 43.39        BLGL
ATOM   1297  CE  LYS   178      -5.780 -19.196  36.897  1.00 45.38        BLGL
ATOM   1298  NZ  LYS   178      -5.125 -20.370  36.252  1.00 47.94        BLGL
ATOM   1299  C   LYS   178      -3.568 -14.217  33.637  1.00 30.97        BLGL
ATOM   1300  O   LYS   178      -4.040 -13.153  34.043  1.00 31.65        BLGL
ATOM   1301  N   MET   179      -2.333 -14.306  33.149  1.00 29.06        BLGL
ATOM   1302  CA  MET   179      -1.485 -13.126  33.062  1.00 26.50        BLGL
ATOM   1303  CB  MET   179      -0.110 -13.481  32.521  1.00 27.08        BLGL
ATOM   1304  CG  MET   179       0.789 -14.179  33.507  1.00 29.22        BLGL
ATOM   1305  SD  MET   179       2.433 -14.378  32.801  1.00 32.04        BLGL
ATOM   1306  CE  MET   179       2.432 -16.100  32.529  1.00 37.19        BLGL
ATOM   1307  C   MET   179      -2.122 -12.106  32.141  1.00 25.11        BLGL
ATOM   1308  O   MET   179      -2.206 -10.924  32.478  1.00 24.38        BLGL
ATOM   1309  N   SER   180      -2.566 -12.572  30.977  1.00 23.38        BLGL
ATOM   1310  CA  SER   180      -3.199 -11.707  29.985  1.00 23.70        BLGL
ATOM   1311  CB  SER   180      -3.725 -12.533  28.812  1.00 23.12        BLGL
ATOM   1312  OG  SER   180      -2.691 -13.297  28.223  1.00 23.86        BLGL
ATOM   1313  C   SER   180      -4.348 -10.933  30.605  1.00 24.08        BLGL
ATOM   1314  O   SER   180      -4.552  -9.756  30.313  1.00 23.86        BLGL
ATOM   1315  N   GLN   181      -5.101 -11.601  31.467  1.00 25.04        BLGL
ATOM   1316  CA  GLN   181      -6.226 -10.965  32.129  1.00 27.04        BLGL
ATOM   1317  CB  GLN   181      -7.064 -12.009  32.864  1.00 29.17        BLGL
ATOM   1318  CG  GLN   181      -7.820 -12.940  31.932  1.00 33.08        BLGL
ATOM   1319  CD  GLN   181      -8.761 -13.860  32.675  1.00 35.97        BLGL
```

Fig. 4 cont.

```
ATOM   1320  OE1 GLN   181      -8.558 -15.077  32.724  1.00 36.76       BLGL
ATOM   1321  NE2 GLN   181      -9.801 -13.280  33.269  1.00 37.03       BLGL
ATOM   1322  C   GLN   181      -5.774  -9.874  33.091  1.00 27.11       BLGL
ATOM   1323  O   GLN   181      -6.459  -8.864  33.252  1.00 28.46       BLGL
ATOM   1324  N   LEU   182      -4.628 -10.080  33.737  1.00 26.80       BLGL
ATOM   1325  CA  LEU   182      -4.086  -9.081  34.655  1.00 25.48       BLGL
ATOM   1326  CB  LEU   182      -2.932  -9.665  35.472  1.00 25.40       BLGL
ATOM   1327  CG  LEU   182      -3.296 -10.736  36.504  1.00 27.62       BLGL
ATOM   1328  CD1 LEU   182      -2.035 -11.268  37.156  1.00 27.60       BLGL
ATOM   1329  CD2 LEU   182      -4.229 -10.149  37.556  1.00 26.92       BLGL
ATOM   1330  C   LEU   182      -3.591  -7.899  33.823  1.00 24.10       BLGL
ATOM   1331  O   LEU   182      -3.739  -6.740  34.211  1.00 23.49       BLGL
ATOM   1332  N   PHE   183      -3.000  -8.211  32.675  1.00 21.91       BLGL
ATOM   1333  CA  PHE   183      -2.512  -7.187  31.770  1.00 22.28       BLGL
ATOM   1334  CB  PHE   183      -1.888  -7.826  30.528  1.00 21.38       BLGL
ATOM   1335  CG  PHE   183      -0.500  -8.347  30.737  1.00 20.19       BLGL
ATOM   1336  CD1 PHE   183      -0.064  -9.469  30.042  1.00 20.38       BLGL
ATOM   1337  CD2 PHE   183       0.385  -7.704  31.597  1.00 22.77       BLGL
ATOM   1338  CE1 PHE   183       1.236  -9.953  30.192  1.00 20.30       BLGL
ATOM   1339  CE2 PHE   183       1.693  -8.174  31.761  1.00 24.59       BLGL
ATOM   1340  CZ  PHE   183       2.120  -9.305  31.054  1.00 23.28       BLGL
ATOM   1341  C   PHE   183      -3.668  -6.283  31.348  1.00 22.44       BLGL
ATOM   1342  O   PHE   183      -3.548  -5.059  31.384  1.00 22.23       BLGL
ATOM   1343  N   ASN   184      -4.792  -6.881  30.954  1.00 22.00       BLGL
ATOM   1344  CA  ASN   184      -5.939  -6.087  30.533  1.00 20.53       BLGL
ATOM   1345  CB  ASN   184      -7.012  -6.964  29.895  1.00 20.92       BLGL
ATOM   1346  CG  ASN   184      -6.677  -7.345  28.474  1.00 21.95       BLGL
ATOM   1347  OD1 ASN   184      -6.162  -6.535  27.708  1.00 24.93       BLGL
ATOM   1348  ND2 ASN   184      -6.983  -8.579  28.108  1.00 26.02       BLGL
ATOM   1349  C   ASN   184      -6.538  -5.293  31.679  1.00 17.99       BLGL
ATOM   1350  O   ASN   184      -7.053  -4.199  31.474  1.00 18.30       BLGL
ATOM   1351  N   ALA   185      -6.458  -5.841  32.884  1.00 16.83       BLGL
ATOM   1352  CA  ALA   185      -6.976  -5.163  34.066  1.00 18.27       BLGL
ATOM   1353  CB  ALA   185      -6.815  -6.048  35.294  1.00 16.14       BLGL
ATOM   1354  C   ALA   185      -6.215  -3.857  34.261  1.00 18.87       BLGL
ATOM   1355  O   ALA   185      -6.812  -2.795  34.422  1.00 17.89       BLGL
ATOM   1356  N   GLY   186      -4.888  -3.945  34.244  1.00 20.07       BLGL
ATOM   1357  CA  GLY   186      -4.073  -2.756  34.409  1.00 19.75       BLGL
ATOM   1358  C   GLY   186      -4.273  -1.834  33.226  1.00 19.07       BLGL
ATOM   1359  O   GLY   186      -4.367  -0.620  33.373  1.00 20.22       BLGL
ATOM   1360  N   SER   187      -4.345  -2.424  32.042  1.00 18.72       BLGL
ATOM   1361  CA  SER   187      -4.534  -1.664  30.819  1.00 18.78       BLGL
ATOM   1362  CB  SER   187      -4.570  -2.618  29.627  1.00 19.99       BLGL
ATOM   1363  OG  SER   187      -4.606  -1.903  28.409  1.00 22.89       BLGL
ATOM   1364  C   SER   187      -5.840  -0.877  30.897  1.00 20.30       BLGL
ATOM   1365  O   SER   187      -5.879   0.311  30.582  1.00 20.23       BLGL
ATOM   1366  N   GLN   188      -6.903  -1.554  31.325  1.00 19.43       BLGL
ATOM   1367  CA  GLN   188      -8.233  -0.960  31.465  1.00 20.10       BLGL
ATOM   1368  CB  GLN   188      -9.192  -1.990  32.093  1.00 21.27       BLGL
ATOM   1369  CG  GLN   188     -10.592  -1.480  32.439  1.00 24.00       BLGL
ATOM   1370  CD  GLN   188     -11.358  -0.973  31.228  1.00 29.54       BLGL
ATOM   1371  OE1 GLN   188     -11.546  -1.695  30.242  1.00 33.67       BLGL
ATOM   1372  NE2 GLN   188     -11.808   0.274  31.295  1.00 28.21       BLGL
ATOM   1373  C   GLN   188      -8.191   0.303  32.322  1.00 20.12       BLGL
ATOM   1374  O   GLN   188      -8.779   1.322  31.984  1.00 19.92       BLGL
ATOM   1375  N   ALA   189      -7.493   0.227  33.442  1.00 20.06       BLGL
ATOM   1376  CA  ALA   189      -7.383   1.366  34.329  1.00 19.56       BLGL
ATOM   1377  CB  ALA   189      -6.587   0.982  35.563  1.00 18.86       BLGL
ATOM   1378  C   ALA   189      -6.728   2.546  33.626  1.00 19.66       BLGL
ATOM   1379  O   ALA   189      -7.150   3.681  33.805  1.00 20.48       BLGL
ATOM   1380  N   VAL   190      -5.697   2.273  32.831  1.00 19.85       BLGL
ATOM   1381  CA  VAL   190      -4.984   3.324  32.108  1.00 21.68       BLGL
ATOM   1382  CB  VAL   190      -3.717   2.755  31.378  1.00 21.13       BLGL
ATOM   1383  CG1 VAL   190      -2.955   3.875  30.675  1.00 17.97       BLGL
ATOM   1384  CG2 VAL   190      -2.809   2.069  32.376  1.00 18.02       BLGL
ATOM   1385  C   VAL   190      -5.922   3.966  31.087  1.00 22.56       BLGL
```

Fig. 4 cont.

```
ATOM   1386  O    VAL  190      -6.041    5.190   31.007  1.00 21.59           BLGL
ATOM   1387  N    ARG  191      -6.590    3.122   30.311  1.00 24.93           BLGL
ATOM   1388  CA   ARG  191      -7.528    3.577   29.297  1.00 24.90           BLGL
ATOM   1389  CB   ARG  191      -8.199    2.375   28.640  1.00 22.96           BLGL
ATOM   1390  CG   ARG  191      -7.687    2.059   27.236  1.00 25.30           BLGL
ATOM   1391  CD   ARG  191      -6.416    1.230   27.171  1.00 24.11           BLGL
ATOM   1392  NE   ARG  191      -5.369    1.936   26.503  1.00 24.46           BLGL
ATOM   1393  CZ   ARG  191      -4.581    1.653   25.474  1.00 21.34           BLGL
ATOM   1394  NH1  ARG  191      -3.733    2.613   25.208  1.00 22.37           BLGL
ATOM   1395  NH2  ARG  191      -4.584    0.551   24.731  1.00 21.45           BLGL
ATOM   1396  C    ARG  191      -8.590    4.492   29.892  1.00 25.14           BLGL
ATOM   1397  O    ARG  191      -8.904    5.535   29.334  1.00 27.85           BLGL
ATOM   1398  N    GLU  192      -9.145    4.098   31.026  1.00 25.90           BLGL
ATOM   1399  CA   GLU  192     -10.170    4.895   31.683  1.00 28.14           BLGL
ATOM   1400  CB   GLU  192     -10.761    4.129   32.865  1.00 28.90           BLGL
ATOM   1401  CG   GLU  192     -11.776    3.079   32.494  1.00 31.91           BLGL
ATOM   1402  CD   GLU  192     -12.200    2.266   33.697  1.00 32.43           BLGL
ATOM   1403  OE1  GLU  192     -12.359    2.874   34.772  1.00 28.80           BLGL
ATOM   1404  OE2  GLU  192     -12.378    1.033   33.569  1.00 34.08           BLGL
ATOM   1405  C    GLU  192      -9.630    6.223   32.190  1.00 28.73           BLGL
ATOM   1406  O    GLU  192     -10.352    7.219   32.278  1.00 31.92           BLGL
ATOM   1407  N    THR  193      -8.355    6.237   32.541  1.00 27.87           BLGL
ATOM   1408  CA   THR  193      -7.741    7.445   33.064  1.00 26.29           BLGL
ATOM   1409  CB   THR  193      -6.416    7.098   33.780  1.00 25.98           BLGL
ATOM   1410  OG1  THR  193      -6.697    6.231   34.884  1.00 27.07           BLGL
ATOM   1411  CG2  THR  193      -5.725    8.350   34.296  1.00 24.23           BLGL
ATOM   1412  C    THR  193      -7.488    8.500   31.990  1.00 25.40           BLGL
ATOM   1413  O    THR  193      -7.827    9.666   32.160  1.00 22.00           BLGL
ATOM   1414  N    ASP  194      -6.909    8.084   30.872  1.00 27.05           BLGL
ATOM   1415  CA   ASP  194      -6.585    9.020   29.810  1.00 27.87           BLGL
ATOM   1416  CB   ASP  194      -5.396    9.870   30.271  1.00 29.53           BLGL
ATOM   1417  CG   ASP  194      -4.956   10.881   29.243  1.00 32.75           BLGL
ATOM   1418  OD1  ASP  194      -4.131   11.746   29.606  1.00 34.57           BLGL
ATOM   1419  OD2  ASP  194      -5.418   10.816   28.081  1.00 35.03           BLGL
ATOM   1420  C    ASP  194      -6.245    8.249   28.546  1.00 27.55           BLGL
ATOM   1421  O    ASP  194      -5.389    7.368   28.565  1.00 29.57           BLGL
ATOM   1422  N    SER  195      -6.917    8.580   27.449  1.00 27.67           BLGL
ATOM   1423  CA   SER  195      -6.690    7.903   26.169  1.00 30.14           BLGL
ATOM   1424  CB   SER  195      -7.748    8.333   25.154  1.00 31.04           BLGL
ATOM   1425  OG   SER  195      -9.041    7.986   25.608  1.00 38.90           BLGL
ATOM   1426  C    SER  195      -5.314    8.137   25.553  1.00 29.28           BLGL
ATOM   1427  O    SER  195      -4.830    7.319   24.773  1.00 26.29           BLGL
ATOM   1428  N    ASN  196      -4.690    9.255   25.903  1.00 30.46           BLGL
ATOM   1429  CA   ASN  196      -3.387    9.600   25.358  1.00 32.52           BLGL
ATOM   1430  CB   ASN  196      -3.147   11.097   25.514  1.00 38.65           BLGL
ATOM   1431  CG   ASN  196      -4.246   11.919   24.892  1.00 45.74           BLGL
ATOM   1432  OD1  ASN  196      -4.436   11.902   23.672  1.00 47.81           BLGL
ATOM   1433  ND2  ASN  196      -4.996   12.637   25.729  1.00 49.19           BLGL
ATOM   1434  C    ASN  196      -2.232    8.838   25.981  1.00 30.86           BLGL
ATOM   1435  O    ASN  196      -1.141    8.779   25.411  1.00 31.65           BLGL
ATOM   1436  N    ILE  197      -2.459    8.260   27.153  1.00 28.33           BLGL
ATOM   1437  CA   ILE  197      -1.403    7.517   27.816  1.00 25.33           BLGL
ATOM   1438  CB   ILE  197      -1.771    7.224   29.282  1.00 24.62           BLGL
ATOM   1439  CG2  ILE  197      -0.720    6.335   29.919  1.00 24.24           BLGL
ATOM   1440  CG1  ILE  197      -1.873    8.542   30.053  1.00 24.08           BLGL
ATOM   1441  CD1  ILE  197      -2.239    8.380   31.513  1.00 24.86           BLGL
ATOM   1442  C    ILE  197      -1.149    6.222   27.064  1.00 23.64           BLGL
ATOM   1443  O    ILE  197      -2.081    5.487   26.748  1.00 23.83           BLGL
ATOM   1444  N    LEU  198       0.116    5.962   26.754  1.00 21.57           BLGL
ATOM   1445  CA   LEU  198       0.483    4.751   26.039  1.00 21.61           BLGL
ATOM   1446  CB   LEU  198       1.787    4.962   25.271  1.00 21.02           BLGL
ATOM   1447  CG   LEU  198       1.683    5.885   24.055  1.00 22.44           BLGL
ATOM   1448  CD1  LEU  198       3.062    6.252   23.554  1.00 22.29           BLGL
ATOM   1449  CD2  LEU  198       0.881    5.188   22.967  1.00 23.53           BLGL
ATOM   1450  C    LEU  198       0.653    3.605   27.013  1.00 21.75           BLGL
ATOM   1451  O    LEU  198       1.250    3.776   28.073  1.00 23.44           BLGL
```

Fig. 4 cont.

```
ATOM   1452  N    VAL   199       0.114    2.441   26.666  1.00 20.49      BLGL
ATOM   1453  CA   VAL   199       0.244    1.266   27.516  1.00 19.26      BLGL
ATOM   1454  CB   VAL   199      -1.040    0.450   27.555  1.00 19.98      BLGL
ATOM   1455  CG1  VAL   199      -0.816   -0.815   28.364  1.00 19.20      BLGL
ATOM   1456  CG2  VAL   199      -2.148    1.282   28.149  1.00 21.20      BLGL
ATOM   1457  C    VAL   199       1.352    0.376   26.979  1.00 18.65      BLGL
ATOM   1458  O    VAL   199       1.329   -0.029   25.818  1.00 16.57      BLGL
ATOM   1459  N    ALA   200       2.314    0.061   27.839  1.00 17.36      BLGL
ATOM   1460  CA   ALA   200       3.436   -0.760   27.432  1.00 17.13      BLGL
ATOM   1461  CB   ALA   200       4.701    0.087   27.427  1.00 15.68      BLGL
ATOM   1462  C    ALA   200       3.645   -1.991   28.299  1.00 16.72      BLGL
ATOM   1463  O    ALA   200       3.403   -1.960   29.501  1.00 15.94      BLGL
ATOM   1464  N    LEU   201       4.079   -3.077   27.661  1.00 17.11      BLGL
ATOM   1465  CA   LEU   201       4.390   -4.332   28.339  1.00 17.16      BLGL
ATOM   1466  CB   LEU   201       3.638   -5.502   27.706  1.00 17.16      BLGL
ATOM   1467  CG   LEU   201       2.114   -5.388   27.753  1.00 17.50      BLGL
ATOM   1468  CD1  LEU   201       1.497   -6.671   27.236  1.00 20.85      BLGL
ATOM   1469  CD2  LEU   201       1.654   -5.132   29.172  1.00 19.12      BLGL
ATOM   1470  C    LEU   201       5.907   -4.497   28.186  1.00 17.78      BLGL
ATOM   1471  O    LEU   201       6.465   -4.279   27.111  1.00 17.49      BLGL
ATOM   1472  N    HIS   202       6.568   -4.874   29.272  1.00 18.05      BLGL
ATOM   1473  CA   HIS   202       8.018   -4.981   29.294  1.00 17.54      BLGL
ATOM   1474  CB   HIS   202       8.519   -4.129   30.460  1.00 17.68      BLGL
ATOM   1475  CG   HIS   202      10.002   -4.110   30.616  1.00 19.94      BLGL
ATOM   1476  CD2  HIS   202      10.998   -4.372   29.741  1.00 20.39      BLGL
ATOM   1477  ND1  HIS   202      10.613   -3.773   31.805  1.00 21.65      BLGL
ATOM   1478  CE1  HIS   202      11.922   -3.831   31.655  1.00 22.99      BLGL
ATOM   1479  NE2  HIS   202      12.183   -4.193   30.411  1.00 23.44      BLGL
ATOM   1480  C    HIS   202       8.569   -6.400   29.402  1.00 18.30      BLGL
ATOM   1481  O    HIS   202       8.272   -7.122   30.354  1.00 18.51      BLGL
ATOM   1482  N    PHE   203       9.386   -6.790   28.429  1.00 16.01      BLGL
ATOM   1483  CA   PHE   203       9.989   -8.114   28.431  1.00 16.62      BLGL
ATOM   1484  CB   PHE   203       9.398   -8.963   27.316  1.00 13.11      BLGL
ATOM   1485  CG   PHE   203       7.912   -9.055   27.375  1.00 17.34      BLGL
ATOM   1486  CD1  PHE   203       7.116   -8.119   26.724  1.00 17.15      BLGL
ATOM   1487  CD2  PHE   203       7.299  -10.037   28.144  1.00 15.95      BLGL
ATOM   1488  CE1  PHE   203       5.738   -8.158   26.840  1.00 16.32      BLGL
ATOM   1489  CE2  PHE   203       5.925  -10.083   28.266  1.00 16.04      BLGL
ATOM   1490  CZ   PHE   203       5.141   -9.140   27.612  1.00 18.54      BLGL
ATOM   1491  C    PHE   203      11.504   -8.033   28.274  1.00 19.65      BLGL
ATOM   1492  O    PHE   203      12.051   -6.987   27.910  1.00 21.99      BLGL
ATOM   1493  N    THR   204      12.188   -9.135   28.552  1.00 17.81      BLGL
ATOM   1494  CA   THR   204      13.634   -9.133   28.426  1.00 18.21      BLGL
ATOM   1495  CB   THR   204      14.314   -8.849   29.798  1.00 17.19      BLGL
ATOM   1496  OG1  THR   204      15.726   -8.736   29.611  1.00 14.37      BLGL
ATOM   1497  CG2  THR   204      14.006   -9.951   30.809  1.00 13.65      BLGL
ATOM   1498  C    THR   204      14.161  -10.428   27.809  1.00 18.61      BLGL
ATOM   1499  O    THR   204      13.394  -11.352   27.534  1.00 16.21      BLGL
ATOM   1500  N    ASN   205      15.469  -10.473   27.580  1.00 17.26      BLGL
ATOM   1501  CA   ASN   205      16.112  -11.622   26.964  1.00 17.80      BLGL
ATOM   1502  CB   ASN   205      15.814  -12.907   27.728  1.00 18.45      BLGL
ATOM   1503  CG   ASN   205      16.601  -13.000   29.001  1.00 18.12      BLGL
ATOM   1504  OD1  ASN   205      16.070  -12.811   30.094  1.00 20.78      BLGL
ATOM   1505  ND2  ASN   205      17.890  -13.266   28.868  1.00 18.03      BLGL
ATOM   1506  C    ASN   205      15.701  -11.784   25.520  1.00 17.89      BLGL
ATOM   1507  O    ASN   205      15.129  -12.800   25.135  1.00 18.21      BLGL
ATOM   1508  N    PRO   206      15.988  -10.771   24.697  1.00 18.39      BLGL
ATOM   1509  CD   PRO   206      16.580   -9.480   25.080  1.00 15.66      BLGL
ATOM   1510  CA   PRO   206      15.657  -10.778   23.273  1.00 19.70      BLGL
ATOM   1511  CB   PRO   206      15.903   -9.334   22.867  1.00 19.33      BLGL
ATOM   1512  CG   PRO   206      17.029   -8.939   23.756  1.00 16.74      BLGL
ATOM   1513  C    PRO   206      16.500  -11.748   22.459  1.00 21.36      BLGL
ATOM   1514  O    PRO   206      16.158  -12.055   21.318  1.00 22.70      BLGL
ATOM   1515  N    GLU   207      17.601  -12.224   23.034  1.00 23.27      BLGL
ATOM   1516  CA   GLU   207      18.478  -13.154   22.324  1.00 25.47      BLGL
ATOM   1517  CB   GLU   207      19.871  -13.210   22.959  1.00 26.18      BLGL
```

Fig. 4 cont.

| | | | | | | | | | |
|---|---|---|---|---|---|---|---|---|---|
| ATOM | 1518 | CG | GLU | 207 | 20.021 | -12.502 | 24.288 | 1.00 30.25 | BLGL |
| ATOM | 1519 | CD | GLU | 207 | 19.242 | -13.139 | 25.413 | 1.00 29.52 | BLGL |
| ATOM | 1520 | OE1 | GLU | 207 | 19.387 | -14.353 | 25.643 | 1.00 33.25 | BLGL |
| ATOM | 1521 | OE2 | GLU | 207 | 18.495 | -12.413 | 26.081 | 1.00 29.56 | BLGL |
| ATOM | 1522 | C | GLU | 207 | 17.924 | -14.561 | 22.258 | 1.00 26.20 | BLGL |
| ATOM | 1523 | O | GLU | 207 | 18.354 | -15.357 | 21.426 | 1.00 29.50 | BLGL |
| ATOM | 1524 | N | THR | 208 | 16.982 | -14.873 | 23.139 | 1.00 25.50 | BLGL |
| ATOM | 1525 | CA | THR | 208 | 16.384 | -16.196 | 23.151 | 1.00 25.38 | BLGL |
| ATOM | 1526 | CB | THR | 208 | 15.419 | -16.349 | 24.314 | 1.00 25.02 | BLGL |
| ATOM | 1527 | OG1 | THR | 208 | 16.108 | -16.063 | 25.532 | 1.00 24.40 | BLGL |
| ATOM | 1528 | CG2 | THR | 208 | 14.871 | -17.765 | 24.361 | 1.00 24.75 | BLGL |
| ATOM | 1529 | C | THR | 208 | 15.628 | -16.435 | 21.853 | 1.00 24.66 | BLGL |
| ATOM | 1530 | O | THR | 208 | 14.689 | -15.711 | 21.531 | 1.00 23.66 | BLGL |
| ATOM | 1531 | N | SER | 209 | 16.047 | -17.455 | 21.114 | 1.00 24.67 | BLGL |
| ATOM | 1532 | CA | SER | 209 | 15.424 | -17.791 | 19.842 | 1.00 25.56 | BLGL |
| ATOM | 1533 | CB | SER | 209 | 15.971 | -19.120 | 19.334 | 1.00 23.59 | BLGL |
| ATOM | 1534 | OG | SER | 209 | 15.290 | -19.524 | 18.166 | 1.00 26.21 | BLGL |
| ATOM | 1535 | C | SER | 209 | 13.896 | -17.862 | 19.885 | 1.00 26.32 | BLGL |
| ATOM | 1536 | O | SER | 209 | 13.321 | -18.668 | 20.632 | 1.00 23.52 | BLGL |
| ATOM | 1537 | N | GLY | 210 | 13.257 | -17.004 | 19.083 | 1.00 26.00 | BLGL |
| ATOM | 1538 | CA | GLY | 210 | 11.803 | -16.966 | 18.977 | 1.00 25.41 | BLGL |
| ATOM | 1539 | C | GLY | 210 | 10.990 | -16.593 | 20.204 | 1.00 26.60 | BLGL |
| ATOM | 1540 | O | GLY | 210 | 9.768 | -16.755 | 20.215 | 1.00 26.52 | BLGL |
| ATOM | 1541 | N | ARG | 211 | 11.659 | -16.080 | 21.231 | 1.00 27.83 | BLGL |
| ATOM | 1542 | CA | ARG | 211 | 11.004 | -15.692 | 22.478 | 1.00 25.31 | BLGL |
| ATOM | 1543 | CB | ARG | 211 | 12.046 | -15.244 | 23.496 | 1.00 26.05 | BLGL |
| ATOM | 1544 | CG | ARG | 211 | 11.487 | -15.024 | 24.881 | 1.00 26.98 | BLGL |
| ATOM | 1545 | CD | ARG | 211 | 12.479 | -14.289 | 25.747 | 1.00 28.49 | BLGL |
| ATOM | 1546 | NE | ARG | 211 | 12.362 | -14.719 | 27.125 | 1.00 32.45 | BLGL |
| ATOM | 1547 | CZ | ARG | 211 | 13.043 | -15.727 | 27.655 | 1.00 34.26 | BLGL |
| ATOM | 1548 | NH1 | ARG | 211 | 13.903 | -16.408 | 26.920 | 1.00 33.07 | BLGL |
| ATOM | 1549 | NH2 | ARG | 211 | 12.850 | -16.067 | 28.924 | 1.00 40.91 | BLGL |
| ATOM | 1550 | C | ARG | 211 | 9.977 | -14.580 | 22.294 | 1.00 24.24 | BLGL |
| ATOM | 1551 | O | ARG | 211 | 8.806 | -14.744 | 22.634 | 1.00 24.47 | BLGL |
| ATOM | 1552 | N | TYR | 212 | 10.413 | -13.440 | 21.768 | 1.00 22.57 | BLGL |
| ATOM | 1553 | CA | TYR | 212 | 9.499 | -12.323 | 21.558 | 1.00 20.27 | BLGL |
| ATOM | 1554 | CB | TYR | 212 | 10.262 | -11.080 | 21.093 | 1.00 18.26 | BLGL |
| ATOM | 1555 | CG | TYR | 212 | 11.063 | -10.409 | 22.188 | 1.00 20.40 | BLGL |
| ATOM | 1556 | CD1 | TYR | 212 | 11.669 | -9.170 | 21.972 | 1.00 19.09 | BLGL |
| ATOM | 1557 | CE1 | TYR | 212 | 12.387 | -8.538 | 22.982 | 1.00 16.98 | BLGL |
| ATOM | 1558 | CD2 | TYR | 212 | 11.204 | -11.001 | 23.445 | 1.00 17.87 | BLGL |
| ATOM | 1559 | CE2 | TYR | 212 | 11.919 | -10.377 | 24.457 | 1.00 15.68 | BLGL |
| ATOM | 1560 | CZ | TYR | 212 | 12.505 | -9.147 | 24.225 | 1.00 16.21 | BLGL |
| ATOM | 1561 | OH | TYR | 212 | 13.200 | -8.514 | 25.235 | 1.00 15.74 | BLGL |
| ATOM | 1562 | C | TYR | 212 | 8.398 | -12.670 | 20.559 | 1.00 20.87 | BLGL |
| ATOM | 1563 | O | TYR | 212 | 7.259 | -12.237 | 20.712 | 1.00 20.22 | BLGL |
| ATOM | 1564 | N | ALA | 213 | 8.734 | -13.449 | 19.537 | 1.00 19.68 | BLGL |
| ATOM | 1565 | CA | ALA | 213 | 7.742 | -13.847 | 18.547 | 1.00 19.79 | BLGL |
| ATOM | 1566 | CB | ALA | 213 | 8.399 | -14.687 | 17.454 | 1.00 17.89 | BLGL |
| ATOM | 1567 | C | ALA | 213 | 6.629 | -14.642 | 19.231 | 1.00 19.99 | BLGL |
| ATOM | 1568 | O | ALA | 213 | 5.451 | -14.479 | 18.911 | 1.00 19.71 | BLGL |
| ATOM | 1569 | N | TRP | 214 | 7.009 | -15.496 | 20.176 | 1.00 20.09 | BLGL |
| ATOM | 1570 | CA | TRP | 214 | 6.039 | -16.309 | 20.900 | 1.00 21.30 | BLGL |
| ATOM | 1571 | CB | TRP | 214 | 6.753 | -17.375 | 21.732 | 1.00 22.71 | BLGL |
| ATOM | 1572 | CG | TRP | 214 | 5.815 | -18.281 | 22.468 | 1.00 24.60 | BLGL |
| ATOM | 1573 | CD2 | TRP | 214 | 5.308 | -18.094 | 23.795 | 1.00 24.97 | BLGL |
| ATOM | 1574 | CE2 | TRP | 214 | 4.449 | -19.183 | 24.074 | 1.00 24.59 | BLGL |
| ATOM | 1575 | CE3 | TRP | 214 | 5.496 | -17.112 | 24.775 | 1.00 25.69 | BLGL |
| ATOM | 1576 | CD1 | TRP | 214 | 5.256 | -19.440 | 22.005 | 1.00 24.97 | BLGL |
| ATOM | 1577 | NE1 | TRP | 214 | 4.436 | -19.989 | 22.966 | 1.00 25.84 | BLGL |
| ATOM | 1578 | CZ2 | TRP | 214 | 3.780 | -19.319 | 25.294 | 1.00 22.78 | BLGL |
| ATOM | 1579 | CZ3 | TRP | 214 | 4.829 | -17.248 | 25.991 | 1.00 27.53 | BLGL |
| ATOM | 1580 | CH2 | TRP | 214 | 3.981 | -18.345 | 26.238 | 1.00 24.84 | BLGL |
| ATOM | 1581 | C | TRP | 214 | 5.167 | -15.453 | 21.816 | 1.00 21.83 | BLGL |
| ATOM | 1582 | O | TRP | 214 | 3.948 | -15.630 | 21.857 | 1.00 20.77 | BLGL |
| ATOM | 1583 | N | ILE | 215 | 5.793 | -14.531 | 22.550 | 1.00 21.49 | BLGL |

Fig. 4 cont.

```
ATOM   1584  CA   ILE  215       5.067 -13.654  23.469  1.00 19.18      BLGL
ATOM   1585  CB   ILE  215       6.038 -12.771  24.300  1.00 19.85      BLGL
ATOM   1586  CG2  ILE  215       5.257 -11.811  25.198  1.00 15.32      BLGL
ATOM   1587  CG1  ILE  215       6.930 -13.651  25.170  1.00 18.25      BLGL
ATOM   1588  CD1  ILE  215       7.930 -12.876  25.975  1.00 15.25      BLGL
ATOM   1589  C    ILE  215       4.104 -12.740  22.725  1.00 19.79      BLGL
ATOM   1590  O    ILE  215       2.964 -12.550  23.146  1.00 18.73      BLGL
ATOM   1591  N    ALA  216       4.565 -12.163  21.621  1.00 19.35      BLGL
ATOM   1592  CA   ALA  216       3.723 -11.275  20.840  1.00 18.57      BLGL
ATOM   1593  CB   ALA  216       4.492 -10.751  19.650  1.00 18.16      BLGL
ATOM   1594  C    ALA  216       2.472 -12.020  20.378  1.00 20.55      BLGL
ATOM   1595  O    ALA  216       1.359 -11.501  20.466  1.00 16.58      BLGL
ATOM   1596  N    GLU  217       2.669 -13.242  19.890  1.00 22.90      BLGL
ATOM   1597  CA   GLU  217       1.569 -14.077  19.419  1.00 24.77      BLGL
ATOM   1598  CB   GLU  217       2.122 -15.338  18.747  1.00 28.27      BLGL
ATOM   1599  CG   GLU  217       1.063 -16.371  18.379  1.00 33.34      BLGL
ATOM   1600  CD   GLU  217      -0.002 -15.823  17.449  1.00 35.08      BLGL
ATOM   1601  OE1  GLU  217      -1.049 -16.485  17.288  1.00 39.18      BLGL
ATOM   1602  OE2  GLU  217       0.208 -14.737  16.875  1.00 35.59      BLGL
ATOM   1603  C    GLU  217       0.623 -14.468  20.560  1.00 24.16      BLGL
ATOM   1604  O    GLU  217      -0.596 -14.464  20.395  1.00 22.67      BLGL
ATOM   1605  N    THR  218       1.195 -14.805  21.713  1.00 24.08      BLGL
ATOM   1606  CA   THR  218       0.412 -15.191  22.878  1.00 23.79      BLGL
ATOM   1607  CB   THR  218       1.334 -15.684  24.027  1.00 25.12      BLGL
ATOM   1608  OG1  THR  218       1.985 -16.896  23.630  1.00 26.14      BLGL
ATOM   1609  CG2  THR  218       0.537 -15.942  25.298  1.00 23.98      BLGL
ATOM   1610  C    THR  218      -0.429 -14.014  23.362  1.00 22.94      BLGL
ATOM   1611  O    THR  218      -1.600 -14.179  23.692  1.00 24.35      BLGL
ATOM   1612  N    LEU  219       0.160 -12.825  23.401  1.00 21.92      BLGL
ATOM   1613  CA   LEU  219      -0.578 -11.644  23.846  1.00 23.28      BLGL
ATOM   1614  CB   LEU  219       0.333 -10.410  23.863  1.00 21.92      BLGL
ATOM   1615  CG   LEU  219       1.462 -10.359  24.893  1.00 18.90      BLGL
ATOM   1616  CD1  LEU  219       2.386  -9.209  24.570  1.00 14.80      BLGL
ATOM   1617  CD2  LEU  219       0.879 -10.220  26.289  1.00 16.33      BLGL
ATOM   1618  C    LEU  219      -1.753 -11.394  22.903  1.00 24.55      BLGL
ATOM   1619  O    LEU  219      -2.850 -11.031  23.322  1.00 25.23      BLGL
ATOM   1620  N    HIS  220      -1.512 -11.603  21.619  1.00 25.34      BLGL
ATOM   1621  CA   HIS  220      -2.539 -11.401  20.622  1.00 25.88      BLGL
ATOM   1622  CB   HIS  220      -1.904 -11.450  19.236  1.00 27.15      BLGL
ATOM   1623  CG   HIS  220      -2.888 -11.366  18.116  1.00 31.81      BLGL
ATOM   1624  CD2  HIS  220      -3.485 -10.300  17.529  1.00 31.02      BLGL
ATOM   1625  ND1  HIS  220      -3.388 -12.486  17.483  1.00 33.38      BLGL
ATOM   1626  CE1  HIS  220      -4.250 -12.111  16.554  1.00 33.29      BLGL
ATOM   1627  NE2  HIS  220      -4.326 -10.791  16.562  1.00 32.86      BLGL
ATOM   1628  C    HIS  220      -3.665 -12.423  20.743  1.00 26.70      BLGL
ATOM   1629  O    HIS  220      -4.839 -12.076  20.617  1.00 25.81      BLGL
ATOM   1630  N    ARG  221      -3.312 -13.679  20.993  1.00 28.18      BLGL
ATOM   1631  CA   ARG  221      -4.314 -14.730  21.133  1.00 30.04      BLGL
ATOM   1632  CB   ARG  221      -3.648 -16.090  21.361  1.00 33.95      BLGL
ATOM   1633  CG   ARG  221      -3.038 -16.680  20.095  1.00 40.22      BLGL
ATOM   1634  CD   ARG  221      -2.052 -17.802  20.368  1.00 47.28      BLGL
ATOM   1635  NE   ARG  221      -2.419 -19.012  19.696  1.00 52.72      BLGL
ATOM   1636  CZ   ARG  221      -1.881 -19.711  18.699  1.00 54.00      BLGL
ATOM   1637  NH1  ARG  221      -2.572 -20.786  18.387  1.00 56.27      BLGL
ATOM   1638  NH2  ARG  221      -0.762 -19.439  18.032  1.00 52.22      BLGL
ATOM   1639  C    ARG  221      -5.263 -14.440  22.276  1.00 29.71      BLGL
ATOM   1640  O    ARG  221      -6.441 -14.790  22.204  1.00 30.75      BLGL
ATOM   1641  N    HIS  222      -4.757 -13.803  23.331  1.00 27.89      BLGL
ATOM   1642  CA   HIS  222      -5.599 -13.482  24.477  1.00 27.09      BLGL
ATOM   1643  CB   HIS  222      -4.844 -13.728  25.782  1.00 26.93      BLGL
ATOM   1644  CG   HIS  222      -4.530 -15.168  26.023  1.00 28.56      BLGL
ATOM   1645  CD2  HIS  222      -5.196 -16.121  26.716  1.00 30.01      BLGL
ATOM   1646  ND1  HIS  222      -3.441 -15.797  25.459  1.00 31.08      BLGL
ATOM   1647  CE1  HIS  222      -3.448 -17.076  25.792  1.00 30.75      BLGL
ATOM   1648  NE2  HIS  222      -4.504 -17.298  26.554  1.00 33.11      BLGL
ATOM   1649  C    HIS  222      -6.159 -12.064  24.456  1.00 26.57      BLGL
```

Fig. 4 cont.

```
ATOM   1650  O    HIS  222      -6.646 -11.564  25.469  1.00 25.69        BLGL
ATOM   1651  N    HIS  223      -6.084 -11.418  23.300  1.00 25.18        BLGL
ATOM   1652  CA   HIS  223      -6.627 -10.082  23.151  1.00 26.33        BLGL
ATOM   1653  CB   HIS  223      -8.147 -10.149  23.214  1.00 30.76        BLGL
ATOM   1654  CG   HIS  223      -8.739 -11.182  22.309  1.00 38.88        BLGL
ATOM   1655  CD2  HIS  223      -9.524 -12.253  22.570  1.00 41.07        BLGL
ATOM   1656  ND1  HIS  223      -8.531 -11.182  20.945  1.00 43.14        BLGL
ATOM   1657  CE1  HIS  223      -9.161 -12.210  20.405  1.00 43.27        BLGL
ATOM   1658  NE2  HIS  223      -9.771 -12.876  21.370  1.00 45.48        BLGL
ATOM   1659  C    HIS  223      -6.149  -9.081  24.186  1.00 26.02        BLGL
ATOM   1660  O    HIS  223      -6.961  -8.345  24.750  1.00 27.73        BLGL
ATOM   1661  N    VAL  224      -4.846  -9.044  24.446  1.00 22.81        BLGL
ATOM   1662  CA   VAL  224      -4.316  -8.096  25.413  1.00 18.14        BLGL
ATOM   1663  CB   VAL  224      -2.912  -8.499  25.895  1.00 16.94        BLGL
ATOM   1664  CG1  VAL  224      -2.312  -7.399  26.758  1.00 12.94        BLGL
ATOM   1665  CG2  VAL  224      -2.998  -9.783  26.676  1.00 15.42        BLGL
ATOM   1666  C    VAL  224      -4.241  -6.742  24.734  1.00 17.57        BLGL
ATOM   1667  O    VAL  224      -3.683  -6.610  23.646  1.00 16.83        BLGL
ATOM   1668  N    ASP  225      -4.808  -5.738  25.386  1.00 16.35        BLGL
ATOM   1669  CA   ASP  225      -4.820  -4.393  24.849  1.00 17.47        BLGL
ATOM   1670  CB   ASP  225      -6.123  -3.707  25.254  1.00 17.33        BLGL
ATOM   1671  CG   ASP  225      -6.172  -2.260  24.843  1.00 19.19        BLGL
ATOM   1672  OD1  ASP  225      -5.722  -1.945  23.717  1.00 21.14        BLGL
ATOM   1673  OD2  ASP  225      -6.672  -1.444  25.643  1.00 19.74        BLGL
ATOM   1674  C    ASP  225      -3.626  -3.562  25.306  1.00 18.47        BLGL
ATOM   1675  O    ASP  225      -3.609  -3.073  26.433  1.00 19.94        BLGL
ATOM   1676  N    TYR  226      -2.626  -3.415  24.440  1.00 17.31        BLGL
ATOM   1677  CA   TYR  226      -1.441  -2.610  24.762  1.00 19.05        BLGL
ATOM   1678  CB   TYR  226      -0.315  -3.483  25.359  1.00 17.31        BLGL
ATOM   1679  CG   TYR  226       0.380  -4.417  24.386  1.00 17.91        BLGL
ATOM   1680  CD1  TYR  226      -0.315  -5.469  23.780  1.00 17.20        BLGL
ATOM   1681  CE1  TYR  226       0.317  -6.338  22.891  1.00 14.85        BLGL
ATOM   1682  CD2  TYR  226       1.737  -4.253  24.076  1.00 15.96        BLGL
ATOM   1683  CE2  TYR  226       2.380  -5.117  23.184  1.00 15.01        BLGL
ATOM   1684  CZ   TYR  226       1.661  -6.156  22.598  1.00 16.47        BLGL
ATOM   1685  OH   TYR  226       2.279  -7.019  21.725  1.00 13.64        BLGL
ATOM   1686  C    TYR  226      -0.944  -1.877  23.513  1.00 17.95        BLGL
ATOM   1687  O    TYR  226      -1.285  -2.251  22.398  1.00 17.24        BLGL
ATOM   1688  N    ASP  227      -0.141  -0.836  23.697  1.00 18.09        BLGL
ATOM   1689  CA   ASP  227       0.361  -0.075  22.557  1.00 20.63        BLGL
ATOM   1690  CB   ASP  227       0.126   1.424  22.760  1.00 23.61        BLGL
ATOM   1691  CG   ASP  227      -1.247   1.736  23.282  1.00 24.31        BLGL
ATOM   1692  OD1  ASP  227      -2.242   1.427  22.597  1.00 26.42        BLGL
ATOM   1693  OD2  ASP  227      -1.327   2.298  24.388  1.00 29.59        BLGL
ATOM   1694  C    ASP  227       1.846  -0.263  22.289  1.00 21.20        BLGL
ATOM   1695  O    ASP  227       2.283  -0.241  21.141  1.00 21.63        BLGL
ATOM   1696  N    VAL  228       2.626  -0.432  23.350  1.00 21.33        BLGL
ATOM   1697  CA   VAL  228       4.069  -0.571  23.205  1.00 18.22        BLGL
ATOM   1698  CB   VAL  228       4.822   0.572  23.961  1.00 16.56        BLGL
ATOM   1699  CG1  VAL  228       6.307   0.511  23.669  1.00 16.51        BLGL
ATOM   1700  CG2  VAL  228       4.268   1.921  23.569  1.00 16.96        BLGL
ATOM   1701  C    VAL  228       4.631  -1.892  23.700  1.00 16.80        BLGL
ATOM   1702  O    VAL  228       4.338  -2.338  24.811  1.00 16.77        BLGL
ATOM   1703  N    PHE  229       5.444  -2.510  22.858  1.00 15.66        BLGL
ATOM   1704  CA   PHE  229       6.115  -3.747  23.213  1.00 16.03        BLGL
ATOM   1705  CB   PHE  229       6.177  -4.694  22.007  1.00 15.71        BLGL
ATOM   1706  CG   PHE  229       6.773  -6.038  22.323  1.00 18.72        BLGL
ATOM   1707  CD1  PHE  229       8.148  -6.193  22.458  1.00 20.15        BLGL
ATOM   1708  CD2  PHE  229       5.957  -7.141  22.537  1.00 19.69        BLGL
ATOM   1709  CE1  PHE  229       8.698  -7.424  22.805  1.00 20.33        BLGL
ATOM   1710  CE2  PHE  229       6.502  -8.376  22.885  1.00 19.99        BLGL
ATOM   1711  CZ   PHE  229       7.873  -8.516  23.020  1.00 20.18        BLGL
ATOM   1712  C    PHE  229       7.517  -3.278  23.608  1.00 15.51        BLGL
ATOM   1713  O    PHE  229       8.336  -2.965  22.747  1.00 16.80        BLGL
ATOM   1714  N    ALA  230       7.781  -3.205  24.909  1.00 14.48        BLGL
ATOM   1715  CA   ALA  230       9.076  -2.740  25.392  1.00 16.32        BLGL
```

Fig. 4 cont.

```
ATOM   1716  CB   ALA   230       8.892   -1.878   26.632  1.00 15.48      BLGL
ATOM   1717  C    ALA   230      10.040   -3.878   25.691  1.00 17.75      BLGL
ATOM   1718  O    ALA   230       9.624   -4.990   26.019  1.00 19.06      BLGL
ATOM   1719  N    SER   231      11.334   -3.588   25.580  1.00 15.44      BLGL
ATOM   1720  CA   SER   231      12.363   -4.583   25.829  1.00 15.19      BLGL
ATOM   1721  CB   SER   231      12.863   -5.165   24.498  1.00 12.54      BLGL
ATOM   1722  OG   SER   231      13.966   -6.035   24.696  1.00  9.34      BLGL
ATOM   1723  C    SER   231      13.554   -4.024   26.601  1.00 16.12      BLGL
ATOM   1724  O    SER   231      13.915   -2.852   26.463  1.00 17.19      BLGL
ATOM   1725  N    SER   232      14.152   -4.865   27.434  1.00 14.04      BLGL
ATOM   1726  CA   SER   232      15.341   -4.463   28.159  1.00 15.04      BLGL
ATOM   1727  CB   SER   232      15.505   -5.272   29.447  1.00 14.50      BLGL
ATOM   1728  OG   SER   232      14.733   -4.727   30.499  1.00 17.36      BLGL
ATOM   1729  C    SER   232      16.485   -4.810   27.216  1.00 15.02      BLGL
ATOM   1730  O    SER   232      16.354   -5.696   26.374  1.00 14.13      BLGL
ATOM   1731  N    TYR   233      17.591   -4.094   27.326  1.00 14.36      BLGL
ATOM   1732  CA   TYR   233      18.738   -4.410   26.506  1.00 16.28      BLGL
ATOM   1733  CB   TYR   233      18.721   -3.697   25.152  1.00 15.72      BLGL
ATOM   1734  CG   TYR   233      19.901   -4.146   24.318  1.00 18.38      BLGL
ATOM   1735  CD1  TYR   233      19.935   -5.428   23.762  1.00 17.95      BLGL
ATOM   1736  CE1  TYR   233      21.072   -5.905   23.102  1.00 17.74      BLGL
ATOM   1737  CD2  TYR   233      21.038   -3.342   24.185  1.00 19.16      BLGL
ATOM   1738  CE2  TYR   233      22.181   -3.809   23.528  1.00 18.72      BLGL
ATOM   1739  CZ   TYR   233      22.188   -5.090   22.991  1.00 20.19      BLGL
ATOM   1740  OH   TYR   233      23.305   -5.552   22.339  1.00 21.28      BLGL
ATOM   1741  C    TYR   233      20.051   -4.096   27.204  1.00 18.26      BLGL
ATOM   1742  O    TYR   233      20.488   -2.941   27.282  1.00 19.11      BLGL
ATOM   1743  N    TYR   234      20.672   -5.148   27.715  1.00 18.61      BLGL
ATOM   1744  CA   TYR   234      21.951   -5.047   28.382  1.00 20.22      BLGL
ATOM   1745  CB   TYR   234      21.838   -5.594   29.794  1.00 18.03      BLGL
ATOM   1746  CG   TYR   234      21.020   -4.689   30.678  1.00 19.42      BLGL
ATOM   1747  CD1  TYR   234      21.536   -3.473   31.130  1.00 17.03      BLGL
ATOM   1748  CE1  TYR   234      20.778   -2.628   31.935  1.00 15.84      BLGL
ATOM   1749  CD2  TYR   234      19.718   -5.035   31.051  1.00 20.59      BLGL
ATOM   1750  CE2  TYR   234      18.950   -4.194   31.854  1.00 18.88      BLGL
ATOM   1751  CZ   TYR   234      19.489   -2.995   32.294  1.00 17.70      BLGL
ATOM   1752  OH   TYR   234      18.745   -2.180   33.108  1.00 17.67      BLGL
ATOM   1753  C    TYR   234      22.896   -5.875   27.538  1.00 20.87      BLGL
ATOM   1754  O    TYR   234      22.858   -7.104   27.570  1.00 23.14      BLGL
ATOM   1755  N    PRO   235      23.749   -5.201   26.756  1.00 21.55      BLGL
ATOM   1756  CD   PRO   235      23.983   -3.751   26.857  1.00 21.91      BLGL
ATOM   1757  CA   PRO   235      24.728   -5.825   25.864  1.00 22.81      BLGL
ATOM   1758  CB   PRO   235      25.551   -4.639   25.367  1.00 22.48      BLGL
ATOM   1759  CG   PRO   235      25.422   -3.640   26.471  1.00 21.97      BLGL
ATOM   1760  C    PRO   235      25.575   -6.912   26.508  1.00 23.83      BLGL
ATOM   1761  O    PRO   235      26.118   -7.762   25.812  1.00 26.44      BLGL
ATOM   1762  N    PHE   236      25.673   -6.894   27.834  1.00 24.38      BLGL
ATOM   1763  CA   PHE   236      26.451   -7.894   28.556  1.00 23.56      BLGL
ATOM   1764  CB   PHE   236      26.439   -7.613   30.069  1.00 22.41      BLGL
ATOM   1765  CG   PHE   236      26.751   -6.190   30.432  1.00 20.97      BLGL
ATOM   1766  CD1  PHE   236      25.769   -5.363   30.960  1.00 22.30      BLGL
ATOM   1767  CD2  PHE   236      28.018   -5.666   30.224  1.00 21.90      BLGL
ATOM   1768  CE1  PHE   236      26.043   -4.031   31.274  1.00 20.76      BLGL
ATOM   1769  CE2  PHE   236      28.304   -4.335   30.534  1.00 22.34      BLGL
ATOM   1770  CZ   PHE   236      27.310   -3.518   31.060  1.00 22.41      BLGL
ATOM   1771  C    PHE   236      25.901   -9.297   28.322  1.00 24.55      BLGL
ATOM   1772  O    PHE   236      26.664  -10.252   28.209  1.00 26.43      BLGL
ATOM   1773  N    TRP   237      24.581   -9.425   28.226  1.00 25.33      BLGL
ATOM   1774  CA   TRP   237      23.971  -10.745   28.067  1.00 26.98      BLGL
ATOM   1775  CB   TRP   237      23.270  -11.144   29.367  1.00 27.82      BLGL
ATOM   1776  CG   TRP   237      23.960  -10.698   30.606  1.00 30.90      BLGL
ATOM   1777  CD2  TRP   237      23.562   -9.632   31.466  1.00 31.06      BLGL
ATOM   1778  CE2  TRP   237      24.489   -9.585   32.535  1.00 31.99      BLGL
ATOM   1779  CE3  TRP   237      22.511   -8.711   31.443  1.00 32.34      BLGL
ATOM   1780  CD1  TRP   237      25.084  -11.238   31.162  1.00 33.44      BLGL
ATOM   1781  NE1  TRP   237      25.408  -10.577   32.324  1.00 32.26      BLGL
```

Fig. 4 cont.

```
ATOM   1782  CZ2 TRP   237      24.396  -8.652  33.570  1.00 32.74      BLGL
ATOM   1783  CZ3 TRP   237      22.417  -7.780  32.477  1.00 34.34      BLGL
ATOM   1784  CH2 TRP   237      23.357  -7.761  33.526  1.00 33.93      BLGL
ATOM   1785  C   TRP   237      22.938 -10.894  26.960  1.00 26.05      BLGL
ATOM   1786  O   TRP   237      22.632 -12.011  26.543  1.00 25.25      BLGL
ATOM   1787  N   HIS   238      22.401  -9.778  26.487  1.00 24.70      BLGL
ATOM   1788  CA  HIS   238      21.333  -9.824  25.504  1.00 20.96      BLGL
ATOM   1789  CB  HIS   238      20.358  -8.703  25.824  1.00 19.05      BLGL
ATOM   1790  CG  HIS   238      19.772  -8.821  27.192  1.00 17.38      BLGL
ATOM   1791  CD2 HIS   238      19.601  -9.900  27.990  1.00 16.73      BLGL
ATOM   1792  ND1 HIS   238      19.291  -7.743  27.896  1.00 20.29      BLGL
ATOM   1793  CE1 HIS   238      18.850  -8.151  29.073  1.00 20.03      BLGL
ATOM   1794  NE2 HIS   238      19.026  -9.456  29.154  1.00 19.52      BLGL
ATOM   1795  C   HIS   238      21.628  -9.863  24.019  1.00 20.65      BLGL
ATOM   1796  O   HIS   238      20.854  -9.354  23.217  1.00 22.38      BLGL
ATOM   1797  N   GLY   239      22.730 -10.489  23.643  1.00 19.61      BLGL
ATOM   1798  CA  GLY   239      23.037 -10.607  22.234  1.00 19.09      BLGL
ATOM   1799  C   GLY   239      23.345  -9.338  21.474  1.00 18.09      BLGL
ATOM   1800  O   GLY   239      23.535  -8.271  22.046  1.00 17.84      BLGL
ATOM   1801  N   THR   240      23.369  -9.476  20.158  1.00 17.37      BLGL
ATOM   1802  CA  THR   240      23.697  -8.387  19.258  1.00 18.95      BLGL
ATOM   1803  CB  THR   240      24.139  -8.949  17.896  1.00 18.49      BLGL
ATOM   1804  OG1 THR   240      23.028  -9.589  17.262  1.00 18.33      BLGL
ATOM   1805  CG2 THR   240      25.239  -9.964  18.076  1.00 14.06      BLGL
ATOM   1806  C   THR   240      22.610  -7.348  19.003  1.00 20.98      BLGL
ATOM   1807  O   THR   240      21.418  -7.604  19.169  1.00 19.90      BLGL
ATOM   1808  N   LEU   241      23.043  -6.165  18.581  1.00 21.55      BLGL
ATOM   1809  CA  LEU   241      22.115  -5.094  18.277  1.00 21.65      BLGL
ATOM   1810  CB  LEU   241      22.874  -3.780  18.086  1.00 20.04      BLGL
ATOM   1811  CG  LEU   241      23.464  -3.205  19.381  1.00 21.24      BLGL
ATOM   1812  CD1 LEU   241      24.455  -2.105  19.074  1.00 18.53      BLGL
ATOM   1813  CD2 LEU   241      22.339  -2.689  20.259  1.00 19.54      BLGL
ATOM   1814  C   LEU   241      21.350  -5.458  17.011  1.00 22.88      BLGL
ATOM   1815  O   LEU   241      20.213  -5.043  16.827  1.00 23.81      BLGL
ATOM   1816  N   LYS   242      21.971  -6.248  16.143  1.00 23.90      BLGL
ATOM   1817  CA  LYS   242      21.322  -6.659  14.902  1.00 25.71      BLGL
ATOM   1818  CB  LYS   242      22.314  -7.426  14.025  1.00 30.56      BLGL
ATOM   1819  CG  LYS   242      21.771  -7.855  12.670  1.00 36.92      BLGL
ATOM   1820  CD  LYS   242      22.735  -8.821  11.983  1.00 43.60      BLGL
ATOM   1821  CE  LYS   242      22.175  -9.333  10.664  1.00 48.93      BLGL
ATOM   1822  NZ  LYS   242      21.895  -8.217   9.709  1.00 51.96      BLGL
ATOM   1823  C   LYS   242      20.108  -7.537  15.208  1.00 24.37      BLGL
ATOM   1824  O   LYS   242      19.070  -7.444  14.551  1.00 23.45      BLGL
ATOM   1825  N   ASN   243      20.248  -8.384  16.219  1.00 23.09      BLGL
ATOM   1826  CA  ASN   243      19.178  -9.279  16.637  1.00 21.13      BLGL
ATOM   1827  CB  ASN   243      19.716 -10.285  17.653  1.00 20.66      BLGL
ATOM   1828  CG  ASN   243      18.639 -11.196  18.185  1.00 22.04      BLGL
ATOM   1829  OD1 ASN   243      18.181 -12.102  17.495  1.00 21.37      BLGL
ATOM   1830  ND2 ASN   243      18.215 -10.951  19.415  1.00 21.96      BLGL
ATOM   1831  C   ASN   243      18.041  -8.477  17.264  1.00 21.16      BLGL
ATOM   1832  O   ASN   243      16.861  -8.684  16.957  1.00 18.33      BLGL
ATOM   1833  N   LEU   244      18.408  -7.557  18.151  1.00 20.72      BLGL
ATOM   1834  CA  LEU   244      17.429  -6.712  18.821  1.00 19.78      BLGL
ATOM   1835  CB  LEU   244      18.131  -5.667  19.695  1.00 18.01      BLGL
ATOM   1836  CG  LEU   244      17.188  -4.669  20.372  1.00 16.83      BLGL
ATOM   1837  CD1 LEU   244      16.393  -5.385  21.463  1.00 13.98      BLGL
ATOM   1838  CD2 LEU   244      17.995  -3.515  20.950  1.00 16.04      BLGL
ATOM   1839  C   LEU   244      16.565  -6.000  17.792  1.00 19.53      BLGL
ATOM   1840  O   LEU   244      15.341  -6.054  17.853  1.00 20.39      BLGL
ATOM   1841  N   THR   245      17.214  -5.332  16.846  1.00 18.73      BLGL
ATOM   1842  CA  THR   245      16.505  -4.606  15.810  1.00 18.66      BLGL
ATOM   1843  CB  THR   245      17.474  -3.996  14.785  1.00 19.64      BLGL
ATOM   1844  OG1 THR   245      18.318  -3.037  15.430  1.00 21.51      BLGL
ATOM   1845  CG2 THR   245      16.697  -3.311  13.664  1.00 17.47      BLGL
ATOM   1846  C   THR   245      15.574  -5.531  15.062  1.00 19.92      BLGL
ATOM   1847  O   THR   245      14.410  -5.219  14.834  1.00 21.53      BLGL
```

Fig. 4 cont.

| ATOM | 1848 | N   | SER | 246 | 16.109 | -6.678  | 14.678 | 1.00 | 20.39 | BLGL |
| ATOM | 1849 | CA  | SER | 246 | 15.361 | -7.661  | 13.927 | 1.00 | 19.04 | BLGL |
| ATOM | 1850 | CB  | SER | 246 | 16.303 | -8.792  | 13.538 | 1.00 | 18.29 | BLGL |
| ATOM | 1851 | OG  | SER | 246 | 15.593 | -9.911  | 13.053 | 1.00 | 23.84 | BLGL |
| ATOM | 1852 | C   | SER | 246 | 14.164 | -8.205  | 14.695 | 1.00 | 20.89 | BLGL |
| ATOM | 1853 | O   | SER | 246 | 13.034 | -8.169  | 14.214 | 1.00 | 22.76 | BLGL |
| ATOM | 1854 | N   | VAL | 247 | 14.411 | -8.703  | 15.899 | 1.00 | 21.65 | BLGL |
| ATOM | 1855 | CA  | VAL | 247 | 13.343 | -9.280  | 16.701 | 1.00 | 21.83 | BLGL |
| ATOM | 1856 | CB  | VAL | 247 | 13.923 | -9.883  | 18.005 | 1.00 | 20.50 | BLGL |
| ATOM | 1857 | CG1 | VAL | 247 | 14.342 | -8.786  | 18.962 | 1.00 | 20.71 | BLGL |
| ATOM | 1858 | CG2 | VAL | 247 | 12.912 | -10.800 | 18.636 | 1.00 | 23.56 | BLGL |
| ATOM | 1859 | C   | VAL | 247 | 12.215 | -8.275  | 17.006 | 1.00 | 22.43 | BLGL |
| ATOM | 1860 | O   | VAL | 247 | 11.031 | -8.631  | 17.000 | 1.00 | 22.15 | BLGL |
| ATOM | 1861 | N   | LEU | 248 | 12.578 | -7.020  | 17.255 | 1.00 | 22.41 | BLGL |
| ATOM | 1862 | CA  | LEU | 248 | 11.584 | -5.990  | 17.538 | 1.00 | 22.55 | BLGL |
| ATOM | 1863 | CB  | LEU | 248 | 12.251 | -4.734  | 18.125 | 1.00 | 20.88 | BLGL |
| ATOM | 1864 | CG  | LEU | 248 | 12.778 | -4.816  | 19.563 | 1.00 | 19.44 | BLGL |
| ATOM | 1865 | CD1 | LEU | 248 | 13.426 | -3.498  | 19.954 | 1.00 | 17.12 | BLGL |
| ATOM | 1866 | CD2 | LEU | 248 | 11.639 | -5.143  | 20.505 | 1.00 | 15.29 | BLGL |
| ATOM | 1867 | C   | LEU | 248 | 10.805 | -5.617  | 16.270 | 1.00 | 23.02 | BLGL |
| ATOM | 1868 | O   | LEU | 248 | 9.597  | -5.381  | 16.318 | 1.00 | 22.01 | BLGL |
| ATOM | 1869 | N   | THR | 249 | 11.496 | -5.570  | 15.136 | 1.00 | 20.49 | BLGL |
| ATOM | 1870 | CA  | THR | 249 | 10.844 | -5.220  | 13.890 | 1.00 | 21.29 | BLGL |
| ATOM | 1871 | CB  | THR | 249 | 11.836 | -5.197  | 12.722 | 1.00 | 22.20 | BLGL |
| ATOM | 1872 | OG1 | THR | 249 | 12.872 | -4.246  | 12.994 | 1.00 | 24.83 | BLGL |
| ATOM | 1873 | CG2 | THR | 249 | 11.128 | -4.808  | 11.440 | 1.00 | 20.47 | BLGL |
| ATOM | 1874 | C   | THR | 249 | 9.739  | -6.214  | 13.573 | 1.00 | 22.84 | BLGL |
| ATOM | 1875 | O   | THR | 249 | 8.706  | -5.842  | 13.020 | 1.00 | 20.69 | BLGL |
| ATOM | 1876 | N   | SER | 250 | 9.956  | -7.481  | 13.920 | 1.00 | 23.97 | BLGL |
| ATOM | 1877 | CA  | SER | 250 | 8.945  | -8.509  | 13.667 | 1.00 | 25.77 | BLGL |
| ATOM | 1878 | CB  | SER | 250 | 9.451  | -9.889  | 14.076 | 1.00 | 27.18 | BLGL |
| ATOM | 1879 | OG  | SER | 250 | 10.487 | -10.310 | 13.213 | 1.00 | 34.71 | BLGL |
| ATOM | 1880 | C   | SER | 250 | 7.686  | -8.196  | 14.446 | 1.00 | 24.53 | BLGL |
| ATOM | 1881 | O   | SER | 250 | 6.590  | -8.207  | 13.892 | 1.00 | 24.89 | BLGL |
| ATOM | 1882 | N   | VAL | 251 | 7.850  | -7.919  | 15.736 | 1.00 | 22.02 | BLGL |
| ATOM | 1883 | CA  | VAL | 251 | 6.713  | -7.592  | 16.581 | 1.00 | 20.32 | BLGL |
| ATOM | 1884 | CB  | VAL | 251 | 7.156  | -7.246  | 18.022 | 1.00 | 19.00 | BLGL |
| ATOM | 1885 | CG1 | VAL | 251 | 5.972  | -6.733  | 18.822 | 1.00 | 19.03 | BLGL |
| ATOM | 1886 | CG2 | VAL | 251 | 7.736  | -8.475  | 18.693 | 1.00 | 17.23 | BLGL |
| ATOM | 1887 | C   | VAL | 251 | 5.968  | -6.401  | 15.984 | 1.00 | 20.70 | BLGL |
| ATOM | 1888 | O   | VAL | 251 | 4.741  | -6.399  | 15.912 | 1.00 | 20.26 | BLGL |
| ATOM | 1889 | N   | ALA | 252 | 6.717  | -5.396  | 15.546 | 1.00 | 20.84 | BLGL |
| ATOM | 1890 | CA  | ALA | 252 | 6.123  | -4.198  | 14.965 | 1.00 | 21.97 | BLGL |
| ATOM | 1891 | CB  | ALA | 252 | 7.203  | -3.175  | 14.663 | 1.00 | 21.24 | BLGL |
| ATOM | 1892 | C   | ALA | 252 | 5.330  | -4.497  | 13.701 | 1.00 | 22.61 | BLGL |
| ATOM | 1893 | O   | ALA | 252 | 4.137  | -4.219  | 13.629 | 1.00 | 23.36 | BLGL |
| ATOM | 1894 | N   | ASP | 253 | 5.999  | -5.069  | 12.711 | 1.00 | 22.58 | BLGL |
| ATOM | 1895 | CA  | ASP | 253 | 5.366  | -5.386  | 11.440 | 1.00 | 23.48 | BLGL |
| ATOM | 1896 | CB  | ASP | 253 | 6.394  | -5.968  | 10.472 | 1.00 | 23.27 | BLGL |
| ATOM | 1897 | CG  | ASP | 253 | 7.403  | -4.946  | 10.019 | 1.00 | 25.67 | BLGL |
| ATOM | 1898 | OD1 | ASP | 253 | 8.372  | -5.346  | 9.337  | 1.00 | 26.60 | BLGL |
| ATOM | 1899 | OD2 | ASP | 253 | 7.224  | -3.744  | 10.344 | 1.00 | 27.47 | BLGL |
| ATOM | 1900 | C   | ASP | 253 | 4.203  | -6.352  | 11.556 | 1.00 | 24.77 | BLGL |
| ATOM | 1901 | O   | ASP | 253 | 3.174  | -6.174  | 10.904 | 1.00 | 25.85 | BLGL |
| ATOM | 1902 | N   | THR | 254 | 4.359  | -7.371  | 12.389 | 1.00 | 24.09 | BLGL |
| ATOM | 1903 | CA  | THR | 254 | 3.317  | -8.374  | 12.537 | 1.00 | 22.38 | BLGL |
| ATOM | 1904 | CB  | THR | 254 | 3.892  | -9.679  | 13.094 | 1.00 | 21.12 | BLGL |
| ATOM | 1905 | OG1 | THR | 254 | 5.000  | -10.096 | 12.287 | 1.00 | 22.06 | BLGL |
| ATOM | 1906 | CG2 | THR | 254 | 2.836  | -10.765 | 13.073 | 1.00 | 20.31 | BLGL |
| ATOM | 1907 | C   | THR | 254 | 2.123  | -7.977  | 13.395 | 1.00 | 23.11 | BLGL |
| ATOM | 1908 | O   | THR | 254 | 0.995  | -8.366  | 13.102 | 1.00 | 26.89 | BLGL |
| ATOM | 1909 | N   | TYR | 255 | 2.345  | -7.201  | 14.444 | 1.00 | 21.45 | BLGL |
| ATOM | 1910 | CA  | TYR | 255 | 1.231  | -6.835  | 15.307 | 1.00 | 20.15 | BLGL |
| ATOM | 1911 | CB  | TYR | 255 | 1.488  | -7.377  | 16.709 | 1.00 | 20.87 | BLGL |
| ATOM | 1912 | CG  | TYR | 255 | 1.670  | -8.876  | 16.701 | 1.00 | 22.40 | BLGL |
| ATOM | 1913 | CD1 | TYR | 255 | 0.568  | -9.728  | 16.568 | 1.00 | 21.45 | BLGL |

Fig. 4 cont.

```
ATOM   1914  CE1 TYR  255       0.731 -11.107  16.494  1.00 21.01      BLGL
ATOM   1915  CD2 TYR  255       2.943  -9.443  16.761  1.00 19.96      BLGL
ATOM   1916  CE2 TYR  255       3.117 -10.822  16.686  1.00 20.59      BLGL
ATOM   1917  CZ  TYR  255       2.008 -11.647  16.554  1.00 21.17      BLGL
ATOM   1918  OH  TYR  255       2.179 -13.009  16.495  1.00 21.44      BLGL
ATOM   1919  C   TYR  255       0.927  -5.357  15.360  1.00 19.29      BLGL
ATOM   1920  O   TYR  255       0.056  -4.923  16.104  1.00 19.71      BLGL
ATOM   1921  N   GLY  256       1.649  -4.585  14.562  1.00 20.06      BLGL
ATOM   1922  CA  GLY  256       1.421  -3.155  14.516  1.00 21.23      BLGL
ATOM   1923  C   GLY  256       1.582  -2.454  15.847  1.00 21.40      BLGL
ATOM   1924  O   GLY  256       0.788  -1.593  16.212  1.00 22.35      BLGL
ATOM   1925  N   LYS  257       2.619  -2.815  16.581  1.00 20.19      BLGL
ATOM   1926  CA  LYS  257       2.845  -2.182  17.861  1.00 21.01      BLGL
ATOM   1927  CB  LYS  257       3.032  -3.244  18.949  1.00 20.86      BLGL
ATOM   1928  CG  LYS  257       1.863  -4.191  19.122  1.00 18.58      BLGL
ATOM   1929  CD  LYS  257       0.615  -3.458  19.566  1.00 17.81      BLGL
ATOM   1930  CE  LYS  257      -0.524  -4.428  19.765  1.00 16.84      BLGL
ATOM   1931  NZ  LYS  257      -1.801  -3.739  20.053  1.00 19.74      BLGL
ATOM   1932  C   LYS  257       4.082  -1.300  17.792  1.00 20.95      BLGL
ATOM   1933  O   LYS  257       4.934  -1.474  16.918  1.00 19.83      BLGL
ATOM   1934  N   LYS  258       4.161  -0.333  18.699  1.00 19.92      BLGL
ATOM   1935  CA  LYS  258       5.329   0.526  18.771  1.00 21.02      BLGL
ATOM   1936  CB  LYS  258       5.037   1.785  19.581  1.00 24.26      BLGL
ATOM   1937  CG  LYS  258       3.850   2.601  19.139  1.00 27.83      BLGL
ATOM   1938  CD  LYS  258       4.143   3.387  17.887  1.00 33.22      BLGL
ATOM   1939  CE  LYS  258       3.297   4.652  17.862  1.00 36.49      BLGL
ATOM   1940  NZ  LYS  258       1.845   4.362  18.036  1.00 38.07      BLGL
ATOM   1941  C   LYS  258       6.322  -0.326  19.559  1.00 21.33      BLGL
ATOM   1942  O   LYS  258       5.923  -1.248  20.276  1.00 21.62      BLGL
ATOM   1943  N   VAL  259       7.607  -0.037  19.430  1.00 18.75      BLGL
ATOM   1944  CA  VAL  259       8.604  -0.786  20.176  1.00 17.87      BLGL
ATOM   1945  CB  VAL  259       9.391  -1.762  19.271  1.00 17.66      BLGL
ATOM   1946  CG1 VAL  259       8.447  -2.789  18.686  1.00 16.47      BLGL
ATOM   1947  CG2 VAL  259      10.118  -0.997  18.171  1.00 16.36      BLGL
ATOM   1948  C   VAL  259       9.572   0.190  20.816  1.00 18.60      BLGL
ATOM   1949  O   VAL  259       9.628   1.362  20.443  1.00 19.89      BLGL
ATOM   1950  N   MET  260      10.328  -0.280  21.794  1.00 18.23      BLGL
ATOM   1951  CA  MET  260      11.295   0.583  22.452  1.00 18.93      BLGL
ATOM   1952  CB  MET  260      10.594   1.741  23.179  1.00 17.82      BLGL
ATOM   1953  CG  MET  260       9.861   1.335  24.450  1.00 18.62      BLGL
ATOM   1954  SD  MET  260       9.338   2.760  25.444  1.00 20.82      BLGL
ATOM   1955  CE  MET  260       9.092   1.989  27.061  1.00 14.70      BLGL
ATOM   1956  C   MET  260      12.109  -0.200  23.461  1.00 18.97      BLGL
ATOM   1957  O   MET  260      11.757  -1.326  23.827  1.00 18.84      BLGL
ATOM   1958  N   VAL  261      13.207   0.401  23.900  1.00 18.49      BLGL
ATOM   1959  CA  VAL  261      14.049  -0.215  24.907  1.00 19.01      BLGL
ATOM   1960  CB  VAL  261      15.545  -0.063  24.567  1.00 18.88      BLGL
ATOM   1961  CG1 VAL  261      16.399  -0.549  25.728  1.00 19.31      BLGL
ATOM   1962  CG2 VAL  261      15.867  -0.867  23.326  1.00 17.95      BLGL
ATOM   1963  C   VAL  261      13.713   0.493  26.218  1.00 17.97      BLGL
ATOM   1964  O   VAL  261      13.854   1.712  26.343  1.00 14.60      BLGL
ATOM   1965  N   ALA  262      13.228  -0.280  27.180  1.00 18.80      BLGL
ATOM   1966  CA  ALA  262      12.846   0.269  28.473  1.00 21.56      BLGL
ATOM   1967  CB  ALA  262      11.777  -0.617  29.107  1.00 20.01      BLGL
ATOM   1968  C   ALA  262      14.047   0.409  29.412  1.00 21.77      BLGL
ATOM   1969  O   ALA  262      14.079   1.297  30.262  1.00 22.42      BLGL
ATOM   1970  N   GLU  263      15.036  -0.464  29.247  1.00 20.47      BLGL
ATOM   1971  CA  GLU  263      16.214  -0.433  30.091  1.00 19.18      BLGL
ATOM   1972  CB  GLU  263      16.099  -1.464  31.211  1.00 18.99      BLGL
ATOM   1973  CG  GLU  263      15.178  -1.102  32.358  1.00 21.05      BLGL
ATOM   1974  CD  GLU  263      15.151  -2.191  33.417  1.00 19.91      BLGL
ATOM   1975  OE1 GLU  263      16.207  -2.819  33.642  1.00 20.67      BLGL
ATOM   1976  OE2 GLU  263      14.087  -2.422  34.029  1.00 22.21      BLGL
ATOM   1977  C   GLU  263      17.483  -0.729  29.319  1.00 19.96      BLGL
ATOM   1978  O   GLU  263      17.497  -1.587  28.440  1.00 20.56      BLGL
ATOM   1979  N   THR  264      18.547  -0.013  29.661  1.00 17.62      BLGL
```

Fig. 4 cont.

| | | | | | | | | | |
|---|---|---|---|---|---|---|---|---|---|
| ATOM | 1980 | CA | THR | 264 | 19.844 | -0.219 | 29.042 | 1.00 15.98 | BLGL |
| ATOM | 1981 | CB | THR | 264 | 19.874 | 0.247 | 27.573 | 1.00 16.21 | BLGL |
| ATOM | 1982 | OG1 | THR | 264 | 20.989 | -0.366 | 26.907 | 1.00 15.60 | BLGL |
| ATOM | 1983 | CG2 | THR | 264 | 20.036 | 1.771 | 27.494 | 1.00 13.52 | BLGL |
| ATOM | 1984 | C | THR | 264 | 20.872 | 0.578 | 29.820 | 1.00 15.21 | BLGL |
| ATOM | 1985 | O | THR | 264 | 20.532 | 1.477 | 30.579 | 1.00 14.74 | BLGL |
| ATOM | 1986 | N | SER | 265 | 22.136 | 0.240 | 29.621 | 1.00 15.34 | BLGL |
| ATOM | 1987 | CA | SER | 265 | 23.229 | 0.936 | 30.280 | 1.00 16.34 | BLGL |
| ATOM | 1988 | CB | SER | 265 | 23.113 | 0.819 | 31.802 | 1.00 16.26 | BLGL |
| ATOM | 1989 | OG | SER | 265 | 23.293 | -0.517 | 32.249 | 1.00 16.64 | BLGL |
| ATOM | 1990 | C | SER | 265 | 24.531 | 0.312 | 29.826 | 1.00 17.34 | BLGL |
| ATOM | 1991 | O | SER | 265 | 24.543 | -0.607 | 29.005 | 1.00 18.70 | BLGL |
| ATOM | 1992 | N | TYR | 266 | 25.629 | 0.836 | 30.349 | 1.00 18.17 | BLGL |
| ATOM | 1993 | CA | TYR | 266 | 26.939 | 0.307 | 30.039 | 1.00 17.93 | BLGL |
| ATOM | 1994 | CB | TYR | 266 | 27.397 | 0.699 | 28.640 | 1.00 15.84 | BLGL |
| ATOM | 1995 | CG | TYR | 266 | 28.485 | -0.218 | 28.131 | 1.00 17.82 | BLGL |
| ATOM | 1996 | CD1 | TYR | 266 | 28.192 | -1.527 | 27.774 | 1.00 18.54 | BLGL |
| ATOM | 1997 | CE1 | TYR | 266 | 29.186 | -2.396 | 27.329 | 1.00 19.26 | BLGL |
| ATOM | 1998 | CD2 | TYR | 266 | 29.816 | 0.210 | 28.035 | 1.00 20.22 | BLGL |
| ATOM | 1999 | CE2 | TYR | 266 | 30.826 | -0.656 | 27.591 | 1.00 19.11 | BLGL |
| ATOM | 2000 | CZ | TYR | 266 | 30.499 | -1.962 | 27.238 | 1.00 19.47 | BLGL |
| ATOM | 2001 | OH | TYR | 266 | 31.472 | -2.836 | 26.784 | 1.00 18.36 | BLGL |
| ATOM | 2002 | C | TYR | 266 | 27.911 | 0.846 | 31.064 | 1.00 18.90 | BLGL |
| ATOM | 2003 | O | TYR | 266 | 27.681 | 1.895 | 31.665 | 1.00 18.09 | BLGL |
| ATOM | 2004 | N | THR | 267 | 28.995 | 0.105 | 31.259 | 1.00 20.38 | BLGL |
| ATOM | 2005 | CA | THR | 267 | 30.037 | 0.462 | 32.210 | 1.00 21.04 | BLGL |
| ATOM | 2006 | CB | THR | 267 | 30.852 | -0.773 | 32.580 | 1.00 20.00 | BLGL |
| ATOM | 2007 | OG1 | THR | 267 | 31.305 | -1.402 | 31.373 | 1.00 19.78 | BLGL |
| ATOM | 2008 | CG2 | THR | 267 | 30.017 | -1.752 | 33.366 | 1.00 19.30 | BLGL |
| ATOM | 2009 | C | THR | 267 | 31.000 | 1.482 | 31.619 | 1.00 21.49 | BLGL |
| ATOM | 2010 | O | THR | 267 | 31.455 | 1.315 | 30.488 | 1.00 24.81 | BLGL |
| ATOM | 2011 | N | TYR | 268 | 31.320 | 2.525 | 32.384 | 1.00 20.55 | BLGL |
| ATOM | 2012 | CA | TYR | 268 | 32.268 | 3.546 | 31.933 | 1.00 20.98 | BLGL |
| ATOM | 2013 | CB | TYR | 268 | 31.724 | 4.958 | 32.205 | 1.00 21.01 | BLGL |
| ATOM | 2014 | CG | TYR | 268 | 31.844 | 5.439 | 33.639 | 1.00 19.32 | BLGL |
| ATOM | 2015 | CD1 | TYR | 268 | 33.019 | 6.027 | 34.105 | 1.00 20.87 | BLGL |
| ATOM | 2016 | CE1 | TYR | 268 | 33.129 | 6.471 | 35.426 | 1.00 20.17 | BLGL |
| ATOM | 2017 | CD2 | TYR | 268 | 30.778 | 5.302 | 34.532 | 1.00 21.37 | BLGL |
| ATOM | 2018 | CE2 | TYR | 268 | 30.873 | 5.739 | 35.853 | 1.00 19.23 | BLGL |
| ATOM | 2019 | CZ | TYR | 268 | 32.049 | 6.322 | 36.295 | 1.00 21.74 | BLGL |
| ATOM | 2020 | OH | TYR | 268 | 32.137 | 6.753 | 37.604 | 1.00 22.30 | BLGL |
| ATOM | 2021 | C | TYR | 268 | 33.597 | 3.364 | 32.664 | 1.00 21.83 | BLGL |
| ATOM | 2022 | O | TYR | 268 | 34.590 | 4.013 | 32.344 | 1.00 18.94 | BLGL |
| ATOM | 2023 | N | THR | 269 | 33.600 | 2.479 | 33.657 | 1.00 22.82 | BLGL |
| ATOM | 2024 | CA | THR | 269 | 34.795 | 2.213 | 34.451 | 1.00 23.10 | BLGL |
| ATOM | 2025 | CB | THR | 269 | 34.970 | 3.271 | 35.573 | 1.00 20.44 | BLGL |
| ATOM | 2026 | OG1 | THR | 269 | 36.161 | 2.989 | 36.311 | 1.00 20.91 | BLGL |
| ATOM | 2027 | CG2 | THR | 269 | 33.791 | 3.250 | 36.524 | 1.00 18.84 | BLGL |
| ATOM | 2028 | C | THR | 269 | 34.693 | 0.834 | 35.083 | 1.00 23.00 | BLGL |
| ATOM | 2029 | O | THR | 269 | 33.607 | 0.376 | 35.403 | 1.00 25.15 | BLGL |
| ATOM | 2030 | N | ALA | 270 | 35.826 | 0.170 | 35.259 | 1.00 24.31 | BLGL |
| ATOM | 2031 | CA | ALA | 270 | 35.825 | -1.158 | 35.853 | 1.00 24.71 | BLGL |
| ATOM | 2032 | CB | ALA | 270 | 37.058 | -1.933 | 35.409 | 1.00 21.17 | BLGL |
| ATOM | 2033 | C | ALA | 270 | 35.810 | -1.019 | 37.361 | 1.00 25.78 | BLGL |
| ATOM | 2034 | O | ALA | 270 | 35.538 | -1.970 | 38.080 | 1.00 29.18 | BLGL |
| ATOM | 2035 | N | GLU | 271 | 36.083 | 0.185 | 37.836 | 1.00 27.12 | BLGL |
| ATOM | 2036 | CA | GLU | 271 | 36.133 | 0.448 | 39.263 | 1.00 29.78 | BLGL |
| ATOM | 2037 | CB | GLU | 271 | 36.914 | 1.742 | 39.495 | 1.00 32.08 | BLGL |
| ATOM | 2038 | CG | GLU | 271 | 36.864 | 2.261 | 40.920 | 1.00 35.54 | BLGL |
| ATOM | 2039 | CD | GLU | 271 | 37.750 | 3.466 | 41.110 | 1.00 36.58 | BLGL |
| ATOM | 2040 | OE1 | GLU | 271 | 38.022 | 4.167 | 40.108 | 1.00 36.10 | BLGL |
| ATOM | 2041 | OE2 | GLU | 271 | 38.160 | 3.714 | 42.262 | 1.00 38.61 | BLGL |
| ATOM | 2042 | C | GLU | 271 | 34.783 | 0.527 | 39.977 | 1.00 30.16 | BLGL |
| ATOM | 2043 | O | GLU | 271 | 33.776 | 0.938 | 39.405 | 1.00 31.60 | BLGL |
| ATOM | 2044 | N | ASP | 272 | 34.782 | 0.125 | 41.242 | 1.00 30.13 | BLGL |
| ATOM | 2045 | CA | ASP | 272 | 33.590 | 0.169 | 42.081 | 1.00 30.63 | BLGL |

Fig. 4 cont.

```
ATOM   2046  CB   ASP  272      33.333   -1.190   42.722  1.00 29.68      BLGL
ATOM   2047  CG   ASP  272      32.488   -1.081   43.968  1.00 29.93      BLGL
ATOM   2048  OD1  ASP  272      31.427   -0.428   43.896  1.00 29.02      BLGL
ATOM   2049  OD2  ASP  272      32.884   -1.640   45.014  1.00 30.80      BLGL
ATOM   2050  C    ASP  272      33.865    1.188   43.178  1.00 31.65      BLGL
ATOM   2051  O    ASP  272      34.705    0.946   44.045  1.00 33.92      BLGL
ATOM   2052  N    GLY  273      33.163    2.318   43.157  1.00 31.58      BLGL
ATOM   2053  CA   GLY  273      33.420    3.340   44.158  1.00 32.18      BLGL
ATOM   2054  C    GLY  273      32.476    3.304   45.333  1.00 31.14      BLGL
ATOM   2055  O    GLY  273      32.407    4.250   46.116  1.00 32.09      BLGL
ATOM   2056  N    ASP  274      31.786    2.184   45.472  1.00 30.99      BLGL
ATOM   2057  CA   ASP  274      30.790    2.002   46.511  1.00 30.40      BLGL
ATOM   2058  CB   ASP  274      29.550    1.377   45.871  1.00 31.29      BLGL
ATOM   2059  CG   ASP  274      28.304    1.620   46.659  1.00 32.35      BLGL
ATOM   2060  OD1  ASP  274      27.319    0.902   46.433  1.00 34.84      BLGL
ATOM   2061  OD2  ASP  274      28.299    2.539   47.495  1.00 38.43      BLGL
ATOM   2062  C    ASP  274      31.264    1.104   47.649  1.00 30.15      BLGL
ATOM   2063  O    ASP  274      31.075    1.408   48.827  1.00 28.39      BLGL
ATOM   2064  N    GLY  275      31.867   -0.017   47.283  1.00 28.33      BLGL
ATOM   2065  CA   GLY  275      32.311   -0.956   48.283  1.00 29.05      BLGL
ATOM   2066  C    GLY  275      31.486   -2.210   48.099  1.00 28.72      BLGL
ATOM   2067  O    GLY  275      31.881   -3.298   48.519  1.00 31.31      BLGL
ATOM   2068  N    HIS  276      30.325   -2.046   47.472  1.00 26.86      BLGL
ATOM   2069  CA   HIS  276      29.431   -3.164   47.191  1.00 24.43      BLGL
ATOM   2070  CB   HIS  276      27.974   -2.726   47.336  1.00 23.89      BLGL
ATOM   2071  CG   HIS  276      26.986   -3.842   47.172  1.00 26.16      BLGL
ATOM   2072  CD2  HIS  276      26.329   -4.297   46.078  1.00 24.85      BLGL
ATOM   2073  ND1  HIS  276      26.595   -4.652   48.217  1.00 26.36      BLGL
ATOM   2074  CE1  HIS  276      25.741   -5.557   47.776  1.00 24.78      BLGL
ATOM   2075  NE2  HIS  276      25.562   -5.363   46.481  1.00 25.01      BLGL
ATOM   2076  C    HIS  276      29.691   -3.597   45.748  1.00 24.24      BLGL
ATOM   2077  O    HIS  276      29.512   -2.808   44.822  1.00 23.66      BLGL
ATOM   2078  N    GLY  277      30.108   -4.844   45.562  1.00 23.41      BLGL
ATOM   2079  CA   GLY  277      30.397   -5.343   44.225  1.00 23.85      BLGL
ATOM   2080  C    GLY  277      29.405   -4.987   43.130  1.00 24.88      BLGL
ATOM   2081  O    GLY  277      28.185   -5.064   43.320  1.00 25.03      BLGL
ATOM   2082  N    ASN  278      29.935   -4.616   41.966  1.00 24.25      BLGL
ATOM   2083  CA   ASN  278      29.114   -4.238   40.822  1.00 22.79      BLGL
ATOM   2084  CB   ASN  278      29.827   -3.150   40.027  1.00 21.96      BLGL
ATOM   2085  CG   ASN  278      29.928   -1.844   40.797  1.00 23.90      BLGL
ATOM   2086  ND2  ASN  278      30.661   -0.934   40.410  1.00 26.25      BLGL
ATOM   2087  OD1  ASN  278      29.177   -1.742   41.889  1.00 21.34      BLGL
ATOM   2088  C    ASN  278      28.748   -5.407   39.910  1.00 23.33      BLGL
ATOM   2089  O    ASN  278      29.408   -6.443   39.898  1.00 22.97      BLGL
ATOM   2090  N    THR  279      27.675   -5.226   39.152  1.00 23.75      BLGL
ATOM   2091  CA   THR  279      27.188   -6.247   38.241  1.00 24.46      BLGL
ATOM   2092  CB   THR  279      25.821   -5.857   37.666  1.00 25.31      BLGL
ATOM   2093  OG1  THR  279      24.874   -5.729   38.728  1.00 27.04      BLGL
ATOM   2094  CG2  THR  279      25.331   -6.910   36.701  1.00 28.22      BLGL
ATOM   2095  C    THR  279      28.137   -6.482   37.078  1.00 24.01      BLGL
ATOM   2096  O    THR  279      28.356   -7.613   36.659  1.00 24.35      BLGL
ATOM   2097  N    ALA  280      28.687   -5.401   36.547  1.00 24.16      BLGL
ATOM   2098  CA   ALA  280      29.599   -5.495   35.422  1.00 24.11      BLGL
ATOM   2099  CB   ALA  280      28.857   -5.182   34.137  1.00 21.63      BLGL
ATOM   2100  C    ALA  280      30.749   -4.522   35.616  1.00 25.17      BLGL
ATOM   2101  O    ALA  280      30.638   -3.565   36.379  1.00 26.21      BLGL
ATOM   2102  N    PRO  281      31.881   -4.766   34.942  1.00 25.93      BLGL
ATOM   2103  CD   PRO  281      32.977   -3.790   34.829  1.00 26.64      BLGL
ATOM   2104  CA   PRO  281      32.106   -5.896   34.037  1.00 27.75      BLGL
ATOM   2105  CB   PRO  281      33.155   -5.353   33.084  1.00 27.25      BLGL
ATOM   2106  CG   PRO  281      34.001   -4.545   33.998  1.00 28.42      BLGL
ATOM   2107  C    PRO  281      32.590   -7.142   34.773  1.00 29.21      BLGL
ATOM   2108  O    PRO  281      33.055   -7.071   35.902  1.00 31.08      BLGL
ATOM   2109  N    LYS  282      32.468   -8.287   34.123  1.00 31.67      BLGL
ATOM   2110  CA   LYS  282      32.902   -9.546   34.705  1.00 35.33      BLGL
ATOM   2111  CB   LYS  282      31.788  -10.169   35.537  1.00 34.90      BLGL
```

Fig. 4 cont.

```
ATOM   2112  CG  LYS   282      31.527  -9.495  36.861  1.00 37.13      BLGL
ATOM   2113  CD  LYS   282      30.496 -10.301  37.636  1.00 38.88      BLGL
ATOM   2114  CE  LYS   282      30.386  -9.846  39.077  1.00 40.27      BLGL
ATOM   2115  NZ  LYS   282      29.540 -10.796  39.851  1.00 42.22      BLGL
ATOM   2116  C   LYS   282      33.270 -10.495  33.583  1.00 38.11      BLGL
ATOM   2117  O   LYS   282      32.931 -10.251  32.429  1.00 39.52      BLGL
ATOM   2118  N   ASN   283      33.967 -11.575  33.920  1.00 42.82      BLGL
ATOM   2119  CA  ASN   283      34.355 -12.558  32.914  1.00 46.20      BLGL
ATOM   2120  CB  ASN   283      35.290 -13.614  33.512  1.00 50.82      BLGL
ATOM   2121  CG  ASN   283      36.534 -13.010  34.122  1.00 56.85      BLGL
ATOM   2122  OD1 ASN   283      36.474 -12.369  35.175  1.00 61.22      BLGL
ATOM   2123  ND2 ASN   283      37.672 -13.200  33.461  1.00 58.97      BLGL
ATOM   2124  C   ASN   283      33.100 -13.246  32.382  1.00 45.60      BLGL
ATOM   2125  O   ASN   283      32.163 -13.532  33.138  1.00 44.14      BLGL
ATOM   2126  N   GLY   284      33.081 -13.507  31.080  1.00 44.05      BLGL
ATOM   2127  CA  GLY   284      31.927 -14.166  30.499  1.00 42.01      BLGL
ATOM   2128  C   GLY   284      30.920 -13.195  29.918  1.00 40.47      BLGL
ATOM   2129  O   GLY   284      30.072 -13.590  29.114  1.00 41.73      BLGL
ATOM   2130  N   GLN   285      30.997 -11.929  30.321  1.00 36.97      BLGL
ATOM   2131  CA  GLN   285      30.081 -10.934  29.794  1.00 32.62      BLGL
ATOM   2132  CB  GLN   285      29.904  -9.781  30.771  1.00 31.11      BLGL
ATOM   2133  CG  GLN   285      29.440 -10.187  32.149  1.00 29.26      BLGL
ATOM   2134  CD  GLN   285      29.234  -8.985  33.046  1.00 27.08      BLGL
ATOM   2135  OE1 GLN   285      29.922  -7.973  32.910  1.00 26.10      BLGL
ATOM   2136  NE2 GLN   285      28.296  -9.091  33.974  1.00 25.79      BLGL
ATOM   2137  C   GLN   285      30.634 -10.397  28.487  1.00 30.85      BLGL
ATOM   2138  O   GLN   285      31.844 -10.301  28.302  1.00 31.43      BLGL
ATOM   2139  N   THR   286      29.735 -10.047  27.581  1.00 29.00      BLGL
ATOM   2140  CA  THR   286      30.119  -9.516  26.292  1.00 26.23      BLGL
ATOM   2141  CB  THR   286      29.000  -9.741  25.280  1.00 26.60      BLGL
ATOM   2142  OG1 THR   286      28.755 -11.147  25.159  1.00 26.51      BLGL
ATOM   2143  CG2 THR   286      29.370  -9.150  23.928  1.00 26.18      BLGL
ATOM   2144  C   THR   286      30.401  -8.030  26.413  1.00 25.38      BLGL
ATOM   2145  O   THR   286      29.553  -7.266  26.859  1.00 25.73      BLGL
ATOM   2146  N   LEU   287      31.596  -7.619  26.016  1.00 25.58      BLGL
ATOM   2147  CA  LEU   287      31.957  -6.219  26.098  1.00 25.95      BLGL
ATOM   2148  CB  LEU   287      33.036  -6.034  27.159  1.00 23.53      BLGL
ATOM   2149  CG  LEU   287      32.593  -6.516  28.539  1.00 22.29      BLGL
ATOM   2150  CD1 LEU   287      33.742  -6.413  29.523  1.00 21.57      BLGL
ATOM   2151  CD2 LEU   287      31.409  -5.692  28.998  1.00 20.26      BLGL
ATOM   2152  C   LEU   287      32.446  -5.739  24.748  1.00 28.08      BLGL
ATOM   2153  O   LEU   287      33.648  -5.666  24.503  1.00 29.85      BLGL
ATOM   2154  N   ASN   288      31.508  -5.406  23.870  1.00 29.45      BLGL
ATOM   2155  CA  ASN   288      31.869  -4.949  22.537  1.00 31.56      BLGL
ATOM   2156  CB  ASN   288      30.641  -4.928  21.632  1.00 35.67      BLGL
ATOM   2157  CG  ASN   288      30.039  -6.306  21.456  1.00 41.56      BLGL
ATOM   2158  OD1 ASN   288      30.766  -7.298  21.320  1.00 42.80      BLGL
ATOM   2159  ND2 ASN   288      28.707  -6.380  21.449  1.00 43.66      BLGL
ATOM   2160  C   ASN   288      32.533  -3.590  22.523  1.00 30.88      BLGL
ATOM   2161  O   ASN   288      33.295  -3.281  21.615  1.00 32.37      BLGL
ATOM   2162  N   ASN   289      32.242  -2.767  23.520  1.00 30.69      BLGL
ATOM   2163  CA  ASN   289      32.849  -1.447  23.583  1.00 29.17      BLGL
ATOM   2164  CB  ASN   289      31.778  -0.364  23.737  1.00 29.80      BLGL
ATOM   2165  CG  ASN   289      31.108  -0.018  22.420  1.00 34.65      BLGL
ATOM   2166  OD1 ASN   289      31.733   0.562  21.529  1.00 36.80      BLGL
ATOM   2167  ND2 ASN   289      29.834  -0.382  22.285  1.00 34.27      BLGL
ATOM   2168  C   ASN   289      33.818  -1.386  24.746  1.00 28.28      BLGL
ATOM   2169  O   ASN   289      33.698  -2.144  25.718  1.00 26.00      BLGL
ATOM   2170  N   PRO   290      34.815  -0.497  24.654  1.00 26.69      BLGL
ATOM   2171  CD  PRO   290      35.116   0.459  23.576  1.00 25.39      BLGL
ATOM   2172  CA  PRO   290      35.783  -0.375  25.740  1.00 24.60      BLGL
ATOM   2173  CB  PRO   290      36.796   0.616  25.184  1.00 23.11      BLGL
ATOM   2174  CG  PRO   290      35.977   1.470  24.294  1.00 24.06      BLGL
ATOM   2175  C   PRO   290      35.098   0.132  27.006  1.00 25.03      BLGL
ATOM   2176  O   PRO   290      34.140   0.916  26.951  1.00 24.16      BLGL
ATOM   2177  N   VAL   291      35.582  -0.334  28.149  1.00 23.84      BLGL
```

Fig. 4 cont.

```
ATOM   2178  CA   VAL  291      35.019   0.083  29.420  1.00 21.28      BLGL
ATOM   2179  CB   VAL  291      35.340  -0.945  30.520  1.00 21.94      BLGL
ATOM   2180  CG1  VAL  291      34.752  -0.488  31.852  1.00 20.42      BLGL
ATOM   2181  CG2  VAL  291      34.775  -2.309  30.114  1.00 17.11      BLGL
ATOM   2182  C    VAL  291      35.607   1.448  29.760  1.00 20.16      BLGL
ATOM   2183  O    VAL  291      36.504   1.574  30.588  1.00 19.20      BLGL
ATOM   2184  N    THR  292      35.100   2.464  29.070  1.00 19.49      BLGL
ATOM   2185  CA   THR  292      35.532   3.842  29.250  1.00 18.74      BLGL
ATOM   2186  CB   THR  292      36.660   4.228  28.251  1.00 18.53      BLGL
ATOM   2187  OG1  THR  292      36.111   4.400  26.939  1.00 17.67      BLGL
ATOM   2188  CG2  THR  292      37.716   3.148  28.196  1.00 17.15      BLGL
ATOM   2189  C    THR  292      34.335   4.759  28.994  1.00 19.39      BLGL
ATOM   2190  O    THR  292      33.275   4.308  28.568  1.00 19.27      BLGL
ATOM   2191  N    VAL  293      34.514   6.048  29.252  1.00 20.06      BLGL
ATOM   2192  CA   VAL  293      33.446   7.005  29.039  1.00 20.55      BLGL
ATOM   2193  CB   VAL  293      33.865   8.406  29.544  1.00 20.16      BLGL
ATOM   2194  CG1  VAL  293      32.857   9.451  29.100  1.00 20.66      BLGL
ATOM   2195  CG2  VAL  293      33.936   8.390  31.074  1.00 16.78      BLGL
ATOM   2196  C    VAL  293      33.051   7.044  27.562  1.00 20.97      BLGL
ATOM   2197  O    VAL  293      31.864   7.124  27.234  1.00 21.53      BLGL
ATOM   2198  N    GLN  294      34.039   6.962  26.674  1.00 20.45      BLGL
ATOM   2199  CA   GLN  294      33.770   6.956  25.238  1.00 21.64      BLGL
ATOM   2200  CB   GLN  294      35.066   7.058  24.431  1.00 25.60      BLGL
ATOM   2201  CG   GLN  294      35.192   8.341  23.619  1.00 29.52      BLGL
ATOM   2202  CD   GLN  294      34.031   8.562  22.666  1.00 29.94      BLGL
ATOM   2203  OE1  GLN  294      33.739   9.696  22.296  1.00 34.05      BLGL
ATOM   2204  NE2  GLN  294      33.371   7.485  22.260  1.00 28.56      BLGL
ATOM   2205  C    GLN  294      33.058   5.672  24.834  1.00 22.39      BLGL
ATOM   2206  O    GLN  294      32.199   5.677  23.950  1.00 19.94      BLGL
ATOM   2207  N    GLY  295      33.444   4.566  25.468  1.00 22.59      BLGL
ATOM   2208  CA   GLY  295      32.814   3.295  25.173  1.00 20.59      BLGL
ATOM   2209  C    GLY  295      31.349   3.362  25.564  1.00 22.43      BLGL
ATOM   2210  O    GLY  295      30.464   3.047  24.767  1.00 23.22      BLGL
ATOM   2211  N    GLN  296      31.099   3.787  26.798  1.00 19.02      BLGL
ATOM   2212  CA   GLN  296      29.750   3.905  27.313  1.00 19.21      BLGL
ATOM   2213  CB   GLN  296      29.789   4.581  28.683  1.00 19.90      BLGL
ATOM   2214  CG   GLN  296      28.467   4.668  29.419  1.00 18.48      BLGL
ATOM   2215  CD   GLN  296      28.572   5.536  30.669  1.00 17.80      BLGL
ATOM   2216  OE1  GLN  296      29.027   6.679  30.595  1.00 16.03      BLGL
ATOM   2217  NE2  GLN  296      28.152   4.999  31.818  1.00 15.03      BLGL
ATOM   2218  C    GLN  296      28.906   4.719  26.336  1.00 19.79      BLGL
ATOM   2219  O    GLN  296      27.777   4.347  26.016  1.00 20.36      BLGL
ATOM   2220  N    ALA  297      29.458   5.825  25.851  1.00 18.99      BLGL
ATOM   2221  CA   ALA  297      28.733   6.669  24.905  1.00 18.45      BLGL
ATOM   2222  CB   ALA  297      29.546   7.916  24.578  1.00 14.36      BLGL
ATOM   2223  C    ALA  297      28.416   5.895  23.630  1.00 19.50      BLGL
ATOM   2224  O    ALA  297      27.301   5.978  23.104  1.00 20.34      BLGL
ATOM   2225  N    ASN  298      29.395   5.142  23.135  1.00 19.83      BLGL
ATOM   2226  CA   ASN  298      29.196   4.352  21.926  1.00 21.45      BLGL
ATOM   2227  CB   ASN  298      30.442   3.524  21.592  1.00 24.97      BLGL
ATOM   2228  CG   ASN  298      31.563   4.358  20.999  1.00 26.63      BLGL
ATOM   2229  OD1  ASN  298      31.329   5.440  20.459  1.00 25.65      BLGL
ATOM   2230  ND2  ASN  298      32.791   3.843  21.078  1.00 27.74      BLGL
ATOM   2231  C    ASN  298      28.027   3.405  22.133  1.00 21.39      BLGL
ATOM   2232  O    ASN  298      27.130   3.306  21.297  1.00 21.38      BLGL
ATOM   2233  N    ALA  299      28.061   2.713  23.266  1.00 19.25      BLGL
ATOM   2234  CA   ALA  299      27.038   1.754  23.633  1.00 17.97      BLGL
ATOM   2235  CB   ALA  299      27.294   1.264  25.030  1.00 16.35      BLGL
ATOM   2236  C    ALA  299      25.638   2.339  23.537  1.00 19.35      BLGL
ATOM   2237  O    ALA  299      24.763   1.771  22.881  1.00 17.73      BLGL
ATOM   2238  N    VAL  300      25.432   3.474  24.201  1.00 20.77      BLGL
ATOM   2239  CA   VAL  300      24.134   4.146  24.202  1.00 20.54      BLGL
ATOM   2240  CB   VAL  300      24.141   5.382  25.141  1.00 19.20      BLGL
ATOM   2241  CG1  VAL  300      22.786   6.081  25.108  1.00 16.54      BLGL
ATOM   2242  CG2  VAL  300      24.467   4.948  26.556  1.00 16.81      BLGL
ATOM   2243  C    VAL  300      23.761   4.597  22.795  1.00 20.62      BLGL
```

Fig. 4 cont.

| | | | | | | | | | |
|---|---|---|---|---|---|---|---|---|---|
| ATOM | 2244 | O | VAL | 300 | 22.643 | 4.383 | 22.332 | 1.00 22.02 | BLGL |
| ATOM | 2245 | N | ARG | 301 | 24.711 | 5.220 | 22.117 | 1.00 19.80 | BLGL |
| ATOM | 2246 | CA | ARG | 301 | 24.485 | 5.699 | 20.770 | 1.00 20.87 | BLGL |
| ATOM | 2247 | CB | ARG | 301 | 25.764 | 6.370 | 20.273 | 1.00 20.72 | BLGL |
| ATOM | 2248 | CG | ARG | 301 | 25.697 | 6.960 | 18.884 | 1.00 19.75 | BLGL |
| ATOM | 2249 | CD | ARG | 301 | 25.963 | 5.909 | 17.841 | 1.00 20.20 | BLGL |
| ATOM | 2250 | NE | ARG | 301 | 25.950 | 6.479 | 16.502 | 1.00 21.66 | BLGL |
| ATOM | 2251 | CZ | ARG | 301 | 25.770 | 5.763 | 15.400 | 1.00 21.05 | BLGL |
| ATOM | 2252 | NH1 | ARG | 301 | 25.593 | 4.453 | 15.484 | 1.00 23.39 | BLGL |
| ATOM | 2253 | NH2 | ARG | 301 | 25.741 | 6.359 | 14.223 | 1.00 19.98 | BLGL |
| ATOM | 2254 | C | ARG | 301 | 24.050 | 4.575 | 19.824 | 1.00 21.51 | BLGL |
| ATOM | 2255 | O | ARG | 301 | 23.190 | 4.774 | 18.967 | 1.00 23.05 | BLGL |
| ATOM | 2256 | N | ASP | 302 | 24.633 | 3.394 | 19.989 | 1.00 20.34 | BLGL |
| ATOM | 2257 | CA | ASP | 302 | 24.306 | 2.262 | 19.138 | 1.00 19.74 | BLGL |
| ATOM | 2258 | CB | ASP | 302 | 25.378 | 1.190 | 19.260 | 1.00 22.07 | BLGL |
| ATOM | 2259 | CG | ASP | 302 | 26.659 | 1.571 | 18.548 | 1.00 26.74 | BLGL |
| ATOM | 2260 | OD1 | ASP | 302 | 27.647 | 0.818 | 18.676 | 1.00 31.70 | BLGL |
| ATOM | 2261 | OD2 | ASP | 302 | 26.686 | 2.618 | 17.857 | 1.00 28.72 | BLGL |
| ATOM | 2262 | C | ASP | 302 | 22.947 | 1.648 | 19.408 | 1.00 20.74 | BLGL |
| ATOM | 2263 | O | ASP | 302 | 22.329 | 1.083 | 18.509 | 1.00 23.13 | BLGL |
| ATOM | 2264 | N | VAL | 303 | 22.482 | 1.740 | 20.644 | 1.00 18.00 | BLGL |
| ATOM | 2265 | CA | VAL | 303 | 21.182 | 1.189 | 20.971 | 1.00 18.00 | BLGL |
| ATOM | 2266 | CB | VAL | 303 | 20.971 | 1.110 | 22.503 | 1.00 17.67 | BLGL |
| ATOM | 2267 | CG1 | VAL | 303 | 19.626 | 0.483 | 22.813 | 1.00 17.30 | BLGL |
| ATOM | 2268 | CG2 | VAL | 303 | 22.075 | 0.299 | 23.132 | 1.00 20.13 | BLGL |
| ATOM | 2269 | C | VAL | 303 | 20.126 | 2.099 | 20.346 | 1.00 18.76 | BLGL |
| ATOM | 2270 | O | VAL | 303 | 19.099 | 1.638 | 19.854 | 1.00 16.54 | BLGL |
| ATOM | 2271 | N | ILE | 304 | 20.392 | 3.401 | 20.367 | 1.00 19.37 | BLGL |
| ATOM | 2272 | CA | ILE | 304 | 19.471 | 4.371 | 19.793 | 1.00 20.60 | BLGL |
| ATOM | 2273 | CB | ILE | 304 | 19.955 | 5.820 | 20.067 | 1.00 21.68 | BLGL |
| ATOM | 2274 | CG2 | ILE | 304 | 19.113 | 6.835 | 19.293 | 1.00 19.25 | BLGL |
| ATOM | 2275 | CG1 | ILE | 304 | 19.853 | 6.108 | 21.567 | 1.00 21.33 | BLGL |
| ATOM | 2276 | CD1 | ILE | 304 | 20.334 | 7.482 | 21.961 | 1.00 21.10 | BLGL |
| ATOM | 2277 | C | ILE | 304 | 19.387 | 4.102 | 18.294 | 1.00 21.62 | BLGL |
| ATOM | 2278 | O | ILE | 304 | 18.316 | 4.130 | 17.695 | 1.00 22.05 | BLGL |
| ATOM | 2279 | N | GLN | 305 | 20.531 | 3.820 | 17.694 | 1.00 21.95 | BLGL |
| ATOM | 2280 | CA | GLN | 305 | 20.579 | 3.523 | 16.279 | 1.00 22.70 | BLGL |
| ATOM | 2281 | CB | GLN | 305 | 22.031 | 3.274 | 15.855 | 1.00 25.34 | BLGL |
| ATOM | 2282 | CG | GLN | 305 | 22.203 | 2.958 | 14.381 | 1.00 28.30 | BLGL |
| ATOM | 2283 | CD | GLN | 305 | 22.031 | 4.178 | 13.505 | 1.00 30.27 | BLGL |
| ATOM | 2284 | OE1 | GLN | 305 | 22.915 | 5.030 | 13.430 | 1.00 30.12 | BLGL |
| ATOM | 2285 | NE2 | GLN | 305 | 20.884 | 4.273 | 12.841 | 1.00 32.34 | BLGL |
| ATOM | 2286 | C | GLN | 305 | 19.736 | 2.278 | 16.006 | 1.00 22.92 | BLGL |
| ATOM | 2287 | O | GLN | 305 | 18.925 | 2.258 | 15.080 | 1.00 23.46 | BLGL |
| ATOM | 2288 | N | ALA | 306 | 19.931 | 1.247 | 16.831 | 1.00 22.84 | BLGL |
| ATOM | 2289 | CA | ALA | 306 | 19.221 | -0.031 | 16.693 | 1.00 21.78 | BLGL |
| ATOM | 2290 | CB | ALA | 306 | 19.708 | -1.019 | 17.743 | 1.00 18.27 | BLGL |
| ATOM | 2291 | C | ALA | 306 | 17.704 | 0.090 | 16.773 | 1.00 22.33 | BLGL |
| ATOM | 2292 | O | ALA | 306 | 16.987 | -0.569 | 16.018 | 1.00 23.37 | BLGL |
| ATOM | 2293 | N | VAL | 307 | 17.219 | 0.919 | 17.691 | 1.00 20.00 | BLGL |
| ATOM | 2294 | CA | VAL | 307 | 15.788 | 1.112 | 17.844 | 1.00 20.55 | BLGL |
| ATOM | 2295 | CB | VAL | 307 | 15.450 | 1.823 | 19.169 | 1.00 20.50 | BLGL |
| ATOM | 2296 | CG1 | VAL | 307 | 13.959 | 2.106 | 19.248 | 1.00 17.36 | BLGL |
| ATOM | 2297 | CG2 | VAL | 307 | 15.878 | 0.960 | 20.337 | 1.00 19.55 | BLGL |
| ATOM | 2298 | C | VAL | 307 | 15.274 | 1.959 | 16.696 | 1.00 21.97 | BLGL |
| ATOM | 2299 | O | VAL | 307 | 14.164 | 1.750 | 16.195 | 1.00 22.69 | BLGL |
| ATOM | 2300 | N | SER | 308 | 16.097 | 2.916 | 16.283 | 1.00 21.64 | BLGL |
| ATOM | 2301 | CA | SER | 308 | 15.750 | 3.818 | 15.197 | 1.00 21.48 | BLGL |
| ATOM | 2302 | CB | SER | 308 | 16.809 | 4.916 | 15.073 | 1.00 22.23 | BLGL |
| ATOM | 2303 | OG | SER | 308 | 16.510 | 5.812 | 14.018 | 1.00 26.06 | BLGL |
| ATOM | 2304 | C | SER | 308 | 15.633 | 3.059 | 13.885 | 1.00 20.97 | BLGL |
| ATOM | 2305 | O | SER | 308 | 14.781 | 3.372 | 13.054 | 1.00 17.14 | BLGL |
| ATOM | 2306 | N | ASP | 309 | 16.490 | 2.057 | 13.709 | 1.00 21.61 | BLGL |
| ATOM | 2307 | CA | ASP | 309 | 16.480 | 1.252 | 12.494 | 1.00 23.50 | BLGL |
| ATOM | 2308 | CB | ASP | 309 | 17.698 | 0.332 | 12.434 | 1.00 25.27 | BLGL |
| ATOM | 2309 | CG | ASP | 309 | 18.971 | 1.069 | 12.064 | 1.00 29.05 | BLGL |

Fig. 4 cont.

```
ATOM   2310  OD1 ASP  309     18.874    2.130   11.401  1.00 26.38      BLGL
ATOM   2311  OD2 ASP  309     20.066    0.576   12.423  1.00 30.01      BLGL
ATOM   2312  C   ASP  309     15.225    0.412   12.339  1.00 24.33      BLGL
ATOM   2313  O   ASP  309     14.972   -0.124   11.265  1.00 26.71      BLGL
ATOM   2314  N   VAL  310     14.450    0.280   13.409  1.00 24.29      BLGL
ATOM   2315  CA  VAL  310     13.219   -0.490   13.344  1.00 23.62      BLGL
ATOM   2316  CB  VAL  310     12.582   -0.647   14.730  1.00 23.06      BLGL
ATOM   2317  CG1 VAL  310     11.232   -1.336   14.606  1.00 21.23      BLGL
ATOM   2318  CG2 VAL  310     13.509   -1.443   15.632  1.00 21.91      BLGL
ATOM   2319  C   VAL  310     12.248    0.247   12.440  1.00 23.63      BLGL
ATOM   2320  O   VAL  310     11.360   -0.352   11.834  1.00 25.38      BLGL
ATOM   2321  N   GLY  311     12.438    1.555   12.343  1.00 23.71      BLGL
ATOM   2322  CA  GLY  311     11.573    2.373   11.519  1.00 23.98      BLGL
ATOM   2323  C   GLY  311     10.628    3.201   12.366  1.00 27.47      BLGL
ATOM   2324  O   GLY  311     10.919    3.565   13.514  1.00 28.40      BLGL
ATOM   2325  N   GLU  312      9.469    3.474   11.783  1.00 27.49      BLGL
ATOM   2326  CA  GLU  312      8.438    4.262   12.419  1.00 27.36      BLGL
ATOM   2327  CB  GLU  312      7.210    4.291   11.514  1.00 32.86      BLGL
ATOM   2328  CG  GLU  312      6.318    5.503   11.705  1.00 43.92      BLGL
ATOM   2329  CD  GLU  312      4.950    5.314   11.071  1.00 50.44      BLGL
ATOM   2330  OE1 GLU  312      4.889    4.793    9.930  1.00 51.60      BLGL
ATOM   2331  OE2 GLU  312      3.939    5.694   11.713  1.00 53.86      BLGL
ATOM   2332  C   GLU  312      8.039    3.746   13.805  1.00 25.87      BLGL
ATOM   2333  O   GLU  312      7.717    4.537   14.683  1.00 27.15      BLGL
ATOM   2334  N   ALA  313      8.067    2.431   14.003  1.00 22.50      BLGL
ATOM   2335  CA  ALA  313      7.671    1.814   15.273  1.00 19.75      BLGL
ATOM   2336  CB  ALA  313      7.480    0.315   15.077  1.00 19.28      BLGL
ATOM   2337  C   ALA  313      8.608    2.054   16.454  1.00 18.86      BLGL
ATOM   2338  O   ALA  313      8.167    2.049   17.602  1.00 15.56      BLGL
ATOM   2339  N   GLY  314      9.897    2.238   16.173  1.00 19.40      BLGL
ATOM   2340  CA  GLY  314     10.868    2.476   17.232  1.00 21.12      BLGL
ATOM   2341  C   GLY  314     10.667    3.878   17.787  1.00 22.30      BLGL
ATOM   2342  O   GLY  314     11.016    4.865   17.135  1.00 23.19      BLGL
ATOM   2343  N   ILE  315     10.122    3.973   18.997  1.00 19.98      BLGL
ATOM   2344  CA  ILE  315      9.841    5.267   19.580  1.00 18.06      BLGL
ATOM   2345  CB  ILE  315      8.457    5.265   20.248  1.00 17.92      BLGL
ATOM   2346  CG2 ILE  315      7.402    4.928   19.221  1.00 16.03      BLGL
ATOM   2347  CG1 ILE  315      8.417    4.242   21.378  1.00 17.81      BLGL
ATOM   2348  CD1 ILE  315      7.113    4.236   22.116  1.00 16.57      BLGL
ATOM   2349  C   ILE  315     10.852    5.818   20.563  1.00 18.49      BLGL
ATOM   2350  O   ILE  315     10.851    7.012   20.836  1.00 19.85      BLGL
ATOM   2351  N   GLY  316     11.719    4.974   21.101  1.00 18.64      BLGL
ATOM   2352  CA  GLY  316     12.692    5.492   22.042  1.00 17.78      BLGL
ATOM   2353  C   GLY  316     13.562    4.510   22.803  1.00 18.38      BLGL
ATOM   2354  O   GLY  316     13.500    3.290   22.618  1.00 17.99      BLGL
ATOM   2355  N   VAL  317     14.381    5.081   23.680  1.00 17.69      BLGL
ATOM   2356  CA  VAL  317     15.312    4.328   24.512  1.00 17.45      BLGL
ATOM   2357  CB  VAL  317     16.727    4.367   23.916  1.00 17.12      BLGL
ATOM   2358  CG1 VAL  317     17.710    3.738   24.882  1.00 16.69      BLGL
ATOM   2359  CG2 VAL  317     16.753    3.642   22.586  1.00 16.13      BLGL
ATOM   2360  C   VAL  317     15.385    4.902   25.921  1.00 17.08      BLGL
ATOM   2361  O   VAL  317     15.386    6.116   26.101  1.00 19.09      BLGL
ATOM   2362  N   PHE  318     15.441    4.032   26.920  1.00 17.11      BLGL
ATOM   2363  CA  PHE  318     15.547    4.488   28.298  1.00 16.85      BLGL
ATOM   2364  CB  PHE  318     14.389    3.976   29.146  1.00 17.66      BLGL
ATOM   2365  CG  PHE  318     13.154    4.821   29.068  1.00 19.59      BLGL
ATOM   2366  CD1 PHE  318     12.208    4.615   28.063  1.00 17.88      BLGL
ATOM   2367  CD2 PHE  318     12.922    5.811   30.017  1.00 18.14      BLGL
ATOM   2368  CE1 PHE  318     11.041    5.383   28.007  1.00 15.40      BLGL
ATOM   2369  CE2 PHE  318     11.760    6.585   29.968  1.00 20.01      BLGL
ATOM   2370  CZ  PHE  318     10.815    6.367   28.960  1.00 16.53      BLGL
ATOM   2371  C   PHE  318     16.839    3.996   28.914  1.00 17.63      BLGL
ATOM   2372  O   PHE  318     17.132    2.802   28.878  1.00 19.56      BLGL
ATOM   2373  N   TYR  319     17.619    4.914   29.471  1.00 17.12      BLGL
ATOM   2374  CA  TYR  319     18.859    4.531   30.127  1.00 17.31      BLGL
ATOM   2375  CB  TYR  319     19.876    5.676   30.103  1.00 15.56      BLGL
```

Fig. 4 cont.

```
ATOM   2376  CG  TYR   319      21.255   5.211  30.495  1.00 17.60      BLGL
ATOM   2377  CD1 TYR   319      22.257   5.060  29.541  1.00 16.51      BLGL
ATOM   2378  CE1 TYR   319      23.503   4.568  29.886  1.00 17.94      BLGL
ATOM   2379  CD2 TYR   319      21.541   4.860  31.815  1.00 17.35      BLGL
ATOM   2380  CE2 TYR   319      22.781   4.366  32.174  1.00 18.20      BLGL
ATOM   2381  CZ  TYR   319      23.761   4.220  31.207  1.00 18.82      BLGL
ATOM   2382  OH  TYR   319      24.993   3.717  31.560  1.00 17.43      BLGL
ATOM   2383  C   TYR   319      18.465   4.214  31.568  1.00 15.84      BLGL
ATOM   2384  O   TYR   319      17.852   5.040  32.231  1.00 17.43      BLGL
ATOM   2385  N   TRP   320      18.811   3.024  32.050  1.00 15.86      BLGL
ATOM   2386  CA  TRP   320      18.448   2.622  33.408  1.00 14.37      BLGL
ATOM   2387  CB  TRP   320      18.286   1.099  33.489  1.00 13.03      BLGL
ATOM   2388  CG  TRP   320      17.673   0.644  34.786  1.00 13.67      BLGL
ATOM   2389  CD2 TRP   320      18.348  -0.001  35.873  1.00 13.63      BLGL
ATOM   2390  CE2 TRP   320      17.408  -0.123  36.930  1.00 16.14      BLGL
ATOM   2391  CE3 TRP   320      19.654  -0.480  36.063  1.00 12.95      BLGL
ATOM   2392  CD1 TRP   320      16.388   0.865  35.210  1.00 10.20      BLGL
ATOM   2393  NE1 TRP   320      16.225   0.413  36.491  1.00 11.94      BLGL
ATOM   2394  CZ2 TRP   320      17.736  -0.706  38.171  1.00 14.00      BLGL
ATOM   2395  CZ3 TRP   320      19.984  -1.057  37.292  1.00 14.81      BLGL
ATOM   2396  CH2 TRP   320      19.023  -1.163  38.332  1.00 15.77      BLGL
ATOM   2397  C   TRP   320      19.428   3.071  34.484  1.00 14.79      BLGL
ATOM   2398  O   TRP   320      20.624   2.786  34.403  1.00 13.40      BLGL
ATOM   2399  N   GLU   321      18.898   3.770  35.487  1.00 14.52      BLGL
ATOM   2400  CA  GLU   321      19.671   4.261  36.630  1.00 16.07      BLGL
ATOM   2401  CB  GLU   321      19.878   3.117  37.634  1.00 16.50      BLGL
ATOM   2402  CG  GLU   321      18.605   2.675  38.362  1.00 15.22      BLGL
ATOM   2403  CD  GLU   321      18.179   3.653  39.439  1.00 15.33      BLGL
ATOM   2404  OE1 GLU   321      17.190   3.375  40.156  1.00 13.74      BLGL
ATOM   2405  OE2 GLU   321      18.840   4.703  39.573  1.00 17.28      BLGL
ATOM   2406  C   GLU   321      21.015   4.890  36.267  1.00 16.30      BLGL
ATOM   2407  O   GLU   321      22.078   4.321  36.533  1.00 19.88      BLGL
ATOM   2408  N   PRO   322      20.985   6.085  35.664  1.00 13.95      BLGL
ATOM   2409  CD  PRO   322      19.800   6.807  35.166  1.00 13.71      BLGL
ATOM   2410  CA  PRO   322      22.207   6.776  35.269  1.00 13.32      BLGL
ATOM   2411  CB  PRO   322      21.727   7.665  34.136  1.00 13.68      BLGL
ATOM   2412  CG  PRO   322      20.397   8.108  34.648  1.00 11.78      BLGL
ATOM   2413  C   PRO   322      22.826   7.588  36.391  1.00 14.16      BLGL
ATOM   2414  O   PRO   322      23.849   8.235  36.191  1.00 17.47      BLGL
ATOM   2415  N   ALA   323      22.215   7.564  37.568  1.00 12.38      BLGL
ATOM   2416  CA  ALA   323      22.742   8.345  38.676  1.00 11.98      BLGL
ATOM   2417  CB  ALA   323      21.979   9.660  38.786  1.00  8.04      BLGL
ATOM   2418  C   ALA   323      22.736   7.619  40.012  1.00 12.24      BLGL
ATOM   2419  O   ALA   323      22.580   8.245  41.060  1.00 10.55      BLGL
ATOM   2420  N   TRP   324      22.910   6.300  39.980  1.00 14.35      BLGL
ATOM   2421  CA  TRP   324      22.933   5.515  41.215  1.00 15.62      BLGL
ATOM   2422  CB  TRP   324      22.422   4.094  40.973  1.00 15.22      BLGL
ATOM   2423  CG  TRP   324      21.843   3.473  42.201  1.00 16.28      BLGL
ATOM   2424  CD2 TRP   324      20.827   2.465  42.257  1.00 18.02      BLGL
ATOM   2425  CE2 TRP   324      20.595   2.181  43.622  1.00 18.70      BLGL
ATOM   2426  CE3 TRP   324      20.086   1.776  41.287  1.00 16.37      BLGL
ATOM   2427  CD1 TRP   324      22.178   3.748  43.494  1.00 17.37      BLGL
ATOM   2428  NE1 TRP   324      21.434   2.978  44.354  1.00 19.41      BLGL
ATOM   2429  CZ2 TRP   324      19.655   1.231  44.044  1.00 19.78      BLGL
ATOM   2430  CZ3 TRP   324      19.154   0.834  41.703  1.00 16.22      BLGL
ATOM   2431  CH2 TRP   324      18.944   0.570  43.071  1.00 18.68      BLGL
ATOM   2432  C   TRP   324      24.378   5.467  41.707  1.00 16.46      BLGL
ATOM   2433  O   TRP   324      24.986   4.405  41.823  1.00 13.25      BLGL
ATOM   2434  N   ILE   325      24.916   6.645  41.994  1.00 18.45      BLGL
ATOM   2435  CA  ILE   325      26.284   6.781  42.453  1.00 20.02      BLGL
ATOM   2436  CB  ILE   325      26.796   8.203  42.189  1.00 19.48      BLGL
ATOM   2437  CG2 ILE   325      26.652   8.518  40.706  1.00 18.33      BLGL
ATOM   2438  CG1 ILE   325      26.021   9.212  43.032  1.00 17.13      BLGL
ATOM   2439  CD1 ILE   325      26.493  10.630  42.843  1.00 14.92      BLGL
ATOM   2440  C   ILE   325      26.448   6.429  43.926  1.00 21.37      BLGL
ATOM   2441  O   ILE   325      25.473   6.373  44.675  1.00 20.25      BLGL
```

Fig. 4 cont.

```
ATOM   2442  N   PRO 326      27.697   6.188  44.358  1.00 22.85      BLGL
ATOM   2443  CD  PRO 326      28.935   6.258  43.557  1.00 21.92      BLGL
ATOM   2444  CA  PRO 326      27.988   5.827  45.750  1.00 23.11      BLGL
ATOM   2445  CB  PRO 326      29.488   5.535  45.724  1.00 21.79      BLGL
ATOM   2446  CG  PRO 326      29.992   6.401  44.613  1.00 23.00      BLGL
ATOM   2447  C   PRO 326      27.604   6.851  46.806  1.00 22.87      BLGL
ATOM   2448  O   PRO 326      27.666   8.055  46.564  1.00 22.51      BLGL
ATOM   2449  N   VAL 327      27.189   6.360  47.975  1.00 22.78      BLGL
ATOM   2450  CA  VAL 327      26.812   7.236  49.083  1.00 24.67      BLGL
ATOM   2451  CB  VAL 327      25.918   6.519  50.133  1.00 26.26      BLGL
ATOM   2452  CG1 VAL 327      24.651   5.996  49.478  1.00 27.07      BLGL
ATOM   2453  CG2 VAL 327      26.691   5.393  50.805  1.00 23.81      BLGL
ATOM   2454  C   VAL 327      28.072   7.697  49.798  1.00 25.35      BLGL
ATOM   2455  O   VAL 327      28.036   8.643  50.582  1.00 25.02      BLGL
ATOM   2456  N   GLY 328      29.176   7.007  49.516  1.00 26.68      BLGL
ATOM   2457  CA  GLY 328      30.459   7.315  50.120  1.00 27.54      BLGL
ATOM   2458  C   GLY 328      31.540   6.412  49.551  1.00 29.31      BLGL
ATOM   2459  O   GLY 328      31.219   5.392  48.938  1.00 29.16      BLGL
ATOM   2460  N   PRO 329      32.830   6.751  49.743  1.00 30.18      BLGL
ATOM   2461  CD  PRO 329      33.277   7.948  50.477  1.00 30.73      BLGL
ATOM   2462  CA  PRO 329      33.989   5.994  49.255  1.00 30.09      BLGL
ATOM   2463  CB  PRO 329      35.166   6.722  49.891  1.00 30.88      BLGL
ATOM   2464  CG  PRO 329      34.685   8.128  49.959  1.00 31.43      BLGL
ATOM   2465  C   PRO 329      33.966   4.520  49.614  1.00 29.93      BLGL
ATOM   2466  O   PRO 329      33.416   4.132  50.639  1.00 30.03      BLGL
ATOM   2467  N   ALA 330      34.582   3.706  48.768  1.00 29.86      BLGL
ATOM   2468  CA  ALA 330      34.614   2.272  48.987  1.00 32.93      BLGL
ATOM   2469  CB  ALA 330      35.343   1.585  47.833  1.00 31.50      BLGL
ATOM   2470  C   ALA 330      35.265   1.911  50.313  1.00 35.35      BLGL
ATOM   2471  O   ALA 330      34.894   0.916  50.940  1.00 35.56      BLGL
ATOM   2472  N   HIS 331      36.228   2.721  50.749  1.00 37.94      BLGL
ATOM   2473  CA  HIS 331      36.922   2.440  52.001  1.00 40.82      BLGL
ATOM   2474  CB  HIS 331      38.282   3.143  52.049  1.00 41.19      BLGL
ATOM   2475  CG  HIS 331      38.195   4.632  52.171  1.00 42.83      BLGL
ATOM   2476  CD2 HIS 331      38.170   5.436  53.261  1.00 42.69      BLGL
ATOM   2477  ND1 HIS 331      38.130   5.469  51.077  1.00 43.41      BLGL
ATOM   2478  CE1 HIS 331      38.073   6.725  51.488  1.00 42.26      BLGL
ATOM   2479  NE2 HIS 331      38.096   6.732  52.809  1.00 42.43      BLGL
ATOM   2480  C   HIS 331      36.130   2.805  53.254  1.00 42.32      BLGL
ATOM   2481  O   HIS 331      36.674   2.788  54.354  1.00 43.73      BLGL
ATOM   2482  N   ARG 332      34.857   3.149  53.105  1.00 43.54      BLGL
ATOM   2483  CA  ARG 332      34.041   3.478  54.264  1.00 43.67      BLGL
ATOM   2484  CB  ARG 332      33.446   4.878  54.152  1.00 46.16      BLGL
ATOM   2485  CG  ARG 332      34.428   6.031  54.232  1.00 51.93      BLGL
ATOM   2486  CD  ARG 332      33.693   7.258  54.754  1.00 55.92      BLGL
ATOM   2487  NE  ARG 332      32.323   7.299  54.240  1.00 62.04      BLGL
ATOM   2488  CZ  ARG 332      31.376   8.138  54.664  1.00 64.85      BLGL
ATOM   2489  NH1 ARG 332      30.154   8.095  54.132  1.00 64.81      BLGL
ATOM   2490  NH2 ARG 332      31.640   9.023  55.622  1.00 65.83      BLGL
ATOM   2491  C   ARG 332      32.899   2.482  54.368  1.00 43.46      BLGL
ATOM   2492  O   ARG 332      31.882   2.766  54.999  1.00 42.10      BLGL
ATOM   2493  N   LEU 333      33.077   1.318  53.748  1.00 43.54      BLGL
ATOM   2494  CA  LEU 333      32.058   0.277  53.739  1.00 44.90      BLGL
ATOM   2495  CB  LEU 333      32.700  -1.104  53.605  1.00 44.71      BLGL
ATOM   2496  CG  LEU 333      32.076  -1.981  52.511  1.00 47.14      BLGL
ATOM   2497  CD1 LEU 333      32.702  -3.370  52.561  1.00 47.53      BLGL
ATOM   2498  CD2 LEU 333      30.561  -2.068  52.691  1.00 46.62      BLGL
ATOM   2499  C   LEU 333      31.154   0.282  54.959  1.00 46.15      BLGL
ATOM   2500  O   LEU 333      29.931   0.378  54.833  1.00 47.20      BLGL
ATOM   2501  N   GLU 334      31.755   0.183  56.139  1.00 47.86      BLGL
ATOM   2502  CA  GLU 334      30.989   0.159  57.384  1.00 48.83      BLGL
ATOM   2503  CB  GLU 334      31.934   0.012  58.584  1.00 51.92      BLGL
ATOM   2504  CG  GLU 334      32.639  -1.345  58.641  1.00 58.71      BLGL
ATOM   2505  CD  GLU 334      31.663  -2.521  58.588  1.00 61.85      BLGL
ATOM   2506  OE1 GLU 334      30.824  -2.642  59.510  1.00 62.23      BLGL
ATOM   2507  OE2 GLU 334      31.734  -3.319  57.622  1.00 63.86      BLGL
```

Fig. 4 cont.

```
ATOM   2508  C    GLU  334      30.083   1.374  57.584  1.00 46.21           BLGL
ATOM   2509  O    GLU  334      28.939   1.246  58.030  1.00 45.37           BLGL
ATOM   2510  N    LYS  335      30.583   2.552  57.251  1.00 44.31           BLGL
ATOM   2511  CA   LYS  335      29.783   3.752  57.415  1.00 43.94           BLGL
ATOM   2512  CB   LYS  335      30.687   4.980  57.370  1.00 48.35           BLGL
ATOM   2513  CG   LYS  335      30.158   6.168  58.168  1.00 51.85           BLGL
ATOM   2514  CD   LYS  335      29.958   5.809  59.653  1.00 56.01           BLGL
ATOM   2515  CE   LYS  335      31.207   5.161  60.270  1.00 57.13           BLGL
ATOM   2516  NZ   LYS  335      32.440   5.982  60.078  1.00 58.45           BLGL
ATOM   2517  C    LYS  335      28.717   3.843  56.318  1.00 42.75           BLGL
ATOM   2518  O    LYS  335      27.664   4.458  56.508  1.00 40.92           BLGL
ATOM   2519  N    ASN  336      28.999   3.229  55.169  1.00 40.89           BLGL
ATOM   2520  CA   ASN  336      28.068   3.233  54.050  1.00 36.25           BLGL
ATOM   2521  CB   ASN  336      28.758   2.764  52.774  1.00 34.22           BLGL
ATOM   2522  CG   ASN  336      29.754   3.770  52.252  1.00 33.73           BLGL
ATOM   2523  OD1  ASN  336      29.698   4.949  52.593  1.00 33.95           BLGL
ATOM   2524  ND2  ASN  336      30.661   3.316  51.401  1.00 34.13           BLGL
ATOM   2525  C    ASN  336      26.883   2.332  54.333  1.00 35.83           BLGL
ATOM   2526  O    ASN  336      25.742   2.702  54.050  1.00 35.07           BLGL
ATOM   2527  N    LYS  337      27.161   1.147  54.882  1.00 34.86           BLGL
ATOM   2528  CA   LYS  337      26.116   0.171  55.209  1.00 33.18           BLGL
ATOM   2529  CB   LYS  337      26.712  -1.023  55.953  1.00 31.58           BLGL
ATOM   2530  CG   LYS  337      27.594  -1.901  55.095  1.00 32.46           BLGL
ATOM   2531  CD   LYS  337      28.112  -3.095  55.881  1.00 33.49           BLGL
ATOM   2532  CE   LYS  337      28.869  -4.046  54.967  1.00 38.20           BLGL
ATOM   2533  NZ   LYS  337      29.366  -5.262  55.679  1.00 41.08           BLGL
ATOM   2534  C    LYS  337      25.042   0.812  56.069  1.00 32.37           BLGL
ATOM   2535  O    LYS  337      23.866   0.477  55.971  1.00 30.10           BLGL
ATOM   2536  N    ALA  338      25.466   1.738  56.917  1.00 32.27           BLGL
ATOM   2537  CA   ALA  338      24.543   2.434  57.793  1.00 32.10           BLGL
ATOM   2538  CB   ALA  338      25.313   3.383  58.712  1.00 30.46           BLGL
ATOM   2539  C    ALA  338      23.533   3.211  56.951  1.00 31.53           BLGL
ATOM   2540  O    ALA  338      22.332   3.174  57.217  1.00 32.87           BLGL
ATOM   2541  N    LEU  339      24.025   3.915  55.937  1.00 29.75           BLGL
ATOM   2542  CA   LEU  339      23.165   4.703  55.064  1.00 28.75           BLGL
ATOM   2543  CB   LEU  339      24.019   5.580  54.149  1.00 29.58           BLGL
ATOM   2544  CG   LEU  339      24.839   6.671  54.842  1.00 29.29           BLGL
ATOM   2545  CD1  LEU  339      25.763   7.358  53.858  1.00 30.28           BLGL
ATOM   2546  CD2  LEU  339      23.889   7.674  55.457  1.00 30.12           BLGL
ATOM   2547  C    LEU  339      22.246   3.824  54.217  1.00 28.58           BLGL
ATOM   2548  O    LEU  339      21.035   4.049  54.154  1.00 28.13           BLGL
ATOM   2549  N    TRP  340      22.828   2.828  53.557  1.00 27.39           BLGL
ATOM   2550  CA   TRP  340      22.052   1.925  52.719  1.00 26.49           BLGL
ATOM   2551  CB   TRP  340      22.900   0.746  52.236  1.00 23.72           BLGL
ATOM   2552  CG   TRP  340      24.091   1.114  51.444  1.00 22.86           BLGL
ATOM   2553  CD2  TRP  340      25.305   0.366  51.336  1.00 23.48           BLGL
ATOM   2554  CE2  TRP  340      26.154   1.077  50.458  1.00 23.45           BLGL
ATOM   2555  CE3  TRP  340      25.760  -0.839  51.895  1.00 23.20           BLGL
ATOM   2556  CD1  TRP  340      24.243   2.214  50.651  1.00 22.87           BLGL
ATOM   2557  NE1  TRP  340      25.480   2.200  50.056  1.00 22.68           BLGL
ATOM   2558  CZ2  TRP  340      27.437   0.626  50.123  1.00 23.93           BLGL
ATOM   2559  CZ3  TRP  340      27.036  -1.288  51.561  1.00 24.91           BLGL
ATOM   2560  CH2  TRP  340      27.859  -0.553  50.682  1.00 23.29           BLGL
ATOM   2561  C    TRP  340      20.891   1.359  53.505  1.00 26.35           BLGL
ATOM   2562  O    TRP  340      19.777   1.252  53.005  1.00 26.95           BLGL
ATOM   2563  N    GLU  341      21.179   0.990  54.743  1.00 27.03           BLGL
ATOM   2564  CA   GLU  341      20.206   0.383  55.629  1.00 27.61           BLGL
ATOM   2565  CB   GLU  341      20.939  -0.239  56.818  1.00 29.81           BLGL
ATOM   2566  CG   GLU  341      20.338  -1.534  57.345  1.00 32.17           BLGL
ATOM   2567  CD   GLU  341      20.490  -2.693  56.384  1.00 34.50           BLGL
ATOM   2568  OE1  GLU  341      20.087  -3.811  56.756  1.00 38.21           BLGL
ATOM   2569  OE2  GLU  341      21.003  -2.503  55.261  1.00 35.23           BLGL
ATOM   2570  C    GLU  341      19.150   1.366  56.112  1.00 27.16           BLGL
ATOM   2571  O    GLU  341      17.967   1.044  56.169  1.00 27.02           BLGL
ATOM   2572  N    THR  342      19.569   2.572  56.452  1.00 27.11           BLGL
ATOM   2573  CA   THR  342      18.624   3.562  56.940  1.00 27.99           BLGL
```

Fig. 4 cont.

```
ATOM   2574  CB   THR   342      19.356    4.706   57.658  1.00  27.99      BLGL
ATOM   2575  OG1  THR   342      20.097    4.174   58.759  1.00  29.52      BLGL
ATOM   2576  CG2  THR   342      18.365    5.731   58.173  1.00  28.27      BLGL
ATOM   2577  C    THR   342      17.732    4.169   55.860  1.00  27.72      BLGL
ATOM   2578  O    THR   342      16.527    4.283   56.047  1.00  27.61      BLGL
ATOM   2579  N    TYR   343      18.319    4.554   54.732  1.00  28.64      BLGL
ATOM   2580  CA   TYR   343      17.544    5.185   53.675  1.00  29.90      BLGL
ATOM   2581  CB   TYR   343      18.260    6.448   53.209  1.00  31.83      BLGL
ATOM   2582  CG   TYR   343      18.573    7.381   54.350  1.00  35.78      BLGL
ATOM   2583  CD1  TYR   343      19.798    7.313   55.013  1.00  36.95      BLGL
ATOM   2584  CE1  TYR   343      20.078    8.151   56.085  1.00  38.42      BLGL
ATOM   2585  CD2  TYR   343      17.631    8.313   54.792  1.00  35.14      BLGL
ATOM   2586  CE2  TYR   343      17.901    9.153   55.864  1.00  36.75      BLGL
ATOM   2587  CZ   TYR   343      19.128    9.067   56.503  1.00  38.36      BLGL
ATOM   2588  OH   TYR   343      19.417    9.904   57.554  1.00  40.88      BLGL
ATOM   2589  C    TYR   343      17.202    4.327   52.469  1.00  28.69      BLGL
ATOM   2590  O    TYR   343      16.524    4.788   51.554  1.00  28.30      BLGL
ATOM   2591  N    GLY   344      17.652    3.081   52.470  1.00  28.37      BLGL
ATOM   2592  CA   GLY   344      17.375    2.204   51.347  1.00  29.03      BLGL
ATOM   2593  C    GLY   344      18.001    2.730   50.068  1.00  28.56      BLGL
ATOM   2594  O    GLY   344      17.425    2.603   48.987  1.00  27.04      BLGL
ATOM   2595  N    SER   345      19.187    3.320   50.199  1.00  27.20      BLGL
ATOM   2596  CA   SER   345      19.903    3.888   49.067  1.00  25.65      BLGL
ATOM   2597  CB   SER   345      20.754    5.061   49.530  1.00  25.43      BLGL
ATOM   2598  OG   SER   345      21.600    4.654   50.582  1.00  31.71      BLGL
ATOM   2599  C    SER   345      20.780    2.853   48.380  1.00  25.28      BLGL
ATOM   2600  O    SER   345      21.554    3.183   47.479  1.00  24.47      BLGL
ATOM   2601  N    GLY   346      20.662    1.604   48.823  1.00  24.37      BLGL
ATOM   2602  CA   GLY   346      21.414    0.518   48.220  1.00  21.46      BLGL
ATOM   2603  C    GLY   346      20.430   -0.252   47.360  1.00  20.92      BLGL
ATOM   2604  O    GLY   346      19.286    0.183   47.216  1.00  21.35      BLGL
ATOM   2605  N    TRP   347      20.834   -1.385   46.795  1.00  18.57      BLGL
ATOM   2606  CA   TRP   347      19.915   -2.145   45.959  1.00  18.47      BLGL
ATOM   2607  CB   TRP   347      20.677   -3.115   45.057  1.00  19.55      BLGL
ATOM   2608  CG   TRP   347      20.976   -4.426   45.700  1.00  24.39      BLGL
ATOM   2609  CD2  TRP   347      20.205   -5.626   45.576  1.00  26.03      BLGL
ATOM   2610  CE2  TRP   347      20.843   -6.616   46.361  1.00  27.34      BLGL
ATOM   2611  CE3  TRP   347      19.035   -5.963   44.878  1.00  25.88      BLGL
ATOM   2612  CD1  TRP   347      22.023   -4.725   46.533  1.00  24.43      BLGL
ATOM   2613  NE1  TRP   347      21.950   -6.039   46.931  1.00  24.87      BLGL
ATOM   2614  CZ2  TRP   347      20.344   -7.926   46.467  1.00  27.61      BLGL
ATOM   2615  CZ3  TRP   347      18.541   -7.268   44.982  1.00  26.42      BLGL
ATOM   2616  CH2  TRP   347      19.195   -8.229   45.770  1.00  25.85      BLGL
ATOM   2617  C    TRP   347      18.910   -2.916   46.807  1.00  17.94      BLGL
ATOM   2618  O    TRP   347      17.820   -3.255   46.347  1.00  16.07      BLGL
ATOM   2619  N    ALA   348      19.296   -3.197   48.047  1.00  19.28      BLGL
ATOM   2620  CA   ALA   348      18.444   -3.918   48.984  1.00  21.94      BLGL
ATOM   2621  CB   ALA   348      18.387   -5.394   48.607  1.00  20.51      BLGL
ATOM   2622  C    ALA   348      18.948   -3.767   50.422  1.00  24.22      BLGL
ATOM   2623  O    ALA   348      20.138   -3.549   50.659  1.00  25.24      BLGL
ATOM   2624  N    THR   349      18.030   -3.870   51.379  1.00  25.44      BLGL
ATOM   2625  CA   THR   349      18.378   -3.774   52.789  1.00  25.50      BLGL
ATOM   2626  CB   THR   349      17.509   -2.738   53.553  1.00  26.44      BLGL
ATOM   2627  OG1  THR   349      16.167   -3.228   53.679  1.00  25.28      BLGL
ATOM   2628  CG2  THR   349      17.500   -1.400   52.823  1.00  24.16      BLGL
ATOM   2629  C    THR   349      18.102   -5.139   53.383  1.00  26.30      BLGL
ATOM   2630  O    THR   349      17.382   -5.942   52.791  1.00  26.26      BLGL
ATOM   2631  N    SER   350      18.671   -5.403   54.551  1.00  27.06      BLGL
ATOM   2632  CA   SER   350      18.463   -6.685   55.208  1.00  26.38      BLGL
ATOM   2633  CB   SER   350      19.252   -6.738   56.514  1.00  23.71      BLGL
ATOM   2634  OG   SER   350      18.812   -5.726   57.400  1.00  21.01      BLGL
ATOM   2635  C    SER   350      16.975   -6.911   55.490  1.00  26.83      BLGL
ATOM   2636  O    SER   350      16.509   -8.046   55.520  1.00  26.17      BLGL
ATOM   2637  N    TYR   351      16.225   -5.830   55.683  1.00  28.04      BLGL
ATOM   2638  CA   TYR   351      14.796   -5.946   55.965  1.00  30.41      BLGL
ATOM   2639  CB   TYR   351      14.208   -4.566   56.244  1.00  32.17      BLGL
```

Fig. 4 cont.

```
ATOM   2640  CG   TYR  351      14.911   -3.829  57.352  1.00 33.63      BLGL
ATOM   2641  CD1  TYR  351      15.961   -2.951  57.083  1.00 35.43      BLGL
ATOM   2642  CE1  TYR  351      16.623   -2.279  58.114  1.00 35.75      BLGL
ATOM   2643  CD2  TYR  351      14.539   -4.020  58.677  1.00 35.69      BLGL
ATOM   2644  CE2  TYR  351      15.193   -3.355  59.717  1.00 36.21      BLGL
ATOM   2645  CZ   TYR  351      16.231   -2.488  59.427  1.00 35.60      BLGL
ATOM   2646  OH   TYR  351      16.865   -1.828  60.451  1.00 36.59      BLGL
ATOM   2647  C    TYR  351      14.012   -6.626  54.836  1.00 30.90      BLGL
ATOM   2648  O    TYR  351      12.921   -7.159  55.055  1.00 30.86      BLGL
ATOM   2649  N    ALA  352      14.572   -6.604  53.633  1.00 30.77      BLGL
ATOM   2650  CA   ALA  352      13.936   -7.220  52.476  1.00 31.75      BLGL
ATOM   2651  CB   ALA  352      14.611   -6.744  51.202  1.00 30.75      BLGL
ATOM   2652  C    ALA  352      13.989   -8.745  52.545  1.00 33.29      BLGL
ATOM   2653  O    ALA  352      13.411   -9.434  51.700  1.00 33.71      BLGL
ATOM   2654  N    ALA  353      14.680   -9.273  53.549  1.00 33.30      BLGL
ATOM   2655  CA   ALA  353      14.804  -10.718  53.706  1.00 33.02      BLGL
ATOM   2656  CB   ALA  353      15.687  -11.033  54.908  1.00 34.24      BLGL
ATOM   2657  C    ALA  353      13.449  -11.409  53.856  1.00 32.34      BLGL
ATOM   2658  O    ALA  353      13.270  -12.545  53.422  1.00 30.15      BLGL
ATOM   2659  N    GLU  354      12.496  -10.716  54.466  1.00 33.65      BLGL
ATOM   2660  CA   GLU  354      11.176  -11.284  54.668  1.00 35.34      BLGL
ATOM   2661  CB   GLU  354      10.345  -10.375  55.578  1.00 35.98      BLGL
ATOM   2662  CG   GLU  354       9.744   -9.163  54.894  1.00 37.66      BLGL
ATOM   2663  CD   GLU  354       8.831   -8.378  55.818  1.00 40.92      BLGL
ATOM   2664  OE1  GLU  354       8.010   -7.584  55.310  1.00 42.14      BLGL
ATOM   2665  OE2  GLU  354       8.935   -8.548  57.055  1.00 41.70      BLGL
ATOM   2666  C    GLU  354      10.437  -11.503  53.343  1.00 36.54      BLGL
ATOM   2667  O    GLU  354       9.614  -12.416  53.228  1.00 36.40      BLGL
ATOM   2668  N    TYR  355      10.735  -10.673  52.345  1.00 36.32      BLGL
ATOM   2669  CA   TYR  355      10.072  -10.778  51.046  1.00 35.27      BLGL
ATOM   2670  CB   TYR  355       9.800   -9.381  50.496  1.00 32.38      BLGL
ATOM   2671  CG   TYR  355       8.715   -9.339  49.445  1.00 32.93      BLGL
ATOM   2672  CD1  TYR  355       9.022   -9.211  48.087  1.00 31.94      BLGL
ATOM   2673  CE1  TYR  355       8.014   -9.141  47.126  1.00 30.60      BLGL
ATOM   2674  CD2  TYR  355       7.372   -9.403  49.812  1.00 31.34      BLGL
ATOM   2675  CE2  TYR  355       6.364   -9.333  48.864  1.00 31.48      BLGL
ATOM   2676  CZ   TYR  355       6.688   -9.198  47.524  1.00 32.10      BLGL
ATOM   2677  OH   TYR  355       5.679   -9.084  46.593  1.00 32.53      BLGL
ATOM   2678  C    TYR  355      10.873  -11.590  50.034  1.00 36.46      BLGL
ATOM   2679  O    TYR  355      10.306  -12.262  49.177  1.00 33.16      BLGL
ATOM   2680  N    ASP  356      12.196  -11.513  50.133  1.00 39.53      BLGL
ATOM   2681  CA   ASP  356      13.079  -12.251  49.241  1.00 42.86      BLGL
ATOM   2682  CB   ASP  356      13.568  -11.355  48.096  1.00 43.64      BLGL
ATOM   2683  CG   ASP  356      14.568  -12.064  47.182  1.00 44.35      BLGL
ATOM   2684  OD1  ASP  356      15.202  -11.382  46.349  1.00 42.98      BLGL
ATOM   2685  OD2  ASP  356      14.715  -13.303  47.293  1.00 45.31      BLGL
ATOM   2686  C    ASP  356      14.278  -12.741  50.045  1.00 45.45      BLGL
ATOM   2687  O    ASP  356      15.302  -12.058  50.133  1.00 47.13      BLGL
ATOM   2688  N    PRO  357      14.165  -13.931  50.650  1.00 46.19      BLGL
ATOM   2689  CD   PRO  357      12.983  -14.810  50.688  1.00 45.78      BLGL
ATOM   2690  CA   PRO  357      15.260  -14.493  51.447  1.00 46.80      BLGL
ATOM   2691  CB   PRO  357      14.578  -15.627  52.196  1.00 46.98      BLGL
ATOM   2692  CG   PRO  357      13.567  -16.109  51.196  1.00 46.25      BLGL
ATOM   2693  C    PRO  357      16.412  -14.990  50.581  1.00 48.11      BLGL
ATOM   2694  O    PRO  357      17.562  -15.006  51.007  1.00 48.32      BLGL
ATOM   2695  N    GLU  358      16.075  -15.381  49.358  1.00 49.36      BLGL
ATOM   2696  CA   GLU  358      17.019  -15.911  48.385  1.00 51.27      BLGL
ATOM   2697  CB   GLU  358      16.257  -16.304  47.125  1.00 53.72      BLGL
ATOM   2698  CG   GLU  358      15.040  -17.170  47.389  1.00 58.04      BLGL
ATOM   2699  CD   GLU  358      15.414  -18.587  47.774  1.00 62.05      BLGL
ATOM   2700  OE1  GLU  358      15.886  -19.331  46.886  1.00 63.62      BLGL
ATOM   2701  OE2  GLU  358      15.244  -18.955  48.961  1.00 64.62      BLGL
ATOM   2702  C    GLU  358      18.142  -14.958  47.995  1.00 52.75      BLGL
ATOM   2703  O    GLU  358      19.319  -15.232  48.240  1.00 53.92      BLGL
ATOM   2704  N    ASP  359      17.768  -13.850  47.366  1.00 53.56      BLGL
ATOM   2705  CA   ASP  359      18.717  -12.847  46.902  1.00 53.46      BLGL
```

Fig. 4 cont.

```
ATOM   2706  CB  ASP  359      18.203 -12.213  45.609  1.00 56.56          BLGL
ATOM   2707  CG  ASP  359      18.748 -12.887  44.366  1.00 58.60          BLGL
ATOM   2708  OD1 ASP  359      18.654 -14.130  44.268  1.00 60.63          BLGL
ATOM   2709  OD2 ASP  359      19.268 -12.166  43.485  1.00 59.51          BLGL
ATOM   2710  C   ASP  359      18.959 -11.751  47.928  1.00 51.60          BLGL
ATOM   2711  O   ASP  359      19.876 -11.837  48.742  1.00 50.90          BLGL
ATOM   2712  N   ALA  360      18.132 -10.713  47.865  1.00 51.06          BLGL
ATOM   2713  CA  ALA  360      18.226  -9.578  48.768  1.00 50.62          BLGL
ATOM   2714  CB  ALA  360      16.945  -8.767  48.697  1.00 49.16          BLGL
ATOM   2715  C   ALA  360      18.471 -10.058  50.193  1.00 50.90          BLGL
ATOM   2716  O   ALA  360      19.164  -9.403  50.973  1.00 49.67          BLGL
ATOM   2717  N   GLY  361      17.896 -11.214  50.515  1.00 52.39          BLGL
ATOM   2718  CA  GLY  361      18.042 -11.794  51.837  1.00 52.85          BLGL
ATOM   2719  C   GLY  361      19.481 -11.858  52.312  1.00 53.39          BLGL
ATOM   2720  O   GLY  361      19.809 -11.331  53.378  1.00 54.42          BLGL
ATOM   2721  N   LYS  362      20.351 -12.496  51.540  1.00 53.32          BLGL
ATOM   2722  CA  LYS  362      21.737 -12.588  51.954  1.00 54.47          BLGL
ATOM   2723  CB  LYS  362      22.081 -14.037  52.329  1.00 57.86          BLGL
ATOM   2724  CG  LYS  362      21.401 -15.120  51.495  1.00 59.76          BLGL
ATOM   2725  CD  LYS  362      22.199 -15.482  50.251  1.00 61.95          BLGL
ATOM   2726  CE  LYS  362      21.745 -16.833  49.698  1.00 63.37          BLGL
ATOM   2727  NZ  LYS  362      22.557 -17.264  48.522  1.00 62.07          BLGL
ATOM   2728  C   LYS  362      22.741 -12.034  50.953  1.00 53.61          BLGL
ATOM   2729  O   LYS  362      23.823 -12.595  50.770  1.00 54.78          BLGL
ATOM   2730  N   TRP  363      22.376 -10.921  50.323  1.00 52.09          BLGL
ATOM   2731  CA  TRP  363      23.236 -10.246  49.357  1.00 49.55          BLGL
ATOM   2732  CB  TRP  363      23.048 -10.816  47.948  1.00 53.13          BLGL
ATOM   2733  CG  TRP  363      23.559 -12.215  47.792  1.00 58.47          BLGL
ATOM   2734  CD2 TRP  363      24.840 -12.716  48.201  1.00 61.21          BLGL
ATOM   2735  CE2 TRP  363      24.867 -14.096  47.894  1.00 62.60          BLGL
ATOM   2736  CE3 TRP  363      25.966 -12.135  48.802  1.00 63.42          BLGL
ATOM   2737  CD1 TRP  363      22.885 -13.277  47.262  1.00 60.70          BLGL
ATOM   2738  NE1 TRP  363      23.663 -14.412  47.320  1.00 62.38          BLGL
ATOM   2739  CZ2 TRP  363      25.981 -14.907  48.168  1.00 63.65          BLGL
ATOM   2740  CZ3 TRP  363      27.076 -12.945  49.076  1.00 64.57          BLGL
ATOM   2741  CH2 TRP  363      27.071 -14.315  48.757  1.00 63.75          BLGL
ATOM   2742  C   TRP  363      22.900  -8.765  49.354  1.00 45.74          BLGL
ATOM   2743  O   TRP  363      23.315  -8.031  48.460  1.00 46.95          BLGL
ATOM   2744  N   PHE  364      22.143  -8.333  50.357  1.00 40.08          BLGL
ATOM   2745  CA  PHE  364      21.748  -6.939  50.478  1.00 36.02          BLGL
ATOM   2746  CB  PHE  364      20.798  -6.763  51.664  1.00 35.97          BLGL
ATOM   2747  CG  PHE  364      21.393  -7.163  52.989  1.00 35.49          BLGL
ATOM   2748  CD1 PHE  364      22.170  -6.264  53.723  1.00 34.51          BLGL
ATOM   2749  CD2 PHE  364      21.194  -8.448  53.493  1.00 34.67          BLGL
ATOM   2750  CE1 PHE  364      22.739  -6.637  54.937  1.00 33.03          BLGL
ATOM   2751  CE2 PHE  364      21.759  -8.834  54.705  1.00 33.39          BLGL
ATOM   2752  CZ  PHE  364      22.534  -7.927  55.429  1.00 33.77          BLGL
ATOM   2753  C   PHE  364      22.978  -6.061  50.655  1.00 33.99          BLGL
ATOM   2754  O   PHE  364      23.998  -6.506  51.181  1.00 34.27          BLGL
ATOM   2755  N   GLY  365      22.881  -4.816  50.208  1.00 30.67          BLGL
ATOM   2756  CA  GLY  365      24.008  -3.915  50.322  1.00 28.90          BLGL
ATOM   2757  C   GLY  365      23.806  -2.610  49.581  1.00 27.08          BLGL
ATOM   2758  O   GLY  365      22.708  -2.058  49.571  1.00 27.26          BLGL
ATOM   2759  N   GLY  366      24.863  -2.122  48.943  1.00 26.06          BLGL
ATOM   2760  CA  GLY  366      24.777  -0.860  48.230  1.00 22.87          BLGL
ATOM   2761  C   GLY  366      24.434  -0.934  46.757  1.00 22.45          BLGL
ATOM   2762  O   GLY  366      23.680  -1.800  46.312  1.00 20.99          BLGL
ATOM   2763  N   SER  367      24.996   0.004  46.002  1.00 22.77          BLGL
ATOM   2764  CA  SER  367      24.779   0.098  44.566  1.00 21.36          BLGL
ATOM   2765  CB  SER  367      25.081   1.511  44.079  1.00 19.13          BLGL
ATOM   2766  OG  SER  367      25.081   1.539  42.665  1.00 20.78          BLGL
ATOM   2767  C   SER  367      25.649  -0.877  43.802  1.00 20.92          BLGL
ATOM   2768  O   SER  367      26.828  -1.040  44.111  1.00 22.00          BLGL
ATOM   2769  N   ALA  368      25.072  -1.518  42.794  1.00 19.58          BLGL
ATOM   2770  CA  ALA  368      25.823  -2.474  41.992  1.00 19.49          BLGL
ATOM   2771  CB  ALA  368      25.069  -3.792  41.921  1.00 18.00          BLGL
```

Fig. 4 cont.

```
ATOM   2772  C    ALA   368      26.058  -1.928  40.595  1.00 19.35      BLGL
ATOM   2773  O    ALA   368      26.610  -2.612  39.735  1.00 19.98      BLGL
ATOM   2774  N    VAL   369      25.656  -0.679  40.387  1.00 19.26      BLGL
ATOM   2775  CA   VAL   369      25.775  -0.041  39.080  1.00 19.71      BLGL
ATOM   2776  CB   VAL   369      24.391   0.041  38.379  1.00 16.72      BLGL
ATOM   2777  CG1  VAL   369      23.863  -1.349  38.093  1.00 13.08      BLGL
ATOM   2778  CG2  VAL   369      23.411   0.804  39.265  1.00 10.69      BLGL
ATOM   2779  C    VAL   369      26.357   1.366  39.124  1.00 20.80      BLGL
ATOM   2780  O    VAL   369      26.139   2.156  38.201  1.00 21.48      BLGL
ATOM   2781  N    ASP   370      27.083   1.693  40.187  1.00 21.01      BLGL
ATOM   2782  CA   ASP   370      27.680   3.024  40.269  1.00 21.96      BLGL
ATOM   2783  CB   ASP   370      28.401   3.226  41.617  1.00 20.78      BLGL
ATOM   2784  CG   ASP   370      29.224   2.016  42.042  1.00 26.31      BLGL
ATOM   2785  OD1  ASP   370      28.640   1.027  42.529  1.00 27.68      BLGL
ATOM   2786  OD2  ASP   370      30.466   2.045  41.893  1.00 31.81      BLGL
ATOM   2787  C    ASP   370      28.649   3.264  39.098  1.00 21.03      BLGL
ATOM   2788  O    ASP   370      28.886   4.405  38.695  1.00 16.48      BLGL
ATOM   2789  N    ASN   371      29.188   2.181  38.542  1.00 20.75      BLGL
ATOM   2790  CA   ASN   371      30.126   2.291  37.431  1.00 21.39      BLGL
ATOM   2791  CB   ASN   371      31.159   1.161  37.506  1.00 19.36      BLGL
ATOM   2792  CG   ASN   371      30.554  -0.202  37.257  1.00 17.69      BLGL
ATOM   2793  OD1  ASN   371      29.412  -0.471  37.631  1.00 16.68      BLGL
ATOM   2794  ND2  ASN   371      31.329  -1.081  36.635  1.00 15.28      BLGL
ATOM   2795  C    ASN   371      29.435   2.298  36.062  1.00 22.85      BLGL
ATOM   2796  O    ASN   371      30.088   2.203  35.018  1.00 21.45      BLGL
ATOM   2797  N    GLN   372      28.109   2.405  36.074  1.00 21.57      BLGL
ATOM   2798  CA   GLN   372      27.355   2.458  34.837  1.00 21.91      BLGL
ATOM   2799  CB   GLN   372      26.432   1.248  34.702  1.00 19.34      BLGL
ATOM   2800  CG   GLN   372      27.186  -0.043  34.541  1.00 19.05      BLGL
ATOM   2801  CD   GLN   372      26.332  -1.154  33.981  1.00 18.53      BLGL
ATOM   2802  OE1  GLN   372      25.802  -1.043  32.881  1.00 16.76      BLGL
ATOM   2803  NE2  GLN   372      26.199  -2.240  34.732  1.00 19.99      BLGL
ATOM   2804  C    GLN   372      26.550   3.750  34.783  1.00 22.49      BLGL
ATOM   2805  O    GLN   372      25.693   3.927  33.920  1.00 24.48      BLGL
ATOM   2806  N    ALA   373      26.842   4.658  35.705  1.00 21.34      BLGL
ATOM   2807  CA   ALA   373      26.155   5.940  35.755  1.00 21.66      BLGL
ATOM   2808  CB   ALA   373      26.301   6.544  37.148  1.00 20.20      BLGL
ATOM   2809  C    ALA   373      26.702   6.914  34.705  1.00 22.35      BLGL
ATOM   2810  O    ALA   373      27.707   6.638  34.038  1.00 21.94      BLGL
ATOM   2811  N    LEU   374      26.025   8.048  34.555  1.00 21.60      BLGL
ATOM   2812  CA   LEU   374      26.454   9.080  33.617  1.00 21.79      BLGL
ATOM   2813  CB   LEU   374      25.273   9.548  32.763  1.00 19.88      BLGL
ATOM   2814  CG   LEU   374      24.631   8.408  31.962  1.00 19.67      BLGL
ATOM   2815  CD1  LEU   374      23.430   8.928  31.196  1.00 19.92      BLGL
ATOM   2816  CD2  LEU   374      25.650   7.809  31.011  1.00 17.34      BLGL
ATOM   2817  C    LEU   374      27.040  10.236  34.431  1.00 22.87      BLGL
ATOM   2818  O    LEU   374      27.314  11.319  33.905  1.00 21.82      BLGL
ATOM   2819  N    PHE   375      27.214   9.981  35.728  1.00 21.81      BLGL
ATOM   2820  CA   PHE   375      27.800  10.937  36.664  1.00 23.69      BLGL
ATOM   2821  CB   PHE   375      26.780  11.387  37.722  1.00 22.43      BLGL
ATOM   2822  CG   PHE   375      25.641  12.195  37.169  1.00 24.54      BLGL
ATOM   2823  CD1  PHE   375      24.652  11.592  36.389  1.00 24.54      BLGL
ATOM   2824  CD2  PHE   375      25.563  13.566  37.407  1.00 22.99      BLGL
ATOM   2825  CE1  PHE   375      23.606  12.343  35.856  1.00 21.26      BLGL
ATOM   2826  CE2  PHE   375      24.521  14.324  36.877  1.00 20.60      BLGL
ATOM   2827  CZ   PHE   375      23.543  13.712  36.101  1.00 22.10      BLGL
ATOM   2828  C    PHE   375      28.928  10.184  37.356  1.00 24.96      BLGL
ATOM   2829  O    PHE   375      28.849   8.963  37.505  1.00 26.41      BLGL
ATOM   2830  N    ASP   376      29.975  10.890  37.771  1.00 24.80      BLGL
ATOM   2831  CA   ASP   376      31.070  10.217  38.449  1.00 24.64      BLGL
ATOM   2832  CB   ASP   376      32.369  11.030  38.382  1.00 25.91      BLGL
ATOM   2833  CG   ASP   376      32.243  12.411  39.007  1.00 26.81      BLGL
ATOM   2834  OD1  ASP   376      31.528  12.566  40.022  1.00 26.23      BLGL
ATOM   2835  OD2  ASP   376      32.885  13.343  38.484  1.00 27.73      BLGL
ATOM   2836  C    ASP   376      30.698   9.969  39.899  1.00 24.00      BLGL
ATOM   2837  O    ASP   376      29.621  10.349  40.344  1.00 22.18      BLGL
```

Fig. 4 cont.

| | | | | | | | | | |
|---|---|---|---|---|---|---|---|---|---|
| ATOM | 2838 | N | PHE | 377 | 31.610 | 9.333 | 40.625 | 1.00 24.93 | BLGL |
| ATOM | 2839 | CA | PHE | 377 | 31.421 | 9.000 | 42.030 | 1.00 26.87 | BLGL |
| ATOM | 2840 | CB | PHE | 377 | 32.652 | 8.256 | 42.530 | 1.00 24.91 | BLGL |
| ATOM | 2841 | CG | PHE | 377 | 32.915 | 6.967 | 41.811 | 1.00 26.64 | BLGL |
| ATOM | 2842 | CD1 | PHE | 377 | 34.185 | 6.394 | 41.837 | 1.00 27.20 | BLGL |
| ATOM | 2843 | CD2 | PHE | 377 | 31.891 | 6.298 | 41.141 | 1.00 27.03 | BLGL |
| ATOM | 2844 | CE1 | PHE | 377 | 34.434 | 5.168 | 41.209 | 1.00 27.98 | BLGL |
| ATOM | 2845 | CE2 | PHE | 377 | 32.127 | 5.073 | 40.511 | 1.00 27.70 | BLGL |
| ATOM | 2846 | CZ | PHE | 377 | 33.402 | 4.505 | 40.546 | 1.00 28.28 | BLGL |
| ATOM | 2847 | C | PHE | 377 | 31.162 | 10.214 | 42.919 | 1.00 28.76 | BLGL |
| ATOM | 2848 | O | PHE | 377 | 30.660 | 10.084 | 44.041 | 1.00 29.47 | BLGL |
| ATOM | 2849 | N | LYS | 378 | 31.500 | 11.393 | 42.410 | 1.00 30.92 | BLGL |
| ATOM | 2850 | CA | LYS | 378 | 31.322 | 12.634 | 43.155 | 1.00 32.99 | BLGL |
| ATOM | 2851 | CB | LYS | 378 | 32.533 | 13.546 | 42.927 | 1.00 36.98 | BLGL |
| ATOM | 2852 | CG | LYS | 378 | 33.889 | 12.924 | 43.274 | 1.00 39.50 | BLGL |
| ATOM | 2853 | CD | LYS | 378 | 34.230 | 13.053 | 44.759 | 1.00 43.64 | BLGL |
| ATOM | 2854 | CE | LYS | 378 | 33.249 | 12.300 | 45.651 | 1.00 45.28 | BLGL |
| ATOM | 2855 | NZ | LYS | 378 | 33.467 | 12.607 | 47.092 | 1.00 46.72 | BLGL |
| ATOM | 2856 | C | LYS | 378 | 30.040 | 13.391 | 42.800 | 1.00 32.50 | BLGL |
| ATOM | 2857 | O | LYS | 378 | 29.803 | 14.487 | 43.309 | 1.00 31.66 | BLGL |
| ATOM | 2858 | N | GLY | 379 | 29.224 | 12.816 | 41.919 | 1.00 32.04 | BLGL |
| ATOM | 2859 | CA | GLY | 379 | 27.975 | 13.453 | 41.544 | 1.00 32.10 | BLGL |
| ATOM | 2860 | C | GLY | 379 | 28.092 | 14.430 | 40.397 | 1.00 33.14 | BLGL |
| ATOM | 2861 | O | GLY | 379 | 27.146 | 15.159 | 40.085 | 1.00 32.60 | BLGL |
| ATOM | 2862 | N | ARG | 380 | 29.261 | 14.451 | 39.771 | 1.00 35.05 | BLGL |
| ATOM | 2863 | CA | ARG | 380 | 29.507 | 15.342 | 38.647 | 1.00 35.69 | BLGL |
| ATOM | 2864 | CB | ARG | 380 | 30.958 | 15.817 | 38.660 | 1.00 40.31 | BLGL |
| ATOM | 2865 | CG | ARG | 380 | 31.123 | 17.323 | 38.592 | 1.00 48.35 | BLGL |
| ATOM | 2866 | CD | ARG | 380 | 32.569 | 17.728 | 38.876 | 1.00 55.04 | BLGL |
| ATOM | 2867 | NE | ARG | 380 | 33.058 | 17.213 | 40.164 | 1.00 61.15 | BLGL |
| ATOM | 2868 | CZ | ARG | 380 | 33.782 | 16.100 | 40.318 | 1.00 61.98 | BLGL |
| ATOM | 2869 | NH1 | ARG | 380 | 34.117 | 15.362 | 39.267 | 1.00 62.74 | BLGL |
| ATOM | 2870 | NH2 | ARG | 380 | 34.178 | 15.720 | 41.529 | 1.00 60.75 | BLGL |
| ATOM | 2871 | C | ARG | 380 | 29.216 | 14.587 | 37.354 | 1.00 34.09 | BLGL |
| ATOM | 2872 | O | ARG | 380 | 29.551 | 13.404 | 37.213 | 1.00 34.62 | BLGL |
| ATOM | 2873 | N | PRO | 381 | 28.590 | 15.265 | 36.386 | 1.00 30.20 | BLGL |
| ATOM | 2874 | CD | PRO | 381 | 28.201 | 16.683 | 36.407 | 1.00 27.18 | BLGL |
| ATOM | 2875 | CA | PRO | 381 | 28.250 | 14.653 | 35.101 | 1.00 28.29 | BLGL |
| ATOM | 2876 | CB | PRO | 381 | 27.395 | 15.723 | 34.438 | 1.00 27.26 | BLGL |
| ATOM | 2877 | CG | PRO | 381 | 28.018 | 16.980 | 34.941 | 1.00 26.31 | BLGL |
| ATOM | 2878 | C | PRO | 381 | 29.453 | 14.278 | 34.260 | 1.00 26.53 | BLGL |
| ATOM | 2879 | O | PRO | 381 | 30.436 | 15.014 | 34.221 | 1.00 27.34 | BLGL |
| ATOM | 2880 | N | LEU | 382 | 29.370 | 13.122 | 33.601 | 1.00 26.02 | BLGL |
| ATOM | 2881 | CA | LEU | 382 | 30.439 | 12.645 | 32.721 | 1.00 24.03 | BLGL |
| ATOM | 2882 | CB | LEU | 382 | 30.475 | 11.116 | 32.656 | 1.00 21.52 | BLGL |
| ATOM | 2883 | CG | LEU | 382 | 30.769 | 10.338 | 33.934 | 1.00 22.08 | BLGL |
| ATOM | 2884 | CD1 | LEU | 382 | 30.549 | 8.867 | 33.678 | 1.00 21.34 | BLGL |
| ATOM | 2885 | CD2 | LEU | 382 | 32.190 | 10.608 | 34.390 | 1.00 21.32 | BLGL |
| ATOM | 2886 | C | LEU | 382 | 30.128 | 13.174 | 31.336 | 1.00 23.10 | BLGL |
| ATOM | 2887 | O | LEU | 382 | 28.964 | 13.412 | 30.996 | 1.00 22.81 | BLGL |
| ATOM | 2888 | N | PRO | 383 | 31.160 | 13.364 | 30.511 | 1.00 22.83 | BLGL |
| ATOM | 2889 | CD | PRO | 383 | 32.593 | 13.134 | 30.744 | 1.00 21.59 | BLGL |
| ATOM | 2890 | CA | PRO | 383 | 30.919 | 13.873 | 29.159 | 1.00 22.58 | BLGL |
| ATOM | 2891 | CB | PRO | 383 | 32.327 | 13.950 | 28.559 | 1.00 22.02 | BLGL |
| ATOM | 2892 | CG | PRO | 383 | 33.101 | 12.953 | 29.345 | 1.00 23.42 | BLGL |
| ATOM | 2893 | C | PRO | 383 | 29.959 | 13.008 | 28.340 | 1.00 22.29 | BLGL |
| ATOM | 2894 | O | PRO | 383 | 29.346 | 13.491 | 27.395 | 1.00 23.29 | BLGL |
| ATOM | 2895 | N | SER | 384 | 29.815 | 11.739 | 28.718 | 1.00 23.07 | BLGL |
| ATOM | 2896 | CA | SER | 384 | 28.918 | 10.830 | 28.014 | 1.00 23.32 | BLGL |
| ATOM | 2897 | CB | SER | 384 | 29.189 | 9.387 | 28.438 | 1.00 23.43 | BLGL |
| ATOM | 2898 | OG | SER | 384 | 28.997 | 9.221 | 29.827 | 1.00 22.72 | BLGL |
| ATOM | 2899 | C | SER | 384 | 27.441 | 11.166 | 28.253 | 1.00 24.76 | BLGL |
| ATOM | 2900 | O | SER | 384 | 26.556 | 10.584 | 27.629 | 1.00 25.96 | BLGL |
| ATOM | 2901 | N | LEU | 385 | 27.166 | 12.094 | 29.160 | 1.00 23.88 | BLGL |
| ATOM | 2902 | CA | LEU | 385 | 25.792 | 12.474 | 29.419 | 1.00 24.72 | BLGL |
| ATOM | 2903 | CB | LEU | 385 | 25.721 | 13.380 | 30.644 | 1.00 22.46 | BLGL |

Fig. 4 cont.

| | | | | | | | | | | |
|---|---|---|---|---|---|---|---|---|---|---|
| ATOM | 2904 | CG | LEU | 385 | 24.332 | 13.873 | 31.055 | 1.00 | 23.33 | BLGL |
| ATOM | 2905 | CD1 | LEU | 385 | 23.424 | 12.687 | 31.367 | 1.00 | 22.86 | BLGL |
| ATOM | 2906 | CD2 | LEU | 385 | 24.458 | 14.778 | 32.268 | 1.00 | 20.09 | BLGL |
| ATOM | 2907 | C | LEU | 385 | 25.250 | 13.207 | 28.193 | 1.00 | 26.26 | BLGL |
| ATOM | 2908 | O | LEU | 385 | 24.041 | 13.255 | 27.958 | 1.00 | 25.15 | BLGL |
| ATOM | 2909 | N | HIS | 386 | 26.161 | 13.763 | 27.404 | 1.00 | 28.46 | BLGL |
| ATOM | 2910 | CA | HIS | 386 | 25.789 | 14.512 | 26.213 | 1.00 | 32.60 | BLGL |
| ATOM | 2911 | CB | HIS | 386 | 26.937 | 15.437 | 25.816 | 1.00 | 37.77 | BLGL |
| ATOM | 2912 | CG | HIS | 386 | 27.172 | 16.539 | 26.799 | 1.00 | 45.65 | BLGL |
| ATOM | 2913 | CD2 | HIS | 386 | 26.393 | 17.016 | 27.801 | 1.00 | 45.94 | BLGL |
| ATOM | 2914 | ND1 | HIS | 386 | 28.330 | 17.291 | 26.820 | 1.00 | 48.26 | BLGL |
| ATOM | 2915 | CE1 | HIS | 386 | 28.254 | 18.180 | 27.795 | 1.00 | 49.16 | BLGL |
| ATOM | 2916 | NE2 | HIS | 386 | 27.089 | 18.033 | 28.405 | 1.00 | 49.07 | BLGL |
| ATOM | 2917 | C | HIS | 386 | 25.392 | 13.656 | 25.025 | 1.00 | 32.02 | BLGL |
| ATOM | 2918 | O | HIS | 386 | 25.011 | 14.184 | 23.979 | 1.00 | 34.90 | BLGL |
| ATOM | 2919 | N | VAL | 387 | 25.467 | 12.341 | 25.177 | 1.00 | 29.53 | BLGL |
| ATOM | 2920 | CA | VAL | 387 | 25.117 | 11.461 | 24.075 | 1.00 | 27.58 | BLGL |
| ATOM | 2921 | CB | VAL | 387 | 25.236 | 9.974 | 24.496 | 1.00 | 27.23 | BLGL |
| ATOM | 2922 | CG1 | VAL | 387 | 24.191 | 9.637 | 25.547 | 1.00 | 25.13 | BLGL |
| ATOM | 2923 | CG2 | VAL | 387 | 25.114 | 9.072 | 23.276 | 1.00 | 23.77 | BLGL |
| ATOM | 2924 | C | VAL | 387 | 23.701 | 11.760 | 23.572 | 1.00 | 26.94 | BLGL |
| ATOM | 2925 | O | VAL | 387 | 23.450 | 11.750 | 22.369 | 1.00 | 26.81 | BLGL |
| ATOM | 2926 | N | PHE | 388 | 22.788 | 12.060 | 24.491 | 1.00 | 25.61 | BLGL |
| ATOM | 2927 | CA | PHE | 388 | 21.403 | 12.339 | 24.136 | 1.00 | 26.79 | BLGL |
| ATOM | 2928 | CB | PHE | 388 | 20.586 | 12.619 | 25.390 | 1.00 | 25.81 | BLGL |
| ATOM | 2929 | CG | PHE | 388 | 20.433 | 11.432 | 26.272 | 1.00 | 26.19 | BLGL |
| ATOM | 2930 | CD1 | PHE | 388 | 21.003 | 11.412 | 27.536 | 1.00 | 27.32 | BLGL |
| ATOM | 2931 | CD2 | PHE | 388 | 19.728 | 10.317 | 25.834 | 1.00 | 25.78 | BLGL |
| ATOM | 2932 | CE1 | PHE | 388 | 20.873 | 10.300 | 28.355 | 1.00 | 27.00 | BLGL |
| ATOM | 2933 | CE2 | PHE | 388 | 19.592 | 9.198 | 26.647 | 1.00 | 26.04 | BLGL |
| ATOM | 2934 | CZ | PHE | 388 | 20.166 | 9.189 | 27.909 | 1.00 | 26.12 | BLGL |
| ATOM | 2935 | C | PHE | 388 | 21.188 | 13.470 | 23.141 | 1.00 | 29.70 | BLGL |
| ATOM | 2936 | O | PHE | 388 | 20.176 | 13.496 | 22.424 | 1.00 | 29.14 | BLGL |
| ATOM | 2937 | N | GLN | 389 | 22.125 | 14.412 | 23.102 | 1.00 | 31.10 | BLGL |
| ATOM | 2938 | CA | GLN | 389 | 22.022 | 15.532 | 22.174 | 1.00 | 32.46 | BLGL |
| ATOM | 2939 | CB | GLN | 389 | 22.603 | 16.797 | 22.793 | 1.00 | 35.41 | BLGL |
| ATOM | 2940 | CG | GLN | 389 | 22.086 | 17.088 | 24.177 | 1.00 | 44.69 | BLGL |
| ATOM | 2941 | CD | GLN | 389 | 22.807 | 18.261 | 24.818 | 1.00 | 50.70 | BLGL |
| ATOM | 2942 | OE1 | GLN | 389 | 22.674 | 19.401 | 24.372 | 1.00 | 52.70 | BLGL |
| ATOM | 2943 | NE2 | GLN | 389 | 23.588 | 17.985 | 25.866 | 1.00 | 53.54 | BLGL |
| ATOM | 2944 | C | GLN | 389 | 22.779 | 15.221 | 20.893 | 1.00 | 30.30 | BLGL |
| ATOM | 2945 | O | GLN | 389 | 22.270 | 15.416 | 19.790 | 1.00 | 31.42 | BLGL |
| ATOM | 2946 | N | TYR | 390 | 23.993 | 14.715 | 21.051 | 1.00 | 28.80 | BLGL |
| ATOM | 2947 | CA | TYR | 390 | 24.851 | 14.403 | 19.917 | 1.00 | 30.88 | BLGL |
| ATOM | 2948 | CB | TYR | 390 | 26.204 | 13.911 | 20.427 | 1.00 | 35.50 | BLGL |
| ATOM | 2949 | CG | TYR | 390 | 26.963 | 14.956 | 21.217 | 1.00 | 41.72 | BLGL |
| ATOM | 2950 | CD1 | TYR | 390 | 28.151 | 14.632 | 21.871 | 1.00 | 45.09 | BLGL |
| ATOM | 2951 | CE1 | TYR | 390 | 28.861 | 15.595 | 22.603 | 1.00 | 47.24 | BLGL |
| ATOM | 2952 | CD2 | TYR | 390 | 26.496 | 16.273 | 21.313 | 1.00 | 42.36 | BLGL |
| ATOM | 2953 | CE2 | TYR | 390 | 27.192 | 17.240 | 22.043 | 1.00 | 45.40 | BLGL |
| ATOM | 2954 | CZ | TYR | 390 | 28.376 | 16.894 | 22.686 | 1.00 | 47.41 | BLGL |
| ATOM | 2955 | OH | TYR | 390 | 29.078 | 17.841 | 23.406 | 1.00 | 46.59 | BLGL |
| ATOM | 2956 | C | TYR | 390 | 24.298 | 13.425 | 18.889 | 1.00 | 29.06 | BLGL |
| ATOM | 2957 | O | TYR | 390 | 24.591 | 13.553 | 17.704 | 1.00 | 29.24 | BLGL |
| ATOM | 2958 | N | VAL | 391 | 23.508 | 12.450 | 19.324 | 1.00 | 27.33 | BLGL |
| ATOM | 2959 | CA | VAL | 391 | 22.943 | 11.488 | 18.381 | 1.00 | 25.21 | BLGL |
| ATOM | 2960 | CB | VAL | 391 | 22.008 | 10.476 | 19.087 | 1.00 | 23.42 | BLGL |
| ATOM | 2961 | CG1 | VAL | 391 | 22.803 | 9.635 | 20.061 | 1.00 | 19.38 | BLGL |
| ATOM | 2962 | CG2 | VAL | 391 | 20.886 | 11.202 | 19.805 | 1.00 | 21.53 | BLGL |
| ATOM | 2963 | C | VAL | 391 | 22.154 | 12.226 | 17.299 | 1.00 | 26.03 | BLGL |
| ATOM | 2964 | O | VAL | 391 | 22.028 | 11.749 | 16.175 | 1.00 | 23.37 | BLGL |
| ATOM | 2965 | N | ASP | 392 | 21.635 | 13.400 | 17.647 | 1.00 | 27.71 | BLGL |
| ATOM | 2966 | CA | ASP | 392 | 20.862 | 14.200 | 16.710 | 1.00 | 30.77 | BLGL |
| ATOM | 2967 | CB | ASP | 392 | 20.134 | 15.323 | 17.448 | 1.00 | 32.83 | BLGL |
| ATOM | 2968 | CG | ASP | 392 | 18.986 | 14.820 | 18.302 | 1.00 | 34.68 | BLGL |
| ATOM | 2969 | OD1 | ASP | 392 | 18.444 | 15.617 | 19.103 | 1.00 | 35.32 | BLGL |

Fig. 4 cont.

| ATOM | 2970 | OD2 | ASP | 392 | 18.618 | 13.636 | 18.167 | 1.00 | 35.22 | BLGL |
|------|------|-----|-----|-----|--------|--------|--------|------|-------|------|
| ATOM | 2971 | C   | ASP | 392 | 21.731 | 14.818 | 15.621 | 1.00 | 33.35 | BLGL |
| ATOM | 2972 | O   | ASP | 392 | 21.467 | 14.650 | 14.430 | 1.00 | 35.61 | BLGL |
| ATOM | 2973 | N   | THR | 393 | 22.777 | 15.526 | 16.035 | 1.00 | 34.96 | BLGL |
| ATOM | 2974 | CA  | THR | 393 | 23.664 | 16.215 | 15.105 | 1.00 | 34.87 | BLGL |
| ATOM | 2975 | CB  | THR | 393 | 23.998 | 17.626 | 15.602 | 1.00 | 35.87 | BLGL |
| ATOM | 2976 | OG1 | THR | 393 | 24.820 | 17.526 | 16.774 | 1.00 | 37.14 | BLGL |
| ATOM | 2977 | CG2 | THR | 393 | 22.726 | 18.392 | 15.952 | 1.00 | 35.93 | BLGL |
| ATOM | 2978 | C   | THR | 393 | 24.991 | 15.518 | 14.908 | 1.00 | 36.53 | BLGL |
| ATOM | 2979 | O   | THR | 393 | 25.462 | 15.358 | 13.787 | 1.00 | 36.72 | BLGL |
| ATOM | 2980 | N   | GLY | 394 | 25.596 | 15.115 | 16.014 | 1.00 | 38.00 | BLGL |
| ATOM | 2981 | CA  | GLY | 394 | 26.896 | 14.481 | 15.961 | 1.00 | 38.77 | BLGL |
| ATOM | 2982 | C   | GLY | 394 | 27.828 | 15.442 | 16.679 | 1.00 | 40.97 | BLGL |
| ATOM | 2983 | O   | GLY | 394 | 27.389 | 16.494 | 17.143 | 1.00 | 40.87 | BLGL |
| ATOM | 2984 | N   | THR | 395 | 29.105 | 15.107 | 16.787 | 1.00 | 43.10 | BLGL |
| ATOM | 2985 | CA  | THR | 395 | 30.043 | 15.990 | 17.461 | 1.00 | 45.02 | BLGL |
| ATOM | 2986 | CB  | THR | 395 | 30.967 | 15.197 | 18.393 | 1.00 | 43.84 | BLGL |
| ATOM | 2987 | OG1 | THR | 395 | 31.206 | 13.896 | 17.840 | 1.00 | 43.18 | BLGL |
| ATOM | 2988 | CG2 | THR | 395 | 30.340 | 15.054 | 19.753 | 1.00 | 41.53 | BLGL |
| ATOM | 2989 | C   | THR | 395 | 30.883 | 16.752 | 16.443 | 1.00 | 48.88 | BLGL |
| ATOM | 2990 | O   | THR | 395 | 31.470 | 16.155 | 15.536 | 1.00 | 49.70 | BLGL |
| ATOM | 2991 | N   | PRO | 396 | 30.941 | 18.089 | 16.578 | 1.00 | 52.29 | BLGL |
| ATOM | 2992 | CD  | PRO | 396 | 30.225 | 18.889 | 17.594 | 1.00 | 52.46 | BLGL |
| ATOM | 2993 | CA  | PRO | 396 | 31.712 | 18.955 | 15.672 | 1.00 | 52.98 | BLGL |
| ATOM | 2994 | CB  | PRO | 396 | 31.537 | 20.343 | 16.291 | 1.00 | 53.36 | BLGL |
| ATOM | 2995 | CG  | PRO | 396 | 30.173 | 20.256 | 16.948 | 1.00 | 52.73 | BLGL |
| ATOM | 2996 | C   | PRO | 396 | 33.188 | 18.543 | 15.578 | 1.00 | 53.94 | BLGL |
| ATOM | 2997 | O   | PRO | 396 | 33.678 | 18.369 | 14.436 | 1.00 | 54.55 | BLGL |
| END  |      |     |     |     |        |        |        |      |       |      |

Fig. 4 cont.

```
                                         9          19         29         39
---------- ---------- -ALTYRGVDW SSVVVEERAG VSYKNTNGNA QPLENILAAN  39 MT
---------- ---------- -ALQYKGVDW SSVMVEERAG VRYKNVNGQE KPLEYILAEN  39 HI
---------- ---------- -ALTYRGADI SSLLLLEDEG YSYKNLNGQT QALETILADA  39 AA
AHRDSGTAKS GLYVEKVSGL RKDFIKGVDV SSIIALEESG VAFYNESGKK QDIFNTLKEA  60 BL
        10         20         30         40         50         60

49         54         61         71         81         91
GVNTVRQRVW VNPAD----- ---GNYNLDY NIAIAKRAKA AGLGVYIDFH YSDTWADPAH  91
GVNMVRQRVW VNPWD----- ---GNYNLDY NIQLARRAKA AGLGLYINFH YSDTWADPAH  91
GINSIRQRVW VNPSD----- ---GSYDLDY NLELAKRVKA AGMSLYLDLH LSDTWADPSD  91
GVNYVRVRIW NDPYDANGNG YGGGNNDLEK AIQIGKRANA NGMKLLADFH YSDFWADPAK 120
        70         80         90        100        110        120

100        110        120        130        140        150
QTMPAGWP-S DIDNLSWKLY NYTLDAANKL QNAGIQPTIV SIGNEIRAGL LWPTGRTENW 150
QTTPAGWP-S DINNLAWKLY NYTLDSMNRF ADAGIQVDIV SIGNEITQGL LWPLGKTNNW 150
QTTPSGWSTT DLGTLKWQLY NYTLEVCNTF AENDIDIEII SIGNEIRAGL LWPLGETSSY 151
QKAPKAWANL NFEDKKTALY QYTKQSLKAM KAAGIDIGMV QVGNETNGGL A----GETDW 176
       130        140        150        160        170        176

160        170        180        190        200        210
ANIARLLHSA AWGIKDSSLS PKPKIMIHLD NGWDWGTQNW WYTNVLKQGT LELSDFDMMG 210
YNIARLLHSA AWGVKDSRLN PKPKIMVHLD NGWNWDTQNW WYTNVLSQGP FEMSDFDMMG 210
SNIGALLHSG AWGVKDSNLA TTPKIMIHLD DGWSWDQQNY FYETVLATGE LLSTDFDYFG 211
AKMSQLFNAG SQAVRETD-- SNILVALHFT NPETSGRYAW IAETLHRH-- --HVDYDVFA 230
       186                   204        214                   230

220        230        240        250        255        265
VSFYPFYSSS ATLSALKSSL DNMAKTWNKE IAVVETNWPI SC-----PNP RYSFPSDVKN 265
VSFYPFYSAS ATLDSLRRSL NNMVSRWGKE VAVVETNWPT SC-----PYP RYQFPADVRN 265
VSYYPFYSAS ATLASLKTSL ANLQSTYDKP VVVVETNWPV SC-----PNP AYAFPSDLSS 266
SSYYPFW--H GTLKNLTSVL TSVADTYGKK VMVAETSYTY TAEDGDGHGN TAPKNGQTLN 288
       238        248        258        268        278        288

275        285        294
IPFSPEGQTT FITNVANIVS SVS-RGVGLF YWEPAWIH-- ---------- ---------- 302
VPFSAAGQTQ YIQSVANVVS SVS-KGVGLF YWEPAWIH-- ---------- ---------- 302
IPFSVAGQQE FLEKLAAVVE ATT-DGLGVY YWEPAWIG-- ---------- ---------- 303
NPVTVQGQAN AVRDVIQAVS DVGEAGIGVF YWEPAWIPVG PAHRLEKNKA LWETYGSGWA 348
       298        308        318        328        338        348

309        318        328
---------- ---NANLGSS CADNTMFSQ- SGQALSSLSV FQRI------ --  332
---------- ---NANLGSS CADNTMFTP- SGQALSSLSV FHRI------ --  332
---------- ---NAGLGSS CADNLMVDYT TDEVYESIET LGEL------ --  334
TSYAAEYDPE DAGKWFGGSA VDNQALFDF- KGRPLPSLHV FQYVDTGTPF KN  399
       358        368        377        387        397
```

Fig. 5

```
                                 9          19         29         39
---------- ---------- -ALTYRGVDW SSVVVEERAG VSYKNTNGNA QPLENILAAN  39  MT
---------- ---------- -ALQYKGVDW SSVMVEERAG VRYKNVNGQE KPLEYILAEN  39  HI
---------- ---------- -ALTYRGADI SSLLLLEDEG YSYKNLNGQT QALETILADA  39  AA
AHRDSGTAKS GLYVEKVSGL RKDFIKGVDV SSIIALEESG VAFYNESGKK QDIFNTLKEA  60  BL
---------- ---------- -ALTYRGADI SSLLIEEDAG ISYKNLNGET QALEDILVNN  39  AT
---------- ---------M NKDFIKGADV SSVIALENSG VTFYNTNGKR QDIFTTLKQA  41  BS
---------- ----NTGVAD NTPFYVGADL SYVNEMESCG ATYRD-QGKK VDPFQLFADK  45  PF
                6          16         26         35         45

49         54         61         71         81         91
GVNTVRQRVW VNPAD----- ---GNYNLDY NIAIAKRAKA AGLGVYIDFH YSDTWADPAH  91
GVNMVRQRVW VNPWD----- ---GNYNLDY NIQLARRAKA AGLGLYINFH YSDTWADPAH  91
GINSIRQRVW VNPSD----- ---GSYDLDY NLELAKRVKA AGMSLYLDLH LSDTWADPSD  91
GVNYVRVRIW NDPYDANGNG YGGGNNDLEK AIQIGKRANA NGMKLLADFH YSDFWADPAK 120
GVNSIRQRVW VDPSD----- ---GSYDLDY NLKLAKRVQA AGMSIYLDLH LSDTWADPSD  91
GVNYVRVRIW NHPYDSNGNG YGGGNNDVQK AIEIGKRATA NGMKVLADFH YSDFWADPAK 101
GADLVRVRLW HNATWT---- ---KYSDLKD VSKTLKRAKN AGMKTLLDFH YSDTWTDPEK  98
    55         61         68         78         88         98

99         109        119        129        139        145
QTMPAGWP-- SDIDNLSWKL YNYTLDAANK LQNAGIQPTI VSIGNEIRAG LLWPTG---- 145
QTTPAGWP-- SDINNLAWKL YNYTLDSMNR FADAGIQVDI VSIGNEITQG LLWPLG---- 145
QTTPSGWST- TDLGTLKWQL YNYTLEVCNT FAENDIDIEI ISIGNEIRAG LLWPLG---- 146
QKAPKAWAN- LNFEDKKTAL YQYTKQSLKA MKAAGIDIGM VQVGNETNGG LA-------- 171
QTTPTGWST- TDIDTLTWQL YNYTLEVCNT FAENDIDVEI VSIGNEISSG LLWPLG---- 146
QKVPKAWAN- LSFEAKKAKL YEYTKQSLQK MIKEGVDIGM VQVGNETTGG FA-------- 152
QFIPKAWAHI TDTKELAKAL YDYTTDTLAS LDQQQLLPNL VQVGNETNIE ILQAEDTLVH 158
    109        118        128        138        148        158

155        165        175        185        195        205
RTENWANIAR LLHSAAWGIK DSSLSPKPKI MIHLDNGWDW GTQNWWYTNV LKQGTLELSD 205
KTNNWYNIAR LLHSAAWGVK DSRLNPKPKI MVHLDNGWNW DTQNWWYTNV LSQGPFEMSD 205
ETSSYSNIGA LLHSGAWGVK DSNLATTPKI MIHLDDGWSW DQQNYFYETV LATGELLSTD 206
GETDWAKMSQ LFNAGSQAVR ETD--SNILV ALHFTNPETS GRYAWIAETL HRH----HVD 225
KTSNYDNIAK LLHSGAWGVK DSDLTTTPKI MIHLDNCWDW DEQEYFYKTV LATGSLLSTD 206
GETDWTKMCQ LFNEGSRAVR ETN--SNILV ALHFTNPETA GRYSFIAETL SKN----KVD 206
GIPNWQRNAT LLNSGVNAVR DYSKKTGKPI QVVLHIAQPE NALWWFKQAK ENG----VID 214
    168        178        188        198        208        214

215        225        235        245        252        260
FDMMGVSFYP FYSSSATLSA LKSSLDNMAK TWNKEIAVVE TNWPISC--- --PNPRYSFP 260
FDMMGVSFYP FYSASATLDS LRRSLNNMVS RWGKEVAVVE TNWPTSC--- --PYPRYQFP 260
FDYFGVSYYP FYSASATLAS LKTSLANLQS TYDKPVVVVE TNWPVSC--- --PNPAYAFP 261
YDVFASSYYP FW--HGTLKN LTSVLTSVAD TYCKKVMVAE TSYTYTAEDG DCHGNTAPKN 283
FDLMGVSYYP FYSSEATLSS LKTSLTNMQS NYDKPVVVVE TNWPVSC--- --PDPEYSFP 261
YDVFASSYYP FW--HGTLQN LTSVLKAVAN TYGKKVMVAE TSYTYTAEDG DCHGNTAPKS 264
YDVIGLSYYP QWS-EYSLPQ LPDAIAELQN TYHKPVMIVE TAYPWTLHNF DQAGNVLGEK 273
    224        233        243        253        263        273
```

Fig. 6

```
           270        280        289        299
SDVKNIPFSP EGQTTFITNV ANIVSSVS-R GVGLFYWEPA WIH------- ----------  302
ADVRNVPFSA AGQTQYIQSV ANVVSSVS-K GVGLFYWEPA WIH------- ----------  302
SDLSSIPFSV AGQQEFLEKL AAVVEATT-D GLGVYYWEPA WIG------- ----------  303
GQTLNNPVTV QGQANAVRDV IQAVSDVGEA GIGVFYWEPA WIPVGPAHRL EKNKALWETY  333
SDLTSIPFSA AGQEEFLEKL AEVVEGVT-D GLGIYYWEPA WID------- ----------  303
GQTLPYPISV QGQATAVRDV MEAVANTGKA GLGVFYWEPA WIPVGPKTQI EKNKVLWETY  314
AVQPEFPASP RGQLTYLLTL TQLVKSAG-- GMGVIYWEPA WVSTRCR--- ----------  318
           283        293        301        311

314        322        332
---------- --------NA NLGSSCADNT MFSQ--SGQA LSSLSVFQRI --------  332
---------- --------NA NLGSSCADNT MFTP--SGQA LSSLSVFHRI --------  332
---------- --------NA GLGSSCADNL MVDYT-TDEV YESIETLGEL --------  334
GSGWATSYAA EYDPEDAGKW FGGSAVDNQA LFDF--KGRP LPSLHVFQYV DTGTPFKN  399
---------- --------NA GLGSSCADNL MVDVN-TDEV LESVTVFEDL --------  334
GSGWASSYAA EYDPEDAGKW YGGSAVDNQA LFDF--NGHP LPSLQVFQYA --------  372
---------- -------TLW GKGSHWENAS FFDATRKNNA LPAFLFFKAD YQASAQAE  359
                      321        331        341        351
```

GALACTANASE VARIANTS

CROSS-REFERENCE TO RELATED APPLICATIONS

This application is a divisional of U.S. application Ser. No. 10/537,746 filed on Jun. 6, 2005, now U.S. Pat. No. 7,537,921, which is a national phase of international application no. PCT/DK2003/00851 filed Dec. 11, 2003, which claims priority or the benefit under 35 U.S.C. 119 of Danish application nos. PA 2002 01968 and PA 2003 00537 filed Dec. 20, 2002 and Apr. 8, 2003, respectively, and U.S. provisional application nos. 60/437,615 and 60/461,230 filed Jan. 2, 2003 and Apr. 8, 2003, respectively, the contents of which are fully incorporated herein by reference.

FIELD OF THE INVENTION

The present invention relates to variants of galactanases of Glycoside Hydrolase Family 53, their production, and their use within the dairy industry.

BACKGROUND OF THE INVENTION

Background Art

The crystallization and preliminary X-ray studies of the galactanase from *Aspergillus aculeatus* is described by Ryttersgaard et al. (Acta. Cryst. (1999), D55, 929-930).

SUMMARY OF THE INVENTION

The invention provides variants of a parent Glycoside Hydrolase Family 53 galactanase, comprising an alteration in at least one of the following positions: -6, -4, -2, 1, 3, 4, 5, 6, 7, 8, 9, 10, 11, 12, 13, 14, 15, 16, 18, 20, 22, 24, 25, 26, 29, 30, 31, 32, 36, 39, 40, 41, 43, 44, 45, 46, 47, 48, 49, 50, 51, 52, 53, 54, 54a, 54e, 54f, 54g, 54h, 55, 56, 57, 58, 61, 62, 65, 69, 77, 79, 80, 81, 82, 83, 84, 85, 86, 87, 88, 89, 90, 91, 92, 93, 94, 95, 96, 97, 101, 106, 107, 110, 113, 114, 126, 131, 132, 133, 134, 135, 136, 137, 138, 139, 140, 141, 142, 144, 145, 146, 147, 150, 153, 157, 159, 163, 169, 171, 172, 176, 177, 178, 179, 180, 181, 182, 183, 184, 185, 186, 187, 188, 189, 191, 192, 194, 198, 200, 203, 204, 209, 210, 211, 212, 213, 214, 215, 216, 217, 218, 219, 220, 221, 222, 223, 224, 225, 226, 227, 228, 229, 230, 231, 232, 233, 234, 241, 242, 243, 244, 245, 246, 247, 248, 249, 250, 252, 252d, 252e, 253, 254, 255, 256, 257, 258, 259, 260, 261, 262, 263, 264, 265, 266, 273, 274, 276, 277, 280, 283, 284, 286, 288, 288a, 289, 292, 293, 294, 295, 296, 297, 298, 299, 300, 301, 302, 302a, 302d, 302j, 302k, 302m, 302n, 302o, 302q, 302r, 302s, 302t, 302u, 302v, 302x, 302y, 302z, 302aa, 302bb, 302cc, 302dd, 302ee, 302ff, 302gg, 302hh, 302ii, 302jj, 303, 304, 305, 306, 307, 308, 309, 310, 311, 312, 313, 314, 315, 316, 317, 318, 319, 320, 321, 322, 323, 324, 325, 326, 327, 328, 329, and 330; wherein
(a) the alteration(s) are independently (i) an insertion of an amino acid immediately downstream of the position, (ii) a deletion of the amino acid which occupies the position, and/or (iii) a substitution of the amino acid which occupies the position; and (b) the variant has galactanase activity.

BRIEF DESCRIPTION OF DRAWINGS

FIG. 1 shows the coordinates for the 3D structure of a GH Family 53 galactanase from *Myceliophthora thermophila* having SEQ ID NO: 1;

FIG. 2 shows the coordinates for the 3D structure of a GH Family 53 galactanase from *Humicola insolens* having SEQ ID NO: 2;

FIG. 3 shows the coordinates for the 3D structure of a GH Family 53 galactanase from *Aspergillus aculeatus* having SEQ ID NO: 3;

FIG. 4 shows the coordinates for the 3D structure of a GH Family 53 galactanase from *Bacillus licheniformis* having SEQ ID NO: 4;

FIG. 5 shows a multiple alignment of SEQ ID NOs: 1-4; and

FIG. 6 shows the alignment of FIG. 5 with three additional galactanase sequences (SEQ ID NOS: 7, 8 and 9) added.

DETAILED DESCRIPTION OF THE INVENTION

3D-Structure Determination

The crystallization and preliminary X-ray studies of the galactanase from *Aspergillus aculeatus* (AAGAL) is described by Ryttersgaard et al. (Acta. Cryst. (1999), D55, 929-930). The galactanases from *Myceliophthora thermophila* (MTGAL) and *Humicola insolens* (HIGAL) (WO 97/32014), and the galactanase from *Bacillus licheniformis* (BLGAL) (WO 00/47711) were crystallized using similar principles.

The 3D-structures were solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure of the *Aspergillus aculeatus* galactanase (AAGAL), as determined by multiple isomorphous replacement to 1.8 Å resolution at 100 K are given in FIG. 1 in standard PDB format (Protein Data Bank, Brookhaven National Laboratory, Brookhaven, Conn.).

The structures of the other three galactanases were solved by Molecular Replacement, using the AAGAL293 structure (to 2.3 Å resolution at 293K) as a search model. Data from 20-2.55 Å, 18-2.14 Å, and 19.67-2.60 Å were used for HIGAL, MTGAL and BLGAL, respectively, within AMoRe (J. Navaza: AMoRe: an Automated package for Molecular Replacement. Acta Crystallogr., A50:157-163, 1994). The respective coordinates are given in FIGS. 2-4 in standard PDB format.

Variant

The term "galactanase variant," or simply "variant," refers to a galactanase comprising one or more alteration(s), such as substitution(s), insertion(s), deletion(s), and/or truncation(s) of one or more specific amino acid residue(s) in one or more specific position(s) in a parent galactanase.

The total number of such alterations is typically not more than thirty, e.g., one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, or thirty of said alterations. In addition, the variant of the invention may include other modifications of the parent enzyme, typically not more than 10, e.g., not more than 5 such modifications.

Nomenclature and Conventions for Designation of Variants

A substitution in a variant is indicated as "original amino acid-position-substituted amino acid." The one letter code is preferably used, but it can of course be translated into the three letter code as desired. The codes X (or Xaa) may be used to indicate any amino acid residue. Accordingly, the notation "D182N" or means, that the variant comprises a substitution of aspartic acid with asparagine acid in the variant amino acid position corresponding to the amino acid in position 182 in MTGAL, when the two are aligned as indicated in FIG. 5.

Where the original amino acid residue may be any amino acid residue, a short hand notation may at times be used indicating only the position, and the substituted amino acid, for example: "Position-substituted amino acid", or "182N". This notation is particular relevant in connection with modification(s) in a series of homologous polypeptides, such as the galactanases of GH Family 53. Similarly when the identity of the substituting amino acid residue(s) is immaterial: "Original amino acid-position;" or "D182".

When both the original amino acid(s) and substituted amino acid(s) may be any amino acid, then only the position is indicated, e.g., "182".

When the original amino acid(s) and/or substituted amino acid(s) may comprise more than one, but not all amino acid(s), then the amino acids are listed, separated by commas: "Original amino acid-position no.-substituted amino acid"; e.g., "H91 D, L, N".

A number of examples of this nomenclature are listed below:

The substitution of aspartic acid for asparagine in position 182 is designated as D182N.

The substitution of any amino acid residue for serine in position 131 is designated as S131X, or S131.

The substitution of proline for any amino acid residue in position 29 would thus be designated X29P, or 29P.

For a modification where the original amino acid(s) and/or substituted amino acid(s) may comprise more than one, but not all amino acid(s), the substitution of aspartic acid, leucine, or asparagine for histidine in position 91 would be indicated by H91D, L, N; which indicates the specific variants H91D, H91L, or H91N.

A deletion of glutamic acid in position 288a will be indicated by E288a*. Correspondingly, the deletion of more than one amino acid residue, such as the deletion of glutamic acid and aspartic acid in positions 252a and 252b will be designated "E252a*+D252b*"

A truncation means an N- or C-terminal shortening of the complete amino acid sequence, i.e., a deletion of one, or usually more, amino acids and the N- or C-terminal end of the peptide. As regards the designation of truncated variants, the general rule for deletions may be used.

The insertion of an additional amino acid residue such as e.g., a valine after F216 is indicated by "F216FV"; or, when more than one amino acid residue is inserted, such as e.g., a valine, alanine, serine, threonine and a glycine after F216 this will be indicated as: "F216FVASTG".

In such cases the inserted amino acid residue(s) are numbered by the addition of lower case letters to the position number of the amino acid residue preceding the inserted amino acid residue(s). In the above example the sequences would thus be:

| Parent: | Variant: | | | | | | |
|---|---|---|---|---|---|---|---|
| 216 | 216 | 216a | 216b | 216c | 216d | 216e | 217 |
| F | F | V | A | S | T | G | Y |

Once all lower case letters from a to z (a, b, c, d, e, f, g, h, i, j, k, l, m, n, o, p, q, r, s, t, u, v, x, y, z) have been used for this purpose, double letters aa, bb, cc etc. onto zz are used, see, e.g., the alignment of FIG. 5, between positions 302 and 303.

In cases where an amino acid residue identical to the existing amino acid residue is inserted, it is clear that degeneracy in the nomenclature arises. If for example a phenylalanine would be inserted after the phenylalanine in the above example this would be indicated by "F216FF".

Given that a proline is present in position 215, the same actual change could just as well be indicated as "P215 PF":

| | Parent: | | Variant: | | |
|---|---|---|---|---|---|
| Numbering I: | 215 | 216 | 215 | 216 | 216a |
| Sequence: | P | F | P | F | F |
| Numbering II: | | | | 215 | 215a | 216 |

Such instances will be apparent to the skilled person, and the indication "F216FF" and corresponding indications for this type of insertions is thus meant to comprise such equivalent degenerate indications.

By analogy, if amino acid sequence segments are repeated in the parent galactanase and/or in the variant, it will be apparent to the skilled person that equivalent degenerate indications are comprised, also when other alterations than insertions are listed such as deletions and/or substitutions. For instance, the deletion of two consecutive amino acids "DG" in the sequence "DGDG" from position 252b-252e, may be written as "D252b*+G252c*" or "D252d*+G252e*" or "G252c*+D252d*":

| | Parent: | | | | Variant: | |
|---|---|---|---|---|---|---|
| Numbering I: | 252b | 252c | 252d | 252e | 252b | 252c |
| Sequence: | D | G | D | G | D | G |
| Numbering II: | | | | | 252d | 252e |
| Numbering III: | | | | | 252b | 252e |

Variants comprising multiple modifications are separated by pluses, e.g., "A90S+H91D" representing modifications in positions 90 and 91 substituting tyrosine and glutamic acid for arginine and glycine, respectively. Thus, "A90S+H91D, N, L" designates the following variants: A90S+H91D, A90S+H91N, and A90S+H91L. Likewise, N303D, H+N305D, H, P designates the following variants: N303D+N305D; N303D+N305H; N303D+N305P; N303H+N305D; N303H+N305H, and N303H+N305P.

This nomenclature is particular relevant relating to modifications aimed at substituting, inserting or deleting amino acid residues having specific common properties, such modifications are referred to as conservative amino acid modification(s).

Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the in reverse.

For the present purposes, the sequence of MTGAL (SEQ ID NO:1) has been selected as the frame of reference, meaning that all variants will be defined on the basis of the amino acid sequence of MTGAL. In particular, each amino acid residue in a galactanase sequence is assigned a number, a position, or a position number, by reference to FIG. 5 herein, viz. the number of the corresponding amino acid residue in the *Myceliophthora thermophila* galactanase backbone (MT; the uppermost line of the alignment of FIG. 5). In this context, the term "corresponding" refers to the amino acid which, according to the alignment, is in the same column as the amino acid residue in question, but in the first row designated "MT".

For example, the variant of the galactanase from *Bacillus licheniformis* (BL) which by reference to SEQ ID NO: 4 may be designated S39C will, for the present purposes, be designated S18C, because S39 of BL corresponds to A18 of MT. As another example, the variant of the galactanase from *Aspergillus aculeatus* which by reference to SEQ ID NO: 3 may be designated D182N will, for the present purposes, be designated D181N, because D182 of AA corresponds to N181 of MT. As a still further example, variant K16P of BL may be designated *-6P, because K16P of BL corresponds to a missing or deleted amino acid in position −6 of MT, still by strict formal reference to FIG. 5.

However, if desired, the variants of the invention may also be defined by reference to their respective "own" backbone, e.g., with reference to SEQ ID NO:1, SEQ ID NO:2, SEQ ID NO: 3, or SEQ ID NO: 4. The corresponding position numbers are easily deduced, in the same way as described above, from FIGS. 5-6 or, for additional galactanase sequences, from a figure which can be prepared according to the principles described herein.

Molecular Dynamics (MD)

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Variants of Amended Properties

Based on the 3D-structure of the galactanase from *Myceliophthora thermophila* of SEQ ID NO: 1, the following variants are contemplated, in which at least one of the below-mentioned residues have been amended and/or at least one of the below-mentioned alterations have been introduced:

i) variants of an amended specific activity, within 10 Å from the active site: Y4, G6, V7, D8, W9, S10, R45, Q46, R47, W49, Y77, D79, F80, H81, Y82, W86, A87, D88, P89, A90, H91, Q92, T93, S131, I132, G133, N134, E135, I136, R137, A138, G139, L140, L141, W142, G145, R146, T147, I153, L157, M176, I177, H178, L179, D180, N181, G182, W183, T187, Q188, W191, Y192, M209, G210, V211, S212, F213, Y214, P215, F216, Y217, A221, L226, I241, A242, V243, V244, E245, T246, N247, W248, F276, I277, V280, V284, G292, L293, F294, Y295, W296, E297, P298, W300, L306, G307, F329;

ii) variants of an amended activity on lactose, within 10 Å from the active site: Y214S, N+N247Y+L306Q; Y214A; F216FVASTGY217; P89W+W86N;

iii) variants of an amended pH-activity profile: H91N, L, D; N313D; N303D, H; N305D, H; A90S+H91D;

iv) variants of an amended thermostability, by insertion of prolines: Y22P, N24P, T25P, A29P, A53P, N56P, T93P, D101P, W142P, T147P, Q198P, L203P, S204P, S219P, S258P, S288P, A304P, A311P, Q318P, A322P, S324P, S325P, S327P;

v) variants of an amended thermostability, by increasing surface hydrophobicity: W107S, H;

vi) variants of an amended thermostability, by amending the surface electrostatic potential: Q126E;

vii) variants of an amended thermostability, by disulfide bridges (double mutations to cysteines): V20C+G320C, N39C+L326C, Y110C+G163C, W150C+N194C, T274C+V328C, I301C+F316C viii) variants of amended thermostability, by improved side-chain packing: 9F, Y, W; 12V, 80F, 82Y, 191Y, W; 213F; 9W+12V; 80F+82Y.

Based on the 3D-structure of the galactanase from *Humicola insolens*, the following variants are contemplated, in which at least one of the below-mentioned residues have been amended and/or at least one of the below-mentioned alterations have been introduced:

i) variants of an amended thermostability, by insertion of prolines: V20P, V25P, E29P, V41P, V50P, W53P, N56P, T94P, A96P, W142P, L169P, W185P, Q198P, M203P, A219P, A221P, T222P, Q258P, A261P, D262P, S288P, N305P, A311P, A322P, S324P, S325P.

ii) variants of an amended thermostability, by disulfide bridges (double mutations to cysteines): T113C+G163C, W185C+S229C, S218C+A221C, R227C+V283C.

Based on the 3D-structure of the galactanase from *Aspergillus aculeatus*, the following variants are contemplated, in which at least one of the below-mentioned residues have been amended and/or at least one of the below-mentioned alterations have been introduced:

i) variants of an amended pH-activity profile: D181N;

ii) variants of an amended thermostability, by insertion of prolines: T3P, Y20P, N24P, L25P, T29P, A31P, V50P, S53P, S56P, T93P, T94P, S96P, W142P, L144P, E146P, T147P, T172P, E200P, S203P, A219P, A256P, A258P, S261P, S264P, I266P, T288P, I301P, A304P, Y318P, E324P;

iii) variants of an amended thermostability, by disulfide bridges (double mutations to cysteines): L13C+L65C, N24C+Q30C, S218C+A221C, A304C+Y318C.

Based on the 3D-structure of the galactanase from *Bacillus licheniformis*, the following variants are contemplated, in which at least one of the below-mentioned residues have been amended and/or at least one of the below-mentioned alterations have been introduced:

i) variants of an amended thermostability, by insertion of prolines: K-6P, S-4P, L-2P, K1P, V20P, S26P, K29P, D31P, A54aP, G54eP, N57P, K93P, A97P, N101P, S171P, S185P, T256P, N260P, N266P, D286P, E288aP, A289P, A302dP, S302yP, Y302zP, A302bbP, E302 ccP, E302ggP, F305P, D311P, F318P;

ii) variants of an amended thermostability, by disulfide bridges (double mutations to cysteines): S18C+Y302qC, G40C+Q330C, V44C+A69C, I48C+A62C, N50C+D84C, G54gC+T302xC, N56C+G302rC, A62C+G146C, K106C+A159C, K114C+A163C, E183C+G221C, T227C+A283C, A234C+V241C, Y250C+Q273C, A302aaC+A302iiC.

Additional variants of the invention which may exhibit amended properties as regards substrate binding and/or substrate specificity are listed below.

According to "Nomenclature for sugar-binding subsites in glycosyl hydrolases", G. J. Davis, K. S. Wilson and B. Henrissart, Biochemical Journal, Volume 321, pages 557 to 559

(1997), so-called subsites may be determined. Such subsites may be labelled from −N to +N (where N is an integer). −N represents the non reducing end and +N the reducing end of the polysaccharide. The cleavage is taking place between the −1 and +1 subsites. The principal constituent of a sugar binding subsite is also called an aromatic platform. That is an aromatic residue, i.e., one of the following: W, H, Y or F.

Subsite −1: W320.
Subsite +1: W237, Y234.

Also the residues in the near vicinity (5 Å) of the above residues may be altered and provide an amended substrate specificity and/or substrate binding. These residues are the following, reference being here had to the position numbering of SEQ ID NOs 1, 2, 3, and 4, respectively (not to the corresponding residue in SEQ ID NO: 1):

```
MTGAL (SEQ ID NO: 1): G6, V7, D8, W9, S10, S11, V12, V13, V14, E15, E16, A18,
V20, Y22, L32, L36, T43, V44, R45, Q46, R47, V48, W49, V50, N51, P52, D54, N56, Y57, Y61,
Y77, D79, F80, H81, Y82, S83, D84, T85, W86, A87, D88, P89, A90, H91, Q92, T93, M94, P95,
G133, N134, E135, I136, R137, G139, L140, L141, W142, H178, L179, D180, N181, G182,
W183, D184, W185, G186, T187, Q188, N189, G210, V211, S212, F213, Y214, P215, F216,
Y217, S218, S219, S220, A221, T222, L223, S224, A225, L226, K227, S228, S229, L230,
D231, N232, M233, I241, A242, V243, V244, E245, T246, N247, W248, P249, I250, C252,
P255, R256, Y257, S258, F259, P260, D262, V263, Q273, F276, I277, V280, I283, L293, F294,
Y295, W296, E297, P298, A299, W300, I301, H302, N303, A304, N305, L306, G307, S308,
S309, C310, A311, D312, N313, T314, M315, F316, S317, Q318, S319, G320, Q321, L326,
F329.

HIGAL (SEQ ID NO: 2): G6, V7, D8, W9, S10, S11, V12, M13, V14, E15, E16, A18, V20,
Y22, L32, L36, M43, V44, R45, Q46, R47, V48, W49, V50, N51, P52, W53, D54, G55, N56,
Y57, N58, Y61, Y77, N79, F80, H81, Y82, S83, D84, T85, W86, A87, D88, P89, A90, H91, Q92,
T93, T94, A96, G133, N134, E135, I136, T137, G139, L141, W142, H178, L179, D180, N181,
G182, W183, N184, W185, D186, T187, Q188, N189, G210, V211, S212, F213, Y214, P215,
F216, Y217, S218, A219, S220, A221, T222, L223, D224, S225, L226, R227, R228, S229,
L230, N231, N232, M233, V241, A242, V243, V244, E245, T246, N247, W248, P249, C252,
P255, R256, Y257, Q258, F259, P260, D262, V263, Q273, Y276, I277, V280, V283, L293,
F294, Y295, W296, E297, P298, A299, W300, I301, H302, N303, A304, N305, L306, G307,
S308, S309, C310, A311, D312, N313, T314, M315, F316, T317, P318, S319, G320, Q321,
L326, F329.

AAGAL (SEQ ID NO: 3): R5, G6, A7, D8, I9, S10, S11, L12, L13, L14, L15, E16, E18,
Y20, Y22, L32, L36, S43, I44, R45, Q46, R47, V48, W49, V50, N51, P52, D54, S56, Y57, Y61,
Y77, D79, L80, H81, L82, S83, D84, T85, W86, A87, D88, P89, S90, D91, Q92, T93, T94, P95,
G134, N135, E136, I137, R138, G140, L142, W143, H179, L180, D181, D182, G183, W184,
S185, W186, D187, Q188, Q189, N190, G211, V212, S213, Y214, Y215, P216, F217, Y218,
S219, A220, S221, A222, T223, L224, A225, S226, L227, K228, T229, S230, L231, A232,
N233, L234, V243, V244, V245, E246, T247, N248, W249, P250, C253, P256, A257, Y258,
A259, F260, P261, D263, L264, Q274, F277, L278, L281, V284, V294, Y295, Y296, W297,
E298, P299, A300, W301, I302, G303, N304, A305, G306, L307, G308, S309, S310, C311,
A312, D313, N314, L315, M316, V317, D318, Y319, T320, D322, V324, Y325, I328, L331.

BLGAL (SEQ ID NO: 4): K26, G27, V28, D29, V30, S31, S32, A35, L36, Y64, V65, R66,
V67, R68, I69, W70, N71, D72, P73, Y74, G80, Y81, G82, G83, G84, N85, N86, L106, D108,
F109, H110, Y111, S112, D113, F114, W115, A116, D117, P118, A119, K120, Q121, K122,
A123, P124, Q161, G163, N164, E165, T166, G169, A171, G172, H202, F203, T204, N205,
P206, E207, T208, R211, Y212, S231, S232, Y233, Y234, P235, F236, W237, H238, G239,
T240, L241, N243, L244, V261, A262, E263, T264, S265, Y266, T267, D274, G275, H276,
G277, N278, T279, A280, P281, K282, N283, G284, Q285, T286, L287, N288, Q296, A299,
V300, V303, V317, F318, Y319, W320, E321, P322, A323, W324, I325, V327, N336, K337,
L339, W340, E341, Y343, G344, S345, G346, W347, A348, T349, S350, Y351, A352, A353,
Y355, D356, P357, E358, D359, A360, G361, K362, W363, F364, G365, G366, S367, A368,
V369, D370, N371, Q372, A373, L374, F375, F388.
```

Based on FIGS. 1-4 the inventors identified subsites as follows:

For MTGAL, HIGAI and AAGAL the following subsites were identified, reference being here had to the position numbering of SEQ ID NOs 1, 2, and 3, respectively (not to the corresponding residue in SEQ ID NO: 1):
Subsite −4: MTGAL none; HIGAL W53; AAGAL none.
Subsite −2: MTGAL W86, W300; HIGAL W86, W300; AAGAL W86, W301.
Subsite −1: MTGAL W296; HIGAL W296; AAGAL W297.
Subsite +1: MTGAL Y217, Y214; HIGAL Y217, Y214; AAGAL Y218, Y215.
Subsite +2: MT W183; HIGAL W183; AAGAL W184.

For BLGAL the following subsites were identified, reference being here had to the position numbering of SEQ ID NO: 4 (not to the corresponding residue in SEQ ID NO: 1):
Subsite −4: W363.
Subsite −3: W347.
Subsite −2: W115.

The above amino acids may be substituted with any other amino acid, e.g., any of the remaining 19 natural amino acids. In the variants of the invention, at least one of the above-mentioned residues have been amended to introduce either of the other nineteen amino acid residues. The above variants are also included in dependent claims, however in the claims they have been renumbered according to the principles outlined above, each position being assigned the number of the corresponding amino acid residue in SEQ ID NO: 1.

Alignments

The program ClustalW (CLUSTAL W: improving the sensitivity of progressive multiple sequence alignment through sequence weighting, position specific gap penalties and weight matrix choice." Julie D. Thompson, Desmond G. Higgins, and Toby J. Gibson, Nucleic Acids Research, 22(22): 4673-4680 (1994)) is used for the purposes of the present invention for pairwise protein sequence alignments, multiple protein sequence alignments and protein profile alignments (version 1.82, default parameters).

For pairwise sequence comparison and calculation of percentage identity, the pairwise alignment parameters were: Slow/Accurate; Gap Open Penalty=10.00; Gap Extension Penalty=0.10; Protein weight matrix=Gonnet series; DNA weight matrix=IUB.

The consensus length is calculated automatically by the program. The number of identical residues (identified with an asterisk) is counted. The percentage of sequence identity is calculated as follows: the number of identical residues is divided by the consensus length and multiplied by 100.

The multiple alignment of FIG. 5 is based on a multiple alignment of the four sequences using Clustalw, but, importantly, it is combined with information derived from the 3D-structures, each position in each backbone being carefully evaluated, and the alignment modified by the present inventors. In other words, the multiple alignment of FIG. 5 is not a simple ClustalW multiple alignment reflecting only sequence homologies, it also reflects structural similarities.

The alignment of FIG. 5 can therefore be used to deduce corresponding variants in other backbones, and these variants are likely to also exhibit the amended property in question. For example, the above-mentioned variant A90S+H91D of MT is transferable to the other backbones or parent galactanases shown in FIG. 5 as follows: According to the FIG. 5 alignment, this variant would correspond to: A90S+H91D of HI; and A90S+K91D of BL. Because AA already has the sequence of S90D91, this variant is not relevant for AA. Another example is variant T288P of AA, which, using the alignment of FIG. 5, translates into S288P in MT and HI, and G288P in BL.

Other galactanase backbones of Glycoside Family 53 are known (see below under parents), and these can be added to the alignment of FIG. 5 as described below, and thereby corresponding variants can be deduced also for these backbones, as just described above.

For aligning a new sequence to the multiple alignment of FIG. 5, the Clustalw option called profile alignment is used as follows: The FIG. 5 multiple alignment is used as profile 1, and then the new sequence as profile 2. Then the program is asked to "Align sequence to 1st. profile," using the following parameters:

Multiple alignment parameters=Slow/Accurate; Gap Open Penalty=10.00; Gap Extension Penalty=0.20; Delay divergent sequences=30%; DNA Transitions Weight: 0.50; Protein weight matrix=Gonnet series; DNA weight matrix=IUB; Use negative matrix=OFF;

Protein Gap Parameters: Toggle Residue-Specific Penalties=ON; Toggle Hydrophilic Penalties=ON; Hydrophilic Residues=GPSNDQEKR; Gap Separation Distance=4; Toggle End Gap Separation=OFF.

In FIG. 6, as an example, three new galactanase sequences have been added to the FIG. 5 alignment. The new galactanases are added at the bottom of the alignment, as rows nos. 5, 6 and 7. The galactanases are: AT (the galactanase of *Aspergillus tubigensis*, (SEQ ID NO: 7)); BS (the galactanase of *Bacillus subtilis* (SEQ ID NO: 8)); and PF (the galactanase of *Pseudomonas fluorescens* (SEQ ID NO: 9)). Thus, using FIG. 6, the above-mentioned variant A90S+H91D of MT translates into A90S+K91D of BS, and E90S+K91D of PF. Because AT already has the sequence of S90D91, this variant is not relevant for AT. Another example is variant T288P of AA, which, using the alignment of FIG. 6, translates into variants T288P of AT, G288P of BS, and G288P of PF.

In the alternative, alignments of sequences and calculation of degree %-identity may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Parent

The term "parent galactanase," or simply "parent," refers to the galactanase on which the variant was based, and also to the galactanase with which the variant is compared and aligned.

The parent may be a naturally occurring (wildtype) galactanase, or it may in turn even be a variant thereof, prepared by any suitable means. For instance, the parent galactanase may be a variant of a naturally occurring galactanase which has been modified or altered in the amino acid sequence. A parent may also be an allelic variant which is any of two or more alternative forms of a gene occupying the same chromosomal locus. Allelic variation arises naturally through mutation, and may result in polymorphism within populations as is well-described in the art. An allelic variant of a polypeptide is a polypeptide encoded by the corresponding allelic variant of a gene.

Galactanase

This section is applicable to the parent galactanases, as well as the variant galactanases of the invention.

Galactanases catalyze the endohydrolysis of 1,4-beta-D-galactosidic linkages in arabinogalactans of type I and/or galactans (see the structure of rhamnogalacturonan I as described in Carpita et al. in Plant J: 3:1-30, 1993).

In the present context, a galactanase is a polypeptide having galactanase activity. Galactanase activity can be measured using a substrate including 1,4-beta-D-galactosidic linkages. Examples of galactanase substrates are arabinogalactans of type I and galactans. Particularly suitable substrates are i) lupin galactan, and potato galactan (commercially available from, e.g., MegaZyme, Australia); as well as ii) AZCL-galactan substrates such as AZCL-potato-galactan, and AZCL-lupin-galactan (also commercially available from MegaZyme, Australia). For the substrates mentioned under i) above, galactanase activity may be measured as release of reducing sugars, whereas for the AZCL-substrates, the galactanase activity is measured spectrophotometrically (formation of a blue colour). In a particular embodiment, the galactanase assay is based on the substrate lupin AZCL galactan.

The person skilled in the art will know how to adapt assay-pH and assay-temperature to the galactanase in question. Examples of assay-pH-values are pH 2, 3, 4, 5, 6, 7, 8, 9, 10, or 11. Examples of assay-temperatures are 20, 25, 30, 35, 37, 40, 45, 50, 55, 60, 65, 70, 75, 80, or 90° C.

A preferred galactanase assay is described in Example 2 herein.

In a particular embodiment, the galactanase is an enzyme classified as EC 3.2.1.89, the official name of which is arabinogalactan-endo-1,4-beta-galactosidase. Alternative names are endo-1,4-beta-galactanase, galactanase, or arabinogalactanase. EC refers to Enzyme Class as described at a) www.chem.qmul.ac.uk/iubmb/enzyme, and/or in b) Enzyme Nomenclature 1992 from NC-IUBMB, Academic Press, San Diego, Calif., published by Academic Press for IUBMB in 1992 (ISBN 0-12-227164-5), as regularly supplemented and updated. For supplements and updates, please consult www.chem.qmul.ac.uk/iubmb/enzyme/supplements, giving details regarding the following supplements: Supplement 1

(1993) (Eur. J. Biochem., 1994 223, 1-5); Supplement 2 (1994) (Eur. J. Biochem., 1995 232, 1-6); Supplement 3 (1995) (Eur. J. Biochem., 1996 237, 1-5); Supplement 4 (1997) (Eur. J. Biochem., 1997, 250, 1-6); Supplement 5 (1999) (Eur. J. Biochem., 1999, 264, 610-650): Supplement 6 (2000); Supplement 7 (2001); and Supplement 8 (2002).

Glycoside Hydrolase (GH) Family 53

The EC-classification referred to above is mainly based on substrate specificity of the enzymes, and does therefore not reflect the structural features of these enzymes. A classification of glycoside hydrolases in families based on amino acid sequence similarities has been proposed a few years ago; see the CAZy(ModO) site at the internet:

Coutinho, P. M. & Henrissat, B. (1999) Carbohydrate-Active Enzymes server at URL: afmb.cnrs-mrs.fr/~cazy/CAZY/index.html; and/or Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23; Henrissat B., A classification of glycosyl hydrolases based on amino-acid sequence similarities. Biochem. J. 280:309-316 (1991); Henrissat B., Bairoch A. New families in the classification of glycosyl hydrolases based on amino-acid sequence similarities. Biochem. J. 293:781-788 (1993); Henrissat B., Bairoch A. Updating the sequence-based classification of glycosyl hydrolases. Biochem. J. 316:695-696 (1996); and/or Davies G., Henrissat B. Structures and mechanisms of glycosyl hydrolases. Structure 3:853-859 (1995).

Glycoside Hydrolase Family 53 is found under the entry relating to Glycosidases and Transglycosidases (or Glycoside Hydrolases).

These are particular embodiments of the GH Family 53 galactanase, i) it is an endo-1,4-beta-galactanase (EC 3.2.1.89);
ii) it has a retaining catalytic mechanism;
iii) it has Glu as a catalytic nucleophile or base;
iv) it has Glu as a catalytic proton donor;
v) its 3D Structure has a fold (beta/alpha)$_8$; and/or
vi) it belongs to GH Clan GH-A.

For the purposes of the present invention, the below glycoside hydrolases of Family 53 are non-limiting examples of a parent galactanase:

| Protein | Organism | GenBank | GenPept | SwissProt | Publication |
|---|---|---|---|---|---|
| galactanase 1 | Aspergillus aculeatus | L34599 | AAA32692.1 | P48842 | Christgau et al, Curr. Genet. 27: 135-141 (1995) |
| endo-1,4-beta-galactanase (GalA) | Aspergillus niger | AJ305303 | CAC83735.1 | Q8X168 | — |
| galactanase GalA | Aspergillus tubingensis | AJ012316 | CAB40555.1 | Q9Y7F8 | Van der Vlugt-Bergmans et al, Biotechnol. Tech. 13: 87-92 (1999) |
| ORF 1 | Bacillus circulans | L03425 | AAA22259.1 | P48843 | SEQ ID NO: 10 of WO 00/47711 |
| ORF BH2023 | Bacillus halodurans | AP001514 NC_002570 | BAB05742.1 NP_242889.1 | Q9KBA5 | Takami et al, Extremophiles 3 (1), 21-28 (1999) |
| ORF yvfO | Bacillus subtilis | Z94043 Z99121 | CAB08009.1 CAB15417.1 | O07013 O07013 O32260 | SEQ ID NO: 14 of WO 00/47711 |
| YvfO | Bifidobacterium longum | AE014643 NC_004307 | AAN24099.1 NP_695463.1 | | Schell et al, Proc. Natl. Acad. Sci. U.S.A. 99 (22), 14422-14427 (2002) |
| galactanase | Cellvibrio japonicus (Pseudomonas cellulosa) | X91885 | CAA62990.1 | P48841 | Braithwaite et al, Biochemistry 36: 15489-15500 (1997) |
| ORF CAC2570 | Clostridium acetobutylicum | AE007755 | AAK80519.1 | Q97G04 | Nolling et al, J. Bacteriol. 183 (16), 4823-4838 (2001) |
| ORF TM1201 | Thermotoga maritima | AE001777 NC_000853 | AAD36276.1 NP_229006.1 | Q9X0S8 | Nelson et al, Nature 399: 323-329 (1999) |

-continued

| Protein | Organism | GenBank | GenPept | SwissProt | Publication |
|---|---|---|---|---|---|
| Sequence 2 from U.S. Pat. No. 6,242,237 | Myceliophthora thermophila | AAE73520 | AAE73520.1 | | U.S. Pat. No. 6,242,237 |
| Sequence 4 from U.S. Pat. No. 6,242,237 | Humicola insolens | AAE73521 | AAE73521.1 | | U.S. Pat. No. 6,242,237 |
| ORF GalA | Xanthomonas axonopodis pv. citri | AE011762 NC_003919 | AAM36180.1 NP_641644.1 | | da Silva et al, Nature 417 (6887), 459-463 (2002) |
| ORF XAC0575 | Xanthomonas axonopodis pv. citri | AE011684 NC_003919 | AAM35464.1 NP_640928.1 | | da Silva et al, Nature 417 (6887), 459-463 (2002) |
| ORF GalA | Xanthomonas campestris pv. campestris | AE012224 NC_003902 | AAM40555.1 NP_636631.1 | | da Silva et al, Nature 417 (6887), 459-463 (2002) |
| ORF GalA | Xanthomonas campestris pv. campestris | AE012483 NC_003902 | AAM42894.1 NP_638970.1 | | da Silva et al, Nature 417 (6887), 459-463 (2002) |
| ORF YPO0853 | Yersinia pestis | AJ414145 NC_003143 | CAC89700.1 NP_404474.1 | Q8ZHN7 | Parkhill et al, Nature 413: 523-527 (2001) |
| ORF Y3238 | Yersinia pestis | AE013925 NC_004088 | AAM86788.1 NP_670537.1 | | Deng et al J. Bacteriol. 184 (16), 4601-4611 (2002) |

Additional examples of a parent galactanase of the invention are the galactanases derived from *Meripilus giganteus* (SEQ ID NO: 2 of WO 97/32013), *Pseudomonas fluorescens*, *Bacillus agaradhaerens* (SEQ ID NO: 12 of WO 00/47711), and *Bacillus licheniformis* (SEQ ID NO: 8 of WO 00/47711).

The present invention specifically includes variants of each and every of the above specific parent galactanases of GH Family 53 corresponding to the claimed variants of MTGAL, HIGAL, AAGAL and BLGAL, such variants being derivable by adding the parent galactanase sequence in question to the FIG. 5 alignment as described above for the construction of FIG. 6, and translating each MTGAL, HIGAL, AAGAL, or BLGAL variant into the parent galactanase in question, using the concept of corresponding amino acid residue as defined above.

In a first embodiment, the parent GH Family 53 galactanase is a fungal galactanase. The fungal galactanase may be derived from a yeast, or from a filamentous fungus. The yeast galactanase may be derived from *Yersinia*, e.g., from *Yersinia pestis*. The filamentous fungal galactanase may be derived from a strain of *Aspergillus*, *Humicola*, *Meripilus*, *Myceliophthora*, or *Thermomyces*. Examples of these strains are *Aspergillus aculeatus*, *Aspergillus niger*, *Aspergillus tubingensis*, *Humicola insolens*, *Meripilus giganteus*, and *Myceliophthora thermophila*.

In a second embodiment, the parent GH Family 53 galactanase is a bacterial galactanase. The bacterial galactanase may be derived from a strain of *Bacillus*, *Bifidobacterium*, *Cellvibrio*, *Clostridium*, *Pseudomonas*, *Thermotoga*, or *Xanthomonas*. Examples of such strains are *Bacillus agaradhaerens*, *Bacillus circulans*, *Bacillus halodurans*, *Bacillus licheniformis*, *Bacillus subtilis*, *Bifidobacterium longum*, *Cellvibrio japonicus*, *Clostridium acetobutylicum*, *Pseudomonas fluorescens*, *Pseudomonas cellulosa*, *Thermotoga maritime*, *Xanthomonas axonopodis* pv. *citri*, and *Xanthomonas campestris* pv. *campestris*.

Particularly preferred parent galactanases are those with the above-mentioned GenBank, GenPept, or SwissProt accession numbers, and those with the above-mentioned SEQ ID NO's.

Further particularly preferred GH Family 53 parent galactanases are the following:

| Strain of origin | Sequence Number (herein) | Abbreviations used herein |
|---|---|---|
| Myceliophthora thermophila | SEQ ID NO: 1 | MTGAL, or MT |
| Humicola insolens | SEQ ID NO: 2 | HIGAL, or HI |
| Aspergillus aculeatus | SEQ ID NO: 3 | AAGAL, or AA |
| Bacillus licheniformis | SEQ ID NO: 4 | BLGAL, or BL |

Preferred subgroups of the above are a) MTGAL, HIGAL, AAGAL; b) MTGAL, HIGAL, BLGAL; and c) MTGAL, HIGAL.

In a third embodiment, the parent galactanase has a percentage identity to SEQ ID NO: 1 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a fourth embodiment, the galactanase variant has a percentage identity to SEQ ID NO: 1 of at least 50%, using the program ClustalW and the settings referred to above. In further particular embodiments, the percentage identity is at least 55, 60, 65, 70, 75, 80, 85, 90, 95, 97, or at least 99%.

In a fifth embodiment, the parent galactanase has a percentage identity to SEQ ID NO: 2 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a sixth embodiment, the galactanase variant has a percentage identity to SEQ ID NO: 2 of at least 50%, using the program ClustalW and the settings referred to above. In further particular embodiments, the percentage identity is at least 55, 60, 65, 70, 75, 80, 85, 90, 95, 97, or at least 99%.

In a seventh embodiment, the parent galactanase has a percentage identity to SEQ ID NO: 3 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In an eighth embodiment, the galactanase variant has a percentage identity to SEQ ID NO: 3 of at least 50%, using the program ClustalW and the settings referred to above. In further particular embodiments, the percentage identity is at least 55, 60, 65, 70, 75, 80, 85, 90, 95, 97, or at least 99%.

In a ninth embodiment, the parent galactanase has a percentage identity to SEQ ID NO: 4 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a tenth embodiment, the galactanase variant has a percentage identity to SEQ ID NO: 4 of at least 50%, using the program ClustalW and the settings referred to above. In further particular embodiments, the percentage identity is at least 55, 60, 65, 70, 75, 80, 85, 90, 95, 97, or at least 99%.

In further particular embodiments of each of the above first to tenth embodiments, the alignment is a full Smith-Waterman alignment with the settings referred to above, preferably made with the FASTA package also referred to above.

It is to be understood that also variants of galactanases are contemplated as the parent enzyme.

Preparation of Galactanase Variants

The galactanase variants may be prepared by any method known in the art, see, e.g., Example 1 herein. Typically, a galactanase variant library is prepared. The term "randomized library", "variant library", or simply "library" refers to such library of galactanase variants. Diversity in the variant library can be generated via mutagenesis of the genes encoding the variants at the DNA triplet level, such that individual codons are variegated e.g., by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes A/S). They also include the use of DNA shuffling techniques to create a library of full length genes, wherein several gene segments are combined, and wherein each segment may be diversified e.g., by spiked mutagenesis (Stemmer, Nature 370, pp. 389-391, 1994 and U.S. Pat. No. 5,811,238; U.S. Pat. No. 5,605,793; and U.S. Pat. No. 5,830,721). One can use a gene encoding a galactanase "backbone" (wildtype parent galactanase) as a template polynucleotide, and combine this with one or more single or double-stranded oligonucleotides as described in WO 98/41623 and in WO 98/41622 (Novozymes A/S). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone galactanase in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g., decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 212) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

The mutated DNA can be expressed by any method known in the art, see, e.g., Example 1. Generally, the host cell may be a unicellular microorganism, e.g., a prokaryote, or a non-unicellular microorganism, e.g., a eukaryote.

Useful unicellular cells are bacteria such as *Bacillus, Streptomyces, E. coli, Pseudomonas* sp., *Lactococcus, Lactobacillus, Leuconostoc, Streptococcus, Pediococcus*, and *Enterococcus*.

Examples of eukaryote cells are non-human animal cells, insect cells, plant cells, or fungal cells. Examples of fungal cells are *Candida, Hansenula, Kluyveromyces, Pichia, Saccharomyces, Schizosaccharomyces, Yarrowia, Acremonium, Aspergillus, Fusarium, Humicola, Mucor, Myceliophthora, Neurospora, Penicillium, Thielavia, Tolypocladium*, and *Trichoderma*.

Applications

The galactanase variants of the invention are useful in animal feed, see, e.g., WO 97/16982. Non-limiting examples of desirable characteristics of galactanase variants for feed applications are: High temperature stability, acid-stability and high specific activity.

The galactanase variants of the invention, e.g., but not exclusively, those of claims 1-4, may also be used to prepare galacto-oligo-saccharides and for hydrolysis of lactose, both of which are relevant for, e.g., the dairy industry. For example, the method of Example 5 can be used for screening of galactanase variants for improved activity on lactose, in particular for improved transglycosylation and/or hydrolytic activity on lactose.

The transglycosylation reactions observed with ONPG (Example 4) can be used for screening of galactanase variants for suitable acceptor affinities. The screening may be a high-through-put screening. This provides valuable knowledge of the affinities of the individual subsites (such as subsites +1, +2, +3, +4) for various acceptors, e.g., galactose (Gal), beta-1,4-galactobiose (Gal2) (Megazyme), beta-1,4-galactotriose (Gal3), beta-1,4-galactotetraose (Gal4), glucose (Glu), arabinose (Ara), galacturonic acid (GalA), maltose (Mal) or maltotriose (Mal3).

The results of Example 3 provides knowledge of individual subsites for galactose (−3 to +3), as well as knowledge of the tendencies to transglycosylate instead of hydrolyse substrates. This knowledge is useful for the designing of galactanase variants of desired properties.

Various references are cited herein, the disclosures of which are incorporated by reference in their entireties.

EXAMPLES

Example 1

Preparation of Galactanase Variants

The D181N mutation was introduced in the AAGAL encoding gene by the use of the mutagenic oligonucleotide 5'-CAT TTG GAC AAC GGC TGG AGC-3' (SEQ ID NO: 5) and the mega-priming method described by Sarkar, G., and Sommer, S. S., 1990. The "Megaprimer" Method of Site-Directed Mutagenesis. BioTechniques, 8: 404-407. The mutations D181N+S90A+D91H were introduced in a similar way.

The resulting variant genes were cloned into plasmid pHD464 as described in Dalbøge H., Heldt-Hansen H. 1994. A novel method for efficient expression cloning of fungal enzyme genes. Mol. Gen. Genet. 243: 253-260, and the correct introduction of the mutations were verified by DNA sequencing.

The A90S+H91D double mutation was introduced in the MTGAL encoding gene essentially as described above by the use of the mutageneic oligonucleotide 5'-GCC GAT CCT TCT GAT CAG ACC ATG CC-3' (SEQ ID NO: 6).

Proteins were expressed in, and secreted from *Aspergillus oryzae* essentially as described in Christensen, T., Wöldike, H., Boel, E., Mortensen, S. B., Hjortshøj, K., Thim, L., Hansen, M. T., 1988. High level expression of recombinant genes in *Aspergillus oryzae*. Bio/Technology 6, 1419-1422.

Example 2

Purification and Characterization of Galactanase Variants

Purification of *Aspergillus aculeatus* Galactanase Variants

The culture supernatant from a fermentation of the *Aspergillus oryzae* strain expressing the site-directed recombinant *Aspergillus* aculeatus galactanase variant D181N (described in Example 1) was filtered through a 0.22 μm filter to remove the mycelia. 1200 ml filtrate was added ammonium sulphate to a concentration of 1.6 M, loaded onto a 50 ml butyl column equilibrated with 25 mM sodium acetate, 1.6 M ammonium sulphate pH 5.0 and eluted using a linear ammonium sulphate decreasing from 1.6 M to 0 M over 10 column volumes. Galactanase activity was measured by mixing 40 μl of fractions with 200 μl 10 mg/ml lupin AZCL-galactan (Megazyme, Australia) in 0.5 M MES pH 6.5 After about 30 min incubation at room temperature, insoluble substrate was removed by centrifugation, and absorbance of supernatant measured at 590 nm. Fractions containing galactanase activity eluted around 1 M ammonium sulphate were pooled and dialysed against 10 mM sodium citrate pH 3.5. Dialysate (400 ml) was diluted to 2000 ml with water and loaded onto a 50 ml S-Sepharose column equilibrated with 10 mM sodium citrate pH 3.5. Galactanase activity did not bind to this column and was concentrated to 80 ml on an Amicon ultrafiltration device with a 10 kDa cut off filter. The concentrate was at least 95% pure estimated from SDS-PAGE.

The culture supernatant from a fermentation of the *Aspergillus oryzae* strain expressing the site-directed recombinant *Aspergillus aculeatus* galactanase variant D181N+S90A+D91H was filtered as described above. 900 ml filtrate was added ammonium sulphate to a concentration of 1.6 M, and eluted from a 50 ml butyl column as described above. Galactanase activity was measured as described above. Fractions containing galactanase activity eluted around 0.35 M ammonium sulphate and were pooled and dialysed against 25 mM sodium acetate pH 5.5. Dialysate (200 ml) was diluted to 275 ml with water, loaded onto a 50 ml Q-Sepharose column equilibrated with 25 mM sodium acetate pH 5.5, and eluted with a linear gradient from 0 to 1 M NaCl over 10 column volumes. Fractions containing galactanase activity (around 0.8 M NaCl) were pooled and concentrated to 10 ml on an Amicon ultrafiltration device with a 10 kDa cut off filter. The concentrate was at least 95% pure estimated from SDS-PAGE.

Purification of *Myceliophthora thermophila* Galactanase Variants

The culture supernatant from a fermentation of the *Aspergillus oryzae* strain expressing the site-directed recombinant *Myceliophthora thermophila* galactanase variant A90S+H91 D (described in Example 1) was filtered through a 0.22 μm filter to remove the mycelia. 1200 ml filtrate was added ammonium sulphate to a concentration of 1.6 M, loaded onto a 50 ml butyl column equilibrated with 25 mM sodium acetate, 1.6 M ammonium sulphate pH 5.0 and eluted using a linear ammonium sulphate decreasing from 1.6 M to 0 M over 10 column volumes. Galactanase activity was measured by mixing 40 μl of fractions with 200 μl 10 mg/ml lupin AZCL-galactan (Megazyme, Australia) in 0.5 M MES pH 6.5 After about 30 min incubation at room temperature, insoluble substrate was removed by centrifugation, and absorbance of supernatant measured at 590 nm. Fractions containing galactanase activity eluted around 1 M ammonium sulphate were pooled and dialysed against 10 mM sodium citrate pH 3.5. Dialysate (400 ml) was diluted to 2000 ml with water and loaded onto a 50 ml S-Sepharose column equilibrated with 10 mM sodium citrate pH 3.5. Galactanase activity did not bind to this column and was concentrated to 80 ml on an Amicon ultrafiltration device with a 10 kDa cut off filter. The concentrate was at least 95% pure estimated from SDS-PAGE.

Characterization of the Purified Variants

The pH profiles of the purified variants described above were established as follows: Galactanase activity at various pH was measured by mixing 500 μl 4 mg/ml lupin AZCL-galactan (Megazyme, Australia) in water with 500 μl buffer (50 mM sodium acetate, 50 mM potassium dihydrogenphosphate, 50 mM boric acid, 1 mM $CaCl_2$, 0.01% Triton X-100 adjusted to pH 2.5, 3.5, 4.5, 5.5, 6.5, 7.5, 8.5 or 9.5 with HCl/NaOH) and 25 μl purified enzyme diluted to about 0.5-2 μg/ml in water. The mixture was incubated 15 min at 37° C., insoluble material was removed by centrifugation, and absorbance in the supernatant was measured at 590 nm.

From the results shown in Table 1 below, it appears that the pH profiles have changed (the profile of the AAGAL variants D181N, and D181N+S90A+D91H have been shifted to the alkaline side; and the pH profile of the MTGAL variant A90S+H91D has been shifted to the acidic side, as compared to the wild types).

TABLE 1

| Galactanase | pH 2.5 | 3.5 | 4.5 | 5.5 | 6.5 | 7.5 | 8.5 | 9.5 |
|---|---|---|---|---|---|---|---|---|
| AAGAL | 73 | 100 | 83 | 47 | 32 | 0 | 2 | 0 |
| AAGAL D181N | 74 | 99 | 100 | 87 | 74 | 35 | 7 | 0 |
| AAGAL D181N + S90A + D91H | 55 | 59 | 71 | 83 | 100 | 90 | 21 | 0 |
| MTGAL | 0 | 12 | 41 | 63 | 90 | 100 | 54 | 7 |
| MTGAL A90S + H91D | 0 | 8 | 51 | 75 | 100 | 95 | 35 | 4 |

Example 3

Activity on Galactooligosaccharides

Preparation of Galactotriose (Gal3), Galactotetraose (Gal4), Methyl-Galactotrioside (MeGal3) and Methyl-Galactotetraoside (MeGal4)

Galactan (lupin) was purchased from Megazyme. All solvents, reagents and TLC-plates (Silica gel 60 $F_{254}$) were purchased from Merck. $^1$H NMR spectra were recorded on a Varian Mercury 400 MHz at 30° C. As reference values CHCl$_3$ in CDCl$_3$ (7.27 ppm) and HDO in D$_2$O (4.67 ppm) were used. Flash chromatography was accomplished using a FLASH 40i chromatography module from Biotage.

Undeca-O-acetyl galactotriose: Arabinofuranosidase treated lupin galactan (0.50 g) was dissolved in 10 mM Bis-Tris buffer pH 6.5 (50 mL) by stirring for 1 h at 37° C. BLGAL was added (250 GalU/mL) and the solution stirred for 3 h at 37° C. and then 5 min at 100° C. TLC (eluent: propanol/ethanol/H$_2$O (7:1:2)) showed a major (Gal3) and a minor product (Gal4) both eluting below commercial galactobiose. After cooling, the solution was concentrated, dried and acetylated and worked up by standard procedures (Ac$_2$O/pyridine, 48 h at room temperature (rt)). The crude product was purified by flash chromatography (eluent: EtOAc/heptane 5:2) to give 0.20 g of pure Gal3 peracetate (mixture of alpha- and beta-anomer (1:2)). $^1$H NMR (selected data, CDCl$_3$): 6.29 ppm (d, $J_{1,2}$=3.5 Hz, H-1 alpha), 5.63 ppm (d, $J_{1,2}$=8.4 Hz, H-1β).

Galactotriose (Gal3): Deacetylation of the acetylated triose was accomplished by stirring overnight in methanol/NaOCH$_3$ (1 mL 1 M NaOCH$_3$ in 3 mL methanol) and then neutralized by addition of Dowex 50 Wx8. Water (2 mL) was added and the resin removed by filtration. The clear solution was concentrated (freeze-drying) to give 0.10 g of solid G3. MS (MALDI-TOF): 527 (M+23, Na). $^1$H NMR (selected data, D$_2$O): 5.20 ppm (d, J=3.6 Hz, H-1 alpha), 4.5-4.6 (3×d, H-1β, H-1', H-1").

Methyl deca-O-acetyl galactotrioside: The acetylated galactotriose (0.24 g) was converted into the bromide by treatment (5 h) with 30% HBr in acetic acid (2.5 mL) and CH$_2$Cl$_2$ (2 mL) at 0° C.→rt. The reaction was worked up by standard procedures and concentrated to give a yellowish syrup (194 mg) of the alpha-bromo compound, which was used without further purification. $^1$H NMR (selected data, CDCl$_3$): 6.57 ppm (d, 1H, $J_{1,2}$=3.8 Hz, H-1). The bromoglycoside (0.19 g, 0.20 mmol) was converted into the methyl glycoside by overnight treatment with Ag$_2$CO$_3$ (60 mg, 22 mmol) in dry methanol (10 mL) (under nitrogen). After work up, the methyl glycoside was purified by flash chromatography (eluent: EtOAc/heptane (3:1)) to give 30 mg of pure compound (colorless oil). $^1$H NMR (selected data, CDCl$_3$): 4.48 ppm, 4.39 ppm and 4.35 ppm (3×d, 3H, $J_{1,2}$=8.0 Hz, H-1, H-1' and H-1"), 3.47 ppm (3H, s, OCH$_3$).

Methyl galactotrioside (MeGal3): The acetylated methyl glycoside (30 mg) was deacetylated as described above to give 10 mg of syrupy material.

Galactotetraose (Gal4): This was prepared as described for Gal3 using 100 GalU/mL. Yield of final deacetylated product: 17 mg.

Methyl galactotetraoside (MeGal4): This compound was prepared in analogy with MeGal3 and 41 mg of MeGal4 was obtained from 1 g of galactan. MS (MALDI-TOF): 704 (M+23, Na).

Activity of HIGAL MTGAL, AAGAL and BLGAL on Galactooligosaccharides

The activity on the galacto-oligosaccharide substrates prepared as described above and on the commercially available galactobiose (Gal2, Megazyme) was studied for the four purified galactanases HIGAL, MTGAL, AAGAL and BLGAL. The buffers and temperatures used were: 25 mM sodium acetate, 0.5 mM CaCl$_2$, 0.005% Triton X-100, pH 6.5 at 37° C. for HIGAL and MTGAL, 50 mM sodium acetate, 1 mM CaCl$_2$, pH 4 at 30° C. for AAGAL and 50 mM Mes, 1 mM CaCl$_2$, pH 6.5 at 30° C. for BLGAL. Enzyme concentrations used were 0.8 µg/ml for HIGAL, 0.2 microgram/ml for MTGAL, and 10 micrograms/ml for AAGAL and BLGAL. With HIGAL and MTGAL substrate concentrations were all 0.25 mg/ml, whereas 0.34 mg/ml Gal2, 0.050 mg/ml Gal3 and 0.067 mg/ml Gal4 were used for AAGAL and BLGAL. Enzyme activity in samples withdrawn after various incubation times was inactivated by heating to 95° C. for 10 min. Compositions of reaction products were analysed using HPAE-PAD (Dionex) applying a PA-100 column and a linear gradient of sodium acetate (0-0.18 M) in 0.15 M NaOH. Response factors of the individual carbohydrates were estimated from reference runs with MeGal3, MeGal4, Gal, Gal2, Gal3 and Gal4. Selected results are shown in Tables 2-8 below (the figures indicating weight percentage of glactooligosaccharides).

Neither of the enzymes HIGAL, MTGAL, AAGAL or BLGAL had any detectable activity on Gal2 in 24 hours. HIGAL, MTGAL and AAGAL degraded Gal3 to Gal2 and Gal, whereas BLGAL had no visible activity on Gal3 after 24 hours. Incubation of HIGAL and MTGAL with MeGal3 (See Tables 2 and 3) gave much higher release of MeGal than MeGal2, indicating that Gal is released from the reducing end of Gal3 with both enzymes. HIGAL and MTGAL degraded Gal4 (also containing about 40% Gal3) (Tables 4 and 5) mainly to Gal and Gal2, whereas Gal3 did not accumulate. Results for HIGAL and MTGAL with MeGal4 (Tables 6 and 7) gave initial release mainly of MeGal, MeGal2 and Gal3 and some Gal2 but little Gal, again indicating that Gal is released mainly from the reducing end of Gal4. The production of Gal from MeGal4 in the later stages of the hydrolysis may be mainly due to hydrolysis of transglycosylation products with no methyl group at the reducing end. BLGAL degrades galactotetraose mainly to galactose and galactotriose. With MeGal4 the main products from BLGAL were MeGal and Gal3, indicating that Gal is released from reducing end of Gal4. With AAGAL the initial products from galactotetraose are about equimolar amounts of galactose, galactobiose and galactotriose, but subsequently the galactotriose is degraded to galactobiose and galactose.

TABLE 2

Degradation of MeGal3 with HIGAL

| | Incubation time (hours) | | | | |
|---|---|---|---|---|---|
| | 0.0 | 0.5 | 2.2 | 5.0 | 72.0 |
| Gal | 0.0 | 0.0 | 2.3 | 3.0 | 17.1 |
| Gal2 | 0.0 | 3.9 | 12.5 | 20.2 | 36.2 |
| Gal3 | 0.0 | 1.2 | 3.3 | 10.6 | 8.0 |
| MeGal | 0.0 | 11.4 | 18.4 | 36.8 | 34.6 |
| MeGal2 | 0.0 | 3.3 | 3.7 | 5.2 | 4.2 |
| MeGal3 | 100.0 | 80.3 | 59.7 | 24.2 | 0.0 |

TABLE 3

Degradation of MeGal3 with MTGAL

| | Incubation time (hours) | | | | |
|---|---|---|---|---|---|
| | 0.0 | 0.5 | 2.2 | 5.0 | 72.0 |
| Gal | 0.0 | 0.0 | 14.1 | 2.2 | 6.5 |
| Gal2 | 0.0 | 0.0 | 8.5 | 10.9 | 37.2 |
| Gal3 | 0.0 | 0.0 | 0.4 | 15.7 | 23.2 |
| MeGal | 0.0 | 10.1 | 27.6 | 17.4 | 28.3 |
| MeGal2 | 0.0 | 2.7 | 1.9 | 3.2 | 3.5 |
| MeGal3 | 100.0 | 87.2 | 47.5 | 50.6 | 1.3 |

TABLE 4

Degradation of Gal4 with HIGAL

| | Incubation time (hours) | | | | |
|---|---|---|---|---|---|
| | 0.0 | 0.5 | 2.2 | 5.0 | 72.0 |
| Gal | 0.0 | 5.8 | 16.7 | 35.6 | 65.2 |
| Gal2 | 0.0 | 8.1 | 21.9 | 34.8 | 33.6 |
| Gal3 | 42.0 | 43.2 | 39.8 | 23.9 | 0.9 |
| Gal4 | 58.0 | 42.9 | 21.6 | 5.7 | 0.2 |

TABLE 5

Degradation of Gal4 with MTGAL

| | Incubation time (hours) | | | | |
|---|---|---|---|---|---|
| | 0.0 | 0.5 | 2.2 | 5.0 | 72.0 |
| Gal | 0.0 | 11.6 | 14.9 | 29.2 | 54.9 |
| Gal2 | 0.0 | 9.9 | 17.4 | 29.1 | 43.5 |
| Gal3 | 42.0 | 27.7 | 45.5 | 29.5 | 1.5 |
| Gal4 | 58.0 | 50.8 | 22.3 | 12.1 | 0.0 |

TABLE 6

Degradation of MeGal4 with HIGAL

| | Incubation time (hours) | | | | |
|---|---|---|---|---|---|
| | 0.0 | 0.5 | 2.0 | 5.0 | 24.0 |
| Gal | 0.0 | 2.3 | 1.6 | 7.4 | 26.4 |
| Gal2 | 0.0 | 6.3 | 5.0 | 13.8 | 25.3 |
| Gal3 | 0.0 | 20.6 | 16.0 | 19.7 | 9.1 |
| Gal4 | 0.0 | 3.3 | 3.2 | 3.2 | 1.7 |
| MeGal | 1.6 | 12.1 | 10.5 | 16.6 | 19.1 |
| MeGal2 | 4.7 | 12.6 | 13.2 | 16.1 | 13.4 |
| MeGal3 | 14.8 | 17.2 | 18.4 | 15.5 | 5.0 |
| MeGal4 | 79.0 | 25.5 | 32.1 | 7.6 | 0.0 |

TABLE 7

Degradation of MeGal4 with MTGAL

| | Incubation time (hours) | | | | |
|---|---|---|---|---|---|
| | 0.0 | 0.5 | 2.0 | 5.0 | 24.0 |
| Gal | 0.0 | 0.9 | 4.8 | 12.4 | 24.2 |
| Gal2 | 0.0 | 3.3 | 10.9 | 20.1 | 32.7 |
| Gal3 | 0.0 | 13.7 | 23.9 | 17.9 | 3.4 |
| Gal4 | 0.0 | 2.5 | 3.7 | 2.9 | 1.1 |
| MeGal | 1.6 | 8.9 | 16.2 | 19.3 | 20.1 |
| MeGal2 | 4.7 | 9.6 | 13.6 | 13.9 | 13.3 |
| MeGal3 | 14.8 | 17.1 | 16.0 | 9.9 | 2.3 |
| MeGal4 | 79.0 | 43.9 | 10.9 | 3.5 | 2.9 |

Example 4

Activity with o-nitrophenyl-β-D-galactopyranoside (ONPG)

The activity of HIGAL and MTGAL with ONPG was tested by mixing 200 microliters (normally 5.5 mg/ml) ONPG in 50 mM sodium acetate, 1 mM $CaCl_2$, 0.01% Triton X-100, pH 6.5 with 25 microliters galactanase (normally 1 mg/ml) in the well of a microtiter plate. Release of o-nitrophenol (ONP) was measured at room temperature at 405 nm every 10 seconds normally for 30 min on a SpectraMaxPlus (Molecular Devices). Effects on the observed release of ONP was studied with varied enzyme concentration, ONPG concentration and with addition of galactose (Gal), beta-1,4-galactobiose (Gal2) (Megazyme), beta-1,4-galactotriose (Gal3), beta-1,4-galactotetraose (Gal4), glucose (Glu), arabinose (Ara), galacturonic acid (GalA), maltose (Mal) or maltotriose (Mal3).

In Tables 8-11 below, incubation times required to increase the observed absorbance at 405 nm by given amounts are listed. Cells marked 'n.r.' indicate that the increase in absorbance was not reached in the experiment. In general, the initial increase in absorbance at 405 nm was very slow, but after a lag phase the rate of ONP release often increased drastically—often approximately exponentially. The most likely explanation for the observed kinetics is that ONPG reacts with the enzyme to give an enzyme-galactosyl intermediate which hydrolyses very slowly. Instead, the Gal of the intermediate is released by transglycosylation, initially with ONPG or added sugar as acceptor. In cases where the rate of ONP release increases, these transglycosylation products are even better acceptors than the initial ones. As seen in Table 8, the rate of ONP release is about proportional to the amount of added enzyme. HIGAL releases ONP faster than MTGAL at identical enzyme dosage. Addition of Gal (5 mg/ml) is seen to slow the ONP release by about a factor of two for MTGAL and a factor of three for HIGAL. Probably, Gal does not significantly slow formation of the enzyme-galactosyl intermediate, which would accumulate even if Gal had high affinity for the −1 or +1 subsite. More likely, Gal inhibits the subsequent transglycosylation, which requires binding of ONPG to the +1 and +2 subsites, e.g., by binding to the +2 subsite. With 50 mg/ml Gal added (results not shown) release of ONP was even slower with only insignificant increase of absorbance at 405 nm in 30 min.

The results in Table 9 show that rate of ONP release is similar with 5 and 10 mg/ml ONPG but slower at 2.5 and especially 1.25 mg/ml ONPG. This indicates that the rate-limiting transglycosylation reaction with ONPG as acceptor has a Km of about 3 mg/ml.

In Table 10 effects of adding 0.5 or 0.05 mg/ml Gal2, Gal3 or Gal4 are given. Contrary to Gal each of these three galactooligosaccharides increases the rate of ONP release. The initial ONP release rates indicate that Gal4 is more efficient than Gal3 as acceptor, and that Gal3 is more efficient than Gal2. With Gal2 and Gal3, ONP release rate increases significantly with incubation time, indicating that transglycosylation products (initially Gal3 and Gal4, respectively) are more efficient acceptors than the added sugars, whereas the release rate is relatively constant with Gal4. These results indicate that HIGAL possesses four significant subsites (+1, +2, +3, +4) on the reducing side of the cleaved bond.

In Table 11 results upon addition of Glu, Ara, Mal, Mal3 and GalA are given. As experiments were run on three different days, and ONP release rate even in identical experiments had been seen to vary slightly (possibly due to variants in temperature), results with only ONPG and HIGAL added run in the same three experiments are shown. It is seen that 5 mg/ml Ara inhibits the transglycosylation, resulting in about three times slower ONP release. 5 mg/ml Glu also has slight inhibitory effect, whereas 50 mg/ml Glu (results not shown) resulted in very little ONP release (<0.02) in 30 min. As with Gal, this indicates binding of these sugars to subsites in the enzyme-galactosyl intermediate, which prevents ONPG to act as acceptor and where the sugars themselves also has little or no acceptor function. With 5 mg/ml Mal or Mal3 no significant effects on ONP release are observed. 5 mg/ml GalA has weak inhibitory effect, whereas 50 mg/ml GalA slows ONP release by about a factor two. From these results ranking of the inhibitory effect of the tested sugars is: Gal~Ara>Glu>GalA>Mal=Mal3=0.

Using HPAE-PAD chromatography (Dionex LC-500 System, PA-100 column, linear gradient of 0-0.6 M sodium acetate in 100 mM NaOH), the production of larger oligosaccharides from transglycosylation upon incubation of HIGAL (110 µg/ml) at room temperature (0.5 to 14 min followed by heat inactivation for 10 min at 95° C. resulting in $A_{405}$: 0.15-0.67) in 50 mM sodium acetate, 1 mM $CaCl_2$, 0.01% Triton X-100, pH 6.5 with ONPG (5 mg/ml) with and without Gal2 (0.05 mg/ml) or Gal3 (0.05 mg/ml) as acceptor was verified.

TABLE 8

Rate of ONP release, MTGAL and HIGAL in varying dosages, and +/− sugar

| | | Enzyme: µg/ml | | | | | | | | | |
|---|---|---|---|---|---|---|---|---|---|---|---|
| | | MTGAL 110 | MTGAL 55 | MTGAL 28 | MTGAL 110 | MTGAL 55 | HIGAL 110 | HIGAL 55 | HIGAL 28 | HIGAL 110 | HIGAL 55 |
| ONPG (5 mg/ml) Sugar: mg/ml | | | | | Gal: 5 | Gal: 5 | | | | Gal: 5 | Gal: 5 |
| Time (min) to increase A405 by: | 0.025 | 14.0 | 29.9 | 40.4 | 26.9 | 40.2 | 9.0 | 20.4 | 41.4 | 32.0 | 57.0 |
| | 0.05 | 20.5 | 42.5 | n.r. | 44.5 | n.r. | 10.3 | 22.9 | 46.5 | 35.7 | n.r. |
| | 0.1 | 26.4 | 54.5 | n.r. | n.r. | n.r. | 11.5 | 25.4 | 51.0 | 41.5 | n.r. |
| | 0.2 | 31.4 | n.r. | n.r. | n.r. | n.r. | 12.7 | 28.0 | 56.5 | 46.7 | n.r. |
| | 0.4 | 34.5 | n.r. | n.r. | n.r. | n.r. | 13.8 | 30.9 | n.r. | 52.7 | n.r. |
| | 0.8 | 39.2 | n.r. | n.r. | n.r. | n.r. | 15.0 | 32.0 | n.r. | 59.0 | n.r. |
| | 1.6 | 43.9 | n.r. | n.r. | n.r. | n.r. | 15.0 | 35.0 | n.r. | n.r. | n.r. |
| | 3.2 | 46.7 | n.r. | n.r. | n.r. | n.r. | 17.7 | 37.9 | n.r. | n.r. | n.r. |

TABLE 9

Rate of ONP release at varying ONPG concentrations

| | | Enzyme: µg/ml | | | |
|---|---|---|---|---|---|
| | | HIGAL: 110 | HIGAL: 110 | HIGAL: 110 | HIGAL: 110 |
| ONPG (mg/ml) Sugar: mg/ml | | 10 | 5 | 2.5 | 1.25 |
| Time (min) to increase A405 by: | 0.025 | 6.3 | 6.0 | 9.7 | 28.7 |
| | 0.05 | 7.7 | 8.0 | 11.3 | n.r. |
| | 0.1 | 8.8 | 9.2 | 12.7 | n.r. |
| | 0.2 | 10.0 | 10.2 | 14.0 | n.r. |
| | 0.4 | 11.2 | 11.3 | 15.5 | n.r. |
| | 0.8 | 12.3 | 12.5 | 17.3 | n.r. |
| | 1.6 | 13.5 | 13.8 | 19.5 | n.r. |
| | 3.2 | 14.7 | 15.3 | 22.8 | n.r. |

TABLE 10

Rate of ONP release, addition of various amounts of various galactooligosaccharides

| | Enzyme: µg/ml | | | | | | |
|---|---|---|---|---|---|---|---|
| | HIGAL: 110 | HIGAL: 110 | HIGAL: 110 | HIGAL: 110 | HIGAL: 110 | HIGAL: 110 | HIGAL: 110 |
| ONPG (mg/ml) | 5 | 5 | 5 | 5 | 5 | 5 | 5 |

TABLE 10-continued

Rate of ONP release, addition of various amounts of various galactooligosaccharides

| | | | | | Enzyme: µg/ml | | | |
|---|---|---|---|---|---|---|---|---|
| | | HIGAL: 110 | HIGAL: 110 | HIGAL: 110 | HIGAL: 110 | HIGAL: 110 | HIGAL: 110 | HIGAL: 110 |
| Sugar: mg/ml | | | Gal2: 0.5 | Gal2: 0.05 | Gal3: 0.5 | Gal3: 0.05 | Gal4: 0.5 | Gal4: 0.05 |
| Initial rate (mOD/min) | | 0.9 | 6 | 2 | 200 | 40 | 700 | 80 |
| Time (min) to increase A405 by: | 0.025 | 10.0 | 2.7 | 5.5 | 0.0 | 0.5 | 0.0 | 0.2 |
| | 0.05 | 11.3 | 3.5 | 6.8 | 0.2 | 1.0 | 0.0 | 0.5 |
| | 0.1 | 12.8 | 4.8 | 8.2 | 0.3 | 1.7 | 0.0 | 0.8 |
| | 0.2 | 14.2 | 6.0 | 9.5 | 0.5 | 2.3 | 0.2 | 1.5 |
| | 0.4 | 15.7 | 7.2 | 10.7 | 0.8 | 3.3 | 0.5 | 2.5 |
| | 0.8 | 17.0 | 8.3 | 11.8 | 1.5 | 4.8 | 1.0 | 3.7 |
| | 1.6 | 18.5 | 9.7 | 13.3 | 2.5 | 6.3 | 2.2 | 5.2 |
| | 3.2 | 20.0 | 11.0 | 15.2 | 3.8 | 7.7 | 5.3 | 7.5 |

TABLE 11

Rate of ONP release, inhibition by sugars

| | | | | | | Enzyme: µg/ml | | | | |
|---|---|---|---|---|---|---|---|---|---|---|
| | | HIGAL: 110 | HIGAL: 110 | HIGAL: 110 | HIGAL: 110 | HIGAL: 110 | HIGAL: 110 | HIGAL: 110 | HIGAL: 110 | HIGAL: 110 |
| ONPG (mg/ml) | | 5 | 5 | 5 | 5 | 5 | 5 | 5 | 5 | 5 |
| Sugar: mg/ml | | | Glu: 5 | Ara: 5 | | Mal: 5 | Mal3: 5 | | GalA: 50 | GalA: 5 |
| Time (min) to increase A405 by: | 0.025 | 8.5 | 12.8 | 26.5 | 11.0 | 11.5 | 11.0 | 8.7 | 13.7 | 9.5 |
| | 0.05 | 9.5 | 14.8 | n.r. | 12.5 | 13.0 | 12.3 | 9.8 | 16.7 | 11.2 |
| | 0.1 | 10.8 | 17.0 | n.r. | 13.8 | 14.3 | 13.8 | 11.0 | 20.0 | 12.7 |
| | 0.2 | 12.0 | 19.3 | n.r. | 15.2 | 15.7 | 15.2 | 12.2 | 23.3 | 14.3 |
| | 0.4 | 13.3 | 21.8 | n.r. | 16.5 | 17.2 | 16.5 | 13.3 | 26.8 | 15.8 |
| | 0.8 | 14.5 | 24.3 | n.r. | 18.0 | 18.7 | 18.0 | 14.7 | n.r. | 17.5 |
| | 1.6 | 15.8 | 27.0 | n.r. | 19.5 | 20.2 | 19.3 | 16.0 | n.r. | 19.3 |
| | 3.2 | 17.3 | n.r. | n.r. | 21.3 | 22.0 | 21.3 | 17.3 | n.r. | 22.5 |

Example 5

Activity on Lactose

HIGAL (60 micrograms/ml) and MTGAL (750 µg/ml) were incubated at 50° C. with lactose (Lac) (100 mg/ml) at pH 4.8 (25 mM sodium citrate), 6.45 (25 mM sodium acetate, 0.5 mM $CaCl_2$, 0.005% Triton X-100) and 8.6 (50 mM Tris, 0.01% Brij 35). 20 microliters samples were withdrawn after 2, 23 and 120 hours, 980 water added and enzyme inactivated by heating to 95° C. for 10 min. After a further 20 time dilution with water, samples were analysed using HPAE-PAD (Dionex LC-500 system, PA-100 column, 0-3 min: 150 mM NaOH, 3-19 min: linear gradient 0-0.18 M sodium acetate in 150 mM NaOH). Response factors for the individual peaks were estimated from standards of Gal, Glu, Lac, Gal2, Gal3 and Gal4.

Under these conditions only MTGAL at pH 4.5 and 6.5 gave significant conversion of Lac. In Tables 12 and 13 weight fractions of the analysed products with MTGAL at pH 4.5 and 6.45 are given. The figures indicate weight % of the products resulting from the incubation. The term DP3 indicates transglycosylation product consisting of three sugar units, and the term DP4+ transglycosylation products consisting of four or more sugar units. Unfortunately, the analysis method used was not able to separate Glu and Gal.

With transglycosylation occurring according to the reaction:

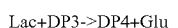

the weight fraction of DP3 should be about three times higher than the weight of the monomer. After 2 hours the ratio is about 1.5 at both pH's indicating that this is not the only reaction taking place. The production of larger oligosaccharides (DP4+) is a result of the initial transglycosylation product functioning as acceptor for further transglycosylation:

Lac+DP3->DP4+Glu

Also, from the increasing amount of Gal/Glu without corresponding increase in transglycosylation products (DP3 and DP4+) after 23 and 120 hours, it is evident that hydrolysis of transglycosylation products takes place. These hydrolysis reactions seem to be slower at pH 6.45 than at pH 4.5.

TABLE 12

Activity of MTGAL on lactose (pH 4.5)

| Incubation time (hours) | 2 | 23 | 120 |
|---|---|---|---|
| Glu/Gal | 1.4 | 12.5 | 38.8 |
| Lac/Gal2 | 96.0 | 78.7 | 51.2 |

TABLE 12-continued

Activity of MTGAL on lactose (pH 4.5)

| Incubation time (hours) | 2 | 23 | 120 |
|---|---|---|---|
| DP3 | 2.0 | 7.0 | 8.9 |
| DP4+ | 0.5 | 1.8 | 1.1 |

TABLE 13

Activity of MTGAL on lactose (pH 6.45)

| Incubation time (hours) | 2 | 23 | 120 |
|---|---|---|---|
| Glu/Gal | 1.0 | 6.5 | 21.0 |
| Lac/Gal2 | 95.7 | 85.3 | 62.6 |
| DP3 | 1.4 | 6.3 | 11.7 |
| DP4+ | 1.9 | 1.9 | 4.7 |

Example 6

Activity on Galactan

Lupin galactan (Megazyme) was incubated with BLGAL (0.1-10 micrograms/ml) at pH 6.5 (50 mM MES, 1 mM CaCl$_2$) and with AAGAL (0.1-10 µg/ml) at pH 4.0 (50 mM sodium acetate, 1 mM CaCl$_2$) at 30° C. Samples were withdrawn after 45 min to 24 hours and enzyme inactivated by heating to 95° C. for 10 min. Reaction products were analyzed using HPAEC-PAD on a Dionex chromatographic system using a CarboPac PA-100 column and a linear gradient 0 to 0.3 M sodium acetate in 0.15 M NaOH. Purified galactooligosaccharides were used to identify products.

With BLGAL the initial main product is galactotetraose with both smaller and larger oligomers also present. Upon longer incubation the fractions of galactose, galactobiose and galactotriose increase and after prolonged incubation only these three oligomers are seen in molar ratios of about 1:0.4:0.9.

AAGAL initially produces a more homogeneous mixture of galactooligomers. Further degradation yields mainly galactose, galactobiose and galactotriose, and finally almost exclusively galactose and galactobiose are seen in a molar ratio of about 2:1. Small peaks probably corresponding to galactobioses and galactotrioses resulting from transglycosylation reactions with glucosidic bonds different from beta-1,4 are also present.

The invention claimed is:

1. A variant of a parent Glycoside Hydrolase Family 53 galactanase, comprising an alteration at a position corresponding to position 295 of SEQ ID NO: 1, wherein
   (a) the variant is at least 80% identical to SEQ ID NO: 1 or 2;
   (b) the alteration is
      (i) an insertion of an amino acid immediately downstream of the position,
      (ii) a deletion of the amino acid which occupies the position, and/or
      (iii) a substitution of the amino acid which occupies the position with a different amino acid; and
   (c) the variant has galactanase activity.

2. The variant of claim 1, wherein the alteration is a substitution.

3. The variant of claim 2, wherein the substitution is Y295A,C,D,E,F,G,H,I,K,L,M,N,P,Q,R,S,T,V,W.

4. The variant of claim 1, wherein the variant is at least 85% identical to SEQ ID NO: 1.

5. The variant of claim 1, wherein the variant is at least 90% identical to SEQ ID NO: 1.

6. The variant of claim 1, wherein the variant is at least 95% identical to SEQ ID NO: 1.

7. The variant of claim 1, wherein the variant is at least 85% identical to SEQ ID NO: 2.

8. The variant of claim 1, wherein the variant is at least 90% identical to SEQ ID NO: 2.

9. The variant of claim 1, wherein the variant is at least 95% identical to SEQ ID NO: 2.

10. The variant of claim 1, which further comprises an alteration at one or more positions selected from the group consisting of:

−6, −4, −2, 1, 3, 4, 5, 6, 7, 8, 9, 10, 11, 12, 13, 14, 15, 16, 18, 20, 22, 24, 25, 26, 29, 30, 31, 32, 36, 39, 40, 41, 43, 44, 45, 46, 47, 48, 49, 50, 51, 52, 53, 54, 54a, 54e, 54f, 54g, 54h, 55, 56, 57, 58, 61, 62, 65, 69, 77, 79, 80, 81, 82, 83, 84, 85, 86, 87, 88, 89, 90, 91, 92, 93, 94, 95, 96, 97, 101, 106, 107, 110, 113, 114, 126, 131, 132, 133, 134, 135, 136, 137, 138, 139, 140, 141, 142, 144, 145, 146, 147, 150, 153, 157, 159, 163, 169, 171, 172, 176, 177, 178, 179, 180, 181, 182, 183, 184, 185, 186, 187, 188, 189, 191, 192, 194, 198, 200, 203, 204, 209, 210, 211, 212, 213, 214, 215, 216, 217, 218, 219, 220, 221, 222, 223, 224, 225, 226, 227, 228, 229, 230, 231, 232, 233, 234, 241, 242, 243, 244, 245, 246, 247, 248, 249, 250, 252, 252d, 252e, 253, 254, 255, 256, 257, 258, 259, 260, 261, 262, 263, 264, 265, 266, 273, 274, 276, 277, 280, 283, 284, 286, 288, 288a, 289, 292, 293, 294, 296, 297, 298, 299, 300, 301, 302, 302a, 302d, 302j, 302k, 302m, 302n, 302o, 302q, 302r, 302s, 302t, 302u, 302v, 302x, 302y, 302z, 302aa, 302bb, 302cc, 302dd, 302ee, 302ff, 302gg, 302hh, 302ii, 302jj, 303, 304, 305, 306, 307, 308, 309, 310, 311, 312, 313, 314, 315, 316, 317, 318, 319, 320, 321, 322, 323, 324, 325, 326, 327, 328, 329, and 330.

11. An animal feed composition, comprising a variant of claim 1.

12. A method for hydrolyzing lactose, comprising treating the lactose with a galactanase variant of claim 1.

* * * * *

SEQUENCE LISTING

```
<160> NUMBER OF SEQ ID NOS: 9

<210> SEQ ID NO 1
<211> LENGTH: 332
<212> TYPE: PRT
<213> ORGANISM: Myceliophthora thermophila
<220> FEATURE:
<221> NAME/KEY: mat_peptide
<222> LOCATION: (1)..()

<400> SEQUENCE: 1

Ala Leu Thr Tyr Arg Gly Val Asp Trp Ser Ser Val Val Val Glu Glu
1               5                   10                  15

Arg Ala Gly Val Ser Tyr Lys Asn Thr Asn Gly Asn Ala Gln Pro Leu
            20                  25                  30

Glu Asn Ile Leu Ala Ala Asn Gly Val Asn Thr Val Arg Gln Arg Val
        35                  40                  45

Trp Val Asn Pro Ala Asp Gly Asn Tyr Asn Leu Asp Tyr Asn Ile Ala
    50                  55                  60

Ile Ala Lys Arg Ala Lys Ala Ala Gly Leu Gly Val Tyr Ile Asp Phe
65                  70                  75                  80

His Tyr Ser Asp Thr Trp Ala Asp Pro Ala His Gln Thr Met Pro Ala
                85                  90                  95

Gly Trp Pro Ser Asp Ile Asp Asn Leu Ser Trp Lys Leu Tyr Asn Tyr
            100                 105                 110

Thr Leu Asp Ala Ala Asn Lys Leu Gln Asn Ala Gly Ile Gln Pro Thr
        115                 120                 125

Ile Val Ser Ile Gly Asn Glu Ile Arg Ala Gly Leu Leu Trp Pro Thr
    130                 135                 140

Gly Arg Thr Glu Asn Trp Ala Asn Ile Ala Arg Leu Leu His Ser Ala
145                 150                 155                 160

Ala Trp Gly Ile Lys Asp Ser Ser Leu Ser Pro Lys Pro Lys Ile Met
```

```
                    165                 170                 175
Ile His Leu Asp Asn Gly Trp Asp Trp Gly Thr Gln Asn Trp Trp Tyr
            180                 185                 190

Thr Asn Val Leu Lys Gln Gly Thr Leu Glu Leu Ser Asp Phe Asp Met
            195                 200                 205

Met Gly Val Ser Phe Tyr Pro Phe Tyr Ser Ser Ala Thr Leu Ser
            210                 215                 220

Ala Leu Lys Ser Ser Leu Asp Asn Met Ala Lys Thr Trp Asn Lys Glu
225                 230                 235                 240

Ile Ala Val Val Glu Thr Asn Trp Pro Ile Ser Cys Pro Asn Pro Arg
                    245                 250                 255

Tyr Ser Phe Pro Ser Asp Val Lys Asn Ile Pro Phe Ser Pro Glu Gly
                260                 265                 270

Gln Thr Thr Phe Ile Thr Asn Val Ala Asn Ile Val Ser Ser Val Ser
            275                 280                 285

Arg Gly Val Gly Leu Phe Tyr Trp Glu Pro Ala Trp Ile His Asn Ala
            290                 295                 300

Asn Leu Gly Ser Ser Cys Ala Asp Asn Thr Met Phe Ser Gln Ser Gly
305                 310                 315                 320

Gln Ala Leu Ser Ser Leu Ser Val Phe Gln Arg Ile
                    325                 330

<210> SEQ ID NO 2
<211> LENGTH: 332
<212> TYPE: PRT
<213> ORGANISM: Humicola insolens
<220> FEATURE:
<221> NAME/KEY: mat_peptide
<222> LOCATION: (1)..()

<400> SEQUENCE: 2

Ala Leu Gln Tyr Lys Gly Val Asp Trp Ser Ser Val Met Val Glu Glu
1               5                   10                  15

Arg Ala Gly Val Arg Tyr Lys Asn Val Asn Gly Gln Glu Lys Pro Leu
                20                  25                  30

Glu Tyr Ile Leu Ala Glu Asn Gly Val Asn Met Val Arg Gln Arg Val
            35                  40                  45

Trp Val Asn Pro Trp Asp Gly Asn Tyr Asn Leu Asp Tyr Asn Ile Gln
        50                  55                  60

Leu Ala Arg Arg Ala Lys Ala Ala Gly Leu Gly Leu Tyr Ile Asn Phe
65                  70                  75                  80

His Tyr Ser Asp Thr Trp Ala Asp Pro Ala His Gln Thr Thr Pro Ala
                85                  90                  95

Gly Trp Pro Ser Asp Ile Asn Asn Leu Ala Trp Lys Leu Tyr Asn Tyr
                100                 105                 110

Thr Leu Asp Ser Met Asn Arg Phe Ala Asp Ala Gly Ile Gln Val Asp
            115                 120                 125

Ile Val Ser Ile Gly Asn Glu Ile Thr Gln Gly Leu Leu Trp Pro Leu
130                 135                 140

Gly Lys Thr Asn Asn Trp Tyr Asn Ile Ala Arg Leu Leu His Ser Ala
145                 150                 155                 160

Ala Trp Gly Val Lys Asp Ser Arg Leu Asn Pro Lys Pro Lys Ile Met
                165                 170                 175

Val His Leu Asp Asn Gly Trp Asn Trp Asp Thr Gln Asn Trp Trp Tyr
            180                 185                 190

Thr Asn Val Leu Ser Gln Gly Pro Phe Glu Met Ser Asp Phe Asp Met
```

```
                    195                 200                 205
Met Gly Val Ser Phe Tyr Pro Phe Tyr Ser Ala Ser Ala Thr Leu Asp
210                 215                 220

Ser Leu Arg Arg Ser Leu Asn Asn Met Val Ser Arg Trp Gly Lys Glu
225                 230                 235                 240

Val Ala Val Val Glu Thr Asn Trp Pro Thr Ser Cys Pro Tyr Pro Arg
                    245                 250                 255

Tyr Gln Phe Pro Ala Asp Val Arg Asn Val Pro Phe Ser Ala Ala Gly
                260                 265                 270

Gln Thr Gln Tyr Ile Gln Ser Val Ala Asn Val Val Ser Ser Val Ser
                275                 280                 285

Lys Gly Val Gly Leu Phe Tyr Trp Glu Pro Ala Trp Ile His Asn Ala
            290                 295                 300

Asn Leu Gly Ser Ser Cys Ala Asp Asn Thr Met Phe Thr Pro Ser Gly
305                 310                 315                 320

Gln Ala Leu Ser Ser Leu Ser Val Phe His Arg Ile
                325                 330
```

<210> SEQ ID NO 3
<211> LENGTH: 334
<212> TYPE: PRT
<213> ORGANISM: Aspergillus aculeatus
<220> FEATURE:
<221> NAME/KEY: mat_peptide
<222> LOCATION: (1)..()

<400> SEQUENCE: 3

```
Ala Leu Thr Tyr Arg Gly Ala Asp Ile Ser Ser Leu Leu Leu Leu Glu
1               5                   10                  15

Asp Glu Gly Tyr Ser Tyr Lys Asn Leu Asn Gly Gln Thr Gln Ala Leu
                20                  25                  30

Glu Thr Ile Leu Ala Asp Ala Gly Ile Asn Ser Ile Arg Gln Arg Val
            35                  40                  45

Trp Val Asn Pro Ser Asp Gly Ser Tyr Asp Leu Asp Tyr Asn Leu Glu
50                  55                  60

Leu Ala Lys Arg Val Lys Ala Ala Gly Met Ser Leu Tyr Leu Asp Leu
65                  70                  75                  80

His Leu Ser Asp Thr Trp Ala Asp Pro Ser Asp Gln Thr Thr Pro Ser
                85                  90                  95

Gly Trp Ser Thr Thr Asp Leu Gly Thr Leu Lys Trp Gln Leu Tyr Asn
                100                 105                 110

Tyr Thr Leu Glu Val Cys Asn Thr Phe Ala Glu Asn Asp Ile Asp Ile
            115                 120                 125

Glu Ile Ile Ser Ile Gly Asn Glu Ile Arg Ala Gly Leu Leu Trp Pro
        130                 135                 140

Leu Gly Glu Thr Ser Ser Tyr Ser Asn Ile Gly Ala Leu Leu His Ser
145                 150                 155                 160

Gly Ala Trp Gly Val Lys Asp Ser Asn Leu Ala Thr Thr Pro Lys Ile
                165                 170                 175

Met Ile His Leu Asp Asp Gly Trp Ser Trp Asp Gln Asn Tyr Phe
                180                 185                 190

Tyr Glu Thr Val Leu Ala Thr Gly Glu Leu Leu Ser Thr Asp Phe Asp
            195                 200                 205

Tyr Phe Gly Val Ser Tyr Tyr Pro Phe Tyr Ser Ala Ser Ala Thr Leu
        210                 215                 220

Ala Ser Leu Lys Thr Ser Leu Ala Asn Leu Gln Ser Thr Tyr Asp Lys
```

```
            225                 230                 235                 240
    Pro Val Val Val Glu Thr Asn Trp Pro Val Ser Cys Pro Asn Pro
                    245                 250                 255

Ala Tyr Ala Phe Pro Ser Asp Leu Ser Ser Ile Pro Phe Ser Val Ala
                260                 265                 270

Gly Gln Gln Glu Phe Leu Glu Lys Leu Ala Ala Val Val Glu Ala Thr
                275                 280                 285

Thr Asp Gly Leu Gly Val Tyr Tyr Trp Glu Pro Ala Trp Ile Gly Asn
                290                 295                 300

Ala Gly Leu Gly Ser Ser Cys Ala Asp Asn Leu Met Val Asp Tyr Thr
    305                 310                 315                 320

Thr Asp Glu Val Tyr Glu Ser Ile Glu Thr Leu Gly Glu Leu
                    325                 330

<210> SEQ ID NO 4
<211> LENGTH: 399
<212> TYPE: PRT
<213> ORGANISM: Bacillus licheniformis

<400> SEQUENCE: 4

Ala His Arg Asp Ser Gly Thr Ala Lys Ser Gly Leu Tyr Val Glu Lys
1               5                   10                  15

Val Ser Gly Leu Arg Lys Asp Phe Ile Lys Gly Val Asp Val Ser Ser
            20                  25                  30

Ile Ile Ala Leu Glu Glu Ser Gly Val Ala Phe Tyr Asn Glu Ser Gly
        35                  40                  45

Lys Lys Gln Asp Ile Phe Asn Thr Leu Lys Glu Ala Gly Val Asn Tyr
    50                  55                  60

Val Arg Val Arg Ile Trp Asn Asp Pro Tyr Asp Ala Asn Gly Asn Gly
65                  70                  75                  80

Tyr Gly Gly Gly Asn Asn Asp Leu Glu Lys Ala Ile Gln Ile Gly Lys
                85                  90                  95

Arg Ala Asn Ala Asn Gly Met Lys Leu Leu Ala Asp Phe His Tyr Ser
            100                 105                 110

Asp Phe Trp Ala Asp Pro Ala Lys Gln Lys Ala Pro Lys Ala Trp Ala
        115                 120                 125

Asn Leu Asn Phe Glu Asp Lys Lys Thr Ala Leu Tyr Gln Tyr Thr Lys
    130                 135                 140

Gln Ser Leu Lys Ala Met Lys Ala Ala Gly Ile Asp Ile Gly Met Val
145                 150                 155                 160

Gln Val Gly Asn Glu Thr Asn Gly Gly Leu Ala Gly Glu Thr Asp Trp
                165                 170                 175

Ala Lys Met Ser Gln Leu Phe Asn Ala Gly Ser Gln Ala Val Arg Glu
            180                 185                 190

Thr Asp Ser Asn Ile Leu Val Ala Leu His Phe Thr Asn Pro Glu Thr
        195                 200                 205

Ser Gly Arg Tyr Ala Trp Ile Ala Glu Thr Leu His Arg His His Val
    210                 215                 220

Asp Tyr Asp Val Phe Ala Ser Ser Tyr Tyr Pro Phe Trp His Gly Thr
225                 230                 235                 240

Leu Lys Asn Leu Thr Ser Val Leu Thr Ser Val Ala Asp Thr Tyr Gly
                245                 250                 255

Lys Lys Val Met Val Ala Glu Thr Ser Tyr Thr Tyr Thr Ala Glu Asp
            260                 265                 270

Gly Asp Gly His Gly Asn Thr Ala Pro Lys Asn Gly Gln Thr Leu Asn
```

```
                275                 280                 285
Asn Pro Val Thr Val Gln Gly Gln Ala Asn Ala Val Arg Asp Val Ile
    290                 295                 300

Gln Ala Val Ser Asp Val Gly Glu Ala Gly Ile Gly Val Phe Tyr Trp
305                 310                 315                 320

Glu Pro Ala Trp Ile Pro Val Gly Pro Ala His Arg Leu Glu Lys Asn
                325                 330                 335

Lys Ala Leu Trp Glu Thr Tyr Gly Ser Gly Trp Ala Ser Tyr Ala
            340                 345                 350

Ala Glu Tyr Asp Pro Glu Asp Ala Gly Lys Trp Phe Gly Gly Ser Ala
            355                 360                 365

Val Asp Asn Gln Ala Leu Phe Asp Phe Lys Gly Arg Pro Leu Pro Ser
370                 375                 380

Leu His Val Phe Gln Tyr Val Asp Thr Gly Thr Pro Phe Lys Asn
385                 390                 395

<210> SEQ ID NO 5
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 5
catttggaca acggctggag c                                          21

<210> SEQ ID NO 6
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 6
gccgatcctt ctgatcagac catgcc                                     26

<210> SEQ ID NO 7
<211> LENGTH: 334
<212> TYPE: PRT
<213> ORGANISM: Aspergillus tubingensis
<220> FEATURE:
<221> NAME/KEY: mat_peptide
<222> LOCATION: (1)..()

<400> SEQUENCE: 7

Ala Leu Thr Tyr Arg Gly Ala Asp Ile Ser Ser Leu Leu Ile Glu Glu
1               5                   10                  15

Asp Ala Gly Ile Ser Tyr Lys Asn Leu Asn Gly Glu Thr Gln Ala Leu
            20                  25                  30

Glu Asp Ile Leu Val Asn Asn Gly Val Asn Ser Ile Arg Gln Arg Val
        35                  40                  45

Trp Val Asp Pro Ser Asp Gly Ser Tyr Asp Leu Asp Tyr Asn Leu Lys
    50                  55                  60

Leu Ala Lys Arg Val Gln Ala Ala Gly Met Ser Ile Tyr Leu Asp Leu
65                  70                  75                  80

His Leu Ser Asp Thr Trp Ala Asp Pro Ser Asp Gln Thr Thr Pro Thr
```

```
                    85                  90                  95
Gly Trp Ser Thr Thr Asp Ile Asp Thr Leu Thr Trp Gln Leu Tyr Asn
                100                 105                 110
Tyr Thr Leu Glu Val Cys Asn Thr Phe Ala Glu Asn Asp Ile Asp Val
            115                 120                 125
Glu Ile Val Ser Ile Gly Asn Glu Ile Ser Ser Gly Leu Leu Trp Pro
        130                 135                 140
Leu Gly Lys Thr Ser Asn Tyr Asp Asn Ile Ala Lys Leu Leu His Ser
145                 150                 155                 160
Gly Ala Trp Gly Val Lys Asp Ser Asp Leu Thr Thr Thr Pro Lys Ile
                165                 170                 175
Met Ile His Leu Asp Asn Gly Trp Asp Trp Asp Glu Gln Glu Tyr Phe
                180                 185                 190
Tyr Lys Thr Val Leu Ala Thr Gly Ser Leu Leu Ser Thr Asp Phe Asp
            195                 200                 205
Leu Met Gly Val Ser Tyr Tyr Pro Phe Tyr Ser Ser Glu Ala Thr Leu
        210                 215                 220
Ser Ser Leu Lys Thr Ser Leu Thr Asn Met Gln Ser Asn Tyr Asp Lys
225                 230                 235                 240
Pro Val Val Val Glu Thr Asn Trp Pro Val Ser Cys Pro Asp Pro
                245                 250                 255
Glu Tyr Ser Phe Pro Ser Asp Leu Thr Ser Ile Pro Phe Ser Ala Ala
                260                 265                 270
Gly Gln Glu Glu Phe Leu Glu Lys Leu Ala Glu Val Val Glu Gly Val
            275                 280                 285
Thr Asp Gly Leu Gly Ile Tyr Tyr Trp Glu Pro Ala Trp Ile Asp Asn
        290                 295                 300
Ala Gly Leu Gly Ser Ser Cys Ala Asp Asn Leu Met Val Asp Val Asn
305                 310                 315                 320
Thr Asp Glu Val Leu Glu Ser Val Thr Val Phe Glu Asp Leu
                325                 330

<210> SEQ ID NO 8
<211> LENGTH: 372
<212> TYPE: PRT
<213> ORGANISM: Bacillus subtilis
<220> FEATURE:
<221> NAME/KEY: mat_peptide
<222> LOCATION: (1)..()

<400> SEQUENCE: 8

Met Asn Lys Asp Phe Ile Lys Gly Ala Asp Val Ser Ser Val Ile Ala
1               5                   10                  15
Leu Glu Asn Ser Gly Val Thr Phe Tyr Asn Thr Asn Gly Lys Arg Gln
                20                  25                  30
Asp Ile Phe Thr Thr Leu Lys Gln Ala Gly Val Asn Tyr Val Arg Val
            35                  40                  45
Arg Ile Trp Asn His Pro Tyr Asp Ser Asn Gly Asn Gly Tyr Gly Gly
        50                  55                  60
Gly Asn Asn Asp Val Gln Lys Ala Ile Glu Ile Gly Lys Arg Ala Thr
65                  70                  75                  80
Ala Asn Gly Met Lys Val Leu Asp Phe His Tyr Ser Asp Phe Trp
                85                  90                  95
Ala Asp Pro Ala Lys Gln Lys Val Pro Lys Ala Trp Ala Asn Leu Ser
                100                 105                 110
Phe Glu Ala Lys Lys Ala Lys Leu Tyr Glu Tyr Thr Lys Gln Ser Leu
```

```
                    115                 120                 125
Gln Lys Met Ile Lys Glu Gly Val Asp Ile Gly Met Val Gln Val Gly
    130                 135                 140

Asn Glu Thr Thr Gly Gly Phe Ala Gly Glu Thr Asp Trp Thr Lys Met
145                 150                 155                 160

Cys Gln Leu Phe Asn Glu Gly Ser Arg Ala Val Arg Glu Thr Asn Ser
                165                 170                 175

Asn Ile Leu Val Ala Leu His Phe Thr Asn Pro Glu Thr Ala Gly Arg
            180                 185                 190

Tyr Ser Phe Ile Ala Glu Thr Leu Ser Lys Asn Lys Val Asp Tyr Asp
        195                 200                 205

Val Phe Ala Ser Ser Tyr Tyr Pro Phe Trp His Gly Thr Leu Gln Asn
    210                 215                 220

Leu Thr Ser Val Leu Lys Ala Val Ala Asn Thr Tyr Gly Lys Lys Val
225                 230                 235                 240

Met Val Ala Glu Thr Ser Tyr Thr Tyr Thr Ala Glu Asp Gly Asp Gly
                245                 250                 255

His Gly Asn Thr Ala Pro Lys Ser Gly Gln Thr Leu Pro Tyr Pro Ile
            260                 265                 270

Ser Val Gln Gly Gln Ala Thr Ala Val Arg Asp Val Met Glu Ala Val
        275                 280                 285

Ala Asn Thr Gly Lys Ala Gly Leu Gly Val Phe Tyr Trp Glu Pro Ala
    290                 295                 300

Trp Ile Pro Val Gly Pro Lys Thr Gln Ile Glu Lys Asn Lys Val Leu
305                 310                 315                 320

Trp Glu Thr Tyr Gly Ser Gly Trp Ala Ser Ser Tyr Ala Ala Glu Tyr
                325                 330                 335

Asp Pro Glu Asp Ala Gly Lys Trp Tyr Gly Gly Ser Ala Val Asp Asn
            340                 345                 350

Gln Ala Leu Phe Asp Phe Asn Gly His Pro Leu Pro Ser Leu Gln Val
        355                 360                 365

Phe Gln Tyr Ala
    370

<210> SEQ ID NO 9
<211> LENGTH: 359
<212> TYPE: PRT
<213> ORGANISM: Pseudomonas fluorscens
<220> FEATURE:
<221> NAME/KEY: mat_peptide
<222> LOCATION: (1)..()

<400> SEQUENCE: 9

Asn Thr Gly Val Ala Asp Asn Thr Pro Phe Tyr Val Gly Ala Asp Leu
1               5                   10                  15

Ser Tyr Val Asn Glu Met Glu Ser Cys Gly Ala Thr Tyr Arg Asp Gln
            20                  25                  30

Gly Lys Lys Val Asp Pro Phe Gln Leu Phe Ala Asp Lys Gly Ala Asp
        35                  40                  45

Leu Val Arg Val Arg Leu Trp His Asn Ala Thr Trp Thr Lys Tyr Ser
    50                  55                  60

Asp Leu Lys Asp Val Ser Lys Thr Leu Lys Arg Ala Lys Asn Ala Gly
65                  70                  75                  80

Met Lys Thr Leu Leu Asp Phe His Tyr Ser Asp Thr Trp Thr Asp Pro
                85                  90                  95

Glu Lys Gln Phe Ile Pro Lys Ala Trp Ala His Ile Thr Asp Thr Lys
```

-continued

```
                      100                 105                 110
 Glu Leu Ala Lys Ala Leu Tyr Asp Tyr Thr Thr Asp Thr Leu Ala Ser
             115                 120                 125

Leu Asp Gln Gln Gln Leu Leu Pro Asn Leu Val Gln Val Gly Asn Glu
             130                 135                 140

Thr Asn Ile Glu Ile Leu Gln Ala Glu Asp Thr Leu Val His Gly Ile
 145                 150                 155                 160

Pro Asn Trp Gln Arg Asn Ala Thr Leu Leu Asn Ser Gly Val Asn Ala
             165                 170                 175

Val Arg Asp Tyr Ser Lys Lys Thr Gly Lys Pro Ile Gln Val Val Leu
             180                 185                 190

His Ile Ala Gln Pro Glu Asn Ala Leu Trp Trp Phe Lys Gln Ala Lys
             195                 200                 205

Glu Asn Gly Val Ile Asp Tyr Asp Val Ile Gly Leu Ser Tyr Tyr Pro
             210                 215                 220

Gln Trp Ser Glu Tyr Ser Leu Pro Gln Leu Pro Asp Ala Ile Ala Glu
 225                 230                 235                 240

Leu Gln Asn Thr Tyr His Lys Pro Val Met Ile Val Glu Thr Ala Tyr
             245                 250                 255

Pro Trp Thr Leu His Asn Phe Asp Gln Ala Gly Asn Val Leu Gly Glu
             260                 265                 270

Lys Ala Val Gln Pro Glu Phe Pro Ala Ser Pro Arg Gly Gln Leu Thr
             275                 280                 285

Tyr Leu Leu Thr Leu Thr Gln Leu Val Lys Ser Ala Gly Gly Met Gly
             290                 295                 300

Val Ile Tyr Trp Glu Pro Ala Trp Val Ser Thr Arg Cys Arg Thr Leu
 305                 310                 315                 320

Trp Gly Lys Gly Ser His Trp Glu Asn Ala Ser Phe Phe Asp Ala Thr
             325                 330                 335

Arg Lys Asn Asn Ala Leu Pro Ala Phe Leu Phe Phe Lys Ala Asp Tyr
             340                 345                 350

Gln Ala Ser Ala Gln Ala Glu
             355
```